(12) United States Patent
Cheng et al.

(10) Patent No.: US 7,279,485 B2
(45) Date of Patent: Oct. 9, 2007

(54) SUBSTITUTED HETEROCYCLIC DERIVATIVES USEFUL AS ANTIDIABETIC AND ANTIOBESITY AGENTS AND METHOD

(75) Inventors: Peter T. W. Cheng, Princeton, NJ (US); Sean Chen, Princeton, NJ (US); Pratik Devasthale, Plainsboro, NJ (US); Charles Z. Ding, Plano, TX (US); Timothy F. Herpin, Princeton, NJ (US); Shung Wu, Princeton, NJ (US); Hao Zhang, Belle Mead, NJ (US); Wei Wang, Princeton, NJ (US); Xiang-Yang Ye, Cranbury, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 574 days.

(21) Appl. No.: 10/616,365

(22) Filed: Jul. 8, 2003

(65) Prior Publication Data
US 2004/0063700 A1   Apr. 1, 2004

Related U.S. Application Data

(60) Provisional application No. 60/394,508, filed on Jul. 9, 2002.

(51) Int. Cl.
| | |
|---|---|
| A01N 43/54 | (2006.01) |
| A01N 43/76 | (2006.01) |
| A61K 31/505 | (2006.01) |
| C07D 239/02 | (2006.01) |
| C07D 413/00 | (2006.01) |

(52) U.S. Cl. .................. 514/275; 514/374; 544/297; 548/235

(58) Field of Classification Search ............... 548/215
See application file for complete search history.

(56) References Cited

U.S. PATENT DOCUMENTS

| 5,846,966 | A | 12/1998 | Rosenblum et al. |
| 6,306,887 | B1 | 10/2001 | Chupak et al. |
| 6,414,002 | B1 | 7/2002 | Cheng et al. |
| 6,653,314 | B2 * | 11/2003 | Cheng et al. ............... 514/256 |
| 6,727,271 | B2 * | 4/2004 | Cheng et al. ............... 514/374 |
| 6,919,358 | B2 * | 7/2005 | Cheng et al. ............... 514/340 |
| 6,967,212 | B2 * | 11/2005 | Cheng et al. ............... 514/365 |
| 7,053,106 | B2 * | 5/2006 | Cheng et al. ............... 514/333 |
| 7,084,162 | B2 * | 8/2006 | Cheng et al. ............... 514/374 |
| 7,105,556 | B2 * | 9/2006 | Cheng et al. ............... 514/374 |

FOREIGN PATENT DOCUMENTS

| EP | 0 520 723 | 6/1994 |
| WO | WO92/22533 | 12/1992 |
| WO | WO97/27847 | 8/1997 |
| WO | WO97/27857 | 8/1997 |
| WO | WO97/28137 | 8/1997 |
| WO | WO97/28149 | 8/1997 |
| WO | WO97/31907 | 9/1997 |
| WO | WO98/00137 | 1/1998 |
| WO | WO98/00403 | 1/1998 |

(Continued)

OTHER PUBLICATIONS

Cobb, J.E. et al., "N-(2-Benzoylphenyl)-L-tyrosine PPARγAgonists. 3. Structure-Activity Relationship and Optimization of the N-Aryl Substituent", J. Med. Chem., vol. 41, pp. 5055-5069 (1998).

Collins, J.L. et al., "N-(2-Benzoylphenyl)-L-tyrosine PPARγAgonists. 2. Structure-Activity Relationship and Optimization of the Phenyl Alkyl Ether Moiety", J. Med. Chem., vol. 41, pp. 5037-5054 (1998).

Henke, B.R. et al., "N-(2-Benzoylphenyl)-L-tyrosine PPARγAgonists. 1. Discovery of a Novel Series of Potent Antihyperglycemic and Antihyperlipidemic Agents", J. Med. Chem., vol. 41, pp. 5020-5036 (1998).

*Primary Examiner*—Zachary C Tucker
(74) *Attorney, Agent, or Firm*—Burton Rodney

(57) ABSTRACT

Substituted heterocyclic derivatives are provided which have the structure

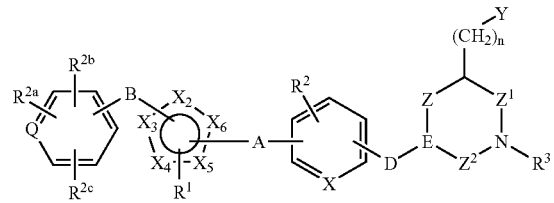

wherein $Z^1$ is $(CH_2)_q$ or C=O;
$Z^2$ is $(CH_2)_p$ or C=O;
D is —CH= or C=O or $(CH_2)_m$ where m is 0, 1, 2 or 3;
n=0, 1 or 2; p=1 or 2; q=0, 1 or 2;
Q is C or N;
X is CH or N;
$X_2$ is C, N, O or S;
$X_3$ is C, N, O or S;
$X_4$ is C, N, O or S;
$X_5$ is C, N, O or S;
$X_6$ is C, N, O or S;
provided that at least one of $X_2$, $X_3$, $X_4$, $X_5$ and $X_6$ is N; and at least one of $X_2$, $X_3$, $X_4$, $X_5$ and $X_6$ is C;
A, B, $R^1$, $R^2$, $R^{2a}$, $R^{2b}$, $R^4$, $R^3$, E, Z and Y are as defined herein.

In addition, a method is provided for treating diabetes, Type 2 diabetes, insulin resistance, hyperglycemia, hyperinsulinemia, elevated blood levels of fatty acids or glycerol, hyperlipidemia, obesity, hypertriglyceridemia, Syndrome X, or atherosclerosis, wherein the substituted heterocyclic derivatives are administered in a therapeutically effective amount to a patient.

11 Claims, No Drawings

FOREIGN PATENT DOCUMENTS

| | | |
|---|---|---|
| WO | WO98/27974 | 7/1998 |
| WO | WO99/08501 | 2/1999 |
| WO | WO99/11255 | 3/1999 |
| WO | WO99/16758 | 4/1999 |
| WO | WO99/20275 | 4/1999 |
| WO | WO 00/08002 | 2/2000 |
| WO | WO 00/64876 | 11/2000 |
| WO | WO 00/64888 | 11/2000 |
| WO | WO 01/38325 | 5/2001 |

* cited by examiner

SUBSTITUTED HETEROCYCLIC DERIVATIVES USEFUL AS ANTIDIABETIC AND ANTIOBESITY AGENTS AND METHOD

This application claims priority from U.S. Provisional Application No. 60/394,508, filed Jul. 9, 2002 which is incorporated herein by reference.

FIELD OF THE INVENTION

The present invention relates to novel substituted heterocyclic derivatives which modulate blood glucose levels, triglyceride levels, insulin levels and non-esterified fatty acid (NEFA) levels, and thus are particularly useful in the treatment of diabetes and obesity, and to a method for treating diabetes, especially Type 2 diabetes, as well as hyperglycemia, hyperinsulinemia, hyperlipidemia, obesity, atherosclerosis and related diseases employing such substituted acid derivatives alone or in combination with another antidiabetic agent and/or a hypolipidemic agent and/or other therapeutic agents.

DESCRIPTION OF THE INVENTION

In accordance with the present invention, substituted heterocyclic derivatives are provided which have the structure

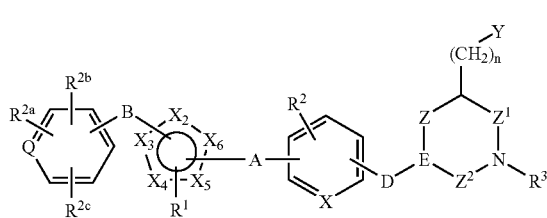

I wherein $Z^1$ is $(CH_2)_q$ or C=O;
$Z^2$ is $(CH_2)_p$ or C=O;
wherein D is —CH= or C=O or $(CH_2)_m$ where m is 0, 1, 2 or 3;
n=0, 1 or 2; p=1 or 2; q=0, 1 or 2;
Q is C or N;
A is $(CH_2)_x$ where x is 1 to 5, or A is $(CH_2)_x^1$, where $x^1$ is 1 to 5 with an alkenyl bond or an alkynyl bond embedded anywhere in the chain, or A is —$(CH_2)_x^2$—O—$(CH_2)_x^3$— where $x^2$ is 0 to 5 and $x^3$ is 0 to 5, provided that at least one of $x^2$ and $x^3$ is other than 0;
B is a bond or is $(CH_2)_x^4$ where $x^4$ is 1 to 5;
X is CH or N;
$X_2$ is C, N, O or S;
$X_3$ is C, N, O or S;
$X_4$ is C, N, O or S;
$X_5$ is C, N, O or S;
$X_6$ is C, N, O or S;
provided that at least one of $X_2$, $X_3$, $X_4$ $X_5$ and $X_6$ is N; and at least one of $X_2$, $X_3$, $X_4$ $X_5$ and $X_6$ is C.
In each of X through $X_6$, as defined above, C may include CH.
$R^1$ is H or alkyl;
$R^2$ is H, alkyl, alkoxy, halogen, amino, substituted amino or cyano;

$R^{2a}$, $R^{2b}$ and $R^{2c}$ may be the same or different and are selected from H, alkyl, alkoxy, halogen, amino, substituted amino or cyano;
$R^3$ is selected from H, alkyl, arylalkyl, aryloxycarbonyl, alkyloxycarbonyl, alkynyloxycarbonyl, alkenyloxycarbonyl, arylcarbonyl, alkylcarbonyl, aryl, heteroaryl, cycloheteroalkyl, heteroarylcarbonyl, heteroaryl-heteroarylalkyl, alkylcarbonylamino, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, arylcarbonylamino, heteroarylcarbonylamino, alkoxycarbonylamino, aryloxycarbonylamino, heteroaryloxycarbonylamino, heteroaryl-heteroarylcarbonyl, alkylsulfonyl, alkenylsulfonyl, heteroaryloxycarbonyl, cycloheteroalkyloxycarbonyl, heteroarylalkyl, aminocarbonyl, substituted aminocarbonyl, alkylaminocarbonyl, arylaminocarbonyl, heteroarylalkenyl, cycloheteroalkyl-heteroarylalkyl; hydroxyalkyl, alkoxy, alkoxyaryloxycarbonyl, arylalkyloxycarbonyl, alkylaryloxycarbonyl, arylheteroarylalkyl, arylalkylarylalkyl, aryloxyarylalkyl, haloalkoxyaryloxycarbonyl, alkoxycarbonylaryloxycarbonyl, aryloxyaryloxycarbonyl, arylsulfinylarylcarbonyl, arylthioarylcarbonyl, alkoxycarbonylaryloxycarbonyl, arylalkenyloxycarbonyl, heteroaryloxyarylalkyl, aryloxyarylcarbonyl, aryloxyarylalkyloxycarbonyl, arylalkenyloxycarbonyl, arylalkylcarbonyl, aryloxyalkyloxycarbonyl, arylalkylsulfonyl, arylthiocarbonyl, arylalkenylsulfonyl, heteroarylsulfonyl, arylsulfonyl, alkoxyarylalkyl, heteroarylalkoxycarbonyl, arylheteroarylalkyl, alkoxyarylcarbonyl, aryloxyheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, arylalkoxycarbonylheteroarylalkyl, heteroarylarylalkyl, arylcarbonylheteroarylalkyl, heteroaryloxyarylalkyl, arylalkenylheteroarylalkyl, arylaminoarylalkyl, aminocarbonylarylarylalkyl;

E is CH or N;
Z is $(CH_2)_x^5$ where $x^5$ is 0 (i.e. a single or a double bond), 1 or 2 (preferably 0 to 1); or Z is $(CH_2)_x^6$ where $x^6$ is 2 to 5 (preferably 2 or 3) where $(CH_2)_x^6$ includes an alkenyl (C=C) bond embedded within the chain or Z is —$(CH_2)_x^7$—O—$(CH_2)_x^8$— where $x^7$ is 0 to 4 (preferably 0 to 2) and $x^8$ is 0 to 4 (preferably 0 to 2);
$(CH_2)_x$, $(CH_2)_x^1$, $(CH_2)_x^2$, $(CH_2)_x^3$, $(CH_2)_x^4$, $(CH_2)_x^5$, $(CH_2)_x^6$, $(CH_2)_x^7$ $(CH_2)_x^8$, $(CH_2)_m$, $(CH_2)_n$, $(CH_2)_p$ and $(CH_2)_q$ may be optionally substituted;
Y is $CO_2R^4$ (where $R^4$ is H or alkyl, or a prodrug ester) or Y is a C-linked 1-tetrazole, a phosphinic acid of the structure P(O) $(OR^{4a})R^5$, (where $R^{4a}$ is H or a prodrug ester, $R^5$ is alkyl or aryl) or a phosphonic acid of the structure P(O) $(OR^{4a})_2$;
and all stereoisomers thereof, prodrug esters thereof, and pharmaceutically acceptable salts thereof.

Thus, the compounds of the invention include the structures:
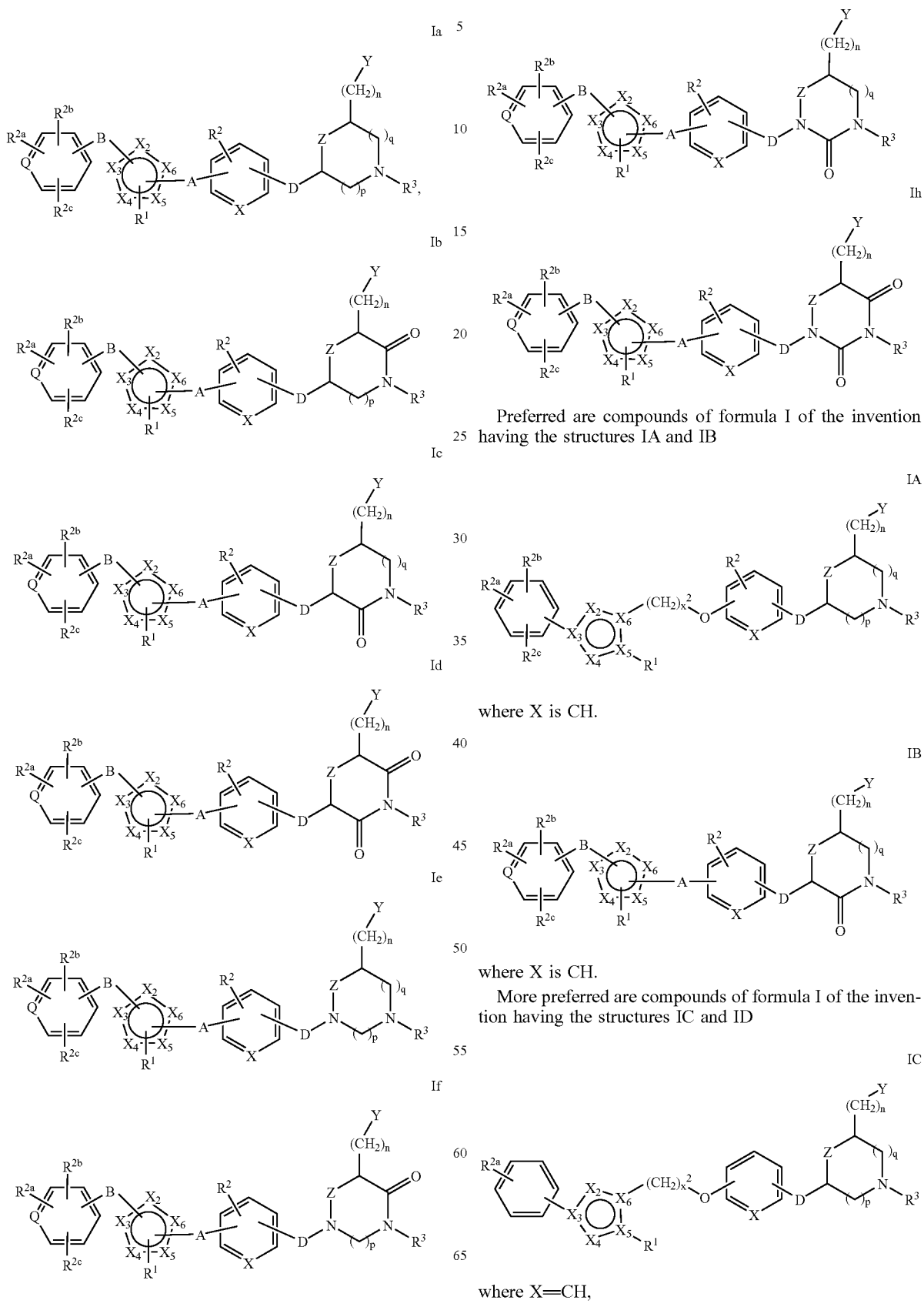
where X is CH.
where X is CH.
Preferred are compounds of formula I of the invention having the structures IA and IB
More preferred are compounds of formula I of the invention having the structures IC and ID
where X=CH,

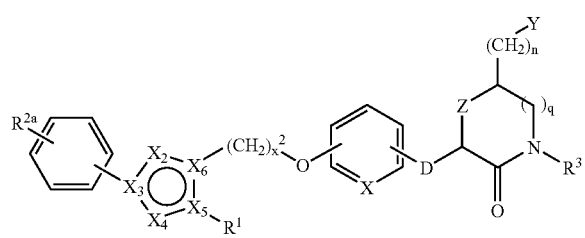

where X is CH, q=0, and Z is a single bond.

In the above compounds IC, it is most preferred that $R^1$ is alkyl, preferably $CH_3$; $R^{2a}$, is alkyl, alkoxy or halogen, $x^2$ is 1 to 3; D is —CH= or $(CH_2)_m$ where m is 0 or $(CH_2)_m$ is $CH_2$ or CH-alkyl, X is CH, $X_2$, $X_3$, $X_4$, $X_5$, and $X_6$ represent a total of 1, 2 or 3 nitrogens; $(CH_2)_n$ is a bond or $CH_2$; p is 1; Z is a bond, q is 1; $R^3$ is alkoxycarbonyl, aryl, heteroaryl, aryloxycarbonyl or arylalkyl; Y is $CO_2R^4$; and n is 0.

In the above compounds ID, it is most preferred that $R^1$ is alkyl, preferably $CH_3$; $R^{2a}$ is alkyl, alkoxy or halogen, $x^2$ is 1 to 3; D is —CH= or $(CH_2)_m$ where m is 0 or $(CH_2)_m$ is $CH_2$ or CH-alkyl, X is CH, $X_2$, $X_3$, $X_4$, $X_5$, and $X_6$ represent a total of 1, 2 or 3 nitrogens; $(CH_2)_n$ is a bond or $CH_2$; Z is a bond, q is 0 or 1; $R^3$ is alkoxycarbonyl, aryl, heteroaryl, aryloxycarbonyl or arylalkyl; Y is $CO_2R^4$; and n is 0.

Examples of

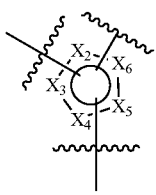

groups present in the compounds of the invention include, but are not limited to

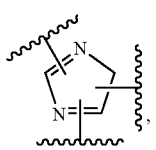

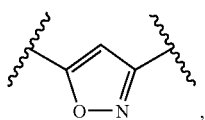

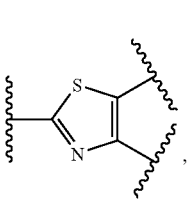

as well as those five-membered rings covered under the definition of heteroaryl set out hereafter, with

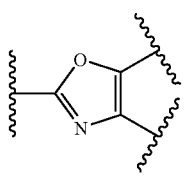

being preferred.

Examples of

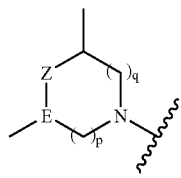

which may be present in the compounds of the invention include, but are not limited to

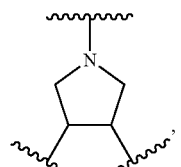

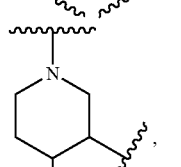

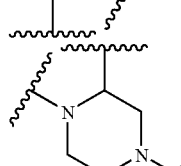

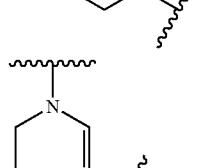

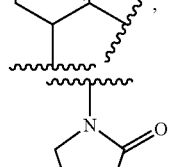

with

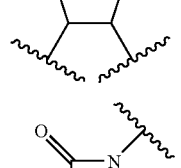

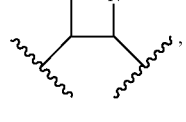

being preferred.

Preferred compounds of the invention include the following:
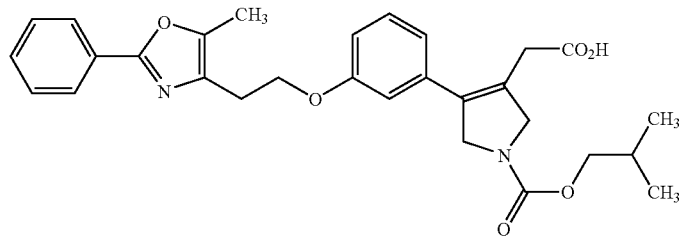
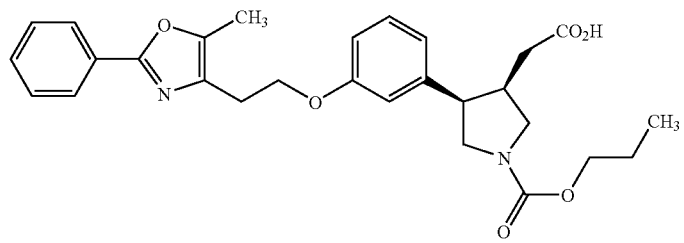
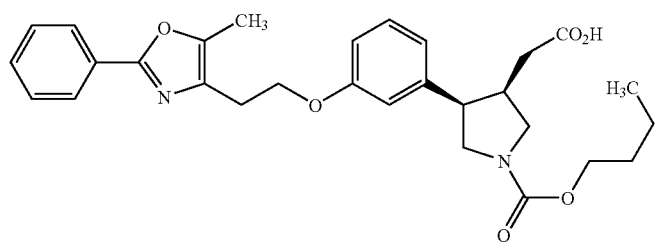
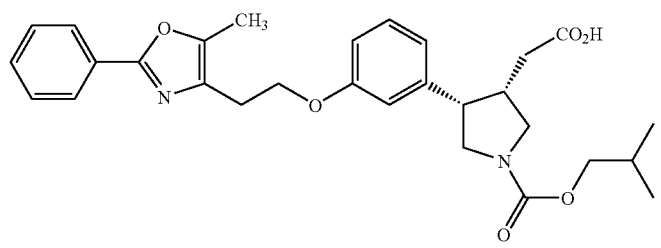
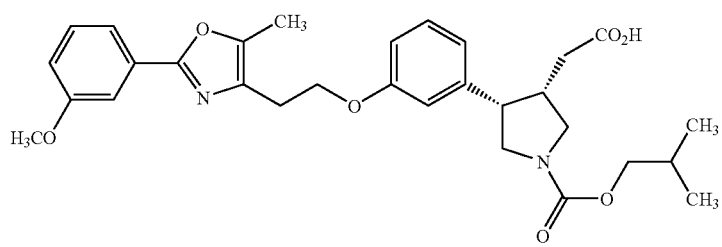
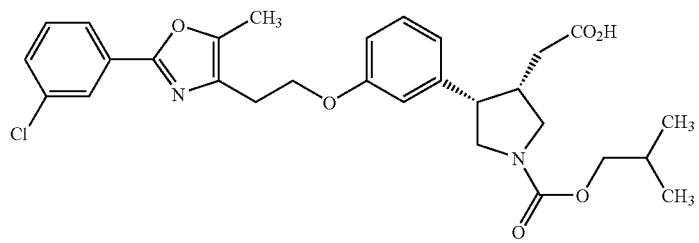

-continued
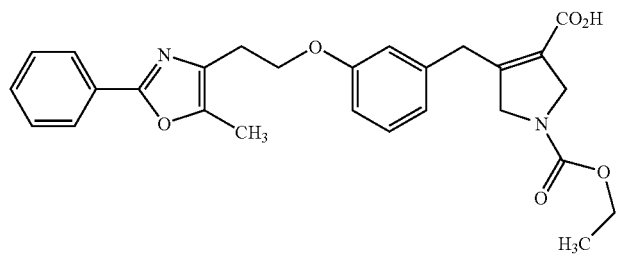
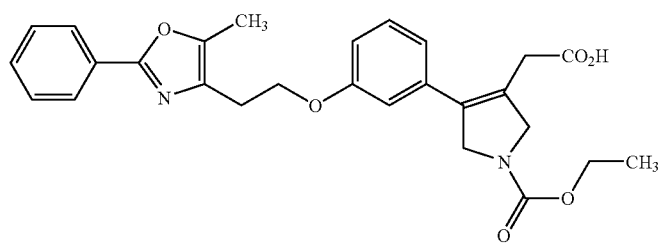
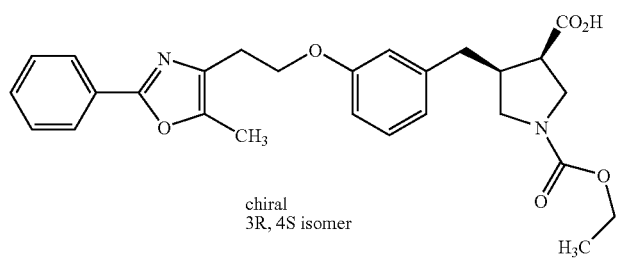
chiral
3R, 4S isomer
chiral
3R, 4S isomer
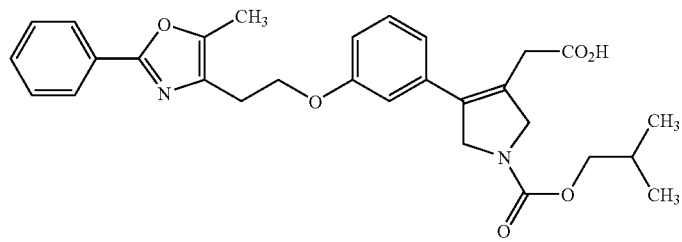
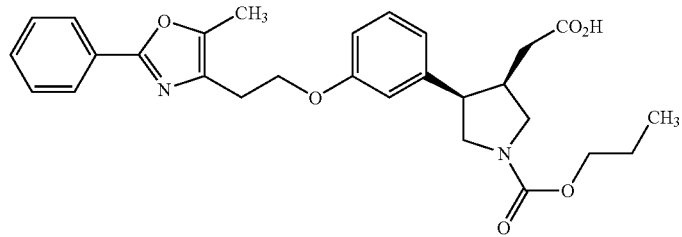

-continued
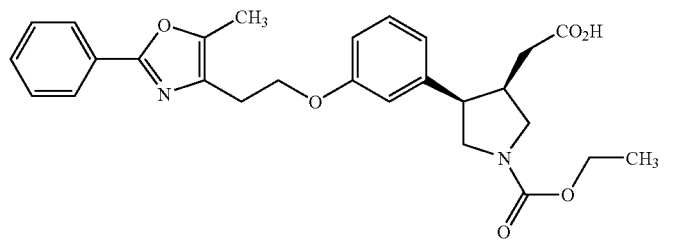
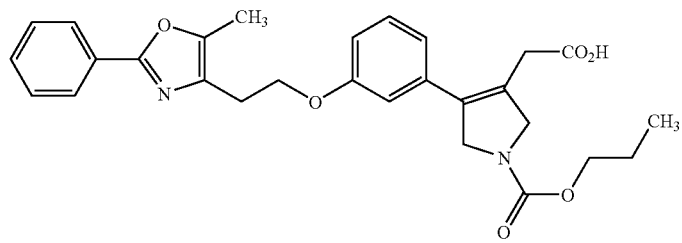
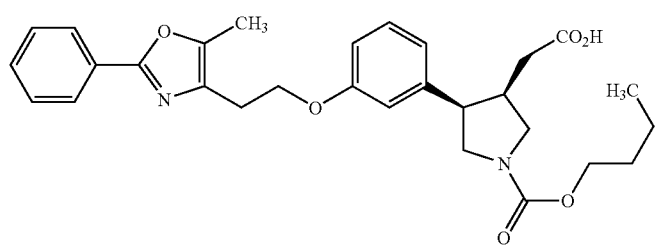
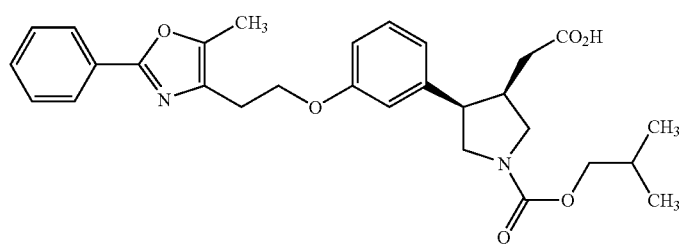
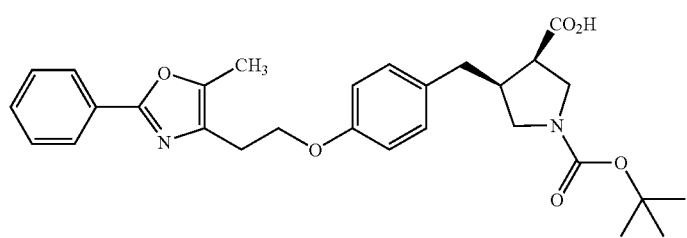
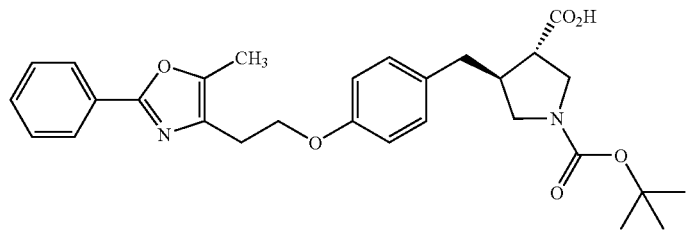
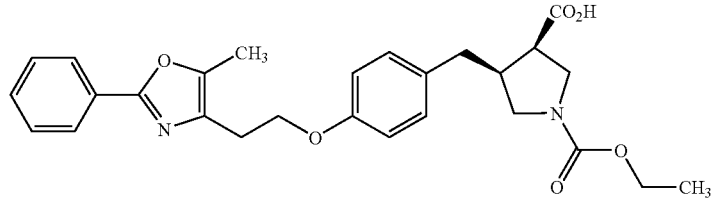

-continued
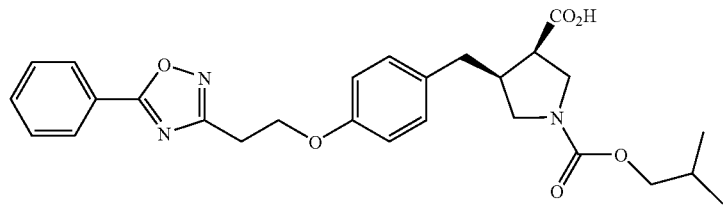
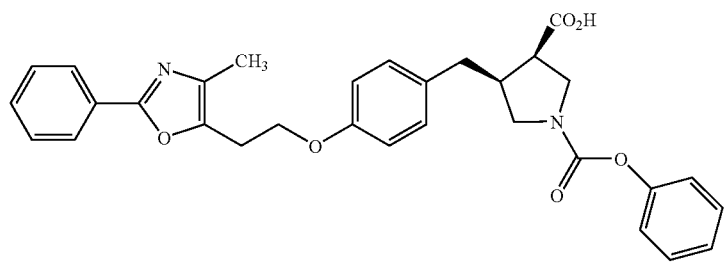
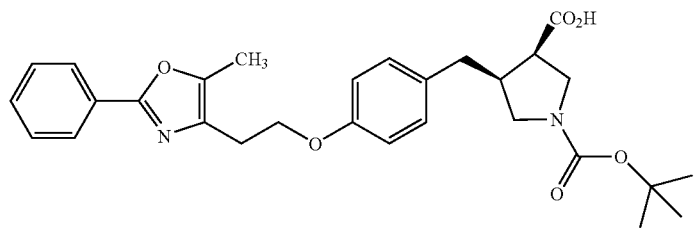
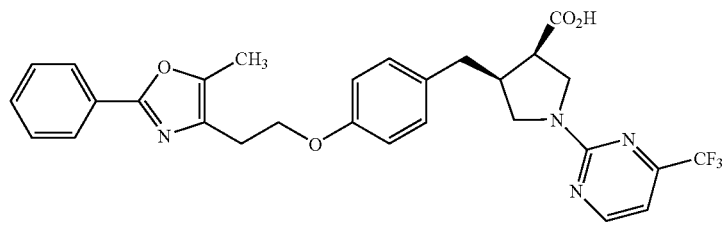
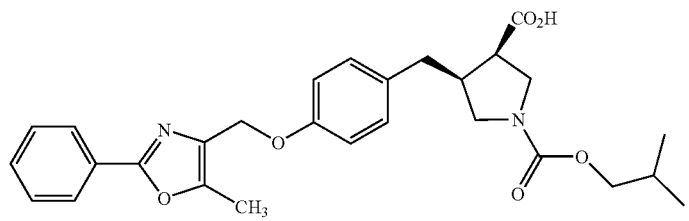
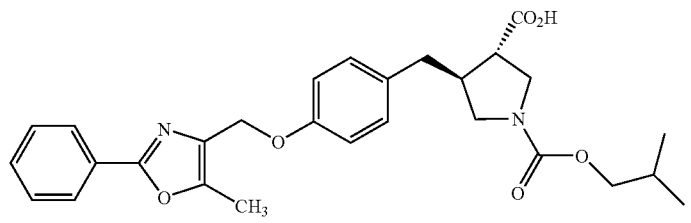
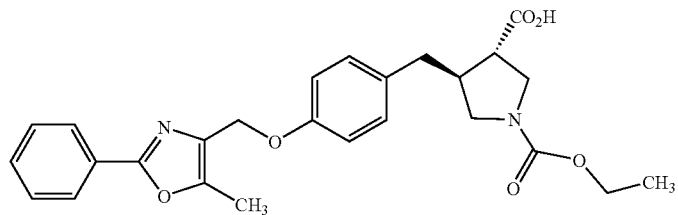

-continued
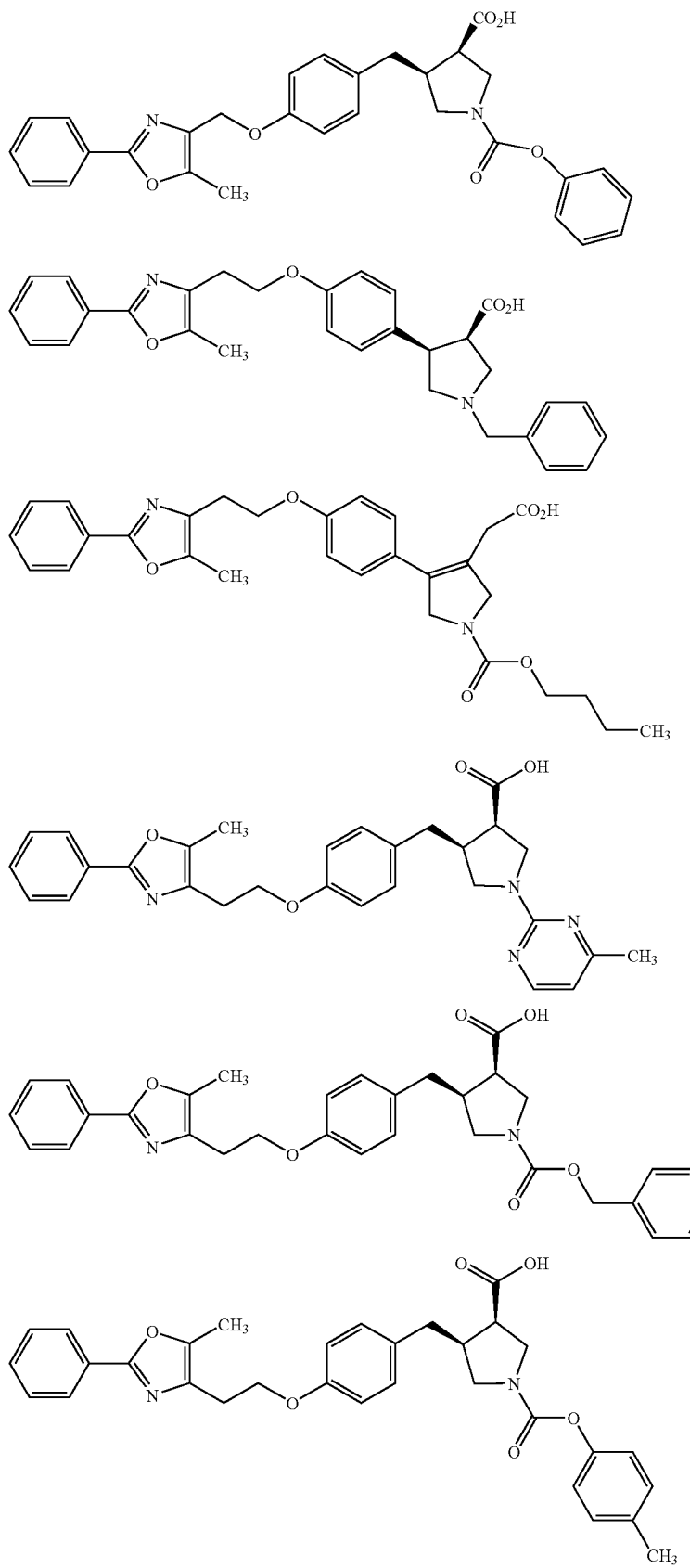

-continued
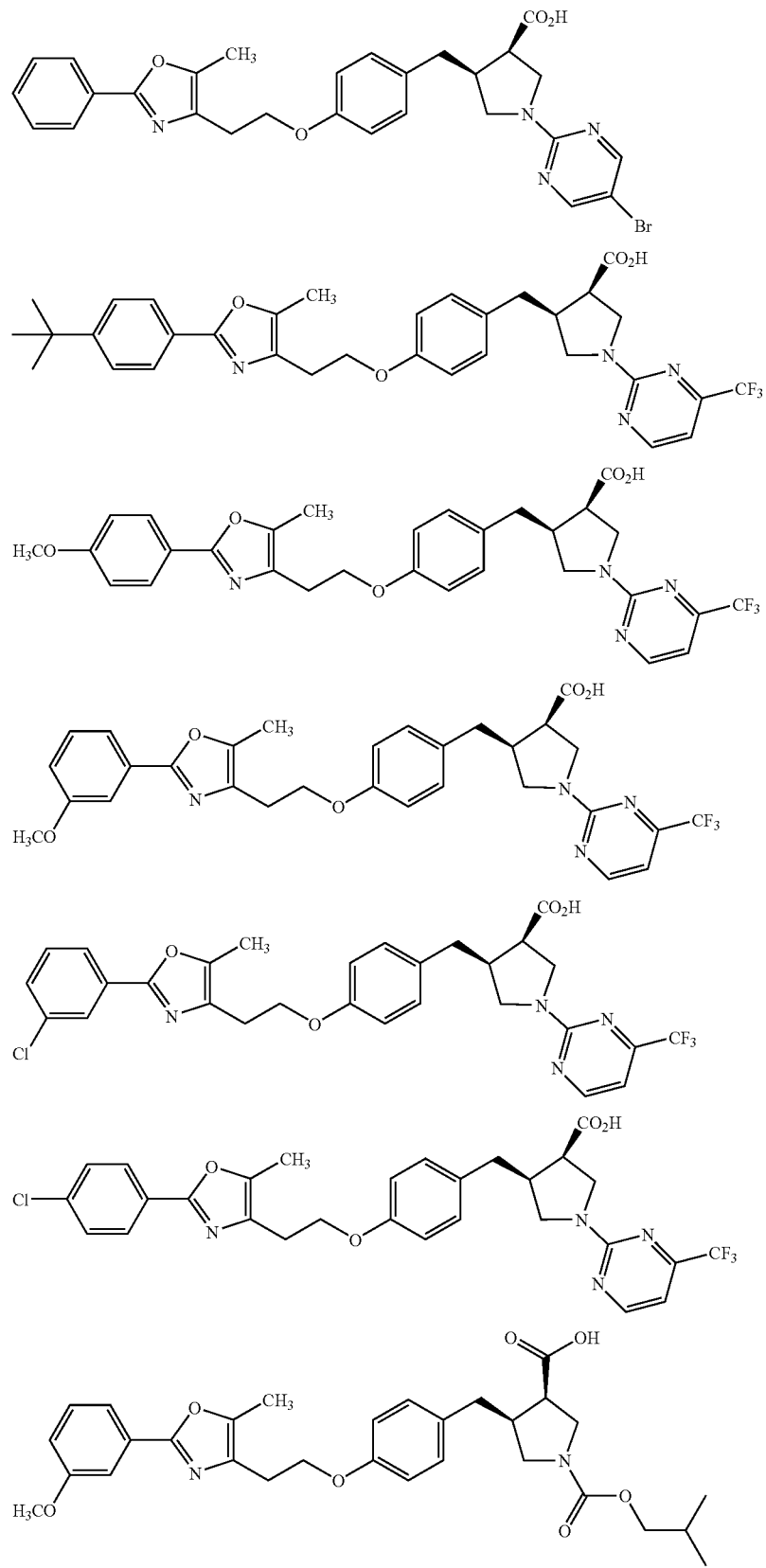

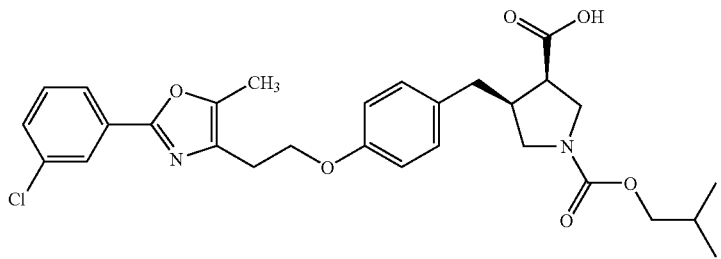
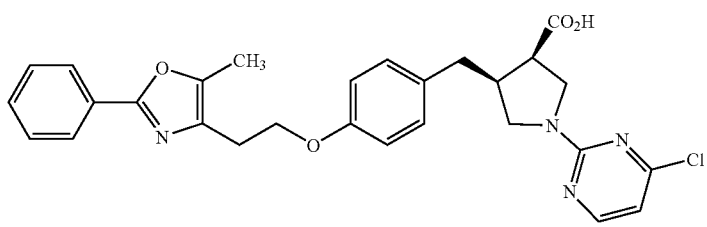
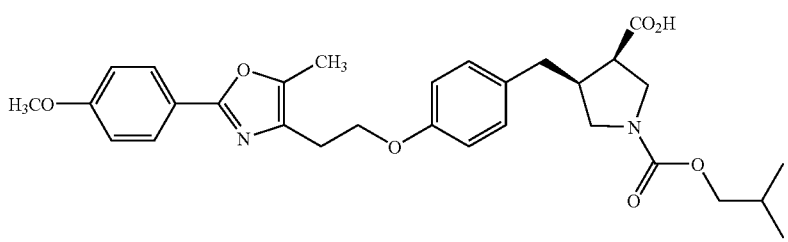
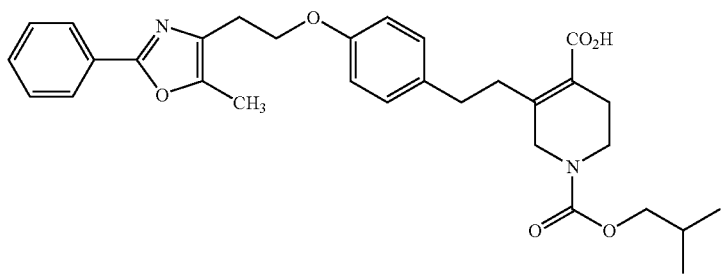
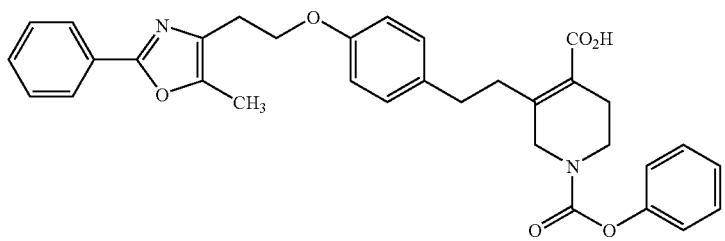
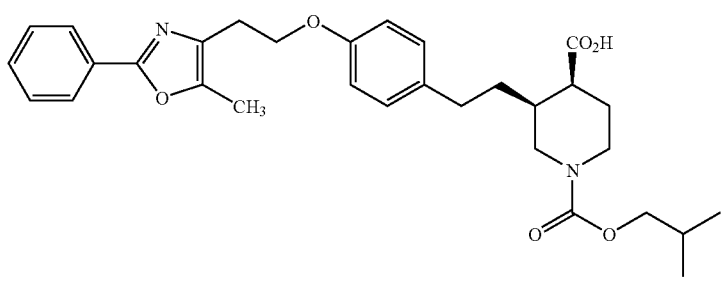

-continued
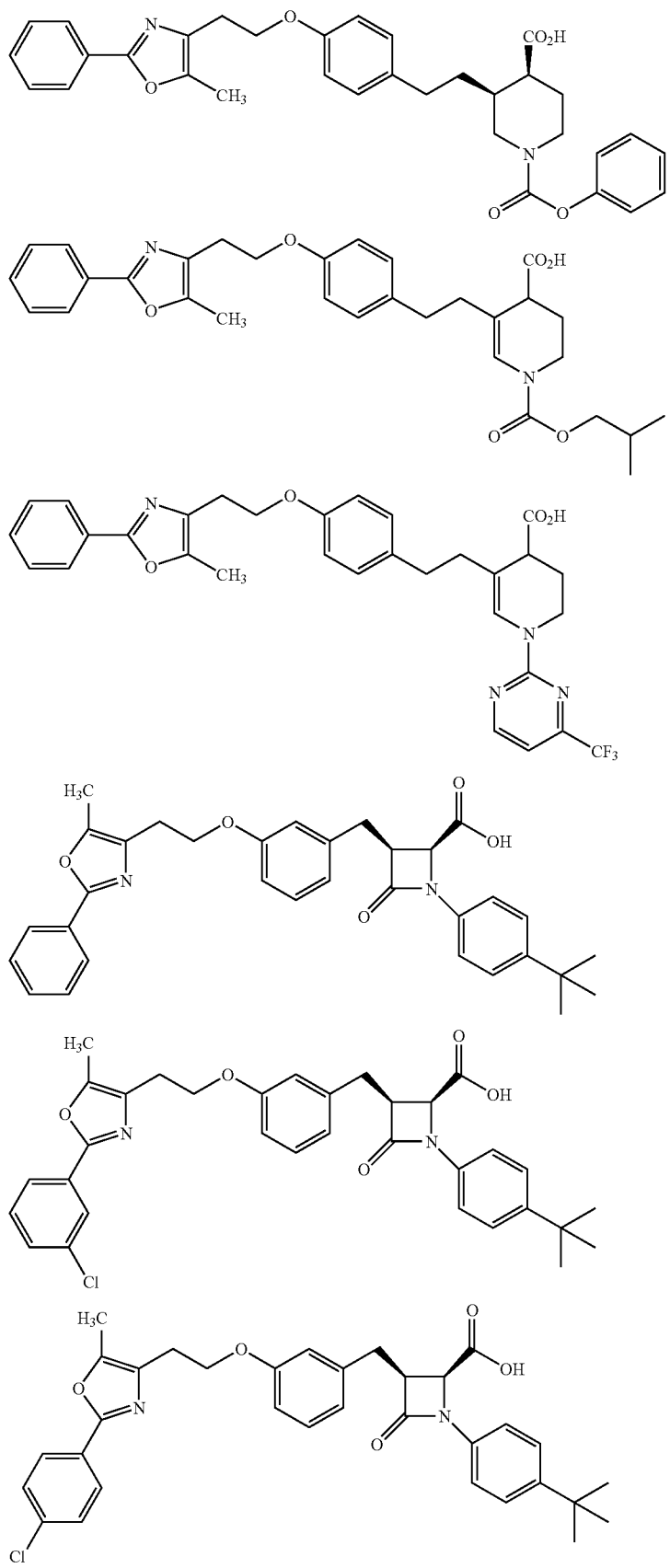

-continued
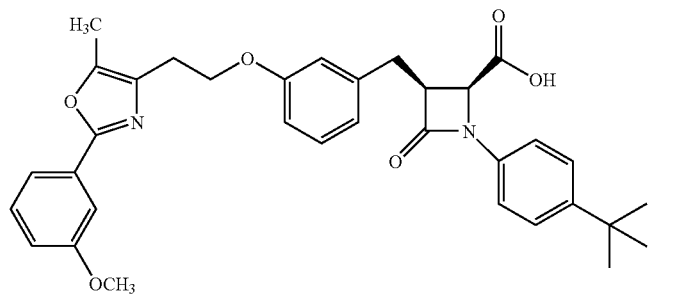
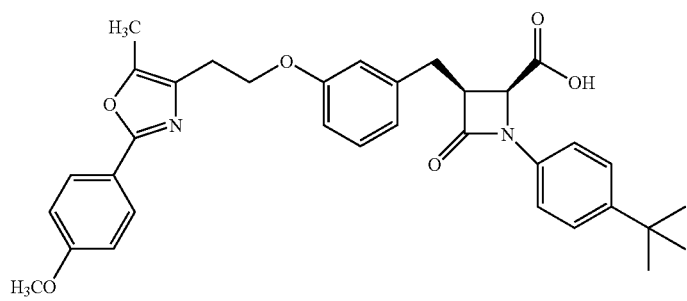
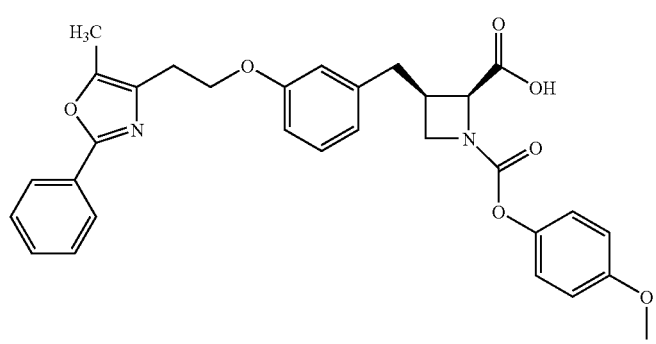
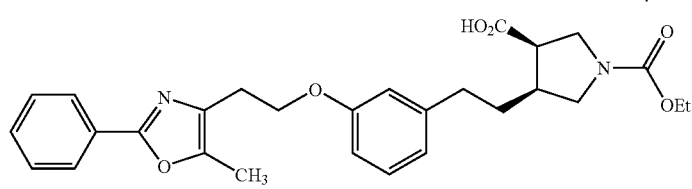
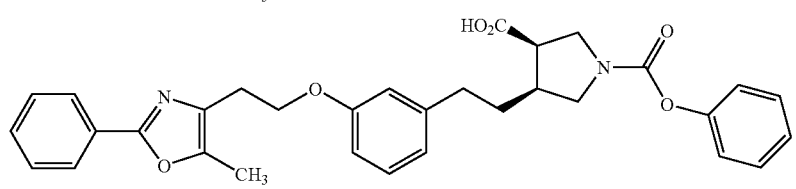
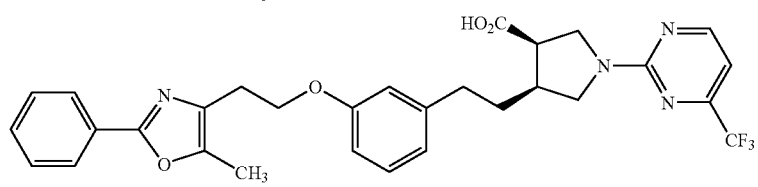
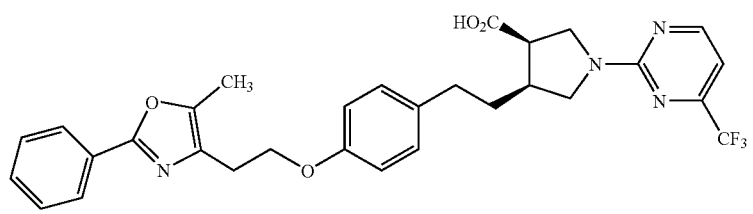

-continued

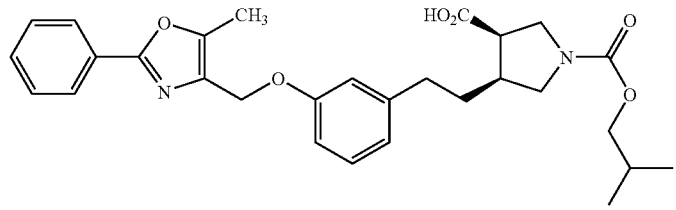

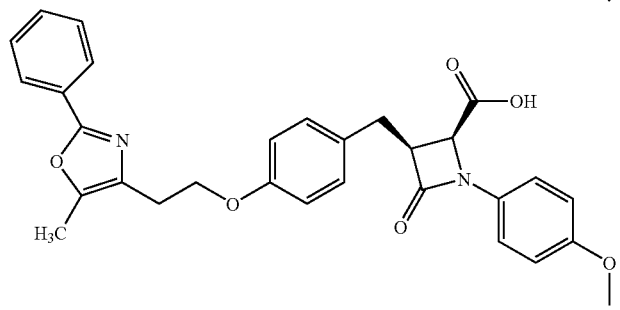

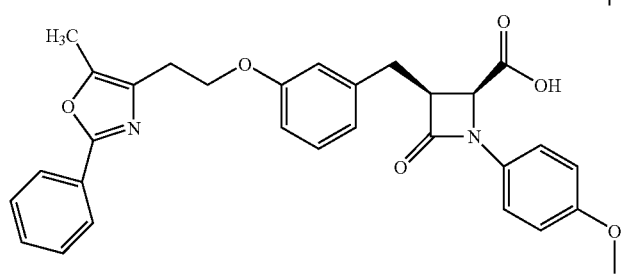

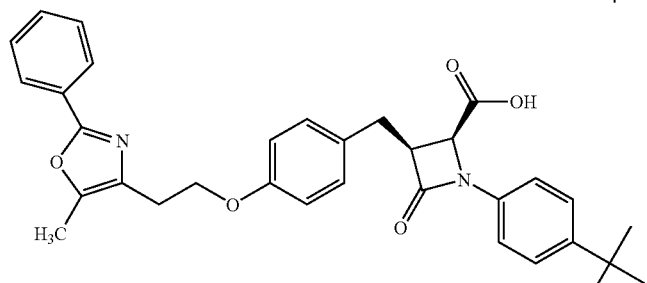

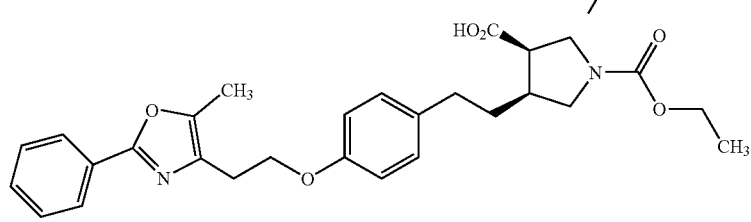

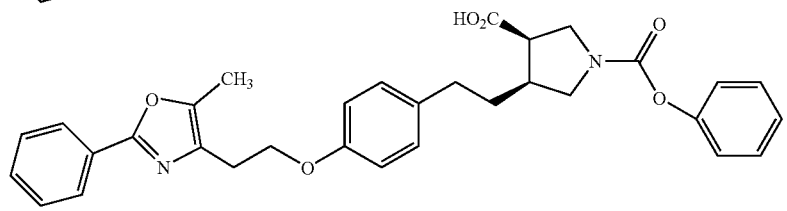

In addition, in accordance with the present invention, a method is provided for treating diabetes, especially Type 2 diabetes, and related diseases such as Type I diabetes, insulin resistance, hyperglycemia, hyperinsulinemia, elevated blood levels of fatty acids or glycerol, hyperlipidemia, obesity, hypertriglyceridemia, inflammation, Syndrome X, diabetic complications, dysmetabolic syndrome, atherosclerosis, and related diseases wherein a therapeutically effective amount of a compound of structure I is administered to a patient in need of treatment.

In addition, in accordance with the present invention, a method is provided for treating early malignant lesions (such as ductal carcinoma in situ of the breast and lobular carcinoma in situ of the breast), premalignant lesions (such as fibroadenoma of the breast and prostatic intraepithelial neoplasia (PIN), liposarcomas and various other epithelial tumors (including breast, prostate, colon, ovarian, gastric and lung), irritable bowel syndrome, Crohn's disease, gastric ulceritis, and osteoporosis and proliferative diseases such as psoriasis, wherein a therapeutically effective amount of a compound of structure I is administered to a patient in need of treatment.

In addition, in accordance with the present invention, a method is provided for treating diabetes and related diseases as defined above and hereinafter, wherein a therapeutically effective amount of a combination of a compound of structure I and another type antidiabetic agent and/or a hypolipidemic agent, and/or lipid modulating agent and/or other type of therapeutic agent, is administered to a human patient in need of treatment.

In the above method of the invention, the compound of structure I will be employed in a weight ratio to the antidiabetic agent (depending upon its mode of operation) within the range from about 0.01:1 to about 100:1; preferably from about 0.5:1 to about 10:1.

The conditions, diseases, and maladies collectively referenced to as "Syndrome X" or Dysmetabolic Syndrome (as detailed in Johanson, *J. Clin. Endocrinol. Metab.*, 1997, 82, 727-734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

DETAILED DESCRIPTION OF THE INVENTION

The compounds of the formula I of the present invention may be prepared according to the following general synthetic schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, Greene, T. W. and Wuts, P. G. M., Protecting Groups in Organic Synthesis, 3$^{rd}$ Edition, 1999 [Wiley]).

The synthesis of some key intermediates required for the synthesis of the compounds in this patent are described in Scheme 1. An alcohol 1 ($R^5(CH_2)_x^2OH$) (which preferably is 2-phenyl-5-methyl-oxazole-4-ethanol) is coupled with a hydroxy aryl- or heteroaryl-aldehyde 2 under standard Mitsunobu reaction conditions (e.g. Mitsunobu, O., *Synthesis*, 1981, 1) to furnish the key intermediate aldehyde 3. Alternatively, the alcohol 1 can be converted to its methanesulfonate ester 4 under standard conditions; the mesylate 4 can then be used to alkylate the hydroxy aryl- or heteroaryl-aldehyde 2 to furnish the aldehyde 3.

A synthesis of the pyrrolidine acids I is shown in Scheme 2. Treatment of the aldehyde 3 with the Horner-Emmons reagent $(CF_3CH_2O)_2P(O)CH_2CO_2CH_3$ 5 (W. C. Still et al., *Tetrahedron Lett.* 1985, 24, 4405-5508) provides the Z-alkenyl ester 6. This Z-alkenyl ester 6 is then reacted with N-trimethylsilylmethyl N-methoxymethyl benzylamine 7 under standard literature conditions (e.g. J. S. Carey, *J. Org. Chem.*, 2001, 66, 2526-2529) to give the corresponding N-benzyl pyrrolidine-ester 8. Deprotection of the N-benzyl group (hydrogenation) gives the key intermediate, pyrrolidine-ester 9. Reaction of pyrrolidine 9 with chloroformate 10

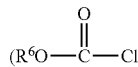

where $R^6$ is any of the $R^3$ groups except H) provides the pyrrolidine-carbamate ester 11. Deprotection of the ester 11 then furnishes the cis-substituted pyrrolidine-carbamate acids I of the invention.

Scheme 3 shows the synthesis of other analogs from the key intermediate pyrrolidine-ester 9. Palladium-mediated reaction of 9 with aryl or heteroaryl bromides (e.g. method of Buchwald et. al., *J. Am. Chem. Soc.*, 2001, 123, 7727) furnishes the N-aryl or N-heteroaryl pyrrolidine acids II of the invention. Reductive amination of 9 (e.g. the procedure of Abdel-Magid et al, *J. Org. Chem.* 1996, 61, 3849) with appropriate aldehydes $R^{3a}CHO$ provides the substituted alkyl pyrrolidine acids III of the invention. Treatment of 9 with diverse acid chlorides $R^{3a}COCl$ in the presence of an appropriate base gives the corresponding amide pyrrolidine acids IV of the invention. Reaction of 9 with diverse isocyanate $R^{3a}N=C=O$ provides the corresponding urea pyrrolidine acids V of the invention. Treatment of 9 with sulfonyl chlorides $R^{3b}SO_2Cl$ furnishes the corresponding sulfonamide pyrrolidine acids VI of the invention. It is understood that these representative reactions of pyrrolidine 9 shown in Scheme 3 are also readily applied to the subsequent key secondary amine intermediates described below to give the corresponding functionalized analogs.

A synthesis of the homologated cis-substituted pyrrolidine acids VII of the invention is shown in Scheme 4. Treatment of aldehyde 3 with a substituted alkynylmetal agent (generated from alkyne 12 in the presence of an appropriate base, e.g. n-butyllithium) furnishes the acetylenic alcohol adduct 13. Alcohol 13 is deoxygenated under standard methods (e.g. Et$_3$SiH/CF$_3$CO$_2$H; e.g. *J. Org. Chem.*, 1990, 55, 555) to give the alkynoate ester 14. The alkynoate ester 14 undergoes selective reduction by standard methods (e.g. H$_2$/Lindlar's catalyst) to give the Z-alkenyl ester 15. This Z-alkenyl unsaturated ester 15 is then reacted with N-trimethylsilylmethyl N-methoxymethyl benzylamine 7 under standard literature conditions (J. S. Carey, *J. Org. Chem.*, 2001, 66, 2526-2529) to give the corresponding N-benzyl pyrrolidine-ester 16. Deprotection of the N-benzyl group (hydrogenation) gives the key intermediate, pyrrolidine-este 17. Reaction of pyrrolidine 17 with chloroformate 10 provides pyrrolidine-carbamate ester 18. Deprotection of the ester 18 then provides the cis-substituted pyrrolidine-carbamate acids VII of the invention.

An alternative synthesis of the key intermediate pyrrolidine ester 17 (for the special case where m=0) is shown in Scheme 4A. Alcohol 13 is acetylated under standard conditions to give the acetylenic acetate 13A, which is then reacted with N-trimethylsilylmethyl N-methoxymethyl benzylamine 7 under standard literature conditions (e.g. J. S. Carey, *J. Org. Chem.*, 2001, 66, 2526-2529) to give the N-benzyl dihydropyrrole 16A. Exhaustive hydrogenation/ hydrogenolysis of the benzylic acetate, the dihydropyrrole and the N-benzyl group then provides the intermediate pyrrolidine-ester 17.

Scheme 5 illustrates a synthetic route to the corresponding trans-substituted pyrrolidine-carbamate acids VIII of the invention. Aldehyde 3 undergoes a Wittig reaction with a phosphoranylidene ester 19 (e.g. "Preparation of Alkenes, A Practical Approach", J. M. J. Williams, Ed., Chapter 2, "The Wittig reaction and related methods", N. J. Lawrence, Oxford University Press, 1996) to give the predominantly E-alkenyl ester 20. The E-alkenyl ester 15 is then reacted with N-trimethylsilyl-methyl N-methoxymethyl benzylamine 7 under standard literature conditions (J. S. Carey, *J. Org. Chem.* 2001, 66, 2526-2529) to give the corresponding trans-substituted N-benzyl pyrrolidine-ester 21. Deprotection of the N-benzyl group (hydrogenation) gives the key intermediate, pyrrolidine-ester 22. Reaction of pyrrolidine 22 with chloroformate 10 provides pyrrolidine-carbamate ester 23. Deprotection of the ester 23 then provides the cis-substituted pyrrolidine-carbamate acids VIII of the invention.

Two alternative synthetic routes to the series of corresponding dihydropyrrole acids V of the invention are shown in Schemes 6-8. The first sequence (Schemes 6 and 7) begins with the acetylation of the hydroxy-acetylenic ester 13 to provide acetylenic acetate 24. Dipolar qycloaddition with the N-trimethylsilylmethyl N-methoxymethyl 4-methoxybenzylamine 25 (prepared as for compound 7 except using 4-methoxybenzylamine instead of benzylamine; J. S. Carey, *J. Org. Chem.* 2001, 66, 2526-2529) furnishes the corresponding dihydropyrrole-ester 26. Deoxygenation of the allylic acetate 26 (e.g. (Ph$_3$P)$_2$PdCl$_2$-mediated; Tsuji, J., et al, *Synthesis*, 1986, 623-727) provide two isomeric alkene products: the β,γ unsaturated ester 27 and the dihydropyrrole ester 28. Deprotection of the 4-methoxybenzylamine (e.g. Yang, B. V., *Synlett*, 1993, 195-196) subsequently furnish the corresponding key amine-ester intermediates 29 and 30 respectively. Reaction of dihydropyrroles 29 and 30 with chloroformate 10 provide the pyrrolidine-carbamate esters 31 and 32 respectively. Deprotection of the esters 31 and 32 then give the dihydropyrrole-carbamate acids IX and X of the invention.

An alternative synthetic sequence (for substrates where deoxygenation of 13 occurs readily to provide 14), involves the reaction of 14 with N-trimethylsilylmethyl N-methoxymethyl 4-methoxybenzylamine 25 (as for Scheme 6) to furnish the corresponding dihydropyrrole-ester 30 directly (shown in Scheme 8). The rest of the synthetic route to provide carbamate acids X of the invention is then identical to that shown in Scheme 5.

The synthesis of dihydropyrrole carbamate-acid analogs XI is shown in Scheme 9. Alkylation of a halogenated phenol or hydroxy-heteroarene 32 with mesylate 4 in the presence of base provides the haloarene 33. Coupling of 33 with silyl-alkyne 34 under standard Sonogashira conditions (ref. Organocopper Reagents, a Practical Approach, R. J. K. Taylor, Ed., Chapter 10, pp 217-236, Campbell, I. B., Oxford University Press, 1994) provides the arylalkyne 35. Removal of the silyl group (e.g. fluoride) followed by treatment with base and an appropriate chloroformate 36 (e.g. methyl chloroformate) furnishes the alkynoate ester 37. Dipolar cycloaddition with N-trimethylsilylmethyl N-methoxymethyl 4-methoxybenzylamine 25 furnishes the corresponding dihydropyrrole-ester 38. Deprotection of the N-methoxybenzyl amine group is achieved under standard conditions to furnish the dihydropyrrole ester 39. This intermediate then is reacted with electrophiles (e.g. chloroformate 10 in the presence of base) to provide carbamates 40. It is understood that reaction of 39 with other electrophiles (analogous to the examples in Scheme 3) can also be similarly achieved. Carbamate-esters 40 are then deprotected to furnish carbamate acids XI of the invention.

The synthesis of homologated dihydropyrrole acid XII is shown in Scheme 10. Dihydropyrrole ester 39 is suitably protected (e.g. PG$_2$ as the t-butyloxy carbamate or as the benzyloxy carbamate) as intermediate 41. Dihydropyrrole ester 41 is reduced by standard literature methods (e.g. diisobutylaluminum hydride) to give the allylic alcohol 42. Halogenation by standard literature methods (e.g. Ph$_3$P/ CBr$_4$ or PBr$_3$ to furnish the bromide; Ph$_3$P/CCl$_4$ to furnish the chloride) furnishes the corresponding allylic halide 43. Carbonylation (ref. Kiji, J. et al, *Bull. Chem. Soc. Jpn.*, 1996, 69, 1029-1031) with carbon monoxide in the presence of a ruthenium catalyst and methanol) of 43 furnishes the dihydropyrrole ester 44. Deprotection of 44 furnishes dihydropyrrole 45, which undergoes reaction with chloroformate 10 to give carbamate ester 46. Deprotection of carbamate ester 46 then furnishes dihydropyrrole acids XII of the invention.

The synthesis of cis-3,4-disubstituted pyrrolidine acids XIII is shown in Scheme 11. Protected dihydropyrrole ester 41 is hydrogenated to furnish the protected cis-3,4-disubstituted pyrrolidine ester 47. Deprotection of the amine gives the pyrrolidine ester 48, which then undergoes reaction with chloroformate 10 to provide the pyrrolidine carbamate ester 49. Deprotection of esters 49 furnishes pyrrolidine carbamate-acids XIII of the invention.

The synthesis of homologated cis-3,4-disubstituted pyrrolidine acids XIV is shown in Scheme 12. Hydrogenation of intermediate dihydropyrrole ester 44 furnishes the cis-3, 4-disubstituted pyrrolidine ester 50, which is then deprotected to provide pyrrolidine-ester 51. Reaction of pyrrolidine 51 with chloroformate 10 furnishes the corresponding pyrrolidine carbamate-ester 52, which is then deprotected to provide the cis-3,4-disubstituted pyrrolidine acids XIV of the invention.

An alternative synthesis of homologated pyrrolidine acids XIV is shown in Scheme 13. The pyrrolidine ester 47 is deprotected to give acid 53. Acid 53 is homologated under a standard Arndt-Eistert protocol (ref. E. Gordon et al., *J. Med. Chem.*, 1988, 31, 2199), which first involves conversion to diazoketone 54 under standard conditions (isobutyl chloroformate followed by diazomethane). Treatment of diazoketone 54 with a silver salt (e.g. silver benzoate) in the presence of methanol provides the homologated pyrrolidine ester 50. Deprotection of pyrrolidine 50 followed by reaction with chloroformate 10 furnishes the carbamate ester 52, which is then deprotected to give homologated pyrrolidine acids XIV of the invention.

The synthesis of ether-containing analogs XV and XVI are shown in Schemes 14-15. In Scheme 14, treatment of the aldehyde 55 with the Horner-Emmons reagent 5 (W. C. Still et al., *Tetrahedron Lett.* 1985, 24, 4405-5508) provides the Z-alkenyl ester 56. This Z-alkenyl ester 56 is then reacted with N-trimethylsilylmethyl N-methoxymethyl benzylamine 7 under standard literature conditions (e.g. J. S. Carey, *J. Org. Chem.*, 2001, 66, 2526-2529) to give the corresponding N-benzyl pyrrolidine-ester 57. Reaction of halo-arene 57 with an appropriate metallating agent (e.g. isopropyl magnesium bromide, reference: P. Knochel et al., *Synthesis*, 2002, 565-569) furnishes the corresponding arylmagnesium reagent, which is then reacted with formaldehyde to provide aryl alcohol 58. Treatment of alcohol 58 with mesylate 4 in the presence of base provides the corresponding ether 59, which is then deprotected to give the pyrrolidine ester 60. Reaction of pyrrolidine 60 with chloroformate 10 provides carbamate ester 61, which is then deprotected to furnish the ether-acids XV of the invention.

In Scheme 15, treatment of the haloaryl pyrrolidine ester 57 aryl with an appropriate vinyl tin reagent (e.g. tributylvinyltin) under Stille coupling conditions (reference: Farina, V., Krishnamurthy, V., and Scott, W. J., *Organic Reactions*, 1997, 50, 1) provides the corresponding vinyl intermediate, which can then undergo hydroboration (e.g. borane-THF) to give the alcohol 62. Treatment of alcohol 62 with mesylate 4 in the presence of base provides the corresponding ether 63, which is then deprotected to furnish pyrrolidine 64. Reaction of pyrrolidine 64 with chloroformate 10 provides carbamate ester 65, which is then deprotected to furnish the ether-pyrrolidine acids XVI of the invention.

The synthesis of carbon-linked analogs XVII is shown in Scheme 16. The halo-aryl pyrrolidine ester 57 is reacted with an appropriate heteroaryl ($R^5$)-substituted acetylene 66 in the presence of an appropriate palladium catalyst (e.g. $(Ph_3P)_2PdCl_2$) and a copper (I) salt (e.g. CuI) in a Sonogashira coupling reaction (ref: Organocopper Reagents, a Practical Approach, R. J. K. Taylor, Ed., Chapter 10, pp 217-236, Campbell, I. B., Oxford University Press, 1994) to furnish the arylacetylene 67. The arylacetylene ester 67 is hydrogenated to provide the corresponding pyrrolidine ester 68. Reaction of pyrrolidine 68 with chloroformate 10 provides carbamate ester 69, which is then deprotected to furnish the alkylaryl pyrrolidine acids XVII of the invention.

The synthesis of piperidine acid analogs XVIII is shown in Scheme 17. Metallation of a halo-arene 70 (e.g. isopropyl magnesium bromide, reference: P. Knochel et al., *Synthesis*, 2002, 565-569, or magnesium/anthracene, ref.) provides the corresponding organomagnesium reagent 71, which is reacted with an appropriate pyridine ester 72 in the presence of a suitable chloroformate 10 and a copper (I) salt (e.g. $CuBr.SMe_2$) to give the corresponding dihydropyridine carbamate ester 73 (e.g. ref. D. J. Wallace et al, *Synthesis*, 2001, 1784-1789). Reduction of the dihydropyridine esters 73 (e.g. hydrogenation) furnishes piperidine carbamate ester 74, which is then deprotected to give the phenol 75. Reaction of phenol 75 with mesylate 4 in the presence of base provides the piperidine carbamate ester 76, which is then deprotected to furnish pyrrolidine carbamate acids XVIII of the invention.

The synthesis of tetrahydropyridine acids XIX is shown in Scheme 18. An appropriately protected piperidone 77 is reacted with aldehyde 78 in the presence of base (standard aldol reaction) followed by deoxygenation to furnish the 2-alkyl piperidone 79. Treatment of 79 with triflic anhydride in the presence of base (e.g. $iPr_2NMg$) under thermodynamic conditions furnishes enol triflate 80. Palladium-mediated carbonylation under standard literature conditions (e.g. S. K. Thompson et al., *J. Org. Chem.*, 1990, 55, 3004) with carbon monoxide in the presence of an alcohol (preferably methanol) furnishes the tetrahydropyridine ester 81. Deprotection of 81 provides phenol 82, which is alkylated with mesylate 4 to give the tetrahydropyridine ester 83. Deprotection of 83, followed by reaction with chloroformate 10, furnishes tetrahydropyridine carbamate ester 84. Deprotection of carbamate ester 84 give tetrahydropyridine carbamate-acids XIX of the invention.

The synthesis of cis 3,4-disubstituted piperidine acids XX is shown in Scheme 19. Tetrahydropyridine ester 83 is reduced (hydrogenation) to give the cis 3,4-disubstituted piperidine ester 85. Deprotection of the piperidine 85, followed by reaction with chloroformate 10, provides piperidine carbamate ester 86. Deprotection of carbamate ester 86 provides cis 3,4-disubstituted piperidine carbamate-acids XX of the invention.

The synthesis of piperazine acids XXI (where in Formula I q=1, Z is a bond, p=2 and E is nitrogen) is shown in Schemes 20A and 20B. In Scheme 20A reductive amination of aldehyde 78 with a readily available monoprotected piperazine ester 87 furnishes the alkylated piperazine ester 88. Deprotection of 88 provides the phenol 89, which is alkylated with mesylate 4 in the presence of base to furnish the alkylated piperazine ester 90. Selective deprotection of the amine followed by reaction with chloroformates 10 provides piperazine carbamate-esters 91. Deprotection of carbamate-esters 91 furnishes piperazine carbamate-acids XXI of the invention.

Alternatively, piperazine carbamate-acids XXI can also be synthesized according to the synthetic sequences shown in Scheme 20B. Reductive amination of the monoprotected piperazine ester 87 with aldehyde 3 directly provides the key intermediate alkylated piperazine ester 90. As described for Scheme 20A, a 3-step sequence involving: 1) selective deprotection of the amine functionality of 90; 2) reaction with chloroformates 10 and 3) deprotection of the acid, furnishes piperazine carbamate-acids XXI of the invention. In addition, complete deprotection of piperazine-ester 90 provides piperazine acid 92, which is then reacted with chloroformates 10 to furnish piperazine carbamate-acids XXI of the invention.

The synthesis of azetidine-acids XXII (in Formula I where Z is a bond, q=0, p=1 and E=CH) is shown in Scheme 21. The hydroxyaryl ester 93 is alkylated with mesylate 4 under basic conditions, then deprotected to provide the acid 94. Acid 94 is converted to the corresponding acid chloride under standard conditions (oxalyl chloride in the presence of a catalytic amount of dimethyl formamide), then is treated with a bis-imine such as 95 under Staudinger conditions (reference: R. M. Adlington et. al., *J. Med. Chem.*, 2001, 44, 1491) to furnish the key intermediate β-lactam aldehyde 96. Protection of the aldehyde 96 (e.g. as the dimethyl acetal) followed by reduction of the resulting β-lactam acetal (e.g. $AlH_2Cl$, reference: B. Alcaide et. al. *J. Org. Chem.*, 1999, 64, 9596) furnishes the corresponding azetidine acetal 97. Deprotection of the azetidine under standard conditions (e.g. ceric ammonium nitrate) followed by reaction with chloroformates 10 furnishes the corresponding azetidine-carbamates. Deprotection of the aldehyde under standard conditions (aqueous acid) followed by a standard oxidation of the aldehyde (e.g. $NaClO_2/H_2NSO_3H$; reference: B. O. Lindgren et. al., *Acta Chem. Scand.*, 1973, 27, 888 or E. Dalcanale et. al., *J. Org. Chem.*, 1986, 51, 567) provides the azetidine carbamate-acids XXII of the invention. Direct oxidation of the intermediate β-lactam aldehyde 96 (e.g. the Lindgren oxidation) furnishes the azetidinone acids XXIII of the invention.

A general method for synthesis of the cis-disubstituted β-lactam acids XXIV and the corresponding trans-disubstituted azetidinone-acids XXV is depicted in Scheme 22. A suitably protected carboxylic acid 98 (e.g., $PG_1$=benzyl) is converted to the acid chloride 99, which upon treatment with a suitably substituted bis-imine (e.g. 95) undergoes a Staudinger reaction (reference: R. M. Adlington et. al., *J. Med. Chem.*, 2001, 44, 1491) to furnish the key intermediate β-lactam aldehyde 100. Oxidation of aldehyde 100 to the corresponding carboxylic acid (e.g. Lindgren oxidation) followed by protection (esterification) provides the β-lactam ester 101. Removal of the N-4-methoxyphenyl group provides the corresponding deprotected β-lactam ester 102, which then is reacted with a variety of diverse aryl boronic acids 103

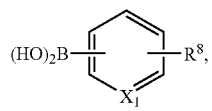

where $R^8$ is H, alkyl, alkoxy, halogen, amino or substituted amino, and $X_1$ is CH or N) under copper-mediated catalysis (Chan, D. M. T. et al. *Tetrahedron Lett.* 1998, 39, 2933; Evans, D. A. et al. *Tetrahedron Lett.* 1998, 39, 2937) to provide the corresponding N-aryl esters 104. Deprotection of the phenol followed by alkylation of the phenol with mesylate 4 under basic conditions provides the alkylated β-lactam ester 105. Appropriate deprotection of the β-lactam ester 105 gives a mixture of the cis-disubstituted azetidinone acids XXIV and the epimerized trans-disubstituted azetidinone acids XXV of the invention.

An alternative synthesis of azetidinone acids XXIII is illustrated in Scheme 23. Deprotection of the phenol moiety of azetidinone-ester 101 provides the phenol 102, which undergoes base-mediated alkylation using mesylate 4 to give the alkylated phenol azetidinone-ester 107. Removal of the final protecting group provides the azetidinone acids XXIII. Yet another route to acids XXIII is shown in Scheme 24). The β-lactam aldehyde intermediate 100 is reduced by standard methods (e.g. $NaBH_4$), after which the phenol is deprotected to give the phenol-azetidinone alcohol 108. Alkylation of 108 with mesylate 4 provides the alkylated phenol azetidinone alcohol 109, which is then oxidized under standard literature conditions (e.g. Jones reagent) to give the azetidinone acids XXIII of the invention.

It should be noted that in Schemes 21-24, a number of the racemic intermediates (e.g. 102 and 107) as well as the final product azetidinone-acids XXIII-XXV, are amenable to separation into their individual enantiomers by chiral preparative HPLC.

An approach to the direct asymmetric synthesis of the key chiral azetidinone intermediate 112 is shown in Scheme 25. A chiral ligand-mediated coupling of the acid chloride 99 with suitably protected carboxy-tosyl imines such as 110 (Ref: Taggi, A. E. et al. *J. Am. Chem. Soc.* 2002, 124, 6626) affords the chiral cis-disubstituted β-lactam 111 with high enantioselectivity. N-deprotection of the tosylated β-lactam 111 furnishes the corresponding β-lactam, which then is reacted with diverse aryl boronic acids 103 under copper-mediated catalysis (Chan, D. M. T. et al. *Tetrahedron Lett.* 1998, 39, 2933; Evans, D. A. et al. *Tetrahedron Lett.* 1998, 39, 2937) to provide the corresponding N-aryl esters 112. The chiral intermediate 112 can be processed as before to furnish chiral azetidinone-acids XXIII-XXV of the invention as described in Schemes 21-24 and 26.

An alternative approach to N-carbamate azetidine acids XXII is shown in Scheme 26. Reduction of the azetidinone-aldehyde intermediate 100 (e.g. with chloroalane) provides the N-aryl azetidine alcohol 113. Deprotection of the N-aryl azetidine to the corresponding azetidine followed by reaction with appropriate chloroformates 10 affords the N-carbamate azetidine alcohols 114. Oxidation of azetidine alcohol 114 to the acid (e.g. Jones reagent) followed by protection of the acid (esterification) provides the azetidine carbamate ester 115. Deprotection of 115 gives the free phenol 116, which undergoes base-mediated reaction with mesylate 4 to give the alkylated azetidine carbamate ester 117. Finally, deprotection of 117 provides the desired carbamate acids XXII of the invention.

The synthesis of the corresponding N-Aryl azetidine acids XXVI is shown in Scheme 27. Reduction of either racemic N-aryl azetidinone ester 104 or chiral N-aryl azetidinone ester 112 (e.g. chloroalane) provides the corresponding azetidine-alcohol 118. Deprotection of the phenol of 118 followed by alkylation with mesylate 4 and finally oxidation (e.g. Jones reagent) provides the N-aryl azetidine acids XXVI of the invention.

The azetidinone acids XXVII and the pyrrolidinone acids XXVIII may be obtained following the general procedure shown in Scheme 28 (literature precedent: Wee, A. G. H.; Liu, B-S.; Zhang, L. *J. Org. Chem.*, 1992, 57(16), 4404; also Wee, A. G. H.; Liu, B. *Tetrahedron Lett.* 1996, 37(2), 145-148). The intermediate aniline 121 can be synthesized either by: a) reductive amination (e.g. with $NaBH(OAc)_3$) of aldehyde 3 with an appropriate aniline or b) an aniline carbamate 119 can be alkylated with an alkyl halide 120 in the presence of a base (e.g. NaH) and then the carbamate can be removed with a nucleophilic base (e.g. KOH). Acylation of aniline 121 with the malonyl acid chloride 122 in the presence of base (e.g. $Et_3N$ or pyridine or DMAP) provides the malonyl amide 123. Treatment of the β-ketoamide 123 with an appropriate diazotization agent (e.g. methanesulfonyl azide) in the presence of base (e.g. DBU) provides the diazoester 124. Rhodium-mediated intramolecular cyclization (by C—H insertion) of diazo-ester 124 provides a mixture of the corresponding azetidinone and pyrrolidinone esters. Deprotection of these esters provides the azetidinone acids XXVII of the invention as a mixture of diastereomers (cis and trans) and the pyrrolidinone acids XXVIII as a mixture of diastereomers (cis and trans) of the invention. The ratio of products XXVII and XXVIII can be controlled by an appropriate choice of the substituent on the aniline moiety.

An alternative synthesis of piperidine carbamate-acids XIX and piperidine N-aryl acids XXIX is shown in Scheme 29. Treatment of an appropriately protected aryl substituted halide 70 with activated zinc provides the aryl zinc reagent 125 (ref: Rieke, R., et al., *J. Org. Chem.*, 1991, 56, 1445-1453). An appropriately protected piperidone ester 126 is converted to the corresponding enol nonaflate 127 under standard literature conditions (ref: Bellina, F. et al, *Tetrahe-* dron, 1999, 55, 2103-2112). Treatment of enol nonaflate 127 with the aryl zinc reagent 125 in the presence of a palladium catalyst (ref: Bellina, F. et al, *Tetrahedron,* 1999, 55, 2103-2112)provides the coupled α,β-unsaturated ester 81. The phenol of 81 is deprotected and alkylated with mesylate 4 (as for Scheme 18) to provide the piperidine ester 83. Hydrogenation and N-deprotection of 83 furnishes the key piperidine ester 128, which is then converted according to the sequence in Scheme 19 to the piperidine carbamate acids XX of the invention.

As shown in Scheme 30, the intermediate piperidine ester 128 can also be reacted with aryl or heteroaryl halides in the presence of a palladium catalyst (e.g. method of Buchwald et. al., *J. Am. Chem. Soc.,* 2001, 123, 7727) to furnish the N-aryl or N-heteroaryl piperidine acids XXIX of the invention. Alternatively, intermediate piperidine ester 128 can also be reacted directly with electron-deficient heteroaryl halides in the presence of base to give N-heteroaryl piperidine acids XXX of the invention.

Scheme 31 shows the synthesis of the α,β-unsaturated piperidine acids. The phenol moiety of the N-protected piperidine ester 81 is deprotected and alkylated with mesylate 4 to provide alkylated phenol 83, which is then deprotected to furnish the key free piperidine intermediate 129. Intermediate 129 is treated with an appropriate chloroformate 10 and deprotected to give piperidine carbamte-acids XIX of the invention (as for Scheme 18). Alternatively, piperidine 129 can be treated with an aryl halide or a heteroaryl halide in the presence of a palladium catalyst (e.g. method of Buchwald et. al., *J. Am. Chem. Soc.,* 2001, 123, 7727) followed by deprotection of the acid to furnish the N-aryl or N-heteroaryl piperidine acids XXXI and XXXII of the invention. In addition, electron-deficient heteroaryl halides can be directly reacted with piperidine intermediate 129 in the presence of base followed by deprotection of the acid to provide N-heteroaryl piperidine acids XXXII of the invention.

The synthesis of β,γ-unsaturated piperidine acids XXXIII-XXXV of the invention is shown in Scheme 32. The piperidine α,β-unsaturated ester intermediate 129 is reacted with a chloroformate 10 to provide the corresponding piperidine carbamate α,β-unsaturated ester 130. Base-mediated deprotection of the acid (ester hydrolysis) furnished the piperidine carbamate β,γ-unsaturated acids XXXIII of the invention. Similarly, reaction of piperidine 129 with aryl halides in the presence of a palladium catalyst (as for Scheme 31) provided the corresponding N-aryl piperidine α,β-unsaturated ester, which upon base hydrolysis furnished the N-aryl piperidine β,γ-unsaturated acids XXXIV of the invention. Reaction of piperidine 129 with π-deficient heteroaryl halides in the presence of base provided the corresponding N-heteroaryl piperidine α,β-unsaturated ester, which upon base hydrolysis furnished the N-heteroaryl piperidine β,γ-unsaturated acids XXXV of the invention.

The preparation of pyrrolidinone acids XXXVI of the invention is shown in Scheme 33. A suitably protected pyrrolidinone ester 130 is deprotonated with an appropriate base (e.g. lithium diisopropylamide) and alkylated with a protected aryl halide 70 to furnish the alkylated pyrrolidinone ester 131. The phenol of pyrrolidinone ester 131 is deprotected and alkylated with mesylate 4 to provide pyrrolidinone ester 132, which is N-deprotected to give the key pyrrolidinone ester intermediate 133. Palladium-mediated arylation with an appropriate arylboronic acid followed by deprotection of the acid provides pyrrolidinone acids XXXVI of the invention.

The preparation of pyrrolidinone acids XXXVII and XXXIX of the invention is shown in Scheme 34. The appropriately protected pyrrolidinone ester 134 is deprotonated with an appropriate base (e.g. lithium diisopropylamide) and alkylated with halide 70 to provide the alkylated lactam ester 135 (ref: Saksena, A. K., et al., Patent PCT WO0208256; August, R. A., *J. Chem. Soc. Perkin* 1, 1996, 507-514). Deprotection of the phenol moiety of 135 followed by alkylation with mesylate 4 in the presence of base gives the alkylated phenol lactam ester 136. N-Deprotection of the lactam provides the key intermediate lactam 137, which is reacted with appropriate aryl boronic acids to provide the corresponding N-aryl lactam ester followed by deprotection of the acid to provide N-aryl pyrrolidinone acids XXXVII of the invention. Alternatively, after lactam 137 is reacted with aryl boronic acids to provide the corresponding N-aryl lactam ester, the lactam is reduced (e.g. 2 step sequence: a) LiBHEt$_3$, b) Et$_3$SiH/BF OEt$_2$; ref: Ezquerra, J., *J. Org. Chem.,* 1995, 60, 2925-2930) to the corresponding pyrrolidine ester, which is then deprotected to give the N-aryl pyrrolidine acids XXXIX of the invention.

The preparation of N-substituted pyrrolidine acids XXXVIII-XXXX of the invention is shown in Scheme 35. The lactam ester 136 is reduced (e.g. 2 step sequence: a) LiBHEt$_3$, b) Et$_3$SiH/BF OEt$_2$) to the corresponding pyrrolidine ester, which then undergoes N-deprotection to provide the key intermediate pyrrolidine ester 139. Reaction of pyrrolidine 139 with chloroformates 10 provide the carbamate pyrrolidine ester 140, which is then deprotected to furnish carbamate pyrrolidine acids XXXVIII of the invention. Reaction of pyrrolidine 139 with aryl halides in the presence of a palladium catalyst (as for Scheme 31) provided the corresponding N-aryl pyrrolidine ester, which upon deprotection of the acid furnished the N-aryl pyrrolidine acids XXXIX of the invention. Reaction of pyrrolidine 139 with π-deficient heteroaryl halides in the presence of base or under palladium catalysis provided the corresponding N-heteroaryl pyrrolidine ester, which upon deprotection of the acid furnished the N-heteroaryl pyrrolidine acids XXXX of the invention.

The synthesis of pyrrolidine acids XLI-XLIII of the invention is shown in Scheme 36. The benzamide-protected α-amino ester 141 is alkylated with mesylate 4 in the presence of base to furnish the alkylated phenol 142. Reduction of the benzamide and ester (e.g. LiAlH$_4$ or LiBH$_4$) followed by Michael reaction of the resultant amine with acrylonitrile in the presence of base to give the β-aminonitrile 143. Chlorination of the alcohol 143 (e.g. with SOCl$_2$) followed by base (e.g. NaN(TMS)$_2$)-mediated intramolecular cyclization provides the cyano-pyrrolidine 144. This sequence is precedented in the literature (R. Achini, *Helv. Chim. Acta,* 1981, 64, 2203-2218). Acid-mediated hydrolysis (e.g. H$_2$SO$_4$) of the nitrile in the presence of an appropriate alcohol provides the corresponding pyrrolidine ester, which is debenzylated (e.g. hydrogenation) to provide the key pyrrolidine ester intermediate 145. Reaction of pyrrolidine 145 with chloroformates 10 provide the corresponding carbamate pyrrolidine ester, which is then deprotected to furnish carbamate pyrrolidine acids XLI of the invention. Reaction of pyrrolidine 145 with aryl halides in the presence of a palladium catalyst (as for Scheme 31) provided the corresponding N-aryl pyrrolidine ester, which upon deprotection of the acid furnished the N-aryl pyrrolidine acids XLII of the invention. Reaction of pyrrolidine 145 with π-deficient heteroaryl halides in the presence of base or under palladium catalysis provided the corresponding N-heteroaryl pyrrolidine ester, which upon deprotection of the acid furnished the N-heteroaryl pyrrolidine acids XLIII of the invention.

An asymmetric synthesis of pyrrolidine acids XLIV and XLV is shown in Scheme 37. The maleimide 146 is reacted with N-trimethylsilylmethyl N-methoxymethyl benzylamine 7 under standard literature conditions (e.g. J. S. Carey, *J. Org. Chem.*, 2001, 66, 2526-2529) to give the corresponding N-benzyl pyrrolidine-ester 147. The imide 147 is then reacted with an appropriately protected aryl Grignard reagent 148; the intermediate hydroxy lactam is reduced (e.g. NaBH$_4$) and thermally-induced intramolecular cyclization provides the lactone 149. Deprotection of the phenol moiety of lactone 149 followed by base-mediated alkylation of the phenol with mesylate 4 provides thealkoxyphenol lactone 150. Deprotection (hydrogenation) of the N-benzyl group with concomitant hydrogenolysis of the benzylic lactone C—O bond provides the pyrrolidine acid 151, which is reprotected with an appropriate alcohol to furnish the key intermediate pyrrolidine ester 152. Reaction of 152 with an appropriate chloroformate 10 and acid deprotection (as for Scheme 4) provides chiral pyrrolidine carbamate acids XLIV of the invention. Reaction of 152 with appropriate aryl halides or heteroaryl halides followed by acid deprotection (as for Scheme 35) provides chiral N-aryl pyrrolidine acids XLV and chiral N-heteroaryl pyrrolidine acids XLVI of the invention respectively.

The synthesis of hydantoin acids XLVII of the invention is shown in Scheme 38. Reductive amination (e.g. NaBH(OAc)$_3$ or NaBH$_3$CN) of aryl aldehyde 3 with an aspartate derivative 153 gives the amino-diester 154. Reaction of amino-diester 154 with appropriate aryl isocyanates 155 with heat results in the formation of hydantoin ester 156. Deprotection of hydantoin ester 156 provides hydantoin acids XLVII of the invention. It should be noted that the use of L- or S-aspartate diesters provides the individual enantiomers of hydantoin acids XLVII of the invention.

The synthesis of piperidine acids XLVIII-L of the invention is shown in Scheme 39. Reaction of the α-carboalkoxy piperidone 157 with nonaflyl fluoride in the presence of base provides the enol nonaflate 158. Palladium mediated coupling of enol nonaflate 158 with the organozinc reagent 125 (as previously described for Scheme 29; ref: (Bellina, F. et al, *Tetrahedron*, 1999, 55, 2103-2112)) provides the coupled α,β-unsaturated ester 159. The phenol of 159 is deprotected and alkylated with mesylate 4 (as for Scheme 18) to provide the piperidine ester 160. N-deprotection of 160 furnishes the key piperidine ester 161, which is then converted according to the sequence in Scheme 37 to the piperidine carbamate acids XLVIII of the invention, the N-aryl piperidine acids XLIX of the invention and N-heteroaryl piperidine acids L of the invention.

The preparation of piperidine acids L1-LIII of the invention is shown in Scheme 40. Treatment of α-carboalkoxy piperidone 157 with triflic anhydride in the presence of base provides enol triflate 162. Palladium-mediated coupling of enol triflate 162 to an appropriately substituted aryl boronic acid 163 (ref: Wustrow, D. J. and Wise, L. D., *Synthesis*, 1991, 993-995) provides the coupled piperidine α,β unsaturated ester 164. Deprotection of the phenol moiety of 164 followed by alkylation with mesylate 4 provides the alkoxy phenol piperidine ester 165, which is then N-deprotected to furnish the free piperidine ester 166.

Piperidine ester 166 is then converted according to the sequences shown in Scheme 37 to the piperidine carbamate acids LI of the invention, the N-aryl piperidine acids LII of the invention and N-heteroaryl piperidine acids LIII of the invention.

Scheme 41 illustrates the synthesis of piperidine acids LIV-LVI of the invention. Reduction (hydrogenation) of the α,β unsaturated ester 166 provides the corresponding piperidine ester 167. Piperidine ester 167 is then converted according to the sequences shown in Scheme 37 to the piperidine carbamate acids LIV of the invention, the N-aryl piperidine acids LV of the invention and N-heteroaryl piperidine acids LVI of the invention.

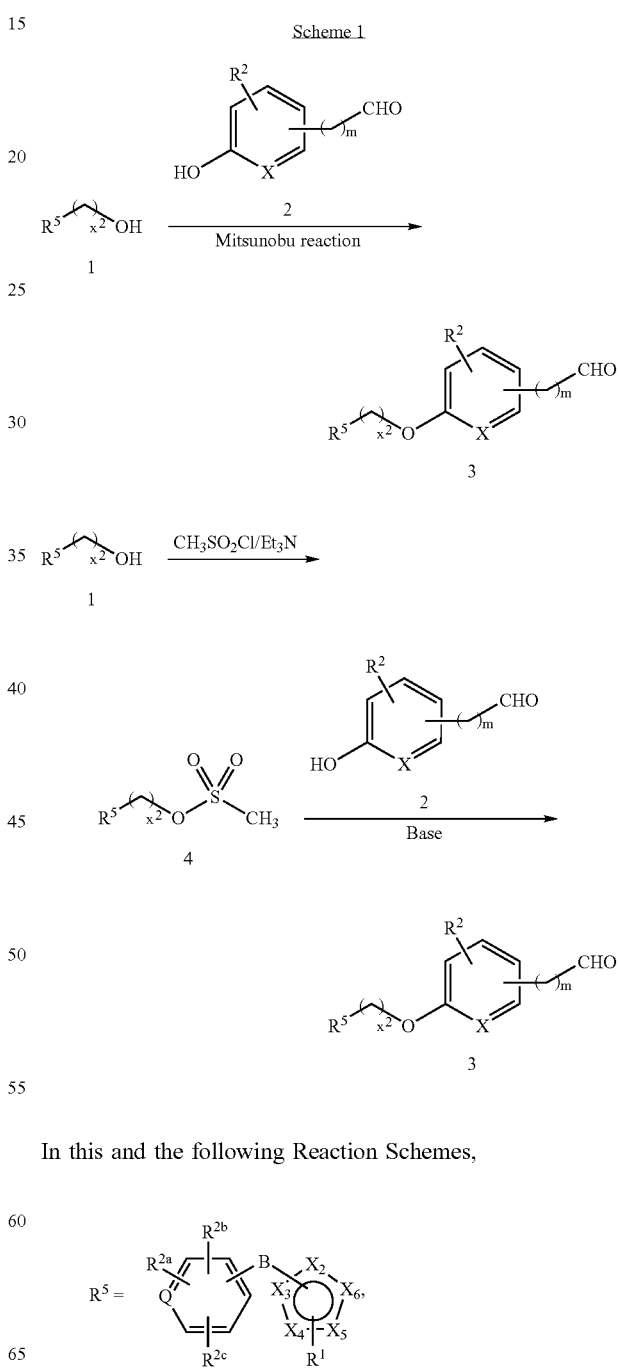

In this and the following Reaction Schemes, preferably
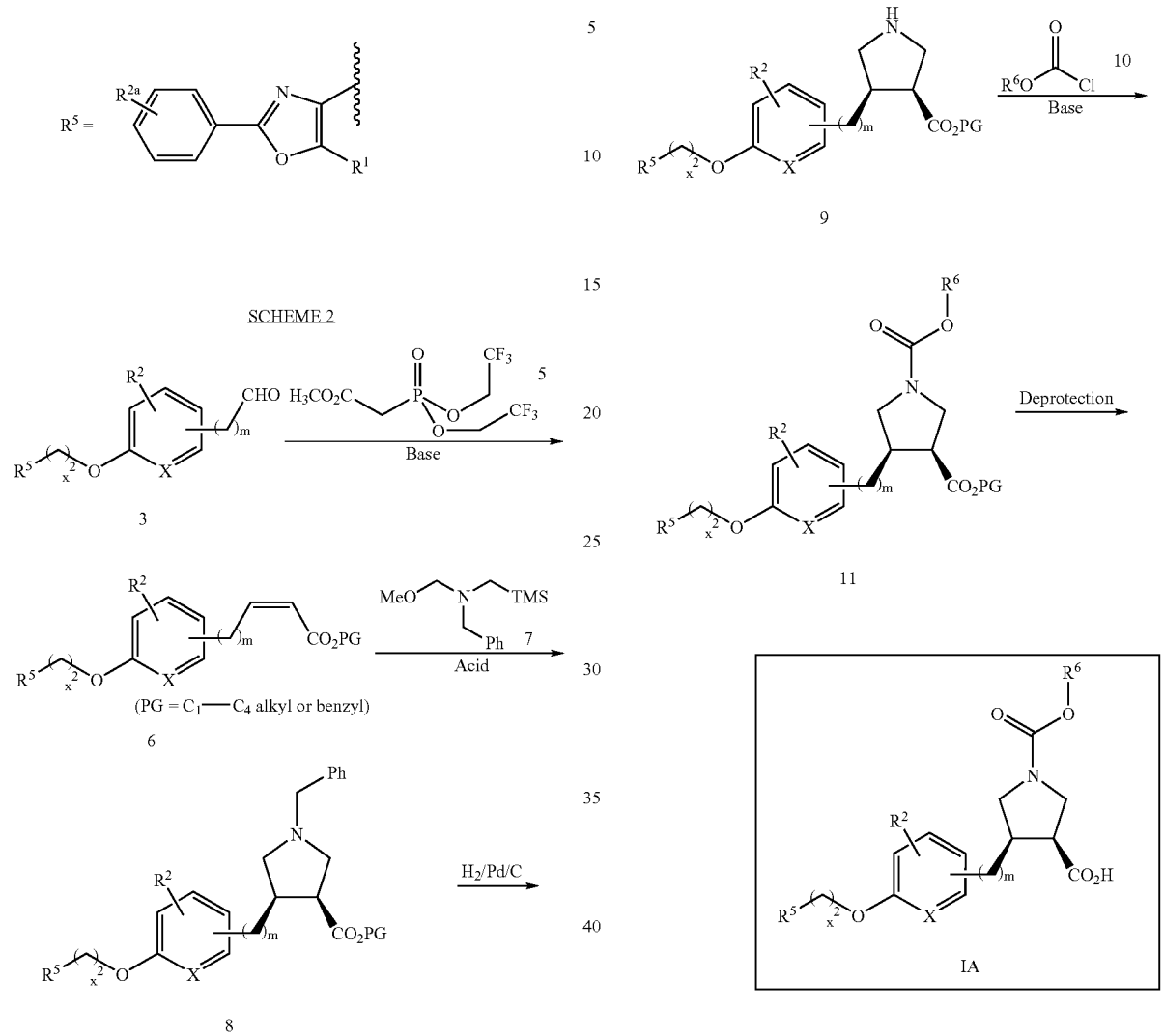
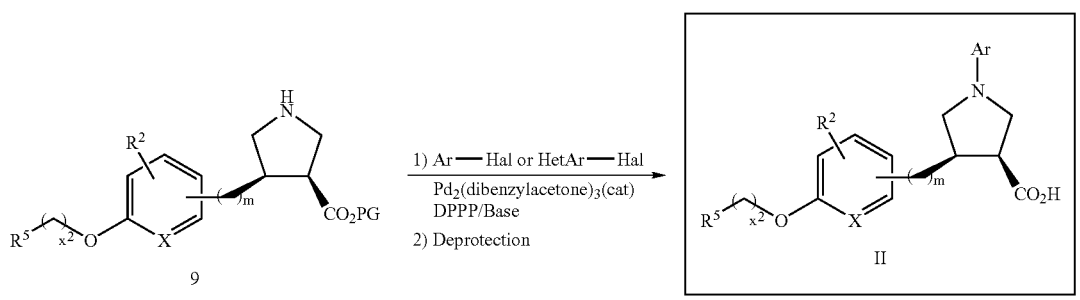

-continued
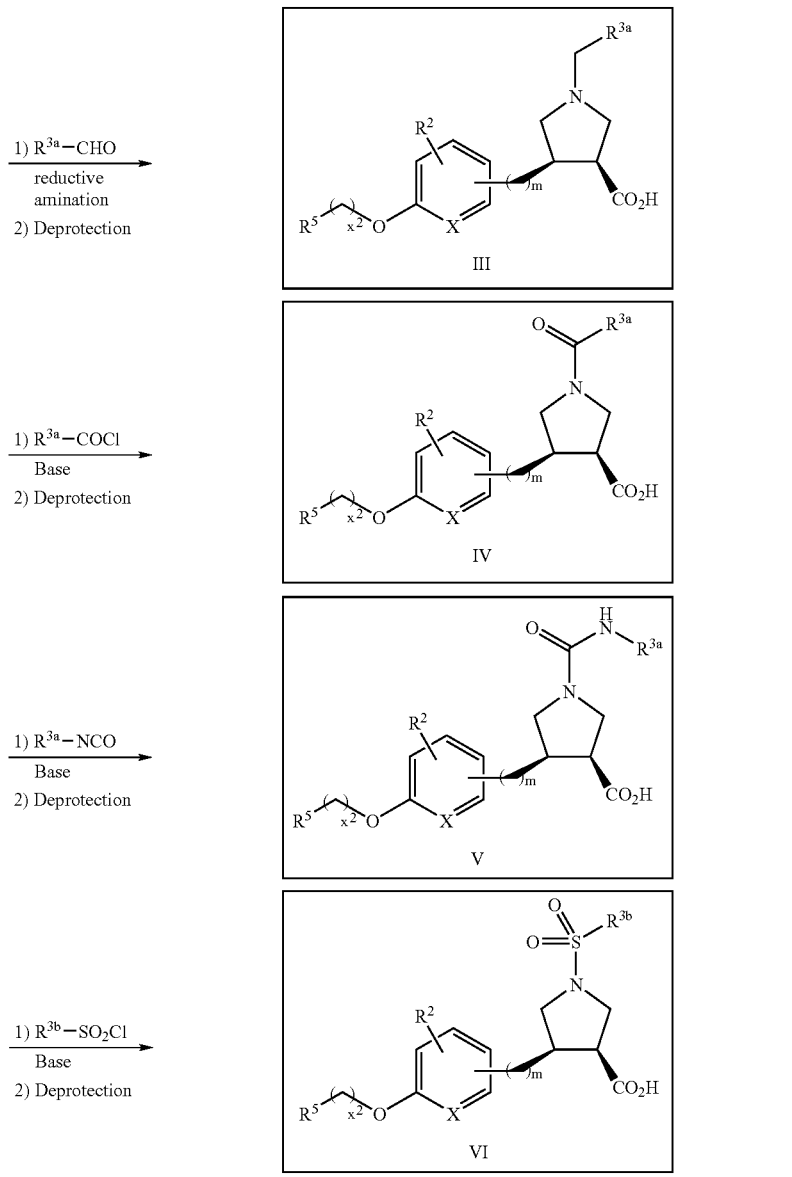
($R^{3a}$ can be any of the $R^3$ groups)
($R^{3b}$ can be any of the $R^3$ groups except H)
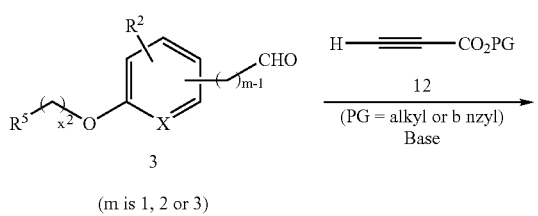
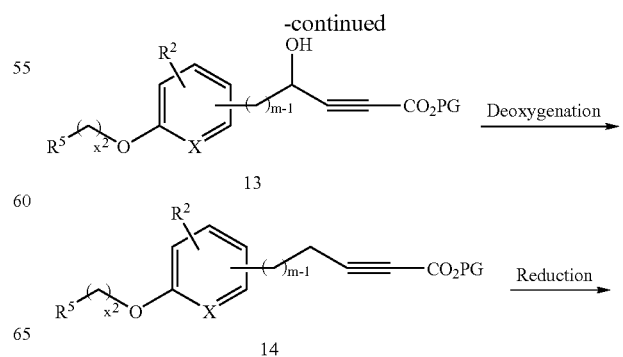

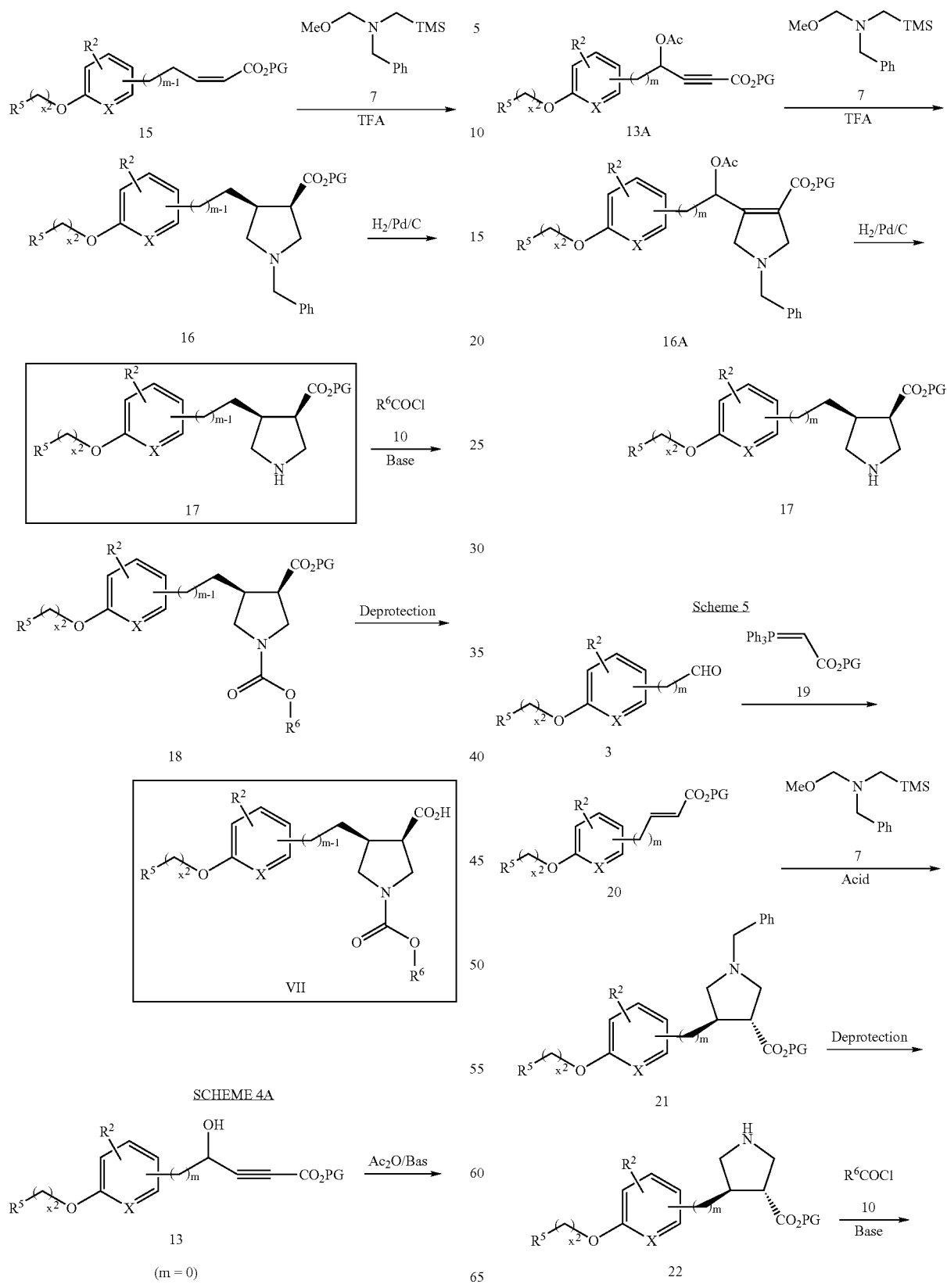

-continued
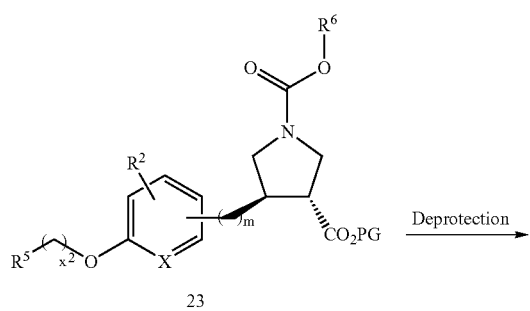
23
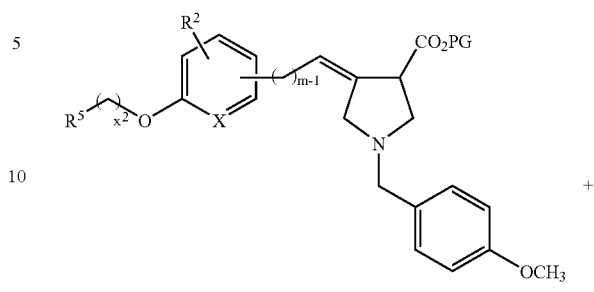
27
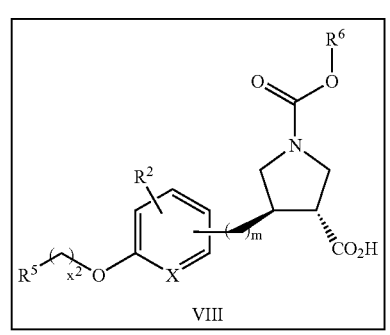
VIII
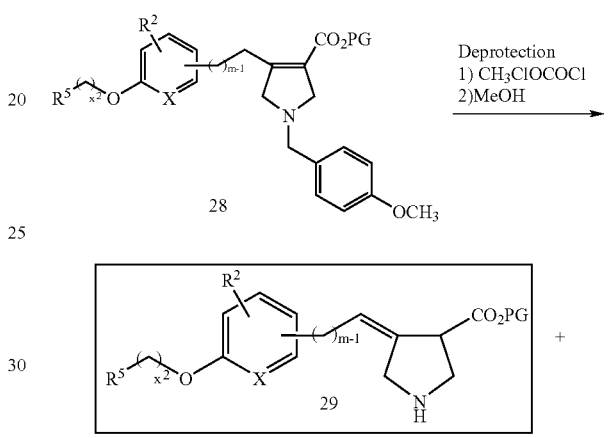
28
29
30
Scheme 6
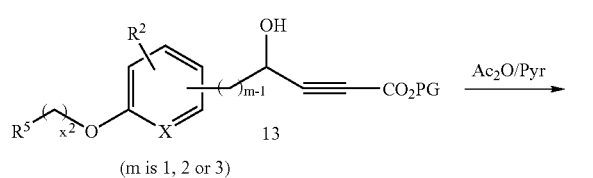
13
(m is 1, 2 or 3)
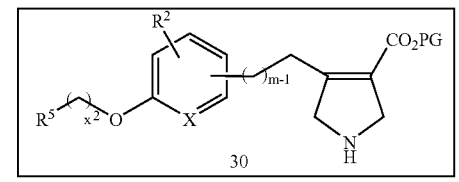
29
30
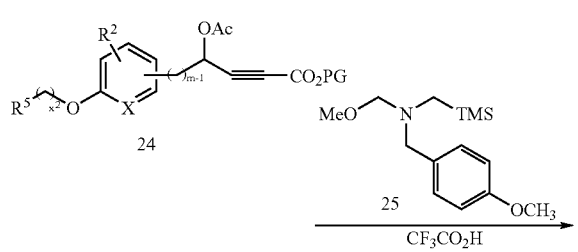
24
25
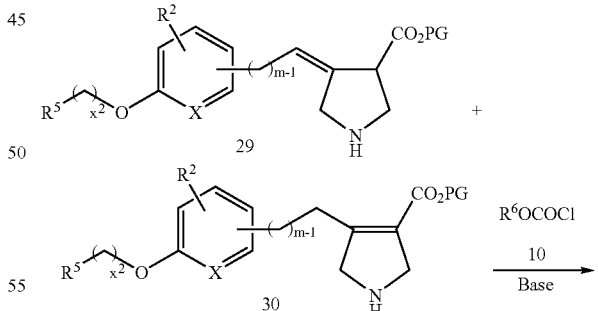
30
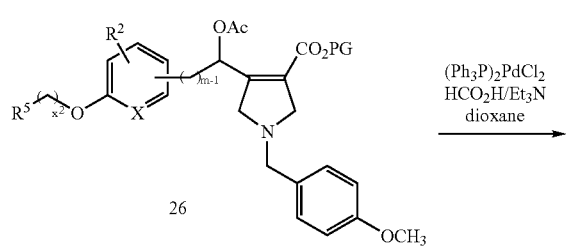
26
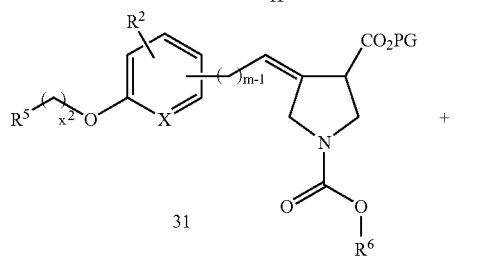
31

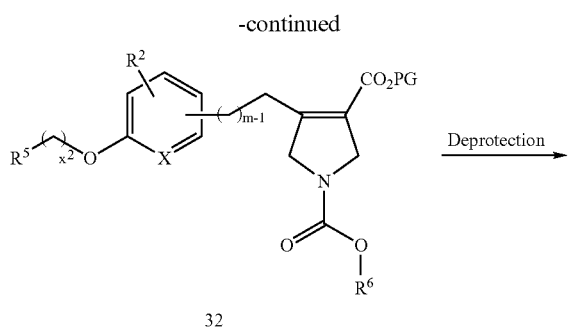
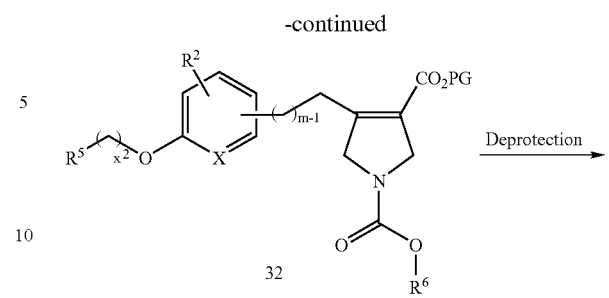
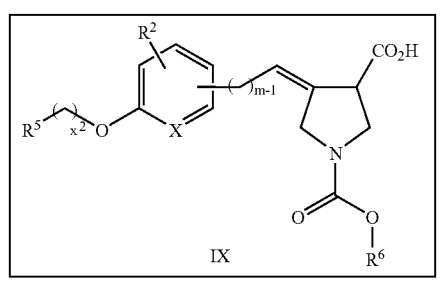
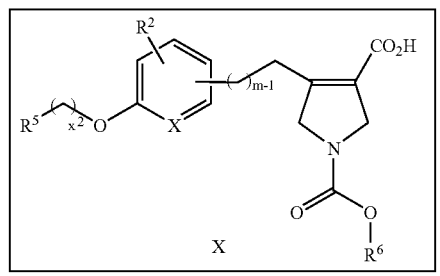
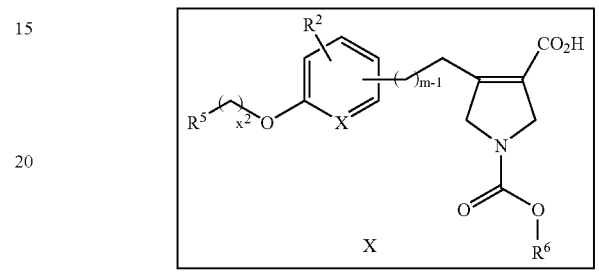
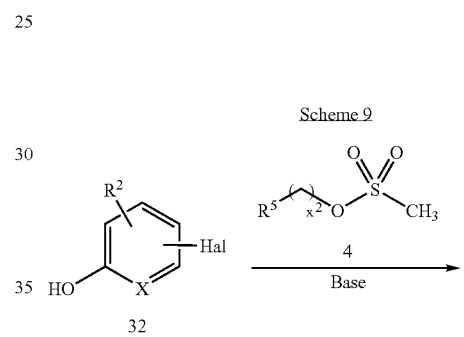
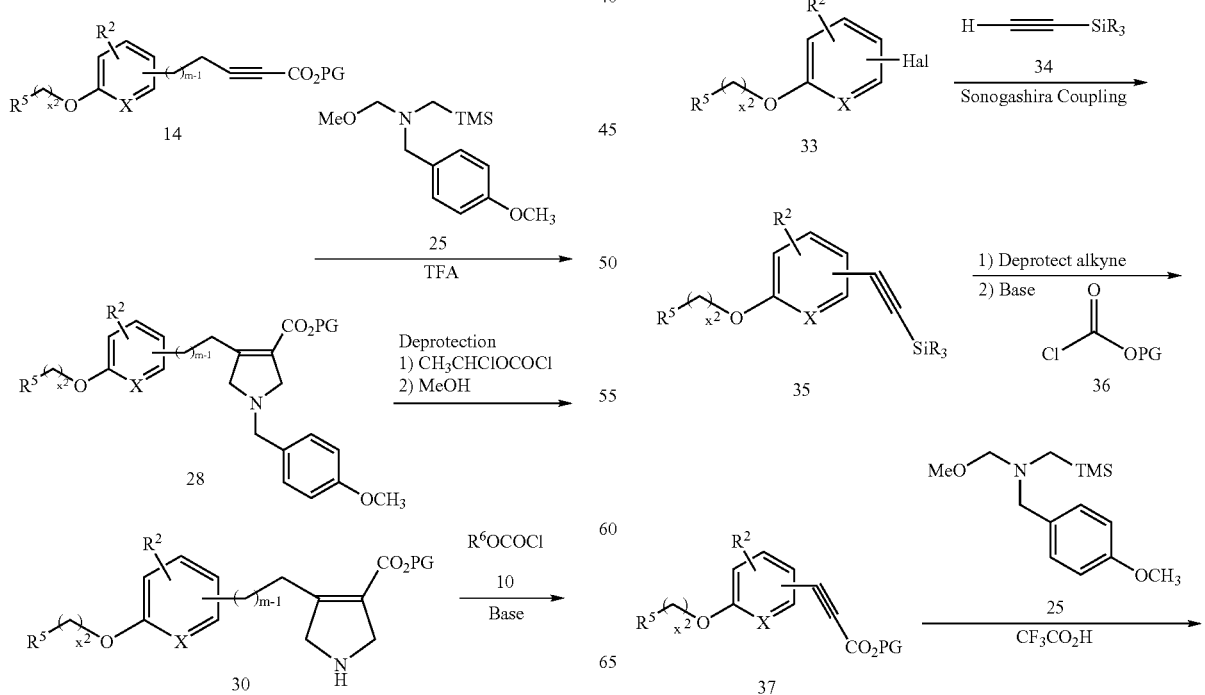

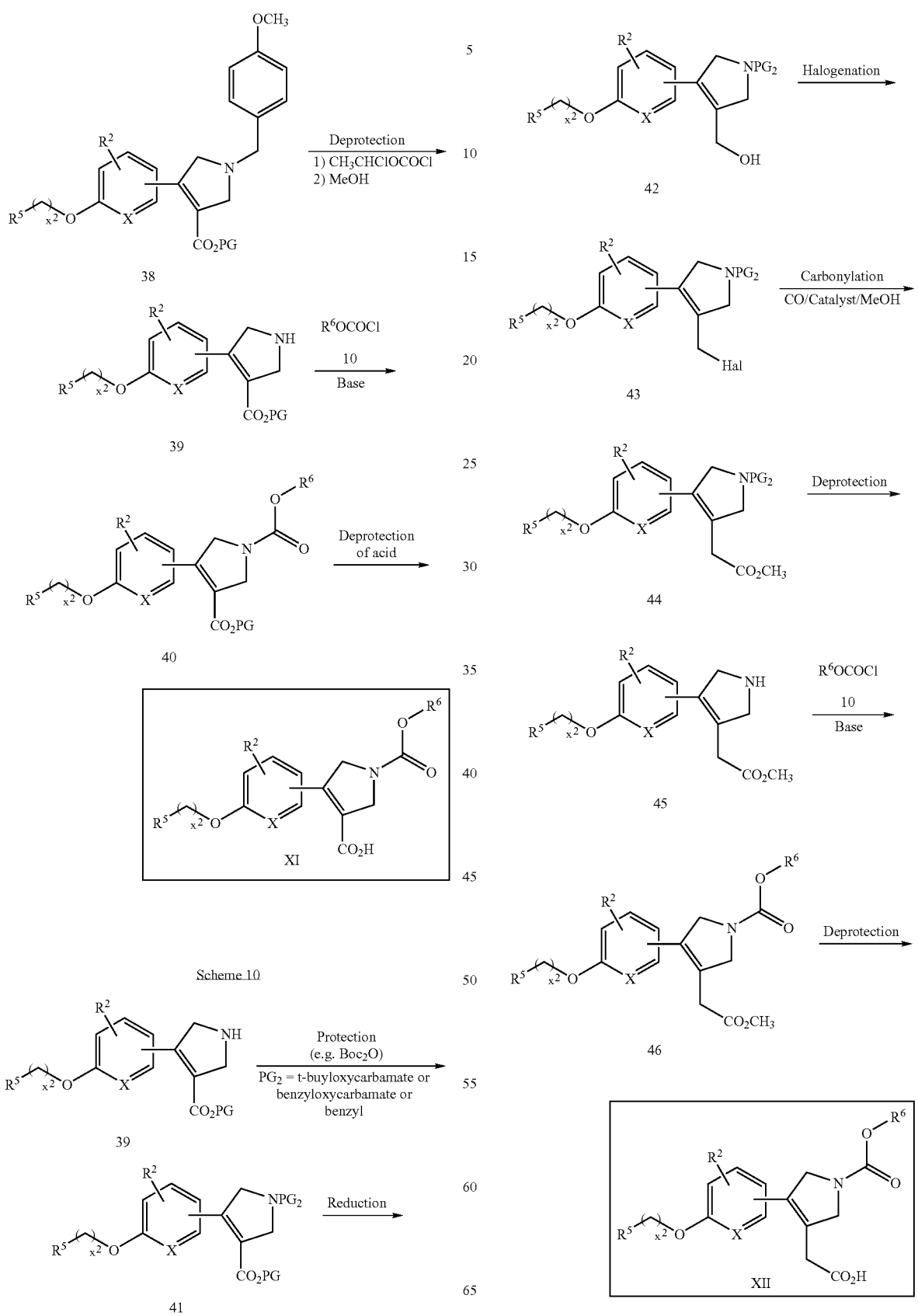

Scheme 11
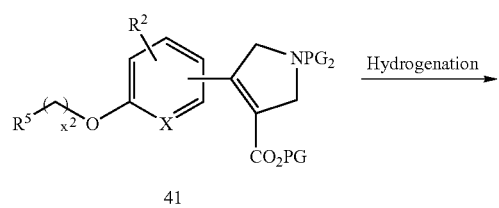
41 →Hydrogenation→
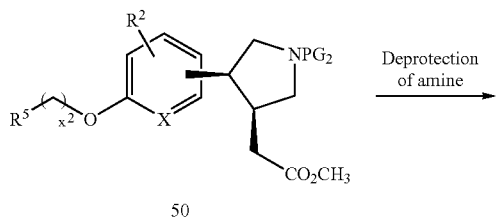
50 →Deprotection of amine→
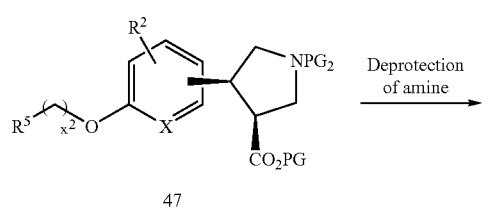
47 →Deprotection of amine→
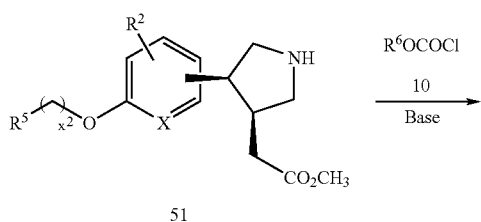
51 →R⁶OCOCl / Base→
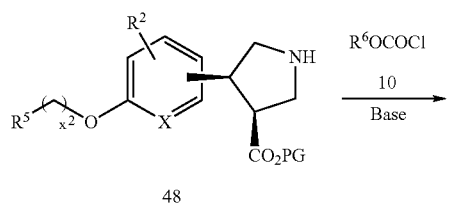
48 →R⁶OCOCl / Base→
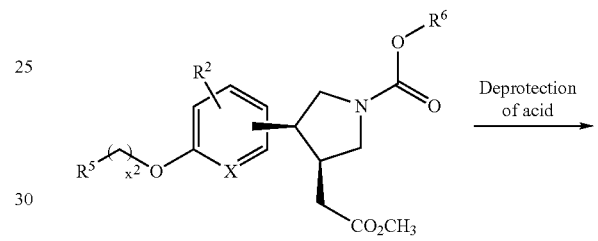
52 →Deprotection of acid→
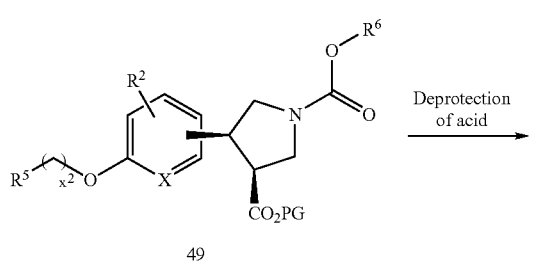
49 →Deprotection of acid→
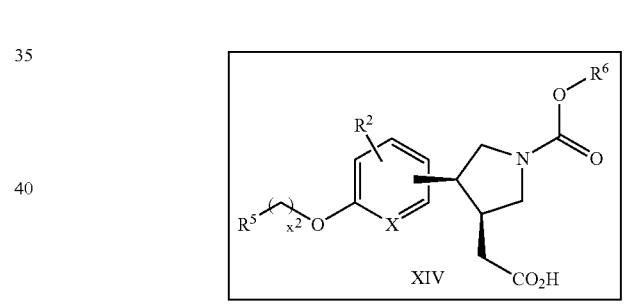
XIV
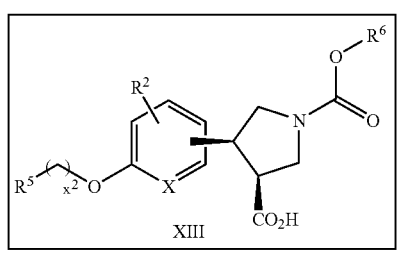
XIII
Scheme 12
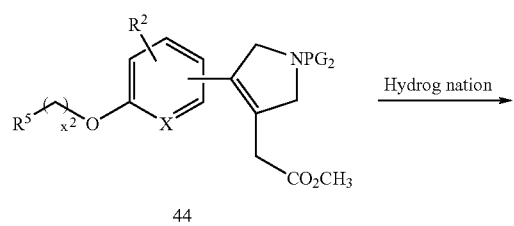
44 →Hydrogenation→
Scheme 13
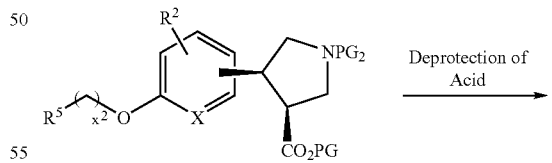
47 →Deprotection of Acid→
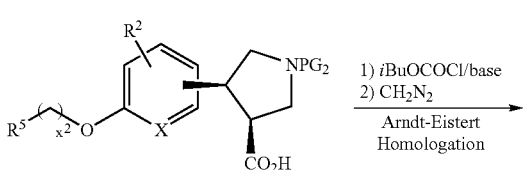
53 →1) iBuOCOCl/base  2) CH₂N₂  Arndt-Eistert Homologation→

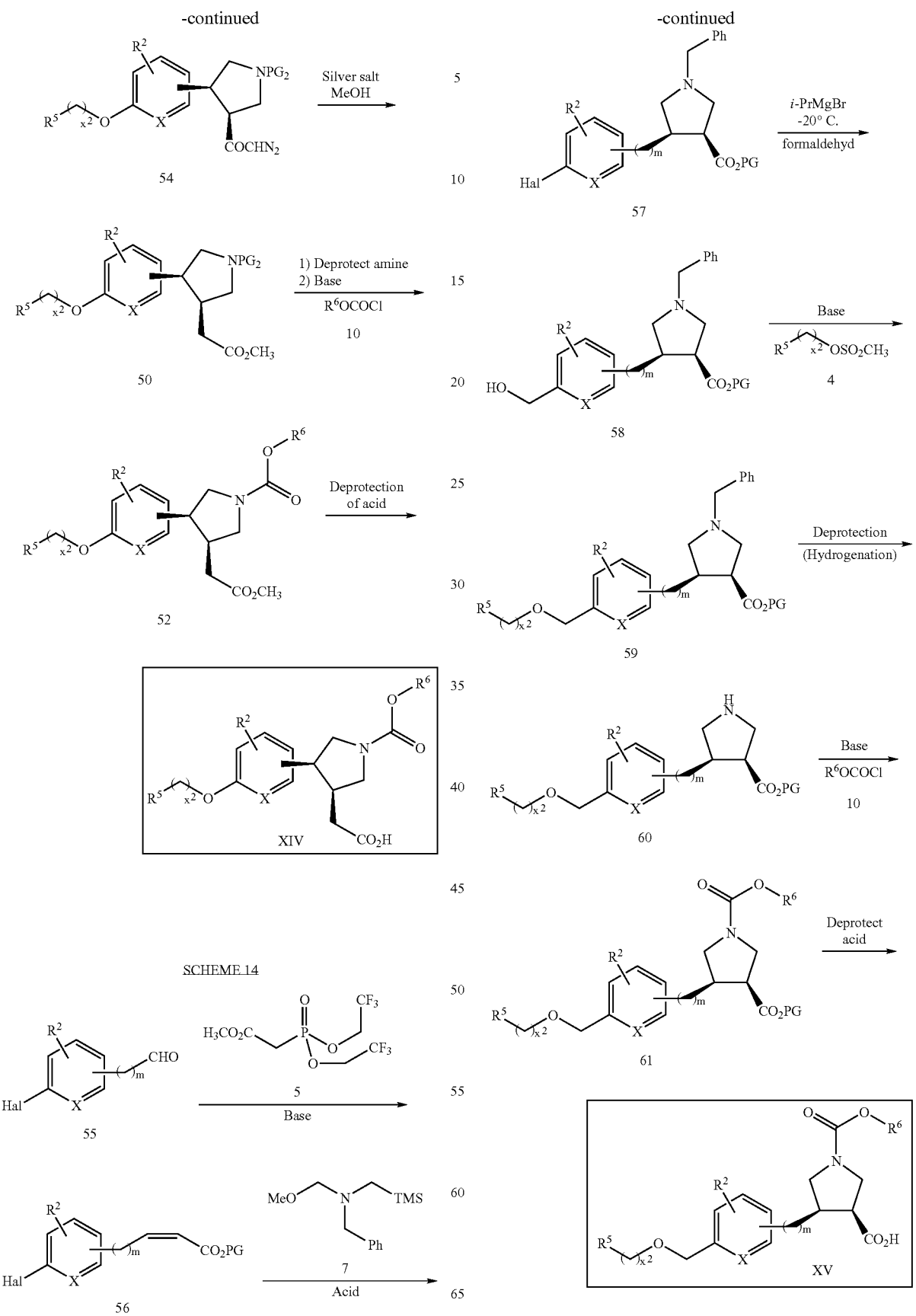

SCHEME 15
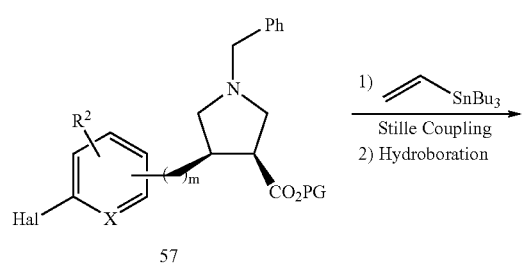
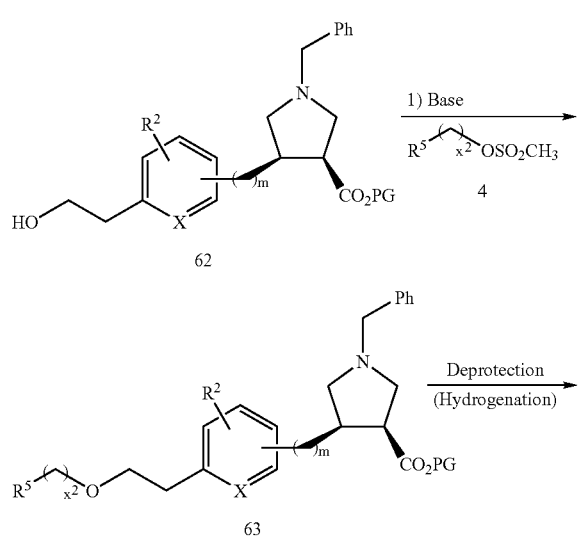
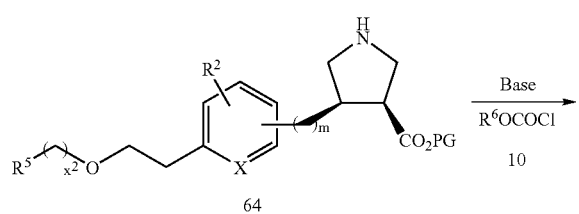
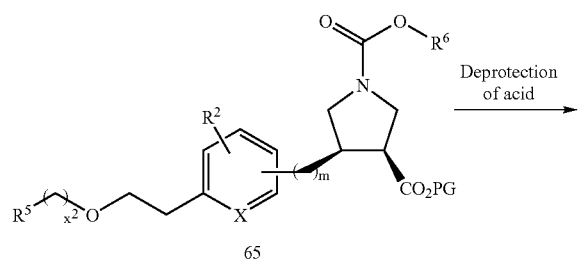
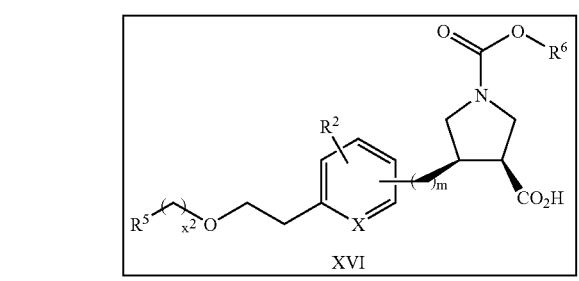
SCHEME 16
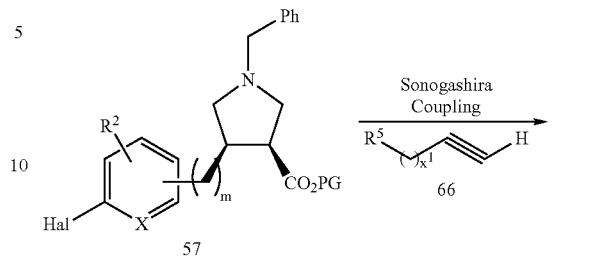
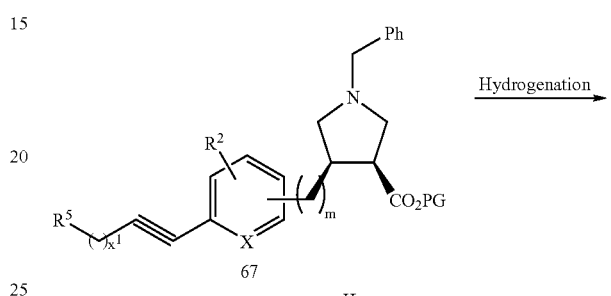
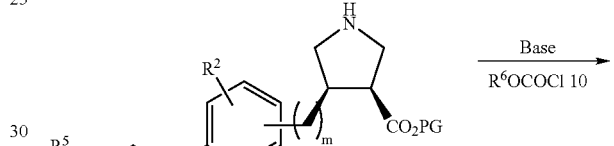
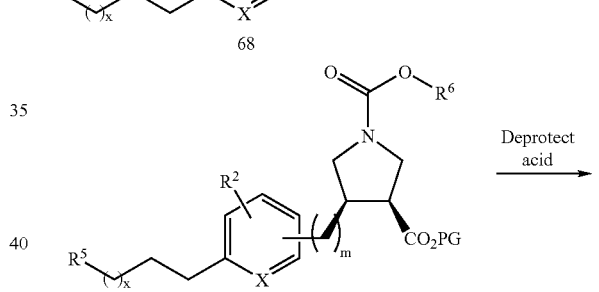

SCHEME 17

70 (PG$_3$ = alkyl or silyl)

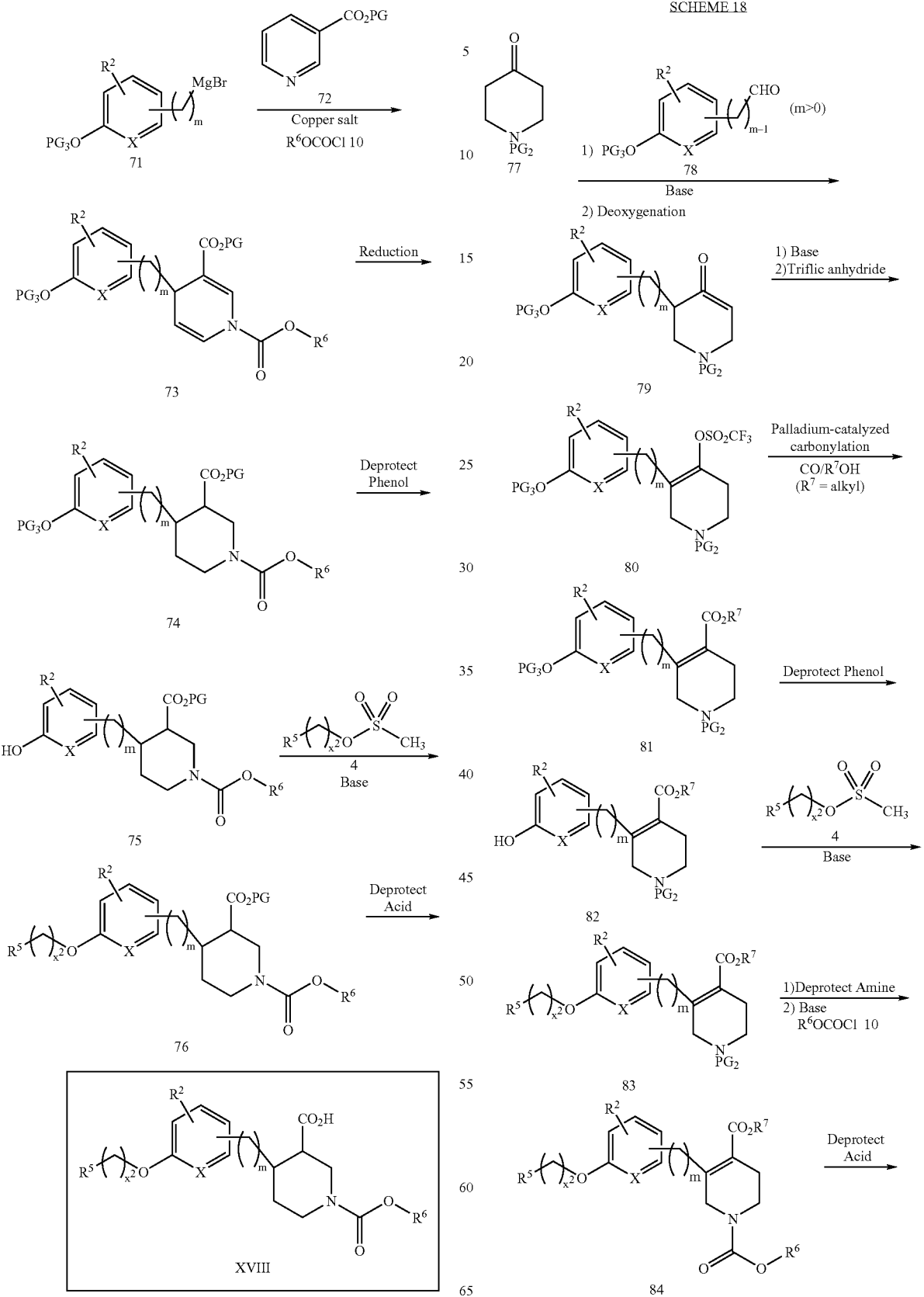

-continued
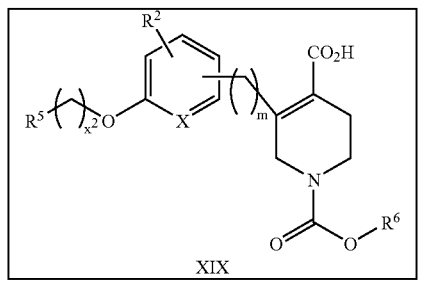
XIX
SCHEME 19
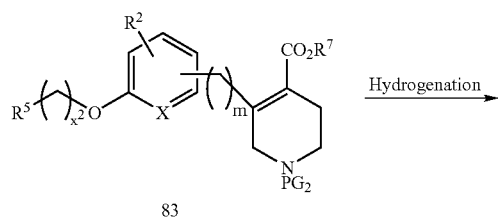
83
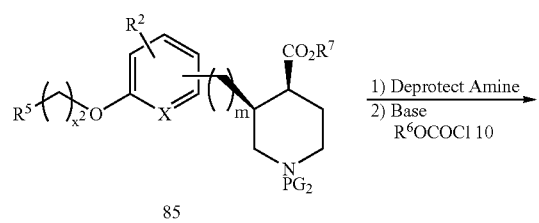
85
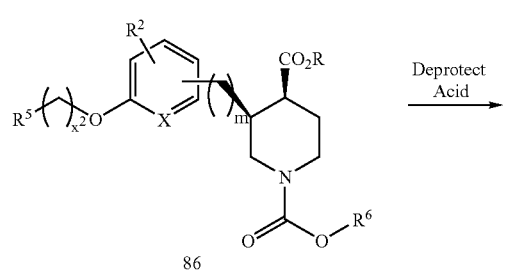
86
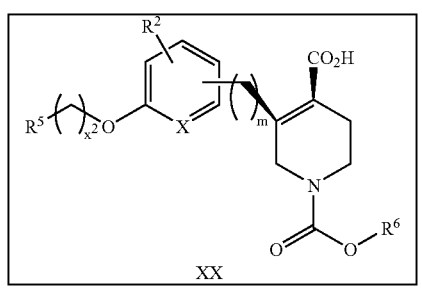
XX
SCHEME 20A
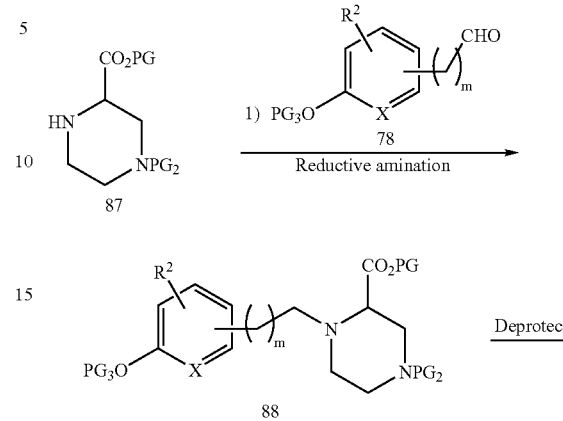
SCHEME 20B
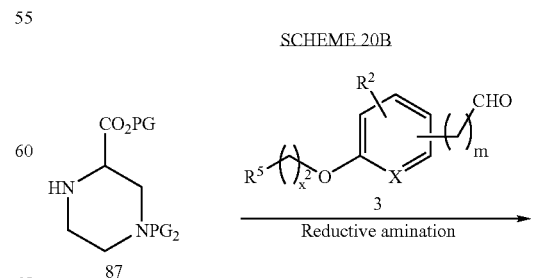
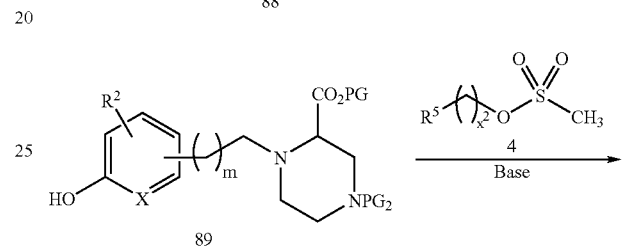
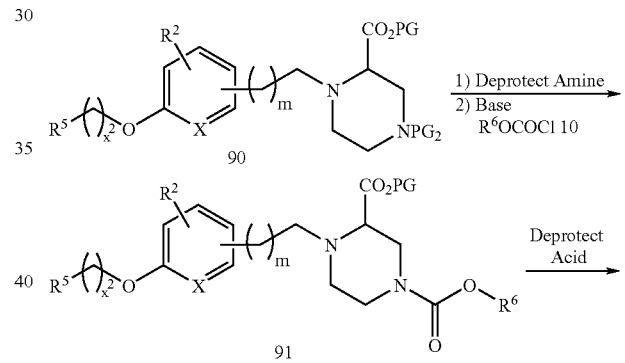
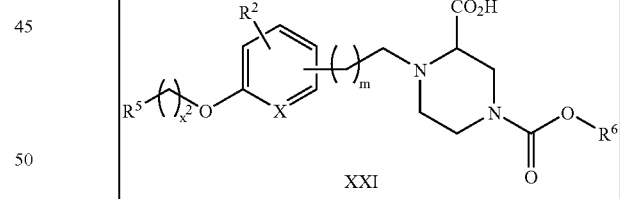
XXI

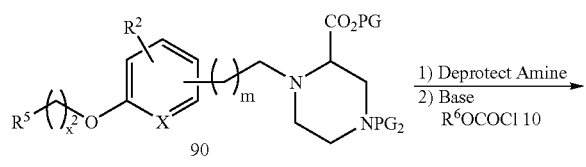
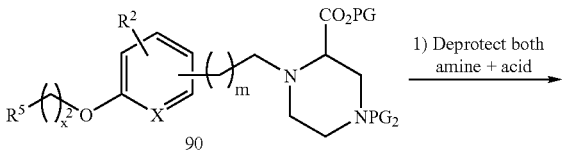
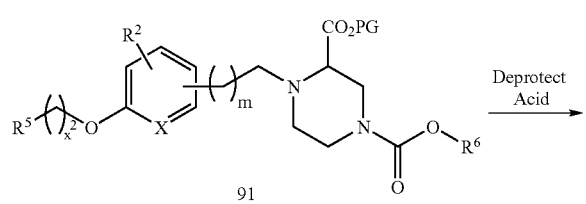
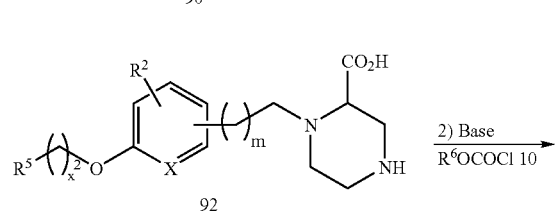
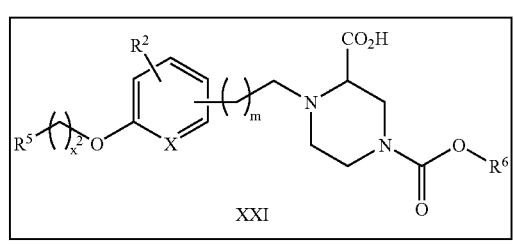
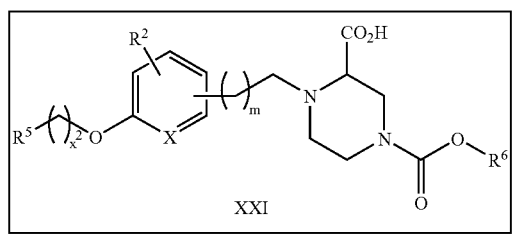
SCHEME 21
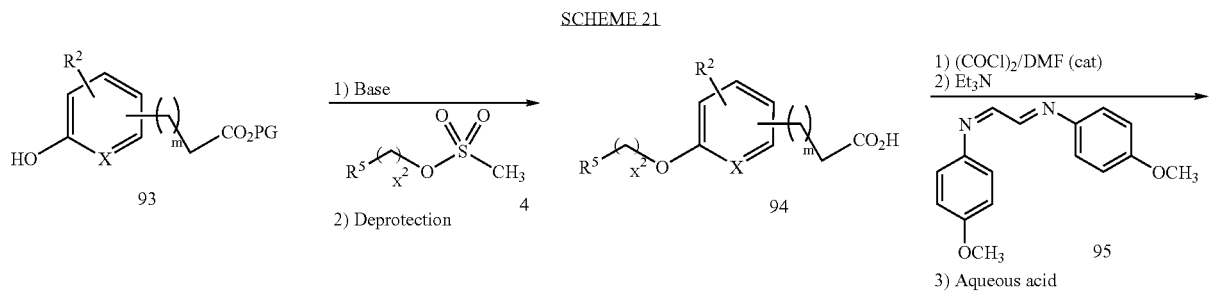
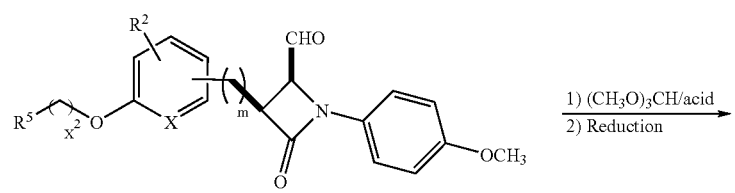
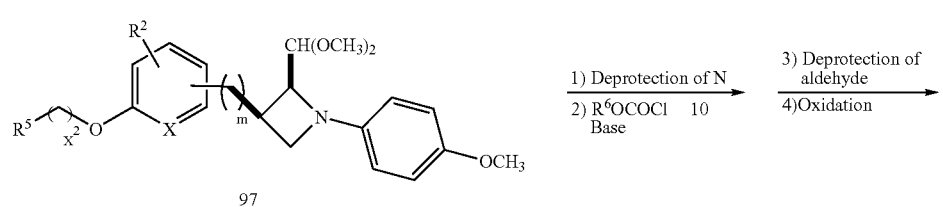

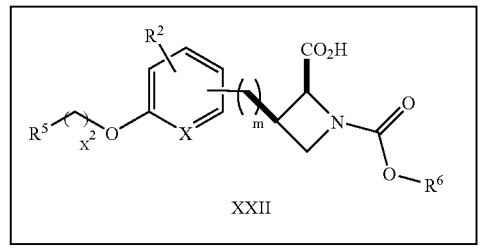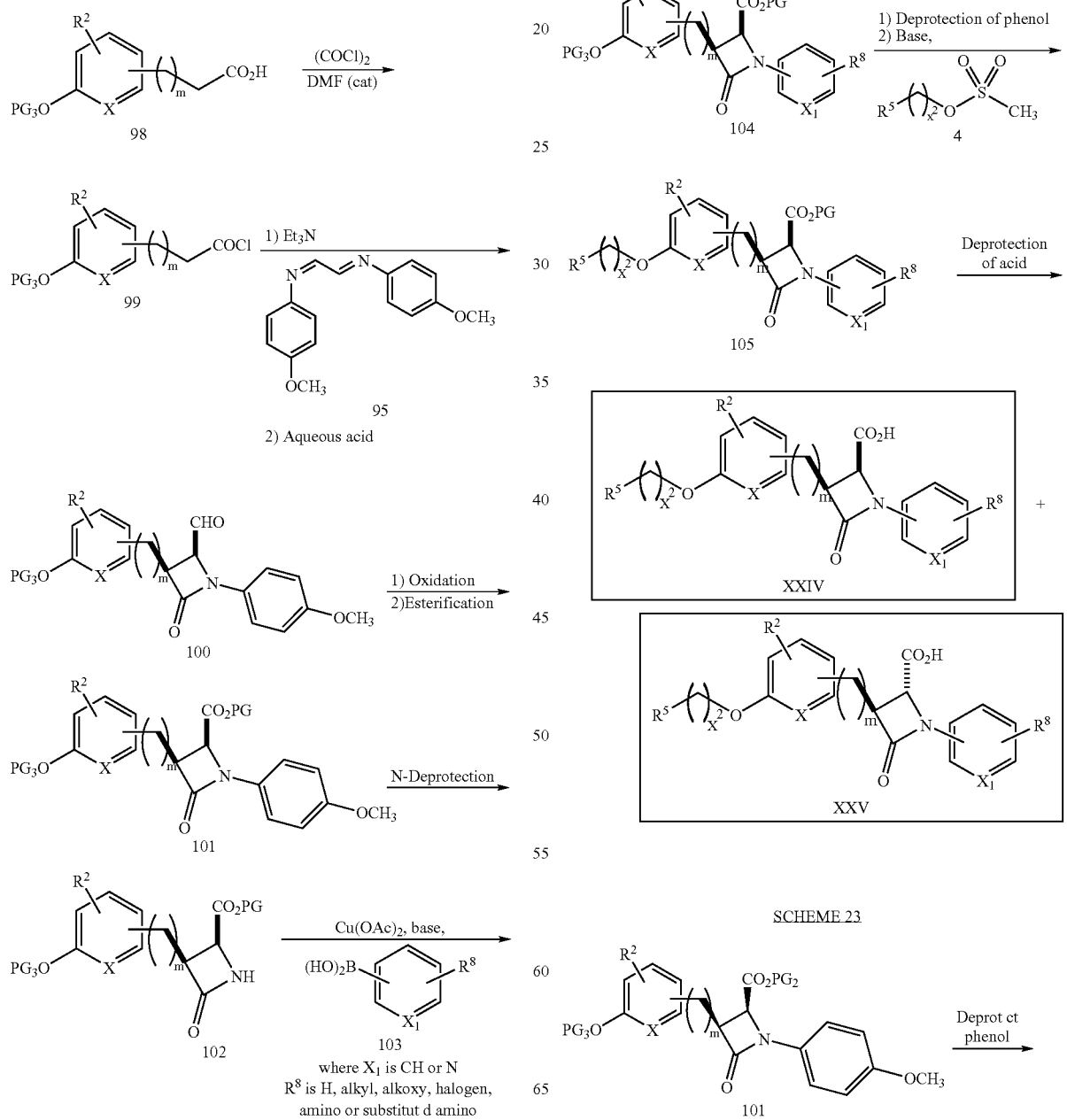

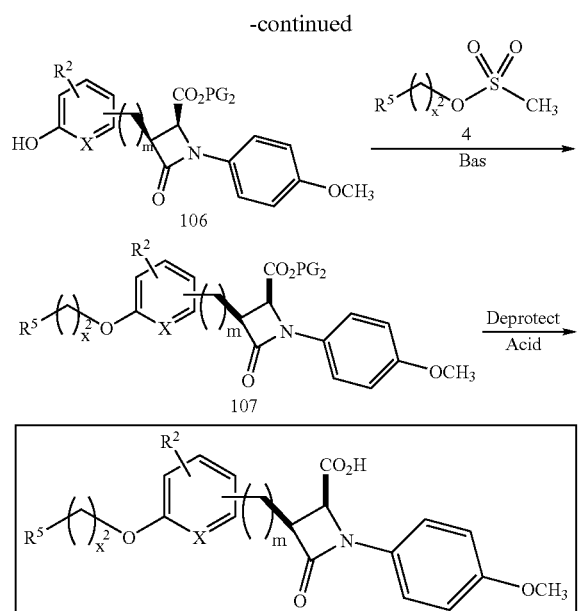
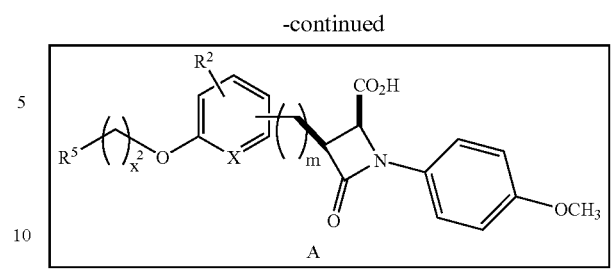
SCHEME 24
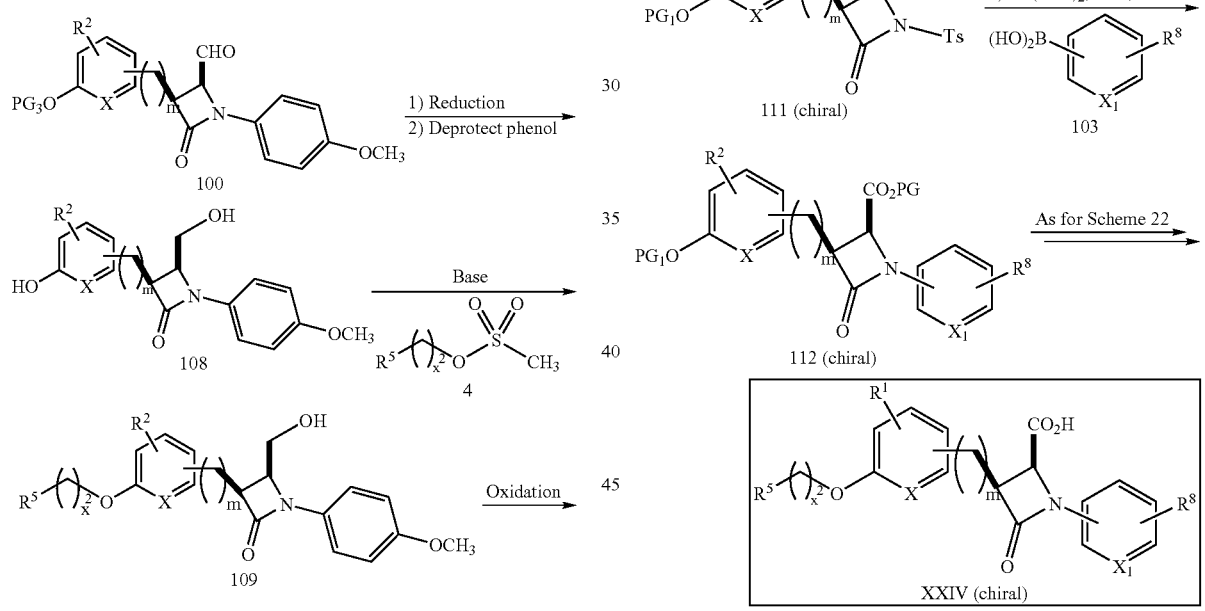
SCHEME 25
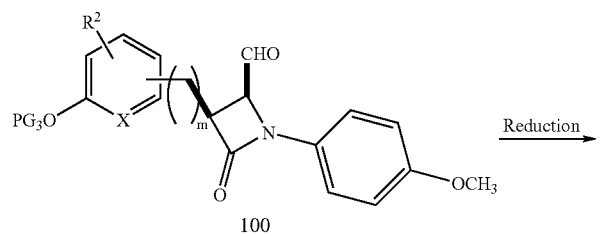
SCHEME 26

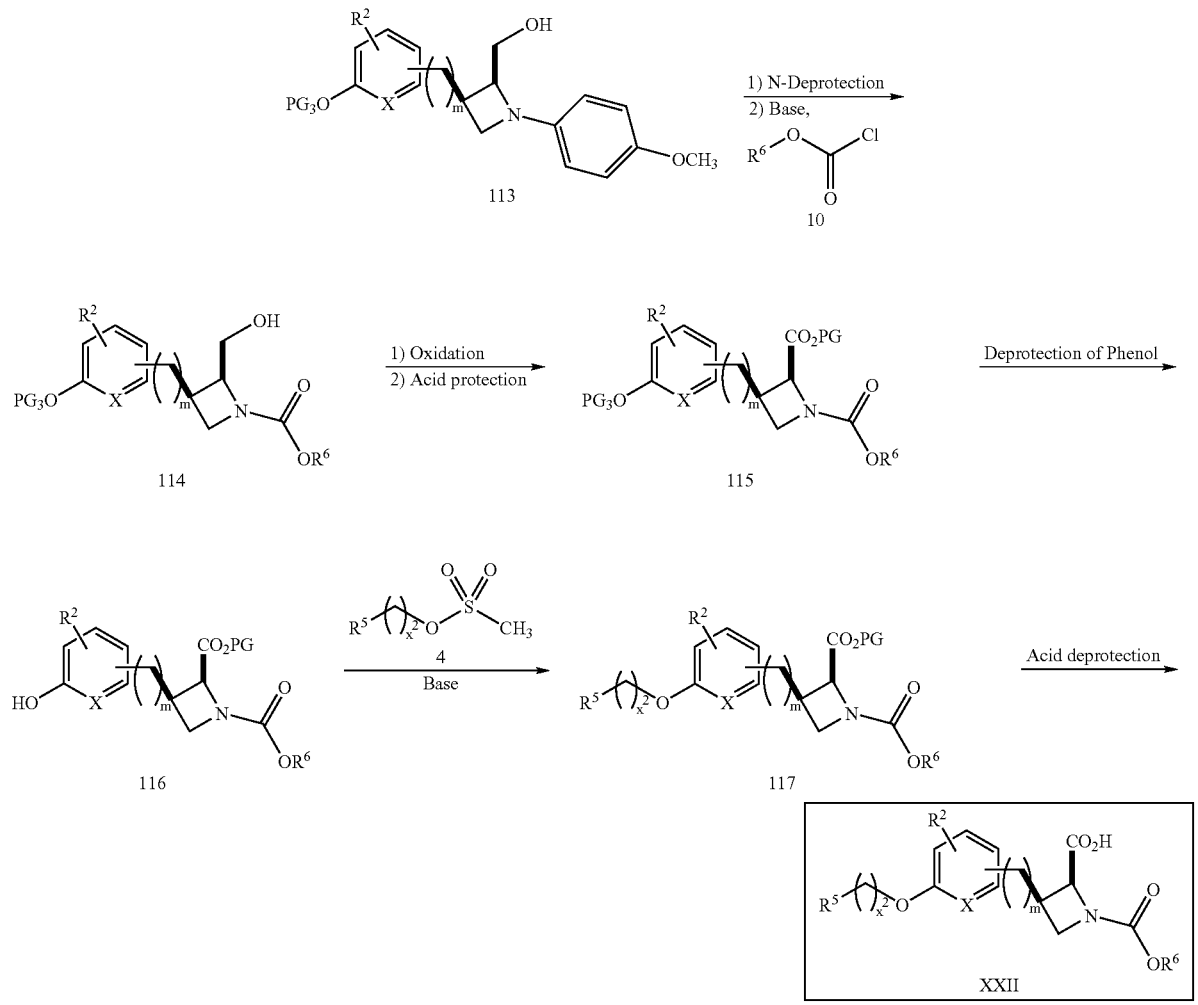
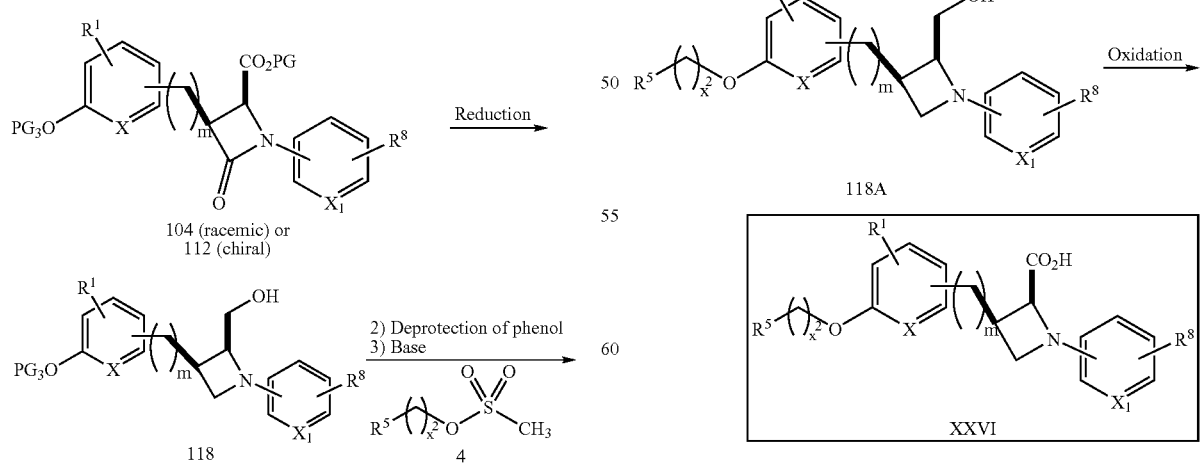
SCHEME 27

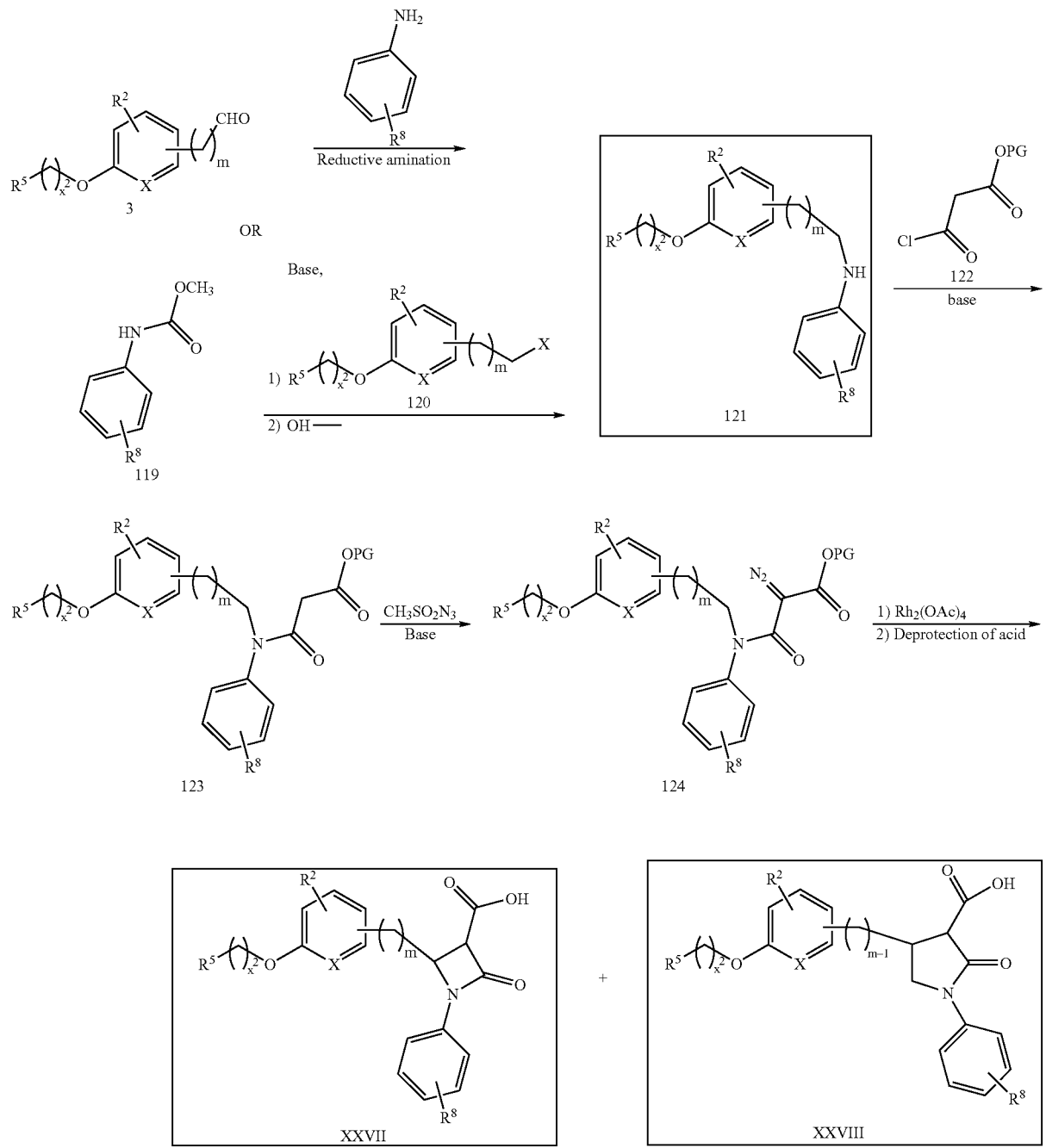
SCHEME 28
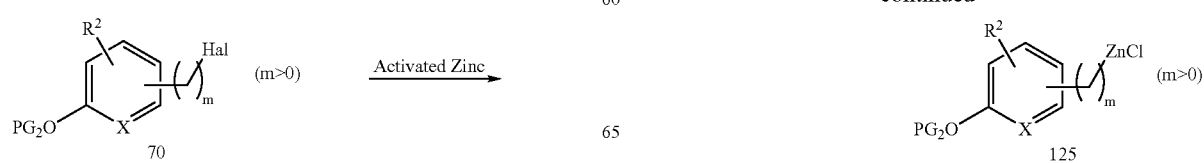
SCHEME 29

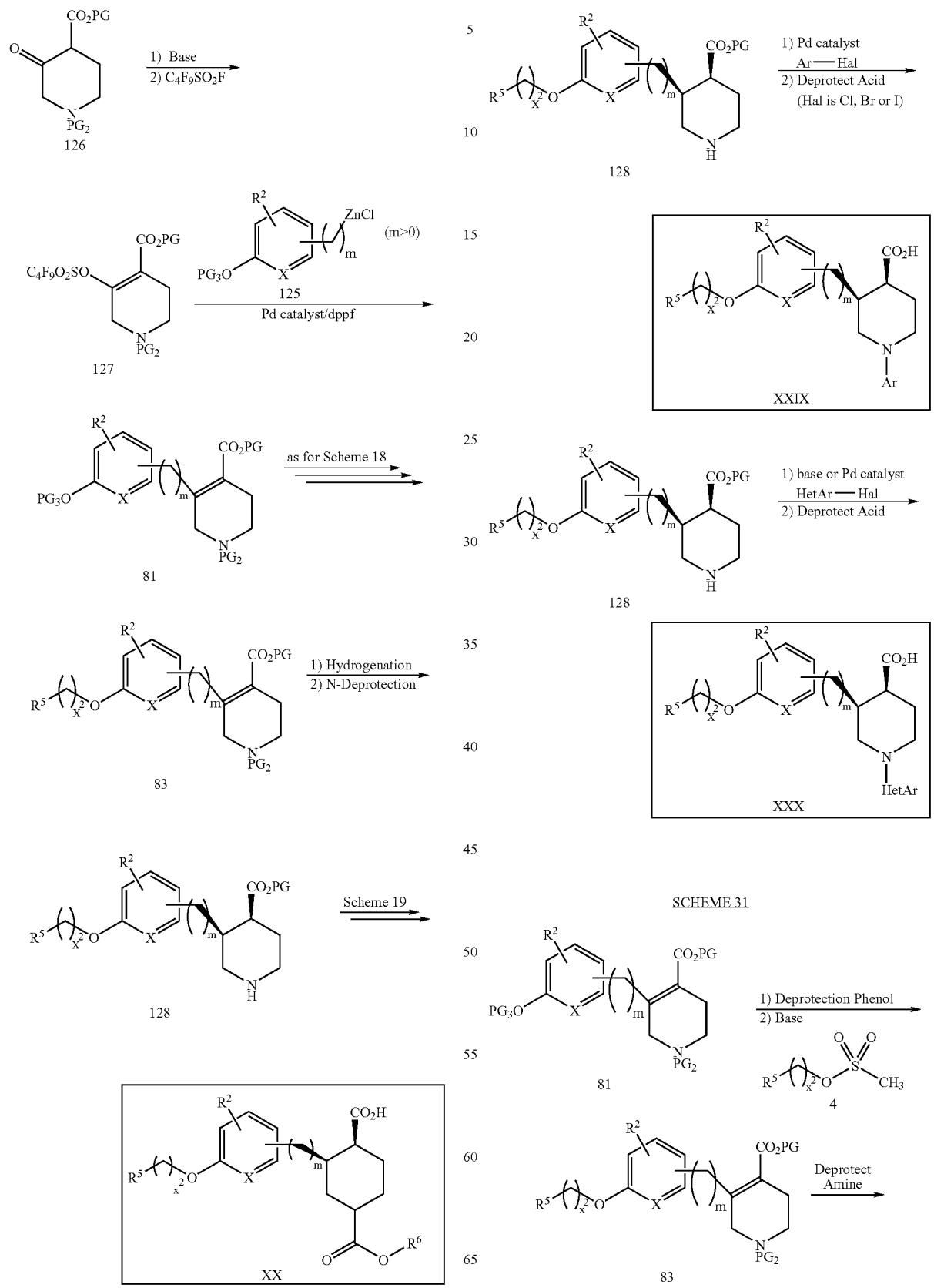

-continued
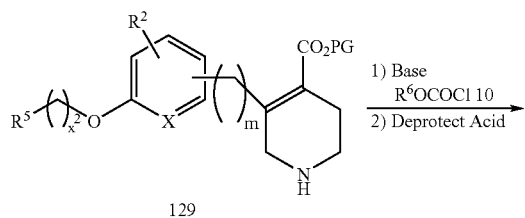
1) Base
R⁶OCOCl 10
2) Deprotect Acid
→
129
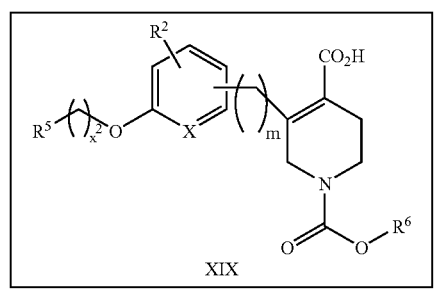
XIX
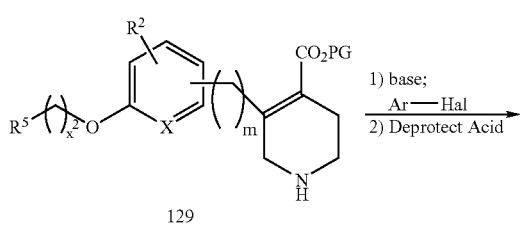
1) base;
Ar—Hal
2) Deprotect Acid
→
129
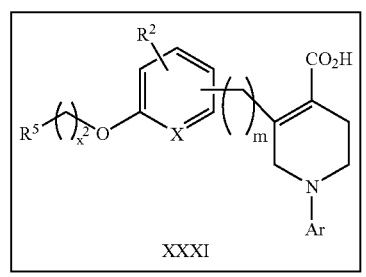
XXXI
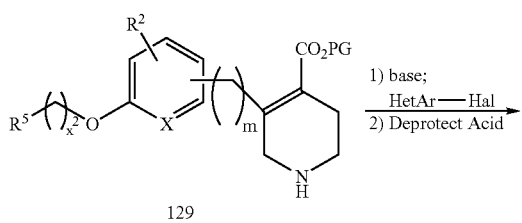
1) base;
HetAr—Hal
2) Deprotect Acid
→
129
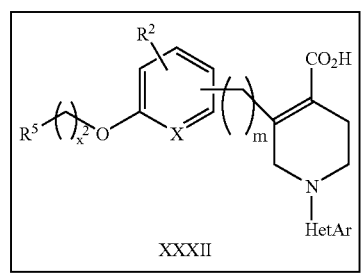
XXXII
SCHEME 32
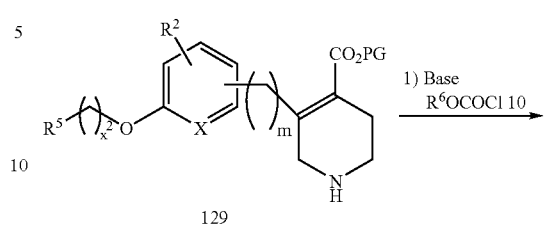
1) Base
R⁶OCOCl 10
→
129
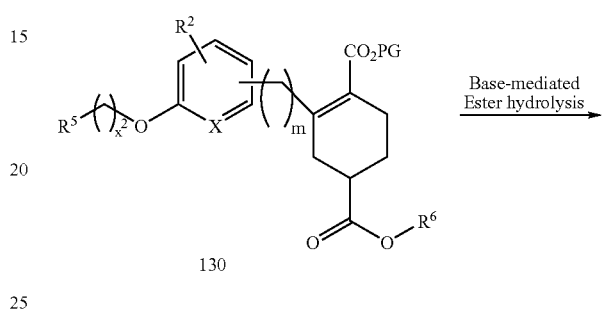
Base-mediated
Ester hydrolysis
→
130
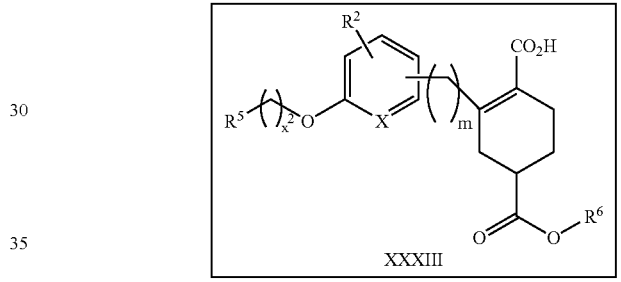
XXXIII
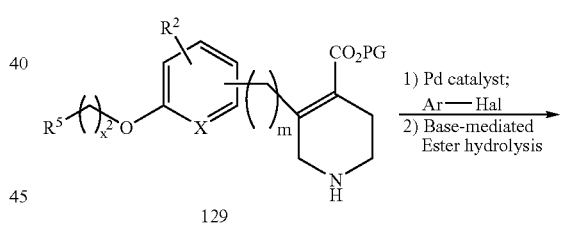
1) Pd catalyst;
Ar—Hal
2) Base-mediated
Ester hydrolysis
→
129
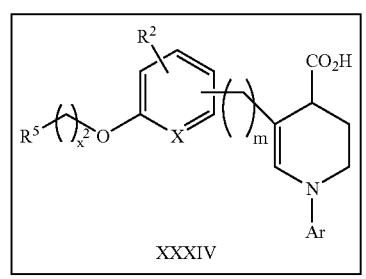
XXXIV
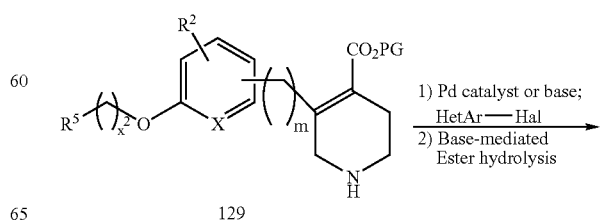
1) Pd catalyst or base;
HetAr—Hal
2) Base-mediated
Ester hydrolysis
→
129

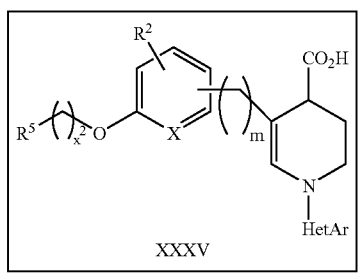
XXXV
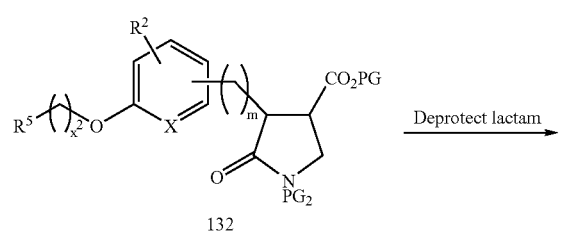
132
Deprotect lactam →
SCHEME 33
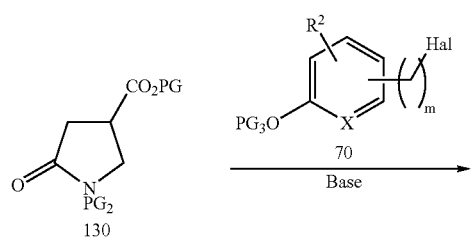
130
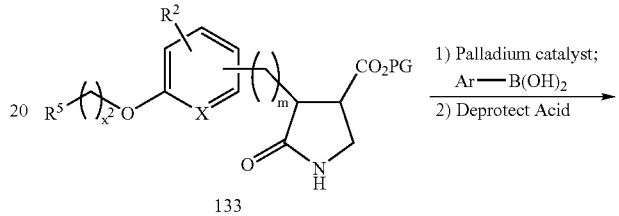
133
1) Palladium catalyst; Ar—B(OH)$_2$
2) Deprotect Acid
→
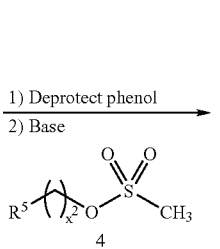
131
1) Deprotect phenol
2) Base
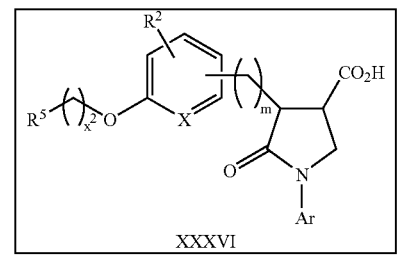
XXXVI
SCHEME 34
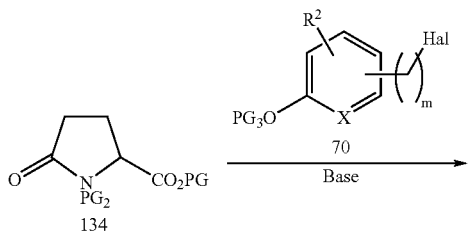
134
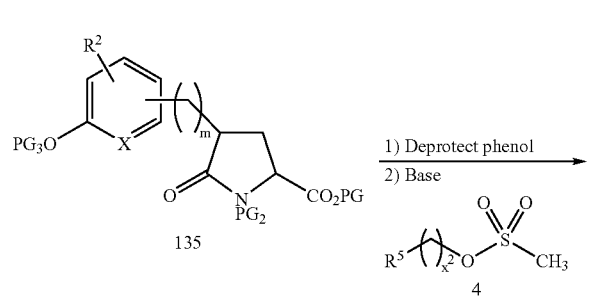
135
1) Deprotect phenol
2) Base
→
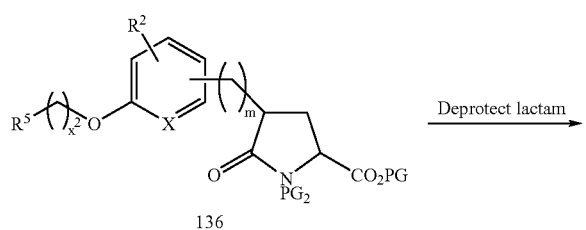
136
Deprotect lactam →

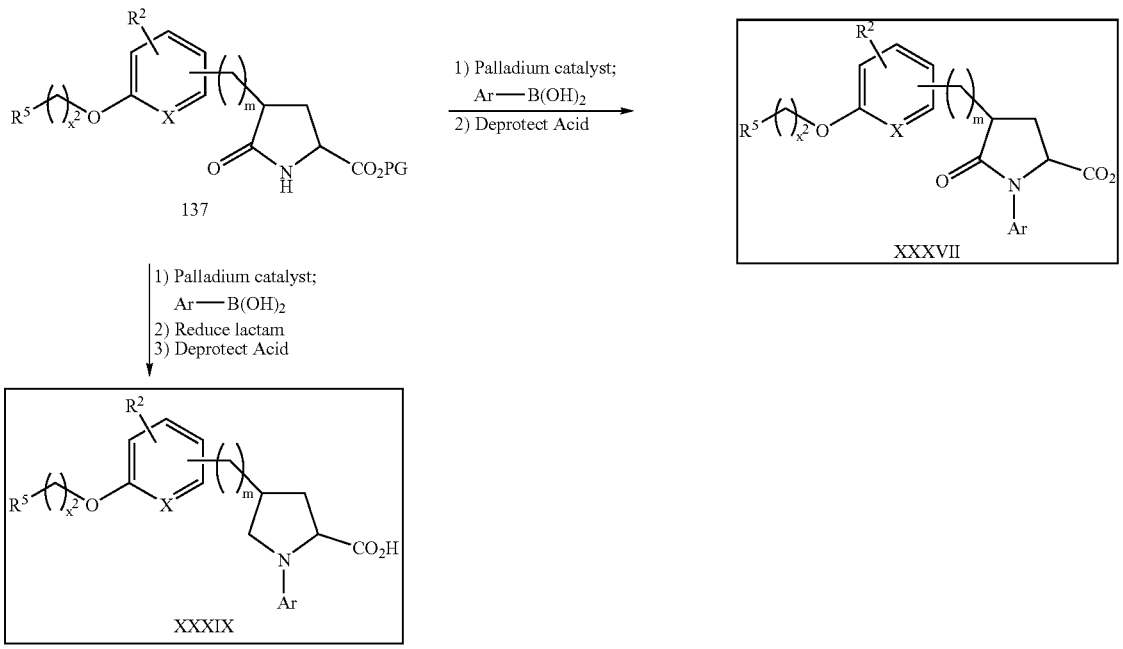
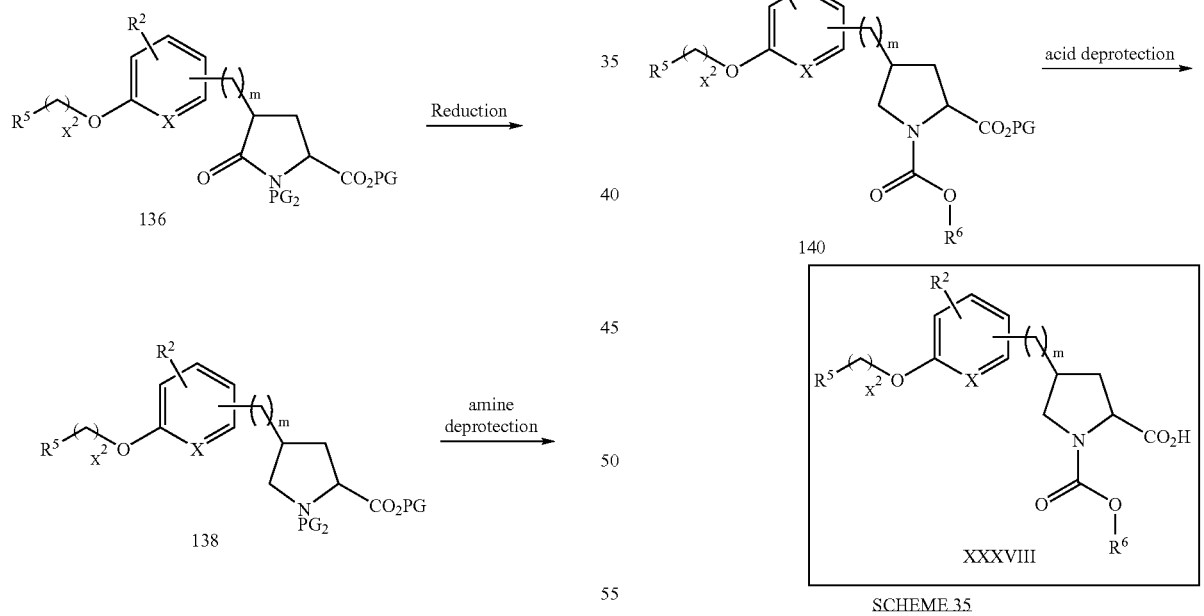
SCHEME 35
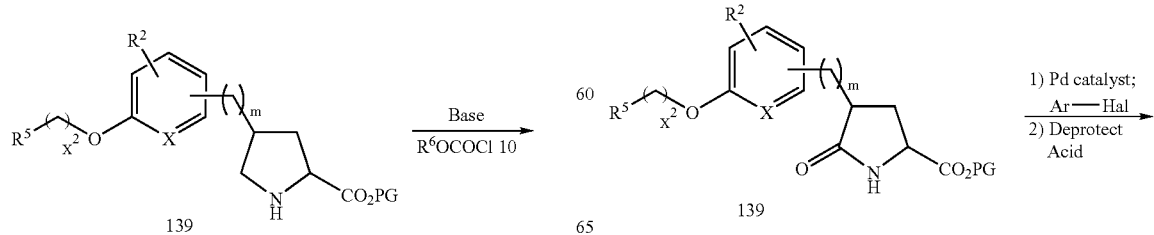

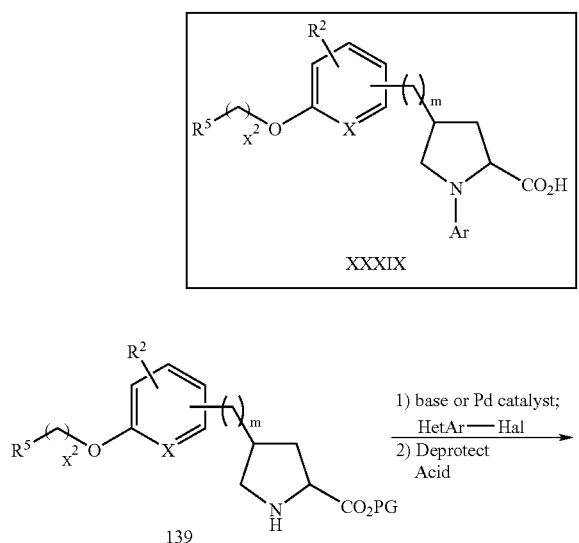
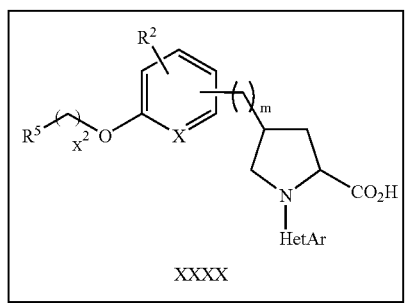
SCHEME 36
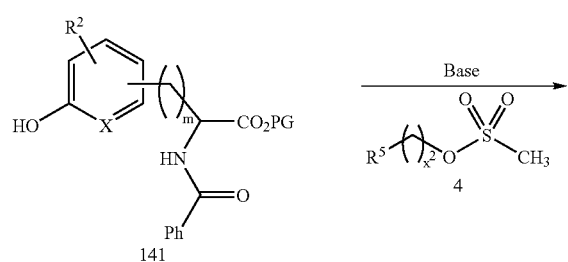
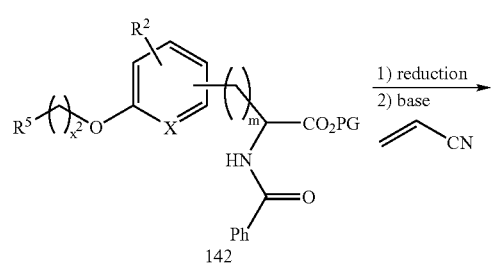
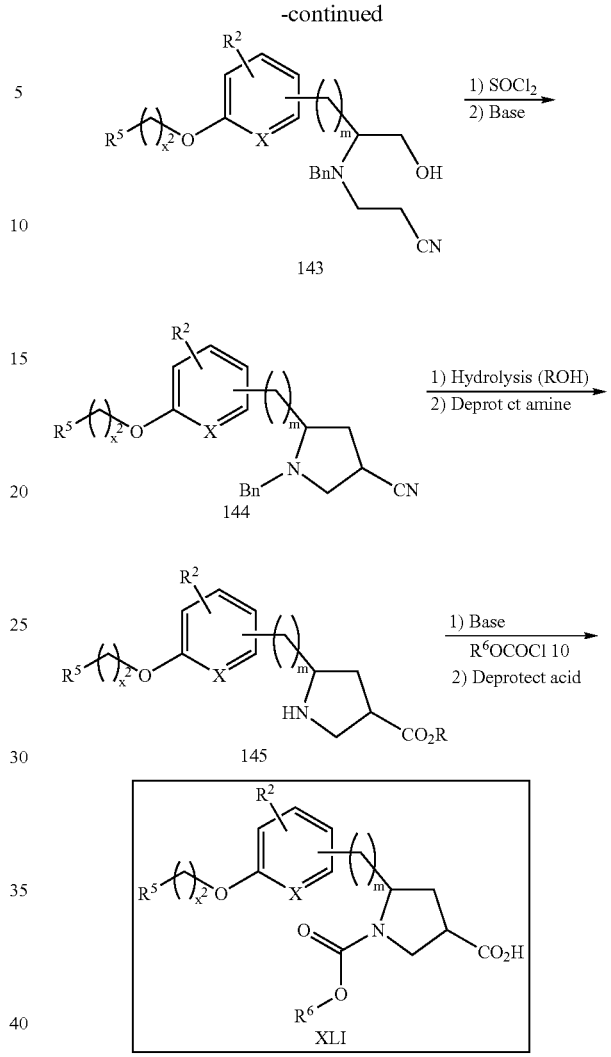
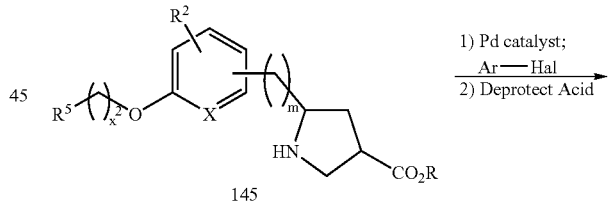
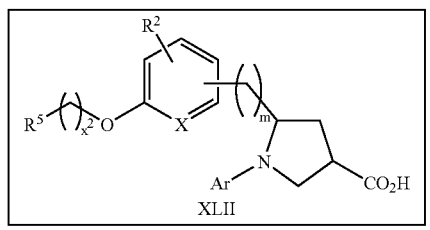
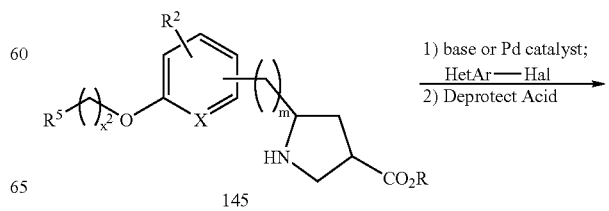

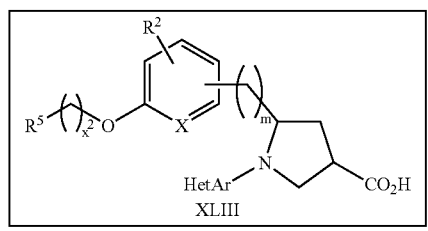
XLIII
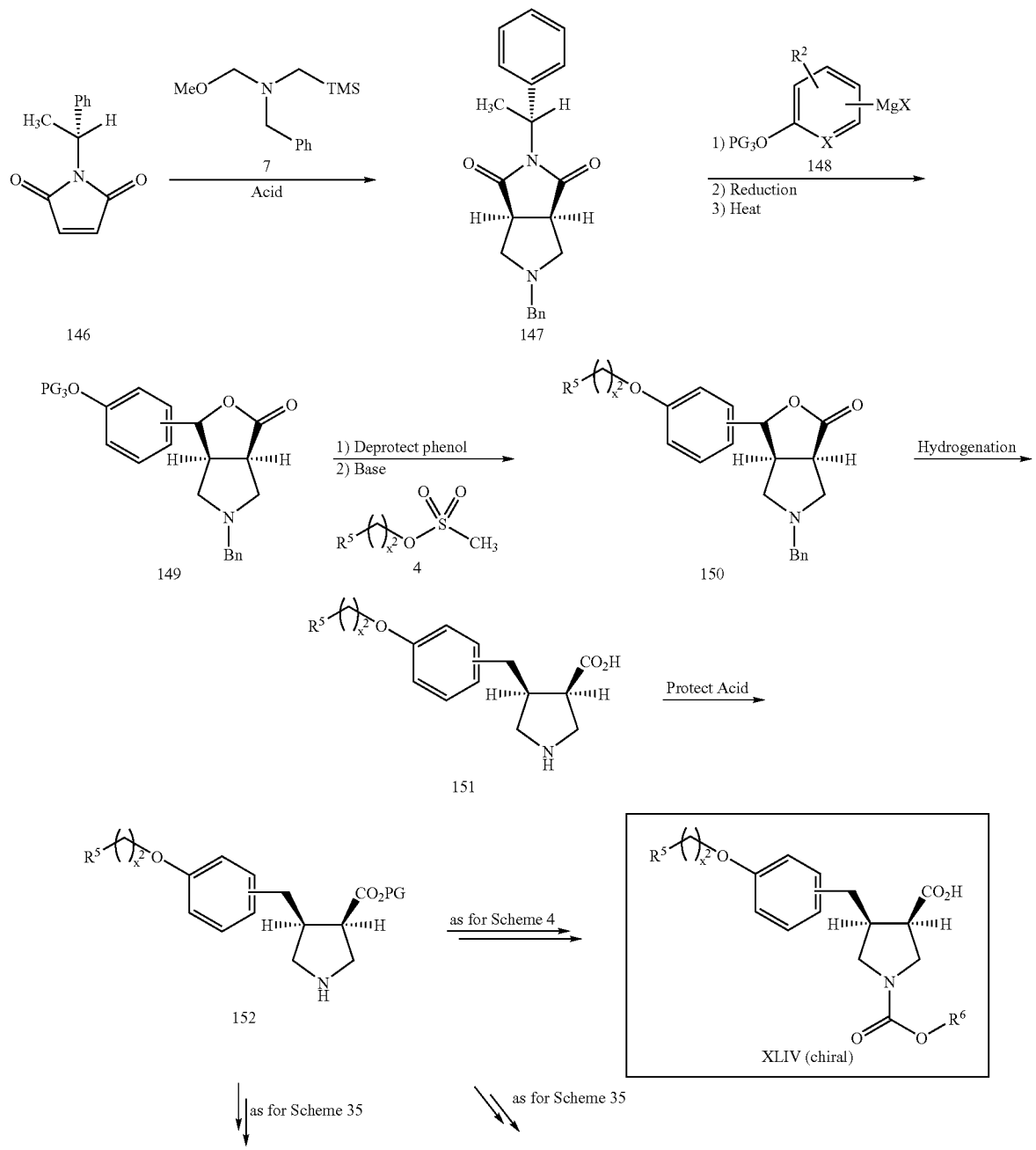
SCHEME 37

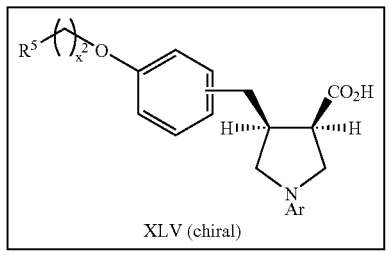
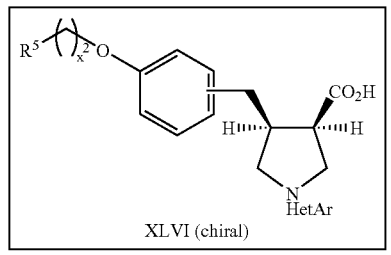
SCHEME 38
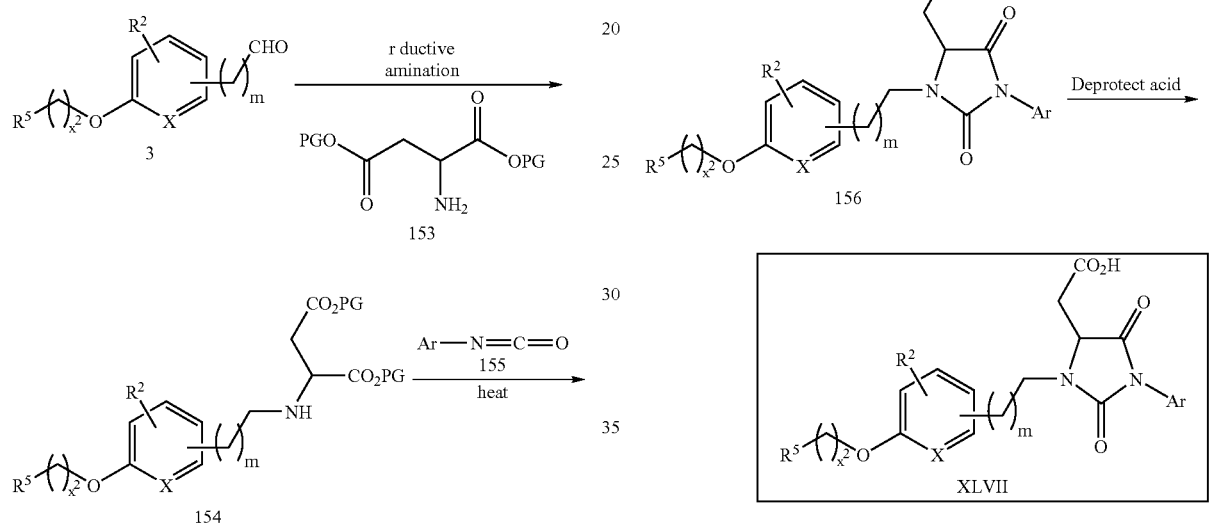
SCHEME 39
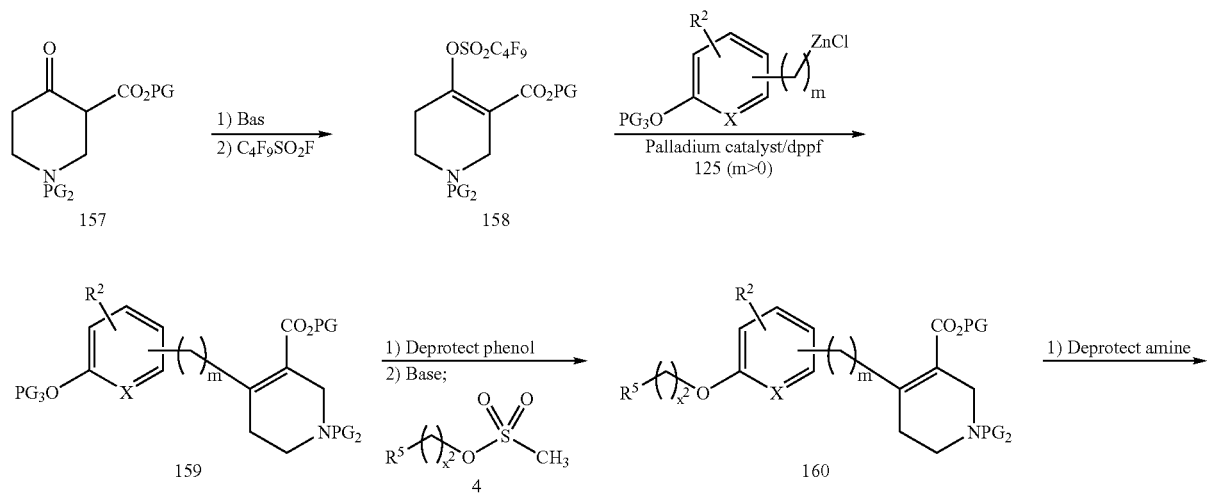

-continued
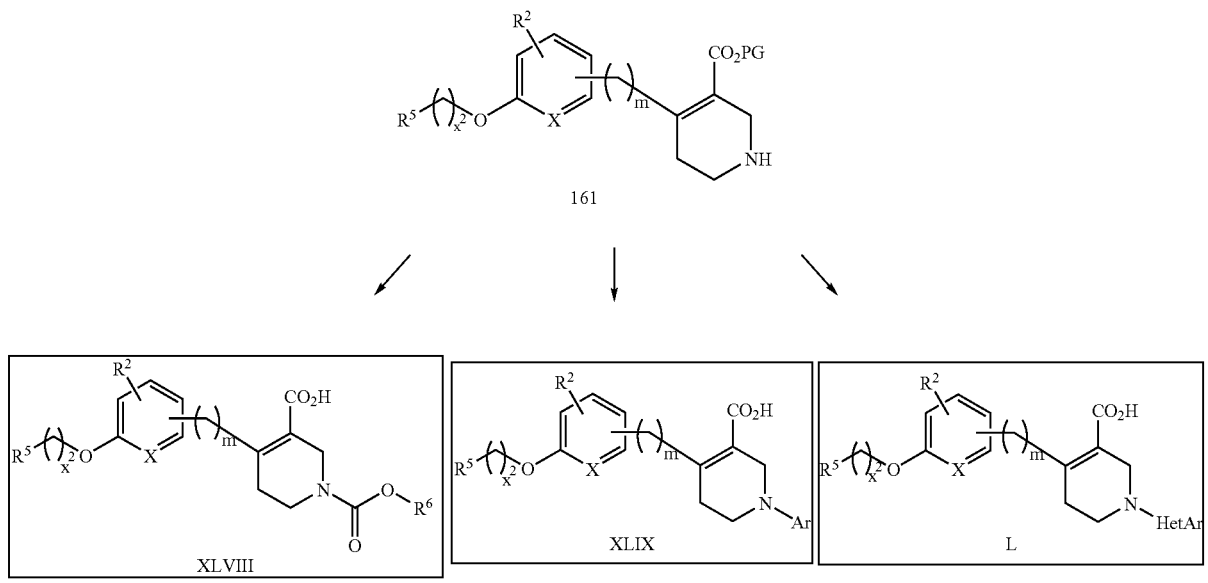
SCHEME 40
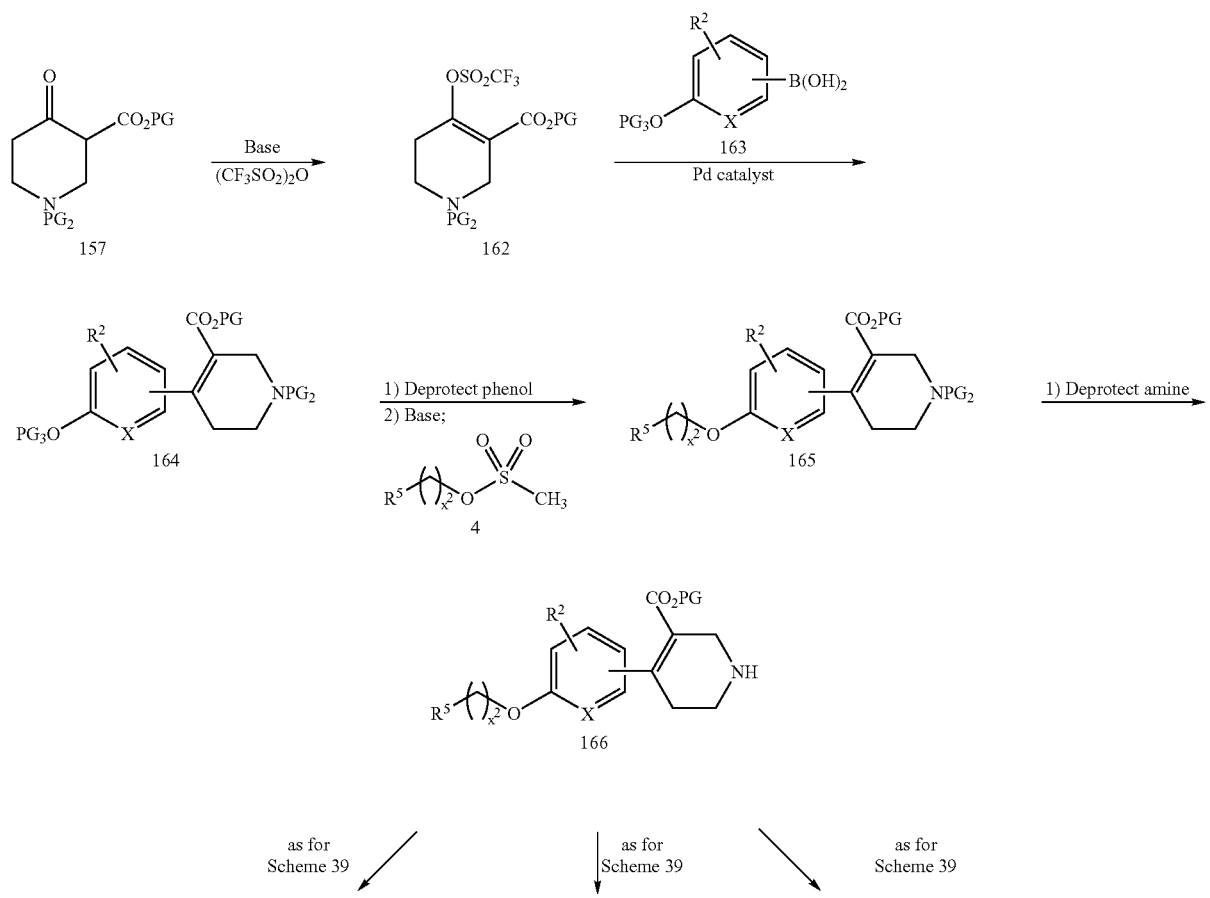

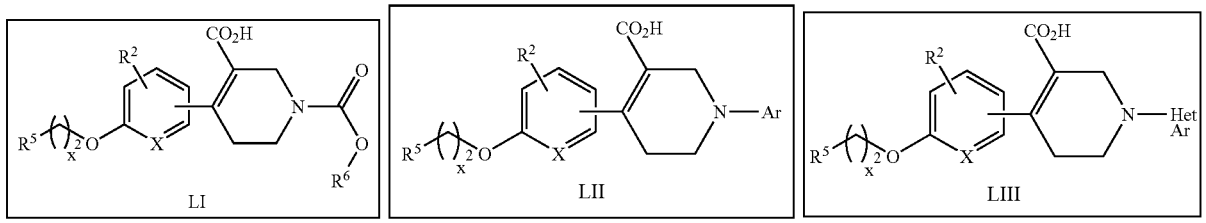

SCHEME 41

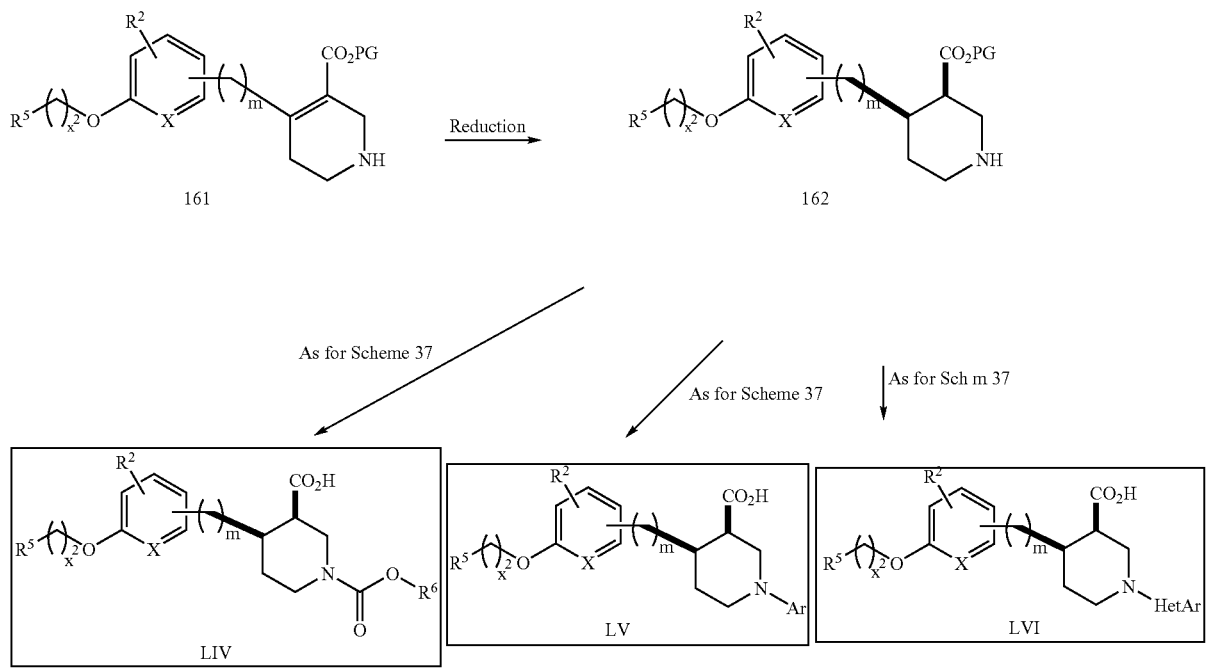

In the above schemes, it will be seen that PG is a protecting group for a carboxylic acid. $PG_2$ is a protecting group for an amine. $PG_3$ is a protecting group for a phenol.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, and may optionally include an oxygen or nitrogen in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio and/or any of the $R^3$ groups.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

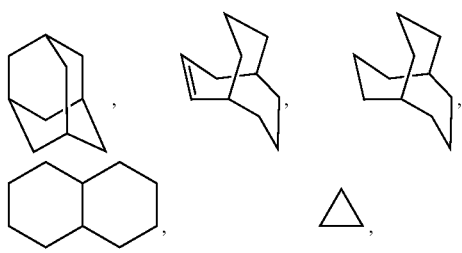

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

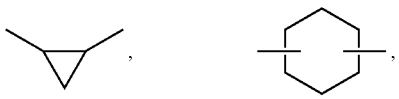

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, and may optionally include an oxygen or nitrogen in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the substituents for alkyl set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, and may optionally include an oxygen or nitrogen in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the substituents for alkyl set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

$(CH_2)_x$, $(CH_2)_x^1$, $(CH_2)_x^2$, $(CH_2)_x^3$, $(CH_2)_x^4$, $(CH_2)_m$, $(CH_2)_n$, $(CH_2)_p$ and $(CH_2)_q$ includes alkylene, allenyl, alkenylene or alkynylene groups, as defined herein, each of which may optionally include an oxygen or nitrogen in the normal chain (in addition to the number of carbon atoms as defined by $x^1$, $x^2$, $x^3$, $x^4$, m, n, p and q) which may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy; the alkyl substituent may be an alkylene moiety of 1 to 4 carbons which may be attached to one or two carbons in the $(CH_2)_x$, $(CH_2)_x^1$, $(CH_2)_x^2$, $(CH_2)_x^3$, $(CH_2)_x^4$, $(CH_2)_x^5$, $(CH_2)_x^6$, $(CH_2)_x^7$, $(CH_2)_x^8$, $(CH_2)_m$, $(CH_2)_n$, $(CH_2)_p$, or $(CH_2)_q$ group to form a cycloalkyl group therewith.

Examples of $(CH_2)_x$, $(CH_2)_x^1$, $(CH_2)_x^2$, $(CH_2)_x^3$, $(CH_2)_x^4$, $(CH_2)_x^5$, $(CH_2)_x^6$, $(CH_2)_x^7$, $(CH_2)_x^8$, $(CH_2)_m$, $(CH_2)_n$, $(CH_2)_p$, $(CH_2)_q$, alkylene, alkenylene and alkynylene include

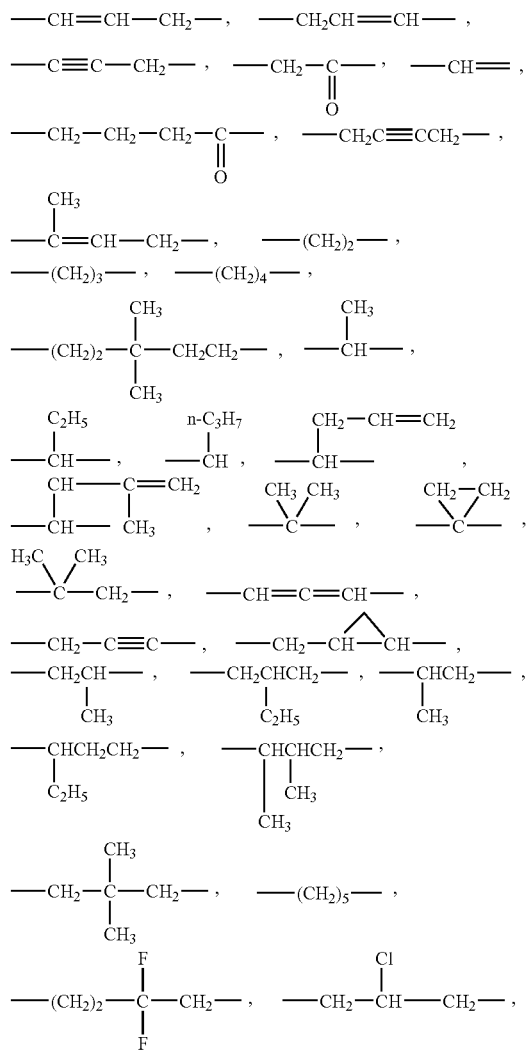

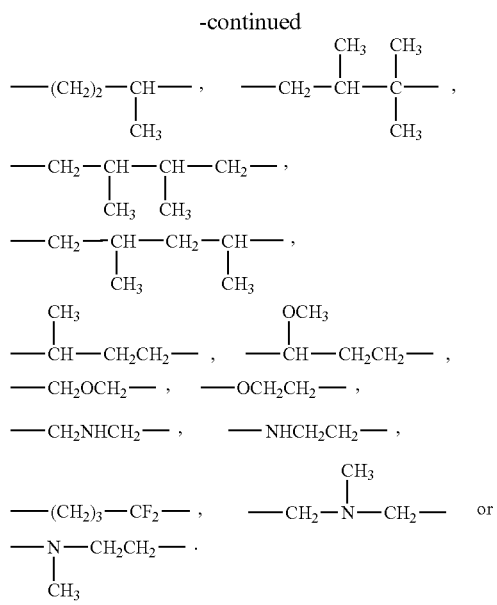

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or the group

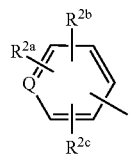

where Q is C, as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

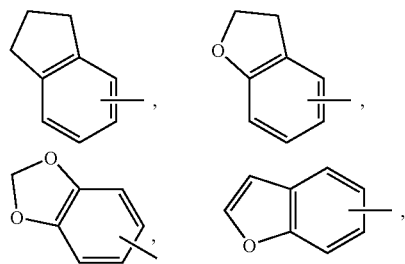

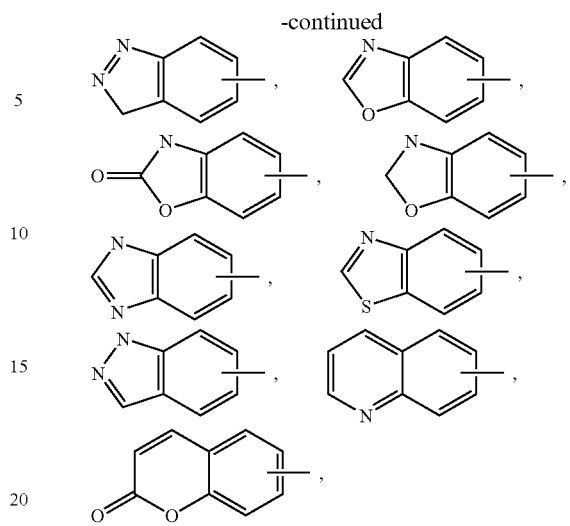

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the substituents for alkyl set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^3$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

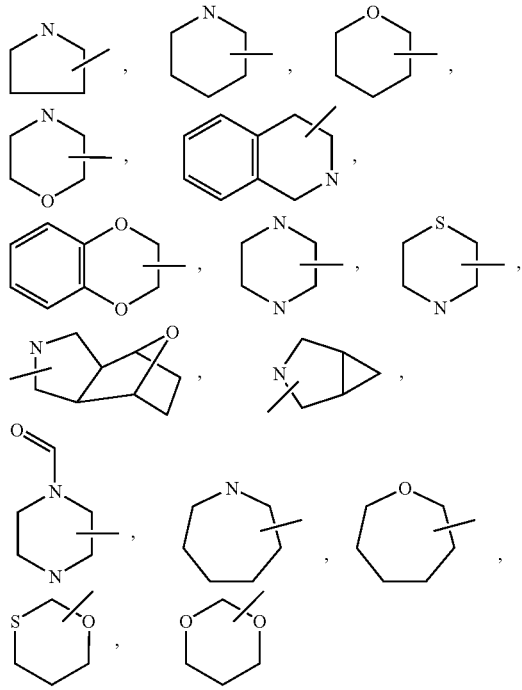

and the like. The above groups may include 1 to 4 substituents such as alkyl, halo, oxo and/or any of of the substituents for alkyl or aryl set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring including

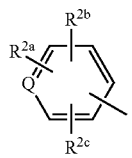

where Q is N, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the the substituents for alkyl or aryl set out above. Examples of heteroaryl groups include the following:

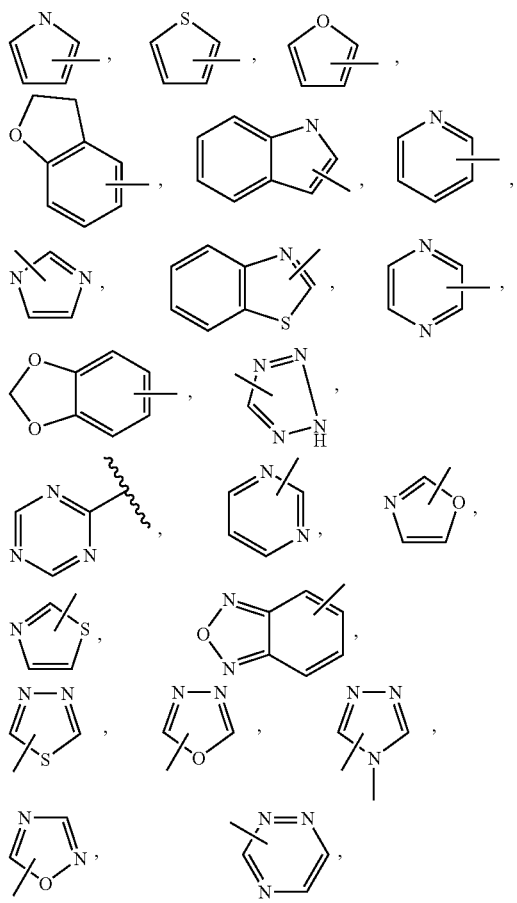

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic and phosphorus acid esters such as methyl, ethyl, benzyl and the like. Other prodrug ester examples of $R^4$ include the following groups:

(1-alkanoyloxy)alkyl such as,

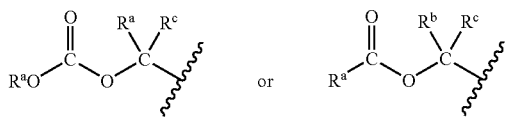

wherein $R^a$, $R^b$ and $R^c$ are H, alkyl, aryl or arylalkyl; however, $R^aO$ cannot be HO.

Examples of such prodrug esters $R^4$ include

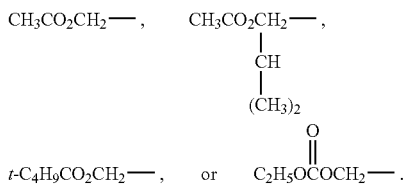

Other examples of suitable prodrug esters $R^4$ include

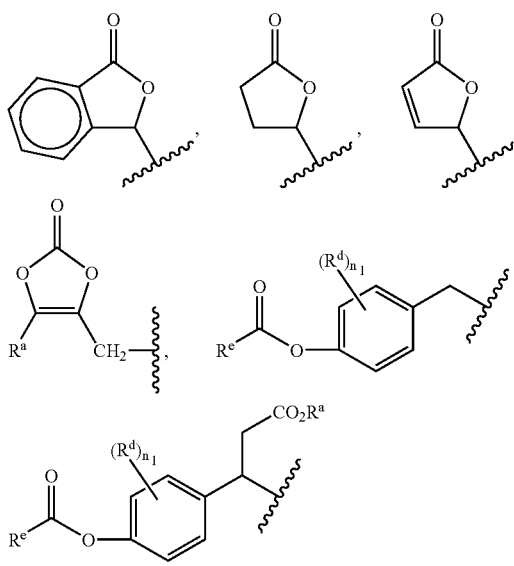

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl)aminomethane (TRIS), N-methyl glucosamine (NMG), triethanolamine and dehydroabietylamine.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more hypolipidemic agents or lipid-lowering agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

Where desired, the compounds of structure I may be used in combination with one or more hypolipidemic agents or lipid-lowering agents and/or one or more other types of therapeutic agents including antidiabetic agents, anti-obesity agents, antihypertensive agents, platelet aggregation inhibitors, and/or anti-osteoporosis agents, which may be administered orally in the same dosage form, in a separate oral dosage form or by injection.

The hypolipidemic agent or lipid-lowering agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors-disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

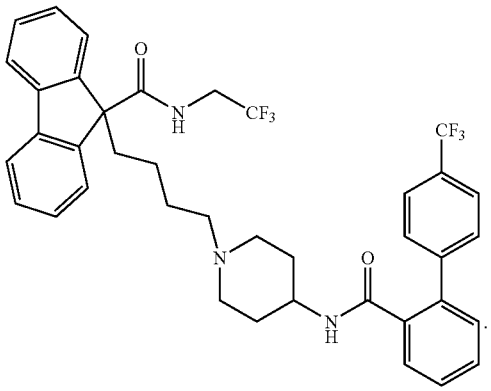

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. No. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinylmethyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J. A. C. S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137 (1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16 (1), 16-30; "RP 73163: a bioavailable alkylsulfinyl-diphenylimidazole ACAT inhibitor", Smith, C., et al, Bioorg. Med. Chem. Lett. (1996), 6 (1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1 (3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8 (6), 359-62, or TS-962 (Taisho Pharmaceutical Co. Ltd) as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The hypolipidemic agent may be an ileal Na+/bile acid cotransporter inhibitor such as disclosed in Drugs of the Future, 24, 425-430 (1999).

The lipid-modulating agent may be a cholesteryl ester transfer protein (CETP) inhibitor such as Pfizer's CP 529, 414 as well as those disclosed in WO/0038722 (i.e. (torcetrapib) and in EP 818448 (Bayer) and EP 992496 and Pharmacia's SC-744 and SC-795, as well as CETi-1 and JTT-705.

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015,201; a beta-lactam cholesterol absorption inhibitor such as disclosed in EP 675714; an HDL upregulator such as an LXR agonist, a PPAR alpha agonist and/or an FXR agonist; a PPAR delta agonist (e.g. GW-501516, ref: Oliver, Jr., W. R., et. al, *Proc. Nat. Acad. Sci. USA,* 2001, 98, 5306-5311), an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050,574, for example, a sphingolipid, such as ceramide, or neutral sphingomyelenase (N-SMase) or fragment thereof.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or rosuvastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or rosuvastatin as well as niacin and/or cholestagel.

The other antidiabetic agent which may be optionally employed in combination with the compound of formula I may be 1,2,3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPARγ agonists such as thiazolidinediones, PPARα agonists such as fibric acid derivatives, PPARδ agonists or antagonists, PPARα/γ dual agonists, aP2 inhibitors, dipeptidyl peptidase IV (DP4) inhibitors, SGLT2 inhibitors, glycogen phosphorylase inhibitors, glucagon-like peptide-1 (GLP-1), PTP-1B (protein tyrosine phosphatase-1B) inhibitors, 11β-HSD 1 (11β-hydroxy-steroid dehydrogenase 1) inhibitors and/or meglitinides, as well as insulin.

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as rosiglitazone (Glaxo SmithKline), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 or balaglitazone (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (Thera Tech), U.S. Pat. Nos. 5,614,492 and 5,631,224 which are incorporated herein by reference.

The other antidiabetic agent may also be a PPAR α/γ dual agonist such as AZ-242/tesaglitazar (Astra/Zeneca; as described: in B. Ljung et. al., *J. Lipid Res.,* 2002, 43, 1855-1863), GW-409544 (Glaxo-Wellcome), KRP-297/MK-767 (Kyorin/Merck; as described in: K. Yajima et. al., *Am. J. Physiol. Endocrinol. Metab.,* 2003, 284: E966-E971) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998) or the compounds (from Bristol-Myers Squibb) described in U.S. Pat. No. 6,414,002.

The antidiabetic agent may be an SGLT2 inhibitor such as disclosed in U.S. provisional application No. 60/158,773, filed Oct. 12, 1999 (attorney file LA49), employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. provisional application No. 60/127,745, filed Apr. 5, 1999, employing dosages as set out herein. Preferred are the compounds designated as preferred in the above application.

The antidiabetic agent may be a DP4 (Dipeptidyl peptidase IV) inhibitor such as disclosed in Provisional Application 60/188,555 filed Mar. 10, 2000, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597-11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537-1540, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a melanocortin receptor (MC4R) agonist, a melanin-concentrating hormone receptor (MCHR) antagonist, a growth hormone secretagogue receptor (GHSR) antagonist, an orexin receptor antagonist, a CCK (cholecystokinin) agonist, a GLP-1 agonists, NPY1 or NPY5 antagonist, a corticotropin releasing factor (CRF) antagonist, a histamine receptor-3 (H3) modulator, a PPARγ modulator, a PPARδ modulator, a beta 3 adrenergic agonist, a lipase inhibitor, a serotonin (and dopamine) reuptake inhibitor, a erotonin receptor agonist (e.g. BVT-933), an aP2 inhibitor, a thyroid receptor agonist and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or CNTF/axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be fenfluramine, dexfenfluramine, fluxoxamine, fluoxetine, paroxetine, sertraline, chlorphentermine, clorofex, clortermine, picilorex, sibutramine, dexamphetamine, phentermine, phenylpropanolamine or mazindol. Other anorectic agents which may be optionally employed in combination with a compound of formula I include CNTF (ciliary neurotrophic factor)/Axokine (Regeneron), BDNF (brain-derived neurotrophic factor), leptin or cannabinoid receptor antagonists, such as SR-141716/rimonabant (Sanofi) or SLV-319 (Solvay).

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432, 971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31-2201 (Hoffman LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]] 3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl)disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, BMS 189,921 ([S—(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physician's Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®). Dosages employed will be as set out in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1-4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following abbreviations are employed in the Examples:
Ph=phenyl
Bn=benzyl
t-Bu=tertiary butyl
Me=methyl
Et=ethyl
TMS=trimethylsilyl
$TMSN_3$=trimethylsilyl azide
$TMSCHN_2$=trimethylsilyl diazomethane
TBS=tert-butyldimethylsilyl
TBDPS=tert-butyldiphenylsilyl
FMOC=fluorenylmethoxycarbonyl
Boc=tert-butoxycarbonyl
Cbz=carbobenzyloxy or carbobenzoxy or benzyloxycarbonyl
THF=tetrahydrofuran
$Et_2O$=diethyl ether
hex=hexanes
EtOAc=ethyl acetate
DMF=dimethyl formamide
MeOH=methanol
EtOH=ethanol
i-PrOH=IPA=isopropanol
DMSO=dimethyl sulfoxide
DME=1,2dimethoxyethane
DCE=1,2dichloroethane
HMPA=hexamethyl phosphoric triamide
HOAc or AcOH=acetic acid
TFA=trifluoroacetic acid
PTSA=pTSOH=para-toluenesulfonic acid
i-$Pr_2$NEt=diisopropylethylamine
$Et_3N$=TEA=triethylamine
$Et_2NH$=diethylamine
NMM=N-methyl morpholine
DMAP=4-dimethylaminopyridine
$NaBH_4$=sodium borohydride
$NaBH(OAc)_3$=sodium triacetoxyborohydride
DIBALH=diisobutyl aluminum hydride
$LiAlH_4$=lithium aluminum hydride
n-BuLi=n-butyllithium
Pd/C=palladium on carbon
$PtO_2$=platinum oxide
KOH=potassium hydroxide
NaOH=sodium hydroxide
LiOH=lithium hydroxide
$K_2CO_3$=potassium carbonate
$NaHCO_3$=sodium bicarbonate
$H_2SO_4$=sulfuric acid
$KHSO_4$=potassium hydrogen phosphate
DBU=1,8-diazabicyclo[5.4.0]undec-7-ene
EDC (or EDC.HCl) or EDCI (or EDCI.HCl) or EDAC=3-ethyl-3'-(dimethylamino)propyl- carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole
BOP reagent=benzotriazol-1-yloxy-tris (dimethylamino) phosphonium hexafluorophosphate
$NaN(TMS)_2$=sodium hexamethyldisilazide or sodium bis (trimethylsilyl)amide
$Ph_3P$=triphenylphosphine
$Pd(OAc)_2$=Palladium acetate
$(Ph_3P)_4Pd°$=tetrakis triphenylphosphine palladium
DIAD=diethyl azodicarboxylate
DIAD=diisopropyl azodicarboxylate
Cbz-Cl=benzyl chloroformate
CAN=ceric ammonium nitrate
$SiO_2$=silica gel
SAX=Strong Anion Exchanger
SCX=Strong Cation Exchanger Ar=argon
N$_2$=nitrogen
min=minute(s)
h or hr=hour(s)
L=liter
mL=milliliter
μL=microliter
μM=micromolar
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
NMR spectral data: s=singlet; d=doublet; m=multiplet; br=broad; t=triplet
mp=melting point
ee=enantiomeric excess The following Examples represent preferred embodiments of the invention.

EXAMPLE 1

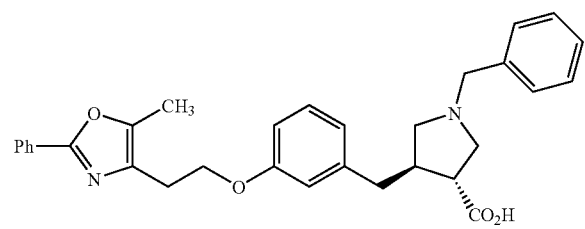

A.

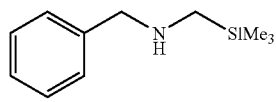

A solution of benzylamine (8.9 mL; 82 mmol) and chloromethyltrimethylsilane (5.0 g; 41 mmol) in MeCN (100 mL) was heated at reflux for 16 h. The reaction was cooled to RT, filtered, and the filtrate was concentrated in vacuo to a volume of ~30 mL. H$_2$O (100 mL) was added and the mixture was extracted with hexane (2×20 mL). The combined organic extracts were washed with H$_2$O (3×20 mL), dried (MgSO$_4$) and concentrated in vacuo to give Part A compound (7.70 g; 49%) as an oil.

B.

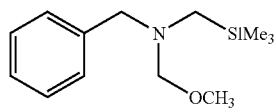

To a 0° C. solution of formaldehyde (4.6 g of a 37% aqueous solution; 55.7 mmol) and 1N aqueous NaOH (5 drops) was added dropwise Part A compound (7.70 g; 39.8 mmol). After the mixture had been stirred at 0° C. for 10 min, MeOH (4 mL) was added, followed by K$_2$CO$_3$ (4.0 g). The mixture was allowed to warm to RT and stirred at RT for 1 h. The organic phase was separated, more K$_2$CO$_3$ (2.0 g) was added, and the reaction was stirred at RT for 12 h. Et$_2$O (20 mL) was then added to the mixture, which was filtered and the filtrate was concentrated in vacuo. The residual oil was distilled at reduced pressure (0.5 mm Hg; 80° C.) to give Part B compound (4.67 g; 49%) as an oil.

C.

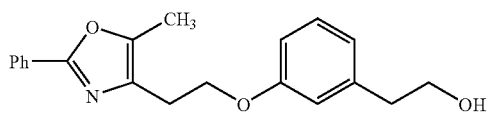

A mixture of 3-hydroxy phenylethanol (4.0 mg; 28 mmol), the mesylate Example 23 Part A compound (8.0 g; 28 mmol)

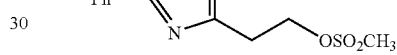

and K$_2$CO$_3$ (15.0 g; 110 mmol) in MeCN (150 mL) was stirred at 90° C. for 5 h. At this point LC/MS showed that the reaction was complete. The reaction was cooled to RT, solids were filtered off, and the filtrate was diluted with EtOAc (100 mL). The solution was successively washed with aqueous 1 M HCl (10 mL), 1 M NaOH (10 mL) and H$_2$O (50 mL), dried (Na$_2$SO$_4$) and concentrated in vacuo. The residue was chromatographed (SiO$_2$; 2:1 hex:EtOAc) to give Part C compound (8.7 g; 96%) as an oil.

D.

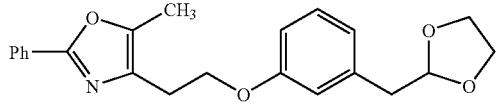

To a solution of Part C compound (4.0 g; 12.3 mmol) in CH$_2$Cl$_2$ (50 mL) were added Florisil™ (8.0 g), pyridinium chlorochromate (4.0 g; 19 mmol) and the reaction was stirred at RT for 3 h. The mixture was then diluted with anhydrous Et$_2$O (200 mL) and filtered. The chromium solid wastes were washed with additional Et$_2$O (3×100 mL); the combined organic filtrates were concentrated in vacuo to give the very crude and impure aldehyde (3.5 g) as an oil. A mixture of the aldehyde (3.5 g), PPTS (500 mg; 0.50 mmol) and ethylene glycol (5.0 mL; 89 mmol) in toluene (50 mL) was heated to reflux in a Dean-Stark apparatus overnight. The reaction was cooled to RT, washed with aqueous Na$_2$CO$_3$ and brine (50 mL each), dried (Na$_2$SO$_4$), and concentrated in vacuo to give an oil. This material was chromatographed (SiO$_2$; 3:1 hexane: EtOAc) to give Part D compound (1.35 g; 30%) as a clear oil.

E.

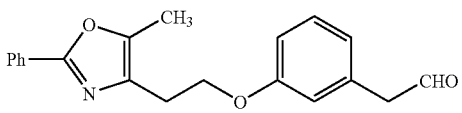

A solution of Part D compound (1.35 g; 3.7 mmol), glacial acetic acid (10 mL) and H₂O (2 mL) was heated at 80° C. for 48 h. H₂O (100 mL) was added and the mixture was extracted with EtOAc (2×20 mL). The combined organic extracts were washed with H₂O (2×100 mL), saturated aqueous NaHCO₃ (2×100 mL), dried (Na₂SO₄), and concentrated in vacuo to give Part E compound (1.24 g; 99%) as a brown oil.

F.

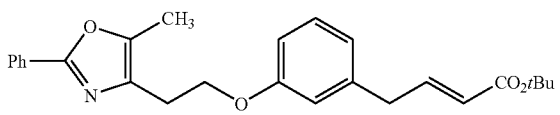

A mixture of Part E compound (500 mg; 1.55 mmol) and tert-butyl (triphenylphosphoranylidene) acetate (600 mg; 1.59 mmol) in toluene (100 mL) was heated to reflux for 1 h. Analytical HPLC showed that the reaction was complete. After cooling, volatiles were removed in vacuo and the residue was chromatographed (SiO₂; hex:EtOAc 3:1) to give Part F compound (390 mg; 60%) as an oil.

G.

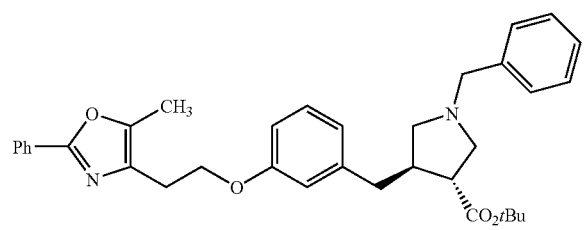

A mixture of Part E compound (100 mg; 0.238 mmol), Part B compound (85 mg; 0.36 mmol) and a catalytic amount of TFA (1 μL) in toluene (1.0 mL) was stirred at RT for 3 h. TLC showed that the reaction was complete at this point. Volatiles were removed in vacuo and the residue was chromatographed (SiO₂; hex:EtOAc 1:1) to provide Part G compound (110 mg; 93%) as an oil.

H.

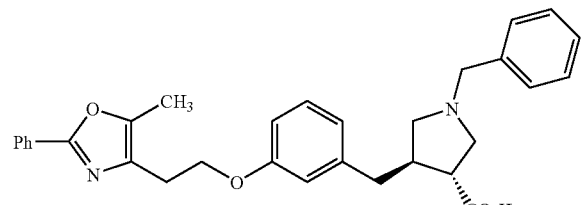

A solution of Part G compound (22 mg; 0.036 mmol) and TFA (1 mL) in CH₂Cl₂ (2 mL) was stirred at RT for 6 h. Volatiles were removed in vacuo and the residue was purified by preparative HPLC (YMC reverse-phase ODS 20×100 mm column; flow rate=20 mL/min; 10 min continuous gradient from 30:70 B:A to 100% B+5 min holdtime at 100% B, where solvent A=90:10:0.1H₂O:MeOH: TFA and solvent B=90:10:0.1 MeOH:H₂O:TFA) to give the racemic title compound (17 mg; 97%). [M+H]⁺=497.2

EXAMPLE 2

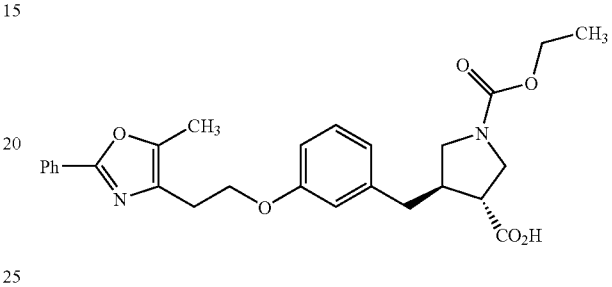

A.

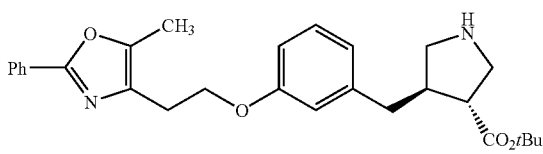

A mixture of Example 1 Part G compound (94 mg; 0.19 mmol) and 10% Pd/C (10 mg) in MeOH (10 mL) under an atmosphere of H₂ was stirred at RT for 3 h. At this point analytical HPLC showed that the reaction was complete. The catalyst was filtered off on a pad of Celite and the filtrate was concentrated in vacuo to give crude Part A compound which was used in the next reaction without further purification.

B.

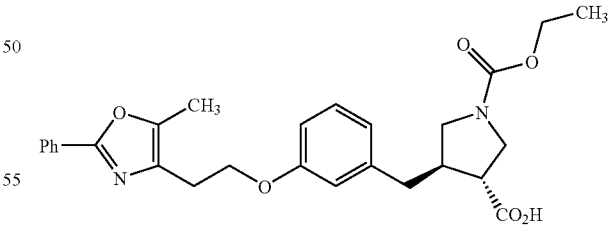

To a 0° C. solution of crude Part A compound (10 mg; 0.022 mmol) and DMAP (150 mg; 1.23 mmol) in pyridine (1 mL) was added dropwise ethyl chloroformate (500 μL; 5.23 mmol). The reaction mixture was stirred at 60° C. for 2 h. At this point TLC indicated that all starting material had been consumed. Volatiles were removed in vacuo; the residue was dissolved in CH₂Cl₂ (1 mL) and TFA (1.5 mL) and the reaction was stirred at RT for 1 h. Volatiles were removed in vacuo and the residue was partitioned between EtOAc (5 mL) and H₂O (3 mL). The organic phase was washed with H₂O (2×3 mL) and concentrated in vacuo. The residue was purified by preparative HPLC (as described for Example 1) to furnish the title compound (5.6 mg; 53%).

[M+H]⁺=479.3

EXAMPLE 3

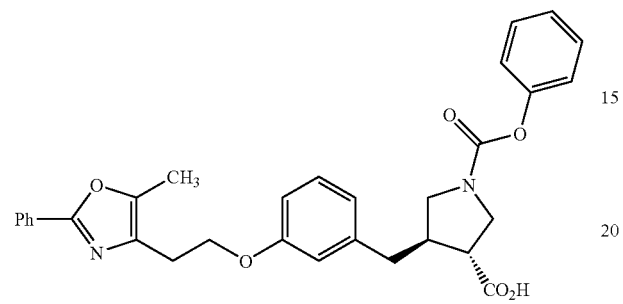

Example 3 (6.6 mg; 57%) was synthesized employing the procedure described in Example 2, except that phenyl chloroformate was used in the sequence instead of ethyl chloroformate.

[M+H⁺]=527.2

EXAMPLE 4

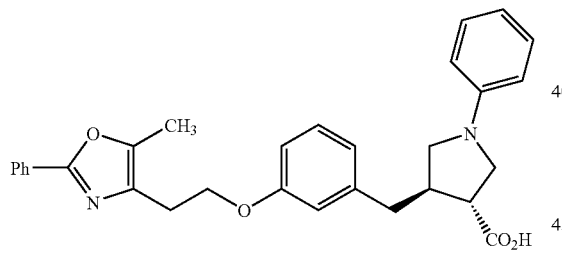

A mixture of Example 2 Part A compound (20 mg; 0.043 mmol), bromobenzene (10 mg; 0.263 mmol), 1,3-bis (diphenylphosphino)propane (DPPP; 2 mg; 4.8×10⁻³ mmol), sodium tert-butoxide (2 mg; 0.018 mmol) and Pd₂(dibenzylacetone)₃ (1 mg; 1×10⁻³ mmol) in toluene (2 mL) was stirred at 90° C. for 6 h. At this point HPLC showed that all starting material had been consumed. The reaction mixture was cooled to RT and partitioned between EtOAc (10 mL) and aqueous 1 N HCl (10 mL). The organic phase was washed with H₂O (2×20 mL), dried (Na₂SO₄), and concentrated in vacuo. The residue was dissolved in TFA:CH₂Cl₂ (1 mL of a 1:1 solution) and the reaction was stirred at RT for 1 h. Volatiles were removed in vacuo and the residue was purified by preparative HPLC (as described for Example 1) to provide the title compound (7 mg; 48%) as an oil.

[M+H]⁺+=483.2

EXAMPLE 5

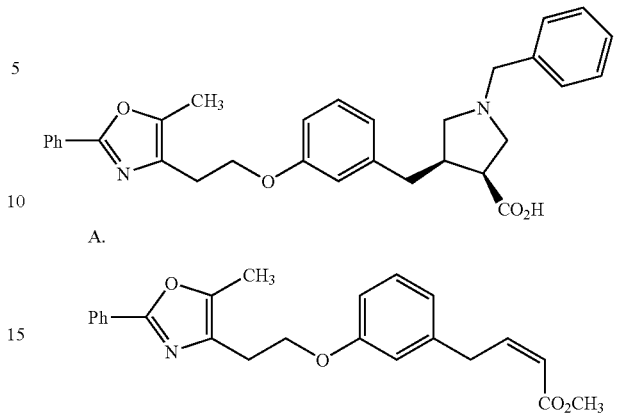

A.

To a −78° C. solution of (CF₃CH₂O)₂P(O)CH₂CO₂CH₃ (1.47 g; 4.62 mmol) and 18-crown-6 (6.10 g; 23 mmol) in anhydrous THF (50 mL) under N₂ was added dropwise potassium hexamethyldisilazide (9.2 mL of a 0.5M solution in toluene; 4.62 mmol). The solution was stirred at −78° C. for 30 min, after which a solution of the aldehyde (Example 1 Part E compound; 1.24 g; 3.86 mmol) in THF (50 mL) was added dropwise. The reaction mixture was stirred for 30 min at −78° C., after which excess saturated aqueous NH₄Cl (50 mL) was added. The mixture was allowed to warm to RT and extracted with Et₂O (3×30 mL). The combined organic extracts were dried (Na₂SO₄), concentrated in vacuo, and the residue was chromatographed (SiO₂; 3:1 hexane:EtOAc) to give Part A compound (343 mg; 23%) as an oil.

B.

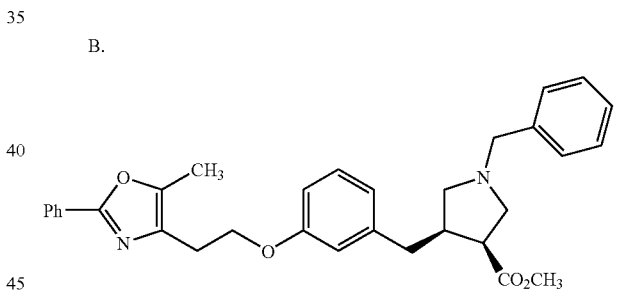

A mixture of Part A compound (343 mg; 0.908 mmol), Example 1 Part B compound (300 mg; 1.26 mmol) and a catalytic amount of TFA (5 µL) in toluene (5.0 mL) was stirred at RT for 3 h. TLC showed that the reaction was complete at this point. Volatiles were removed in vacuo and the residue was chromatographed (SiO₂; hex:EtOAc 1:1) to provide Part B compound (450 mg; 98%) as an oil.

C.

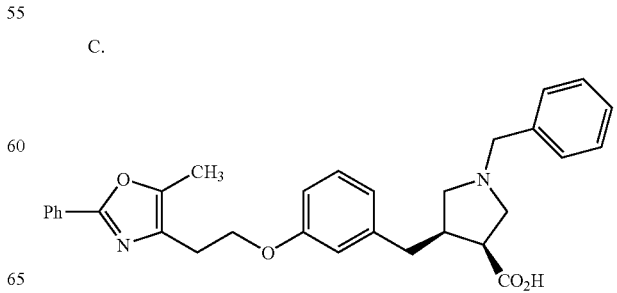

A solution of Part B compound (27 mg; 0.053 mmol), aqueous LiOH (1 mL of a 1 M solution) and THF (2 mL) was stirred at RT for 5 h. At this point, LC/MS indicated that the reaction was complete. The mixture was acidified with aqueous HCl (5 mL of a 1 M solution) and extracted with EtOAc (10 mL). The organic phase was washed with H$_2$O (2×5 mL), dried (Na$_2$SO$_4$) and concentrated in vacuo. The residue was purified by preparative HPLC (as described for Example 1) to give the title compound (24 mg; 91%) as a white lyophilate.

[M+H]$^+$=497.3

EXAMPLE 6

A.

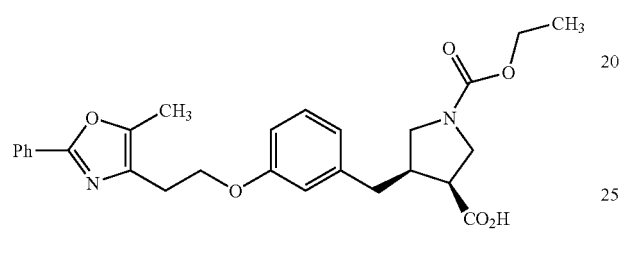

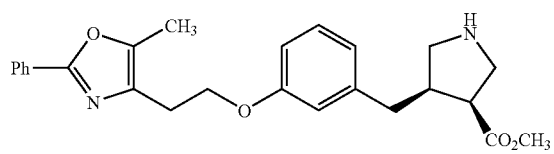

A mixture of Example 5 Part B compound (580 mg; 1.17 mmol) and 10% Pd/C (50 mg) in MeOH (25 mL) under an atmosphere of H$_2$ was stirred at RT for 18 h. At this point analytical HPLC showed that the reaction was complete. The catalyst was filtered off (using a pad of Celite®) and the filtrate was concentrated in vacuo to give crude Part A compound (400 mg; 81%) as an oil which was used in the next reaction without further purification.

B.

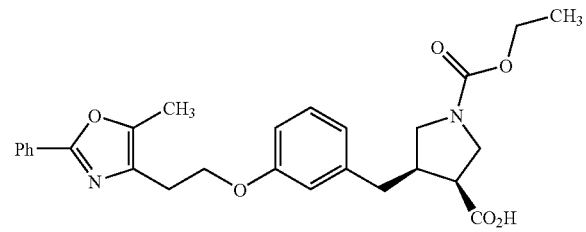

To a 0° C. solution of crude Part A compound (10 mg; 0.022 mmol) and DMAP (150 mg; 1.23 mmol) in CH$_2$Cl$_2$ (1 mL) was added dropwise ethyl chloroformate (500 μL; 5.23 mmol). The reaction mixture was then stirred at RT for 5 h. At this point TLC indicated that all starting material had been consumed. Volatiles were removed in vacuo and the residue was dissolved in a solution of THF (1 mL) and aqueous LiOH (1 mL of a 1 M solution) and the reaction was stirred at RT for 12 h. The reaction mixture was acidified with aqueous HCl (2 mL of a 1 M solution) and extracted with EtOAc (10 mL). The organic phase was washed with H$_2$O (2×5 mL), dried (Na$_2$SO$_4$) and concentrated in vacuo. The residue was purified by preparative HPLC (as described for Example 1) to give the title compound (6.0 mg; 56%) as a white lyophilate.

[M+H]$^+$=479.3

EXAMPLE 7

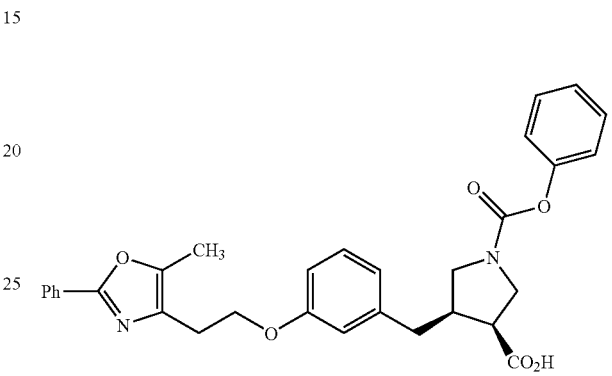

Example 7 compound (6.2 mg; 53%) was synthesized employing the procedure described in Example 6, except that phenyl chloroformate was used in the sequence instead of ethyl chloroformate.

[M+H]$^+$=479.3

EXAMPLE 8

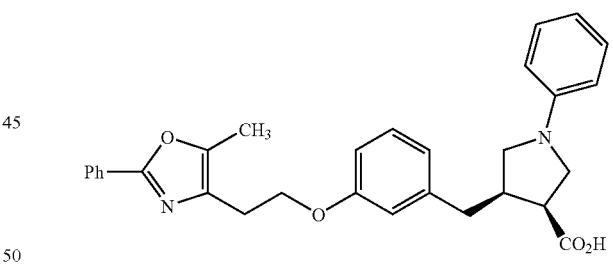

A mixture of Example 6 Part A compound (30 mg; 0.071 mmol), phenylboronic acid (15 mg; 0.123 mmol), Cu(OAc)$_2$ (4 mg; 0.022 mmol), myristic acid (3 mg; 0.013 mmol) and 2,6 lutidine (10 μL; 0.056 mmol) in toluene (2 mL) was stirred at RT for 24 h in air. At this point HPLC showed that product had been formed. The reaction mixture was eluted through an SiO$_2$ cartridge with 1:1 hexane:EtOAc. The combined eluent fractions were concentrated in vacuo and the residue was taken up in aqueous LiOH (0.5 mL of a 1 M solution) and THF (1 mL). The reaction was stirred at RT for 2 h; TLC indicated that the reaction was complete at this point. Volatiles were removed in vacuo and the residue was purified by preparative HPLC (as described for Example 1) to provide the title compound (6 mg; 17%) as an oil.

[M+H]$^+$=483.2

EXAMPLE 9

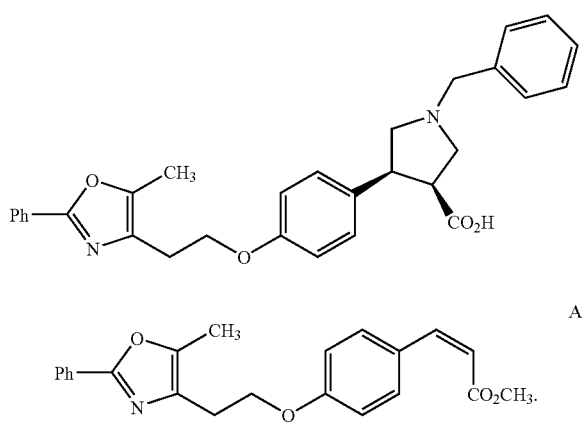

To a −78° C. solution of (CF$_3$CH$_2$O)$_2$P(O)CH$_2$CO$_2$CH$_3$ (372 mg; 1.17 mmol) and 18-crown-6 (1.55 g; 5.85 mmol) in anhydrous THF (5 mL) under N$_2$ was added dropwise potassium hexamethyldisilazide. (2.34 mL of a 0.5 M solution in toluene; 1.17 mmol). The solution was stirred at −78° C. for 30 min, after which a solution of the aldehyde Example 47 Part B compound (300 mg; 0.977 mmol)

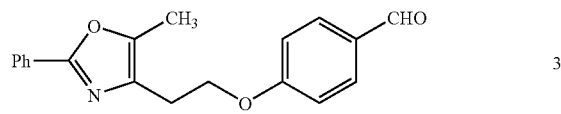

in THF (5.5 mL) was added dropwise. The reaction mixture was stirred for 30 min at −78° C., after which excess saturated aqueous NH$_4$Cl (50 mL) was added. The mixture was allowed to warm to RT and extracted with Et$_2$O (3×30 mL). The combined organic extracts were dried. (Na$_2$SO$_4$), concentrated in vacuo, and the residue was chromatographed (SiO$_2$; 3:1 hexane:EtOAc) to give Part A compound (317 mg; 89%) as an oil.

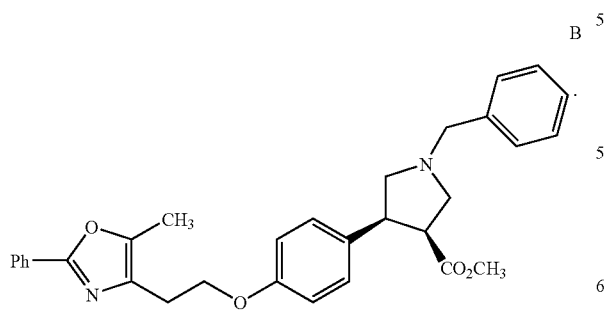

A mixture of Part A compound (317 mg; 0.87 mmol), Example 1 Part B compound (300 mg; 1.26 mmol) and a catalytic amount of TFA (5 μL) in toluene (5.0 mL) was stirred at RT for 3 h. TLC showed that the reaction was complete at this point. Volatiles were removed in vacuo and the residue was chromatographed (SiO$_2$; hex:EtOAc 1:1) to provide Part B compound (400 mg; 92%) as an oil.

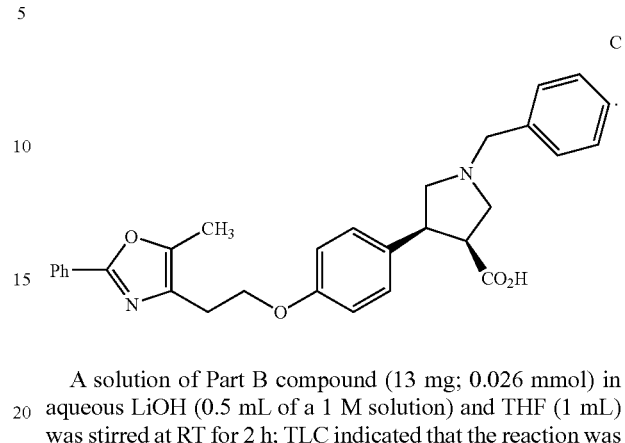

A solution of Part B compound (13 mg; 0.026 mmol) in aqueous LiOH (0.5 mL of a 1 M solution) and THF (1 mL) was stirred at RT for 2 h; TLC indicated that the reaction was complete at this point. The reaction mixture was acidified with aqueous HCl (2 mL of a 1 M solution) and extracted with EtOAc (10 mL). The organic phase was washed with H$_2$O (2×5 mL), dried (Na$_2$SO$_4$) and concentrated in vacuo. The residue was purified by preparative HPLC (as described for Example 1) to provide the title compound (6 mg; 48%) as an oil.

[M+H]$^+$=483.2

EXAMPLE 10

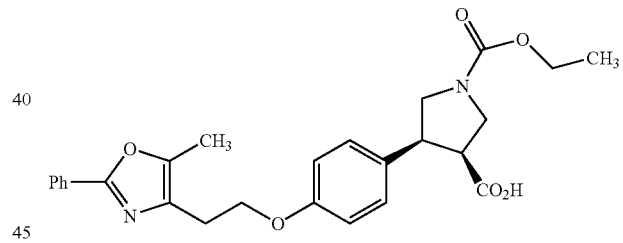

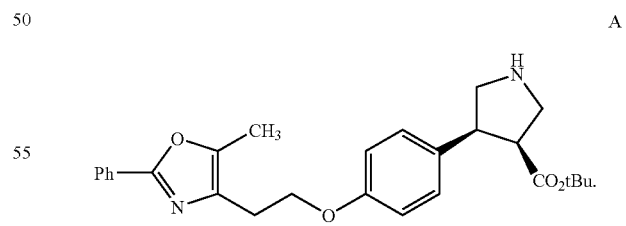

A mixture of Example 9 Part B compound (400 mg; 0.805 mmol) and 10% Pd/C (50 mg) in MeOH (15 mL) under an atmosphere of H$_2$ was stirred at RT for 5 h. At this point analytical HPLC showed that the reaction was complete. The catalyst was filtered off (using a pad of Celite®) and the filtrate was concentrated in vacuo to give crude Part A compound (280 mg; 85%) as an oil which was used in the next reaction without further purification.

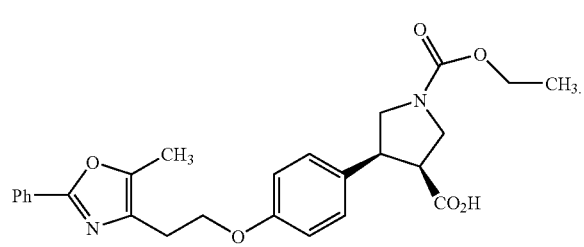

To a 0° C. solution of crude Part A compound (15 mg; 0.037 mmol) and DMAP (13 mg; 0.1 mmol) in CH$_2$Cl$_2$ (1 mL) was added dropwise ethyl chloroformate (7 μL; 0.06 mmol). The reaction mixture was then stirred at RT for 3 h. At this point HPLC indicated that all starting material had been consumed. TFA in CH$_2$Cl$_2$ was added (1 mL of a 1:1 solution) and the reaction was stirred at RT for 1 h. Volatiles were removed in vacuo and the residue was purified by preparative HPLC (as described for Example 1) to give the title compound (6.4 mg; 36%) as an oil.

[M+H]$^+$=465.3

EXAMPLE 11

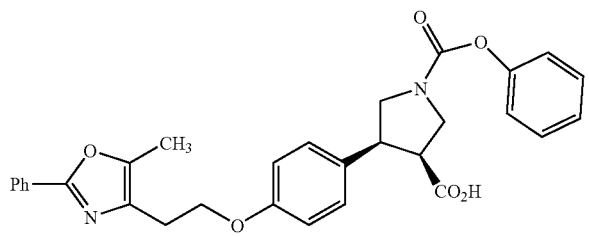

The racemic title compound (2.7 mg; 14%) was prepared employing the procedure described in Example 10, except that phenyl chloroformate (8 μL; 0.06 mmol) was used in the sequence instead of ethyl chloroformate.

[M+H]$^+$=513.4

EXAMPLE 13

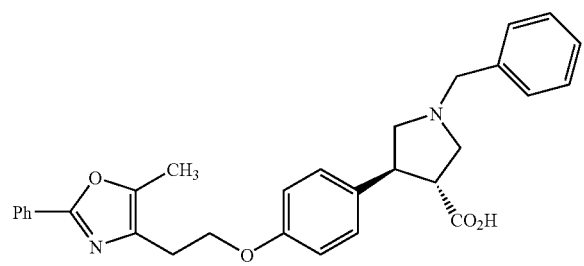

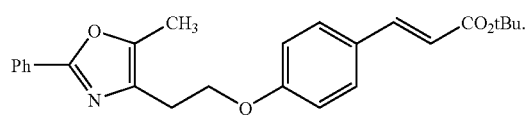

A mixture of Ph$_3$P=CHCO$_2$tBu (200 mg; 0.53 mmol) and the aldehyde Example 47 Part B compound (150 mg; 0.49 mmol)

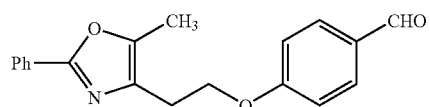

in toluene (20 mL) was heated at 100° C. for 2 h. At this point LC/MS indicated that all starting aldehyde had been consumed. The reaction mixture was cooled to RT and volatiles were removed in vacuo. The residue was chromatographed (SiO$_2$; 3:1 hexane:EtOAc) to provide Part A compound (120 mg; 60%) as a clear oil.

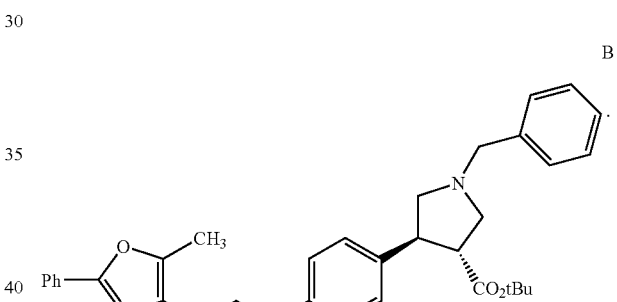

A mixture of Part A compound (120 mg; 0.30 mmol), Example 1 Part B compound (100 mg; 0.421 mmol) and a catalytic amount of TFA (5 μL) in CH$_2$Cl$_2$ (5.0 mL) was stirred at RT for 24 h. HPLC showed that the reaction was complete at this point. Volatiles were removed in vacuo and the residue was chromatographed (SiO$_2$; hex:EtOAc 3:1) to provide Part B compound (143 mg; 88%) as an oil.

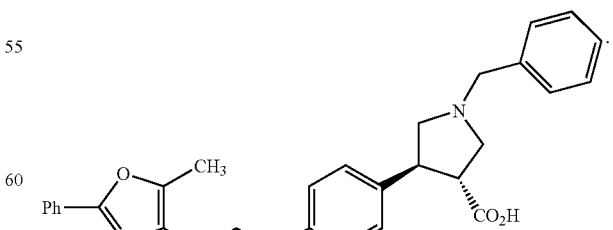

A solution of Part B compound (20 mg; 0.037 mmol) in aqueous LiOH (0.5 mL of a 1 M solution) and THF (1 mL) was stirred at RT for 2 h; TLC indicated that the reaction was complete at this point. The reaction mixture was acidified with aqueous HCl (2 mL of a 1 M solution) and extracted with EtOAc (10 mL). The organic phase was washed with H$_2$O (2×5 mL), dried (Na$_2$SO$_4$) and concentrated in vacuo. The residue was purified by preparative HPLC (as described for Example 1) to provide the title compound (6 mg; 33%) as an oil.

[M+H]$^+$=483.2

EXAMPLE 14

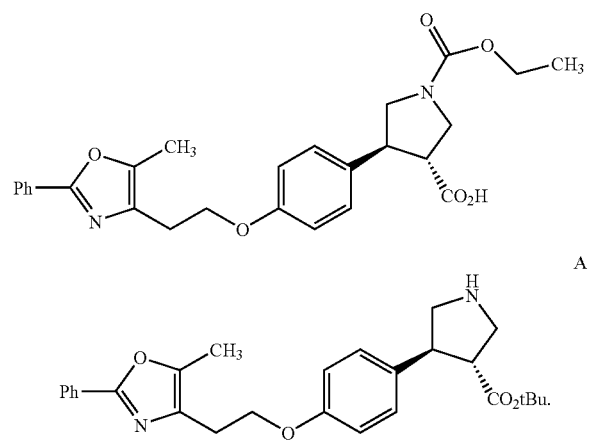

A mixture of Example 10 Part B compound (143 mg; 0.265 mmol) and 10% Pd/C (30 mg) in MeOH (10 mL) under an atmosphere of H$_2$ was stirred at RT for 3 h. At this point analytical HPLC showed that the reaction was complete. The catalyst was filtered off (using a pad of Celite®) and the filtrate was concentrated in vacuo to give crude Part A compound (82 mg; 69%) as an oil which was used in the next reaction without further purification.

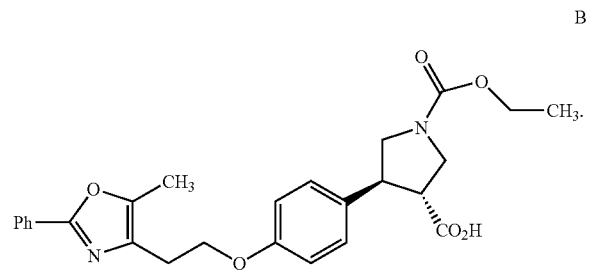

To a 0° C. solution of crude Part A compound (15 mg; 0.033 mmol) and DMAP (15 mg; 0.122 mmol) in CH$_2$Cl$_2$ (1 mL) was added dropwise ethyl chloroformate (7 μL; 0.06 mmol). The reaction mixture was then stirred at RT for 3 h. At this point HPLC indicated that all starting material had been consumed. TFA in CH$_2$Cl$_2$ was added (1 mL of a 1:1 solution) and the reaction was stirred at RT for 1 h. Volatiles were removed in vacuo and the residue was purified by preparative HPLC (as described for Example 1) to give the title compound (16 mg; 57%) as an oil.

[M+H]$^+$=465.3

EXAMPLE 15

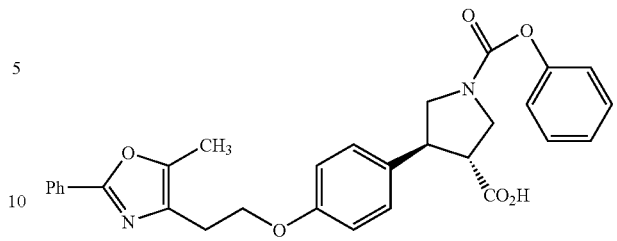

Example 15 compound (19 mg; 62%) was prepared employing the procedure as described in Example 11, except that phenyl chloroformate (8 μL; 0.04 mmol) was used in the sequence instead of ethyl chloroformate.

[M+H]$^+$=513.4

EXAMPLE 16

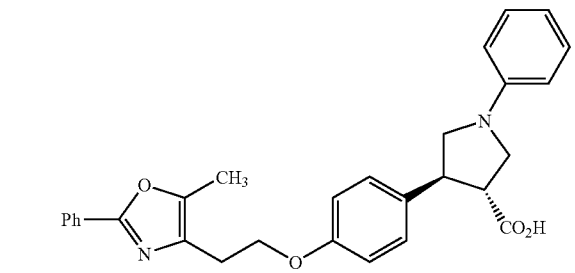

The procedure of Example 8 was essentially followed to prepare the title compound.

A mixture of Example 14 Part A compound (40 mg; 0.089 mmol), phenylboronic acid (12 mg; 0.10 mmol), Cu(OAc)$_2$ (1 mg; 5.5×10$^{-3}$ mmol), myristic acid (1 mg; 4.3×10$^{-3}$ mmol) and 2,6 lutidine (18 μL; 0.16 mmol) in toluene (1 mL) was stirred at RT for 24 h in air. At this point HPLC showed that product had been formed. The reaction mixture was filtered, and the filtrate was concentrated in vacuo. The residue was dissolved in a solution of TFA/CH$_2$Cl$_2$ (1 mL of a 1:1 mixture). The reaction was stirred at RT for 1 h; TLC indicated that the reaction was complete at this point. Volatiles were removed in vacuo and the residue was purified by preparative HPLC (as described for Example 1) to provide the title compound (4 mg; 9%) as an oil.

[M+H]$^+$=469.2.

EXAMPLE 17

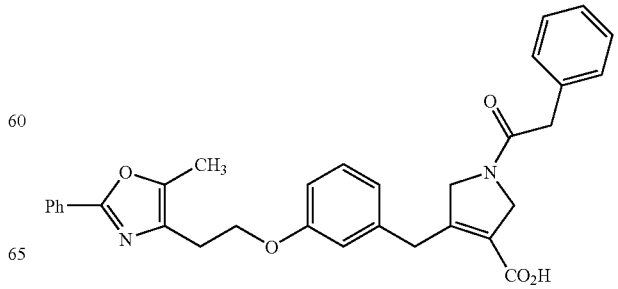

-continued

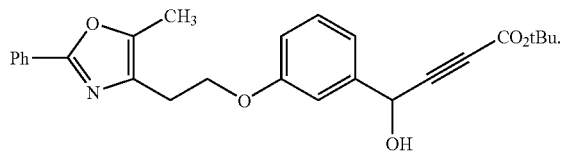
A

To a −74° C. solution of tert-butyl propiolate (0.808 g; 6.4 mmol) in anhydrous THF (10 mL) was added n-BuLi (2.60 mL of a 2.5 M solution in hexane) dropwise. The reaction mixture was stirred at −74° C. for 30 min, after which a solution of the aldehyde Example 436 Part A compound (1.79 g; 5.83 mmol)

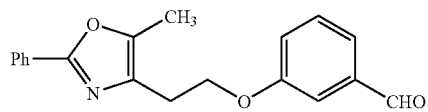

in anhydrous THF (10 mL) was added dropwise at −74° C. (temperature reached −68° C. during addition). The reaction mixture was stirred at −70° C. for 1 h, after which it was quenched by dropwise addition of saturated aqueous $NH_4Cl$ (10 mL). The mixture was allowed to warm to RT, then extracted with EtOAc (2×20 mL). The combined organic extracts were washed with water, dried ($Na_2SO_4$) and concentrated in vacuo to provide crude Part A compound, which was used in the next step without further purification.

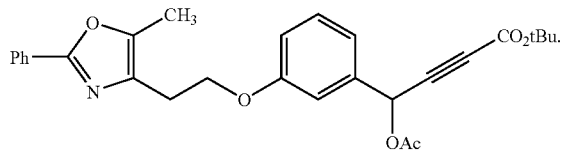
B

To a solution of Part A compound (1.75 g; 4.08 mmol) in $CH_2Cl_2$ (10 mL) were successively added acetic anhydride (0.75 g; 8.2 mmol), pyridine (1.16 g; 16.3 mmol) and DMAP (10 mg). The reaction was stirred at RT for 2 h, after which LC/MS indicated that the reaction was complete. EtOAc (150 mL) was added and the solution was washed with aqueous 1 M HCl (2×) and $H_2O$, then concentrated in vacuo. The residual oil was chromatographed ($SiO_2$; 3:1 hexane:EtOAc) to provide Part B compound (1.79 g; 92%) as an oil.

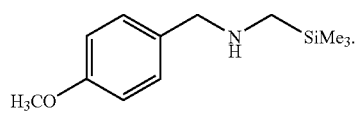
C

A solution of 4-methoxybenzylamine (11.2 g; 82 mmol) and $Me_3SiCH_2Cl$ (5.0 g; 41 mmol) in MeCN (50 mL) was refluxed under an atmosphere of $N_2$ for 16 h. The reaction mixture was then cooled to RT and filtered. The filtrate was concentrated in vacuo to ~30 mL in volume. $H_2O$ (100 mL) was added and the mixture was extracted with hexane (2×20 mL). The combined organic extracts were washed with $H_2O$ (3×20 mL), dried ($MgSO_4$) and concentrated in vacuo to provide crude Part C compound (7.6 g; 41%) as an oil, which was used in the next step without further purification.

D

To a 0° C. solution of 37% aqueous formaldehyde (2.8 g; 34 mmol) was added dropwise crude Part C compound (7.6 g; 34 mmol) followed by 5 drops of aqueous 1 N NaOH (in order to neutralize the formic acid in the formaldehyde). The reaction mixture was stirred at 0° C. for 10 min, after which MeOH (5 mL) was added in one portion. $K_2CO_3$ (4 g) was added to absorb the aqueous phase, after which the mixture was stirred at RT for 1 h and then filtered. Additional $K_2CO_3$ (2 g) was added to the filtrate and the mixture was stirred at RT for an additional 12 h. $Et_2O$ (20 mL) was then added and the mixture was filtered; the filtrate was concentrated in vacuo and the residual oil was distilled under reduced pressure (bp=80° C. @ 0.5 mm Hg) to give Part D compound (4.2 g; 46%) as a clear oil.

E

A mixture of Part B compound (130 mg; 0.273 mmol), Part D compound (73 mg; 0.273 mmol) and TFA (catalytic amount; several drops) in $CH_2Cl_2$ (2 mL) was stirred at RT for 2 h. At this point the reaction was complete by TLC. Volatiles were removed in vacuo and the mixture was chromatographed ($SiO_2$; 3:1 hexane:EtOAc) to provide Part E compound (171 mg; 98%) as an oil.

F.

A solution of Part E compound (360 mg; 0.564 mmol), $(Ph_3P)_2PdCl_2$ (4 mg; 0.006 mmol) and formic acid/$Et_3N$ (0.50 mL of a 1:1 4M solution in dioxane; 1.69 mmol) in dioxane (5 mL) was refluxed $N_2$ for 30 min. At this point LC-MS indicated that all starting material had been consumed. The reaction mixture was cooled to RT, diluted with EtOAc (5 mL) and washed with $H_2O$ (2×10 mL). The organic phase was dried ($Na_2SO_4$) and concentrated in vacuo. The residue was chromatographed (ISCO chromatography apparatus; 25 g $SiO_2$ column; continuous gradient from hexane->70:30 hexane:EtOAc) to provide Part F compound (114 mg; 35%) in addition to the pyrrole (Part G compound; 80 mg; 25%)

(Part G compound)

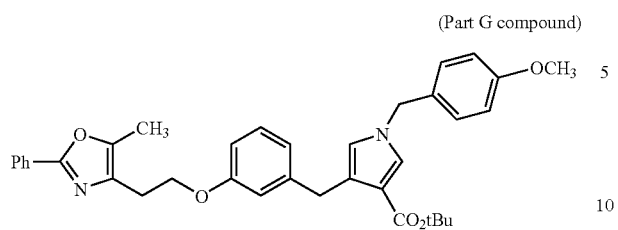

as well as the pyrrolidine (Part H compound; 25 mg; 8%)

(Part H compound)

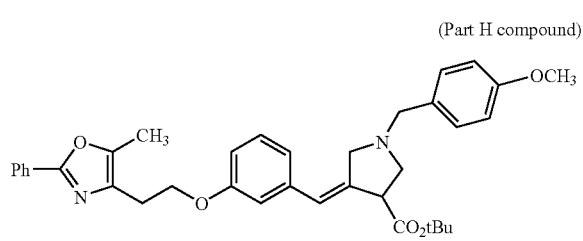

as byproducts.

I.

H·CF₃CO₂H

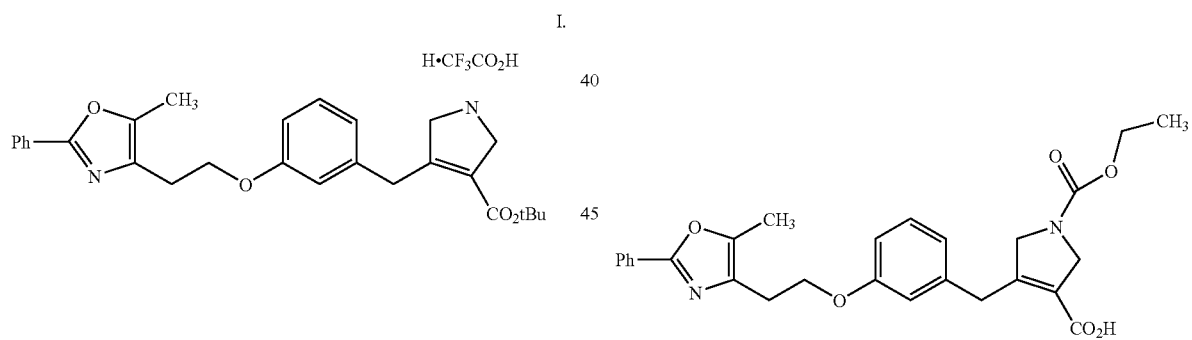

To a −78° C. solution of Part F compound (114 mg; 0.1969 mmol) in CH₂Cl₂ (1 mL) was added CH₃CHClOCOCl (45 μL; 0.40 mmol) The reaction mixture was stirred at −78° C. for 30 min, then was allowed to warm to RT and stirred at RT for 1 h. At this point, HPLC indicated that all starting material had been consumed. Volatiles were removed in vacuo and MeOH (5 mL) was added; the solution was then stirred at RT for 8 h. Volatiles were removed in vacuo and the residue was purified by preparative HPLC (YMC reverse-phase ODS 30×250 mm column; flow rate 25 mL/min; 30 min continuous gradient from 30:70 B:A to 100% B+10 min hold-time at 100% B, where solvent A=90:10:0.1H₂O:MeOH:TFA and solvent B=90:10: 0.1 MeOH:H₂O:TFA) to provide Part I compound (81 mg; 89%) as a TFA salt.

A solution of Part I compound (18 mg; 0.032 mmol), phenyl chloroformate (6.3 μL; 0.05 mmol) and DMAP (11 mg; 0.09 mmol) in CH₂Cl₂ (3 mL) was stirred at RT for 30 min. EtOAc (10 mL) was then added and the mixture was successively washed with H₂O (2×20 mL) and aqueous 1 N HCl (10 mL), then dried (Na₂SO₄). Volatiles were removed in vacuo and the residual oil was dissolved in TFA/CH₂Cl₂ (1 mL of a 1:1 mixture) and the reaction was stirred at RT for 1 h, after which volatiles were removed in vacuo. The residue was purified by preparative HPLC (as described for Example 1) to provide the title compound (13 mg; 78%) as an oil.

[M+H]⁺=525.1

EXAMPLE 18

A solution of Example 17 Part J compound (25 mg; 0.054 mmol), ethyl chloroformate (11 mg; 0.10 mmol) and DMAP (61 mg; 0.50 mmol) in CH₂Cl₂ (2 mL) was stirred at RT for 30 min. EtOAc (10 mL) was then added and the mixture was successively washed with H₂O (2×20 mL) and aqueous 1 N HCl (10 mL), then dried (Na₂SO₄). Volatiles were removed in vacuo and the residual oil was dissolved in TFA/CH₂Cl₂ (1 mL of a 1:1 mixture) and the reaction was stirred at RT for 1 h, after which volatiles were removed in vacuo. The residue was purified by preparative HPLC (using the same conditions as described for Example 1) to provide Example 16 compound (17 mg; 66%) as an oil.

[M+H]⁺=477.1

EXAMPLE 19

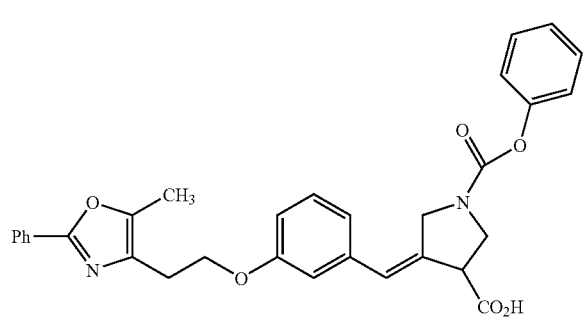

Example 19 compound was prepared from Example 17 Part G compound (16 mg; 0.035 mmol) with phenyl chloroformate (13 µL; 0.10 mmol) using the 2-step sequence as employed in the synthesis of Example 17 from Example 17 Part J compound. Example 19 compound was obtained (9 mg; 49%) as a white solid after preparative HPLC (using the same conditions as described in Example 1).

[M+H]$^+$=525.1

EXAMPLE 19A

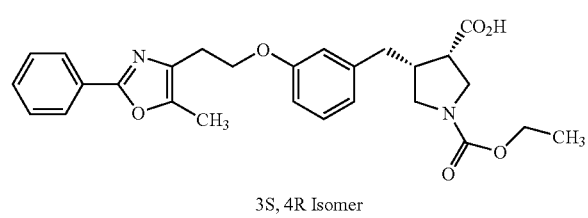

3S, 4R Isomer

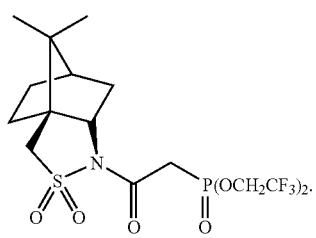

To a RT solution of D-(1S)-(−)-2,10-camphorsultam (1.0 g; 4.64 mmol) in anhydrous toluene (5 mL) under an atmosphere of argon was added Me$_3$Al (2.3 mL of a 2.0 M solution in toluene; 4.6 mmol). The solution was stirred at RT for 1 h, after which (CF$_3$CH$_2$O)$_2$P(O)CH$_2$CO$_2$CH$_3$ (1.50 g; 4.71 mmol) was added. The reaction was stirred at 75° C. for 3 days, cooled to RT, and partitioned between saturated aqueous NH$_4$Cl (50 mL) and Et$_2$O (25 mL). The organic phase was dried (MgSO$_4$) and concentrated in vacuo. The residue was chromatographed (SiO$_2$; hexane:EtOAc 3:1) and further purified by preparative HPLC (YMC ODS reverse phase 30×250 mm column; flow rate=25 mL/min; 30 min continuous gradient from 80:20 A:B to 100% B; where A=90:10:0.1H$_2$O:MeOH:TFA; B 90:10:0.1 MeOH:H$_2$O: TFA, then 15 min hold at 100% B) to give Part A compound (491 mg; 21%) as an oil.

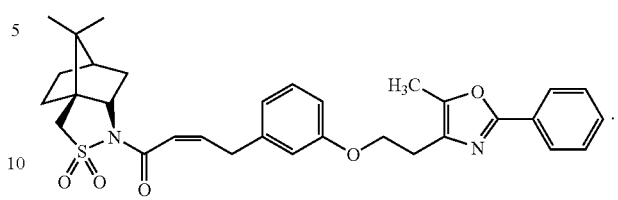

To a −78° C. solution of Part A compound (491 mg; 0.98 mmol) and 18-crown-6 (2.1 g; 8 mmol) in THF (20 mL) under an atmosphere of N$_2$ was added dropwise a solution of KN(TMS)$_2$ (2.35 mL of a 0.5 M solution in toluene; 1.18 mmol). The reaction was stirred at −78° C. for 30 min, after which a solution of the aldehyde (Example 1 Part E compound; 377 mg; 1.18 mmol) in THF (5 mL) was added and the reaction was stirred at −78° C. for a further 30 min. Saturated aqueous NH$_4$Cl (5 mL) was then added slowly and the reaction was allowed to warm to RT. The mixture was extracted with Et$_2$O (3×30 mL), dried (Na$_2$SO$_4$) and concentrated in vacuo. The crude product was chromatographed (SiO$_2$; hexane:EtOAc 3:1) to provide Part B compound (Z-isomer; 100 mg; 18%) as an oil. In addition the isomeric Part C compound (Part C compound)

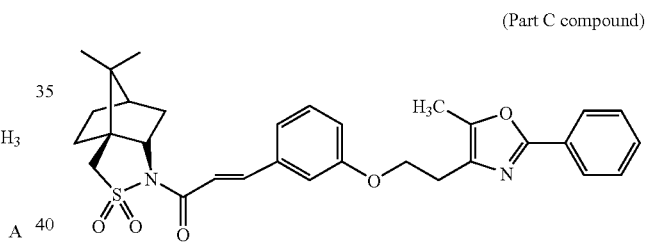

(E-isomer; 50 mg; 9%) was also obtained.

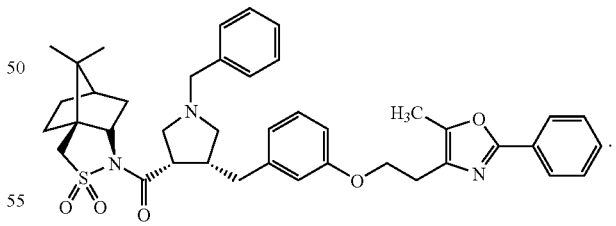

A mixture of Part B compound (100 mg; 0.178 mmol), Example 1 Part B compound (100 mg; 0.421 mmol) and a catalytic amount of TFA (5 µL) in toluene (2.0 mL) was stirred at RT for 3 h. TLC showed that the reaction was complete. The reaction mixture was partitioned between EtOAc (10 mL) and saturated aqueous NaHCO$_3$ (20 mL). The organic phase was dried (Na$_2$SO$_4$) and concentrated in vacuo. The residue was chromatographed (SiO$_2$; hex:EtOAc 3:1) to provide Part C compound (56 mg; 45%) as an oil.

D

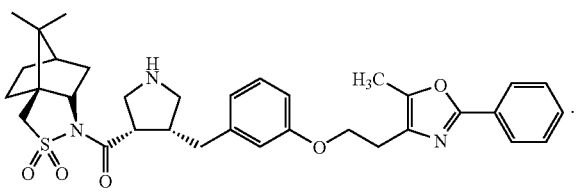

A mixture of Part C compound (56 mg; 0.081 mmol) and 10% Pd/C (30 mg) in MeOH (5 mL+1 drop of HOAc) was stirred under an atmosphere of $H_2$ at RT for 5 h. The mixture was filtered, and the filtrate was concentrated in vacuo to give Part D compound (42 mg; 85%) as an oil.

E

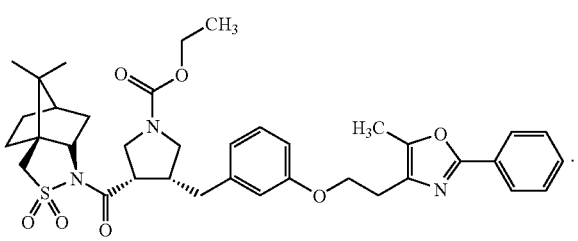

A mixture of Part D compound (20 mg; 0.033 mmol), DMAP (12 mg; 0.1 mmol) and ethyl chloroformate (5 mg; 0.05 mmol) in $CH_2Cl_2$ (1 mL) was stirred at RT for 30 min, then was partitioned between EtOAc (10 mL) and $H_2O$ (20 mL). The organic phase was washed with $H_2O$ and aqueous 1 M HCl (10 mL each), dried ($Na_2SO_4$) and concentrated in vacuo. The residue was chromatographed ($SiO_2$; continuous gradient from 100% hexane to 30:70 hexane:EtOAc over 25 min) to give Part E compound (4 mg; 18%) as an oil.

F

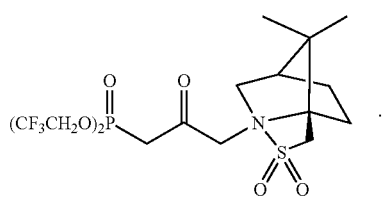

3S, 4R isomer

A solution of Part E compound (4 mg; 5.9×10$^{-3}$ mmol) in aqueous LiOH (1 mL of a 1 N solution) and THF (2 mL) was stirred at RT for 3 h, then was partitioned between excess aqueous 1 M HCl and EtOAc. The organic phase was washed with $H_2O$, dried ($Na_2SO_4$) and concentrated in vacuo. The residue was purified by preparative HPLC (as described for the synthesis of Example 1) to give the title compound (0.9 mg; 32%).

[M+H]$^+$=479.2

Chiral analytical HPLC (Daicel Chiralcel OJ-H 4.6×250 mm column): flow rate=1 mL/min; isocratic conditions=80:20 A:B, where A=heptane+0.1% TFA and B=50:50:0.1 MeOH: EtOH:TFA; detector wavelength=220 nm; retention time=20.0 min; ee=95%

The rest of the material was the chiral epimerized trans isomer:

EXAMPLE 19B COMPOUND

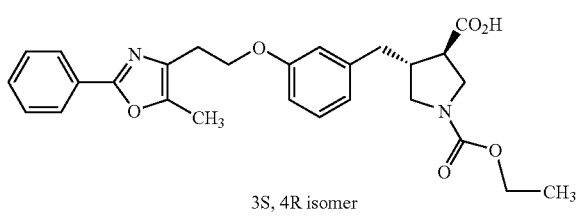

3S, 4R isomer

Example 20 compound (0.5 mg; 16%) was prepared from Example 19A Part D compound (using the same sequence as the synthesis of Example 19A from Example 19A Part D compound). [M+H]+=527.2

Chiral analytical HPLC (Daicel Chiralcel OD 4.6×250 mm column): flow rate=1 mL/min; isocratic conditions=85:15 A:B, where A=heptane+0.1% TFA; B 50:50:0.1 MeOH: EtOH:TFA; detector wavelength=220 nm; retention time=21.3 min; ee=93%

EXAMPLE 21

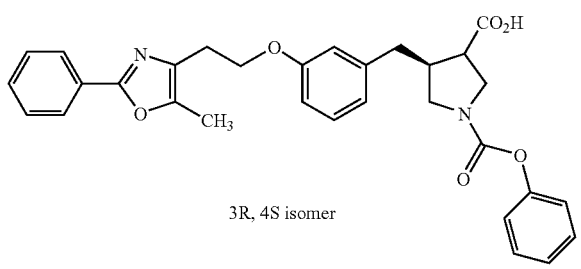

3R, 4S isomer

A

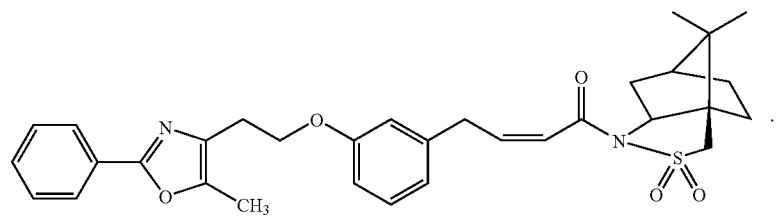

Part A compound (630 mg; 27%) was synthesized in exactly the same way as Example 19 Part A compound except that L-(1S)-(−)-2,10-camphorsultam (1.0 g) was used in place of D-(1R)-(+)-2,10-camphorsultam.

B

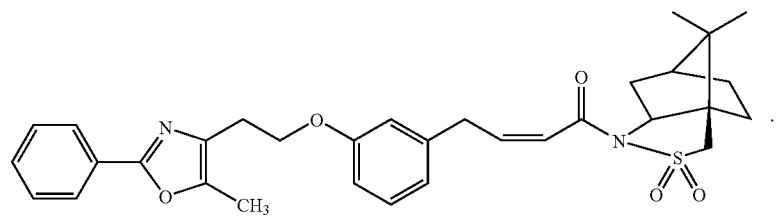

To a –78° C. solution of Part A compound (630 mg; 1.26 mmol) and 18-crown-6 (2.66 g; 10.1 mmol) in anhydrous THF (25 mL) under N₂ was added dropwise a solution of KN(TMS)₂ (2.51 mL of a 0.5 M solution in toluene; 1.26 mmol). The reaction was stirred at –78° C. for 15 min, after which a solution of Example 1 Part E compound (610 mg; 1.90 mmol) in THF (5 mL) was added dropwise. The reaction was stirred at –78° C. for a further 30 min, then quenched by cautious addition of excess H₂O. The reaction was allowed to warm to RT and partitioned between saturated aqueous NH₄Cl and EtOAc. The organic phase was washed with H₂O and brine, dried (MgSO₄) and concentrated in vacuo. The residue was chromatographed (SiO₂; continuous gradient from 100% hexane to 100% EtOAc over 50 min) to provide the Z-olefin Part B compound (293 mg; 28%) as an oil. In addition, the corresponding E-olefin Part C compound (149 mg; 14%) was also obtained.

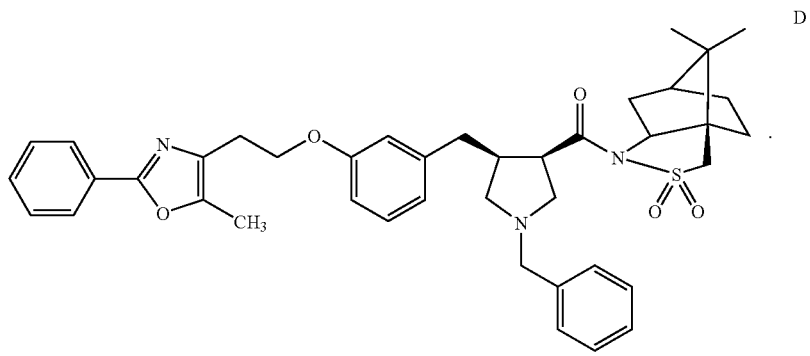

To a solution of Part B compound (290 mg; 0.517 mmol) in toluene (1.3 mL) were successively added Example 1 Part B compound (270 mg; 1.14 mmol) and a catalytic amount of TFA (1 µL). The reaction was stirred at RT for 3 h, then was partitioned between EtOAc and saturated aqueous NaHCO₃. The organic phase was washed with brine, dried (MgSO₄) and concentrated in vacuo. The residue was chromatographed (SiO₂; continuous gradient from 100% hexane to 100% EtOAc over 40 min) to provide Part D compound (176 mg; 49%) as well as a diastereomeric product (41 mg; 11%), which corresponds to Example 19 Part C compound.

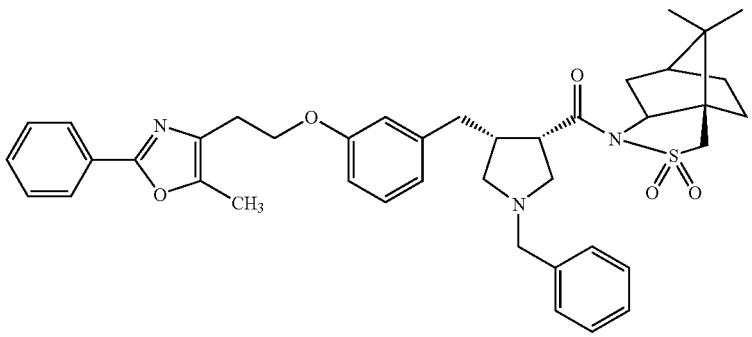

(Ex. 19 Part C Compound)

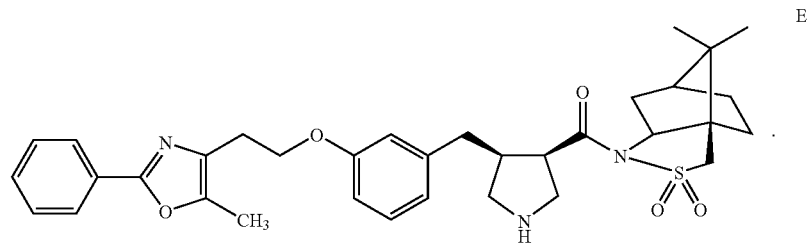

A mixture of Part D compound (87 mg; 0.126 mmol) and 10% Pd/C (42 mg) in MeOH:EtOAc (2.5 mL of a 4:1 solution) was stirred under an atmosphere of H$_2$ at RT for 24 h. The mixture was filtered and the filtrate was concentrated in vacuo to give Part E compound (70 mg; 92%) as an oil.

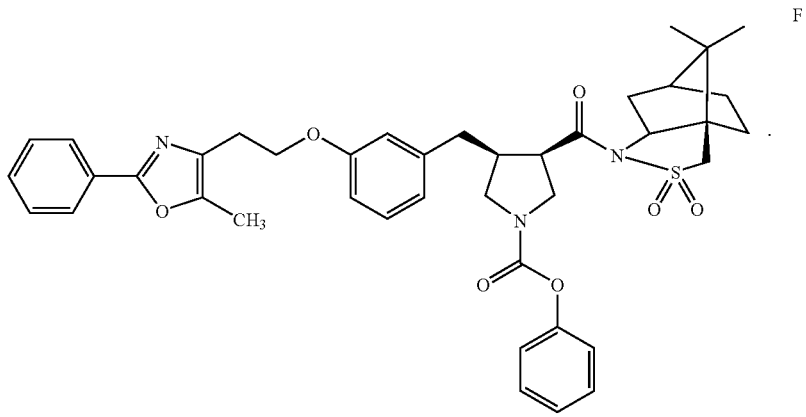

A mixture of Part E compound (35 mg; 0.058 mmol), Et$_3$N (16 µL; 0.12 mmol), DMAP (one crystal) and phenyl chloroformate (15 µL; 0.12 mmol) in CH$_2$Cl$_2$ (1 mL) was stirred at RT for 2 h, then was partitioned between aqueous 1 N HCl and EtOAc. The organic phase was washed with H$_2$O and brine, dried (MgSO$_4$) and concentrated in vacuo. The residue was chromatographed (SiO$_2$; continuous gradient from 100% hexane to 100% EtOAc over 35 min) to give Part F compound (30 mg; 72%) as an oil.

G

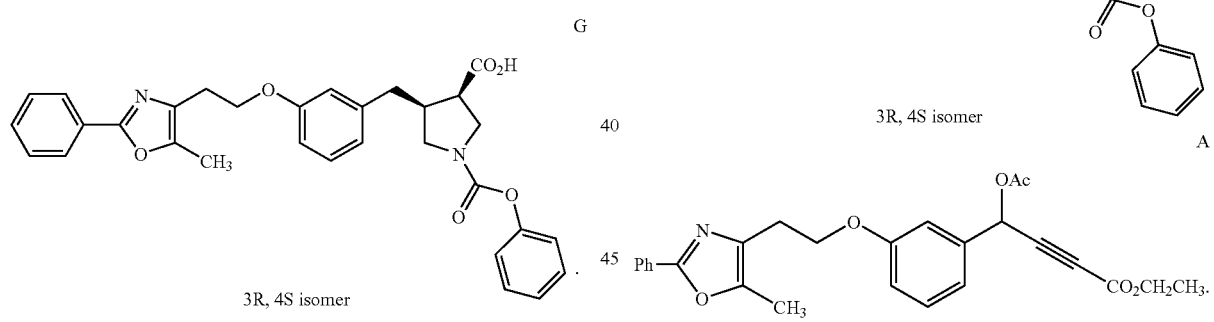

3R, 4S isomer

A mixture of Part F compound (15 mg; 0.021 mmol) and LiOH.H$_2$O (40 mg; 0.95 mmol) in THF/H$_2$O (4 mL of a 2:1 solution) was stirred at RT for 18 h. EtOAc was added and the reaction acidified to pH ~2 with aqueous 1 N HCl. The organic phase was washed with brine, dried (Na$_2$SO$_4$) and concentrated in vacuo. The residue was chromatographed (SiO$_2$; stepwise gradient from 1:1 hex:EtOAc to 10:10:1 hex:EtOAc:acetic acid) to give the title compound (6.5 mg; 60%) as a white solid.

[M+H]$^+$=527.6

Chiral analytical HPLC (Daicel Chiralcel OD 4.6×250 mm column): flow rate=1 mL/min; isocratic conditions=85:15 A:B, where A=heptane+0.1% TFA; B=50:50:0.1 MeOH:EtOH:TFA; detector wavelength=220 nm; retention time=15.6 min; ee=99%

EXAMPLE 21

Alternative Synthesis

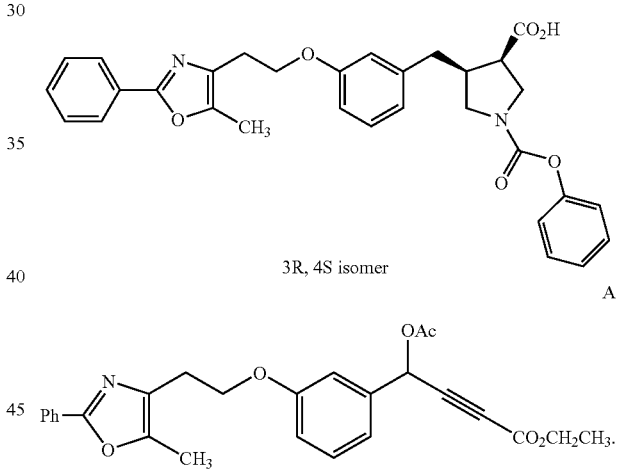

3R, 4S isomer

A

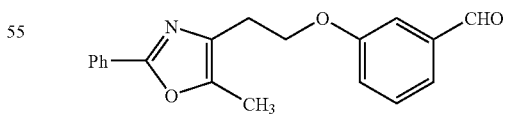

To a RT solution of ethyl trimethylsilylpropynoate (2.65 g; 15.6 mmol) and aldehyde Example 436 Part A compound (4.0 g; 13.0 mmol)

in CH$_2$Cl$_2$ (100 mL) were successively added potassium fluoride (910 mg; 15.6 mmol) and 18-crown-6 (1.26 g; 4.7 mmol). The reaction mixture was stirred at RT for 18 h, after which a solution of concentrated HCl (5 mL) in MeOH (20 mL) was added slowly. The solution was stirred for 3 h at RT, then washed with aqueous 1 N HCl and brine. The organic phase was dried (MgSO$_4$) and concentrated in vacuo. The residue was dissolved in CH₂Cl₂ (40 mL) and acetyl chloride (1.20 g; 15.6 mmol) and Et₃N (2.2 mL; 15.6 mmol) were successively added slowly to this solution. The reaction was stirred at RT for 30 min, then washed with brine and saturated aqueous NaHCO₃. The organic phase was dried (MgSO₄) and concentrated in vacuo. The crude product was chromatographed (SiO₂; heptane:EtOAc 7:3) to give Part A compound (3.26 g; 56%) as a pale yellow oil.

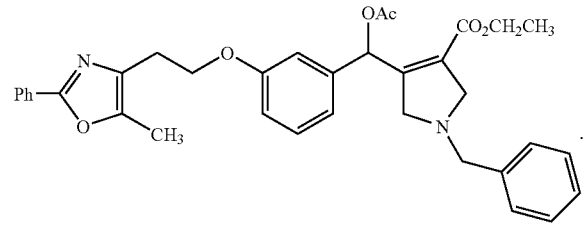

B

To a RT solution of Part A compound (2.50 g; 5.60 mmol) in CH₂Cl₂ (40 mL) was added a solution of Example 1 Part B compound (1.70 g; 7.2 mmol) in CH₂Cl₂ (40 mL). The solution was stirred at RT for 10 min, after which TFA (0.50 mL) was added dropwise. The reaction was stirred at RT for 1 h, after which HPLC indicated that 30% of Part A compound still remained. Additional Example 1 Part A compound (0.57 g; 2.4 mmol) was added and the reaction was stirred for 30 min longer. The solution was washed with saturated aqueous NaHCO₃, dried (MgSO₄) and concentrated in vacuo. The residue was chromatographed (SiO₂; heptane:EtOAc 6:4) to give crude Part B compound (2.3 g) as a pale yellow oil.

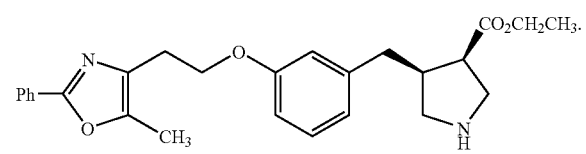

C

A mixture of crude Part B compound (2.3 g), 10% Pd/C (600 mg) and concentrated HCl (5 drops) in MeOH (40 mL) was stirred under an atmosphere of H₂ (60 psi) for 96 h. The catalyst was filtered off (Celite®) and the filtrate was concentrated in vacuo; the residue was partitioned between EtOAc and aqueous 1 N NaOH. The organic phase was dried (Na₂SO₄) and concentrated in vacuo. The residue was chromatographed (SiO₂; CH₂Cl₂:MeOH 10:1) to give racemic Part C compound (1.70 mg; 70% for 2 steps) as a pale yellow oil. The individual enantiomers were separated at this point by preparative HPLC under the following conditions: Chiralcel OD chiral column, 5 cm×50 cm; 20 μM; Flow rate=45 mL/min; isocratic solvent system=80% heptane+ 0.1% Et₂NH & 20% IPA+0.1% Et₂NH. Part C compound (1.72 g) was chromatographed in 3 runs. The first fraction elutes under these conditions @45 min-1 hour and was subsequently determined to be the (3R, 4S) enantiomer (see below) (Part D compound).

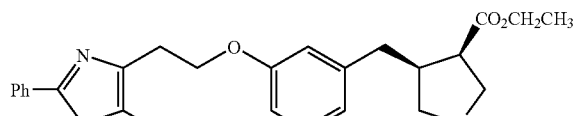

(Part D compound)

3R, 4S enantiomer

The second fraction elutes under these conditions@1 hour-1 hour 15 min. This fraction was subsequently determined to be the (3S, 4R) enantiomer (see below) (Part E compound).

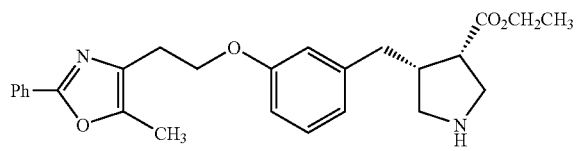

(Part E compound)

3S, 4R enantiomer

EXAMPLE 22

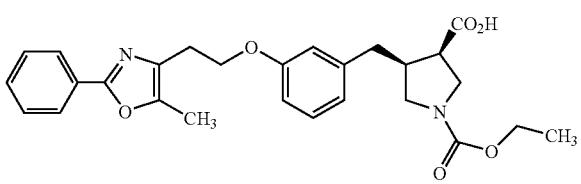

The title compound (4.3 mg; 16% for 2 steps) was prepared from Example 21 Part E compound using the same 2-step sequence as for the synthesis of Example 21.

[M+H]⁺=479.5

Chiral analytical HPLC (Daicel Chiralcel OD 4.6×250 mm column): flow rate=1 mL/min; isocratic conditions=80:20 A:B, where A=heptane+0.1% TFA; B=50:50:0.1 MeOH: EtOH:TFA; detector wavelength=220 nm; retention time=14.6 min; ee=99% o

EXAMPLE 23

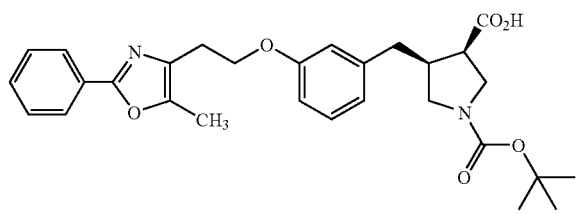

-continued

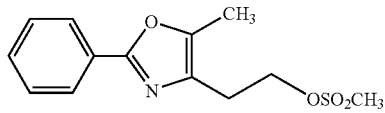

5

To a −5° C. solution of 5-phenyl-2-methyl-oxazole-4-ethanol (20.00 g, 0.098 mol) in CH$_2$Cl$_2$ (100 mL) was added methanesulfonyl chloride (12.40 g, 0.108 mol) in one portion (exothermic reaction). After recooling to −5° C., Et$_3$N (11.1 g, 0.110 mol) was added slowly over 30 min (internal temperature<3° C.). The reaction was allowed to warm to RT and stirred for 1 h (reaction monitored by analytical HPLC), at which point starting material had been consumed. The reaction was washed with aqueous HCl (2×50 mL of a 3N solution). The combined aqueous layers were extracted with CH$_2$Cl$_2$ (50 mL). The combined organic extracts were successively washed with satd. aqueous NaHCO$_3$ and brine (50 mL each), dried (Na$_2$SO$_4$), and concentrated to ~30 mL volume. Methyl tert-butyl ether (120 mL) was added and the mixture was stirred; a white solid was formed. The mixture was cooled to −20° C. for complete crystallization. The product was filtered and vacuum-dried to give Part A compound (23.3 g, 85%) as a white solid. The mother liquor was concentrated in vacuo and recrystallized from methyl tert butyl ether/heptane to give a second crop of Part A compound (3.3 g, 12%; total yield=97%).

B

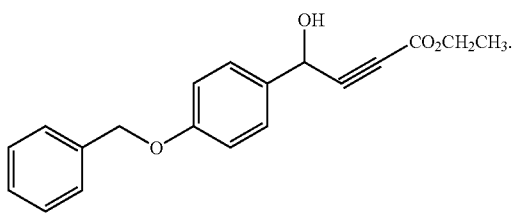

To a −78° C. solution of ethyl propynoate (10.0 g; 100 mmol) in anhydrous THF (200 mL) was added dropwise n-BuLi (40 mL of a 2.5 M solution in hexane; 100 mmol) over 30 min. The reaction was stirred at −78° C. for 30 min, after which a solution of 4-benzyloxybenzaldehyde (21.0 g; 100 mmol) in THF (100 mL) was added dropwise. The reaction was stirred at −78° C. for 1 h, excess saturated aqueous NH$_4$Cl was cautiously added to quench the reaction, and the mixture was allowed to warm to RT. Volatiles were removed in vacuo and the residue was partitioned between EtOAc and saturated aqueous NH$_4$Cl. The organic phase was dried (Na$_2$SO$_4$) and concentrated in vacuo; the residue was chromatographed (SiO$_2$; continuous gradient from 100% hex to 100% EtOAc over 50 min) to give Part B compound (7.0 g; 23%) as an oil.

[M+H]$^+$=311; $^1$H NMR (CDCl$_3$) δ 7.35 (m, 7H), 6.95 (d, J=8.4 Hz, 2H), 5.47 (d, J=6 Hz, 1 h), 5.05 (s, 2H), 4.20 (q, J=7.2 Hz, 2H), 1.27 (t, J=7.2 Hz, 3H). $^{13}$C NMR (CDCl$_3$) δ 159.6, 137.4, 131.6, 129.0, 128.6, 128.4, 127.8, 115.6, 87.3, 78.2, 70.5, 64.3, 62.6, 14.4.

C

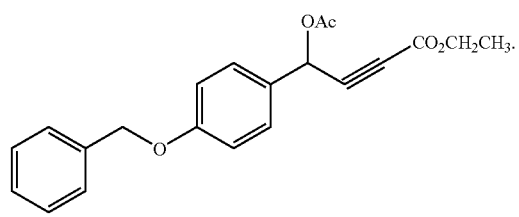

To a 0° C. solution of Part B compound (4.50 g; 14.5 mmol) in CH$_2$Cl$_2$ (50 mL) were successively added pyridine (1.80 mL; 22.3 mmol) and acetyl chloride (1.30 mL; 18.1 mmol). The reaction was stirred at 0° C. for 2 h, then was partitioned between CH$_2$Cl$_2$ and 5% aqueous HCl. The organic phase was washed with brine, dried (MgSO$_4$) and concentrated in vacuo to give Part C compound (5.0 g; 95%) as an oil.

[M+H]$^+$=353; $^1$H NMR (CDCl$_3$) δ 7.40 (m, 7H), 6.98 (d, 2H), 6.47 (s, 1H), 5.07 (s, 2H), 4.24 (q, J=7.2 Hz, 2H), 2.08 (s, 3H), 1.30 (t, J=7.2 Hz, 3H). $^{13}$C NMR (CDCl$_3$) δ 169.8, 160.1, 153.4, 137.0, 129.8, 129.0, 128.5, 128.0, 127.8, 115.6, 83.4, 78.5, 70.5, 64.9, 62.6, 21.2, 14.5.

D

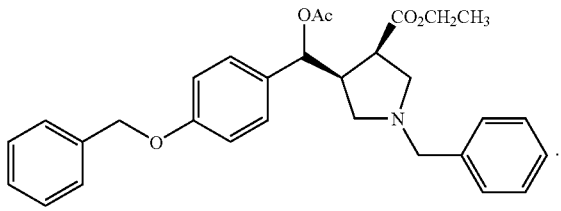

To a RT solution of Part C compound (1.0 g; 2.84 mmol) in toluene (2 mL) were successively added Example 1 Part B compound (900 mg; 3.8 mmol) and TFA (100 μL); a highly exothermic reaction occurred. The reaction was stirred at RT for 2 h, then was concentrated in vacuo. The residue was chromatographed (SiO$_2$; continuous gradient from 100% hex to 100% EtOAc over 50 min) to give Part D compound (700 mg; 72%) as a light yellow oil.

[M+H]+=486; $^1$H NMR (CDCl$_3$) δ 7.32 (m, 12H), 6.88 (d, J=8.4 Hz, 2H), 4.98 (s, 2H), 4.15 (q, J=7.2 Hz, 2H), 3.66 (m, 6H), 2.01 (s, 3H), 1.19 (t, 3H). $^{13}$C NMR (CDCl$_3$) δ 169.5, 163.3, 158.6, 150.8, 138.8, 136.8, 130.4, 128.5, 128.5, 128.4, 127.9, 127.8, 127.4, 127.1, 114.8, 70.8, 70.0, 60.5, 60.3, 60.0, 21.0, 14.2.

E

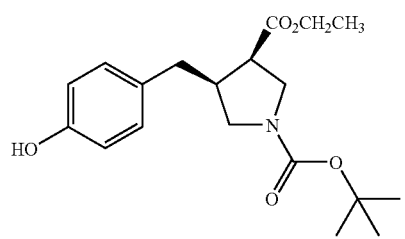

A mixture of Part D compound (700 mg; 1.44 mmol) and 10% Pd/C (100 mg) in HOAc (5 mL) and TFA (1 mL) was stirred under an atmosphere of $H_2$ (balloon) for 48 h. The catalyst was filtered off on Celite and the filtrate was concentrated in vacuo. The crude product was dissolved in THF (20 mL) and saturated aqueous $NaHCO_3$ (pH=9); di-tert butyl dicarbonate (320 mg; 145 mmol) was added. The reaction was stirred at RT for 2 h, then was concentrated in vacuo; the residue was partitioned between EtOAc and saturated aqueous $NaHCO_3$. The organic phase was washed with brine, dried ($MgSO_4$) and concentrated in vacuo. The residue was chromatographed ($SiO_2$; continuous gradient from 100% hex to 100% EtOAc over 50 min) to give Part E compound (300 mg; 60%) as an oil.

F

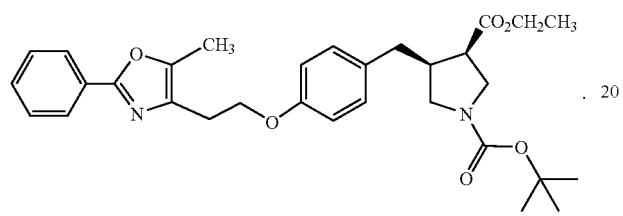

A mixture of Part E compound (50 mg; 0.14 mmol), Part A compound (50 mg; 0.17 mmol) and $K_2CO_3$ (23 mg; 0.17 mmol) in MeCN (5 mL) was stirred at 85° C. for 18 h. The reaction was cooled to RT and volatiles were removed in vacuo and partitioned between EtOAc and saturated aqueous $NH_4Cl$. The organic phase was dried ($MgSO_4$) and concentrated in vacuo. The residue was chromatographed ($SiO_2$; continuous gradient from 100% hex to 100% EtOAc over 50 min) to give crude Part F compound.

An alternative procedure for the synthesis of Part F compound is as follows:

To a RT solution of Part E compound (700 mg; 2.0 mmol) and 5-phenyl-2-methyl-oxazole-4-ethanol (500 mg, 2.46 mol) in toluene (15 mL) was added cyanomethylenetributylphosphine (500 μL; 2.0 mmol) dropwise. The mixture was heated at 88° C. in an oil bath for 2 h, cooled to RT and concentrated in vacuo. The residue was chromatographed ($SiO_2$; continuous gradient from 100% hex to 100% EtOAc over 50 min) to give Part F compound (800 mg; 75%). $[M+H]^+=536.6$

G

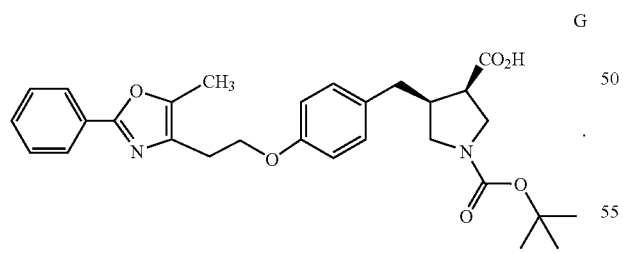

A solution of crude Part F compound and $LiOH \cdot H_2O$ (25 mg; 0.61 mmol) in THF (2 mL), MeOH (1 mL) and $H_2O$ (0.3 mL) was stirred at 0° C. for 2 h, then was quenched with saturated aqueous $NH_4Cl$ and concentrated in vacuo. The residue was partitioned between saturated aqueous $NH_4Cl$ and EtOAc. The organic phase was dried ($Na_2SO_4$) and concentrated in vacuo; the residue was purified by preparative HPLC (as described for Example 1) and lyophilized to give the title compound (5.0 mg; 7%) as a solid.

$[M+H]^+=507.4$ $^1H$ NMR ($CD_3OD$) δ 7.85 (m, 2H), 7.37 (m, 3H), 6.99 (d, 2H; J=8.4 Hz), 6.77 (m, 2H), 4.13 (m, 2H), 3.51 (m, 1H), 3.35 (m, 1H), 3.15 (m, 2H), 3.00 (m, 1H), 2.87 (t, 2H; J=8.4 Hz), 2.70 (m, 1H), 2.55 (m, 1H), 2.32 (m, 1H), 2.27 (s, 2H), 1.35 (2S, 9H).

In addition, a second, later eluting fraction from the preparative HPLC of the above crude product was identified as the epimerized trans-isomer Example 24 compound (5.0 mg; 7%):

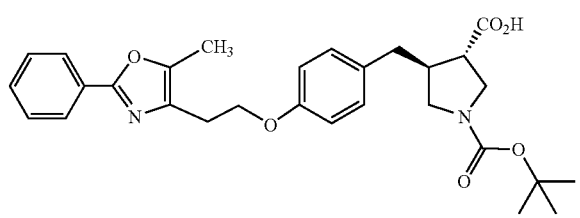

$[M+H]^+=507.4$ $^1H$ NMR ($CD_3OD$) δ 7.94 (m, 2H), 7.4 (m, 3H), 7.09 (d, 2H; J=6.4 Hz), 6.84 (d, J=8.0 Hz, 2H), 4.22 (m, 2H), 3.60 (m, 1H), 3.45 (m, 1H), 3.35 (m, 1H), 3.05 (m, 1H), 2.95 (t, 2H; J=6.4 Hz), 1.80 (m, 2H), 2.60 (m, 2H), 2.37 (s, 3H), 1.4 (s, 9H).

EXAMPLE 25

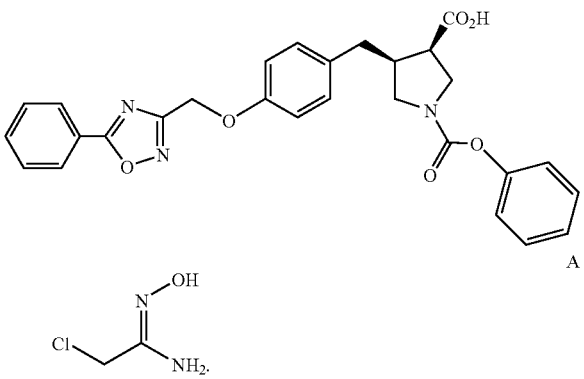

A

To a vigorously stirred mixture of chloroacetonitrile (7.5 g; 0.10 mmol) and hydroxylamine hydrochloride (6.95 g; 0.10 mmol) in $H_2O$ (25 mL) was carefully added $Na_2CO_3$ (5.3 g; 0.05 mmol) while maintaining the reaction temperature at ≦30° C. The mixture was then stirred at 30° C. for 15 min, then was extracted with $Et_2O$ (2×80 mL). The combined organic extracts were dried ($Na_2SO_4$) and concentrated in vacuo to give Part A compound (6.9 g; 64%) as a white solid.

B

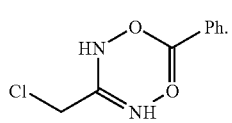

To a 0° C. mixture of Part A compound (1.0 g; 9.0 mmol) and $K_2CO_3$ (870 mg; 6.3 mmol) in acetone (45 mL) was added dropwise a solution of benzoyl chloride (1.0 mL; 9.0 mmol) in acetone (5 mL). The reaction was allowed to warm to RT and stirred at RT for 30 min. Volatiles were removed in vacuo and the residue was partitioned between H$_2$O and EtOAc. The organic phase was washed with brine, dried (MgSO$_4$) and concentrated in vacuo to give crude Part B compound (1.50 g; 76%) as a white solid.

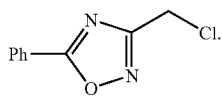

A solution of crude Part B compound (1.50 g) in HOAc (25 mL) was heated to reflux for 1.5 h, after which volatiles were removed in vacuo. The residue was partitioned between H$_2$O (40 mL) and EtOAc (50 mL); the organic phase was washed with H$_2$O (2×40 mL), saturated aqueous NaHCO$_3$ (2×40 mL) and brine (40 mL), dried (MgSO$_4$) and concentrated in vacuo. The residue was chromatographed (SiO$_2$; continuous gradient from 4:1 to 7:3 hexane:EtOAc) to give Part C compound (840 mg; 61%) as a white solid.

D

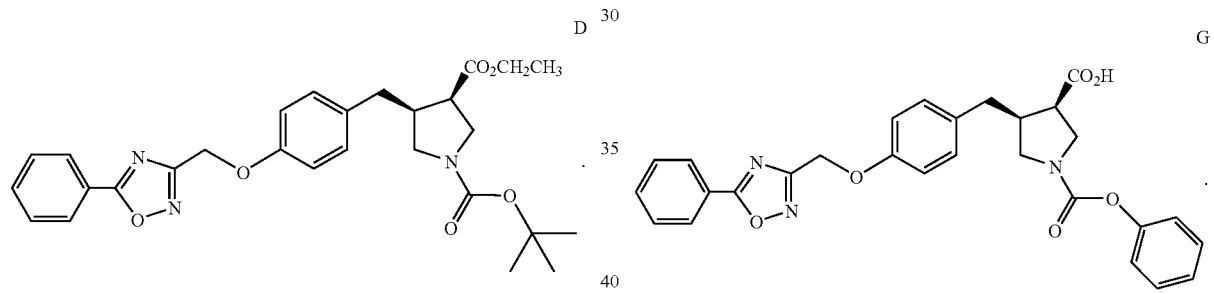

A mixture of crude Part C compound (120 mg; 0.60 mmol), Example 23 Part E compound (100 mg; 0.30 mmol) and K$_2$CO$_3$ (83 mg; 0.60 mmol) in MeCN (3 mL) was heated at 90° C. for 8 h. After cooling to RT, the mixture was filtered. The filtrate was concentrated in vacuo and the residue was chromatographed (SiO$_2$; continuous gradient from 9:1 to 3:1 hex:EtOAc) to give Part D compound (140 mg; 96%) as a syrup. [M+H]$^+$=508.3; [M+Na]$^+$=530.3

E

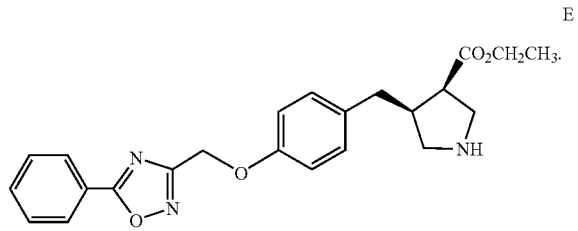

A solution of Part D compound (140 mg; 0.28 mmol) and HCl (700 µL of a 4 M solution in dioxane) in CH$_2$Cl$_2$ (5 mL) was stirred at RT for 2 h, then was concentrated in vacuo to give crude Part E compound (100 mg; 82%) as a white solid.

F

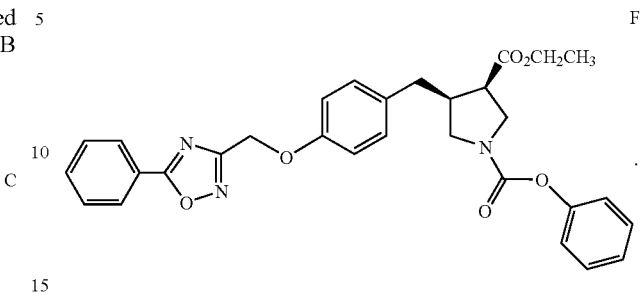

A solution of crude Part E compound (25 mg; 0.056 mmol), phenyl chloroformate (9 µL; 0.067 mmol) and NaHCO$_3$ (24 mg; 0.28 mmol) in H$_2$O and THF (2 mL each) was stirred at RT for 1 h, then was partitioned between H$_2$O and EtOAc (3 mL each). The organic phase was dried (MgSO$_4$) and concentrated in vacuo. The residue was chromatographed (SiO$_2$; continuous gradient from 9:1 to 3:1 hex:EtOAc) to give Part F compound (27 mg; 91%) as a white solid. [M+H]$^+$=528.2

G

A solution of Part F compound (27 mg; 0.05 mmol) and LiOH. H$_2$O (11 mg; 0.25 mmol) in THF and H$_2$O (1 mL each) was stirred at RT overnight, then the pH was adjusted to 3 with aqueous 1 N HCl. The mixture was partitioned between H$_2$O and EtOAc. The organic phase was dried (Na$_2$SO$_4$) and concentrated in vacuo; the residue was purified by preparative HPLC (as described for Example 1 except that a continuous gradient from 1:1 Solvent A:Solvent B to 100% B over 10 min was used, followed by 5 min hold at 100% B) to give two compounds. The compound with the shorter retention time was lyophilized from 1,4 dioxane to give the title compound (11 mg; 41%) as a white solid.

[M+H]$^+$=500.0

$^1$H NMR (CD$_3$OD): δ 8.14 (m, 2H), 7.65 (m, 1H), 7.58 (m, 2H), 7.35 (m, 2H), 7.20 (m, 3H), 7.08 (m, 2H), 7.03 (m, 2H), 5.24 (s, 2H), 3.90 (m, 0.5H), 3.75 (m, 1H), 3.56 (m, 1H), 3.29-3.50 (m, 2.5H), 2.75-2.92 (m, 2H), 2.54 (m, 1H)

The second compound (longer retention time) was determined to be the corresponding epimerized transisomer. This compound was lyophilized from dioxane to give Example 26 compound (6 mg; 23%) as a white solid.

EXAMPLE 26

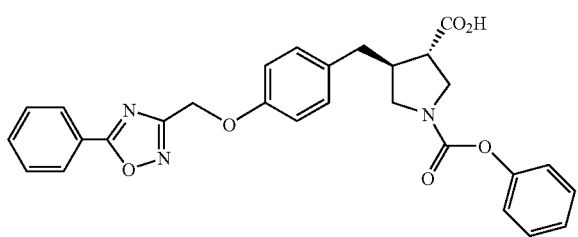

[M+H]$^+$=500.0

$^1$H NMR (CD$_3$OD): δ 8.14 (m, 2H), 7.65 (m, 1H), 7.58 (m, 2H), 7.35 (m, 2H), 7.20 (m, 3H), 7.08 (m, 2H), 7.03 (m, 2H), 5.24 (s, 2H), 3.90 (m, 0.5H), 3.75 (m, 1H), 3.65 (m, 1H), 3.50 (m, 0.5H), 3.32 (m, 0.5H), 3.22 (m, 0.5H) 2.85-2.97 (m, 2H), 2.78 (m, 1H), 2.65 (m, 1H).

EXAMPLE 27

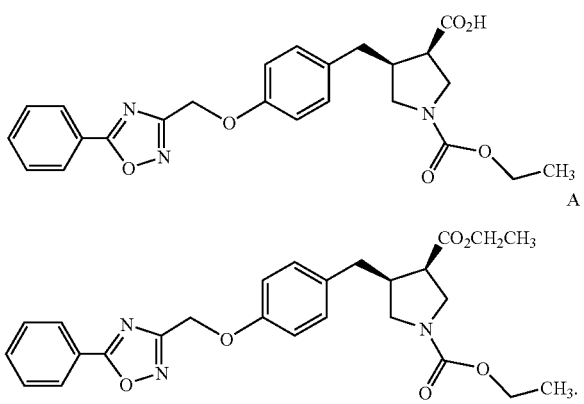

Example 25 Part E compound (25 mg; 0.056 mmol) and ethyl chloroformate (7 μL; 0.067 mmol) were reacted (using the same experimental procedure as for the preparation of Example 25 Part F compound) to give Part A compound (20 mg; 74%) as a white solid. [M+H]$^+$=480.21

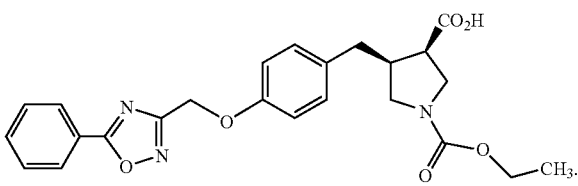

A solution of Part A compound (20 mg; 0.042 mmol) and LiOH. H$_2$O (9 mg; 0.21 mmol) in THF and H$_2$O (1 mL each) was stirred at RT overnight, after which the pH was adjusted to ~3 with aqueous 1 N HCl. The mixture was partitioned between H$_2$O and EtOAc. The organic phase was dried (Na$_2$SO$_4$) and concentrated in vacuo; the residue was purified by preparative HPLC (as described for Example 25) to give two compounds. The compound with the shorter retention time was lyophilized from 1,4 dioxane to give the title compound (9.3 mg; 49%) as a white solid.

[M+H]$^+$=452.1

Analytical HPLC: retention time=4.91 min (YMC S5 ODS 4.6×50 mm column; continuous gradient from 50:50 A:B to 100% B over 8 min; A=90:10:0.1H$_2$O:MeOH:TFA; B=90:10:0.1 MeOH:H$_2$O:TFA; flow rate=2.5 mL/min)

$^1$H NMR (CD$_3$OD): δ 8.14 (m, 2H), 7.65 (m, 1H), 7.60 (m, 2H), 7.14 (m, 2H), 7.01 (m, 2H), 5.24 (s, 2H), 4.10 (m, 2H), 3.68 (m, 1H), 3.50 (m, 1H), 3.20-3.33 (m, 2H), 3.15 (m, 1H), 2.85 (m, 1H), 2.70 (m, 1H), 2.45 (m, 1H), 1.22 (m, 3H)

The second compound (longer retention time) was determined to be the corresponding epimerized transisomer. This compound was lyophilized from dioxane to give Example 28 compound (3.2 mg; 17%) as a white solid.

EXAMPLE 28

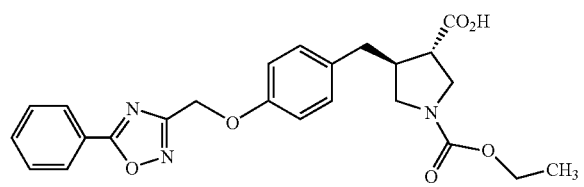

[M+H]$^+$=452.0 retention time=5.14 min (YMC S5 ODS 4.6×50 mm column; continuous gradient from 50:50 A-B to 100% B over 8 min; A=90:10:0.1H$_2$O:MeOH:TFA; B=90:10:0.1 MeOH:H$_2$O:TFA; flow rate=2.5 mL/min)

$^1$H NMR (CD$_3$OD): δ 8.14 (m, 2H), 7.67 (m, 1H), 7.59 (m, 2H), 7.16 (m, 2H), 7.01 (m, 2H), 5.24 (s, 2H), 4.08 (m, 2H), 3.67 (m, 1H), 3.55 (m, 1H), 3.42 (m, 1H), 3.10 (m, 1H), 2.90 (m, 1H), 2.82 (m, 1H), 2.68 (m, 1H), 2.60 (m, 1H), 1.22 (m, 3H)

EXAMPLE 29

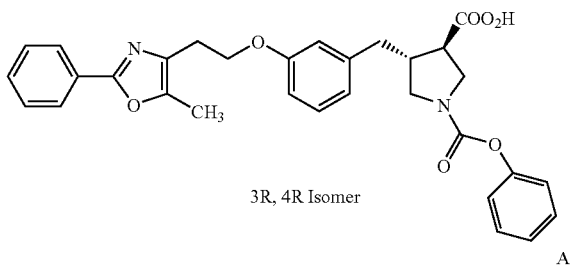

3R, 4R Isomer

To a RT solution of L-(1R)-(+)-2,10-camphorsultam (1.0 g; 4.64 mmol) in anhydrous toluene (5 mL) under an atmosphere of N$_2$ was added Me$_3$Al (3.0 mL of a 2.0 M solution in toluene; 6.0 mmol). The solution was stirred at RT for 2 h, after which Ph$_3$P=CHCO$_2$CH$_3$ (1.70 g; 5.0 mmol) was added. The reaction was stirred at 150° C. in a sealed tube for 2 h, cooled to RT, and partitioned between H₂O and EtOAc (50 mL each). The organic phase was washed with H₂O (2×50 mL), dried (Na₂SO₄) and concentrated in vacuo. The residue was chromatographed (SiO₂; hexane:EtOAc 3:1) to give Part A compound (1.0 g; 39%) as an oil.

A mixture of Part C compound (35 mg; 0.058 mmol) and 10% Pd/C (5 mg) in MeOH (5 mL) and HOAc (200 µL) was stirred under an atmosphere of H₂ (balloon) for 5 h. Solids were removed by filtration through Celite® and the filtrate was concentrated in vacuo to give Part D compound (25 mg; 71%) as an oil.

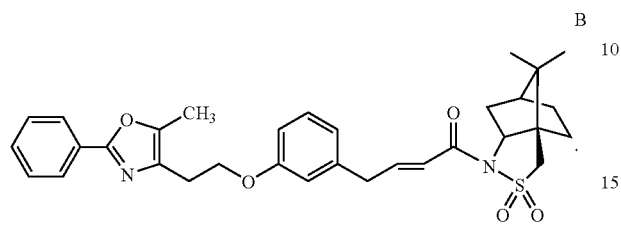
B

A solution of Part A compound (200 mg; 0.39 mmol) and the aldehyde (Example 1 Part E compound; 110 mg; 0.35 mmol) in toluene (20 mL) was heated at reflux for 2 h, then was concentrated in vacuo. The residue was chromatographed (SiO₂; hex:EtOAc 3:1) to give Part B compound (51 mg; 23%) as an oil.

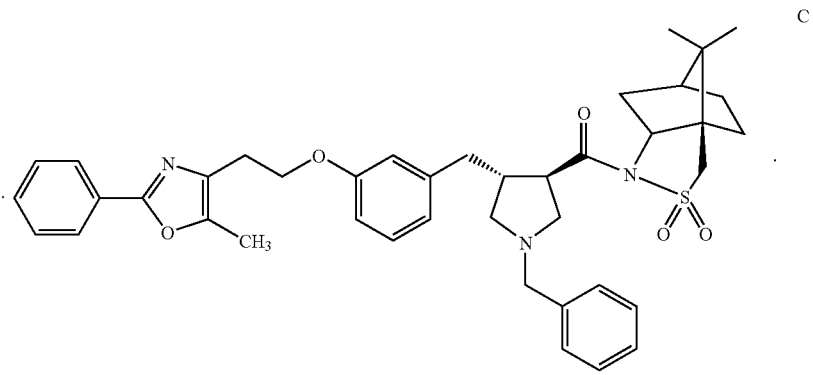
C

To a solution of Part B compound (51 mg; 0.090 mmol) in toluene (2 mL) were successively added Example 1 Part B compound (36 mg; 0.15 mmol) and a catalytic amount of TFA (1 µL). The reaction was stirred at RT for 3 h, then was partitioned between EtOAc (10 mL) and saturated aqueous NaHCO₃ (20 mL). The organic phase was dried (Na₂SO₄) and concentrated in vacuo. The residue was chromatographed (SiO₂; hex:EtOAc 3:1) to provide Part C compound (35 mg; 56%) as an oil.

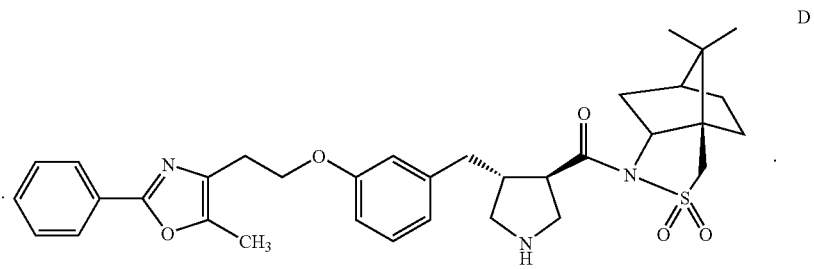
D

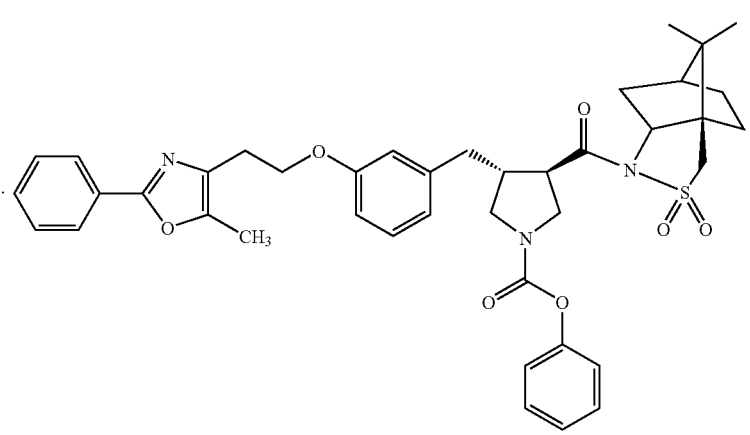

E

A mixture of Part D compound (25 mg; 0.033 mmol), DMAP (13 mg; 0.1 mmol) and phenyl chloroformate (78 mg; 0.5 mmol) in CH$_2$Cl$_2$ (3 mL) was stirred at RT for 30 min, then was partitioned between EtOAc and H$_2$O (20 mL each) The organic phase was washed with H$_2$O and aqueous 1 M HCl (10 mL each), dried (Na$_2$SO$_4$) and concentrated in vacuo. The residue was chromatographed (SiO$_2$; continuous gradient from 100% hexane to 30:70 hexane:EtOAc over 25 min) to give Part E compound (17 mg; 57%) as an oil.

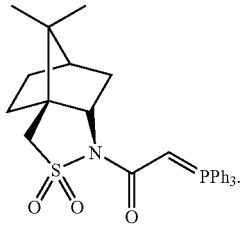

A

D-(1S)-(−)-2,10-camphorsultam (1.0 g; 4.64 mmol) was reacted with Ph$_3$P=CHCO$_2$CH$_3$ (1.70 g; 5.0 mmol) and Me3Al (3 mL of a 2 M solution in toluene) in exactly the same way as Example 29 Part A to give Part A compound (1.0 g; 39%) as an oil.

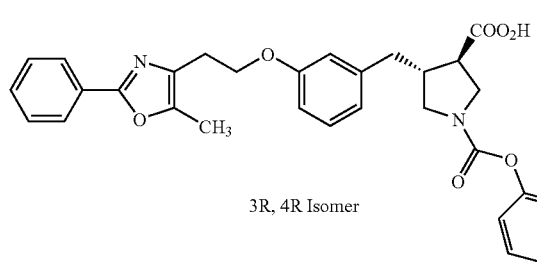

F 3R, 4R Isomer

A solution of Part A compound (17 mg; 0.024 mmol) in aqueous 1 N LiOH (0.5 mL; 0.50 mmol) and THF (1.5 mL) was stirred at RT for 6 h, then was partitioned between aqueous 1 N HCl (1 mL) and EtOAc (2 mL). The organic phase was dried (Na$_2$SO$_4$) and concentrated in vacuo; the residue was purified by preparative HPLC (as described for Example 25) to give the title compound (6 mg; 47%) as a white solid.

[M+H]$^+$=527.0

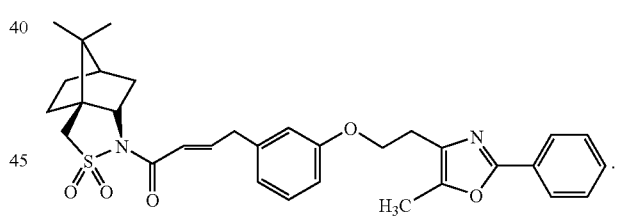

B

Part A compound (200 mg; 0.39 mmol) was reacted with the aldehyde Example 1 Part E compound (110 mg; 0.35 mmol) in the same way as Example 29 Part B to give Part B compound (45 mg; 20%) as an oil.

EXAMPLE 30

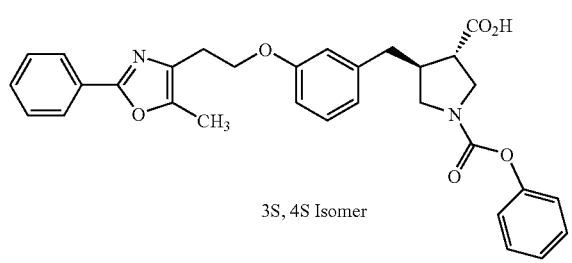

3S, 4S Isomer

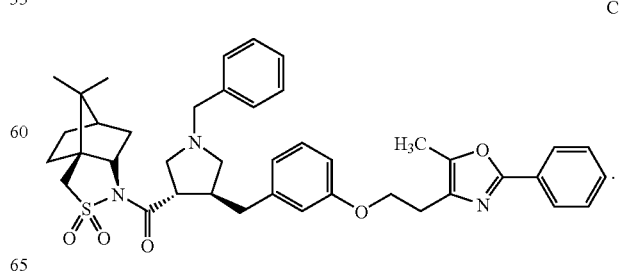

C

Part B compound (45 mg; 0.08 mmol) was reacted with Example 1 Part B compound (36 mg; 0.15 mmol) in the same way as Example 29 Part C to give Part C compound (28 mg; 51%) as an oil.

C

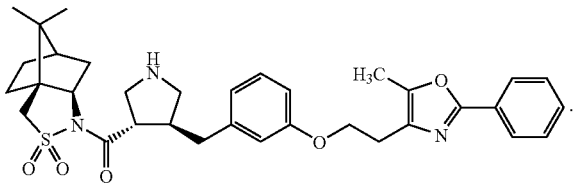

Part C compound (28 mg; 0.046 mmol) was used (the same procedure as described in Example 29 Part D) to prepare Part D compound (20 mg; 72%) as an oil.

D

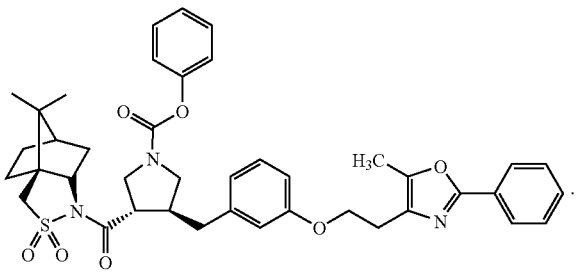

Part D compound (20 mg; 0.033 mmol) was reacted with phenyl chloroformate (78 mg; 0.50 mmol) in the same manner as Example 29 Part E to provide Part E compound (18 mg; 75%) as an oil.

E

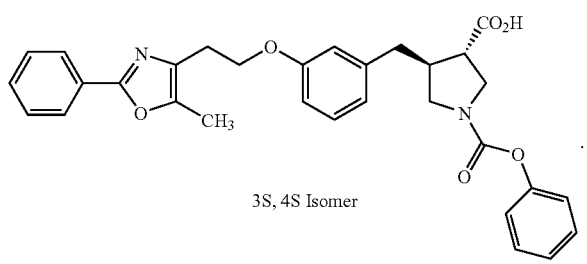

3S, 4S Isomer

Part E compound (18 mg; 0.025 mmol) was treated with aqueous LiOH (0.5 mL of a 1 M solution) in the same manner as Example 29 Part F to provide the title compound (7 mg; 53%) as a solid.

$[M+H]^+=527.0$

EXAMPLE 31

A

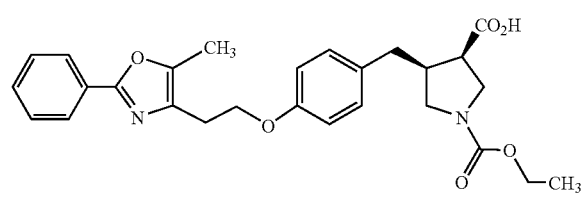

D

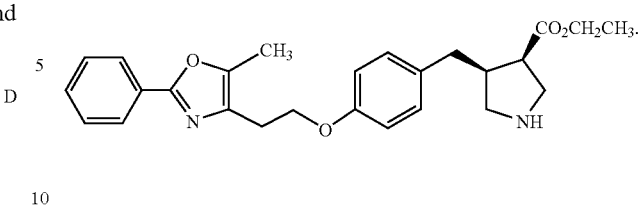

To a RT solution of Example 23 Part F compound (30 mg; 0.056 mmol) in $CH_2Cl_2$ (1 mL) was added HCl (250 μL of a 4 M solution in dioxane). The reaction was stirred at RT for 30 min, then was concentrated in vacuo to give crude Part A compound.

B

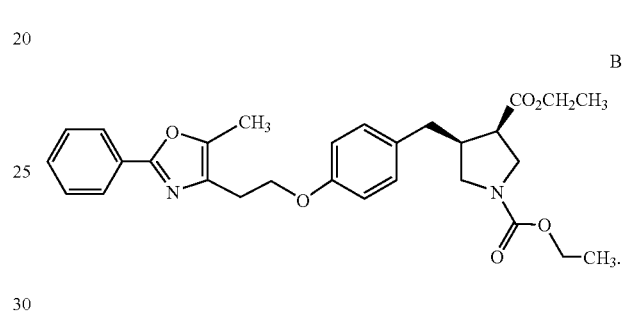

A mixture of crude Part A compound, ethyl chloroformate (50 μL; 0.52 mmol), THF (5 mL) and saturated aqueous $NaHCO_3$ (sufficient to adjust the pH to ~9) was stirred at RT for 30 min, then was concentrated in vacuo. The residue was partitioned between $H_2O$ and $Et_2O$. The aqueous phase was extracted with $Et_2O$; the combined organic extracts were dried ($MgSO_4$) and concentrated in vacuo to give crude Part B compound (25 mg; 76%) as an oil.

C

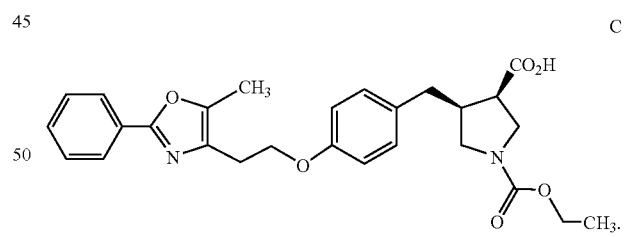

A mixture of Part B compound (5 mg; 0.01 mmol) in HOAc (500 μL) and aqueous HCl (150 μL of a 20% solution) was stirred at 80° C. for 18 h, then was cooled to RT and concentrated in vacuo. The residue was partitioned between EtOAc and saturated aqueous $NH_4Cl$. The organic phase was dried ($Na_2SO_4$) and concentrated in vacuo. The residue was lyophilized from dioxane to give the title compound (5 mg; 100%) as an oil.

$[M+H]^+=478.2$

EXAMPLE 32

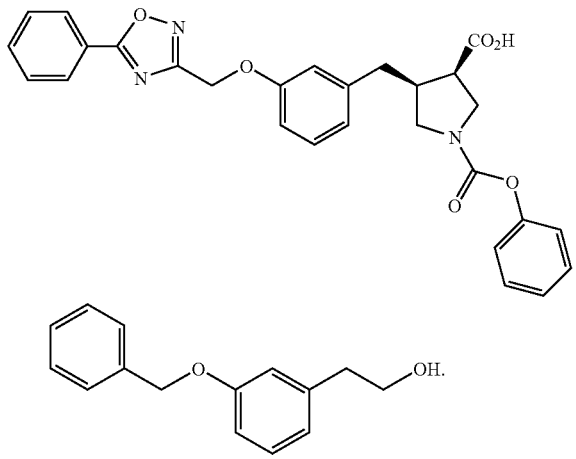

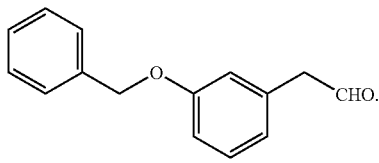

A mixture of 3-hydroxyphenyl ethanol (30.0 g; 0.217 mol), benzyl bromide (28.4 mL; 0.239 mol) and $K_2CO_3$ (45 g; 0.326 mol) in MeCN (500 mL) was stirred at RT for 48 h, then was filtered. The filtrate was concentrated in vacuo; the residue was recrystallized from hexane to give Part A compound (49 g; 99%) as a white solid.

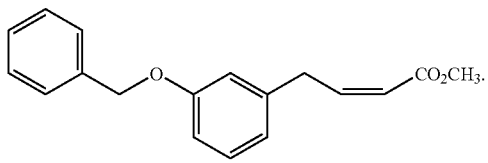

To a mixture of Part A compound (40 g; 175 mmol) and Florisil (180 g) in $CH_2Cl_2$ (1 L) was added pyridinium chlorochromate (40 g; 186 mmol) in portions. The reaction was stirred at RT for 3.5 h, then was filtered through Florisil. To the filtrate was added more pyridinium chlorochromate (20 g; 93 mmol) and Florisil (70 g). The reaction was stirred at RT for another 2 h, then was filtered through Florisil. The filtrate was concentrated in vacuo to give crude Part B compound (34 g; 86%) as an oil.

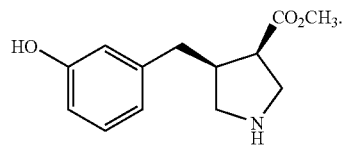

To a -78° C. solution of $(CF_3CH_2O)_2POCH_2CO_2CH_3$ (29.1 g; 91.5 mmol) and 18-crown-6 (25 g; 95.4 mmol) in anhydrous THF (600 mL) under Ar was added dropwise $KN(TMS)_2$ (186 mL of a 1 M solution in toluene). The reaction was stirred at -78° C. for 10 min, after which a solution of Part B compound (17.3 g; 76.5 mmol) in THF (100 mL) was added dropwise by cannula over 15 min. The reaction was stirred at -78° C. for 2 h, then was quenched by cautious slow addition of saturated aqueous $NH_4Cl$ (150 mL). The mixture was allowed to warm to RT, then extracted with EtOAc. The organic phase was washed with $H_2O$ (150 mL), dried ($MgSO_4$) and concentrated in vacuo. The residue was chromatographed ($SiO_2$; stepwise gradient from 10:1 to 4:1 hex:EtOAc) to remove the crown ether. The crude product was chromatographed ($SiO_2$; continuous gradient from 10:1 to 5:1 hex:EtOAc) to give Part C compound (6.5 g; 30%) as a pale yellow oil.

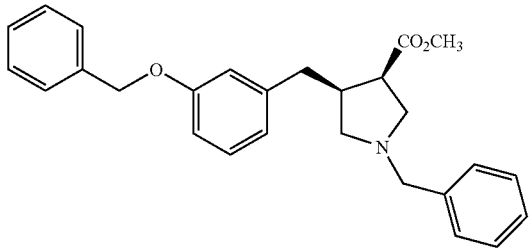

To a 0° C. solution of Part C compound (3.90 g; 13.8 mmol) and Example 1 Part B compound (5.0 g; 20.7 mmol) in toluene (40 mL) was added TFA (200 μL) dropwise. The reaction was stirred at 0° C. for 30 min, then was partitioned between EtOAc (150 mL) and saturated aqueous $NaHCO_3$ (100 mL). The organic phase was washed with brine (100 mL), dried ($MgSO_4$) and concentrated in vacuo. The residue was chromatographed ($SiO_2$; continuous gradient from 4:1 to 1:1 hex:EtOAc) to give Part D compound (5.50 g; 96%) as an oil.

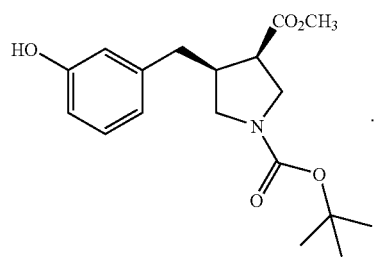

Acetic acid salt

A mixture of Part D compound (5.50 g; 13.3 mmol), 10% Pd/C (300 mg) and HOAc (1.13 mL; 20 mmol) in EtOH (100 mL) was stirred an atmosphere of $H_2$ (balloon) for 26 h. The catalyst was filtered off (Celite®) and the filtrate was concentrated in vacuo to give Part E compound (3.60 g; 92%) as an oil.

A mixture of Part E compound (3.60 g; 12.2 mmol), di-tert butyl dicarbonate (2.66 g; 24.4 mmol) and $NaHCO_3$ (2.05 g; 24.4 mmol) in THF and H₂O (100 mL each) was stirred at RT for 1 h, then was partitioned between EtOAc (150 mL) and H₂O (100 mL). The organic phase was washed with brine (100 mL), dried (MgSO₄) and concentrated in vacuo. The residue was chromatographed (SiO₂; continuous gradient from 4:1 to 3:2 hex:EtOAc) to give Part F compound (3.70 g; 91%) as a syrup.

G

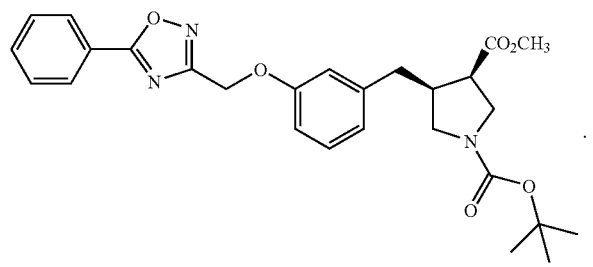

A mixture of Part F compound (150 mg; 0.43 mmol), Example 25 Part C compound (120 mg; 0.62 mmol), and K₂CO₃ (118 mg; 0.86 mmol) in MeCN (6 mL) was heated at 80° C. for 16 h, then was cooled to RT and filtered. The filtrate was concentrated in vacuo and the residue was chromatographed (SiO₂; continuous gradient from 9:1 to 7:3 hex:EtOAc) to give Part G compound (200 mg; 94%) as a syrup.

H

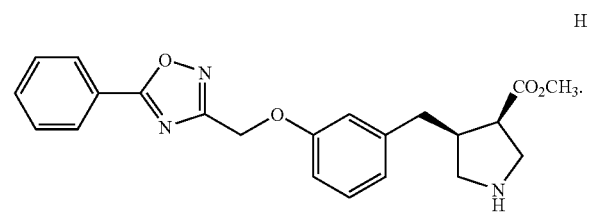

A mixture of Part G compound (200 mg; 0.41 mmol) in HCl/dioxane (1.0 mL of a 4 M solution) and CH₂Cl₂ (4 mL) was stirred at RT for 1 h, then was concentrated in vacuo to give Part H compound (165 mg; 92%) as a white solid which was used in the next step without further purification.

I

A mixture of Part H compound (23 mg; 0.052 mmol), phenyl chloroformate (8 μL; 0.062 mmol) and NaHCO₃ (22 mg; 0.26 mmol) in THF and H₂O (1 mL each) was stirred at RT for 1 h, then was partitioned between H₂O (5 mL) and EtOAc (10 mL). The organic phase was dried (MgSO₄) and concentrated in vacuo. The residue was purified by preparative HPLC (as described for Example 25) to give Part I compound (20 mg; 75%) as a colorless syrup.

J

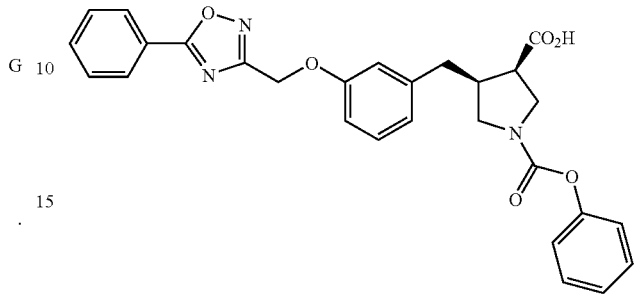

A mixture of Part I compound (20 mg; 0.039 mmol) in conc. HCl (0.2 mL) and HOAc (1 mL) was heated at 70° C. for 18 h, then was cooled to RT and concentrated in vacuo. The residue was purified by preparative HPLC (as described for Example 25) and lyophilized from dioxane to give the title compound (10 mg; 51%) as a white solid.

$[M+H]^+ = 500.0$

EXAMPLE 33

Example 32 Part H compound (23 mg; 0.052 mmol) and ethyl chloroformate (6 μL; 0.062 mmol) were reacted (using the same 2-step sequence as described for the synthesis of Example 32) to give the title compound (7.7 mg; 33% for 2 steps) as a white solid.

$[M+H]^+ = 452.0$

EXAMPLE 34

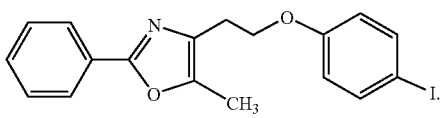

A mixture of 4-iodophenol (3.27 g; 14.9 mmol), K$_2$CO$_3$ (3 g; 21.7 mmol) and the mesylate Example 47 Part A compound (3.0 g; 10.7 mmol) in MeCN (50 mL) was heated at reflux overnight under N$_2$. The reaction was cooled to RT and partitioned between EtOAc and H$_2$O (200 mL each). The organic phase was washed with aqueous NaOH (2×20 mL of a 1 M solution) and H$_2$O, dried (Na$_2$SO$_4$) and concentrated in vacuo. The residue was chromatographed (SiO$_2$; continuous gradient from 100% hex to 7:3 hex:EtOAc over 20 min, then at 7:3 hex:EtOAc for 15 min) to give Part A compound (2.50 g; 57%) as a white solid.

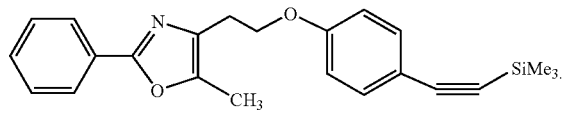

A mixture of Part A compound (2.24 g; 5.53 mmol), Cu(I)I (42 mg; 0.221 mmol), (Ph$_3$P)$_2$PdCl$_2$ (78 mg; 0.11 mmol), K$_2$CO$_3$ (3.05 g; 22.1 mmol) and trimethylsilylacetylene (3.9 mL; 27.7 mmol) in THF (20 mL) was stirred at RT in a sealed tube for 60 h. The dark mixture was filtered, and the filtrate was concentrated in vacuo. The residue was chromatographed (SiO$_2$; continuous gradient from 100% hex to 4:1 hex:EtOAc over 25 min, then at 4:1 hex:EtOAc for 10 min) to give Part B compound (2.04 g; 98%) as a brown solid.

C

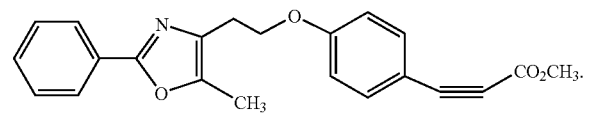

A solution of Part B compound (2.04 g; 5.44 mmol) and tetrabutylammonium fluoride (5.44 mL of a 1 M solution in THF) in THF (60 mL) was stirred at RT for 30 min, then was concentrated in vacuo. The residue was chromatographed (SiO$_2$; 100% hex to 3:1 hex:EtOAc) to give Part C compound (1.50 g; 91%) as a slightly yellow solid.

D

To a −78° C. solution of Part C compound (875 mg; 2.89 mmol) in THF (10 mL) was added dropwise methyllithium (3.0 mL of a 1.4 M solution in Et$_2$O; 4.20 mmol). The reaction was stirred at −78° C. for 30 min, after which dimethyl carbonate (900 µL; 10.6 mmol) was added dropwise. Stirring was continued at −78° C. for 30 min, after which the reaction was allowed to warm to RT (30 min) and stirred at RT for 30 min. Excess saturated aqueous NH$_4$Cl was added to quench the reaction and the mixture was partitioned with EtOAc (150 mL). The organic phase was dried (MgSO$_4$) and concentrated in vacuo. The residue was chromatographed (SiO$_2$; gradient from 100% hex to 3:1 hex:EtOAc over 10 min; 3:1 hex:EtOAc for 5 min, gradient from 3:1 to 2:1 hex:EtOAc over 5 min, then at 2:1 hex:EtOAc for 10 min) to give Part D compound (800 mg; 77% as a white solid).

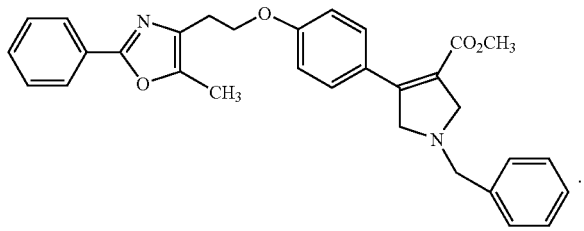

To a RT solution of Part D compound (700 mg; 2.2 mmol) in toluene (5 mL) were successively added TFA (100 µL) and Example 1 Part B compound (678 mg; 2.86 mmol) over 2 min. The reaction was stirred at RT for 10 min, after which additional Example 1 Part B compound (290 mg; 1.23 mmol) was added over 15 min. A final aliquot of Example 1 Part B compound (290 mg; 1.23 mmol) was added over 30 min. At this point (by analytical HPLC) there was 53% desired product, 15% of the bis-addition adduct and 12% unreacted starting material. The mixture was partitioned between EtOAc and saturated NaHCO$_3$ (20 mL each). The organic phase was concentrated in vacuo and chromatographed (SiO$_2$; continuous gradient from 100% hex to 85:15 hex:EtOAc over 15 min, 85:15 hex:EtOAc for 3 min, then continuous gradient from 85:15 to 3:2 hex:EtOAc over 5 min, then at 3:2 hex:EtOAc for 5 min) to give Part E compound (596 mg; 62%) as an viscous oil.

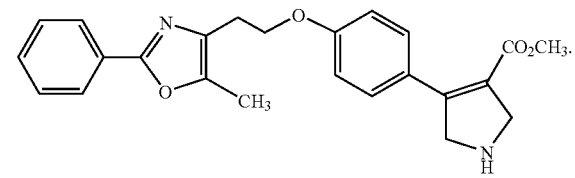

To a −78° C. solution of Part E compound (122 mg; 0.247 mmol) in CH$_2$Cl$_2$ (3 mL) was added CH$_3$CHClOCOCl (53 µL; 0.49 mmol) dropwise. The mixture was stirred at −78° C. for 30 min, then was warmed to RT and stirred at RT for 3 h, then concentrated in vacuo. The residue was dissolved in MeOH (3 mL) and the mixture was stirred at RT for 72 h, then concentrated in vacuo to give crude Part F compound as a foam which was used in the next step without further purification.

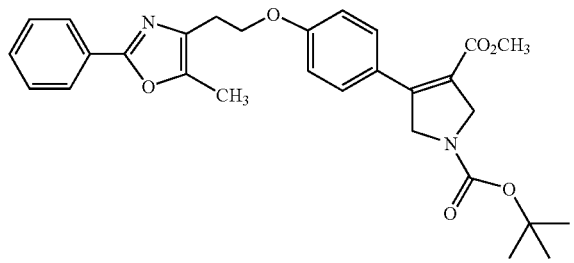

G

A mixture of crude Part F compound, NaHCO₃ (84 mg; 1.0 mmol) and di-tert butyl dicarbonate (84 mg; 0.38 mmol) in THF/H₂O (3 mL of a 1:1 solution) was stirred at RT for 2 h, then was partitioned between EtOAc and H₂O (20 mL). The organic phase was concentrated in vacuo and the residue was chromatographed (SiO₂; continuous gradient from 100% hex to 85:15 hex:EtOAc over 10 min, 85:15 hex:EtOAc for 3 min, 85:15 to 3:2 hex:EtOAc over 10 min and 3:2 hex:EtOAc for 5 min) to give Part G compound (55 mg; 44% for 2 steps) as an oil. In addition Part E compound (30 mg; 25%) was also recovered.

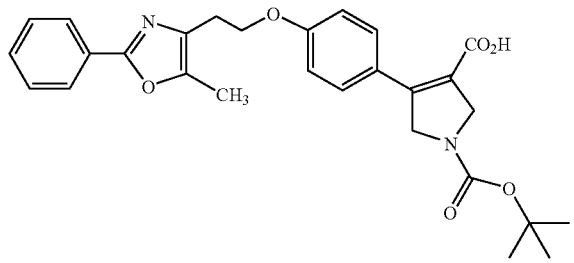

H

A mixture of Part G compound (55 mg; 0.11 mmol) and LiOH.H₂O (10 mg; 0.23 mmol) in THF/H₂O (1.6 mL of a 1:1 solution) was stirred at RT for 16 h, after which the pH was adjusted to ~5 by addition of aqueous 1 M HCl. The mixture was extracted with EtOAc (10 mL). The organic phase was concentrated in vacuo, and the residue was chromatographed (SiO₂; 3:1 hex:EtOAc, then 100% EtOAc, then 10:1 EtOAc:MeOH) to give the title compound (45 mg; 80%) as a foam.
[M+H]⁺=491

EXAMPLE 35

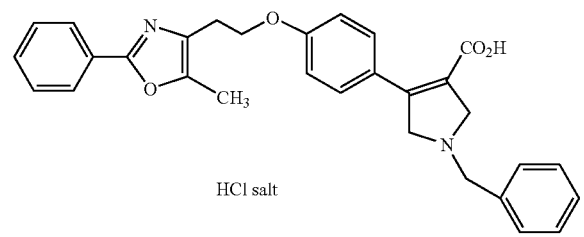

HCl salt

A mixture of Example 34 Part E compound (20 mg; 0.040 mmol) and LiOH.H₂O (8 mg; 0.19 mmol) in THF/H₂O (1.6 mL of a 1:1 solution) was stirred at RT for 20 h, after which the pH was adjusted to ~5 with aqueous 1 M HCl. The THF was removed in vacuo and the mixture was extracted with EtOAc (10 mL). The organic phase was concentrated in vacuo to give a white solid, which was further purified by crystallization from MeOH. This material was dissolved in CH₂Cl₂ (1 mL) and HCl in dioxane (4 drops of a 4 N solution) was added. Volatiles were removed in vacuo to give the title compound (10 mg; 48%) as a white solid.
[M+H]⁺=481

EXAMPLE 36

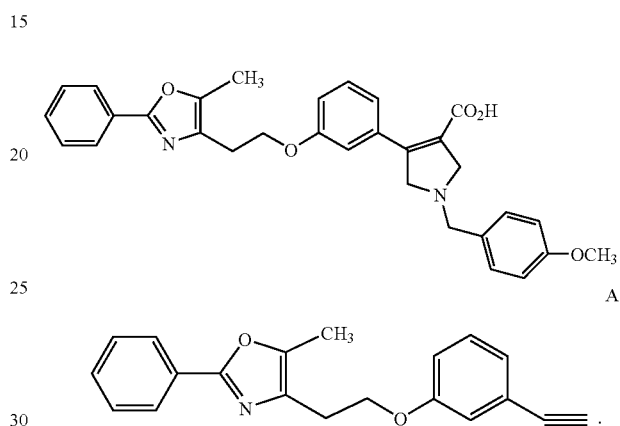

A

A mixture of 3-hydroxyphenylacetylene (1.0 μg; 8.46 mmol), K₂CO₃ (4.0 g; 30 mmol) and the mesylate Example 47 Part A compound (3.0 g; 10.7 mmol) in MeCN (10 mL) was heated at 90° C. for 5 h under N₂. The reaction was cooled to RT and the solids were filtered off; the filtrate was partitioned between EtOAc and H₂O (100 mL each). The organic phase was washed with aqueous HCl and NaOH (10 mL each of a 1 M solution), dried (Na₂SO₄) and concentrated in vacuo. The residue was chromatographed (SiO₂; 3:1 hex:EtOAc) to give Part A compound (1.25 g; 49%) as white crystals.

B.

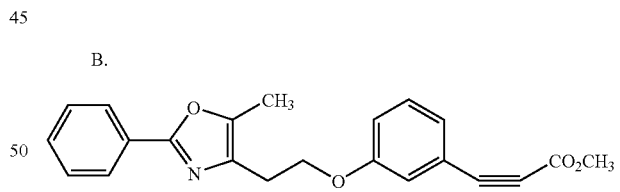

To a −78° C. solution of Part A compound (1.09 g; 3.59 mmol) in anhydrous THF (10 mL) was added methyllithium (3.2 mL of a 1.4 M solution in Et₂O) dropwise. The reaction was stirred at −78° C. for 2 h, after which anhydrous dimethyl carbonate (1 mL; 12 mmol) was added in one portion. The reaction was allowed to warm to RT and stirred at RT for 30 min, after which saturated aqueous NH₄Cl (5 mL) was added. The mixture was partitioned between EtOAc and H₂O (50 mL each). The organic phase was washed with H₂O (2×50 mL), dried (Na₂SO₄) and concentrated in vacuo. The residue was chromatographed (SiO₂; 3:1 hexane:EtOAc) to give Part B compound (1.07 g; 83%) as an oil.

C.

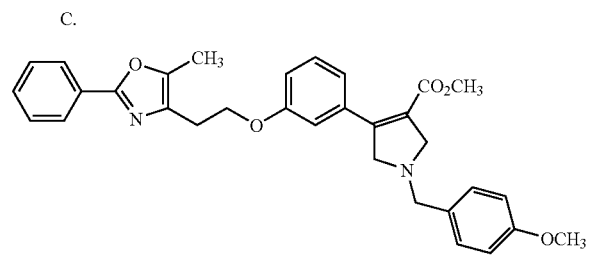

A mixture of Part B compound (1.07 g; 3.0 mmol), Example 17 Part D compound (0.79 g; 3.0 mmol) and TFA (1 drop) in toluene (10 mL) was stirred at RT for 3 h, then was concentrated in vacuo. The residue was chromatographed (SiO$_2$; hex:EtOAc 1:1) to give Part C compound (1.01 g; 64%) as white crystals.

D.

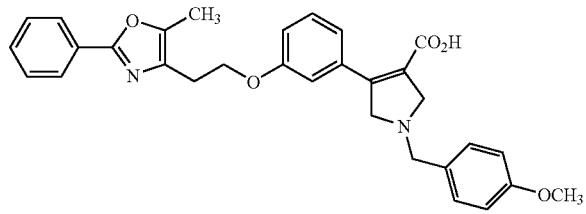

A solution of Part C compound (500 mg; 0.953 mmol) in HOAc/concentrated HCl (5 mL of a 4:1 solution) was stirred at 66° C. for 30 h. The reaction was cooled to RT and partitioned between ice water (100 mL) and EtOAc (20 mL). The aqueous phase was extracted with EtOAc (2×20 mL); the combined organic extracts were washed with H$_2$O (2×50 mL), pH 4 aqueous buffer (50 mL), dried (Na$_2$SO$_4$), and concentrated in vacuo to a volume of ~5 mL. The precipitate was filtered off and dried in vacuo to give the title compound (310 mg; 63%) as a white solid.

[M+H]$^+$=511.2

EXAMPLE 37

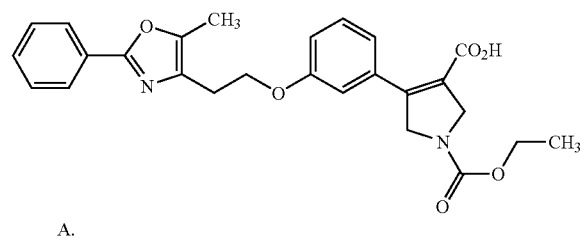

A.

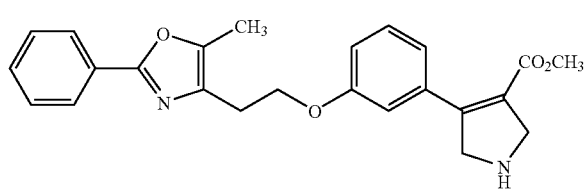

To a −78° C. solution of Example 36 Part C compound (474 mg; 0.90 mmol) in anhydrous CH$_2$Cl$_2$ (0.5 mL) was added CH$_3$CHClOCOCl (140 μL; 1.8 mmol) The reaction mixture was stirred at −78° C. for 30 min, then was warmed to −20° C. and stirred at −20° C. for 1 h. Volatiles were removed in vacuo and MeOH (10 mL) was added; the solution was then stirred at RT for 8 h. Volatiles were removed in vacuo to give crude Part A compound (450 mg; 99%) as an oil which was used in the next step without further purification.

B.

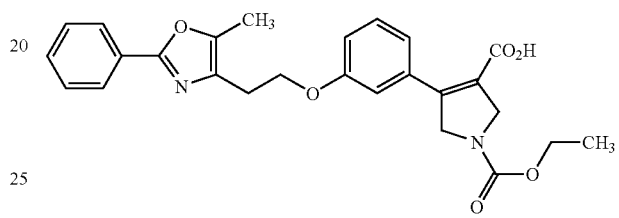

To a 0° C. solution of Part A compound (50 mg; 0.123 mmol) in THF (1 mL) was added saturated aqueous NaHCO$_3$ (1 mL), followed by ethyl chloroformate (22 mg; 0.20 mmol). The reaction was stirred at 0° C. for 15 min, then was partitioned between EtOAc and H$_2$O (5 mL each). The organic phase was washed with H$_2$O (5 mL), dried (MgSO$_4$) and concentrated in vacuo. A mixture of this crude carbamate-ester and acetic acid/concentrated HCl (4:1) was heated at 80° C. for 18 h; the reaction was cooled to RT and concentrated in vacuo. The mixture was extracted with EtOAc (10 mL). The organic phase was concentrated in vacuo, and the residue was purified by preparative HPLC (as described for Example 1) to give the title compound (10 mg; 17%) as a white solid.

[M+H]$^+$=463.2

EXAMPLE 38

The title compound (16 mg; 26%) was prepared from Example 37 Part A compound (50 mg; 0.123 mmol) using the same sequence as for Example 37 except that phenyl chloroformate (31 mg; 0.20 mmol) was used instead of ethyl chloroformate.

EXAMPLE 39

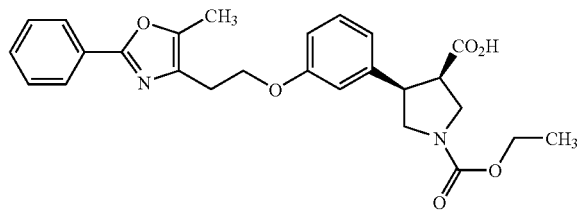

A suspension of Example 37 compound (5 mg; 0.011 mmol) and 10% Pd/C (5 mg) in MeOH (2 mL) was stirred at RT under an atmosphere of $H_2$ (balloon) for 2 h. The catalyst was filtered off using Celite® and the filtrate was concentrated in vacuo. The residue was purified by preparative HPLC (as described for the purification of Example 1) to give the title compound (1.0 mg; 20%) as a white solid.
[M+H]+465.2

EXAMPLE 40

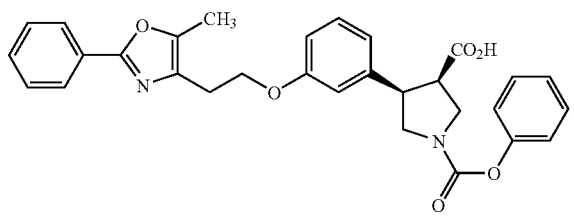

The title compound (3.0 mg; 60%) was prepared from Example 38 compound (5 mg; 0.0098 mmol) according to the procedure described for the synthesis of Example 39.
[M+H]$^+$=513.2

EXAMPLE 41

A.

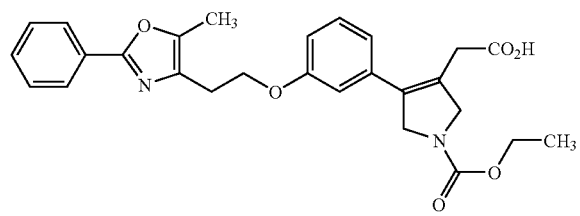

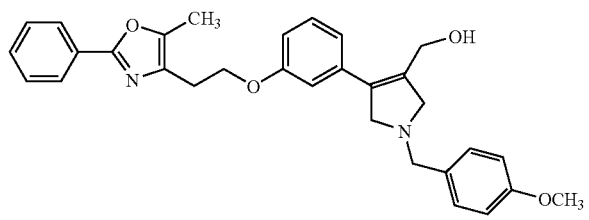

To a −70° C. solution of Example 36 compound (500 mg; 0.952 mmol) in anhydrous THF (10 mL) was added dropwise DIBALH (2.4 mL of a 1 M solution in hexane; 2.4 mmol). The reaction was stirred at −70° C. for 20 min, then was warmed to RT and stirred at RT for 2 h, then cooled to −70° C. and finally quenched by dropwise addition of MeOH (1 mL). The mixture was allowed to warm to RT, then aqueous Rochelle salt (10 mL of a 1 M solution) was added and stirring was continued for 1 h. The mixture was partitioned between $H_2O$ and $Et_2O$ (20 mL each). The aqueous phase was extracted with additional $Et_2O$ (20 mL); the combined organic extracts were dried ($Na_2SO_4$) and concentrated in vacuo. The residue was chromatographed ($SiO_2$; EtOAc:hex:$Et_3N$ 3:1:0.08) to give Part A compound (374 mg; 79%) as an oil.

B.

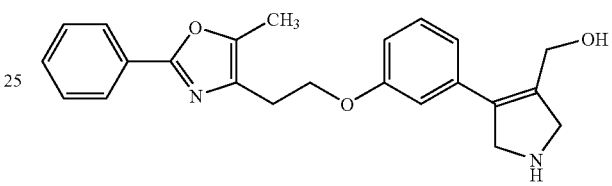

To a −78° C. solution of Part A compound (261 mg; 0.53 mmol) in $CH_2Cl_2$ (5 mL) was added $CH_3CHClOCOCl$ (143 mg; 1.0 mmol). The reaction mixture was stirred at −78° C. for 30 min, then was allowed to warm to RT and stirred at RT for 1 h. At this point, HPLC indicated that all starting material had been consumed. Volatiles were removed in vacuo and MeOH (10 mL) was added; the solution was then stirred at RT for 8 h. Volatiles were removed in vacuo to give crude Part B compound (100 mg; 51%) as an oil which was used in the next step without further purification.

C.

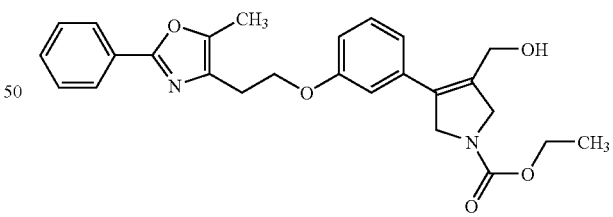

A solution of crude Part B compound (100 mg; 0.27 mmol) and ethyl chloroformate (47 μL; 0.50 mmol) in saturated aqueous $NaHCO_3$ (2 mL) and THF (1 mL) was stirred at 0° C. for 15 min, then was partitioned between $H_2O$ and EtOAC (5 mL each). The organic phase was washed with $H_2O$ (5 mL), dried ($Na_2SO_4$) and concentrated in vacuo. The residue was purified by preparative HPLC (as described for the purification of Example 1) to give Part C compound (30 mg; 25%) as an oil.

D.

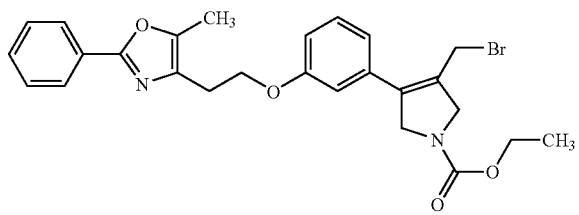

To a 0° C. mixture of Part C compound (30 mg; 0.067 mmol) and polyvinylpyridine (300 mg) in CH$_2$Cl$_2$ (1 mL) was added phosphorus tribromide (134 μL of a 1 M solution in CH$_2$Cl$_2$; 0.134 mmol) dropwise over 5 min. The reaction was allowed to warm to RT and stirred at RT for 30 min, then was filtered. The filtrate was partitioned between CH$_2$Cl$_2$ (20 mL) and H$_2$O (50 mL). The organic phase was washed with saturated aqueous NaHCO$_3$ (2×20 mL), dried (Na$_2$SO$_4$) and concentrated in vacuo. The residue was chromatographed (SiO$_2$; hex:EtOAc 3:1) to give Part D compound (13 mg; 38%) as an oil.

E.

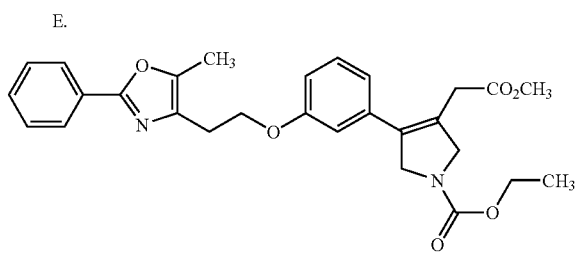

A mixture of Part D compound (13 mg; 0.025 mmol), (Ph$_3$P)$_4$Pd° (5 mg; 4.3×10$^{-3}$ mmol) and KHCO$_3$ (100 mg; 1.0 mmol) in anhydrous MeOH (5 mL) in an autoclave was pressurized to 100 psi with carbon monoxide (flushed 3× with CO). The reaction mixture was stirred at RT for 3 days, after which the CO gas was released and the mixture was filtered. The filtrate was concentrated in vacuo and the residue was chromatographed (SiO$_2$; 3:1 hex:EtOAc) to give Part E compound (9.3 mg; 76%) as an oil.

F.

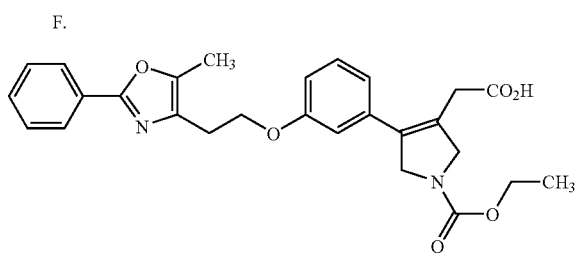

A mixture of Part E compound (9.3 mg; 0.019 mmol) and aqueous LiOH (0.5 mL of a 1 N solution) in THF (1 mL) was stirred at RT for 2 h, after which the reaction was partitioned between EtOAc (10 mL) and aqueous 1 M HCl (5 mL). The organic phase was washed with H$_2$O (3×10 mL) and concentrated in vacuo. The residue was purified by preparative HPLC (as described for Example 1) to give the title compound (8.3 mg; 92%) as an oil.

[M+H]$^+$=477.2

EXAMPLE 42

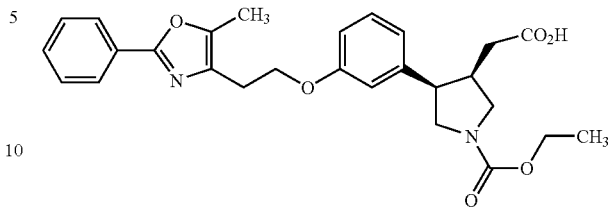

A suspension of Example 41 compound (4 mg; 0.01 mmol) and 10% Pd/C (2 mg) in MeOH (1 mL) was stirred at RT under an atmosphere of H$_2$ (balloon) for 2 h. The catalyst was filtered off on Celite® and the filtrate was concentrated in vacuo to give the title compound (3 mg; 60%) as a white solid.

[M+H]$^+$=479.2

EXAMPLE 43

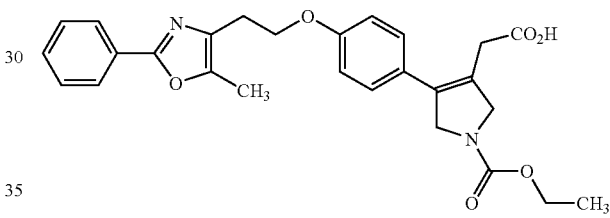

A.

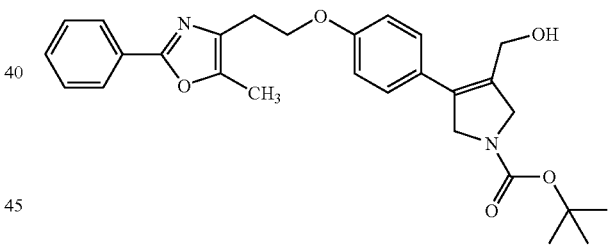

To a −78° C. solution of Example 34 Part G compound (420 mg; 0.833 mmol) in anhydrous THF (8 mL) under argon was added dropwise DIBALH (1.8 mL of a 1 M solution in hexane; 1.8 mmol). The reaction was stirred at −78° C. for 5 min, then was allowed to warm to RT and stirred at RT for 30 min. Since starting material still remained, the reaction was cooled to −78° C. and more DIBALH (0.4 mL of a 1 M solution in hexane; 0.4 mmol) was added, after which the reaction was warmed to RT and stirred at RT for 1.5 h. The reaction was cooled to −78° C. and MeOH (0.5 mL) was added dropwise, followed by Rochelle's salt (2.35 g in 10 mL H$_2$O). The mixture was allowed to warm to RT and stirred at RT for 1.5 h, after which EtOAc (20 mL) was added and stirring was continued for 10 min. The organic phase was concentrated in vacuo and chromatographed (SiO$_2$; 2:1 to 1:2 hex:EtOAc, then 100% EtOAc) to give Part A compound (352 mg; 88%) as a solid foam.

B.

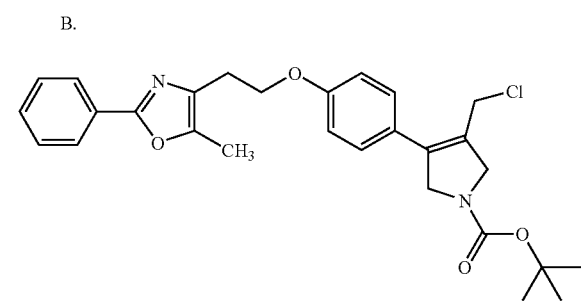

To a RT solution of Part A compound (25 mg; 0.053 mmol) in $CH_2Cl_2$ (0.5 mL) was added $CCl_4$ (35 mg; 0.228 mmol) and $Ph_3P$ (24 mg; 0.092 mmol). The reaction was stirred at RT overnight and concentrated in vacuo; the residue was chromatographed ($SiO_2$; hex to 2:1 hex:EtOAc) to give Part B compound (10 mg; 38%) as an oil.

C.

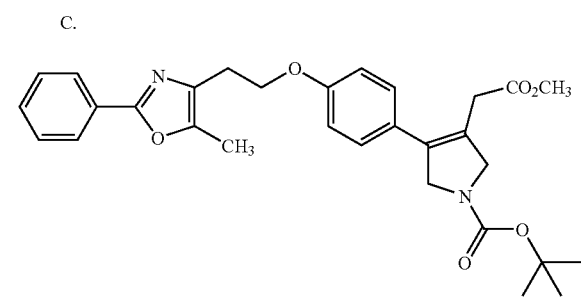

To a mixture of $(Ph_3P)_4Pd°$ (9 mg; 0.0078 mmol) and $KHCO_3$ (50 mg; 0.50 mmol) in anhydrous MeOH (1 mL) was added a solution of Part C compound (10 mg; 0.020 mmol) in EtOAc (0.8 mL). The reaction mixture was place in an autoclave and pressurized to 100 psi with carbon monoxide. The reaction mixture was stirred at RT for 2 h, after which the CO gas was released and the mixture was filtered. The filtrate was concentrated in vacuo and the residue was chromatographed ($SiO_2$; 2:1 hex:EtOAc) to give Part C compound (8 mg; 76%) as an oil.

D.

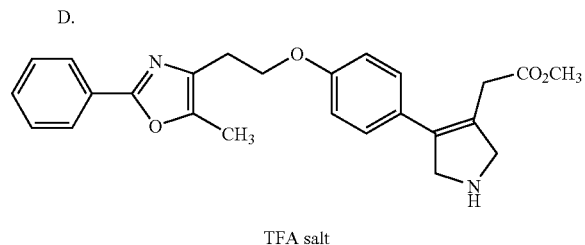

TFA salt

A solution of Part C compound (12 mg; 0.023 mmol) in TFA (0.2 mL) and $CH_2Cl_2$ (1 mL) was stirred at RT for 2.5 h, then was concentrated in vacuo to give Part D compound as an oil, which was used in the next step without further purification.

E.

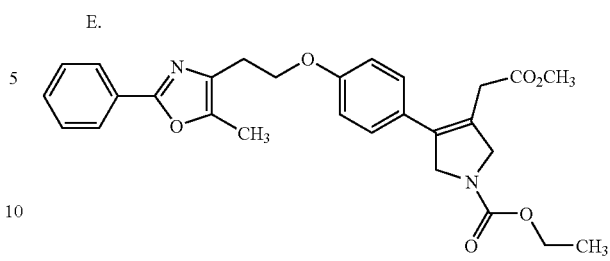

To a solution of Part D compound in THF (0.7 mL) was added a solution of $NaHCO_3$ (8 mg; 0.095 mmol) in $H_2O$ (0.7 mL), followed by ethyl chloroformate (3 µL; 0.030 mmol). The reaction was stirred at RT for 2.5 h, then partitioned between EtOAc and $H_2O$ (10 mL each). The organic phase was dried ($MgSO_4$) and concentrated in vacuo. The residue was chromatographed ($SiO_2$; 2:1 hex: EtOAc) to give Part E compound (9.5 mg; 84% for 2 steps) as an oil.

F.

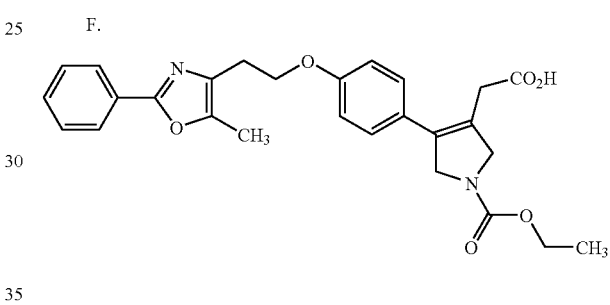

A mixture of Part E compound (9.5 mg; 0.019 mmol) and $LiOH.H_2O$ (7 mg; 0.17 mmol) in $THF/H_2O$ (1.4 mL of a 1:1 solution) was stirred at RT for 2 h, after which the pH was adjusted to ~5 with aqueous 1 M HCl. The mixture was extracted with EtOAc (10 mL). The organic phase was concentrated in vacuo, and the residue was chromatographed ($SiO_2$; 1:1 hex:EtOAc, 100% EtOAc, then 10:1 EtOAc:MeOH), then further purified by preparative HPLC (conditions as described for Example 1 compound, except that a continuous gradient from 30:70 A:B to 100% B over 10 min was used) to give the title compound (4.2 mg; 46%) as a white foam.

$[M+H]^+=477$

EXAMPLE 44

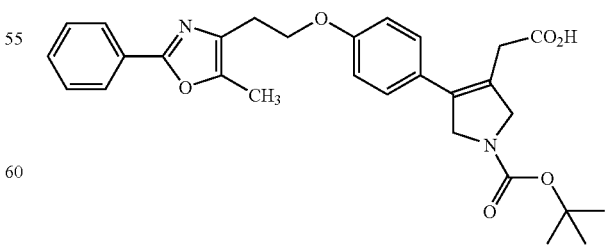

A mixture of Example 43 Part C compound (10 mg; 0.019 mmol) and $LiOH.H_2O$ (2 mg; 0.048 mmol) in $THF/H_2O$ (1.4 mL of a 1:1 solution) was stirred at RT for 16 h, after which the pH was adjusted to ~5 with aqueous 1 M HCl. The mixture was extracted with EtOAc (10 mL). The organic phase was concentrated in vacuo, and the residue was chromatographed (SiO$_2$; 3:1 hex:EtOAc, then 100% EtOAc, then 10:1 EtOAc:MeOH) to give the title compound (6 mg; 62%) as a foam.

[M+H]$^+$=504.2

EXAMPLE 45

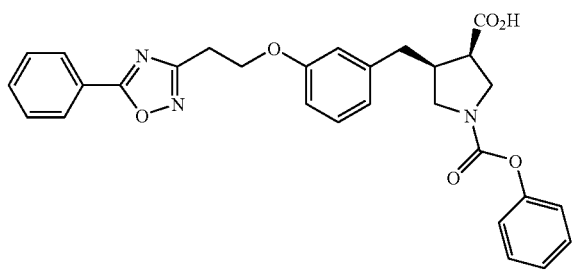

A.

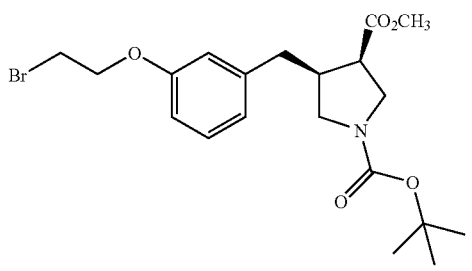

A mixture of Example 32 Part F compound (1.20 g; 3.6 mmol), K$_2$CO$_3$ (1.0 g; 7.2 mmol) and 1,2 dibromoethane (3.1 mL; 36 mmol) in MeCN (50 mL) was heated at reflux for 46 h. Two additional portions of K$_2$CO$_3$ (0.5 g at 12 & 36 h) were added during this time. The reaction was cooled to RT and filtered; the filtrate was concentrated in vacuo. The residue was chromatographed (SiO$_2$; continuous gradient from 100% hex to 3:7 hex:EtOAc) to give Part A compound (1.10 g; 70%) as a syrup.

B.

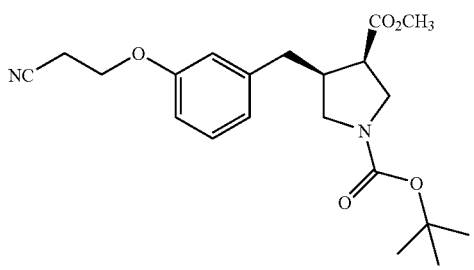

A mixture of Part A compound (1.05 g; 2.4 mmol) and tetrabutylammonium cyanide (1.27 g; 4.8 mmol) in CH$_2$Cl$_2$ (25 mL) was stirred at RT for 18 h, then was concentrated in vacuo. The residue was chromatographed (SiO$_2$; stepwise gradient from 4:1 to 3:2 hex:EtOAc) to give Part B compound (900 mg; 98%) as a syrup. [M+Na]$^+$=411.2

C.

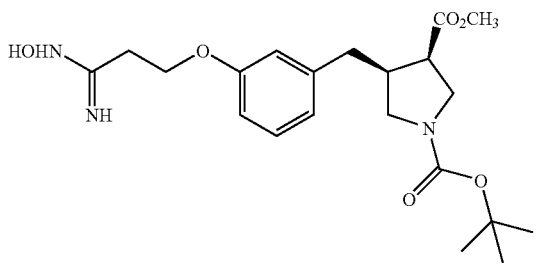

A mixture of Part B compound (200 mg; 0.52 mmol), aqueous NH$_2$OH (136 mg of a 50% solution) in MeOH (6 mL) and H$_2$O (3 mL) was stirred at 95° C. for 3 h, then was cooled to RT and concentrated in vacuo. The residue was partitioned between H$_2$O and EtOAc; the organic phase was dried (MgSO$_4$) and concentrated in vacuo to give crude Part C compound (200 mg; 92%) as a white solid, which was used in the next step without further purification. [M+H]+ 422.3

D.

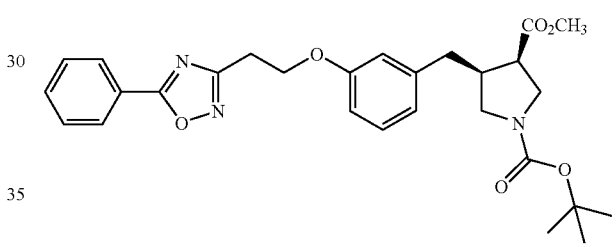

A mixture of Part C compound (90 mg; 0.22 mmol) and benzoyl chloride (30 μL; 0.26 mmol) in pyridine (5 mL) was stirred at reflux for 4 h, then was cooled to RT and concentrated in vacuo. The residue was partitioned between EtOAc (10 mL) and H$_2$O (5 mL); the organic phase was washed with brine (5 mL), dried (MgSO$_4$) and concentrated in vacuo. The residue was chromatographed (SiO$_2$; continuous gradient from 9:1 to 5:1 hex:EtOAc) to give Part D compound (70 mg; 65%) as a syrup.

[M+H]$^+$=508.3

E.

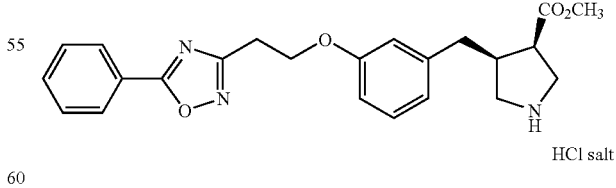

HCl salt

A mixture of Part D compound (70 mg; 0.14 mmol) in HCl/dioxane (1 mL of a 4 M solution; 4.0 mmol) and CH$_2$Cl$_2$ (3 mL) was stirred at RT for 2.5 h, then was concentrated in vacuo to give Part E compound (50 mg; 79%), which was used in the next step without further purification.

F.

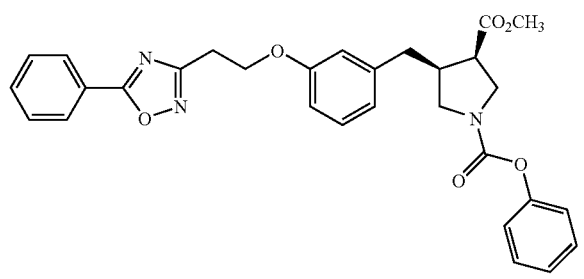

A mixture of Part E compound (25 mg; 0.055 mmol), phenyl chloroformate (8 μL; 0.11 mmol) and NaHCO$_3$ (23 mg; 0.28 mmol) in THF/H$_2$O (2 mL of a 1:1 solution) was stirred at RT for 1 h, then was partitioned between EtOAc and H$_2$O (5 mL each). The organic phase was dried (MgSO$_4$) and concentrated in vacuo. The residue was purified by preparative HPLC (as described for the purification of Example 26) to give Part F compound (19 mg; 66%) as a syrup. [M+H]$^+$=528.2

G.

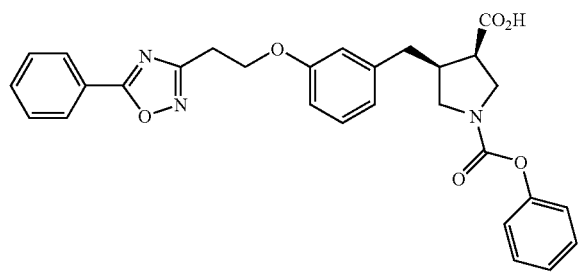

A mixture of Part F compound (19 mg; 0.036 mmol) in concentrated HCl/glacial HOAc (2 mL of a 1:4 solution) was stirred at 70° C. for 16 h, then was cooled to RT and concentrated in vacuo. The residue was purified by preparative HPLC (as described for the purification of Part F compound) and lyophilized from dioxane to give the title compound (17 mg; 92%) as a white solid.

[M+H]$^+$=514.2

EXAMPLE 46

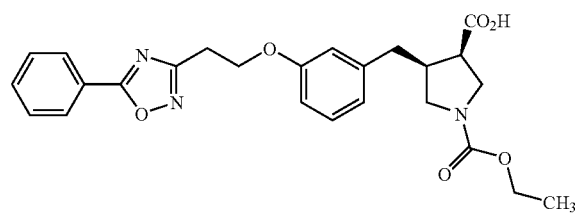

-continued

A.

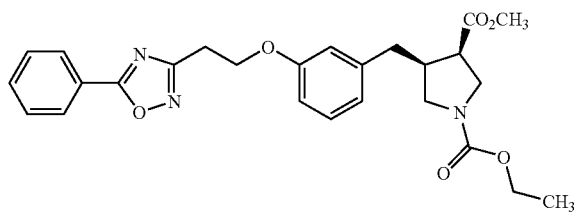

A mixture of Example 45 Part E compound (25 mg; 0.055 mmol), phenyl chloroformate (6 μL; 0.11 mmol) and NaHCO$_3$ (23 mg; 0.28 mmol) in THF/H$_2$O (2 mL of a 1:1 solution) was stirred at RT for 1 h, then was partitioned between EtOAc and H$_2$O (5 mL each). The organic phase was dried (MgSO$_4$) and concentrated in vacuo. The residue was purified by preparative HPLC (as described for the purification of Example 26) to give Part A compound (18 mg; 69%) as a syrup. [M+H]$^+$=480.2

B

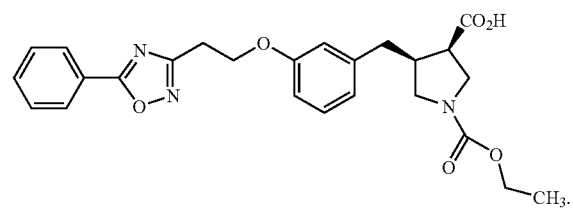

A mixture of Part A compound (18 mg; 0.038 mmol) in concentrated HCl/glacial HOAc (2 mL of a 1:4 solution) was stirred at 70° C. for 16 h, then was cooled to RT and concentrated in vacuo. The residue was purified by preparative HPLC (as described for the purification of Part F compound) and lyophilized from dioxane to give the title compound (17 mg; 97%) as a white solid.

[M+H]$^+$=466.2

EXAMPLE 47

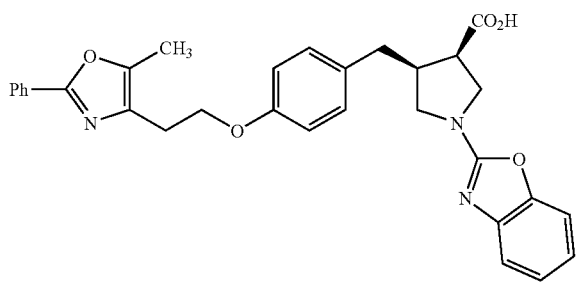

A

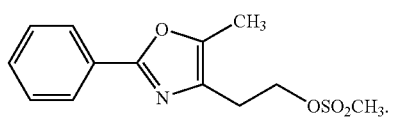

To a −5° C. solution of 5-phenyl-2-methyl-oxazole-4-ethanol (20.0 g, 0.098 mol) in CH$_2$Cl$_2$ (100 mL) was added methanesulfonyl chloride (12.40 g, 0.108 mol) in one portion (exothermic reaction). After recooling to −5° C., Et$_3$N .(11.1 g, 0.110 mol) was added slowly over 30 min (internal temperature <3° C.). The reaction was allowed to warm to RT and stirred for 1 h (reaction monitored by analytical HPLC), at which point starting material had been consumed. The reaction was washed with aqueous HCl (2×50 mL of a 3N solution). The combined aqueous layers were extracted with CH$_2$Cl$_2$ (50 mL). The combined organic extracts were successively washed with satd. aqueous NaHCO$_3$ and brine (50 mL each), dried (Na$_2$SO$_4$), and concentrated to ~30mL volume. Methyl tert-butyl ether (120 mL) was added and the mixture was stirred; a white solid was formed. The mixture was cooled to −20° C. for complete crystallization. The product was filtered and vacuum-dried to give the product mesylate (23.3 g, 85%) as a white solid. The mother liquor was concentrated in vacuo and recrystallized from methyl tert butyl ether/heptane to give a second crop of product mesylate (3.3 g, 12%; total yield=97%).

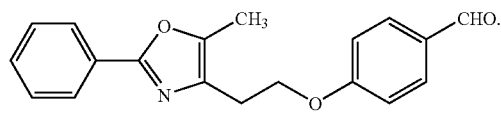

B

A mixture of Part A compound (13.6 g, 0.048 mol), 4-hydroxybenzaldehyde (7.09 g, 0.058 mol) and K$_2$CO$_3$ (9.95 g, 0.072 mol) in DMF (110 mL) was heated at 100° C. for 2 h (reaction complete by analytical HPLC). The mixture was allowed to cool to RT and then poured into ice-water (400 mL) and stirred for 30 min. The solid product was filtered and washed with cold water (3×25 mL) and dried in vacuo at 50°-60° C. overnight. The crude product was crystallized from MTBE-Hexane to give (12.2 g, 82%; 2 crops) Part B compound as a white solid.

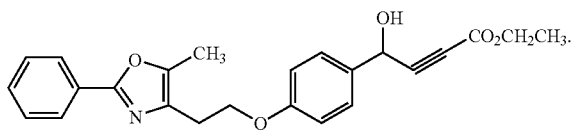

C

To a RT solution of Part B compound (2.70 g; 8.80 mmol), ethyl trimethylsilylpropynoate (2.0 mL; 10.5 mmol) in CH$_2$Cl$_2$ (40 mL) was added KF (570 mg; 9.8 mmol) and catalytic 18-crown-6 (50 mg; 0.20 mmol). The reaction mixture was stirred at 45° C. for 18 h, at which point the reaction was complete by analytical HPLC. The reaction was extracted with aqueous 1 N HCl, dried (Na$_2$SO$_4$) and concentrated in vacuo. MeOH (50 mL) and TFA (2 mL) were added and the mixture was stirred at RT for 4 h, then concentrated in vacuo and partitioned between Et$_2$O and saturated aqueous NaHCO$_3$. The organic phase was dried (Na$_2$SO$_4$) and concentrated in vacuo to give Part C compound (3.50 g; 90%) which was used in the next step without further purification.

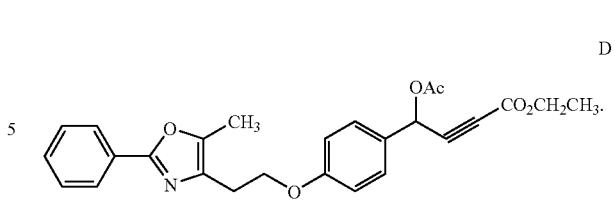

D

To a 0° C. solution of Part C compound (3.50 g; 8.6 mmol) in CH$_2$Cl$_2$ (20 mL) were successively added pyridine (1.0 mL; 12.3 mmol) and acetyl chloride (0.8 mL; 11.2 mmol). The reaction was stirred at 0° C. for 30 min, then extracted with aqueous 10% HCl and saturated aqueous NaHCO$_3$. The organic phase was dried (MgSO$_4$) and concentrated in vacuo to give Part D compound (4.0 g; 98%) as an oil which was used in the next step without further purification.

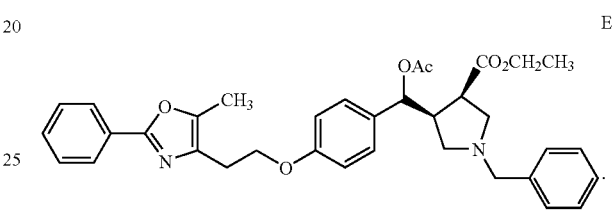

E

To a RT solution of Part D compound (4.0 g; 8.9 mmol) and Example 1 Part B compound (3.0 g; 12.6 mmol) in toluene (15 mL) was slowly added TFA (100 μL). An exothermic reaction ensued, and the reaction was stirred at RT for 3 h, then was concentrated in vacuo. The residue was chromatographed (SiO$_2$; continuous gradient from 100% hex to 100% EtOAc) to give Part E compound (2.5 g; 48%) as an oil.

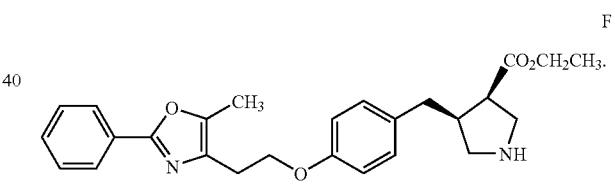

F

A mixture of Part E compound (2.50 g; 4.3 mmol) and 10% Pd/C (500 mg) in glacial HOAc (20 mL) was stirred under an atmosphere of H$_2$ (65 psi) in a pressurized vessel for 48 h. The catalyst was filtered off and the filtrate was concentrated in vacuo. The residue was partitioned between EtOAc and saturated aqueous NaHCO$_3$. The organic phase was dried (Na$_2$SO$_4$) and concentrated in vacuo to give Part F compound (1.70 g; 90%; acetic acid salt) as an oil.

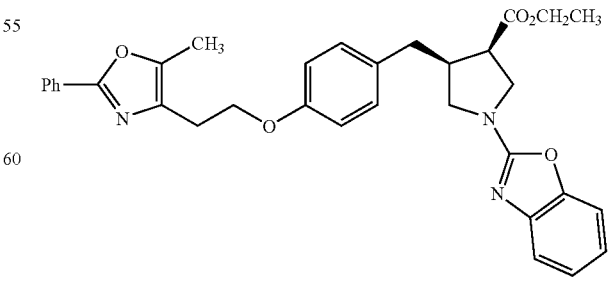

A mixture of Part F compound (25 mg; 0.057 mmol), 2-chlorobenzoxazole (10 mg; 0.065 mmol) and Et$_3$N (20 μL;

0.14 mmol) in toluene (1 mL) was stirred at 120° C. in a sealed tube for 3 h, then was cooled to RT and concentrated in vacuo. The residue was partitioned between Et₂O and saturated aqueous NaHCO₃; the organic phase was dried (MgSO₄) and concentrated in vacuo. The residue was chromatographed (SiO₂; continuous gradient from 100% hex to 100% EtOAc) to give Part G compound (20 mg; 63%) as an oil.

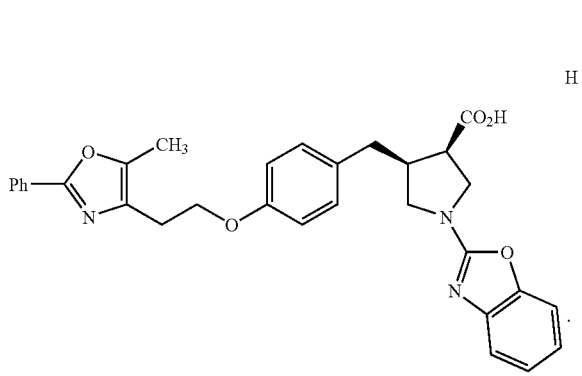

H

A mixture of Part G compound (10 mg; 0.018 mmol) in glacial HOAc (1 mL) and 20% aqueous HCl (0.25 mL) was heated at 80° C. for 18 h, then was cooled to RT and concentrated in vacuo. The residue was partitioned between CH₂Cl₂ and saturated aqueous NH₄Cl. The organic phase was dried (Na₂SO₄) and concentrated in vacuo; the residue was purified by preparative HPLC (as described for the purification of Example 26) and lyophilized from H₂O to give the title compound (5 mg; 55%) as a white solid.

[M+H]⁺=524.6

¹H NMR (CD₃OD) δ 7.85 (m, 2H), 7.37 (m, 4H), 7.20 (m, 2H), 7.07 (m, 3H), 6.79 (d, J=8.8 Hz, 2H), 4.12 (t, J=6.4 Hz, 2H), 3.95 (m, 1 h), 3.80 (m, 1H), 3.55 (m, 1H), 3.45 (m, 1H), 3.30 (m, 1H), 2.87 (m, 4H), 2.45 (m, 1H).

EXAMPLE 48

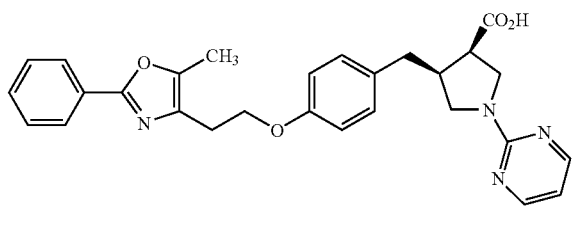

A

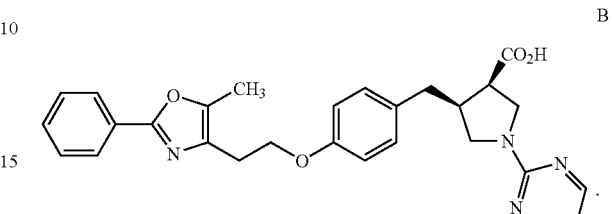

A mixture of Example 47 Part F compound (17 mg; 0.039 mmol) and 2-chloro-pyrimidine (25 mg; 0.22 mmol) and Et₃N (30 μL; 0.22 mmol) was heated in a sealed tube at 130° C. for 3 h, then was cooled to RT and concentrated in vacuo. The residue was partitioned between Et₂O and saturated aqueous NaHCO₃ (20 mL each). The organic phase was dried (MgSO₄) and concentrated in vacuo to give crude Part A compound, which was used in the next step without further purification.

B

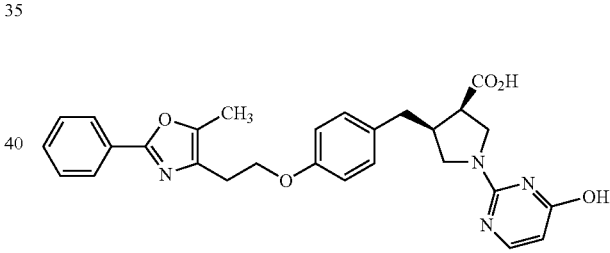

A mixture of crude Part A compound in glacial HOAc (1 mL) and 20% aqueous HCl (0.25 mL) was stirred at 85° C. for 18 h, then was cooled to RT and concentrated in vacuo. The residue was partitioned between CH₂Cl₂ and saturated aqueous NH₄Cl. The organic phase was dried (Na₂SO₄) and concentrated in vacuo; the residue was purified by preparative HPLC (as described for the purification of Example 1 except that an 8 min gradient was employed instead of a 10 min gradient) and lyophilized from H₂O to give the title compound (10 mg; 50%) as a brown solid.

[M+H]⁺=485.2

EXAMPLE 49

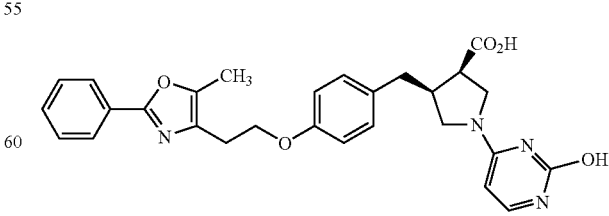

The title compound (1.2 mg; 4%) was prepared from Example 47 Part F compound (25 mg; 0.058 mmol) and 2,4-dichloro-pyrimidine (10 mg; 0.067 mmol) using the same procedure as for the preparation of Example 48.

[M+H]⁺=501.2

Also recovered was 0.8 mg (3%) of the regioisomeric product Example 49A compound

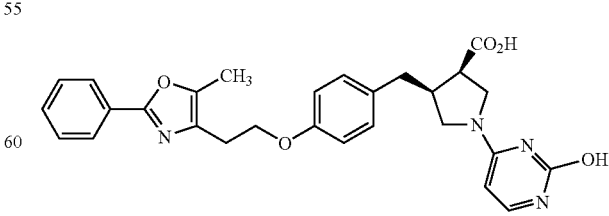

Example 49A compound

[M+H]⁺=501.2

EXAMPLE 50

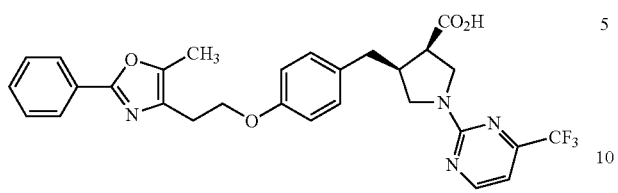

The title compound (15 mg; 50%) was prepared from Example 47 Part F compound (25 mg; 0.057 mol) and 2-chloro-4-trifluoromethyl-pyrimidine (10 mg; 0.054 mmol) using the same sequence as described for the synthesis of Example 48.

[M+H]$^+$=553.2

EXAMPLE 51

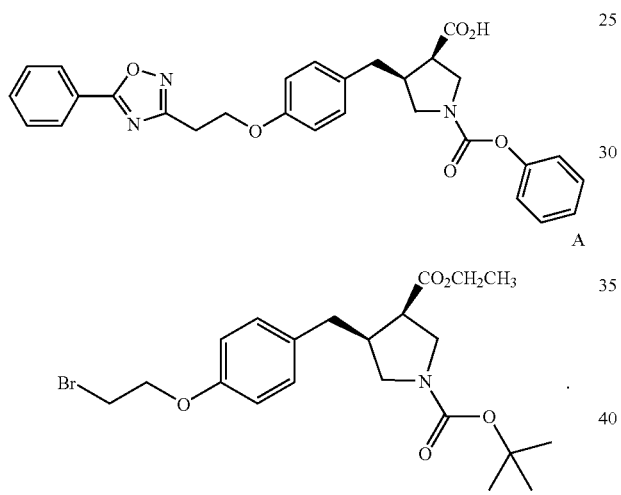

A

A mixture of Example 23 Part E compound (1.05 g; 3.0 mmol), K$_2$CO$_3$ (1.66 g; 12 mmol) and 1,2 dibromoethane (2.6 mL; 30 mmol) in MeCN (25 mL) was heated at reflux for 40 h. Two additional portions of K$_2$CO$_3$ (1.5 g at 12 and 36 h) were added during this time. The reaction was cooled to RT and filtered; the filtrate was concentrated in vacuo. The residue was chromatographed (SiO$_2$; stepwise gradient from 9:1 to 3:1 hex:EtOAc) to give Part A compound (1.05 g; 76%) as a syrup.

B

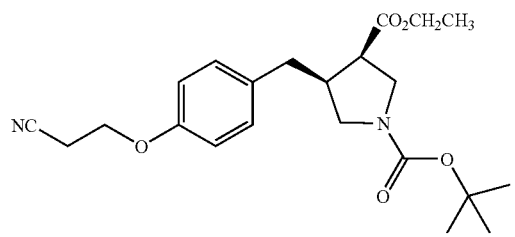

A mixture of Part A compound (1.04 g; 2.3 mmol) and tetrabutylammonium cyanide (1.23 g; 4.6 mmol) in CH$_2$Cl$_2$ (10 mL) was stirred at RT for 64 h, then was concentrated in vacuo. The residue was chromatographed (SiO$_2$; stepwise gradient from 9:1 to 7:3 hex:EtOAc) to give Part B compound (860 mg; 94%) as a syrup. [M+H]$^+$=403.4

C

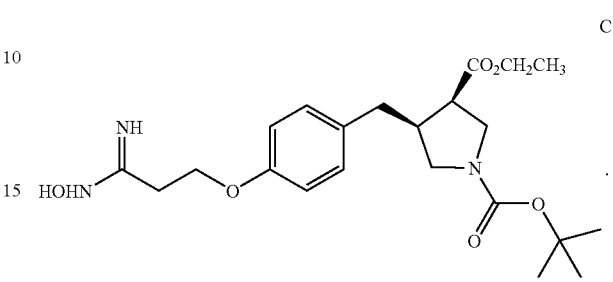

A mixture of Part B compound (160 mg; 0.40 mmol), aqueous NH$_2$OH (105 mg of a 50% solution) in MeOH (4 mL) and H$_2$O (2 mL) was stirred at 95° C. for 3 h, then was cooled to RT and concentrated in vacuo. The residue was partitioned between H$_2$O and EtOAc; the organic phase was dried (MgSO$_4$) and concentrated in vacuo to give crude Part C compound (165 mg; 95%) as a white solid, which was used in the next step without further purification. [M+H]$^+$=436.4

D

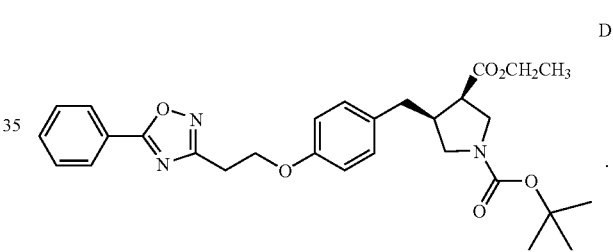

A mixture of Part C compound (95 mg; 0.22 mmol) and benzoyl chloride (30 µL; 0.26 mmol) in pyridine (5 mL) was stirred at 130° C. for 4 h, then was cooled to RT and concentrated in vacuo. The residue was partitioned between EtOAc and aqueous 1 M HCl (4 mL each); the organic phase was washed with brine (4 mL), dried (MgSO$_4$) and concentrated in vacuo. The residue was chromatographed (SiO$_2$; stepwise gradient from 9:1 to 4:1 hex:EtOAc) to give Part D compound (85 mg; 75%) as a syrup. [M+H]$^+$=522.4

E

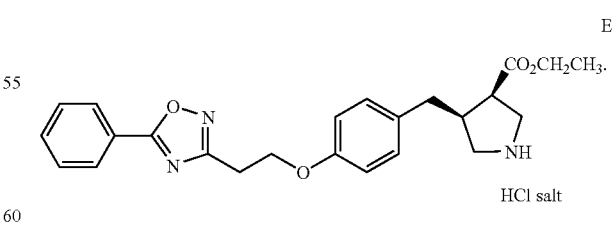

HCl salt

A mixture of Part D compound (85 mg; 0.16 mmol) in HCl/dioxane (0.6 mL of a 4 M solution; 2.4 mmol) and CH$_2$Cl$_2$ (3 mL) was stirred at RT for 2 h, then was concentrated in vacuo to give Part E compound (75 mg; 100%) as a white solid, which was used in the next step without further purification.

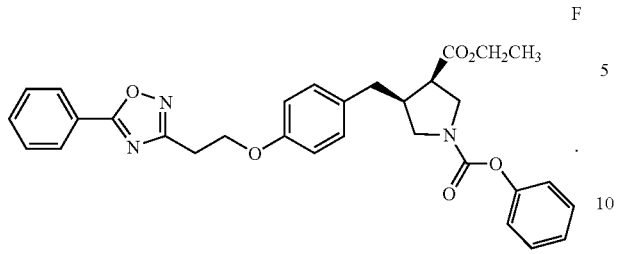

F

A mixture of Part E compound (25 mg; 0.055 mmol), phenyl chloroformate (8 µL; 0.11 mmol) and NaHCO₃ (23 mg; 0.28 mmol) in THF/H₂O (2 mL of a 1:1 solution) was stirred at RT for 1 h, then was partitioned between EtOAc and H₂O (4 mL each) The organic phase was dried (MgSO₄) and concentrated in vacuo. The residue was purified by preparative HPLC (as described for the purification of Example 26) to give Part F compound (21 mg; 71%) as a solid.

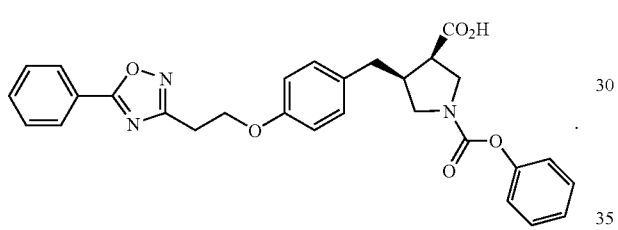

G

A mixture of Part F compound (21 mg; 0.039 mmol) in concentrated HCl/glacial HOAc (2.4 mL of a 1:5 solution) was stirred at 70° C. for 16 h, then was cooled to RT and concentrated in vacuo. The residue was purified by preparative HPLC (as described for the purification of Part F compound) and lyophilized from dioxane to give the title compound (14 mg; 70%) as a white solid.

$[M+H]^+=514.2$

EXAMPLE 52

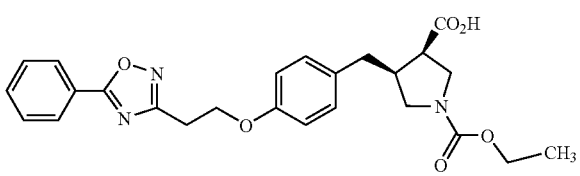

The 2-step sequence used to synthesize Example 51 from Example 51 Part E compound was also used to prepare the title compound (15 mg; 59% for 2 steps) from Example 51 Part E compound (25 mg; 0.055 mmol) and ethyl chloroformate (6 µL; 0.066 mmol).

$[M+H]^+=466.2$

EXAMPLE 53

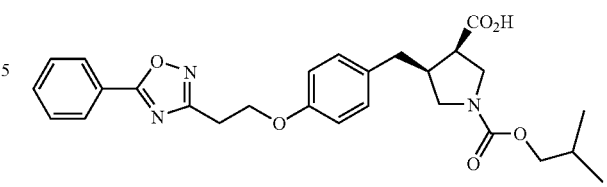

The 2-step sequence used to synthesize Example 51 from Example 51 Part E compound was also used to prepare the title compound (15 mg; 52% for 2 steps) from Example 0.51 Part E compound (25 mg; 0.055 mmol) and isobutyl chloroformate (9 µL; 0.066 mmol).

$[M+H]^+=494.2$

EXAMPLE 54

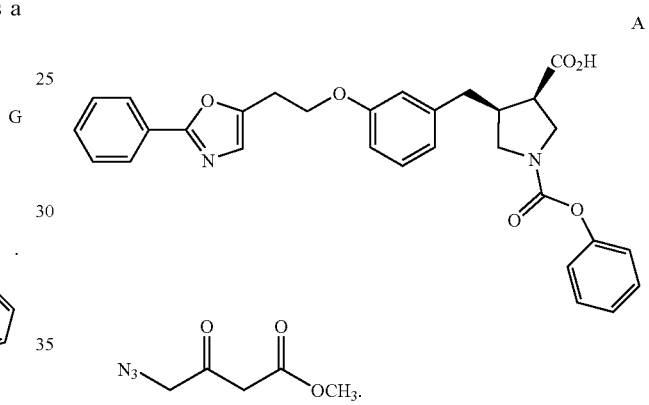

A

A mixture of methyl 4-chloroacetoacetate (400 mg; 2.6 mmol) and sodium azide (136 mg; 2.1 mmol) in acetone (6 mL) was diluted with H₂O (~1 mL) until the azide had dissolved. The mixture was heated at 50° C. for 1 h, stirred overnight at RT, then was heated at 50° C. for 2 h. The reaction was cooled to RT and the acetone was removed in vacuo. The aqueous phase was extracted with CH₂Cl₂; the combined organic extracts were dried (MgSO₄) and concentrated in vacuo. The residue was chromatographed (SiO₂; continuous gradient from 100% hex to 3:2 hex:EtOAc) to give Part A compound (237 mgs; 72%).

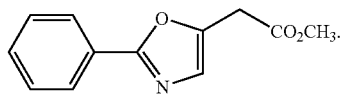

B

A mixture of Part A compound (237 mg; 1.51 mmol) and resin-bound Ph₃P (1.56 g of 3 mmol/g resin; 4.68 mmol) in dioxane (5 mL) was shaken for 10 min at RT. Benzoyl chloride (263 mg; 1.87 mmol) was then added and the reaction was heated at 75° C. for 2 h, then cooled to RT and filtered. The filtrate was concentrated in vacuo and the residue was chromatographed (SiO₂; continuous gradient from 100% hex to 1:1 hex:EtOAc; compound was pre-loaded onto the column with Celite®) to give Part B compound (95 mg; 28%) as a pale yellow oil.

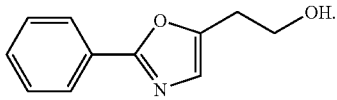

C

A solution of LiAlH₄ in THF (2.0 mL of a 1 M solution; 2.0 mmol) was added dropwise to Part B compound (95 mg; 0.44 mol) at RT. The reaction was stirred overnight at RT, then was cooled to 0° C. and quenched cautiously with H₂O. Aqueous 3 N NaOH was added and the mixture was concentrated in vacuo. The residue was partitioned between CH₂Cl₂ and H₂O. The aqueous phase was extracted with CH₂Cl₂; the combined organic extracts were dried (Na₂SO₄) and concentrated in vacuo. The residue was chromatographed (SiO₂; continuous gradient from 100% hex to 100% EtOAc; compound preloaded onto column with. CH₂Cl₂) to provide Part C compound (100 mg; 100%) as a colorless oil.

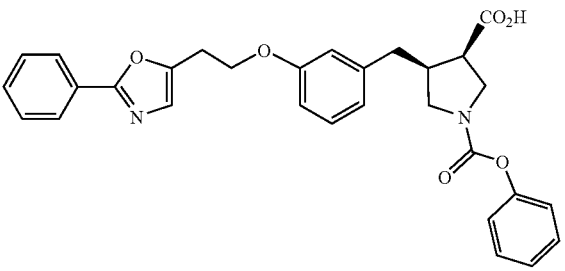

D

A RT mixture of Example 32 Part F compound (100 mg; 0.298 mmol) and 4 M HCl/dioxane (1 mL; 4 mmol) in CH₂Cl₂ (1 mL) was stirred at RT for 2 h, then was concentrated in vacuo. A mixture of the residue (crude pyrrolidine-phenol) and phenyl chloroformate (60 μL; 0.461 mmol) in saturated aqueous NaHCO₃ (1.5 mL) and THF (1 mL) was stirred at RT overnight, after which the THF was removed in vacuo. The aqueous phase was extracted with CH₂Cl₂ (3×). The combined organic extracts were dried (MgSO₄) and concentrated in vacuo; the residue was chromatographed (SiO₂; continuous gradient from 100% hex to 100% EtOAc) to give Part D compound (110 mg; 100%) as a colorless oil.

E

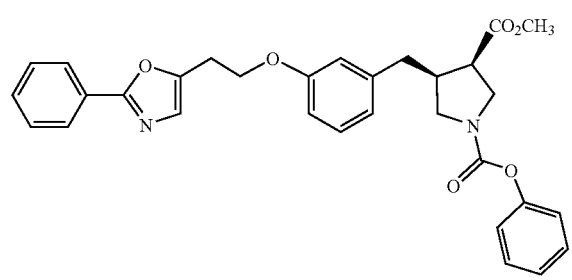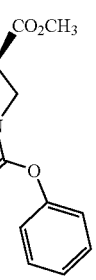

A mixture of Part C compound (25 mg; 0.132 mmol), Part D compound (35 mg; 0.098 mmol) and cyanomethylene tributylphosphorane (60 μL; 0.25 mmol) in toluene (500 μL) at 70° C. was shaken overnight, then was concentrated in vacuo. The residue was chromatographed (SiO₂; continuous gradient from 100% hex to 2:3 hex:EtOAc) to give Part E compound (9 mg; contaminated with 50% Part D compound; 13%) as a yellow oil. [M+H]⁺=527.3

F

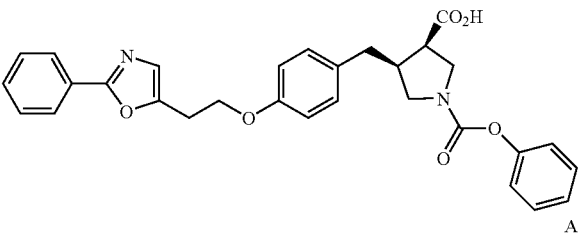

A mixture of Part E compound (4.5 mg; 0.008 mmol) in concentrated HCl (100 μL) and HOAc (400 μL) was heated at 70° C. for 24 h, then was cooled to RT and concentrated in vacuo. The residue was purified by preparative HPLC (as for the purification of Example 26) to give the title compound (2 mg; 40%) as a solid.

[M+H]⁺=513.1

EXAMPLE 55

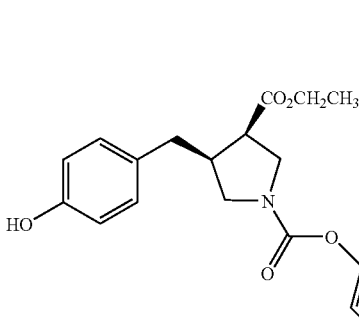

A

A RT-mixture of Example 23 Part E compound (100 mg; 0.271 mmol) and 4 M HCl/dioxane (1 mL; 4 mmol) in CH₂Cl₂ (1 mL) was stirred at RT for 2 h, then was concentrated in vacuo. A mixture of the residue (crude pyrrolidine-phenol) and phenyl chloroformate (60 μL) in saturated aqueous NaHCO₃ (1.5 mL) and THF (1 mL) was stirred at RT overnight, then the THF was removed in vacuo. The aqueous phase was extracted with CH₂Cl₂ (3×). The combined organic extracts were dried (MgSO₄) and concentrated in vacuo; the residue was chromatographed (SiO₂; continuous gradient from 100% hex to 100% EtOAc) to give Part A compound (65 mg; 62%) as a colorless oil.

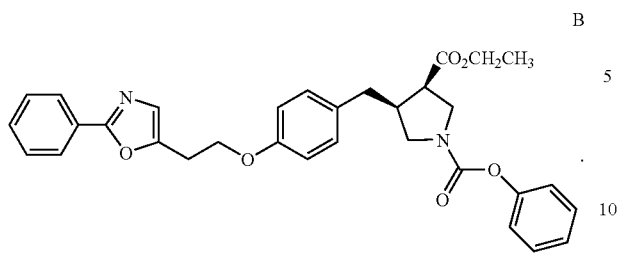
B

A mixture of Example 54 Part C compound (25 mg; 0.132 mmol), Part A compound (35 mg; 0.095 mmol) and cyanomethylene tributylphosphorane (60 μL; 0.248 mmol) in toluene (500 μL) at 70° C. was shaken overnight, then was concentrated in vacuo. The residue was chromatographed (SiO$_2$; continuous gradient from 100% hex to 2:3 hex:EtOAc) to give Part B compound (30 mg; contaminated with 50% Part A compound; 43%) as a yellow oil. [M+H]$^+$=541.4

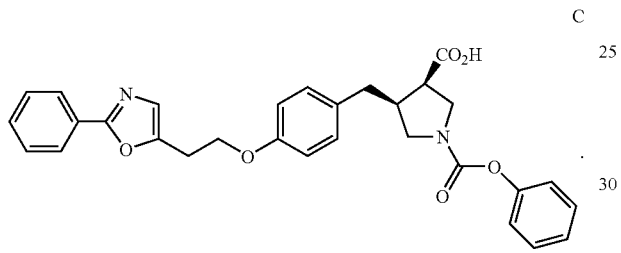
C

A mixture of Part B compound (15 mg; 0.027 mmol) in concentrated HCl (100 μL) and HOAc (400 μL) was stirred at 70° C. for 24 h, then was cooled to RT and concentrated in vacuo. The residue was purified by preparative HPLC (as for the purification of Example 26) to give the title compound (3 mg; 20%) as a solid.

[M+H]$^+$=513.1

EXAMPLE 56

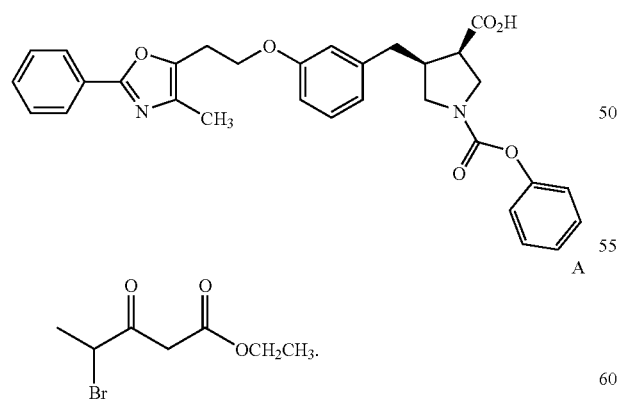
A

To a 0° C. solution of ethyl propionylacetate (10.0 g, 69.4 mmol) in CHCl$_3$ (60 mL) was added dropwise a solution of Br$_2$ (3 .6 mL; 69.4 mmol) in CHCl$_3$ (20 mL) and the resulting mixture was stirred at 0° C. for 0.5 h. The reaction was allowed to warm to RT and stirred at RT for 0.5 h. Air was then bubbled into the mixture for 1 h. Volatiles were then removed in vacuo to yield an oily residue to provide crude Part A compound (15.3 g, >95% yield) as an oil which was used in the next reaction without further purification.

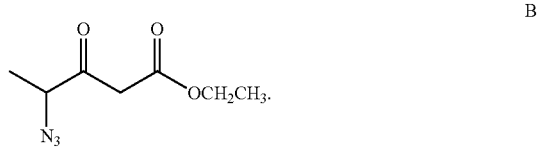
B

A mixture of Part A compound (400 mg; 1.79 mmol) and sodium azide (136 mg; 2.09 mmol) in acetone (6 mL) and H$_2$O (1 mL) was stirred at RT for 1 h, then at 50° C. for 1 h. Analytical HPLC indicated that the starting material had been consumed at this point. The acetone was removed in vacuo and the aqueous phase was extracted with CH$_2$Cl$_2$. The combined organic extracts were dried (MgSO$_4$) and concentrated in vacuo; the residue was chromatographed (SiO$_2$; continuous gradient from 100% hex to 1:1 hex:EtOAc) to give Part B compound (280 mg; 85%) as a pale yellow oil.

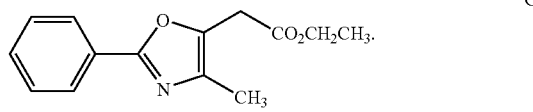
C

A mixture of Part B compound (100 mg; 0.54 mmol) and resin-bound Ph$_3$P (540 mg of 3 mmol/g resin; 1.62 mmol) in dioxane (4 mL) was shaken for 10 min at RT. Benzoyl chloride (84 mg; 0.60 mmol) was then added and the reaction was heated at 75° C. for 2 h, then cooled to RT and filtered. The filtrate was concentrated in vacuo and the residue was chromatographed (SiO$_2$; continuous gradient from 100% hex to 1:1 hex:EtOAc; the compound was pre-loaded onto the column with Celite®) to give Part C compound (280 mg; 85%) as a pale yellow oil.

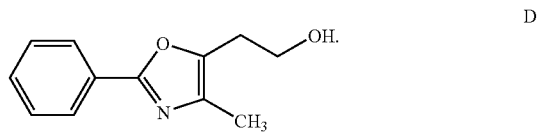
D

A solution of LiAlH$_4$ in THF (1 mL of a 1 M solution; 1 mmol) was added dropwise to Part C compound (75 mg; 0.30 mol) at 0° C. The reaction was warmed to RT and stirred overnight at RT, then was cooled to 0° C. and quenched cautiously with H$_2$O. Aqueous 3 N NaOH was added and the mixture was concentrated in vacuo. The residue was partitioned between CH$_2$Cl$_2$ and H$_2$O. The aqueous phase was extracted with CH$_2$Cl$_2$; the combined organic extracts were dried (Na$_2$SO$_4$) and concentrated in vacuo. The residue was chromatographed (SiO$_2$; continuous gradient from 100%, hex to 100% EtOAc; compound pre-loaded onto column with CH$_2$Cl$_2$) to provide Part D compound (55 mg; 89%) as a colorless oil.

E

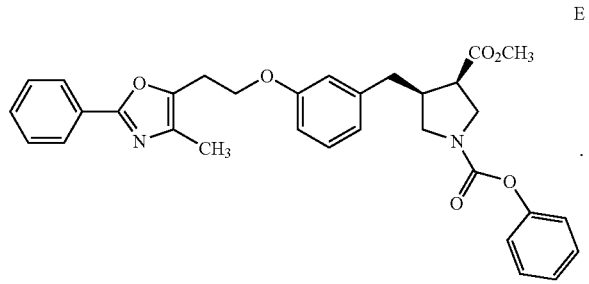

A mixture of Part D compound (25 mg; 0.123 mmol), Example 54 Part D compound (35 mg; 0.098 mmol) and cyanomethylene tributylphosphorane (60 µL; 0.248 mmol) in toluene (500 µL) at 70° C. was shaken overnight, then was concentrated in vacuo The residue was chromatographed (SiO$_2$; continuous gradient from 100% hex to 2:3 hex:EtOAc) to give Part E compound (33 mg; contaminated with 10% Example 54 Part D compound; 60%) as a yellow oil.

[M+H]$^+$=541.4

F

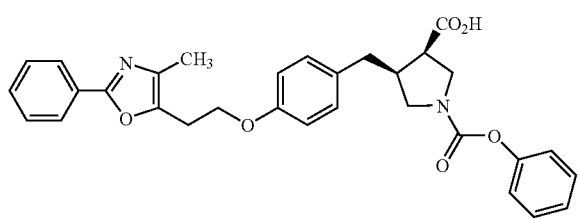

A mixture of Part E compound (16 mg; 0.031 mmol) in concentrated HCl (100 µL) and acetic acid (400 µL) was heated at 70° C. for 24 h, then was cooled to RT and concentrated in vacuo. The residue was purified by preparative HPLC (as for the purification of Example 26) to give the title compound (7.5 mg; 45%) as a solid.

[M+H]$^+$=527.1

EXAMPLE 57

A

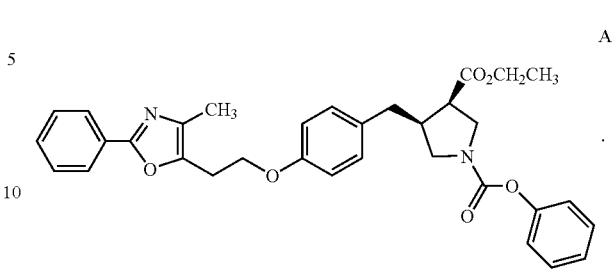

A mixture of Example 56 Part D compound (25 mg; 0.123 mmol), Example 55 Part A compound (35 mg; 0.095 mmol) and cyanomethylene tributylphosphorane (60 µL; 0.248 mmol) in toluene (500 µL) at 70° C. was shaken overnight, then was concentrated in vacuo. The residue was chromatographed (SiO$_2$; continuous gradient from 100% hex to 2:3 hex:EtOAc) to give Part A compound (27 mg; contaminated with 12% Example 56 Part D compound; 43%) as a yellow oil.

[M+H]$^+$=555.4

B

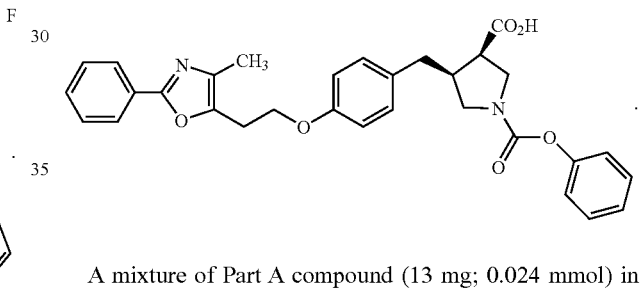

A mixture of Part A compound (13 mg; 0.024 mmol) in concentrated HCl (100 µL) and HOAc (400 µL) was heated at 70° C. for 24 h, then was cooled to RT and concentrated in vacuo. The residue was purified by preparative HPLC (as for the purification of Example 26) to give the title compound (7.5 mg; 60%) as a solid.

[M+H]$^+$=527.1

EXAMPLE 58

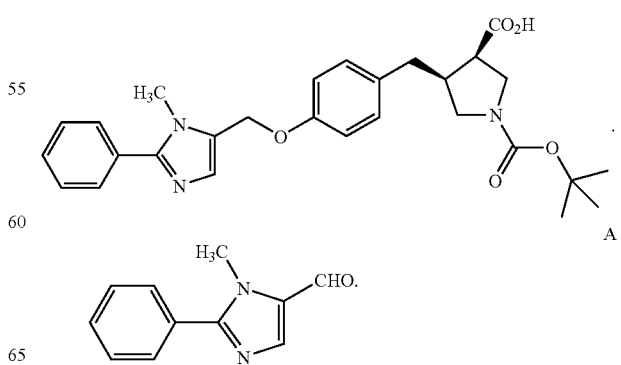

To a solution of 4-formyl-2-phenylimidazole (100 mg, 0.58 mmol) in CH$_2$Cl$_2$ (2 mL) was added aqueous KOH (2 mL of a 30% solution), followed by dimethyl sulfate (66 μL, 0.70 mmol), and tetrabutylammonium bromide (10 mg; 0.039 mmol). The reaction mixture was stirred overnight at RT and then was partitioned between ETOAc and water; the organic phase was washed with brine and then concentrated in vacuo. The residue was chromatographed (SiO$_2$; continuous gradient from 1:1 hexane:EtOAc to 100% EtOAc) to give 1-methyl-2-phenyl-imidazole-5-carboxaldehyde as a solid (35 mg; 32%; 1$^{st}$ eluted fraction; Part A compound) and Part B compound

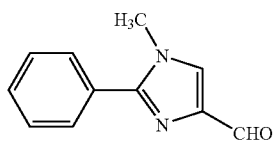

(45 mg; 42%; second eluted fraction) as a solid.

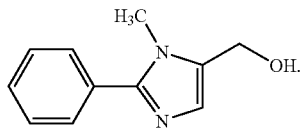

C

To a solution of Part A compound (50 mg, 0.27 mmol) in MeOH (2 mL) was added NaBH$_4$ (30 mg; 0.79 mmol). The mixture was stirred at RT for 1 h, after which the reaction was quenched with excess saturated aqueous NH$_4$Cl (1 mL). Volatiles were removed in vacuo, and the residue was partitioned between saturated aqueous NaHCO$_3$ and EtOAc. The organic phase was washed with brine, dried (Na$_2$SO$_4$) and concentrated in vacuo to give Part C compound as a white solid (37 mg, 75%).

A mixture of Example 23 Part E compound (50 mg; 0.14 mmol), Part C compound (40 mg; 0.21 mmol) and cyanomethylene tributylphosphorane (50 mg; 0.21 mmol) in toluene (1.5 mL) was stirred at 88° C. for 3 h, then was cooled to RT and concentrated in vacuo. The residue was chromatographed (SiO$_2$; continuous gradient from 3:2 to 1:4 hex:EtOAc) to give Part D compound (30 mg; 40%) as an oil.

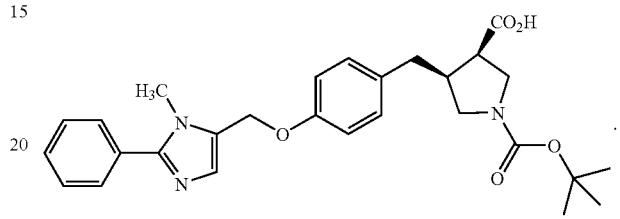

E

A mixture of Part D compound (30 mg; 0.057 mmol) and LiOH.H$_2$O (30 mg; 0.71 mmol) in MeOH (0.3 mL), THF (1 mL) and H$_2$O (0.5 mL) was stirred at RT for 1 h, after which saturated aqueous NH$_4$Cl (1 mL) was added. Volatiles were removed in vacuo and the residue was partitioned between EtOAc and H$_2$O. The aqueous phase was extracted with EtOAc; the combined organic extracts were dried (Na$_2$SO$_4$) and concentrated in vacuo. The residue was purified by preparative HPLC (as for the purification of Example 26 except that a continuous gradient from 40:60 A:B to 100% B was used) to give the title compound (5 mg; 17%) as a solid.

[M+H]$^+$=527.1

In addition, the epimerized compound, Example 59, was also obtained (5 mg; 17%) as a solid.

EXAMPLE 59

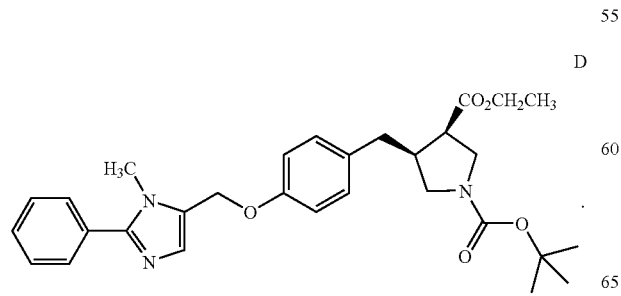

D

[M+H]$^+$=527.1

EXAMPLE 60

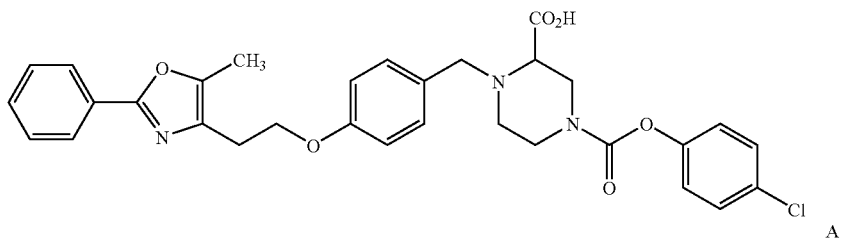

A

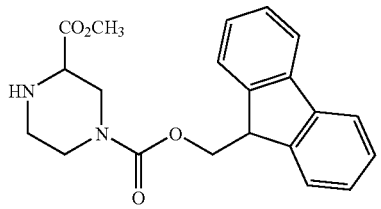

HCl gas was bubbled through a solution of N-1-Boc-N-4-Fmoc-2-piperazine carboxylic acid (5.0 g; 11 mmol) in MeOH (250 mL) at RT for 5 min. The reaction was stirred at RT for 5 h, then was concentrated in vacuo. The residue was partitioned between EtOAc and 1N aqueous NaOH. The organic phase was dried (MgSO$_4$) and concentrated in vacuo to give Part A compound (3.8 g; 95%) as an oil.

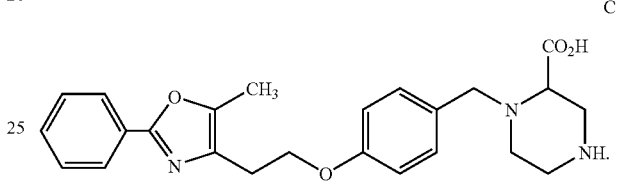

C

To a RT solution of Part A compound (1.0 g; 2.7 mmol) and the aldehyde Example 47 Part B compound (840 mg; 2.7 mmol)

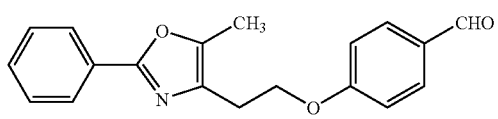

in CH$_2$Cl$_2$ (150 mL) were successively added HOAc (1 mL) and NaBH(OAc)$_3$ (930 mg; 4.7 mmol). The reaction was stirred at RT for 1 h and then washed with saturated aqueous NaHCO$_3$. The organic phase was dried (MgSO$_4$) and concentrated in vacuo to furnish Part B compound (1.74 g; 97%) as an oil.

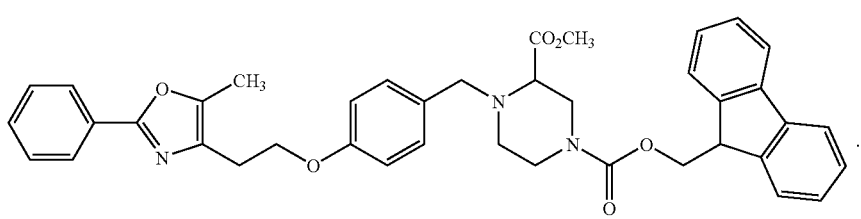

B

A solution of Part B compound (1.74 g; 2.65 mmol) and KOH (740 mg; 13.2 mmol) in MeOH/H$_2$O (40 mL of a 1:1 solution) was stirred at RT for 18 h. Volatiles were removed in vacuo, and the residue was purified by preparative HPLC (YMC reverse-phase ODS 30×250 mm column; detection at 220 nm; flow rate=25 mL/min; continuous gradient from 100% A to 100% B over 30 min+10 min hold time at 100% B, where A=90:10:0.1 H$_2$O:MeOH:TFA and B=90:10:0.1 MeOH:H$_2$O:TFA) to provide Part C compound (510 mg; 40%) as an oil.

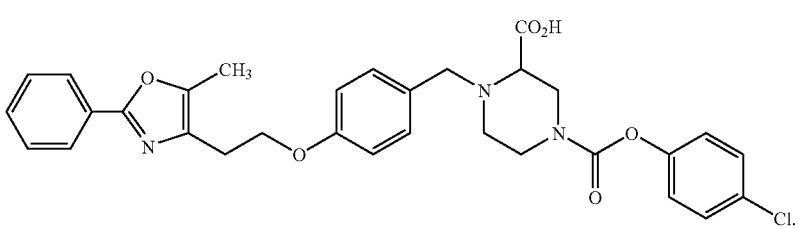

D

To a RT solution of Part C compound (50 mg; 0.11 mmol) and 4-chlorophenyl chloroformate (28 mg; 0.14 mmol) in CH$_2$Cl$_2$ (2 mL) was added Et$_3$N (70 µL; 0.52 mmol). The reaction was stirred at RT for 16 h and then was concentrated in vacuo. The residue was purified by preparative HPLC (YMC reverse-phase ODS 20×100 mm column; detection at 220 nm; flow rate=20 mL/min; continuous gradient from 100% A to 100% B over 30 min+10 min hold time at 100% B, where A 90:10:0.1 H₂O:MeOH:TFA and B 90:10:0.1 MeOH:H₂O:TFA) to provide the title compound (28 mg; 44%) as a solid.

[M+H]⁺=577.2

EXAMPLES 61-71

Examples 61 through 71 were prepared in a similar fashion to Example 60 (from Example 60 Part C compound) using a variety of chloroformates.

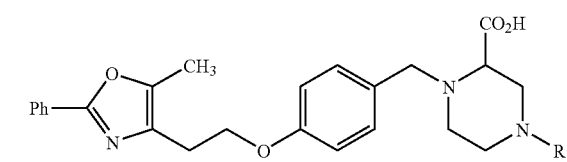

| Example # | R | [M + H]⁺ |
|---|---|---|
| 61 | 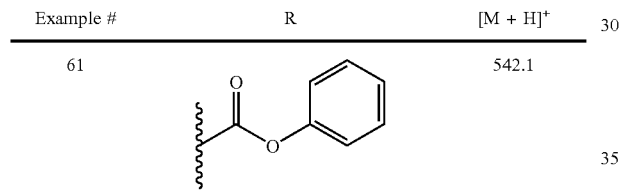 | 542.1 |
| 62 | 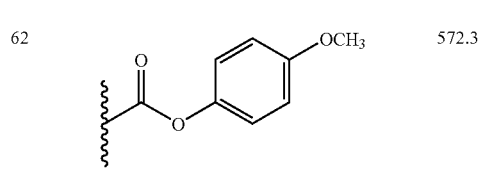 | 572.3 |
| 63 | 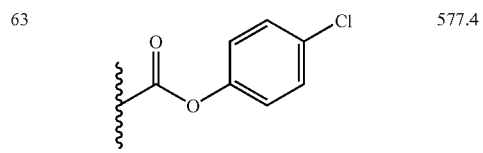 | 577.4 |
| 64 | 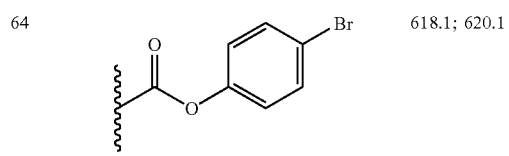 | 618.1; 620.1 |
| 65 |  | 560.2 |

-continued

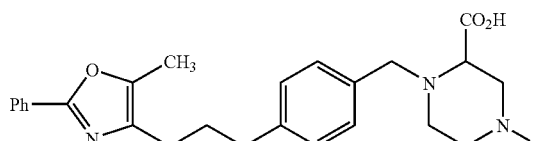

| Example # | R | [M + H]⁺ |
|---|---|---|
| 66 | 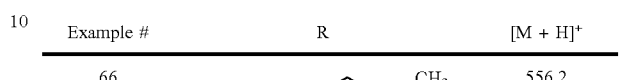 | 556.2 |
| 67 | 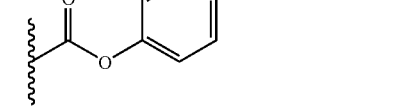 | 600.2 |
| 68 | 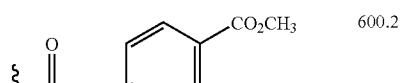 | 610.2 |
| 69 | 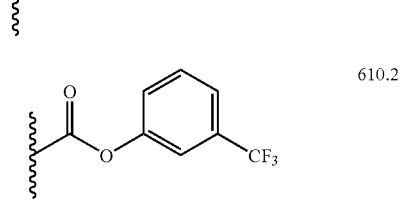 | 577.4 |
| 70 | 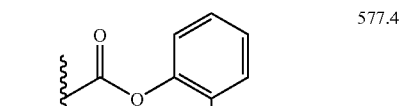 | 572.2 |
| 71 | 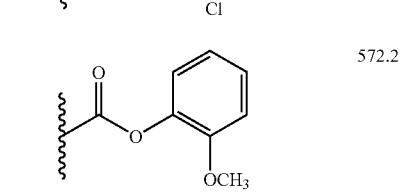 | 592.2 |

EXAMPLES 72-73

Examples 72 and 73 were prepared using an analogous synthetic sequence to that used for the synthesis of Example 60. The only difference was that the aldehyde used was Example 436 Part A compound

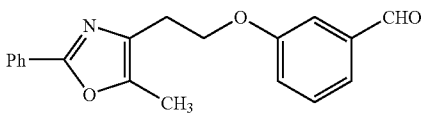

instead of the aldehyde in Example 60.

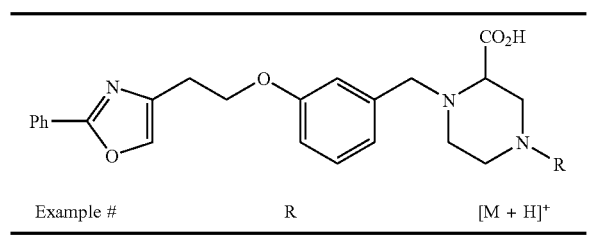
| Example # | R | [M + H]+ |
|---|---|---|
| 72 | 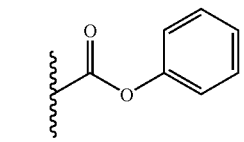 | 542.4 |
| 73 | 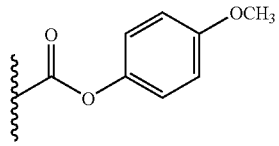 | 572.2 |
EXAMPLES 74-88
Following the general sequence for the preparation of Example 45 compound (using appropriately substituted benzoyl chlorides instead of benzoyl chloride), the following compounds of the invention were prepared from Example 45 Part C compound.
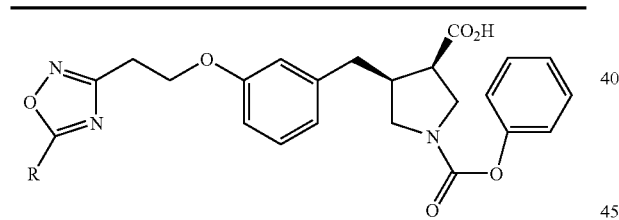
| Example No. | R | [M + H]+ |
|---|---|---|
| 74 | 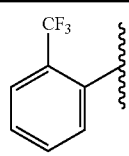 | 528.4 |
| 75 | 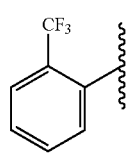 | 582.4 |
| 76 | 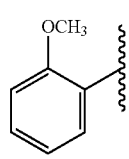 | 544.4 |
-continued
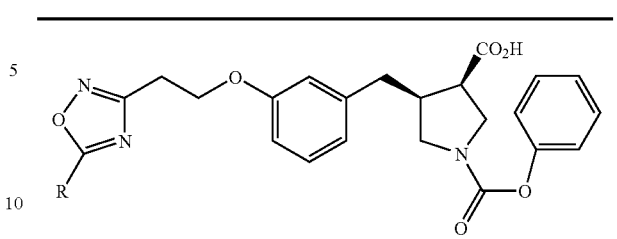
| Example No. | R | [M + H]+ |
|---|---|---|
| 77 | | 528.5 |
| 78 | 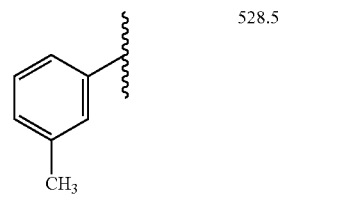 | 582.4 |
| 79 | 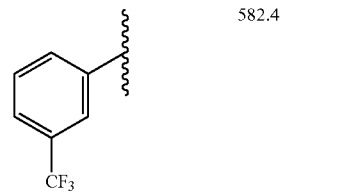 | 598.4 |
| 80 | | 544.4 |
| 81 | 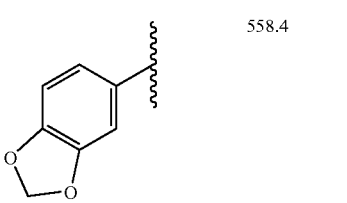 | 558.4 |
| 82 | 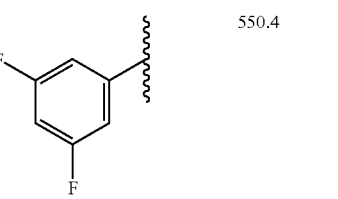 | 550.4 |

-continued

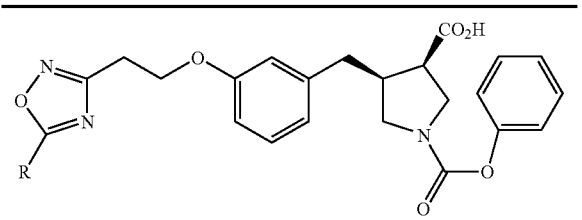

| Example No. | R | [M + H]+ |
|---|---|---|
| 83 | 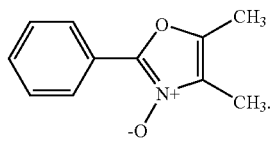 4-CH3-C6H4- | 528.5 |
| 84 | 4-tBu-C6H4- | 570.5 |
| 85 | 4-F3C-C6H4- | 582.4 |
| 86 | 4-F3CO-C6H4- | 598.4 |
| 87 | 4-H3CO-C6H4- | 544.4 |
| 88 | 4-Cl-C6H4- | 548.4 |

EXAMPLE 89

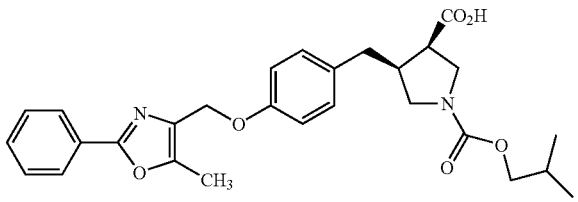

-continued

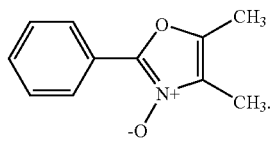
A

To a solution of benzaldehyde (23.8 g, 234 mmol) in EtOAc (150 mL; pre-saturated with HCl gas) was added 2,3-butanedione mono-oxime (25.0 g, 234 mmol) in one portion and the resulting solution was stirred at RT for 12 h. Analytical HPLC indicated that all starting materials had been consumed. The reaction mixture was concentrated in vacuo to yield Part A compound as a white solid, which was used in the next step without further purification.

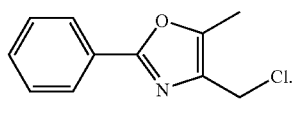
B

To a solution of Part A compound in CHCl3 (200 mL) was added dropwise POCl3 (30 mL, 320 mmol). The reaction was stirred for 12 h at 50° C., then was concentrated in vacuo. The brown residue was partitioned between EtOAc (300 mL) and 1N aqeuous NaOH. The organic phase was washed with brine, dried, (MgSO4) and concentrated in vacuo. The residue was chromatographed (SiO2; Et2O) to give Part B compound (41.5 g; 86%) as a light brown solid (>95% pure by analytical HPLC and $^1$H-NMR analysis).

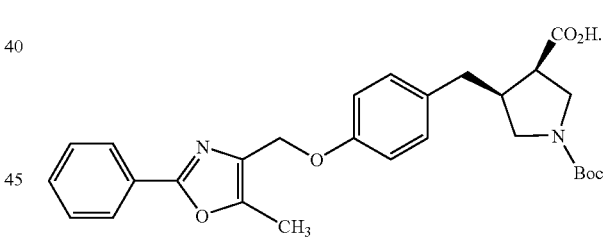
C

A mixture of Example 23 Part E compound (140 mg; 0.4 mmol),

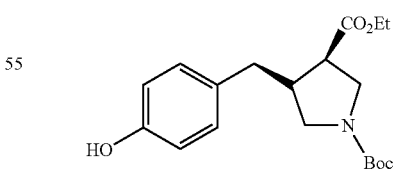

Part B compound (124 mg; 0.6 mmol) and K2CO3 (83 mg; 0.6 mmol) in CH3CN (10 mL) was stirred at 95° C. for 2 h. The solids were filtered off, and the filtrate was concentrated in vacuo. The residue was chromatographed (SiO2; 9:1 to 4:1 hex:EtOAc) to give Part C compound (180 mg; 86%) as an oil.

D
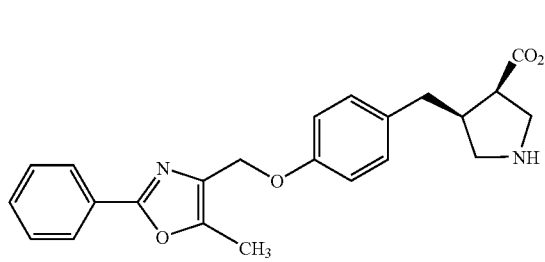

F
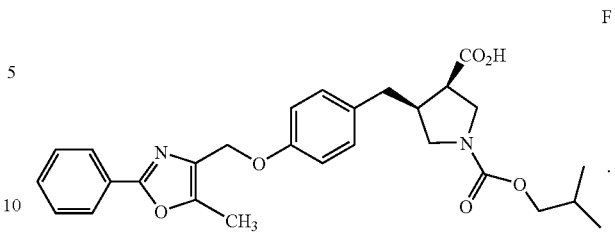

To a solution of Part C compound (180 mg; 0.35 mmol) in CH$_2$Cl$_2$ (5 mL) was added HCl in dioxane (0.5 mL of a 4M solution; 2 mmol). The reaction was stirred at RT for 2 h, then was concentrated in vacuo to give crude Part D compound (152 mg; 96%) as a white solid, which was used in the next reaction without further purification.

E
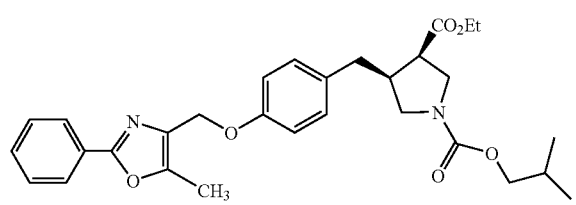

A solution of Part D compound (25 mg; 0.055 mmol), isobutyl chloroformate (11 µL; 0.083 mmol) and NaHCO$_3$ (18 mg; 0.22 mmol) in 1:1 THF:H$_2$O (3 mL) was stirred at RT for 30 min, then was partitioned between EtOAc and H$_2$O. The organic phase was dried (MgSO$_4$) and concentrated in vacuo. The residue was purified by preparative HPLC (YMC reverse-phase ODS 20×100 mm column; detection at 220 nm; flow rate=20 mL/min; continuous gradient from 50% A to 100% B over 10 min+3 min hold time at 100% B, where A=90:10:0.1 H$_2$O:MeOH:TFA and B=90:10:0.1 MeOH:H$_2$O:TFA) to give Part E compound (20 mg; 70%) as an oil.

A solution of Part E compound (20 mg; 0.04 mmol) and LiOH (6 mg; 0.16 mmol) in THF H$_2$O (2 mL of 1:1 solution) was stirred at RT for 18 h. The reaction was acidified to pH 3 with 1 M aqueous HCl and extracted with EtOAc (2×). The combined organic extracts were dried (Na$_2$SO$_4$) and concentrated in vacuo. The residue was purified by preparative HPLC (YMC reverse-phase ODS 20×100 mm column; detection at 220 nm; flow rate=20 mL/min; continuous gradient from 50% A to 100% B over 10 min+3 min hold time at 100% B, where A=90:10:0.1 H$_2$O:MeOH:TFA and B=90:10:0.1 MeOH:H$_2$O:TFA) to give the title compound as a white solid (7.3 mg; 39%). [M+H]$^+$=493.5

In addition, a second fraction from the preparative HPLC of the above crude product was identified as the epimerized trans-isomer Example 90 compound (white solid; 3.6 mg; 19%).

[M+H]$^+$=493.5

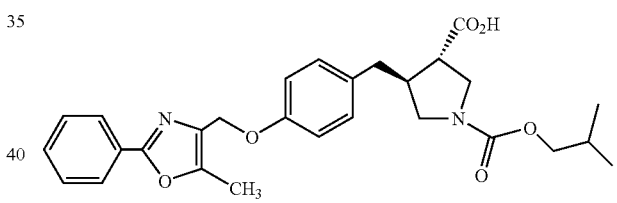

Following the general procedure for the synthesis of Examples 89 and 90, the following compounds (Examples 91-94) of the invention were prepared:

| Example No. | Structure | [M + H]$^+$ |
|---|---|---|
| 91 | ![structure] racemic cis | 465.5 |

| Example No. | Structure | [M + H]+ |
|---|---|---|
| 92 | 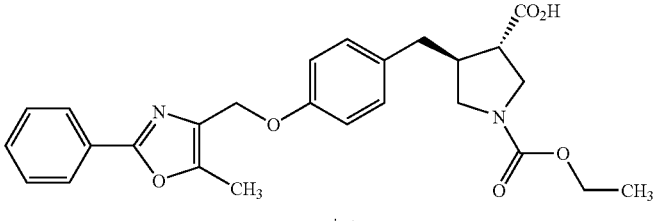<br>racemic trans | 465.5 |
| 93 | 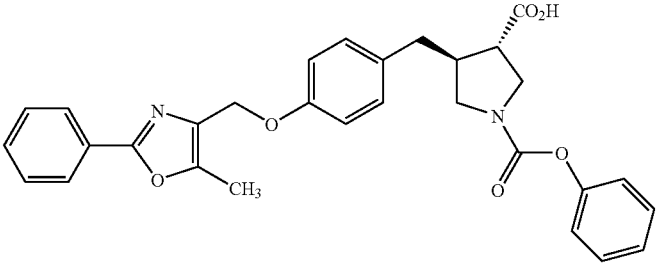<br>racemic cis | 513.5 |
| 94 | 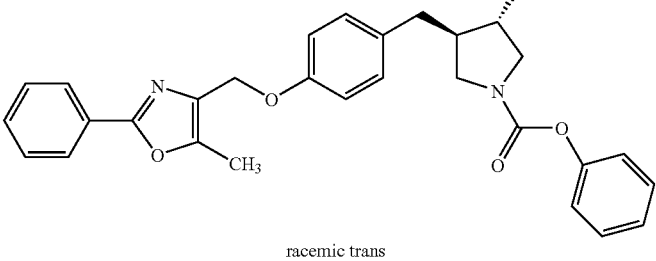<br>racemic trans | 513.5 |
EXAMPLES 95-97
Following the general procedure for the synthesis of Example 89, except that Example 32 Part F compound (the methyl ester)
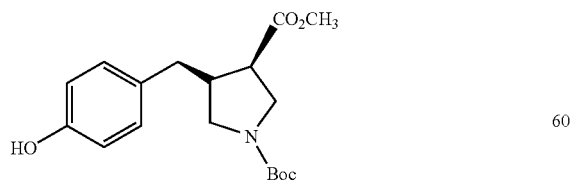
was used instead of Example 23 Part E compound (the ethyl ester), the following compounds of the invention were prepared:

| Example No. | Structure | [M + H]+ |
|---|---|---|
| 95 | cis racemate | 465.5 |
| 96 | cis racemate | 493.5 |
| 97 | cis racemate | 513.5 |

EXAMPLE 98

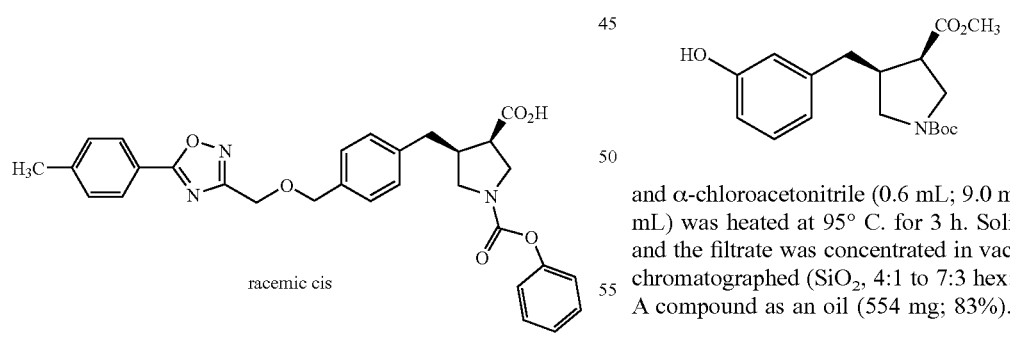

racemic cis

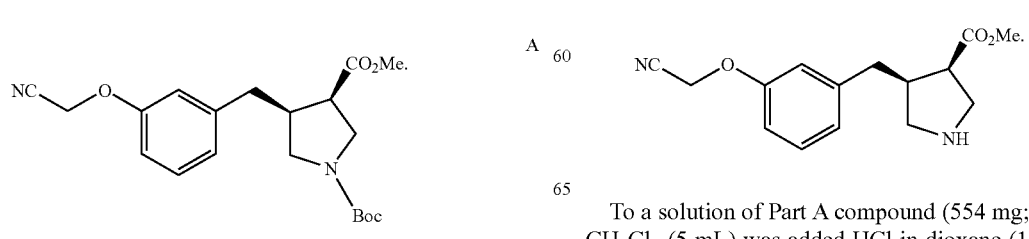

A mixture of Example 32 Part F compound (600 mg; 1.8 mmol), $K_2CO_3$ (1.2; 9.0 mmol) and α-chloroacetonitrile (0.6 mL; 9.0 mmol) in $CH_3CN$ (10 mL) was heated at 95° C. for 3 h. Solids were filtered off, and the filtrate was concentrated in vacuo. The residue was chromatographed ($SiO_2$, 4:1 to 7:3 hex:EtOAc) to give Part A compound as an oil (554 mg; 83%).

To a solution of Part A compound (554 mg; 1.5 mmol) in $CH_2Cl_2$ (5 mL) was added HCl in dioxane (1 mL of a 4 M solution; 4 mmol). The reaction mixture was stirred at RT for 3 h. Volatiles were removed in vacuo to give crude Part B compound (425 mg; 92% yield) as a white solid, which was used in the next reaction without further purification.

C

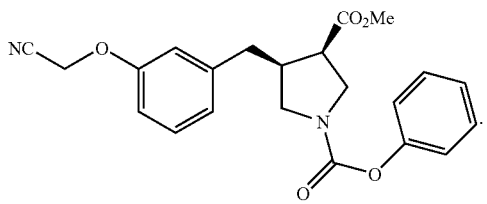

A solution of Part B compound (425 mg; 1.4 mmol), phenyl chloroformate (205 µL; 1.7 mmol) and NaHCO$_3$ (470 mg; 5.6 mmol) in THF/H$_2$O (10 mL of a 1:1 solution) was stirred at RT for 1 h, then was partitioned between EtOAc and H$_2$O. The organic phase was washed with brine, dried (MgSO$_4$) and concentrated in vacuo. The residue was chromatographed (SiO$_2$; 4:1 to 7:3 hex:EtOAc) to give Part C compound as an oil (500 mg; 93%).

D

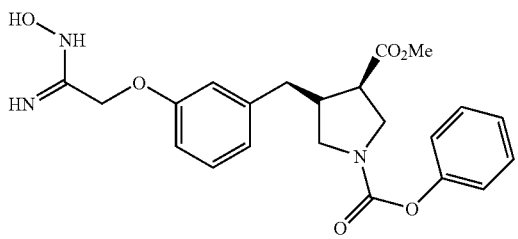

A solution of Part C compound (500 mg; 1.3 mmol), and NH$_2$OH (420 mg; 3.3 mmol) in MeOH (10 mL) and H$_2$O (5 mL) was stirred at 95° C. for 3 h. Volatiles were removed in vacuo, and the residue was lyophilized from dioxane to give Part D compound (493 mg; 91%) as a solid, which was used in the next reaction without further purification.

E

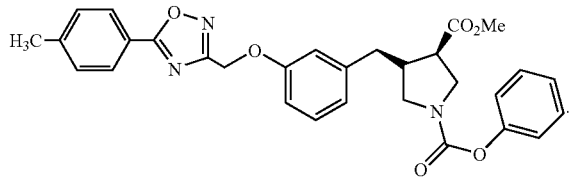

To a solution of Part D compound (25 mg; 0.06 mmol) in pyridine (1 mL) was added p-methyl benzoyl chloride (9 µL; 0.07 mmol). The reaction was stirred at 115° C. for 4 h, then was cooled to RT and concentrated in vacuo to give crude Part E compound, which was used in the next step without further purification.

F

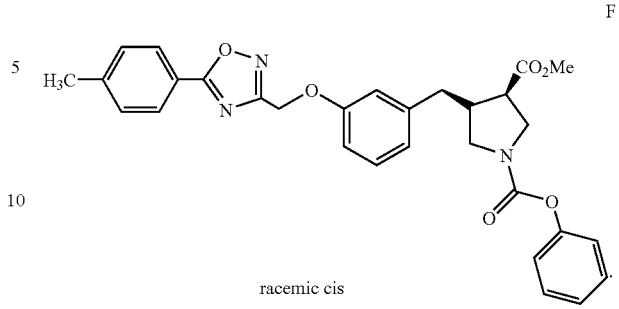

racemic cis

A solution of crude Part E compound and LiOH (9 mg; 0.2 mmol) in THF/H$_2$O (2 mL of a 1:1 solution) was stirred at RT for 18 h, then was acidified to pH 3 with excess 1M aqueous HCl. The aqueous phase was extracted with EtOAc (2×). The combined organic extracts were dried (MgSO$_4$) and concentrated in vacuo. The residue was purified by preparative HPLC (YMC reverse-phase ODS 20×100 mm column; detection at 220 nm; flow rate=20 mL/min; continuous gradient from 50% A to 100% B over 10 min+3 min hold time at 100% B, where A=90:10:0.1 H$_2$O:MeOH:TFA and B=90:10:0.1 MeOH:H$_2$O:TFA) to give the title compound as a white solid (8.5 mg; 28% yield for 2 steps). [M+H]$^+$=514.6

EXAMPLES 99-105

Following the general procedure for the synthesis of Example 98, the following compounds of the invention were prepared.

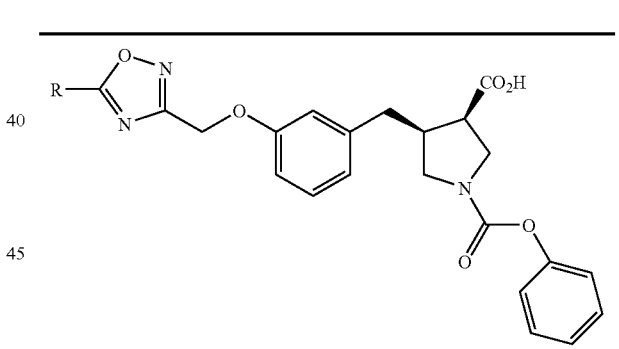

| Example No. | R | [M + H]$^+$ |
|---|---|---|
| 99 | 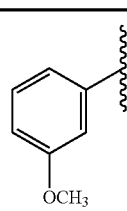 | 530.6 |
| 100 | 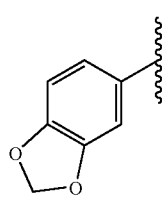 | 544.5 |

-continued

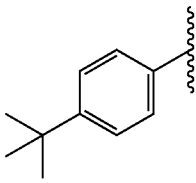

| Example No. | R | [M + H]+ |
|---|---|---|
| 101 | 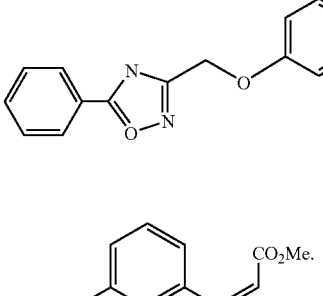 | 556.6 |
| 102 | 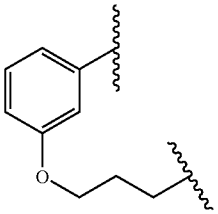 | 558.6 |
| 103 | 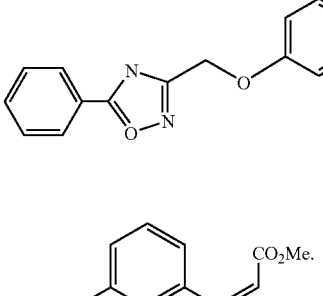 | 584.5 |
| 104 | 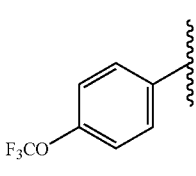 | 584.5 |
| 105 | 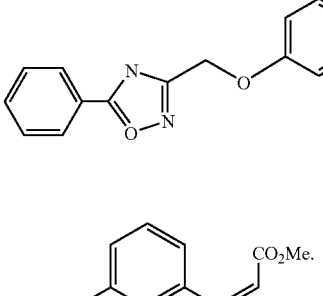 | 530.6 |

EXAMPLE 106

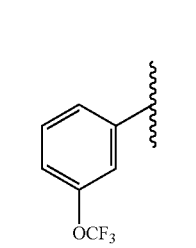

A

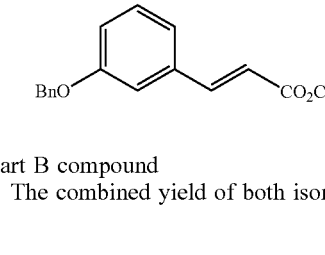

To a −78° C. solution of methyl bis(trifluoroethyl) phosphonoacetate (1.3 g; 4.1 mmol) in dry THF (10 mL) under Ar was added NaH (141 mg of a 60% dispersion in mineral oil; 3.6 mmol) in one portion, and the mixture was stirred at −78° C. for 30 min. A solution of 3-benzyloxy-benzaldehyde (500 mg; 2.4 mmol) in dry THF (5 mL) was then added dropwise and the reaction was stirred for 3 h at −78° C. The reaction was then quenched by dropwise addition of saturated aqueous NH$_4$Cl, warmed to RT and partitioned between EtOAc and H$_2$O. The organic phase was washed with brine, dried (MgSO$_4$) and concentrated in vacuo. The residue was chromatographed (SiO$_2$; 100% hex to 85:15 hex:EtOAc) to give Part A compound (the desired cis isomer; 470 mg) as an oil.

In addition, Part B compound, the trans isomer (60 mg) was also obtained as an oil.

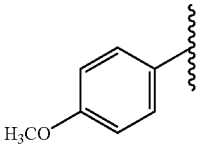

Part B compound
The combined yield of both isomers was 96%.

C

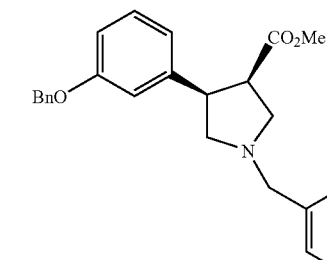

To a solution of Part A compound (470 mg; 1.8 mmol), and Example 1 Part B compound (622 mg; 2.7 mmol) in toluene (15 mL) was added TFA (50 µL) dropwise. The mixture was stirred at RT for 1 h, then was partitioned between EtOAc and saturated aqueous NaHCO₃ The organic phase was dried (MgSO₄) and concentrated in vacuo. The residue was chromatographed (SiO₂; 100% hex to 7:3 hex:EtOAc) to give Part C compound (650 mg; 92%) as an oil.

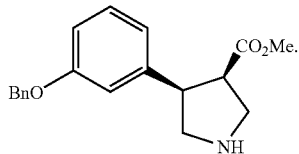

D

To a 0° C. solution of Part C compound (600 mg; 1.5 mmol) in DCE (5 mL) was added dropwise 1-chloroethyl chloroformate (321 µL; 3.0 mmol) and the reaction mixture was heated at 60° C. for 2 h. Volatiles were removed in vacuuo, and the residue was dissolved in MeOH (5 mL) and heated at 60° for 1 h. Volatiles were removed in vacuo, and the residue was lyophilized (dioxane) to give crude Part D compound (590 mg) as a white solid, which was used in the next step without further purification.

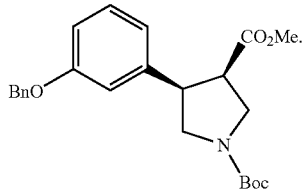

E

A solution of Part D compound (590 mg; 1.7 mmol), di-tert-butyl dicarbonate (327 mg; 1.5 mmol), and NaHCO₃ (252 mg; 3.0 mmol) in THF/H₂O (10 mL of a 1:1 solution) was stirred at RT for 1 h, then was partitioned between EtOAc and H₂O. The organic phase was washed with brine, dried (MgSO₄), and concentrated in vacuo. The residue was chromatographed (SiO₂; 9:1 to 4:1 hex:EtOAc) to give Part E compound as an oil (530 mg; 86% yield for 2 steps).

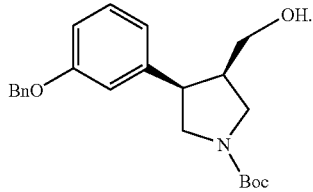

F

To a −78° C. solution of Part E compound (530 mg; 1.3 mmol) in dry THF (5 mL) was added dropwise LiAlH₄ in THF. (1.3 mL of a 1 M solution; 1.3 mmol). The mixture was warmed to 0° C. and stirred at 0° C. for 30 min, then was cautiously quenched by dropwise addition of EtOAc and saturated aqueous sodium potassium tartrate, and finally partitioned between EtOAc and H₂O. The organic phase was dried (MgSO₄) and concentrated in vacuo. The residue was chromatographed (SiO₂; 4:1 to 3:2 hex:EtOAc) to give Part F compound (390 mg; 79%) as an oil.

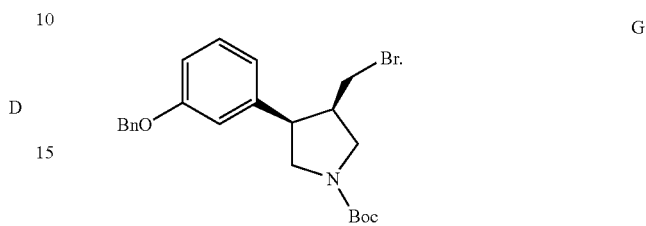

G

To a 0° C. solution of Part F compound (250 mg; 0.7 mmol), and Ph₃P (206 mg; 0.8 mmol) in CH₂Cl₂ (4 mL) was added dropwise a solution of CBr₄ (323 mg; 1.0 mmol) in CH₂Cl₂ (1 mL). The mixture was stirred at RT for 2 h and then heated at reflux for 2 h. After cooling to RT, volatiles were removed in vacuuo, and the residue was chromatographed (SiO₂, 9:1 to 7:3 hex:EtOAc) to give Part G compound (169 mg; 70%).

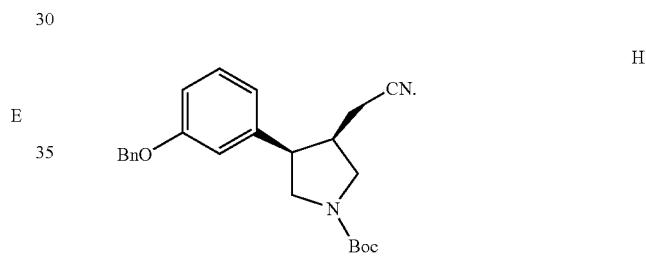

H

A solution of Part G compound (169 mg; 0.4. mmol) and tetrabutylammonium cyanide (406 mg; 1.6 mmol) in CH₂Cl₂ (10 mL) was stirred at RT for 18 h, then was heated to reflux for 2 h. Volatiles were removed in vacuo, and the residue was chromatographed (SiO₂; 9:1 to 7:3 hex:EtOAc) to give Part H compound (45 mg; 65%).

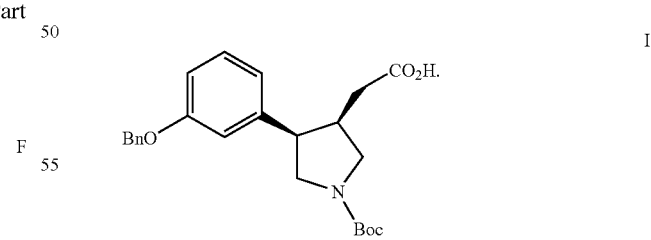

I

A solution of Part H compound (2.9 g; 7.4 mmol) and 30% aqueous KOH (10 mL) in MeOH (20 mL) was heated at 100° C. for 5 h, then was cooled to RT, acidified to pH 5 with aqueous 1M HCl and finally partitioned between EtOAc and H₂O. The organic phase was washed with brine, dried (MgSO₄) and concentrated in vacuo to give crude Part I compound (2.8 g; 93%), which was used in the next reaction without further purification.

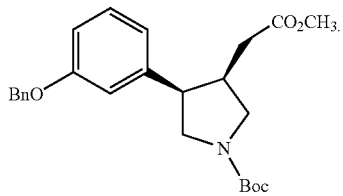

J

To a −78° C. solution of Part I compound (2.8 g; 6.9 mmol) in MeOH (30 mL) was added dropwise a solution of TMSCHN₂ in hexane (17.1 mL of a 2 M solution; 34.2 mmol), then was allowed to warm to RT and stirred at RT for 5 h. Volatiles were removed in vacuuo, and the residue was chromatographed (SiO₂; 100% hex to 3:7 hex:EtOAc) to give Part J compound (2.5 g; 86%) as an oil.

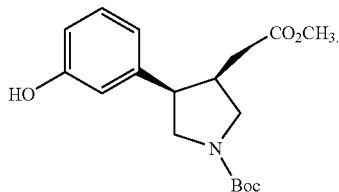

K

A mixture of Part J compound (1.0 g; 2.4 mmol), and 10% Pd/C (80 mg) in MeOH (30 mL) and glacial HOAc (5 drops) was stirred at RT for 4 h under an atmosphere of H₂ (balloon), then was neutralized with excess NaHCO₃ and filtered. The filtrate was concentrated in vacuo to give Part K compound as an oil (730 mg; 93%).

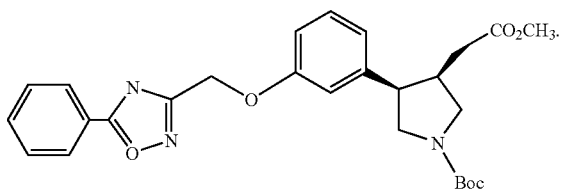

L

A mixture of Part K compound (120 mg; 0.4 mmol), Example 25 Part C compound (116 mg; 0.6 mmol)

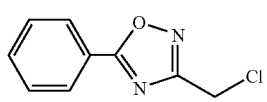

and K₂CO₃ (100 mg; 0.8 mmol) in CH₃CN (6 mL) was heated at 95° C. for 2 h, then was cooled to RT. Solids were filtered off, and the filtrate was concentrated in vacuo. The residue was chromatographed (SiO₂; 95:5 to 85:15 hex: EtOAc) to give Part L compound (160 mg; 91%) as an oil.

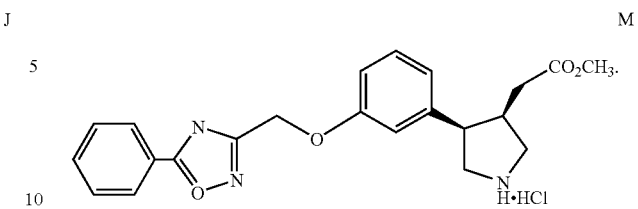

M

A solution of Part L compound (145 mg; 0.3 mmol) and HCl in dioxane (0.5 mL of a 4M solution; 2.0 mmol) in CH₂Cl₂ (4 mL) was stirred at RT for 2 h. Volatiles were removed in vacuo to give Part M compound (126 mg; 100%) as a white solid

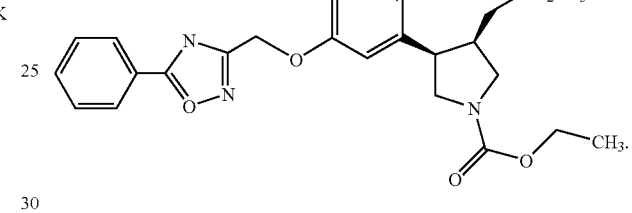

N

A solution of Part M compound (20 mg; 0.05 mmol), ethyl chloroformate (6 μL, 0.07 mmol) and NaHCO₃ (16 mg; 0.2 mmol) in THF/H₂O (2 mL of a 1:1 solution) was stirred at RT for 1 h, then was partitioned between EtOAc and H₂O. The organic phase was dried (MgSO₄) and concentrated in vacuo to give Part N compound, which was used in the next step without further purification.

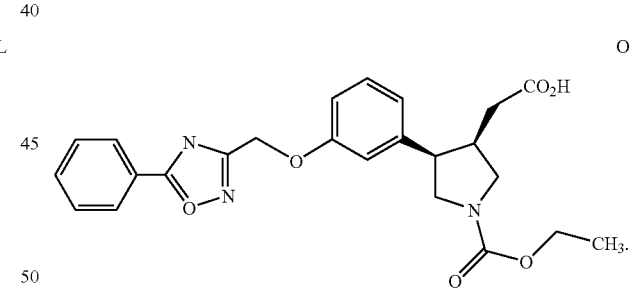

O

A solution of Part N compound and LiOH (10 mg; 0.24 mmol) in THF/H₂O (2 mL of a 1:1 solution) was stirred at RT for 2 h, then was acidified to pH 2 with aqueous 1 M HCl, and finally partitioned between EtOAc and H₂O. The organic phase was dried (MgSO₄) and concentrated in vacuo. The residue was purified by preparative HPLC (YMC reverse-phase ODS 20×100 mm column; detection at 220 nm; flow rate 20 mL/min; continuous gradient from 50% A to 100% B over 10 min+4 min hold time at 100% B, where A=90:10:0.1 H₂O:MeOH:TFA and B=90:10:0.1 MeOH: H₂O:TFA) and lyophilized from dioxane to furnish the title compound as a white solid (15 mg; 71% yield). [M+H]⁺= 452.5

EXAMPLES 107-111
Following the procedure for the synthesis of Example 106, the following compounds of the invention were prepared.
| Example No. | R | [M + H]+ |
|---|---|---|
| 107 | 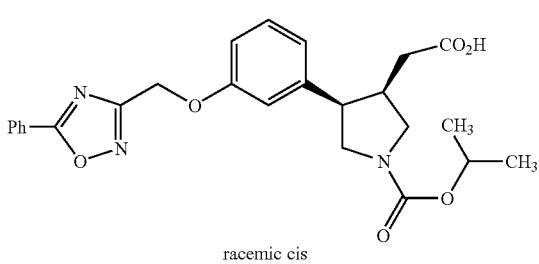 racemic cis | 466.5 |
| 108 | 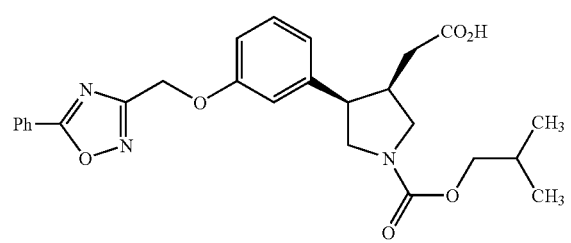 racemic cis | 480.5 |
| 109 | 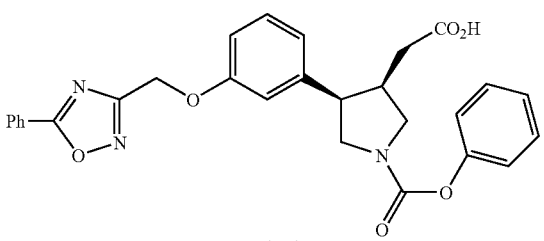 racemic cis | 500.5 |
| 110 | 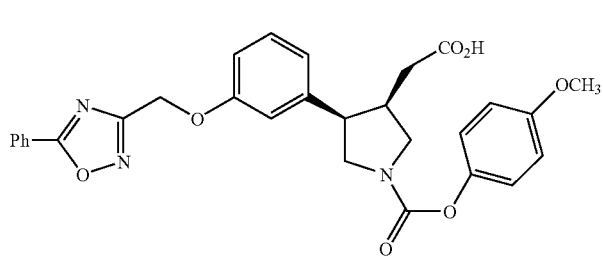 racemic cis | 530.6 |
| 111 | 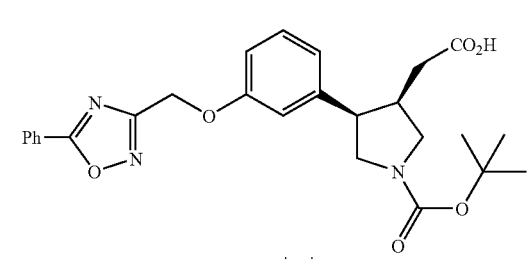 racemic cis | 480.5 |

EXAMPLE 112

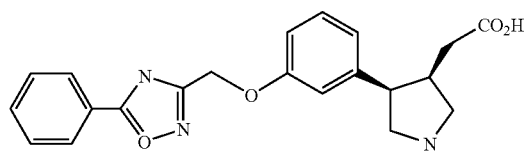

A solution of Example 106 Part M compound (26 mg; 0.06 mmol),

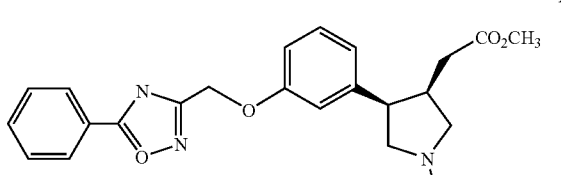

2-chloro-4-(trifluoromethyl) pyrimidine (10 µL, 0.07 mmol) and Et₃N (21 µL; 0.15 mmol) in toluene (5 mL) was heated at 80° C. for 30 min. Volatiles were removed in vacuo, and the residue was partitioned between EtOAc and H₂O. The organic phase was dried (MgSO₄) and concentrated in vacuo to give crude Part A compound, which was used in the next step without further purification.

A solution of crude Part A compound and LiOH (10 mg; 0.24 mmol) in THF/H₂O (2 mL of a 1:1 solution) was stirred at RT for 2 h, then was acidified to pH 2 with aqueous 1 M HCl, and finally partitioned between EtOAc and H₂O. The organic phase was dried (MgSO₄) and concentrated in vacuo. The residue was purified by preparative HPLC (YMC reverse-phase ODS 20×100 mm column; detection at 220 nm; flow rate=20 mL/min; continuous gradient from 50% A to 100% B over 10 min+4 min hold time at 100% B, where A=90:10:0.1 H₂O:MeOH:TFA and B=90:10:0.1 MeOH:H₂O:TFA) and lyophilized from dioxane to furnish the title compound as a white solid (31 mg; 97%). [M+H]⁺=526.0

EXAMPLE 113

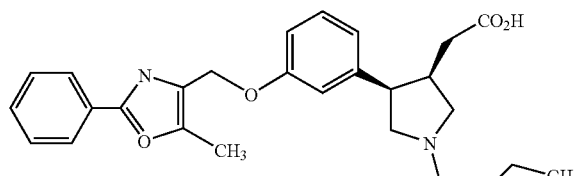

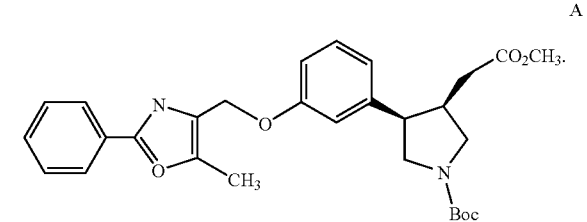

A mixture of Example 106 Part K compound (120 mg; 0.4 mmol),

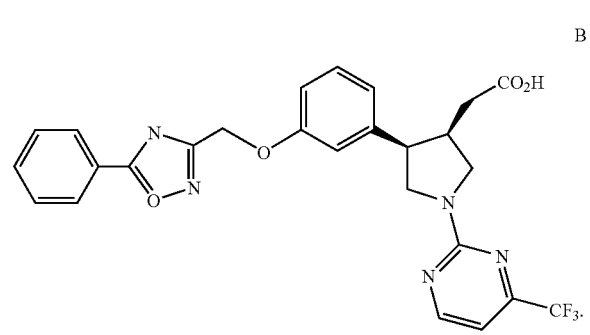

Example 89 Part B compound (112 mg; 0.6 mmol)

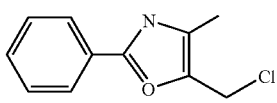

and K₂CO₃ (100 mg; 0.8 mmol) in CH₃CN (6 mL) was heated at 95° C. for 2 h, then cooled to RT. Solids were filtered off, and the filtrate was concentrated in vacuo. The residue was chromatographed (SiO₂; 95:5 to 85:15 hex:EtOAc) to give Part A compound (145 mg; 80%) as an oil.

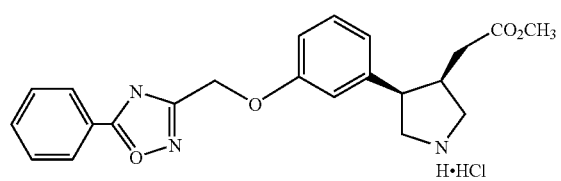

A solution of Part A compound (133 mg; 0.3 mmol) and HCl in dioxane (0.5 mL of a 4M solution; 2.0 mmol) in CH$_2$Cl$_2$ (4 mL) was stirred at RT for 2 h, then was concentrated in vacuo to give Part B compound as a white solid (110 mg; 95%), which was used in the next step without further purification.

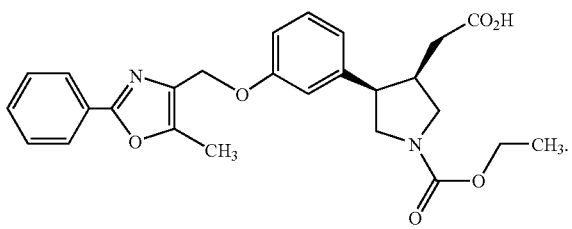

D

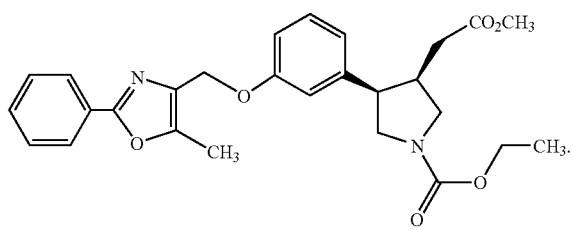

C

A solution of Part B compound (16 mg; 0.04 mmol), 2-ethyl chloroformate (5 μL, 0.06 mmol), and NaHCO$_3$ (15 mg; 0.2 mmol) in THF/H$_2$O (2 mL of a 1:1 solution) was stirred at RT for 1 h. Volatiles were removed in vacuo, and the residue was partitioned between EtOAc and H$_2$O. The organic phase was dried (MgSO$_4$) and concentrated in vacuo to give Part C compound, which was used in the next step without further purification.

A solution of Part C compound and LiOH H$_2$O (10 mg; 0.24 mmol) in 1:1 THF:H$_2$O (2 mL) was stirred at RT for 2 h, then was acidified to pH 2 with 1 M aqueous HCl, and finally partitioned between EtOAc and H$_2$O. The organic phase was dried (MgSO$_4$) and concentrated in vacuo. The residue was purified by preparative HPLC (YMC reverse-phase ODS 20×100 mm column; detection at 220 nm; flow rate=20 mL/min; continuous gradient from 50% A to 100% B over 10 min+4 min hold time at 100% B, where A=90:10:0.1 H$_2$O:MeOH:TFA and B=90:10:0.1 MeOH:H$_2$O:TFA) and lyophilized from dioxane to furnish the title compound (11 mg; 66%) as a white solid. [M+H]$^+$=465.5

EXAMPLES 114-118

Following the procedure for the synthesis of Example 113, the following compounds of the invention were prepared.

| Example No. | R | [M + H]$^+$ |
|---|---|---|
| 114 | ![structure] racemic cis | 479.6 |
| 115 | ![structure] racemic cis | 493.6 |
| 116 | ![structure] racemic cis | 513.6 |

| Example No. | R | [M + H]+ |
|---|---|---|
| 117 | 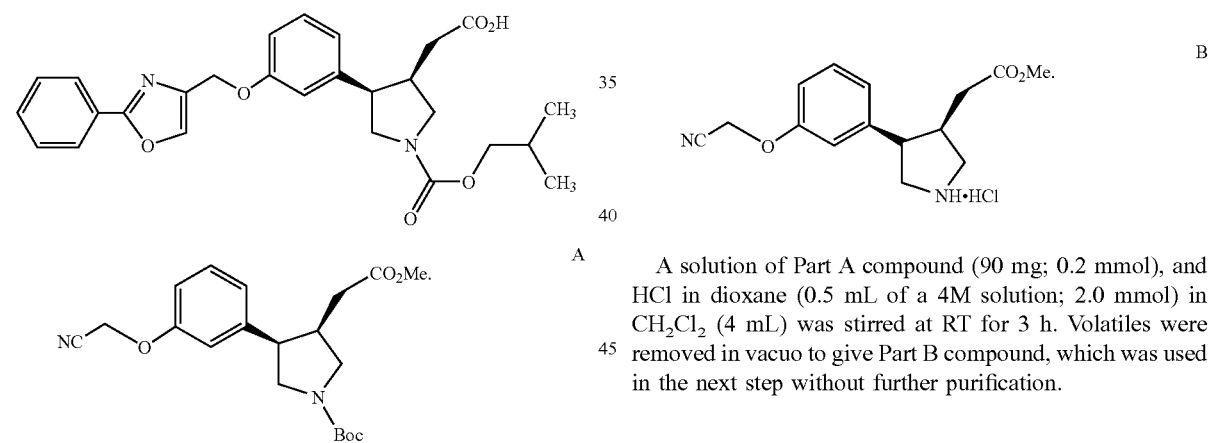
racemic cis | 543.6 |
| 118 | 
racemic cis | 493.6 |

EXAMPLE 119

A solution of Example 106 Part K compound (150 mg; 0.5 mmol)

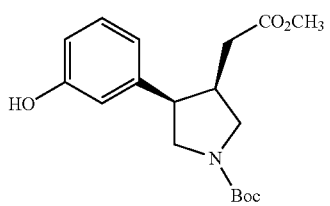

α-Chloroacetonitrile (140 μL; 2.5 mmol) and K₂CO₃ (310 mg; 2.5 mmol) in CH₃CN (15 mL) was heated at 90° C. for 2 h. Solids were filtered off and the filtrate was concentrated in vacuo. The residue was chromatographed (SiO₂; 85:15 hex: EtOAc) to give Part A compound: (90 mg; 54%) as an oil.

A solution of Part A compound (90 mg; 0.2 mmol), and HCl in dioxane (0.5 mL of a 4M solution; 2.0 mmol) in CH₂Cl₂ (4 mL) was stirred at RT for 3 h. Volatiles were removed in vacuo to give Part B compound, which was used in the next step without further purification.

A mixture of Part C compound, isobutyl chloroformate (37 μL; 0.3 mmol) and NaHCO₃ (80 mg; 1.0 mmol) in 1:1 THF:H₂O (4 mL) was stirred at RT for 30 min, then was partitioned between EtOAc and H₂O. The organic phase was dried (MgSO₄) and concentrated in vacuo. The residue was chromatographed (SiO₂; 3:1 hex:EtOAc) to give Part C compound (30 mg; 33%) as an oil.

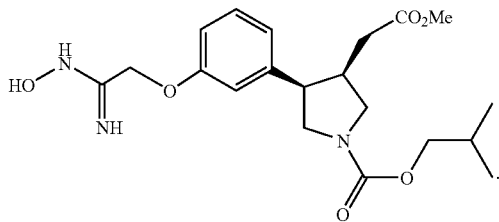

D

A solution of Part C compound (90 mg; 0.2 mmol), and 50% $NH_2OH/H_2O$ (75 mg) in MeOH (6 mL) and $H_2O$ (3 mL) was heated at 90° C. for 3 h. Volatiles were removed in vacuo, and the residue was lyophilized from dioxane to give Part D compound as a pink solid (75 mg), which was used in the next step without further purification.

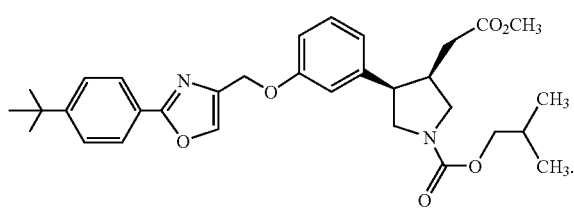

E

A solution of Part C compound (15 mg; 0.04 mmol) and 4-tert-butyl-benzoyl chloride (8 μL; 0.04 mmol) in pyridine (1 mL) was heated at 115° C. for 4 h, then was cooled to RT. Volatiles were removed in vacuo, and the residue was purified by preparative HPLC (YMC reverse-phase ODS 20×100 mm column; detection at 220 nm; flow rate=20 mL/min; continuous gradient from 50% A to 100% B over 10 min+5 min hold time at 100% B, where A=90:10:0.1$H_2O$:MeOH:TFA and B=90:10:0.1 MeOH:$H_2O$:TFA) to furnish Part E compound.

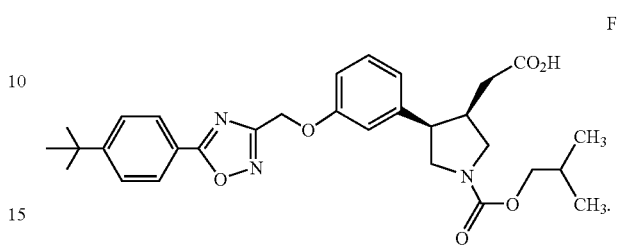

F

A solution of Part E compound and LiOH.$H_2O$ (15 mg) in 1:1 THF:$H_2O$ (2 mL) was stirred at RT for 4 h, then was acidified with aqueous 1 M HCl. Volatiles were removed in vacuo and the residue was purified by preparative HPLC (YMC reverse-phase ODS 20×100 mm column; detection at 220 nm; flow rate=20 mL/min; continuous gradient from 50% A to 100% B over 10 min+5 min hold time at 100% B, where A=90:10:0.1 $H_2O$:MeOH:TFA and B=90:10:0.1 MeOH:$H_2O$:TFA) and lyophilized from dioxane to furnish the title compound as a white lyophilate (2.0 mg; 10% yield for 2 steps).

$[M+H]^+$=536.6

EXAMPLES 120-122

Following the general procedure for the synthesis of Example 119, the following compounds of the invention were prepared.

| Example No. | R | $[M + H]^+$ |
|---|---|---|
| 120 | *(racemic cis structure shown)* | 524.6 |
| 121 | *(racemic cis structure shown)* | 564.5 |

| Example No. | R | [M + H]+ |
|---|---|---|
| 122 | 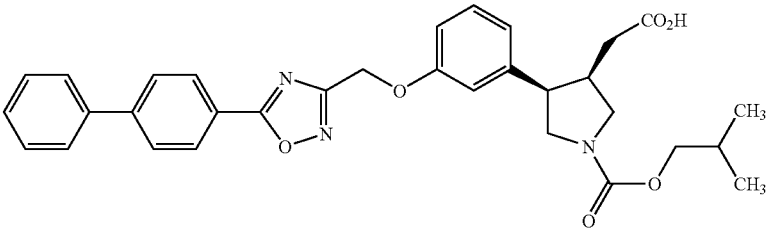 racemic cis | 556.6 |

EXAMPLE 123

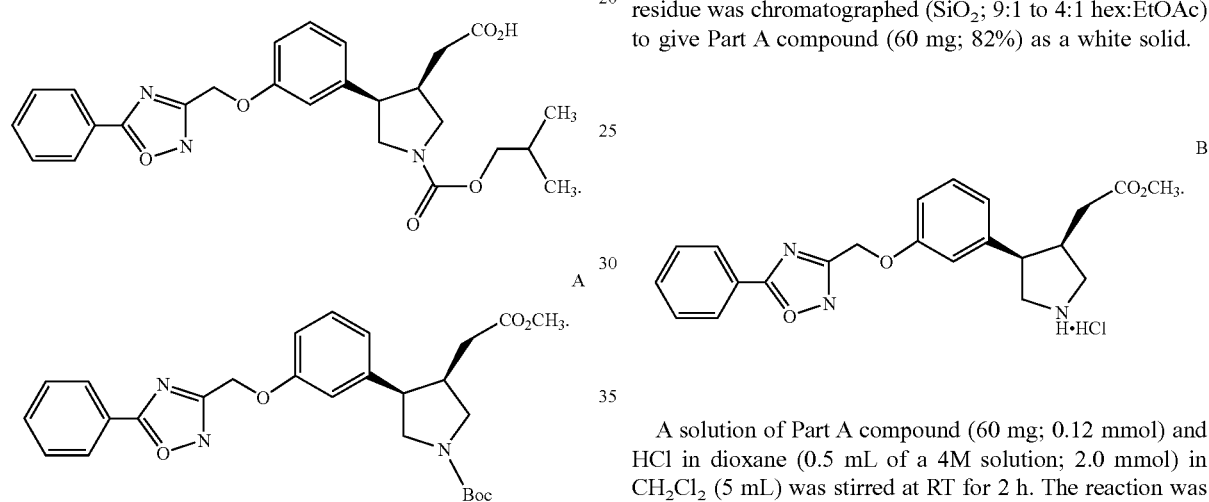

A mixture of Example 106 Part K compound (50 mg; 0.15 mmol)

and 5-Chloromethyl-3-phenyl-[1,2,4]oxadiazole (58 mg; 0.3 mmol),

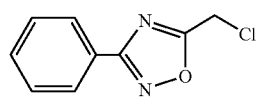

and $K_2CO_3$ (41 mg; 0.3 mmol) in $CH_3CN$ (10 mL) was heated at 90° C. for 2 h, then cooled to RT. Solids were filtered off, and the filtrate was concentrated in vacuo. The residue was chromatographed ($SiO_2$; 9:1 to 4:1 hex:EtOAc) to give Part A compound (60 mg; 82%) as a white solid.

A solution of Part A compound (60 mg; 0.12 mmol) and HCl in dioxane (0.5 mL of a 4M solution; 2.0 mmol) in $CH_2Cl_2$ (5 mL) was stirred at RT for 2 h. The reaction was concentrated to give Part B compound as a white solid (45 mg; 86%), which was used in the next step without further purification.

A solution of Part B compound (15 mg, 0.04 mmol), isobutyl chloroformate (7 µL, 0.06 mmol), and $NaHCO_3$ (12 mg; 0.16 mmol) in 1:1 THF:$H_2O$ (2 mL) was stirred at RT for 30 min. Volatiles were removed in vacuo, and the residue was partitioned between EtOAc and $H_2O$. The organic phase was dried ($MgSO_4$) and concentrated in vacuo to give Part C compound, which was used in the next step without further purification.

EXAMPLE 126

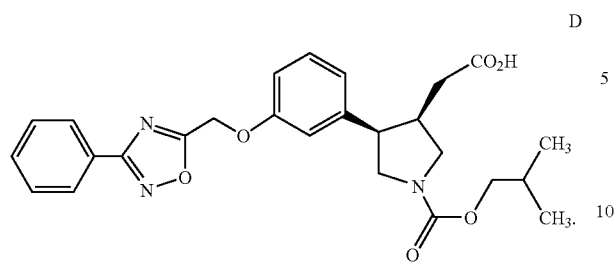

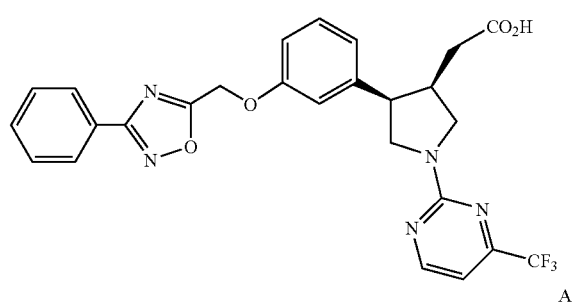

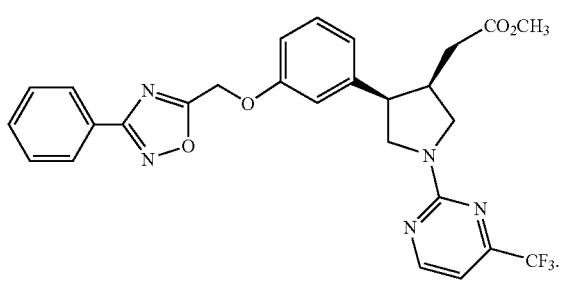

A solution of crude Part C compound and LiOH.H₂O (8 mg; 0.2 mmol) in 1:1 THF:H₂O (2 mL) was stirred at RT for 6 h, then was acidified to pH 2 with aqueous 1 M HCl, and finally was partitioned between EtOAc and H₂O. The organic phase was dried (MgSO₄) and concentrated in vacuo. The residue was purified by preparative HPLC (YMC reverse-phase ODS 20×100 mm column; detection at 220 nm; flow rate=20 mL/min; continuous gradient from 50% A to 100% B over 10 min+5 min hold time at 100% B, where A=90:10:0.1 H₂O:MeOH:TFA and B=90:10:0.1 MeOH: H₂O:TFA) and lyophilized from dioxane to furnish the title compound (11 mg; 66%) as a white solid.
[M+H]⁺=480.0

A solution of Example 123 Part B compound (30 mg; 0.07 mmol)

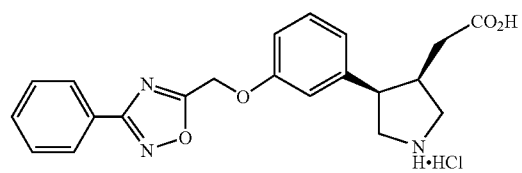

EXAMPLES 124-125

Following the general procedure for the synthesis of Example 123, the following compounds of the invention were prepared.

2-chloro-4-(trifluoromethyl) pyrimidine (22 μL, 0.14 mmol), and Et₃N (39 μL; 0.28 mmol) in toluene (8 mL) was heated at 85° C. for 1 h. Volatiles were removed in vacuo,

| Example No. | R | [M + H]⁺ |
|---|---|---|
| 124 | ![racemic cis structure] racemic cis | 556.6 |
| 125 | ![racemic cis structure] racemic cis | 536.6 | and the residue was chromatographed (SiO$_2$; 9:1 to 4:1 hex:EtOAc) to give Part A compound (36 mg; 96%) as a white solid.

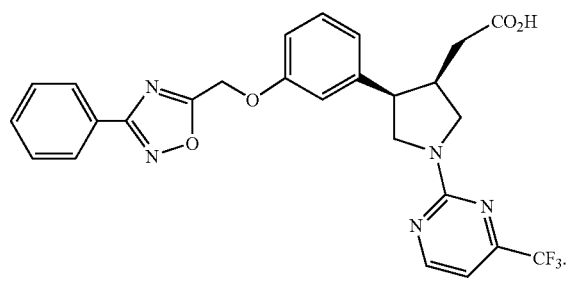

B

A solution of Part A compound (36 mg; 0.07 mmol) and LiOH.H$_2$O (14 mg; 0.4 mmol) in 1:1 THF:H$_2$O (2 mL) was stirred at RT for 18 h, then was acidified to pH 2 with aqueous 1M HCl, and finally was partitioned between EtOAc and H$_2$O. The organic phase was dried (MgSO$_4$) and concentrated in vacuo. The residue was purified by preparative HPLC (YMC reverse-phase ODS 20×100 mm column; detection at 220 nm; flow rate=20 mL/min; continuous gradient from 50% A to 100% B over 10 min+5 min hold time at 100% B, where A=90:10:0.1H$_2$O:MeOH:TFA and B=90:10:0.1 MeOH:H$_2$O:TFA) and lyophilized from dioxane to give the title compound as a white solid (33 mg; 94%).

[M+H]$^+$=526.0

EXAMPLES 127-130

Following the general procedure for the synthesis of Example 126, the following compounds of the invention were prepared (Example 129 was prepared using Example 89 Part B compound and Example 130 was prepared using Example 23 Part A compound).

| Example No. | R | [M + H]$^+$ |
|---|---|---|
| 127 | (racemic cis) | 602.6 |
| 128 | (racemic cis) | 582.6 |
| 129 | (racemic cis) | 539.5 |

-continued

| Example No. | R | [M + H]+ |
|---|---|---|
| 130 | 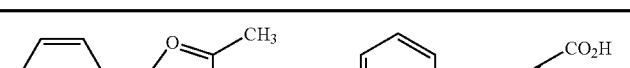 racemic cis | 553.6 |

EXAMPLE 131

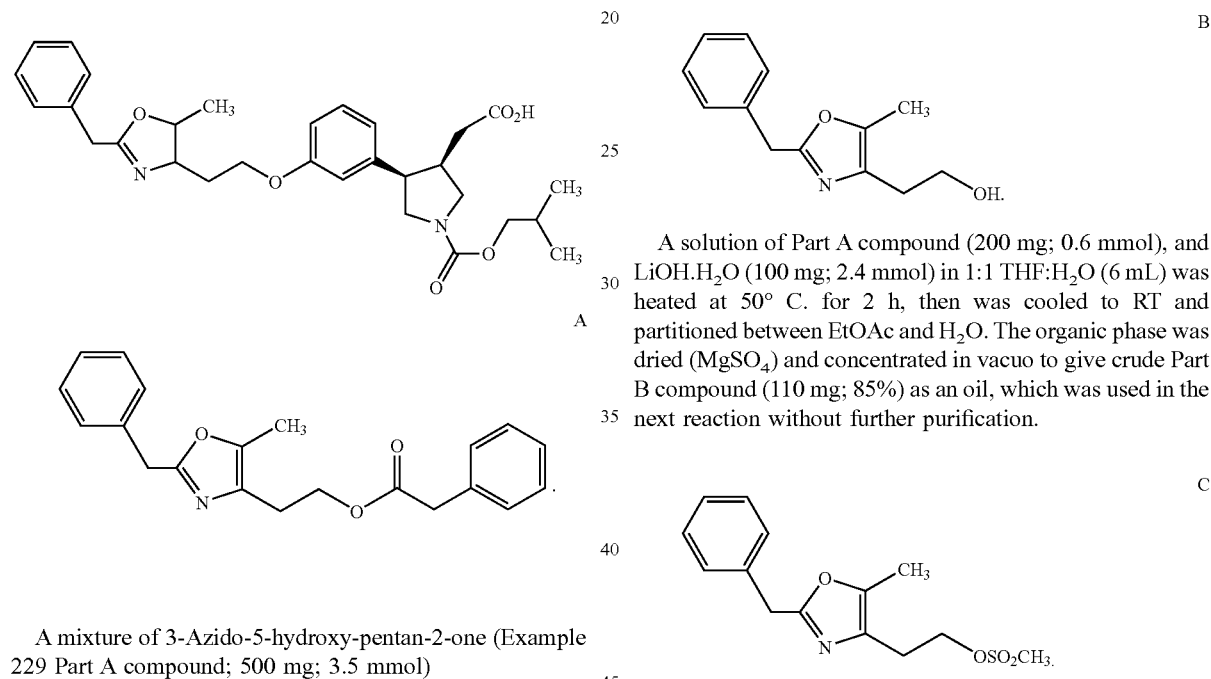

A mixture of 3-Azido-5-hydroxy-pentan-2-one (Example 229 Part A compound; 500 mg; 3.5 mmol)

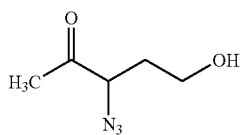

and polymer-bound Ph₃P (1.75 g; 5.25 mmol) in dry dioxane (10 mL) was stirred at RT for 10 min, after which benzylcarbonyl chloride (0.9 mL; 7.0 mmol) was added dropwise. The reaction was heated at 80° C. for 18 h, cooled to RT and the resin was filtered off. The filtrate was concentrated in vacuo, and the residue was purified by preparative HPLC (YMC reverse-phase ODS 30×250 mm column; detection at 220 nm; flow rate=20 mL/min; continuous gradient from 50% A to 100% B over 30 min+7 min hold time at 100% B, where A=90:10:0.1 H₂O:MeOH:TFA and B=90:10:0.1 MeOH:H₂O:TFA) to give Part A compound as an oil (200 mg; 17%).

A solution of Part A compound (200 mg; 0.6 mmol), and LiOH.H₂O (100 mg; 2.4 mmol) in 1:1 THF:H₂O (6 mL) was heated at 50° C. for 2 h, then was cooled to RT and partitioned between EtOAc and H₂O. The organic phase was dried (MgSO₄) and concentrated in vacuo to give crude Part B compound (110 mg; 85%) as an oil, which was used in the next reaction without further purification.

To a 0° C. solution of Part B compound (75 mg; 0.4 mmol) and Et₃N (100 μL; 0.8 mmol) in CH₂Cl₂ (5 mL) was added dropwise methanesulfonyl chloride (32 μL; 0.5 mmol). The reaction was warmed to RT and stirred at RT for 1.5 h, then was partitioned between CH₂Cl₂ and aqueous 1M HCl. The organic phase was washed with saturated aqueous NaHCO₃ and brine, dried (MgSO₄) and concentrated in vacuo. The residue was chromatographed (SiO₂; 9:1 to 7:3 hex:EtOAc) to give Part C compound (95 mg; 93%) as an oil.

A solution of Example 106 Part K compound (270 mg; 0.8 mmol) and HCl in dioxane (1.0 mL of a 4M solution; 4.0 mmol) in CH$_2$Cl$_2$ (3 mL) was stirred at RT for 2 h. Volatiles were removed in vacuo to give crude Part D compound, which was used in the next step without further purification.

E

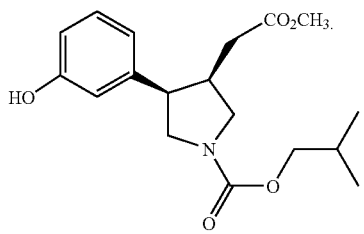

A solution of crude Part D compound, isobutyl chloroformate (90 μL, 0.68 mmol) and NaHCO$_3$ (336 mg; 4.0 mmol) in THF/H$_2$O (6 mL of a 1:1 solution) was stirred at RT for 30 min, then was partitioned between EtOAc and H$_2$O. The organic phase was dried (MgSO$_4$) and concentrated in vacuo. The residue was chromatographed (SiO$_2$; 3:1 hex:EtOAc) to give Part E compound (200 mg; 74% for two steps) as an oil.

F

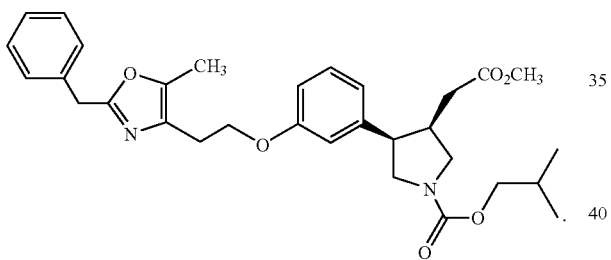

A mixture of Part C compound (30 mg; 0.1 mmol), Part D compound (15 mg; 0.05 mmol), and K$_2$CO$_3$ (10 mg; 0.075 mmol) in CH$_3$CN (1 mL) was heated at 95° C. for 30 h. Volatiles were removed in vacuo, and the residue was partitioned between EtOAc and H$_2$O. The organic phase was dried (MgSO$_4$) and concentrated in vacuo. The residue was purified by preparative HPLC (YMC reverse-phase ODS 20×100 mm column; detection at 220 nm; flow rate =20 mL/min; continuous gradient from 50% A to 100% B over 10 min+5 min hold time at 100% B, where A=90:10:0.1H$_2$O:MeOH:TFA and B=90:10:0.1 MeOH:H$_2$O:TFA) to give Part F compound (13 mg; 48% yield).

G

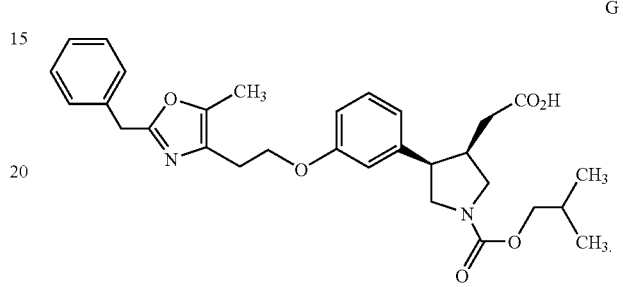

A solution of Part D compound (13 mg; 0.02 mmol) and LiOH.H$_2$O (10 mg; 0.1 mmol) in 1:1 THF:H$_2$O (1 mL) was stirred at RT for 18 h, then was acidified to pH 1 with 1 M aqueous HCl and finally partitioned between EtOAc and H$_2$O. The organic phase was dried (MgSO$_4$) and concentrated in vacuo. The residue was lyophilized from dioxane to give the title compound (9 mg; 39%) as a white solid. [M+H]$^+$=521.6

EXAMPLES 132-143

Following the general procedure for the synthesis of Example 31, the following compounds of the invention were prepared. All the appropriate aryloxazole-ethanol reagents were prepared according to the general procedure for the synthesis of Example 231 Part A compound.

| Example No. | R | [M + H]$^+$ |
|---|---|---|
| 132 | ![structure] | 563.7 | racemic cis

-continued

| Example No. | R | [M + H]+ |
|---|---|---|
| 133 | 4-methoxyphenyl-oxazole(5-methyl)-CH2CH2-O-phenyl-pyrrolidine(N-CO-O-CH2CH(CH3)2)-CH2CO2H, racemic cis | 537.6 |
| 134 | 3-methoxyphenyl-oxazole(5-methyl)-CH2CH2-O-phenyl-pyrrolidine(N-CO-O-CH2CH(CH3)2)-CH2CO2H, racemic cis | 537.6 |
| 135 | 3-chlorophenyl-oxazole(5-methyl)-CH2CH2-O-phenyl-pyrrolidine(N-CO-O-CH2CH(CH3)2)-CH2CO2H, racemic cis | 542.1 |
| 136 | 4-trifluoromethylphenyl-oxazole(5-methyl)-CH2CH2-O-phenyl-pyrrolidine(N-CO-O-CH2CH(CH3)2)-CH2CO2H, racemic cis | 575.6 |
| 137 | 3-trifluoromethylphenyl-oxazole(5-methyl)-CH2CH2-O-phenyl-pyrrolidine(N-CO-O-CH2CH(CH3)2)-CH2CO2H, racemic cis | 575.6 |

-continued
| Example No. | R | [M + H]+ |
|---|---|---|
| 138 | 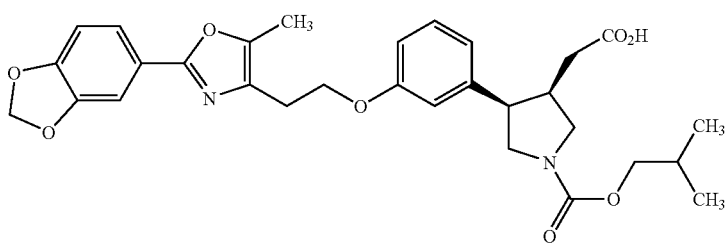<br>racemic cis | 551.6 |
| 139 | 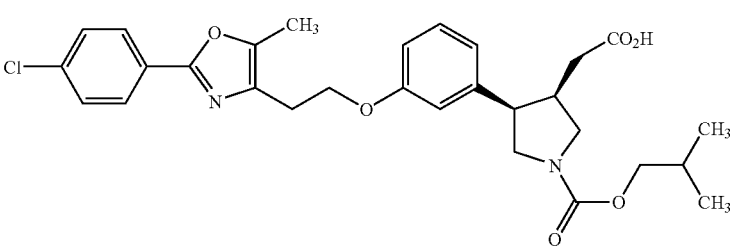<br>racemic cis | 542.1 |
| 140 | <br>cis enantiomer #1 | 542.1 |
| 141 | 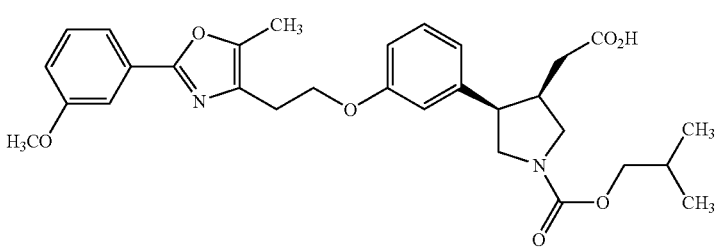<br>cis enantiomer #1 | 537.6 |
| 142 | 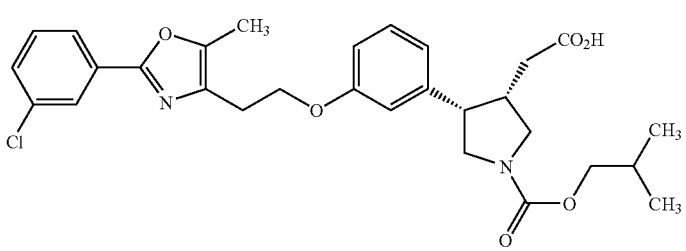<br>cis enantiomer #2 | 542.1 |

| Example No. | R | [M + H]⁺ |
| --- | --- | --- |
| 143 | 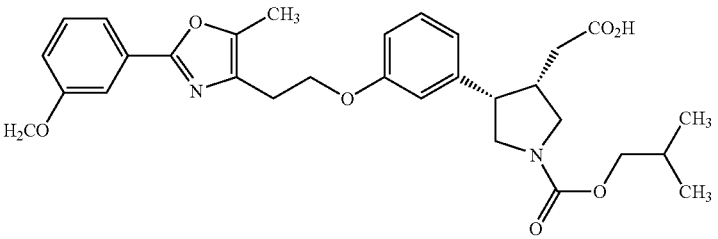 cis enantiomer #2 | 537.6 |

EXAMPLE 144

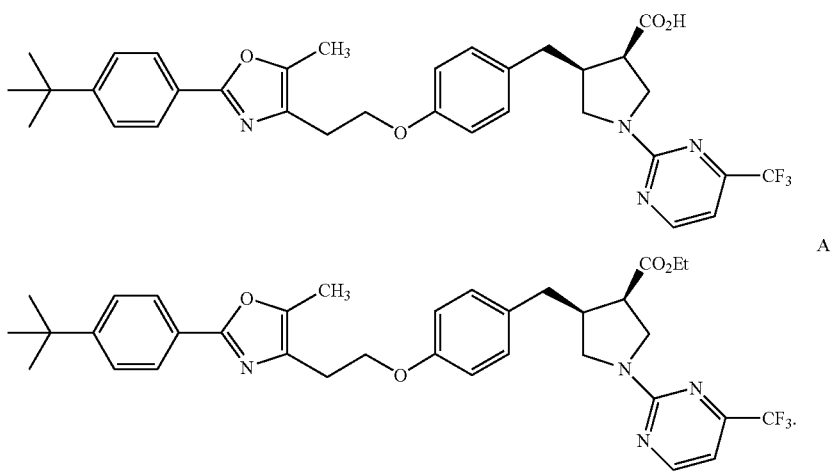

A mixture of chiral 4-(3-hydroxy-phenyl)-1-(4-trifluoromethyl-pyrimidin-2-yl)-pyrrolidine-3-carboxylic acid ethyl ester (24 mg; 0.06 mmol; obtained from chiral prep HPLC separation of Example 243 Part A compound),

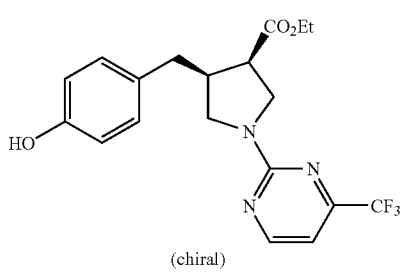

methanesulfonic acid 2-[2-(4-tert-butylphenyl)-5-methyl-oxazol-4-yl]-ethyl ester (41 mg; 0.12 mmol; The oxazole-ethanol was prepared according to the general procedure described for the synthesis of Example 231 Part A compound. The mesylate was prepared from the alcohol according to the general procedure described for the synthesis of Example 23 Part A compound.),

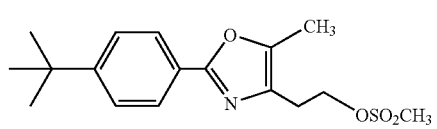

and K₂CO₃ (14 mg; 0.09 mmol) in CH₃CN (1 mL) was heated at 90° C. for 18 h. More K₂CO₃ (14 mg; 0.09 mmol) was added and the heating was continued at 90° C. for an additional 18 h. The reaction was then cooled to RT and volatiles were removed in vacuo. The residue was taken up in MeOH (2 mL), sonicated and filtered. The filtrate was concentrated in vacuo and the residue was purified by preparative HPLC (YMC reverse-phase ODS 20×100 mm column; detection at 220 nm; flow rate=20 mL/min; continuous gradient from 30% A to 100% B over 10 min+6 min hold time at 100% B, where A=90:10:0.1H₂O:MeOH:TFA and B=90:10:0.1 MeOH:H₂O:TFA) to give Part A compound (cis diastereomer; 7.6 mg; 22%).

A second product isolated was Part B compound (trans diastereomer; 20 mg; 57%).

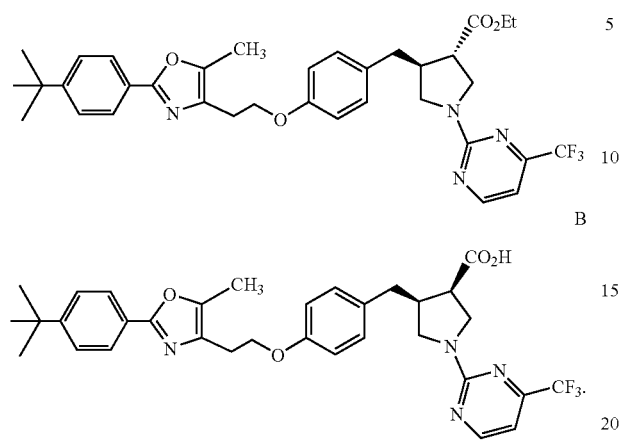

B

A solution of Part A compound (7.6 mg; 0.01 mmol) and conc. HCl/HOAc (1 mL of a 1:9 solution) was heated at 80° C. for 6 h, then was cooled to RT. Volatiles were removed in vacuo and the residue was purified by preparative HPLC (YMC reverse-phase ODS 20×100 mm column; detection at 220 nm; flow rate=20 mL/min; continuous gradient from 30% A to 100% B over 10 min+5 min hold time at 100% B, where A=90:10:0.1H$_2$O:MeOH:TFA and B=90:10:0.1 MeOH:H$_2$O:TFA) and was lyophilized from dioxane to give the title compound as a white solid (2.5 mg; 34% yield). [M+H]$^+$=609.6

EXAMPLE 145

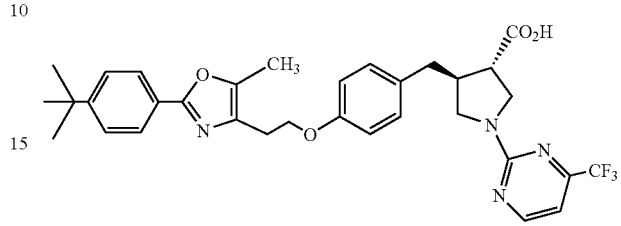

Following the same procedure as for Example 144 Part C, Example 144 Part B compound was converted to the title compound. [M+H]$^+$=609.6

EXAMPLES 146-147

Following the general procedure for the synthesis of Examples 144 and 145, the following compounds of the invention were prepared from the enantiomer

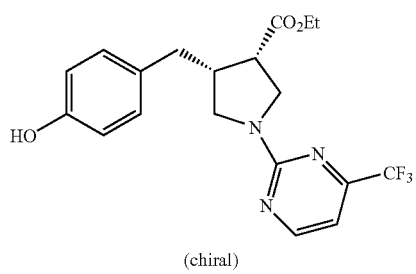

(chiral)

| Example No. | R | [M + H]$^+$ |
|---|---|---|
| 146 | 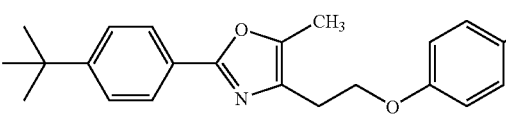 #2 trans enantiomer | 609.6 |
| 147 | 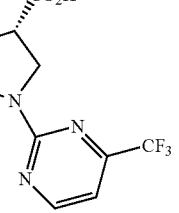 #2 trans enantiomer | 609.6 |

EXAMPLE 148

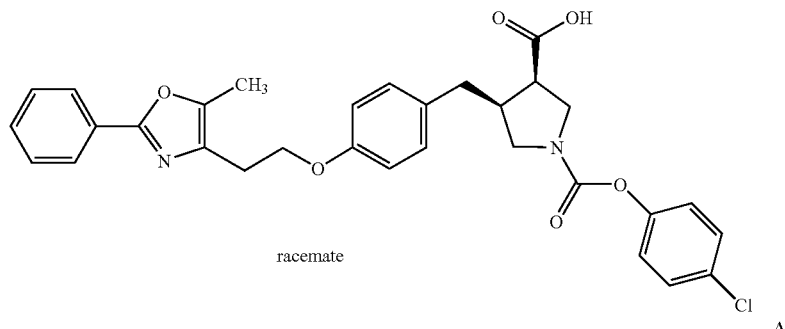
racemate

A solution of Example 23 Part F compound (240 mg; 0.45 mmol) in HOAc (20 mL) and aqueous HCl (20% solution; 5 mL) was stirred at 85° C. for 4 h, then was cooled to RT and concentrated in vacuo to give Part A compound (200 mg; 100%) as an oil.

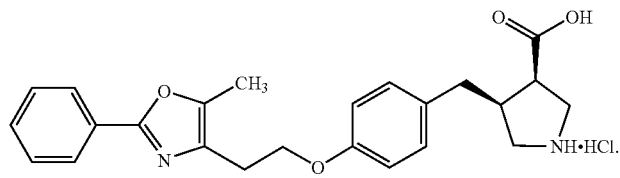
racemate

B

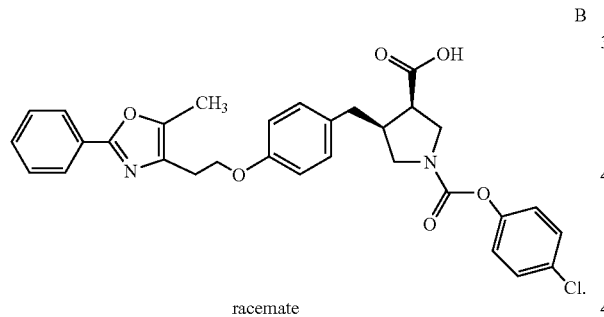
racemate

A mixture of part A compound (20 mg; 0.037 mmol), NaHCO$_3$ (8 mg; 0.09 mmol) and 4-chlorophenyl chloroformate (10 µL; 0.074 mmol) in THF (0.5 mL) and water (50 µL) was stirred at RT for 1 h, then concentrated in vacuo. The residue was partitioned between EtOAc (2 mL) and saturated KHSO$_4$ (1 mL). The organic phase was washed with brine (1 mL), dried (Na$_2$SO$_4$), and concentrated in vacuo; the residue was purified by preparative HPLC (as described for Example 1) and lyophilized (water) to give the title compound (18.3 mg; 66%) as an oil.

[M+H]$^+$=561.2

EXAMPLES 149-157

Compounds 149-157 of the invention were prepared (from Example 148 part A compound) in a similar fashion to the synthesis of Example 148 using appropriate chloroformates.

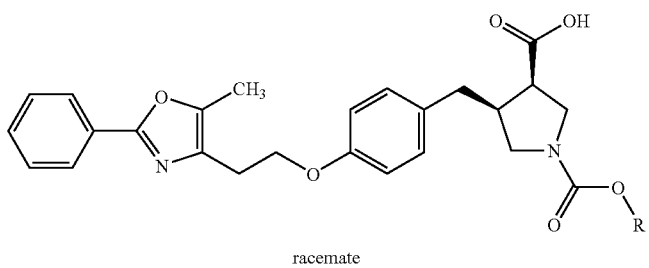
racemate

| Example # | R | [M + H]$^+$ |
|---|---|---|
| 149 | ~~CH$_2$–phenyl~~ | 541.3 |

-continued
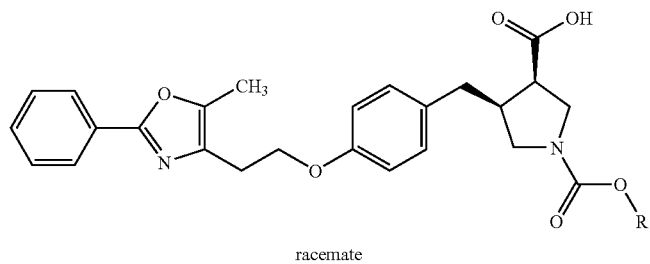
racemate
| Example # | R | [M + H]+ |
|---|---|---|
| 150 | isobutyl | 507.3 |
| 151 | n-propyl | 493.3 |
| 152 | n-butyl | 507.3 |
| 153 | 4-methylphenyl | 541.3 |
| 154 | 4-methoxyphenyl | 557.2 |
| 155 | 2-methoxyethyl | 509.3 |
| 156 | neopentyl | 521.3 |
| 157 | phenyl | 527.2 |

EXAMPLES 158-163

Examples 158-163 of the invention were prepared (from Example 148 part A compound) in a similar fashion to the synthesis of Example 148 using appropriate acylating reagents.

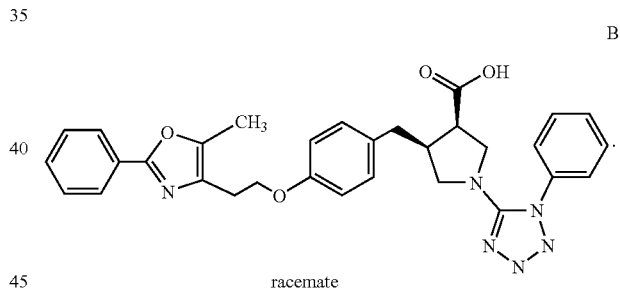

| Example # | R | Reagent | [M + H]+ |
|---|---|---|---|
| 158 | cyclohexyl-C(=O)- | cyclohexanecarbonyl chloride | 517.2 |
| 159 | PhSO2- | PhSO2Cl | 547.2 |
| 160 | Et2N-C(=O)- | Et2N-C(=O)Cl | 506.3 |
| 161 | t-Bu-C(=O)- | t-Bu-C(=O)Cl | 491.1 |
| 162 | neopentyl-C(=O)- | neopentyl-C(=O)Cl | 505.1 |
| 163 | t-Bu-NH-C(=O)- | t-Bu-N=C=O | 506.1 |

EXAMPLE 164

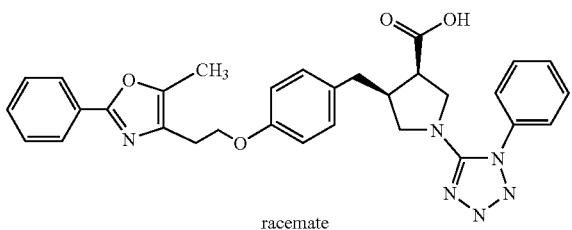
racemate

A

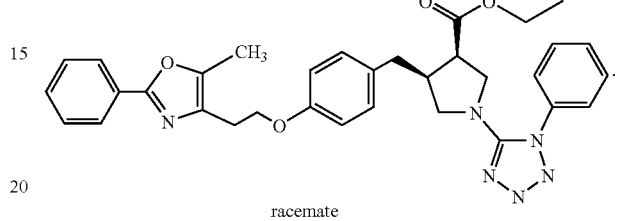
racemate

A solution of Example 31 Part A compound (5 mg; 0.012 mmol), 5-chloro-1-phenyl-tetrazole (15 µL; 0.11 mmol), Et₃N (40 µL; 0.29 mmol) in toluene (1 mL) was stirred at 120° C. in a sealed tube for 18 h; then was cooled to RT and concentrated in vacuo. The residue was partitioned between EtOAc (10 mL) and brine (5 mL). The organic layer was dried (Na₂SO₄) and concentrated in vacuo; the residue was purified by preparative HPLC (as described for Example 1) and lyophilized (water) to give Part A compound (5 mg; 75%) as an oil.

B racemate

A solution of Part A compound (5 mg; 0.0087 mmol) in HOAc (0.8 mL) and aqueous HCl (0.2 mL of a 20% solution) was stirred at 88° C. for 4 h; then was cooled to RT and concentrated in vacuo. The residue was purified by preparative HPLC (as described for Example 1) and lyophilized (water) to give the title compound (2 mg; 42%) as an oil.

[M+H]⁺=551.2

¹H NMR (CD₃OD): δ 7.86 (m, 2H), 7.38 (m, 8H), 6.87 (m, 2H), 6.69 (m, 2H), 4.12 (t, J=7 Hz, 2H), 3.49 (m, 1H), 3.40 (m, 1H), 3.06 (m, 1H), 3.01 (m, 2H), 2.88 (t, J=7 Hz, 2H), 2.67 (m, 1H), 2.58 (m, 1H), 2.36 (m, 1H), 2.28 (s, 3H)

EXAMPLES 165-169

Examples 165 through 169 of the invention were prepared in a similar fashion to the synthesis of Example 164 (from Example 31 Part A compound) using appropriate heteroaryl chlorides.

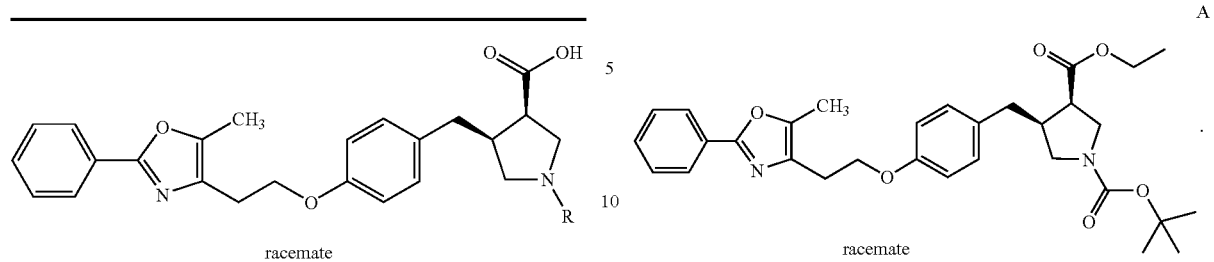

racemate

| Example # | R | [M + H]+ |
|---|---|---|
| 165 | thiazole-N+(=O)O- | 535.2 |
| 166 | thiazole-Br | 568.1 |
| 167 | pyridine-Cl, CF3 | 586.1 |
| 168 | pyrimidine-CH3 | 499.2 |
| 169 | pyrimidine-OCH3 | 514.2 |

EXAMPLE 170

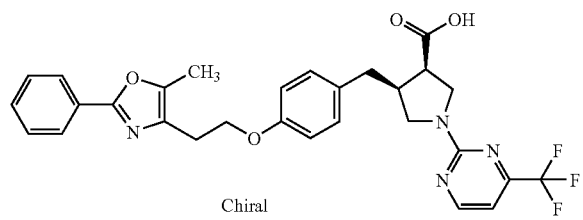

Chiral

-continued

A racemate

A mixture of Example 23 Part E compound (1.00 g; 2.9 mmol), 5-phenyl-2-methyl-oxazole-4-ethanol (700 mg; 3.4 mmol) and cyanomethylene tributylphosphorane (830 mg; 3.5 mmol) in toluene (15 mL) was stirred at 85° C. for 4 h, then was cooled to RT and concentrated in vacuo. The residue was chromatographed (SiO₂; continuous gradient from 7:3 to 3:7 hex:EtOA) to give Part A compound (1.30 g; 85%) as an oil.

B racemate

A solution of Part A compound (1.3 g; 2.4 mmol) in DCE (10 mL) and HCl in dioxane (2.5 mL of a 4M solution; 10 mmol) was stirred at RT for 3 h; then was concentrated in vacuo. The residue was partitioned between EtOAc (30 mL) and saturated aqueous NaHCO₃ (10 mL). The organic layer was dried (Na₂SO₄) and concentrated in vacuo to give Part B compound (530 mg; 50%; racemate) as a colorless oil.

C 3R, 4S nantiomer

The individual enantiomers of racemic Part B compound (530 mg; 1.2 mmol) were separated by preparative HPLC using the following conditions: ChiralPak AD chiral column, 5 cm×50 cm, 20µ; Isocratic solvent system: 15:85 A:B (A=50% MeOH+50% EtOH+0.1% Et₂NH; B=100% heptane+0.1% Et₂NH); Injection volume=10 mL MeOH; Detection wavelength=220 nm; Flow rate=50 mL/min. The enantiomer that eluted off the column first was Part C compound (245 mg; 46 mg), which was isolated as an oil. Analytical chiral HPLC conditions: ChiralPak AD chiral column 4.6×250 mm; Isocratic solvent system: 15% A+85% B, where Solvent A=50% MeOH+50% EtOH+0.1% Et₂NH; Solvent B=100% heptane+0.1% Et₂NH; Detection wavelength=254 nm; Flow rate=1 mL/min; Retention time=13.3 min. [α] (0.48w/v%)$_{MeOH}^{589}$=+10.9°.

The other enantiomer from Part B compound (that eluted off the column later than Part C compound) was identified as Part D compound (245 mg; 46%), which was isolated as an oil. Under the identical chiral analytical HPLC conditions as for Part C compound, the retention time of Part D compound=26.7 min. [α] (0.50w/v%)$_{MeOH}^{589}$=−12.3°.

D

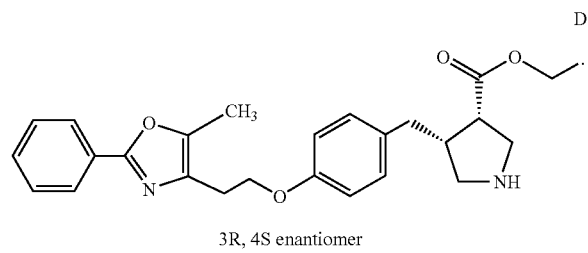

3R, 4S enantiomer

E

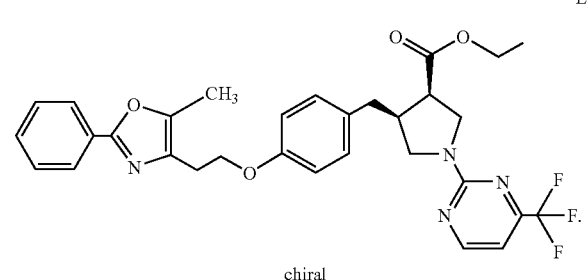

chiral

A solution of Part C compound (225 mg; 0.52 mmol), 2-chloro-4-trifluoromethylpyrimidine (77 μL; 0.64 mmol), Et$_3$N (130 μL; 0.93 mmol) in toluene (4.5 mL) was stirred at 60° C. in a sealed tube for 3 h; then was cooled to RT and concentrated in vacuo. The residue was partitioned between EtOAc (10 mL) and brine (5 mL). The organic layer was dried (Na$_2$SO$_4$) and concentrated in vacuo; the residue was chromatographed (SiO$_2$; continuous gradient from 100% hex to 1:1 hex:EtOAc) to provide Part E compound (300 mg; 100%) as a colorless oil.

F

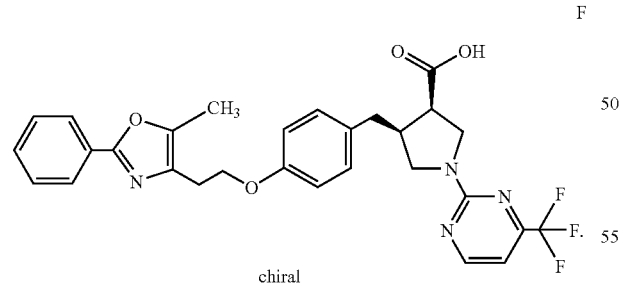

chiral

A solution of Part E compound (300 mg; 0.52 mmol) in HOAc (4 mL) and aqueous HCl (1 mL of a 20% solution) was stirred at 70° C. for 18 h; then was cooled to RT and concentrated in vacuo. The residue was partitioned between EtOAc (30 mL) and water (10 mL). The organic layer was washed with brine (10 mL), dried (Na$_2$SO$_4$) and concentrated in vacuo; the residue was purified by preparative HPLC (as described for Example 1) and lyophilized (dioxane) to give the title compound (230 mg; 81%) as a white solid.

[M+H]$^+$=553.2

[α] (0.96w/v%)$_{MeOH}^{589}$=−70.8°

Analytical chiral HPLC: Chiralpak AD chiral column 4.6×250 mm, 10μ; Isocratic solvent system: 3:7 A:B, where Solvent A=100% IPA+0.1% TFA; Solvent B=100% heptane Detection=254 nm; Flow rate=2 mL/min; Retention time=6.7 min.

$^1$H NMR (CD$_3$OD): δ 8.41 (m, 1H), 7.85 (m, 2H), 7.36 (m, 3H), 7.00 (d, J=9 Hz, 2H), 6.76 (m, 3H), 4.13 (m, 2 H), 3.81 (m, 1H), 3.62 (m, 1H), 3.51 (m, 2H), 3.18 (m, 1H), 2.87 (m, 2H), 2.73 (m, 2H), 2.41 (m, 1H), 2.28 (s, 3H)

Alternative Synthesis of Example 170 Part C Compound:

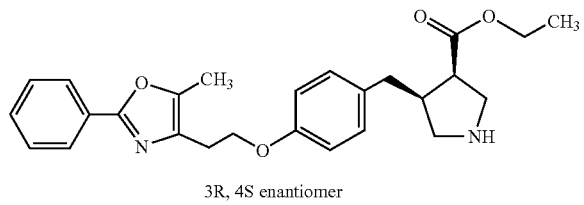

3R, 4S enantiomer

Crude Example 184 Part G compound was purified by HPLC (YMC reverse-phase ODS 20×100 mm column; flow rate=20 mL/min; 10 min continuous gradient from 20:100 B:A to 100% B+2 min hold-time at 100% B, where solvent A=90:10:0.1H$_2$O:MeOH:TFA and solvent B=90:10:0.1 MeOH:H$_2$O:TFA) to give pure Example 184 Part G compound as a white lyophilate. To a solution of the lyophilate in EtOH (10 mL) was added HCl in dioxane (3 mL of a 1 N solution), and the reaction was stirred for 24 h at RT, then was concentrated in vacuo. The residue was purified by HPLC (YMC reverse-phase ODS 20×100 mm column; flow rate=20 mL/min; 10 min. continuous gradient from 25:100 B:A to 100% B+2 min hold-time at 100% B, where solvent A=90:10:0.1H$_2$O:MeOH:TFA and solvent B=90:10:0.1 MeOH:H$_2$O:TFA) to give material which was identical in every respect to pure Example 170 Part C compound (13 mg; 33%). [α]$_{Methanol}^{589\ nm}$=+14.27° (c=XX mg/mL)

EXAMPLE 171

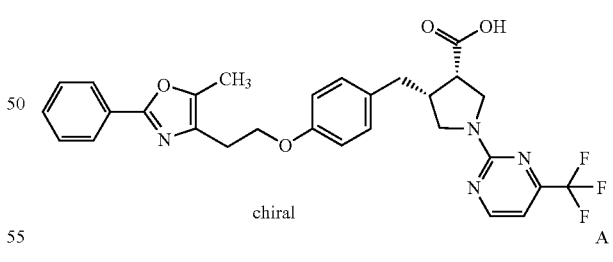

chiral

A

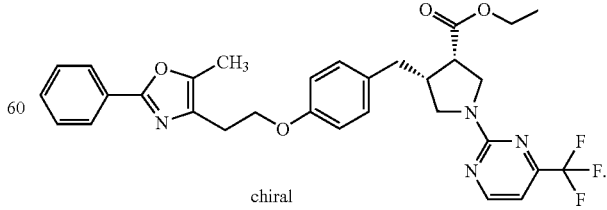

chiral

Part A compound (300 mg; 100%) was prepared from Example 170 Part D compound (225 mg; 0.52 mmol) using the same procedure as described for the synthesis of Example 170 Part E compound.

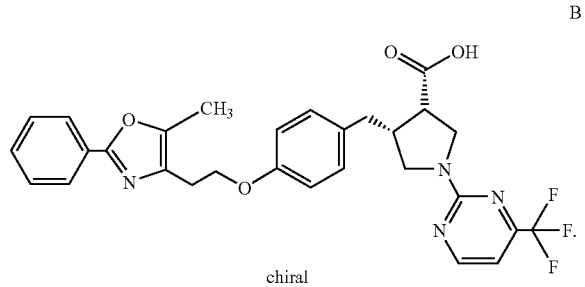

chiral

The title compound was prepared from Part A compound (225 mg; 0.52 mmol) using the procedure employed in the synthesis of Example 170 Part F compound. The title compound was obtained (180 mg; 63%) as a white solid after preparative HPLC (using the same conditions as described in Example 1)

[M+H]$^+$=553.2

[α] (0.96w/v%)$_{MeOH}^{589}$=+70.4°

Analytical chiral HPLC: Chiralpak AD chiral column; 4.6×250 mm, 10μ; Isocratic solvent system: 30% A+70% B, where Solvent A=100% IPA+0.1% TFA; Solvent B=100% heptane Detection=254 nm; Flow rate=2 mL/min Retention time=10.1 min.

$^1$H NMR (CD$_3$OD): δ 8.41 (m, 1H), 7.85 (m, 2H), 7.36 (m, 3H), 7.00 (d, J=9 Hz, 2H), 6.76 (m, 3H), 4.13 (m, 2H), 3.81 (m, 1H), 3.62 (m, 1H), 3.51 (m, 2H), 3.18 (m, 1H), 2.87 (m, 2H), 2.73 (m, 2H), 2.41 (m, 1H), 2.28 (s, 3H)

EXAMPLE 172

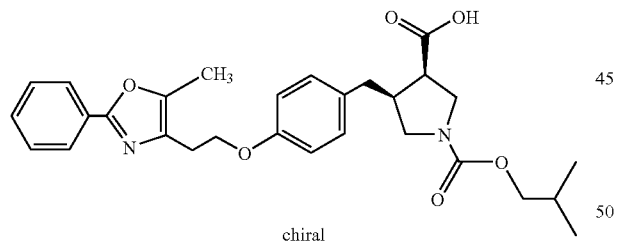

chiral

The title compound was prepared from the reaction of Example 170 Part C compound (131 mg; 0.30 mmol) with isobutyl chloroformate (50 μL; 0.45 mmol) using the same 2-step sequence as employed in the synthesis of Example 148 from Example 170 Part C compound. The title compound was obtained (75 mg; 44%) as a white solid after preparative HPLC (using the same conditions as described in Example 1)

[M+H]$^+$=507.2

$^1$H NMR (CD$_3$OD): δ 7.86 (m, 2H), 7.37 (m, 3H), 6.99 (m, 2H), 7.75 (m, 2H), 4.13 (m, 2H), 3.72 (m, 2H), 3.58 (m, 1H), 3.41 (m, 1H), 3.21 (m, 3H), 3.03 (m, 1H), 2.87 (m, 2H), 2.71 (m, 1H), 2.59 (m, 1H), 2.33 (m, 1H), 1.80 (s, 3H), 0.81 (q, J=7 Hz, 6H)

EXAMPLE 173

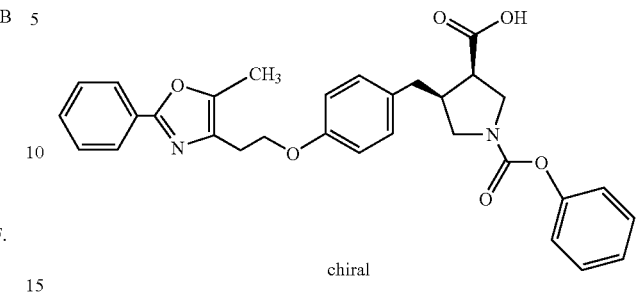

chiral

The title compound was prepared from the reaction of Example 170 Part C compound (109 mg; 0.25 mmol) with phenyl chloroformate (50 μL; 0.45 mmol) using the same 2-step sequence as employed in the synthesis of Example 148 from Example 170 Part-C compound. The title compound was obtained (80 mg; 61%) as a white solid after preparative HPLC (using the same conditions as described for the purification of Example 1 compound)

[M+H]$^+$=527.2

$^1$H NMR (CD$_3$OD): δ 7.85 (m, 2H), 7.37 (m, 3H), 7.26 (m, 2H), 7.10 (m, 1H), 7.00 (m, 4H), 6.78 (m, 2H), 4.13 (m, 2H), 3.80 (m, 1H), 3.65 (m, 1H), 3.45 (m, 1H), 3.24 (m, 1H), 3.11 (m, 1H), 2.87 (m, 2H), 2.74 (m, 1H), 2.66 (m, 1H), 2.42 (m, 1H), 2.27 (d, J=5 HZ, 3H)

EXAMPLE 174

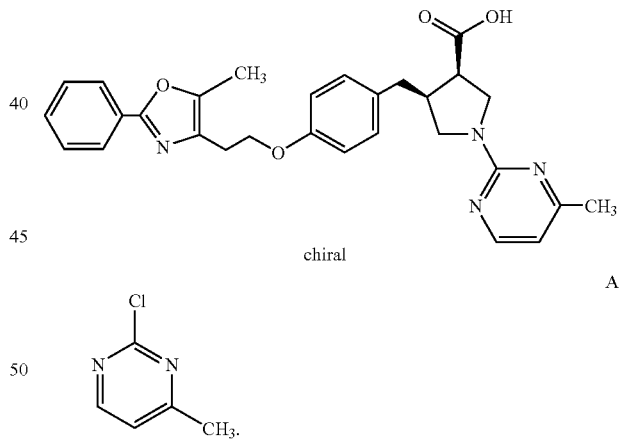

To a −40° C. suspension of 2-chloropyrimidine (2.8 mL; 24.6 mmol) in Et$_2$O (75 mL) was added a solution of methyl lithium in Et$_2$O (20 mL of a 1.4 M solution; 28 mmol). The mixture was stirred at −40° C. for 30 min, then was allowed to warm to 0° C. and stirred at 0° C. for 30 min. After cooling to −40° C., a solution of HOAc (1.7 mL), water (0.3 mL) and THF (10 mL) was added dropwise, followed by a solution of DDQ (7.0 g in 25 mL THF). The mixture was allowed to warm to RT and was stirred at RT for 10 min, then cooled to 0° C. Aqueous NaOH (1.2 g in 10 mL of H$_2$O) was added, and the mixture was stirred at 0° C. for 10 min. The organic phase was dried (MgSO$_4$/K$_2$CO$_3$) and concentrated in vacuo to give Part A compound (1.1 g; 35%) as a solid.

EXAMPLE 176

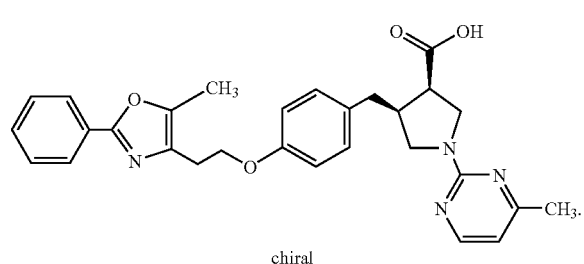
chiral

The title compound was prepared from the reaction of Example 170 Part C compound (100 mg; 0.24 mmol) with Part A compound (34 mg; 0.26 mmol) using the same 2-step sequence as employed in the synthesis of Example 170 from Example 170 Part C compound. The title compound was obtained (90 mg; 78%) as a white solid after preparative HPLC (using the same conditions as described in Example 1).

[M+H]$^+$=499.2

Analytical chiral HPLC: Chiral AD column; 4.6×250 mm, 10μ%; Isocratic solvent system: 20% A+80% B; Solvent A=100% IPA+0.1% TFA; Solvent B=100% heptane+0.1% TFA; Detection=261 nm; Flow rate 1 mL/min; Retention time=10.86 min.

$^1$H NMR (CD$_3$OD): δ 8.13 (m, 1H), 7.94 (m, 2H), 7.46 (m, 3H), 7.14 (m, 2H), 6.86 (m, 3H), 4.22 (t, J=6 Hz, 2H), 4.12 (m, 1H), 3.83 (m, 1H), 3.57 (m, 1H), 3.42 (m, 1H), 3.32 (m, 1H), 2.97 (m, 4H), 2.55 (m, 4H), 2.39 (s, 3H)

EXAMPLE 175

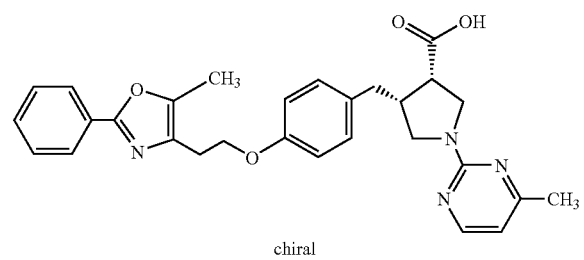
chiral

The title compound was prepared from Example 170 Part D compound (60 mg; 0.14 mmol) with Example 174 Part A compound (23 mg; 0.18 mmol) using the 2-step sequence as employed in the synthesis of Example 170 from Example 170 Part D compound. The title compound was obtained (50 mg; 73%) as a white solid after preparative HPLC (using the same conditions as described in Example 1)

[M+H]$^+$=499.2

Chiral Analytical HPLC: Chiralpak AD chiral column; 4.6×250 mm, 10μ; Isocratic solvent system: 20% A+80% B; Solvent A 100% IPA+0.1% TFA; Solvent B=100% heptane+0.1% TFA; Detection=261 nm; Flow rate=1 mL/min Retention time 17.32 min.

$^1$H NMR (CD$_3$OD): δ 8.17 (m, 1H), 7.94 (m, 2H), 7.45 (m, 3H), 7.13 (m, 2H), 6.85 (m, 3H), 4.20 (t, J=6 Hz, 2H), 4.11 (m, 1H), 3.83 (m, 1H), 3.57 (m, 1H), 3.42 (m, 1H), 3.32 (m, 1H), 2.97 (m, 4H), 2.55 (m, 4H), 2.39 (s, 3H)

EXAMPLE 176

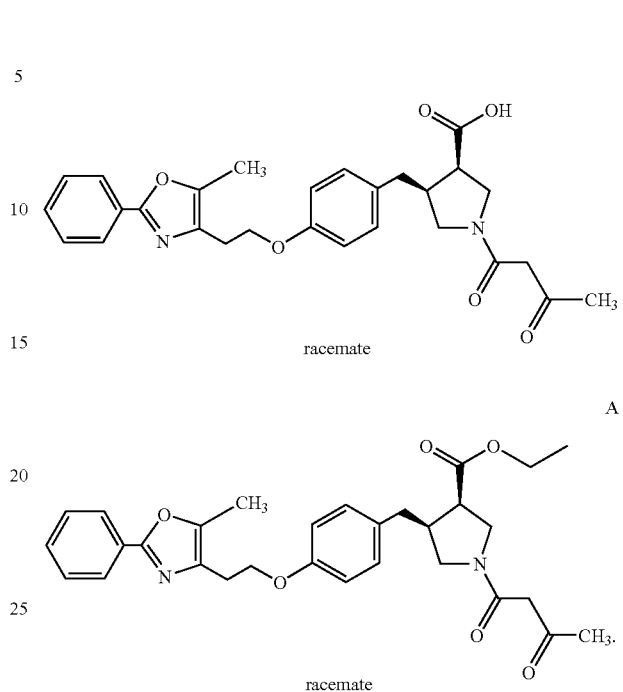
racemate

A solution of Example 31 Part A compound (600 mg; 1.38 mmol) and diketene (126 μL; 1.7 mmol) in MeCN (4 mL) was stirred at 70° C. for 4 h, then was cooled to RT and concentrated in vacuo. The residue was chromatographed (SiO$_2$; continuous gradient from 100% EtOAc to 1:4 MeOH/EtOAc) to give Part A compound (450 mg; 63%) as an oil.

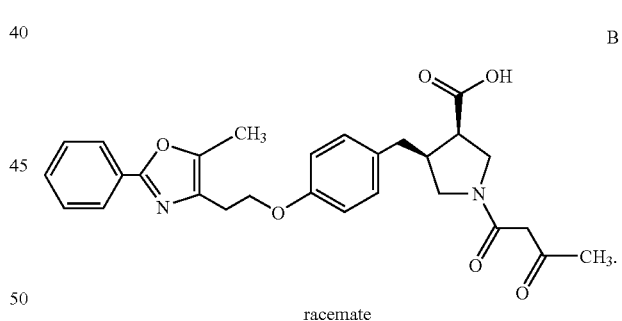
racemate

A solution of Part A compound (15 mg; 0.029 mmol) in HOAc (0.8 mL) and aqueous HCl (0.2 mL of a 20% solution) was stirred at 70° C. for 18 h; then was cooled to RT and concentrated in vacuo. The residue was purified by preparative HPLC (as described for Example 1) and lyophilized (water) to give the title compound (8 mg; 56%) as an oil.

[M+H]$^+$=491.2

$^1$H NMR (CD$_3$OD): δ 7.86 (m, 2H), 7.37 (m, 3H), 7.00 (m, 2H), 6.76 (m, 2H), 4.13 (t, J=6 Hz, 2H), 3.67 (m, 1H), 3.59 (m, 1H), 3.26 (m, 2H), 3.20 (m, 2H), 3.15 (m, 1H), 3.05 (m, 1H), 2.87 (m, 2H), 2.70 (m, 1H), 2.37 (m, 1H), 2.28 (s, 3H), 2.10 (m, 3H)

EXAMPLE 177

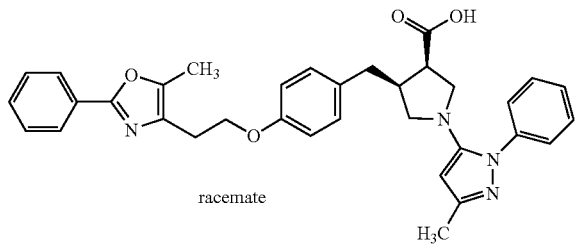

To a solution of Example 176 Part A compound (100 mg; 0.19 mmol) and phenylhydrazine (19 µL; 0.19 mmol) in EtOH (1 mL), was added methanesulfonic acid (6 µL). The mixture was stirred at RT for 3 h; then pyridine (100 µL) was added and the mixture was concentrated in vacuo. The residue was dissolved in pyridine (1 mL) and POCl$_3$ (54 µL; 0.58 mmol) was added. The mixture was stirred at RT for 18 h, after which the reaction was quenched by adding water (0.2 mL). The mixture was partitioned between EtOAc (10 mL) and saturated aqueous NaHCO$_3$ (5 mL). The organic layer was dried (Na$_2$SO$_4$) and concentrated in vacuo; the residue was purified by preparative HPLC (as described for Example 1) and lyophilized (water) to give the title compound (18 mg; 17%) as an oil.

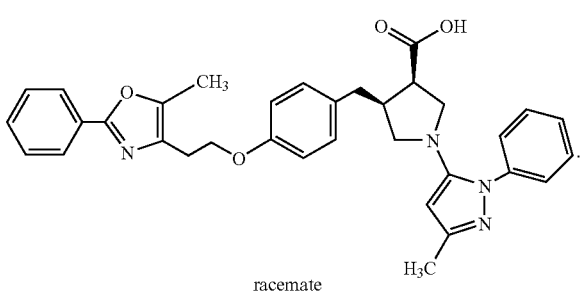

Example 177 title compound (3.4 mg; 71%) was prepared from Part A compound (5 mg; 0.008 mmol) using the same procedure as described in Example 164 title compound.

[M+H]$^+$=563.3

$^1$H NMR (CD$_3$OD): δ 7.95 (m, 2H), 7.53 (m, 5H), 7.46 (m, 4H), 7.94 (m, 2H), 6.78 (m, 2H), 4.20 (t, J=6 Hz, 2H), 3.42 (m, 1H), 3.36 (m, 1H), 3.24 (m, 1H), 2.97 (m, 5H), 2.76 (m, 1H), 2.67 (m, 1H), 2.39 (s, 3H), 2.32 (s, 3H)

EXAMPLE 178

A solution of Example 170 Part E compound (30 mg; 0.052 mmol) and LiOH.H$_2$O (15 mg; 0.35 mmol) in THF (0.8 mL), MeOH (0.3 mL) and H$_2$O (0.3 mL) was stirred at RT for 2.5 h, then was concentrated in vacuo. The residue was partitioned between aqueous HCl (5 mL of a 1N solution) and EtOAc (20 mL). The organic phase was washed with brine (5 mL), dried (Na$_2$SO$_4$) and concentrated in vacuo; the residue was purified by preparative HPLC (as described for Example 1) and lyophilized (dioxane) to give the title compound (3 mg; 11%) as a white solid.

[M+H]$^+$=553.3

$^1$H NMR (CD$_3$OD): δ 8.41 (m, 1H), 7.85 (m, 2H), 7.37 (m, 3H), 7.05 (d, J=8 Hz, 2H), 6.77 (d, J=8 Hz, 2H), 6.69 (s, 1H), 4.14 (m, 2H), 3.81 (m, 1H), 3.71 (m, 2H), 2.94 (m, 2H), 2.85 (m, 4H), 2.62 (m, 1H), 2.27 (m, 3H)

EXAMPLE 179

A solution of Example 171 Part A compound (50 mg; 0.087 mmol) and LiOH.H$_2$O (15 mg; 0.35 mmol) in THF (1 mL), MeOH (0.2 mL) and H$_2$O (0.2 mL) was stirred at RT for 3 h, then was concentrated in vacuo. The residue was partitioned between aqueous HCl (5 mL of a 1N solution) and EtOAc (20 ml). The organic phase was washed with brine (5 mL), dried (Na$_2$SO$_4$) and concentrated in vacuo; the residue was purified by preparative HPLC (as described for Example 1) and lyophilized (dioxane) to give the title compound (10 mg; 21%) as a white solid.

[M+H]$^+$=553.3

$^1$H NMR (CDCl$_3$): δ 8.40 (m, 1H), 7.92 (m, 2H), 7.26 (m, 3H), 7.02 (d, J=8 Hz, 2H), 6.75 (d, J=8 Hz, 2H), 6.69 (d, J=5 Hz, 1H), 4.14 (m, 2H), 3.90 (m, 1H), 3.71 (m, 2H), 2.94 (m, 2H), 2.85 (m, 4H), 2.62 (m, 1H), 2.31 (m, 3H)

EXAMPLE 180

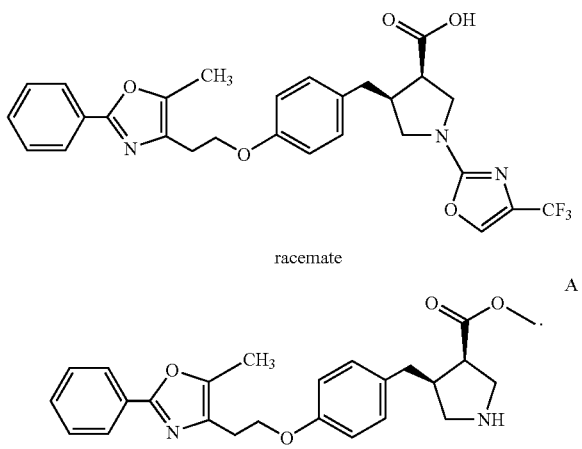
racemate

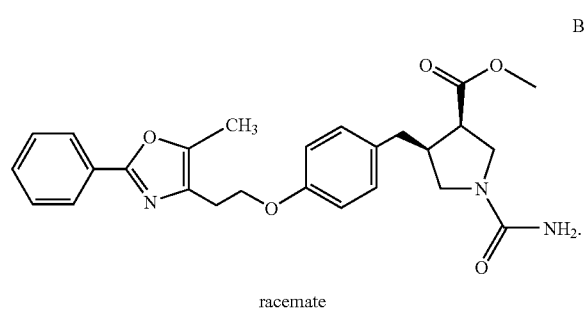
racemate

Part A compound was synthesized in a similar fashion as Example 31 Part A compound from Example 23 Part F compound from the corresponding methyl ester (which was synthesized exactly according to the sequence used for the synthesis of Example 23 Part F compound except that methyl propynoate was used in the synthesis of the methyl ester of Example 23 Part B compound).

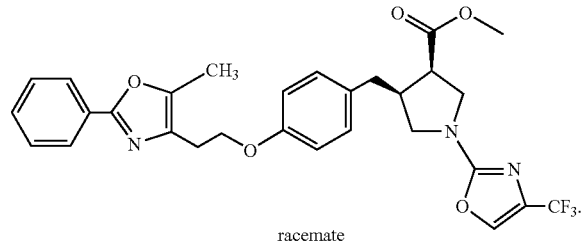
racemate

A solution of Part A compound (50 mg; 0.12 mmol) and trimethylsilylisocyanate (20 μL; 0.14 mmol) in THF (1 mL) was stirred at RT for 18 h. Volatiles were removed in vacuo and the residue was partitioned between EtOAc (10 mL) and brine (5 mL). The organic layer was dried (Na$_2$SO$_4$) and concentrated in vacuo to give Part B compound (60 mg; 100%) as an oil.

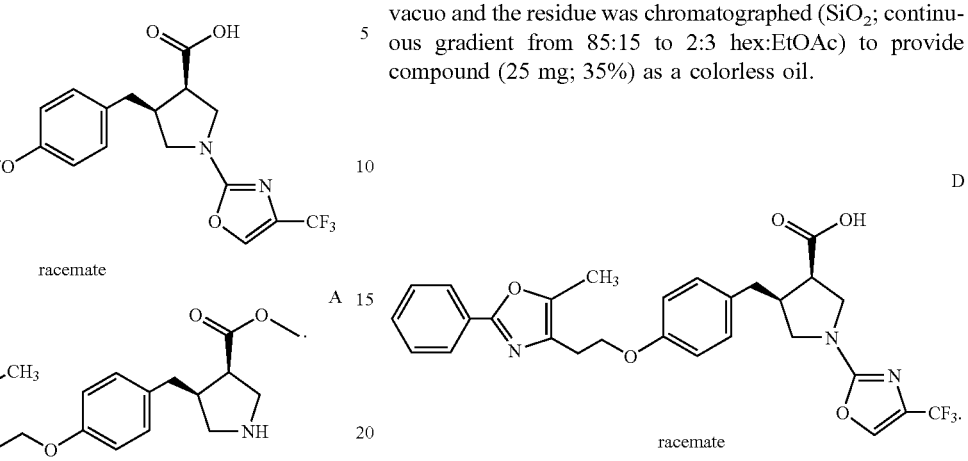
racemate

A solution of Part B compound (60 mg; 0.13 mmol) and bromotrifluoroacetone (17 μL; mmol) in toluene (1.5 mL) was stirred at 80° C. for 3 h. Volatiles were removed in vacuo and the residue was chromatographed (SiO$_2$; continuous gradient from 85:15 to 2:3 hex:EtOAc) to provide compound (25 mg; 35%) as a colorless oil.

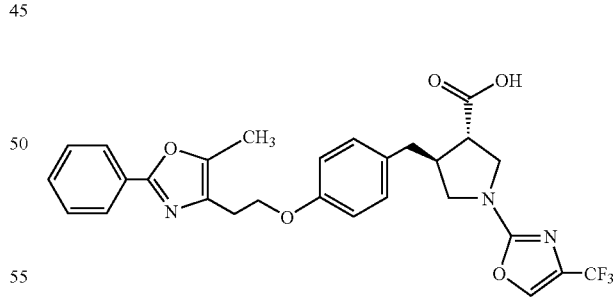
racemate

A solution of Part C compound (8 mg; 0.014 mmol) and LiOH.H$_2$O (4 mg; 0.092 mmol) in THF (0.33 mL), MeOH (0.15 mL) and H$_2$O (0.15 mL) was stirred at RT for 1 h, then was concentrated in vacuo. The residue was partitioned between aqueous HCl (5 mL) and EtOAc (20 mL). The organic phase was dried (Na$_2$SO$_4$) and concentrated in vacuo; the residue was purified by preparative HPLC (as described for Example 1) and lyophilized (dioxane) to give the title compound (2.1 mg; 27%) as a solid.

[M+H]$^+$=542.3

$^1$H NMR (CD$_3$OD): δ 7.95 (m, 2H), 7.84 (m, 1H), 7.46 (m, 3H), 7.12 (d, J=8 Hz, 2H), 6.86 (d, J=8 Hz, 2H), 4.22 (t, J=4 Hz, 2H), 3.83 (m, 1H), 3.69 (m, 1H), 3.45 (m, 1H), 3.38 (m, 1H), 3.24 (m, 1H), 2.96 (t, J=8 Hz, 2H), 2.84 (m, 2H), 2.49 (m, 1H), 2.37 (m, 3H)

In addition, a second, slower eluting fraction from the preparative HPLC of the crude hydrolysis product mixture was identified as the epimerized trans-isomer Example 181 (2.0 mg; 26%):

EXAMPLE 181

[M+H]$^+$=542.3

$^1$H NMR (CD$_3$OD): δ 7.95 (m, 2H), 7.84 (m, 1H), 7.46 (m, 3H), 7.12 (d, J=8 Hz, 2H), 6.86 (d, J=8 Hz, 2H), 4.22 (t, J=4 Hz, 2H), 3.81 (m, 1H), 3.72 (m, 1H), 3.54 (m, 1H), 3.30 (m, 1H), 2.97 (m, 3H), 2.90 (m, 1H), 2.80 (m, 1H), 2.63 (m, 1H), 2.37 (m, 3H)

EXAMPLE 182

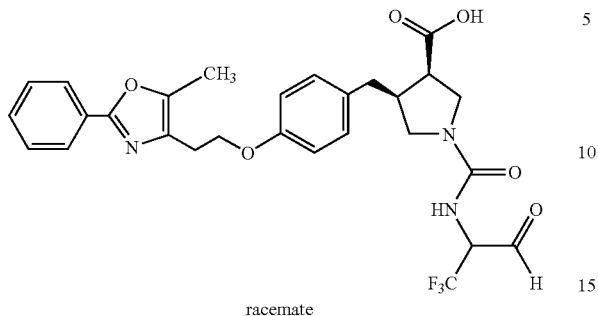

racemate solution of Example 180 Part C compound (15 mg; 0.03 mmol) in HOAc (0.8 mL) and aqueous HCl (0.2 mL of a 20% solution) was stirred at 70° C. for 3 days. The mixture was concentrated in vacuo and the residue was purified by preparative HPLC (as described for Example 1) and lyophilized (water) to give the title compound (13 mg; 86%) as an oil.

[M+H]$^+$=559.2

EXAMPLE 183

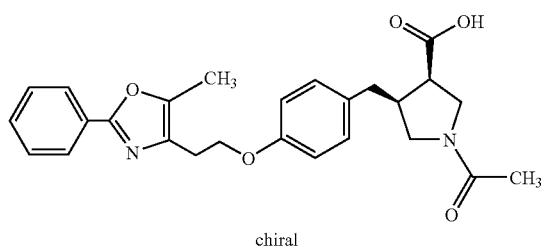

chiral

The title compound (5 mg; 9.6%) was prepared employing the same procedure as described in Example 164 Part B compound from Example 170 Part C compound (50 mg; 0.12 mmol).

[M+H]$^+$=449.4

$^1$H NMR (CD$_3$OD): δ 8.01 (m, 2H), 7.53 (m, 3H), 7.15 (t, J=9 Hz, 2H), 6.91 (m, 2H), 4.27 (t, J=4 Hz, 2H), 3.84 (m, 1H), 3.74 (m, 1H), 3.65 (m, 1H), 3.49 (m, 1H), 3.29 (m, 1H), 3.17 (m, 1H), 3.03 (m, 2H), 2.73 (m, 1H), 2.51 (m, 1H), 2.45 (m, 3H), 2.03 (m, 3H)

EXAMPLE 184

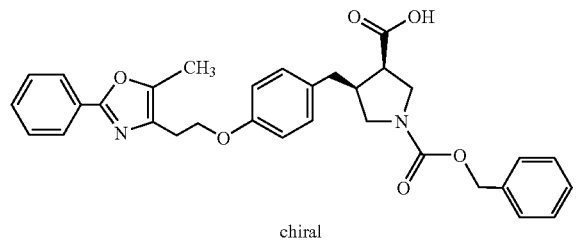

chiral

-continued

A

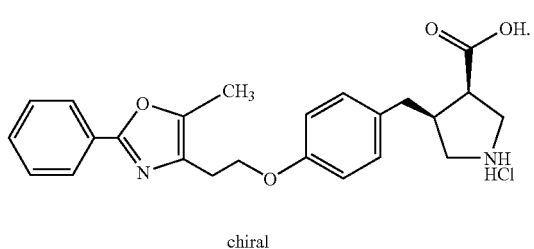

chiral

Part A compound (186 mg; 100%) was prepared from Example 170 Part C compound (200 mg; 0.46 mmol) using the procedure described in Example 148 Part A compound.

B

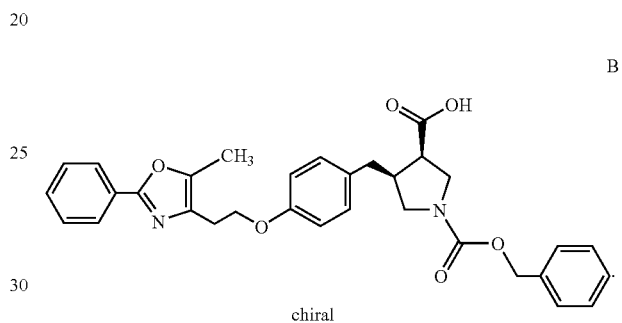

chiral

The title compound was prepared from the reaction of Part A compound (15 mg; 0.035 mmol) with benzyl chloroformate (15 μL; 0.14 mmol) using the procedure as employed in the synthesis of Example 148. The title compound was obtained (10 mg; 54%) as an oil after preparative HPLC (using the same conditions as described in Example 1)

[M+H]$^+$=541.3

$^1$H NMR (CD$_3$OD): δ 7.95 (m, 2H), 7.48 (m, 3H), 7.33 (m, 5H), 7.05 (m, 2H), 6.83 (m 2H), 5.10 (m, 2H), 4.22 (t, J=4 Hz, 2H), 3.71 (m, 1H), 3.52 (m, 1H), 3.30 (m, 2H), 3.12 (m, 1H), 2.96 (m, 2H), 2.78 (m, 1H), 2.69 (m, 1H), 2.42 (m, 1H), 2.37 (m, 3H)

[α] (0.97w/v%)$_{MeOH}^{589}$=−33.7°

An alternative synthesis of Example 184 compound is shown using the following sequence:

C

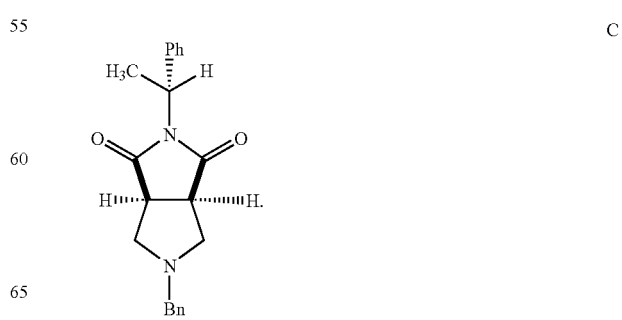

To a 0° C. solution of (R)-(+)-(1-phenylethyl) maleimide (3 g; 15 mmol)

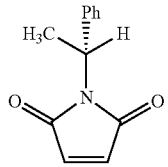

and Example 1 Part B compound (4.56 g; 19.2 mmol) in CH₂Cl₂ (50 mL) was added TFA (0.1 mL) The solution was allowed to warm to RT and stirred at RT for 2 h, then was concentrated in vacuo. The residue was chromatographed (SiO₂; 4:1 hex:EtOAc) to give Part C compound (4.2 g; 84%) as a white solid.

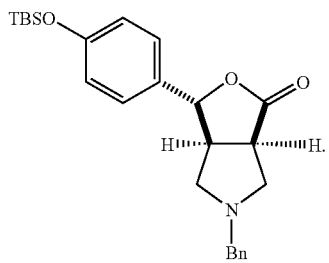

D

To a −20° C. (CCl₄/dry ice bath) solution of Part C Compound (1.5 g; 4.4 mmol) in THF (5 mL) was 4-tert-butyldimethylsilyloxyphenyl magnesium bromide in THF (15 mL of a 0.58 M solution) over 1 h using a syringe pump. The reaction was complete by HPLC 30 min after the addition had been completed, after which EtOH (30 mL) was added followed by NaBH₄ (0.42 g; 11 mmol). The mixture was stirred for 2 h at 0° C. and for 18 h at RT. The mixture was concentrated in vacuo and the residue was partitioned between EtOAc and aqueous 10% K₂CO₃. The organic layer was dried (MgSO₄) and concentrated in vacuo. The residue was dissolved in toluene (50 mL) and the mixture was stirred at 110° C. for 8 h, then was cooled to RT and concentrated in vacuo. The residue was chromatographed (SiO₂; 9:1 hex:EtOAc) to give Part D compound as a clear oil (0.92 g; 45%).

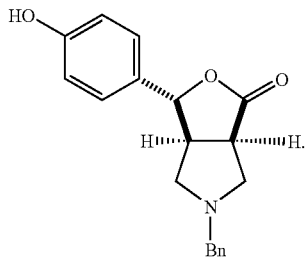

E

To a 0° C. solution of Part D compound (500 mg; 1.18 mmol) in THF (5 mL) was added (n-Bu)₄NF (1.3 mL of a 1 M solution in THF; 1.0 mmol). The mixture was stirred at 0° C. for 30 min, then was concentrated in vacuo to give crude Part E compound (360 mg; 99%) as an oil.

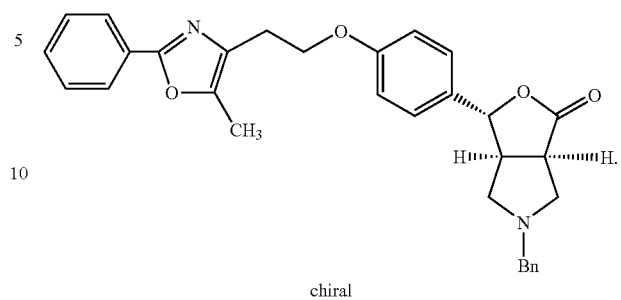

F chiral

A mixture of crude Part E compound (360 mg; 1.2 mmol) in MeCN (10 mL), Example 23 Part A compound (400 mg; 1.42 mmol) and K₂CO₃ (196 mg; 1.42 mmol) was stirred at 85° C. for 18 h, then was cooled to RT and concentrated in vacuo. The residue was partitioned between EtOAc (20 mL) and brine (10 mL). The organic layer was separated, dried (Na₂SO₄) and concentrated in vacuo; the residue was chromatographed (SiO₂; gradient from 100% hex to 3:7 hex:EtOAc) to give Part F compound (320 mg; 55%) as a colorless oil.

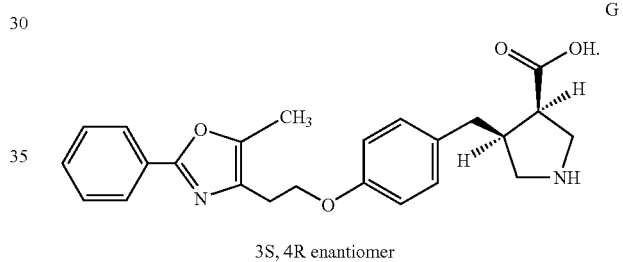

G 3S, 4R enantiomer

A mixture of Part F compound (600 mg; 1.2 mmol) and 10% Pd/C (30 mg) in HOAc (24 mL) was stirred under an atmosphere of H₂ (60 psi) for 18 h. The mixture was filtered through Celite®; the Celite® pad was washed with MeOH (30 mL). The combined filtrates were concentrated in vacuo to give Part G compound (500 mg; 100%) as an oil. This material was confirmed to be the 3S, 4R enantiomer by conversion to Example 170 Part C compound (see Example 170).

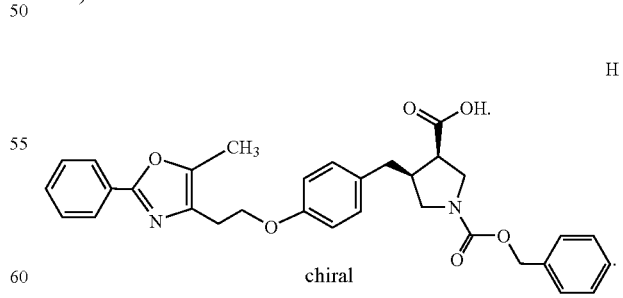

H chiral

The title compound (130 mg; 75%) was prepared from the reaction of Part G compound (130 mg; 0.32 mmol) with benzyl chloroformate (46 μL; 0.32 mmol) using the same procedure as described for the synthesis of Example 148 Part B compound.

EXAMPLE 185

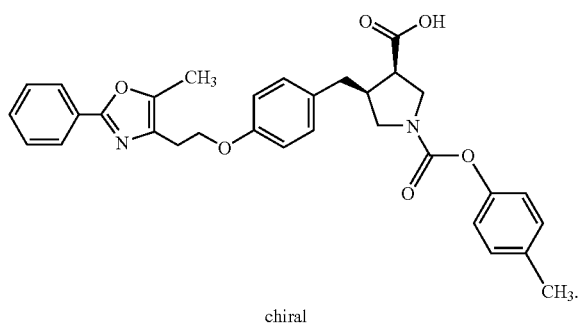

chiral

The title compound was prepared from Example 184 Part A compound (15 mg; 0.035 mmol) with p-tolyl chloroformate (10 μL; 0.09 mmol) using the procedure as employed in the synthesis of Example 148. The title compound (10 mg; 54%) was obtained as an oil after preparative HPLC (using the same conditions as described in Example 1).

[M+H]$^+$=541.3

$^1$H NMR (CD$_3$OD): δ 7.95 (m, 2H), 7.47 (m, 3H), 7.13 (m, 4H), 6.95 (m, 2H), 6.86 (m 2H), 4.22 (t, J=4 Hz, 2H), 3.86 (m, 1H), 3.74 (m, 1H), 3.52 (m, 1H), 3.33 (m, 1H), 3.20 (m, 1H), 2.98 (m, 2H), 2.84 (m, 1H), 2.75 (m, 1H), 2.49 (m, 1H), 2.36 (m, 3H), 2.31 (s, 3H)

[α] (0.69w/v%)$_{MeOH}$$^{589}$=−50.6°

Example 185 (135 mg; 78%) was also prepared from Example 184 Part E compound (130 mg; 0.32 mmol) with p-tolyl chloroformate (50 μL; 0.35 mmol) using the same procedure as described for the synthesis of Example 148 Part B compound.

EXAMPLE 186

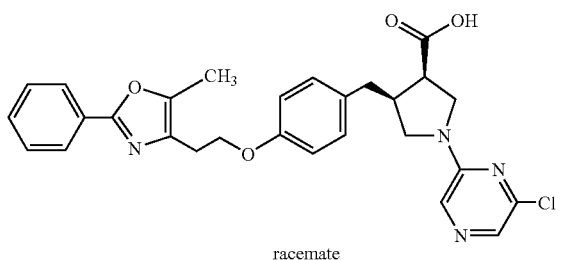

racemate

The title compound (5 mg; 20%) was prepared from Example 180 Part A compound (20 mg; 0.048 mmol) with 2,6-dichloropyrazine (15 mg; 0.10 mmol) using the same procedure as described for the synthesis of Example 164.

[M+H]$^+$=519.2

EXAMPLE 187

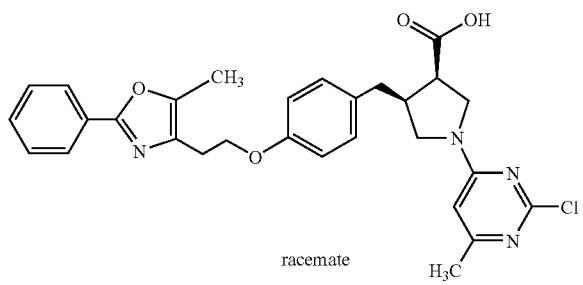

racemate

The title compound (6 mg; 18%) was prepared from Example 148 Part A compound (25 mg; 0.062 mmol) with 2,4-dichloro-6-methylpyrimidine (15 mg; 0.092 mmol) using the procedure described in Example 164 Part A compound.

[M+H]$^+$=533.1

$^1$H NMR (CD$_3$OD): δ 7.95 (m, 2H), 7.46 (m, 3H), 7.12 (m, 2H), 6.87 (d, J=4 Hz, 2H), 6.50 (m, 1H), 4.21 (m, 2H), 4.07 (m, 1H), 3.83 (m, 1H), 3.70 (m, 1H), 3.62 (m, 1H), 3.51 (m, 1H), 3.37 (m, 1H), 2.97 (m, 2H), 2.90 (m, 1H), 2.50 (m, 1H), 2.37 (s, 3H), 2.34 (m, 3H)

A second compound (later fraction), identified as Example 188 (3 mg; 9%) was also obtained from the preparative HPLC purification.

[M+H]$^+$=533.1

$^1$H NMR (CD$_3$OD): δ 7.95 (m, 2H), 7.46 (m, 3H), 7.12 (m, 2H), 6.87 (d, J=4 Hz, 2H), 6.67 (m, 1H), 4.24 (m, 2H), 3.97 (m, 1H), 3.74 (m, 1H), 3.54 (m, 1H), 3.43 (m, H), 3.30 (m, 2H), 2.97 (m, 2H), 2.86 (m, 1H), 2.50 (m, 1H), 2.38 (m, 6H)

EXAMPLE 188

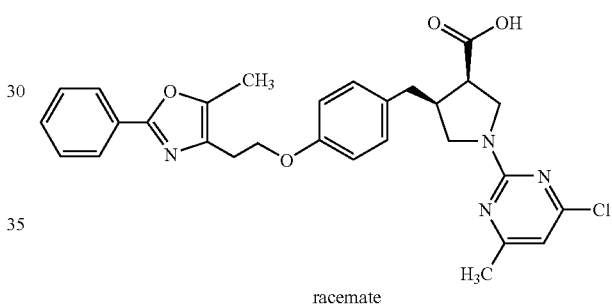

racemate

EXAMPLE 189

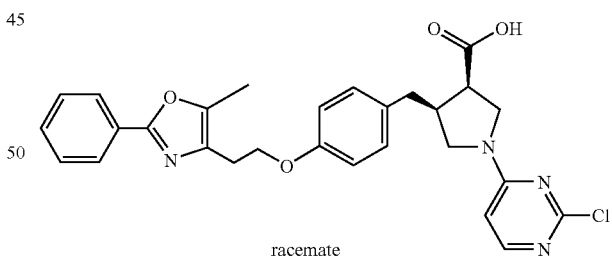

racemate

The title compound (5 mg; 18%) was prepared from Example 148 Part A compound (20 mg; 0.050 mmol) with 2,4-dichloropyrimidine (15 mg; 0.10 mmol) using the same procedure as described for the synthesis of Example 164 Part A compound.

[M+H]$^+$=519.2

A second compound (later fraction, identified as Example 190 (2 mg; 8%) was also obtained from the preparative HPLC purification. [M+H]$^+$=519.1

EXAMPLE 190

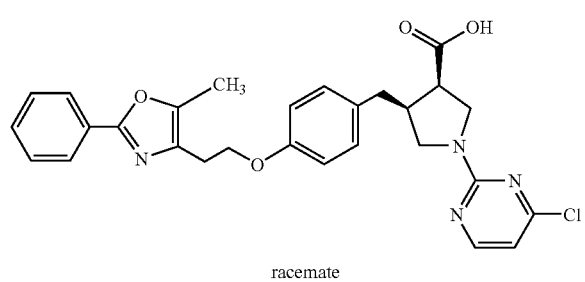

racemate

EXAMPLE 191

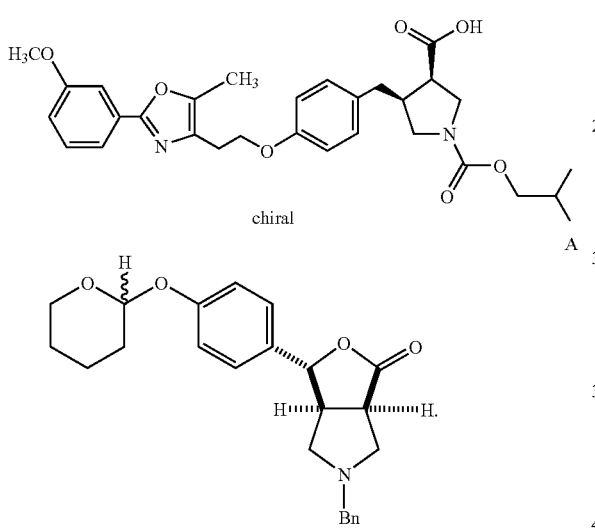

Part A compound was synthesized from (R)-(+)-(1-phenylethyl)maleimide employing the identical synthetic sequence used for the synthesis of Example 184 Part D compound except that 4-tetrahydropyranyloxy-phenyl magnesium bromide was used instead of of 4-tert-butyldimethylsilyloxy-phenyl magnesium bromide.

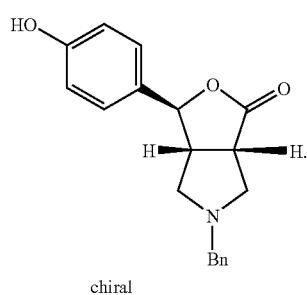

A solution of Part A compound (200 mg; 0.51 mmol) in CH$_2$Cl$_2$ (5 mL) at RT and p-toluenesulfonic acid.H$_2$O (116 mg; 0.61 mmol) was stirred at RT for 4 h; then was concentrated in vacuo to give crude Part B compound (150 mg; 96%).

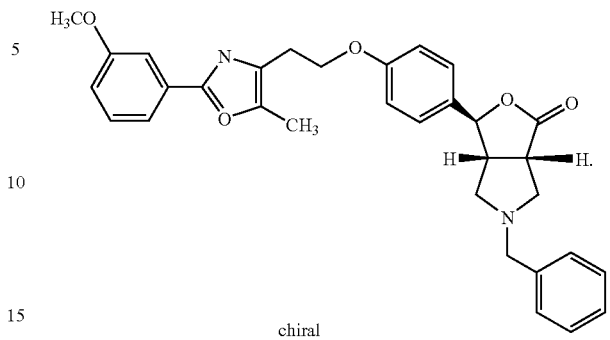

Part C compound (30 mg; 58%) was prepared by the reaction of crude Part B compound (30 mg; 0.097 mmol) with the mesylate Example 277 Part E compound (33 mg; 0.11 mmol) using the procedure described in Example 184 Part F compound.

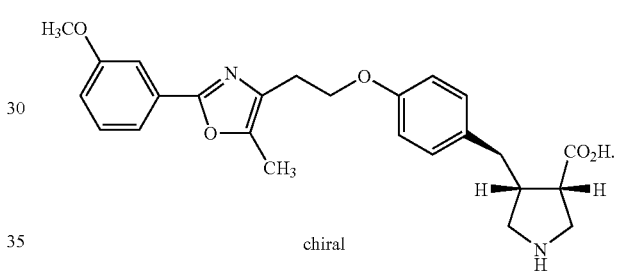

Part D compound (20 mg; 100%) was prepared from Part C compound (30 mg; 0.057 mmol) using the procedure described for the preparation of Example 184 Part G compound.

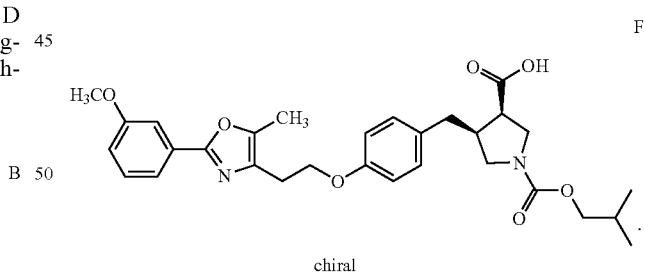

The title compound (20 mg; 65%) was prepared from Part D compound (20 mg; 0.057 mmol) and isobutyl chloroformate (8 μL; 0.057 mmol) using the same procedure as described for the synthesis of Example 148 compound.

[M+H]$^+$=537.4

$^1$H NMR (CD$_3$OD): δ 7.51 (m, 2H), 7.37 (m, 1H), 7.07 (d, J=8 Hz, 2H), 7.01 (d, J=8 Hz, 1H), 6.84 (d, J=8 Hz, 2H), 4.21 (m, 2H), 3.84 (s, 3H), 3.81 (m, 2H), 3.67 (m, 1H), 3.50 (m, 1H), 3.29 (m, 2H), 3.12 (m, 1H), 2.95 (m, 2H), 2.79 (m, 1H), 2.68 (m, 1H), 2.42 (m, 1H), 2.36 (s, 3H), 1.89 (m, 1H), 0.89 (dd, J=6 Hz, 6H)

EXAMPLE 192

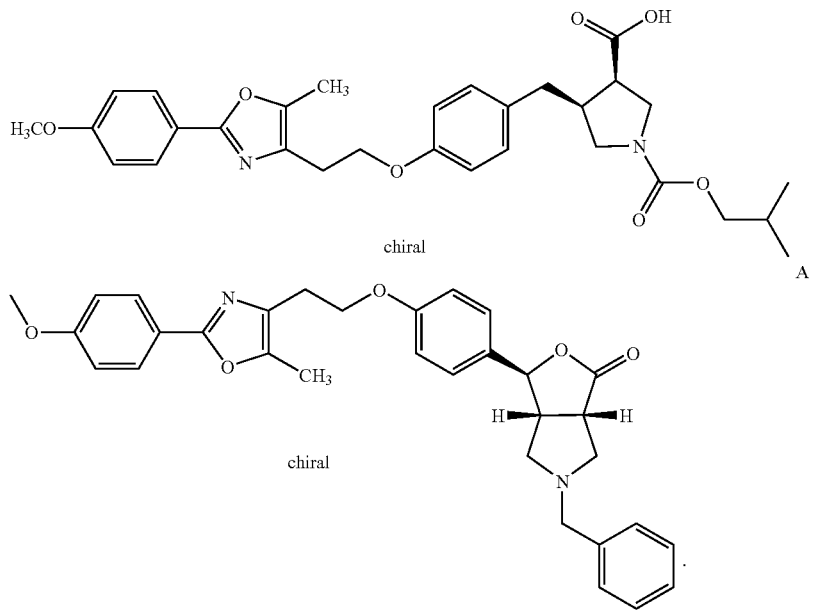

Part A compound (30 mg; 58%) was prepared by the reaction of Example 191 Part B compound (30 mg; 0.097 mmol) with the mesylate Example 264 Part B compound (33 mg; 0.11 mmol) using the procedure described for the preparation of Example 184 Part F compound.

Part B compound (20 mg; 100%) was prepared from Part A compound (30 mg; 0.057 mmol) using the procedure described in Example 184 Part G compound.

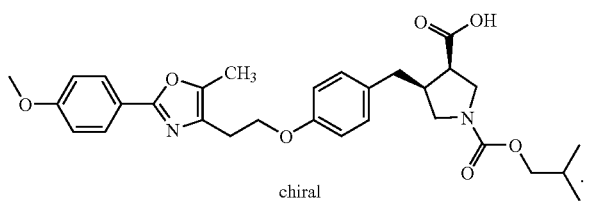

Part C compound (15 mg; 49%) was prepared from Part B compound (20 mg; 0.057 mmol) with isobutyl chloroformate (8 µL; 0.057 mmol) using the procedure described for the synthesis of Example 148.

$[M+H]^+=537.3$

EXAMPLE 193

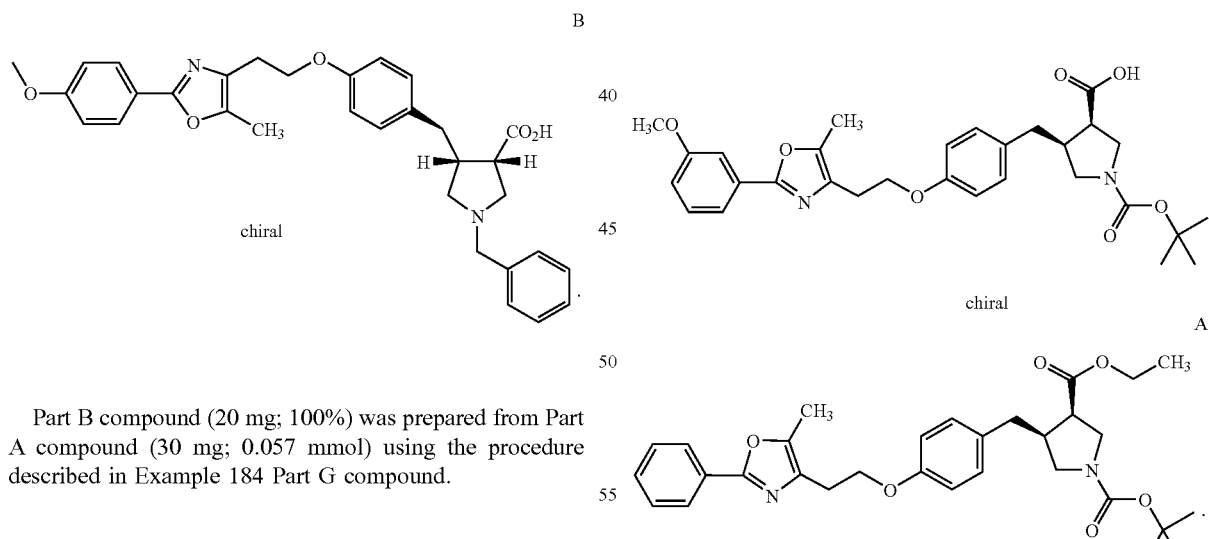

Part A compound (the 3R, 4S enantiomer; 200 mg; 25%) was isolated from racemic Example 23 Part F compound (800 mg; 1.50 mmol) by preparative HPLC using the following conditions: ChiralPak AD column, 5 cm×50 cm, 20 µ; Isocratic solvent system: 10% A:90% B (A=100% IPA+0.1% HOAc; B=100% hex+0.1% HOAc); Injection volume=10 mL in IPA; Detection=220 nm; Flow rate=50 mL/min. Analytical chiral HPLC: Chiralpak AD column 4.6×250 mm Isocratic solvent system: 10% A+90% B; Solvent A=100% IPA+0.1% HOAc; Solvent B=100% hex+ 0.1% HOAc; Detection=254 nm; Flow rate=1 mL/min Retention time =5.7 min.

B

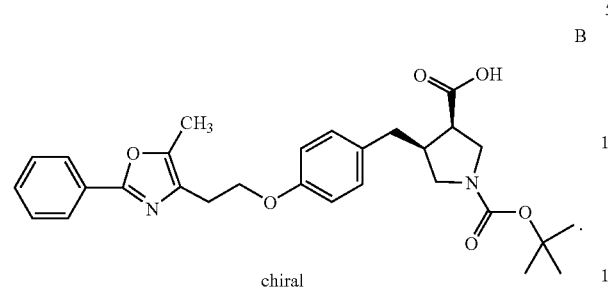

chiral

A solution of Part A compound (5 mg; 0.0094 mmol) in HOAc (1 mL) and aqueous HCl (0.25 mL of a 20% solution) was stirred at 85° C. for 18 h. Volatiles were removed in vacuo, and the residue was dissolved in THF (1 mL). Saturated aqueous NaHCO$_3$ (0.5 mL) and di-tert-butyl dicarbonate (10 mg; 0.046 mmol) were added. The reaction was stirred at RT for 3 h, then was quenched by the addition of saturated aqueous NH$_4$Cl (0.5 mL). The mixture was partitioned between EtOAc (50 mL) and saturated-aqueous NH$_4$Cl (10 mL). The organic phase was dried (Na$_2$SO$_4$) and concentrated in vacuo. The residue was purified by preparative HPLC (as described for Example 1) and lyophilized (water) to give the title compound (3 mg; 63%) as a white solid.

[M+H]$^+$=506.6

Part B compound was also prepared from Example 170 Part C compound using the following synthetic route:

A solution of Example 170 Part C compound (350 mg; 0.81 mmol) in HOAc (4 mL) and aqueous HCl (1 mL of a 20% solution) was stirred at 85° C. for 6 h. Volatiles were removed in vacuo and the residue was dissolved in THF (5 mL); the pH was adjusted to ~9 with saturated aqueous NaHCO$_3$, after which (Boc)$_2$O (280 mg; 1.28 mmol) was added. The reaction was stirred at RT for 18 h, then was quenched with saturated aqueous NH$_4$Cl solution (50 mL) to adjust the pH to ~3-4. The organic phase was dried (Na$_2$SO$_4$), and concentrated in vacuo. The residue was chromatographed (SiO$_2$; continuous gradient from 100% hex to 100% EtOAc) to give a yellow oil, which was lyophilized from dioxane to give the title compound (250 mg; 61%) as a light yellow solid.

[M+H]$^+$=506.6

[α] (12 mg/2 mL)$_{MeOH}^{589}$=−33.67°

EXAMPLE 194

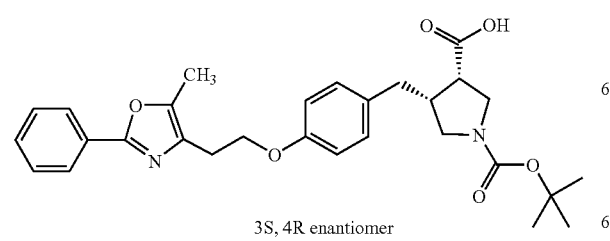

3S, 4R enantiomer

The title compound (150 mg; 61%) was prepared from Example 170 Part D compound (210 mg; 0.48 mmol) using the same procedure as described in the second synthetic route for the preparation of Example 193 compound.

[M+H]$^+$=506.6

[α] (8.8 mg/2 mL)$_{MeOH}^{589}$=+33.93

EXAMPLE 195

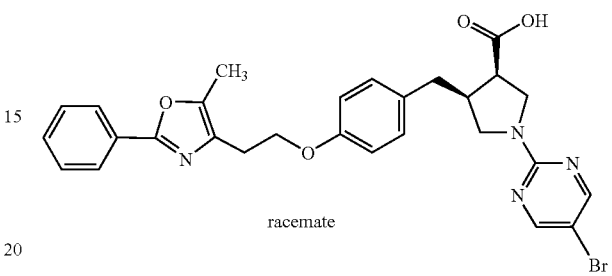

racemate

The title compound (34 mg; 51%) was prepared from Example 180 Part A compound (50 mg; 0.12 mmol) and 2-chloro-5-bromopyrimidine (100 mg) using the 2-step procedure employed in the synthesis of Example 164.

[M+H]$^+$=563.2

EXAMPLE 196

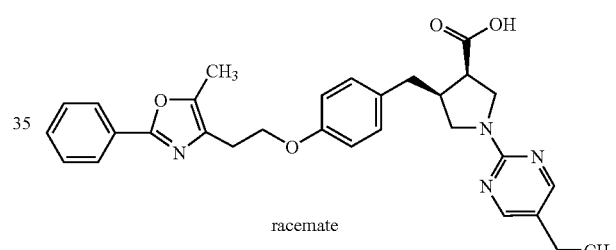

racemate

The title compound (31 mg; 51%) was prepared from Example 180 Part A compound (50 mg; 0.12 mmol) with 2-chloro-5-ethylpyrimidine (100 mg) using the same 2-step procedure as employed in the synthesis of Example 164.

[M+H]$^+$=513.3

EXAMPLE 197

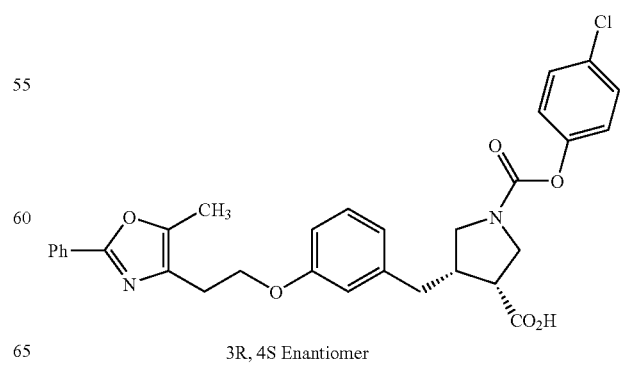

3R, 4S Enantiomer

-continued

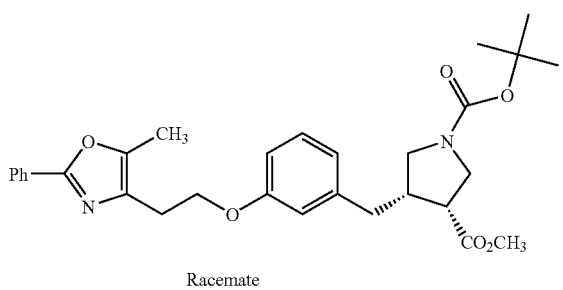

Racemate

To a mixture of Example 32 Part F compound (1.66 g; 4.9 mmol) and 2-(5-methyl-2-phenyl-oxazol-4-yl)-ethanol (1.11 g, 5.4 mmol) in toluene (40 mL) was added cyanomethylenetributylphosphine (3.58 g; 14.8 mmol) dropwise. The mixture was heated at 80° C. for 3 h, cooled to RT, concentrated in vacuo and partitioned between EtOAc and water. The organic phase was washed with water (2×) and brine, dried (Na$_2$SO$_4$) and concentrated in vacuo. The residue was chromatographed (SiO$_2$; stepwise gradient from hexane to hex:EtOAc 2:3) to give Part A compound (2.44 g; 95%) as an oil.

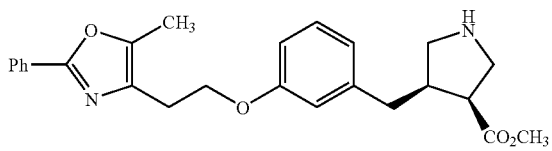

racemate

A solution of Part A compound (2.34 g; 4.49 mmol) and 4M HCl in dioxane (50 mL) in CH$_2$Cl$_2$ (50 ml) was stirred at RT for 4.5 h, concentrated in vacuo and partitioned between EtOAc and saturated aqueous NaHCO$_3$. The organic layer was washed with saturated aqueous NaHCO$_3$ (2×), water and brine, dried (Na$_2$SO$_4$) and concentrated in vacuo to give Part B compound (1.72 g; 91%) as an orange oil.

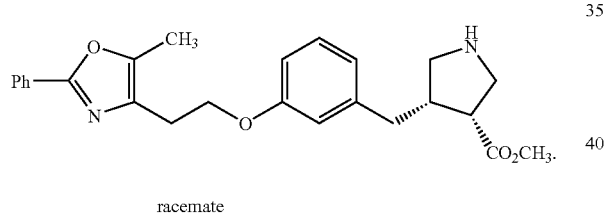

3R, 4S, enantiomer

The individual enantiomers of Part B compound were separated by preparative HPLC using a CHIRALCEL OD column from Chiral Technologies Inc (5 cm ID×50 cm, 20 µ): flow rate=45 mL/min; isocratic conditions=80:20 A:B, where A=heptane+0.1% Et$_2$NH; B=iPrOH+0.1% Et$_2$NH; detector wavelength=279 nm. The first fraction from the chiral preparative HPLC was identified as the desired 3R,4S enantiomer (760 mg; Part C compound). Chiral analytical HPLC using a Daicel Chiralcel OD 4.6×500 mm column: flow rate=1 mL/min; isocratic conditions=80:20 A:B, where A=heptane+0.1% Et$_2$NH; B=IPA+0.1% Et$_2$NH; detector wavelength=279 nm; retention time=21 min. Optical rotation=+13.36°

The second (slower-eluting) fraction (660 mg) from the chiral prep HPLC separation was identified as the opposite enantiomer (Part D compound). Chiral analytical HPLC (same conditions as above) retention time=29 min.

Optical rotation=−13.6°

(Part D Compound)

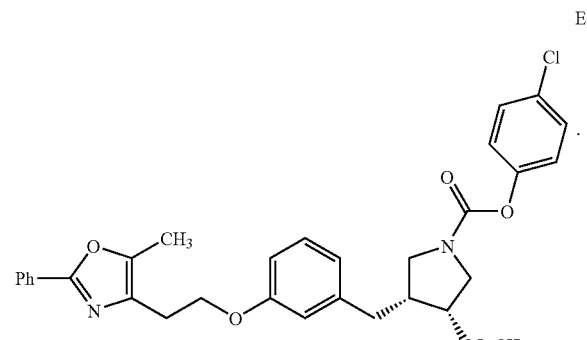

3S, 4R enantiomer

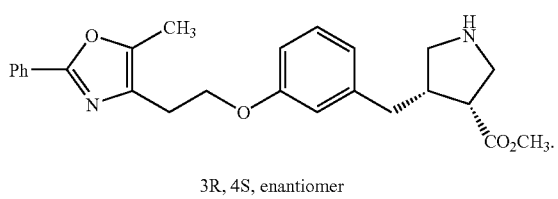

3R, 4S Enantiomer

To a 0° C. solution of Part C3R,4S enantiomer (10.0 mg; 0.0238 mmol) and aqueous saturated NaHCO$_3$ (0.50 mL) in THF (0.50 mL) was added 4-chlorophenyl chloroformate (4.0 µL; 0.0286 mmol). The reaction was stirred at 0° C. for 30 min, then was allowed to warm to RT and stirred overnight at RT. Volatiles were removed in vacuo, and the residue was partitioned between EtOAc and water. The aqueous layer was extracted with EtOAc (2×). The combined organic extracts were washed with water (1×) and brine (1×), dried (Na$_2$SO$_4$) and concentrated in vacuo to give Part E compound, which was used in the next reaction without further purification.

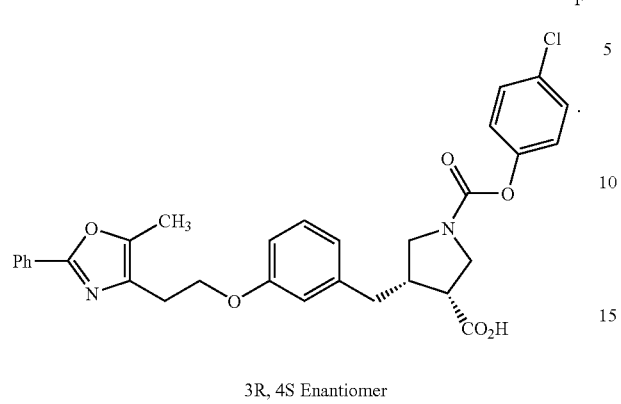

3R, 4S Enantiomer

A solution of Part E compound in HOAc (0.80 mL) and concentrated HCl (0.20 mL) was shaken at 70° C. for 6.5 h, then cooled to RT and concentrated in vacuo. The residue was purified by preparative HPLC (YMC Combiprep ODS-A 30×50 mm column; flow rate=35 mL/min; 8 min continuous gradient from 20:80 B:A to 100% B, where solvent A=90:10:0.1 H$_2$O:MeOH:TFA and solvent B=90:10:0.1 MeOH:H$_2$O:TFA) to give the title compound (6.3 mg; 47%).

[M+H]$^+$=561.23

EXAMPLES 198–219

Examples 198 through 219 were prepared in a similar fashion to Example 197 (from Example 197 Part C compound) using appropriate chloroformates.

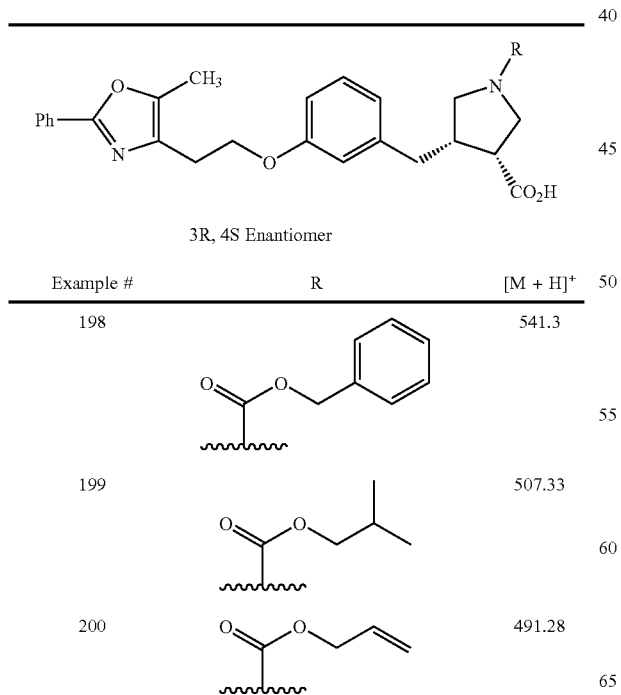

3R, 4S Enantiomer

| Example # | R | [M + H]$^+$ |
|---|---|---|
| 198 | (benzyl carbonate) | 541.3 |
| 199 | (isobutyl carbonate) | 507.33 |
| 200 | (allyl carbonate) | 491.28 |

-continued

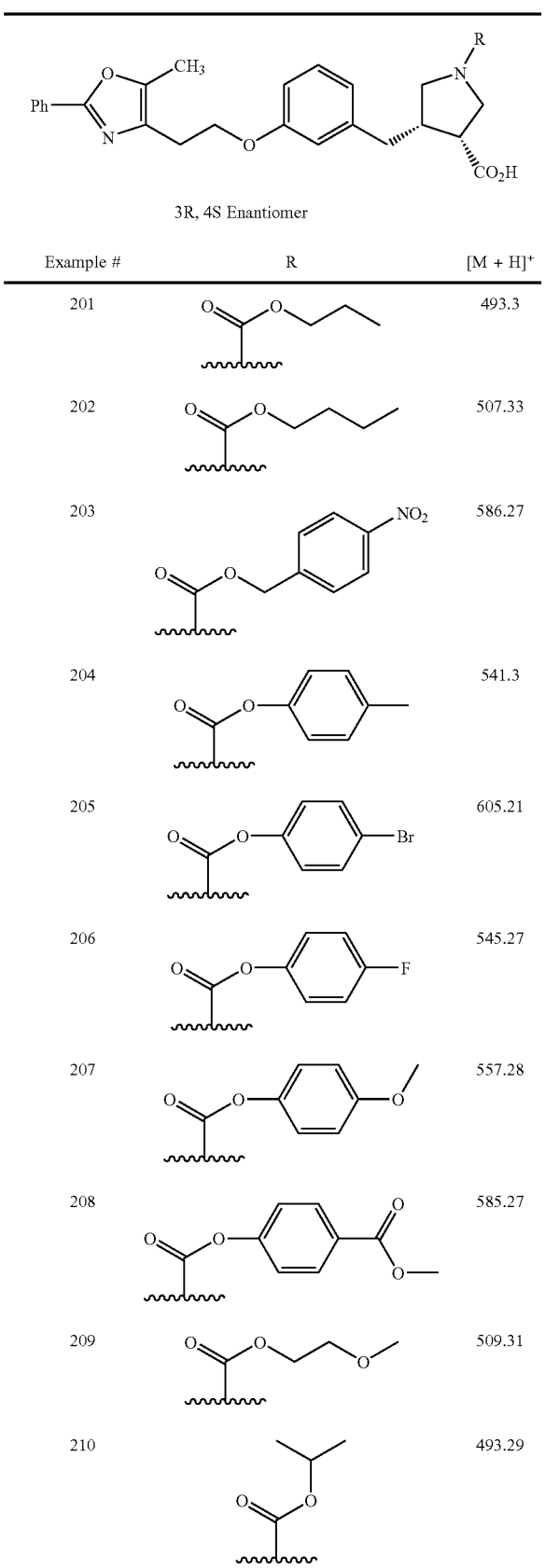

3R, 4S Enantiomer

| Example # | R | [M + H]$^+$ |
|---|---|---|
| 201 | (n-propyl carbonate) | 493.3 |
| 202 | (n-butyl carbonate) | 507.33 |
| 203 | (4-nitrobenzyl carbonate) | 586.27 |
| 204 | (4-methylphenyl carbonate) | 541.3 |
| 205 | (4-bromophenyl carbonate) | 605.21 |
| 206 | (4-fluorophenyl carbonate) | 545.27 |
| 207 | (4-methoxyphenyl carbonate) | 557.28 |
| 208 | (4-methoxycarbonylphenyl carbonate) | 585.27 |
| 209 | (2-methoxyethyl carbonate) | 509.31 |
| 210 | (isopropyl carbonate) | 493.29 |

-continued

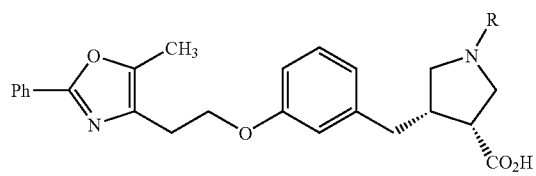

3R, 4S Enantiomer

| Example # | R | [M + H]+ |
|---|---|---|
| 211 | propargyl ester | 489.26 |
| 212 | neopentyl ester | 521.34 |
| 213 | 2-chlorobenzyl ester | 575.25 |
| 214 | 2-fluoroethyl ester | 497.27 |
| 215 | 2-methoxyphenyl ester | 557.28 |
| 216 | 2-chlorophenyl ester | 561.22 |
| 217 | 4-carboxyphenyl ester | 569.21 |
| 218 | 2-chloroethyl ester | 513.22 |
| 219 | methyl ester | 465.29 |

EXAMPLE 220

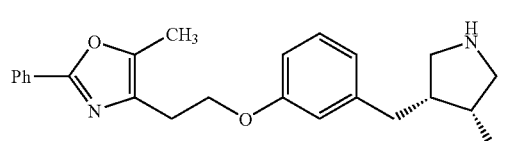

3R, 4S Enantiomer

A

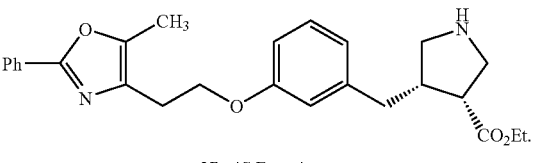

3R, 4S Enantiomer

The racemic Example 21 Part C compound (970 mg) was purified by chiral preparative HPLC using the same condition as described in Example 197 Part C. The desired 3R,4S enantiomer shown above was obtained (140 mg; chiral analytical HPLC retention time=16 min).

B

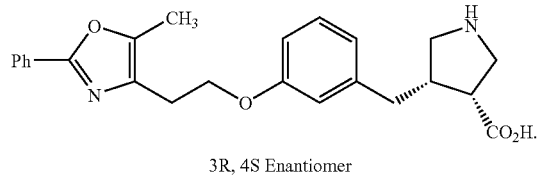

3R, 4S Enantiomer

A solution of chiral Part A compound (10 mg; 0.0230 mmol) in HOAC (800 μL) and concentrated HCl (200 μL) was shaken at 70° C. overnight. Concentration of the reaction solution in vacuo yielded the pure title compound (10.1 mg; 94%).

[M+H]+=407.44

EXAMPLE 221

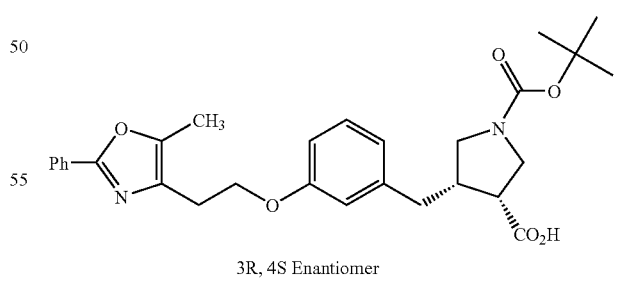

3R, 4S Enantiomer

To a 0° C. solution of Example 220 (6.1 mg; 0.015 mmol) in saturated aqueous NaHCO$_3$ (0.50 mL) and THF (0.50 mL) was added di-tert-butyl dicarbonate (4 mg; 0.017 mmol). The reaction was stirred at 0° C. for 10 min, then was allowed to warm to RT and stirred at RT for 2.5 h. Volatiles were removed in vacuo; water and EtOAc were added. The mixture was cooled to 0° C. and the aqueous phase was acidified to pH 1 with saturated aqueous KHSO$_4$ and extracted with EtOAc (2×). The combined organic extracts were washed with water (2×) and brine, dried (Na$_2$SO$_4$) and concentrated in vacuo. The residue was purified by preparative HPLC (as described for Example 197 Part F) to yield the title compound (3.2 mg, 42%).

[M+H]$^+$=507.30

EXAMPLE 222

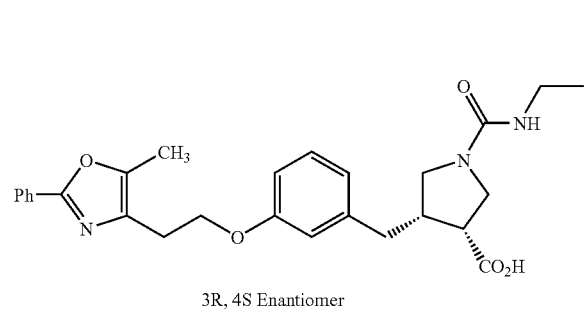

3R, 4S Enantiomer

To a solution of Example 220 (9.3 mg; 0.023 mmol) in THF (250 μL) and saturated aqueous NaHCO$_3$ (250 μL) was added ethyl isocyanate (2.18 μL; 0.0276 mmol) at RT. The reaction was stirred at RT overnight. More ethyl isocyanate (2.2 μL) was added to drive the reaction to completion (6 h), after which volatiles were removed in vacuo. The residue was dissolved in water, cooled to 0° C. and acidified to pH 1 with saturated aqueous KHSO$_4$. A white precipitate formed. The aqueous phase was extracted with EtOAc (3×). The combined organic extracts were washed with water (2×) and brine, dried (Na$_2$SO$_4$), filtered and concentrated in vacuo. The residue was purified by preparative HPLC (Phenomenex Luna 5μ 21.2×100 mm column; flow rate=20 mL/min; 10 min continuous gradient from 20:80 B:A to 100% B, where solvent A=90:10:0.1 H$_2$O:MeOH:TFA and solvent B=90:10:0.1 MeOH:H$_2$O:TFA) to give the title compound (9.6 mg; 87%).

[M+H]$^+$=478.49

EXAMPLE 223

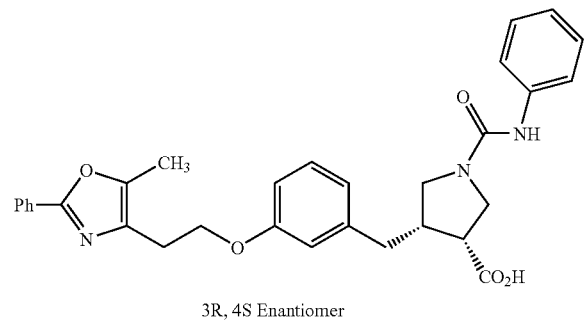

3R, 4S Enantiomer

To a solution of Example 220 (9.3 mg; 0.023 mmol) in THF (250 μL) and saturated aqueous NaHCO$_3$ (250 μL) was added phenyl isocyanate (3.75 μL; 0.0345 mmol) at RT. The reaction was stirred at room temperature overnight and then concentrated down. The solid residue was redissolved into water, cooled in an ice bath, and acidified to pH 1.0 with saturated aqueous KHSO$_4$. This acidic solution was extracted with EtOAc (3×). The combined extracts were washed with water (2×) and brine, dried over anhydrous sodium sulfate, filtered and concentrated. The product was purified by preparative HPLC (as described for Example 222) to yield the title compound (9.1 mg; 75%).

[M+H]$^+$=526.49

EXAMPLE 224

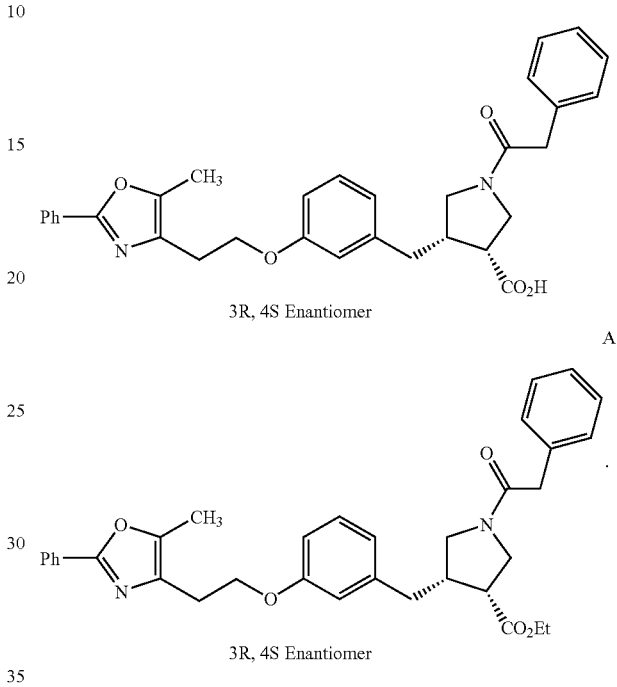

3R, 4S Enantiomer

To a solution of Example 220 Part A compound (10 mg; 0.0230 mmol) in CH$_2$Cl$_2$ (500 μL) was added TEA (4.8 μL; 0.035 mmol) and phenylacetyl chloride (3.7 μL; 0.028 mmol). The reaction was stirred at RT for 3 h, then was concentrated in vacuo. The residue was partitioned between EtOAc and water; the organic phase was washed with water (2×) and brine, dried (Na$_2$SO$_4$) and concentrated in vacuo to give Part A compound (12.5 mg) as a yellow oil, which was used in the next step without further purification.

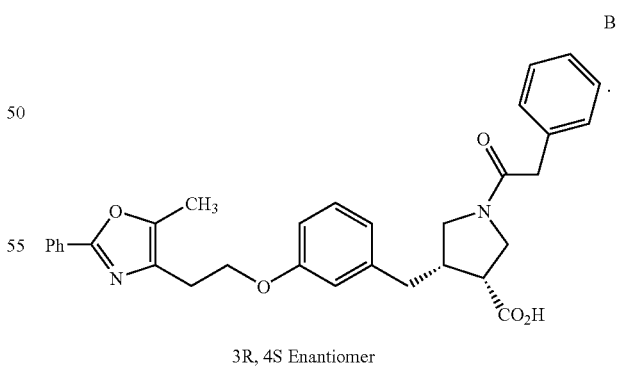

3R, 4S Enantiomer

A solution of Part A compound in HOAc (800 μL) and concentrated HCl (200 μL). The reaction was shaken at 70° C. for 13.5 h, then cooled to RT and concentrated in vacuo. The residue was purified by preparative HPLC (as described for Example 222) to yield the title compound (5.0 mg; 41%) as a solid.

[M+H]$^+$=525.50.

EXAMPLE 225

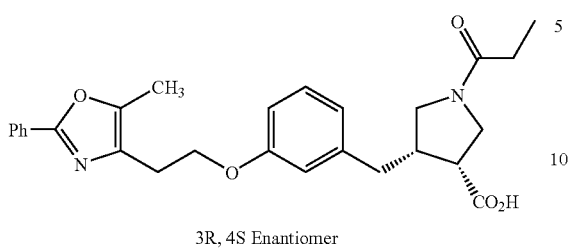

3R, 4S Enantiomer

Example 225 (7.1 mg; 65%) was synthesized employing the procedure described in Example 224, except that butyryl chloride was used in the sequence instead of phenylacetyl chloride.

[M+H]$^+$=477.50.

EXAMPLE 226

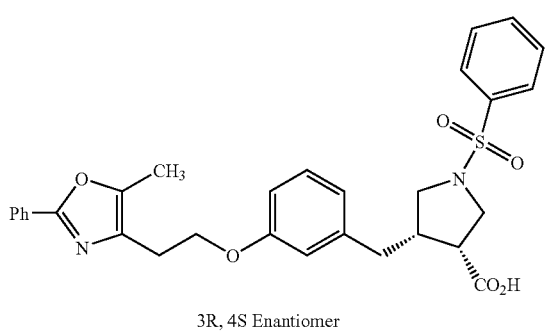

3R, 4S Enantiomer

A solution of Example 220 (9.3 mg; 0.023 mmol) and phenylsulfonyl chloride (4.4 µL; 0.035 mmol) in THF (250 µL) and saturated aqueous NaHCO$_3$ (250 µL) was stirred at RT for 3.5 h, then was concentrated in vacuo. The residue was taken up in water, cooled to 0° C., and acidified to pH 1 with saturated aqueous KHSO$_4$ (precipitate formation). The mixture was extracted with EtOAc (3×). The combined organic extracts were washed with water (2×) and brine, dried (Na$_2$SO$_4$) and concentrated in vacuo. The residue was purified by preparative HPLC (as described for Example 222) to yield the title compound (8.1 mg; 64%).

[M+H]$^+$=547.46

EXAMPLE 227

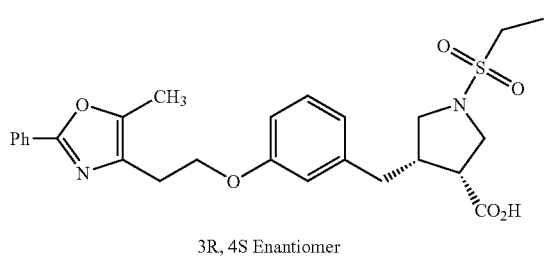

3R, 4S Enantiomer

Example 227 (4.4 mg; 38%) was synthesized employing the procedure described in Example 226, except that ethane sulfonyl chloride was used in the sequence instead of phenyl sulfonyl chloride. [M+H]$^+$=499.46

EXAMPLE 228

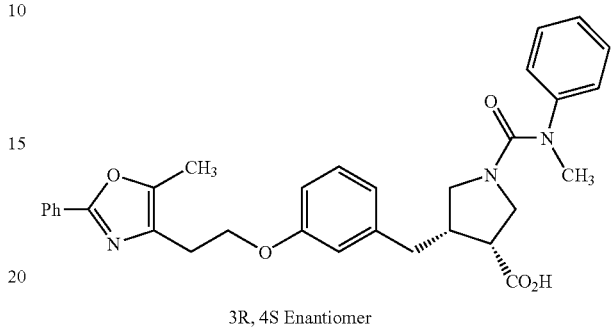

3R, 4S Enantiomer

To a RT solution of Example 220 (9.3 mg; 0.023 mmol) in THF (250 µL) and saturated aqueous NaHCO$_3$ (250 µL) was added N-methyl-N-phenylcarbamoyl chloride (4.7 mg; 0.028 mmol). The reaction was stirred at RT for 3.5 h, then was concentrated in vacuo. The residue was dissolved into water, cooled to 0° C., and acidified to pH 1.0 with saturated aqueous KHSO$_4$ (precipitate formation). The mixture was extracted with EtOAc (3×). The combined organic extracts were washed with water (2×) and brine, dried (Na$_2$SO$_4$) and concentrated in vacuo. The product was purified by preparative HPLC (as described for Example 222) to yield the title compound (6.5 mg; 52%) as a solid.

[M+H]$^+$=540.24

EXAMPLE 229

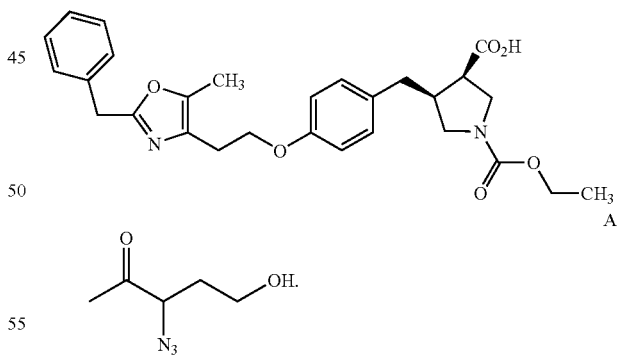

A mixture of 3-chloro-5-hydroxy-2-pentanone (5 g; 36.7 mmol) and sodium azide (4.8 g; 73.8 mmol) in acetone (100 mL) and H$_2$O (~30 mL) was stirred at 50° C. for 2.5 h. The reaction was cooled to RT and the acetone was removed in vacuo. The aqueous phase was extracted with CH$_2$Cl$_2$; the combined organic extracts were dried (Na$_2$SO$_4$) and concentrated in vacuo. The residue was chromatographed (SiO$_2$; continuous gradient from 100% hex to 100% EtOAc) to give Part A compound (4.38 g; 82%).

B

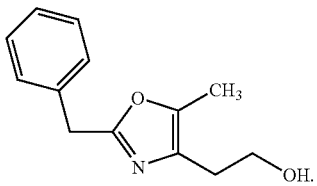

A mixture of Part A compound (500 mg; 3.50 mmol) and resin-bound Ph₃P (1.50 g of 3 mmol/g resin; 4.50 mmol) in dioxane (20 mL) was shaken for 10 min at RT. Phenylacetyl chloride (1 g; 6.50 mmol) was added and the reaction was heated at 80° C. for 18 h, then cooled to RT and filtered. A mixture of the filtrate in MeOH (20 mL) and aqueous LiOH (6 mL of a 2N solution) was shaken at 70° C. for 15 min. and more aqueous LiOH 2N was added until the pH of the solution remained at 9. The mixture was concentrated in vacuo and partitioned between water and CH₂Cl₂; the aqueous layer was extracted with CH₂Cl₂ The combined organic extracts were dried (Na₂SO₄) and concentrated in vacuo. The residue was chromatographed (SiO₂; continuous gradient from 20% hex/EtOAc to 100% EtOAc) to give Part B compound (140 mg; 19%) as a pale yellow oil.

[M+H]+=-218; ¹H NMR (CDCl₃) δ 7.31 (m, 5H), 4.03 (s, 2H), 3.87 (t, J=6.0 Hz, 2H), 2.64 (t, J 6.0 Hz, 2H 2.19 (s, 3H).

C

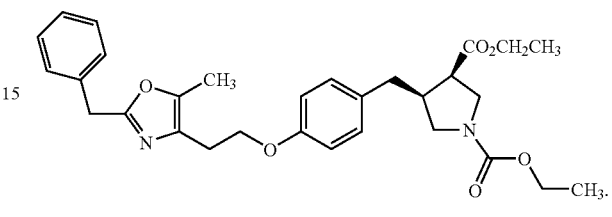

A mixture of Example 23 Part D compound (4.8 g; 10 mmol) and 10% Pd/C (500 mg) in HOAc (100 mL) was stirred under an atmosphere of H₂ (60 psi) for 18 h. The catalyst was filtered off on Celite® and the filtrate was concentrated in vacuo. The residue was azeotroped with toluene, then was treated with 1N HCl in dioxane (50 mL) for 10 min. and concentrated in vacuo to afford Part C compound (3.3 g; 95%) as an orange oil which was used in the next step without further purification.

[M+H]+=250.11

D

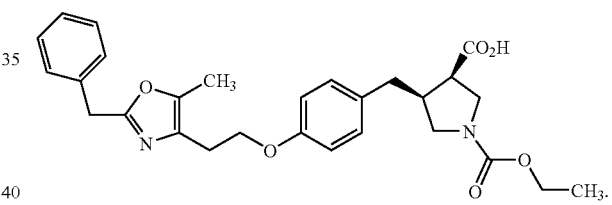

To a mixture of part C compound (300 mg, 1.05 mmol) in THF (3 mL) and saturated aqueous Na₂CO₃ (5 mL) was added ethyl chloroformate (120 μL, 1.30 mmol), and the reaction was stirred overnight at RT. The THF was removed in vacuo and the aqueous solution was extracted with CH₂Cl₂; the combined organic extracts were dried (Na₂SO₄) and concentrated in vacuo. The residue was chromatographed (SiO₂; continuous gradient from 100% hex to 100% EtOAc) to give Part D compound (110 mg; 32%).

[M+H]+=322.18

E

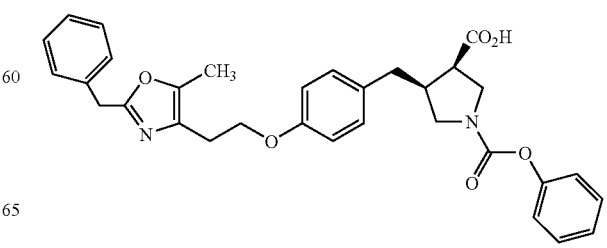

A mixture of Part D compound (13 mg, 40 μmol), part B compound (10.3 mg, 48 μmol), cyanomethylene tributylphosphine (30 μL, 120 μmol) in toluene (0.5 mL) was heated at 70° C. for 18 h. The mixture was concentrated in vacuo and the resulting residue was chromatographed (SiO₂; continuous gradient from 100% hex to 60% EtOAc) to give part E compound as an oil. ([M+H]+521.24)

F

A solution of Part E compound in 25% concentrated HCl in HOAc (1 mL) was heated at 70° C. for 8 h. Volatiles were removed in vacuo and the residue was purified by HPLC (as described for Example 1) and lyophilized (water with 2-4% methanol) to give the title compound (5.0 mg; 26% over 2 steps) as a white solid.

[M+H]+=493.20

EXAMPLE 230

A.

-continued

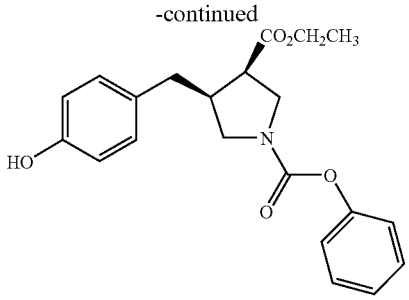

To a mixture of Example 229 part C compound (300 mg, 1.05 mmol), THF (3 mL) and saturated aqueous $Na_2CO_3$ (5 mL) was added phenyl chloroformate (160 μL, 1.30 mmol). The reaction was stirred overnight at RT, after which the THF was removed in vacuo and the resulting aqueous solution was extracted with $CH_2Cl_2$. The combined organic extracts were dried ($Na_2SO_4$) and concentrated in vacuo. The residue was chromatographed ($SiO_2$; continuous gradient from 100% hex to 100% EtOAc) to give Part A compound (140 mg; 36%) as a colorless oil.

[M+H]+=370.14

B.

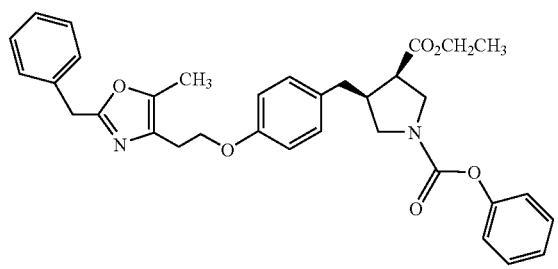

A mixture of Part A compound (15 mg, 40 μmol), Example 229 part B compound (10.3 mg, 48 μmol), cyanomethylene tributylphosphine (30 μL, 120 μmol) in toluene (0.5 mL) was heated at 70° C. for 18 h. Volatiles were removed in vacuo and the residue was chromatographed ($SiO_2$; continuous gradient from 100% hexane to 60:4 hex:EtOAc) to give Part B compound as an oil.

[M+H]+=569.18

C.

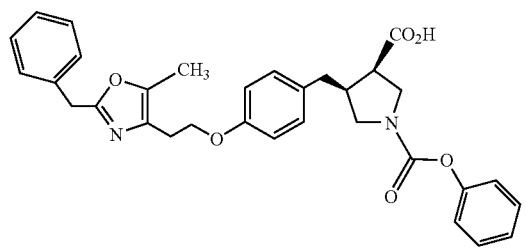

A solution of Part B compound in 25% concentrated HCl in HOAC (1 mL) was heated at 70° C. for 20 h. The mixture was concentrated in vacuo and the residue was purified by preparative HPLC (as described for Example 1) and lyophilized (water with 2-4% methanol) to give the title compound (10.5 mg; 48% over 2 steps) as a white solid.

[M+H]+=541.18

EXAMPLE 231

A.

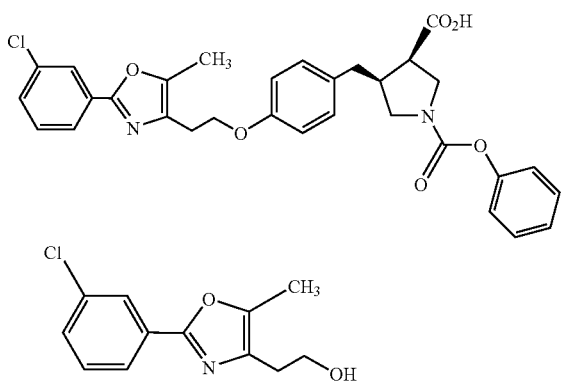

A mixture of example 229 part A compound (500 mg; 3.50 mmol) and resin-bound $Ph_3P$ (1.50 g of 3 mmol/g resin; 4.50 mmol) in dioxane (20 mL) was shaken for 10 min at RT. 3-chlorobenzoyl chloride (1.22 g; 6.50 mmol) was then added and the reaction was heated at 80° C. for 18 h, then cooled to RT, filtered and concentrated in vacuo. The residue was dissolved in MeOH (10 mL) and THF (10 mL) and aqueous LiOH (6 mL of a 2N solution) was added. The mixture was shaken at 50° C. and more aqueous LiOH was added until the pH of the solution remained constant at 9. The mixture was then heated at 50° C. for 6 h, cooled to RT and concentrated. The residue was partitioned between $H_2O$ and $CH_2Cl_2$; the combined organic extracts were dried ($Na_2SO_4$) and concentrated in vacuo. The residue was chromatographed ($SiO_2$; continuous gradient from 20% hex/EtOAc to 100% EtOAc) to give Part A compound (80 mg; 9%).

[M+H]+=260.36;

B.

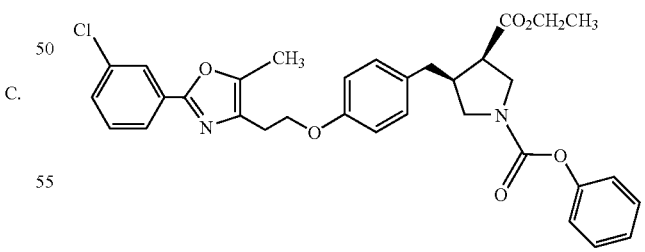

A mixture of Example 230 part A compound (15 mg, 40 μmol), part A compound (11.4 mg, 48 μmol) and cyanomethylene tributylphosphine (30 μL, 120 μmol) in toluene (0.5 mL) was heated at 70° C. for 18 h. The mixture was concentrated in vacuo and the resulting residue was chromatographed ($SiO_2$; continuous gradient from 100% hex to 60:40 EtOAc) to give Part B compound.

[M+H]+=589.44

C.

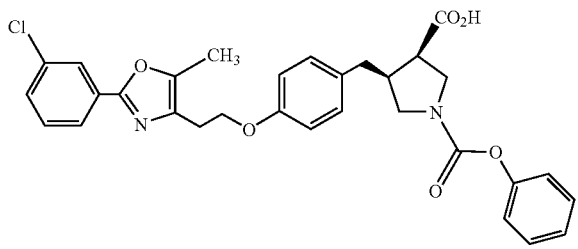

A solution of Part B compound in concentrated HCl/HOAc (1 mL of a 1:3 mixture) was heated at 70° C. for 18 h. The mixture was concentrated in vacuo and the residue was purified by preparative HPLC (as described for Example 1) and lyophilized (water with 2-4% methanol) to give the title compound (5.6 mg; 25% for 2 steps) as a white solid.
[M+H]+=561.63

EXAMPLE 232

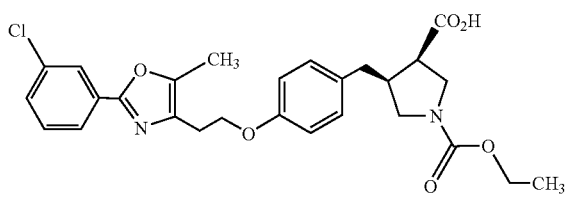

A mixture of example 229 part D compound (13 mg, 40 µmol), example 231 part A compound (11.4 mg, 48 µmol) and cyanomethylene tributylphosphine (30 µL, 120 µmol) in toluene (0.5 mL) was heated at 70° C. for 18 h. The mixture was concentrated in vacuo and the resulting residue was chromatographed (SiO$_2$; continuous gradient from 100% hex to 60% EtOAc) to give the ethyl ester of part E compound ([M+H]+=541.46). This ester was dissolved in 25% concentrated HCl in acetic acid (1 mL) and heated at 70° C. for 18 h. The mixture was concentrated and the residue was purified by HPLC (as described for Example 1) and lyophilized (water with 2-4% methanol) to give the title compound (3.5 mg; 18%) as a white solid.
[M+H]+=513.54

EXAMPLE 233

A.

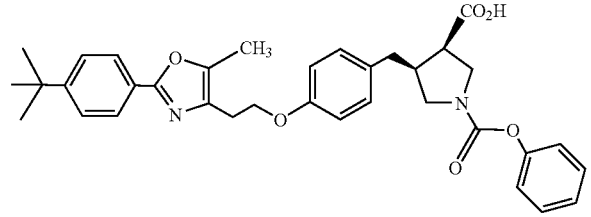

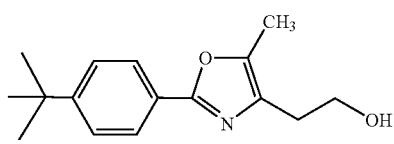

Part A compound was synthesized according to the general procedure described for the synthesis of Example 231 Part A compound except that 4-tert-butylbenzoyl chloride was used instead of 3-chlorobenzoyl chloride.

B.

The title compound (11 mg; 50%) was prepared from Part A compound and Example 230 part A compound (15 mg; 40 µmol) using the same sequence as for Example 231 except that 4-tert-butylbenzoyl chloride (1.37 g; 6.50 mmol) was used instead of 3-chlorobenzoyl chloride.
[M+H]+=583.64

EXAMPLE 234

The title compound (7 mg; 30%) was prepared from example 229 part D compound (13 mg, 40 µM),using the same sequence as for Example 232 except that 4-tert-butylbenzoyl chloride (1.37 g; 6.50 mmol) was used instead of 3-chlorobenzoyl chloride.
[M+H]+=535.64

EXAMPLES 235-241

Examples 235-241 of the invention were prepared in a similar fashion to Example 43 (from Example 43 Part D compound) using a variety of chloroformates.

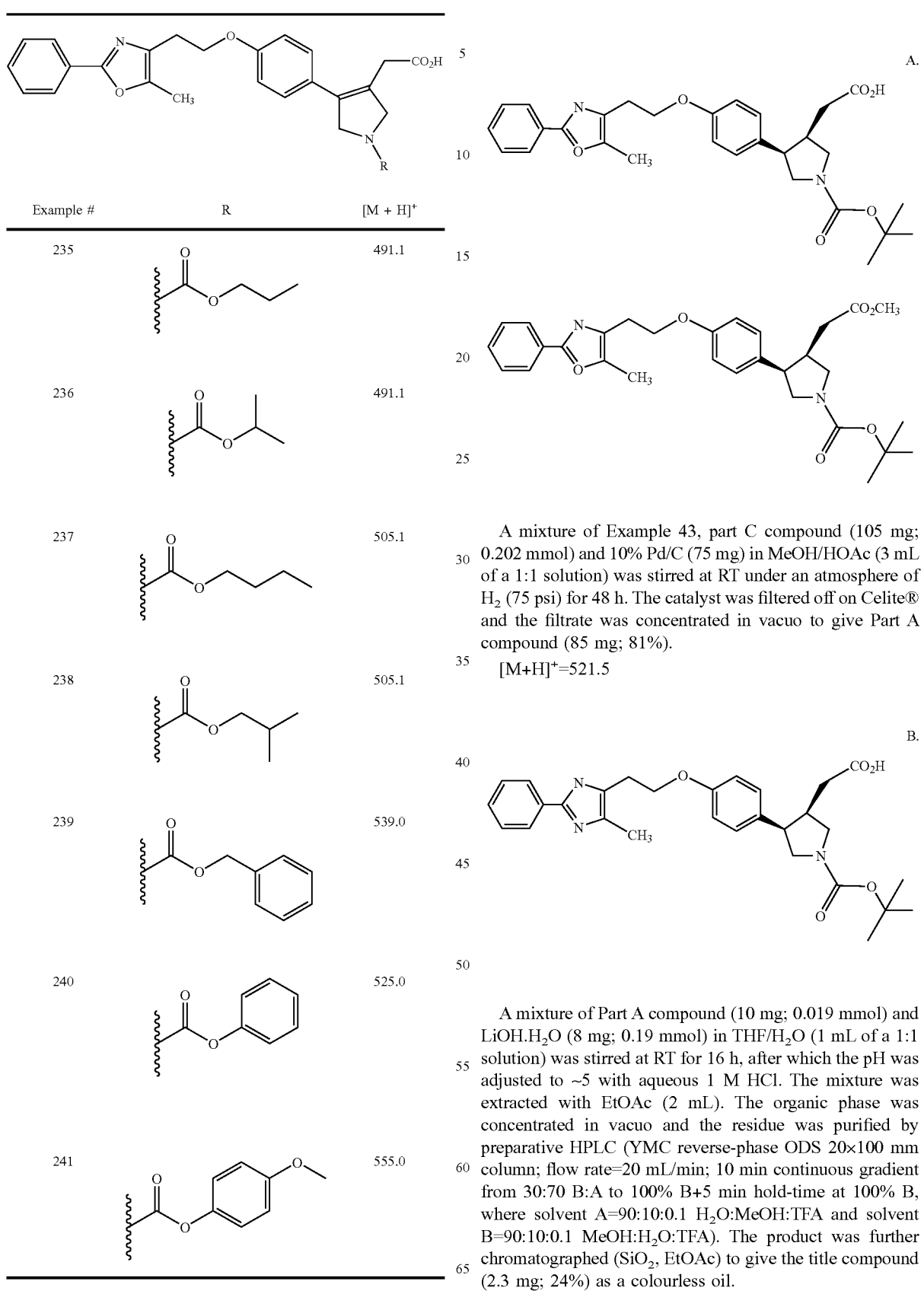

| Example # | R | [M + H]+ |
|---|---|---|
| 235 | propyl ester | 491.1 |
| 236 | isopropyl ester | 491.1 |
| 237 | butyl ester | 505.1 |
| 238 | isobutyl ester | 505.1 |
| 239 | benzyl ester | 539.0 |
| 240 | phenyl ester | 525.0 |
| 241 | 4-methoxyphenyl ester | 555.0 |

EXAMPLE 242

A.

A mixture of Example 43, part C compound (105 mg; 0.202 mmol) and 10% Pd/C (75 mg) in MeOH/HOAc (3 mL of a 1:1 solution) was stirred at RT under an atmosphere of H$_2$ (75 psi) for 48 h. The catalyst was filtered off on Celite® and the filtrate was concentrated in vacuo to give Part A compound (85 mg; 81%).

[M+H]$^+$=521.5

B.

A mixture of Part A compound (10 mg; 0.019 mmol) and LiOH.H$_2$O (8 mg; 0.19 mmol) in THF/H$_2$O (1 mL of a 1:1 solution) was stirred at RT for 16 h, after which the pH was adjusted to ~5 with aqueous 1 M HCl. The mixture was extracted with EtOAc (2 mL). The organic phase was concentrated in vacuo and the residue was purified by preparative HPLC (YMC reverse-phase ODS 20×100 mm column; flow rate=20 mL/min; 10 min continuous gradient from 30:70 B:A to 100% B+5 min hold-time at 100% B, where solvent A=90:10:0.1 H$_2$O:MeOH:TFA and solvent B=90:10:0.1 MeOH:H$_2$O:TFA). The product was further chromatographed (SiO$_2$, EtOAc) to give the title compound (2.3 mg; 24%) as a colourless oil.

[M+H]$^+$=507.1

EXAMPLE 243

A.

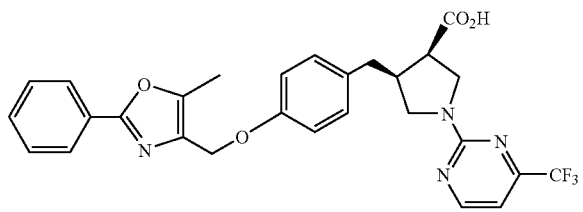

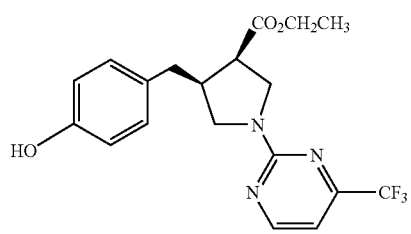

A mixture of Example 229 Part C compound (920 mg; 3.69 mmol)

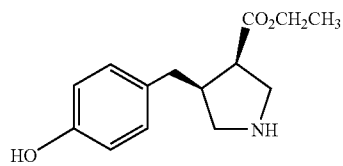

and 2-chloro-4-(trifluoromethyl)pyrimidine (0.53 mL; 4.43 mmol) and Et₃N (1.03 mL; 7.38 mmol) in toluene (12.3 mL) was stirred at 80° C. for 2 h, after which the reaction was partitioned between EtOAc (65 mL) and aqueous 1 M HCl (25 mL). The organic phase was washed with H₂O (2×65 mL) and brine (70 mL), dried (MgSO₄) and concentrated in vacuo. The residue was chromatographed (SiO₂; continuous gradient from 90% hex to 100% EtOAc) to give Part A compound (918 mg; 63%) as a colorless oil.

B.

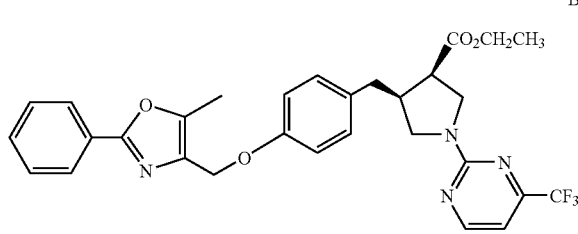

A mixture of 4-chloromethyl-5-methyl-2-phenyloxazole (12.6 mg; 0.0608 mmol),

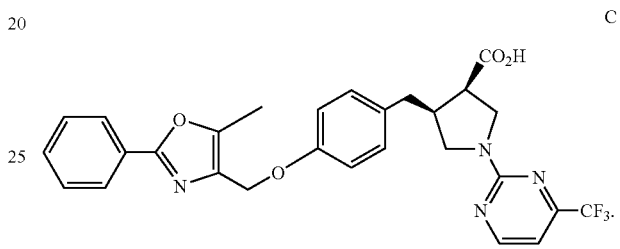

Part A compound (12 mg; 0.0304 mmol) and K₂CO₃ (8.4 mg; 0.0608 mmol) in CH₃CN (1 mL) was stirred at 70° C. for 15 h, after which the reaction was partitioned between EtOAc (10 mL) and H₂O (5 mL). The organic phase was washed with brine (20 mL), dried (MgSO₄) and concentrated in vacuo to provide crude Part B compound as an oil, which was used in the next step without further purification.

C.

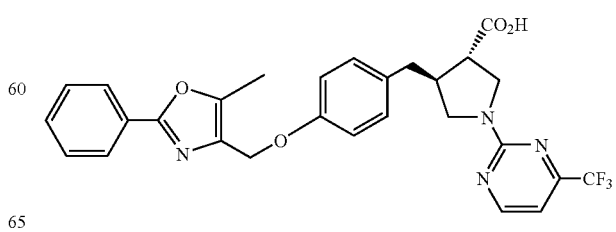

A solution of Part B compound LiOH.H₂O (5.1 mg) in THF (1 mL) and H₂O (0.5 mL) was stirred at RT for 16 h and then heated to 70° C. for an additional 6 h, after which the reaction mixture was cooled to RT and the pH was adjusted to ~2 with aqueous 1 N HCl. The mixture was partitioned between EtOAc (10 mL) and H₂O (5 mL). The organic phase was washed with brine (20 mL), dried (MgSO₄) and concentrated in vacuo; the residue was purified by preparative HPLC (as described for Example 1 except that a continuous gradient from 30:70 Solvent A:Solvent B to 100% B over 10 min was used, followed by 4 min hold at 100% B) to give two compounds. The compound with the shorter retention time on HPLC was lyophilized from 1,4-dioxane to give the title compound (1.8 mg; 11% for two steps) as a white solid.

$[M+H]^+=539.0$

The second compound (longer retention time) was determined to be the corresponding epimerized transisomer of Example 243. This compound was also lyophilized from 1,4-dioxane to give Example 244 (1.1 mg; 6.7% for 2 steps) as a white solid.

EXAMPLE 244

$[M+H]^+=539.0$

EXAMPLE 245

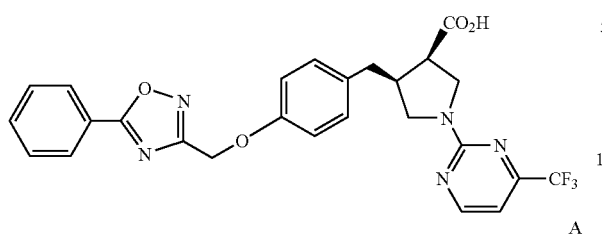
A

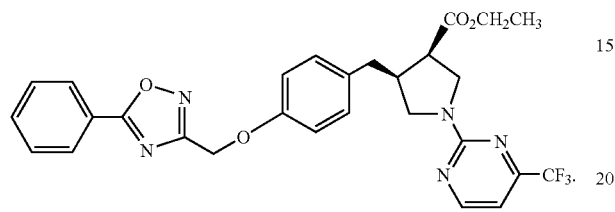

A mixture of Example 25 Part C compound (11.8 mg; 0.0608 mmol), Example 243 Part A compound (12 mg; 0.0304 mmol) and K$_2$CO$_3$ (8.4 mg; 0.0608 mmol) in CH$_3$CN (1 mL) was stirred at 70° C. for 15 h, then was cooled to RT and partitioned between EtOAc (10 mL) and H$_2$O (5 mL). The organic phase was washed with brine (20 mL), dried (MgSO$_4$) and concentrated in vacuo to provide crude Part A compound as an oil, which was used in the next step without further purification.

B

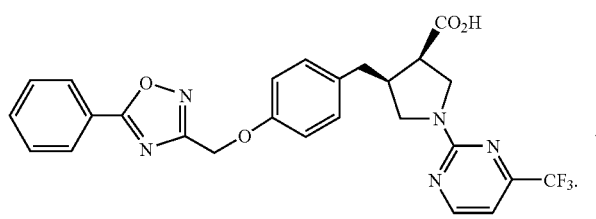

A solution of crude Part A compound in HOAc/concentrated HCl (1.2 mL of a 9:1 solution) was stirred at 70° C. for 17 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give the title compound (2.0 mg; 13% for 2 steps) as a white solid.

[M+H]$^+$=526.0

EXAMPLE 246

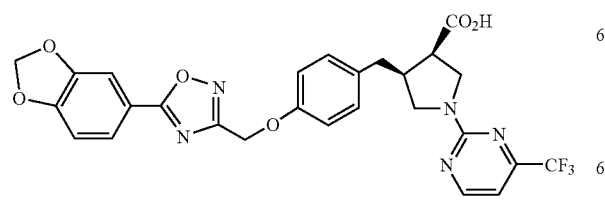

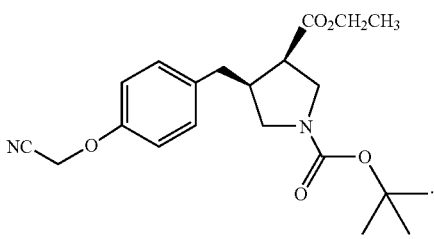
A

A mixture of Example 23 Part E compound (640 mg; 1.83 mmol), α-chloroacetonitrile (0.232 mL; 3.66 mmol) and K$_2$CO$_3$ (506 mg; 3.66 mmol) in CH$_3$CN (9.2 mL) at 70° C. was stirred for 18 h, then was cooled to RT and partitioned between EtOAc (150 mL) and H$_2$O (80 mL). The organic phase was washed with brine (20 mL), dried (MgSO$_4$) and concentrated in vacuo. The residue was chromatographed (SiO$_2$; continuous gradient from 100% hex to 100% EtOAc over 55 min) to give Part A compound (590 mg; 83%) as an oil.

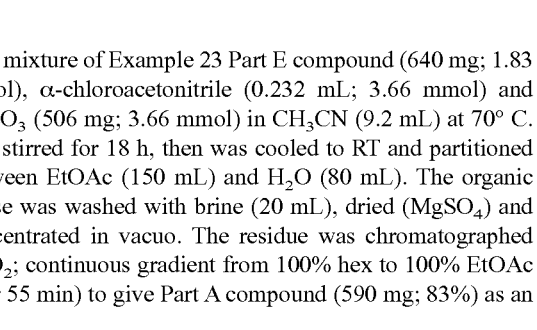
B

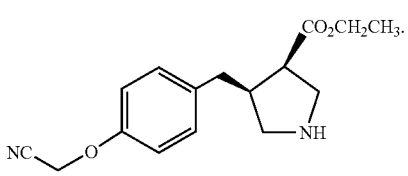

A solution of Part A compound (590 mg; 1.52 mmol) and HCl (0.76 mL of a 4 M solution in dioxane) in CH$_2$Cl$_2$ (4 mL) was stirred at RT for 3 h, then was concentrated in vacuo to give crude Part B compound (355 mg; 81%) as an oil.

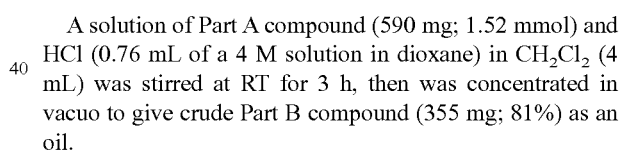
C

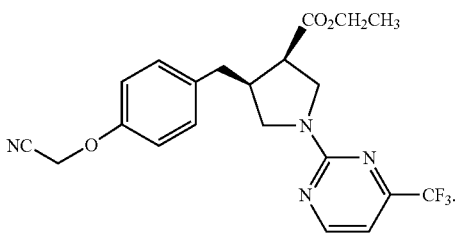

A mixture of Part B compound (355 mg; 1.23 mmol) and 2-chloro-4-(trifluoromethyl)pyrimidine (0.298 mL; 2.47 mmol) and Et$_3$N (0.344 mL; 2.47 mmol) in toluene (5 mL) was stirred at 80° C. for 2 h, after which the reaction was partitioned between EtOAc (35 mL) and aqueous 1 M HCl (15 mL) The organic phase was washed with H$_2$O (2×35 mL) and brine (40 mL), dried (MgSO$_4$) and concentrated in vacuo. The residue was chromatographed (SiO$_2$; continuous gradient from 90% hex to 100% EtOAc) to give Part C compound (246 mg; 46%) as a colorless oil.

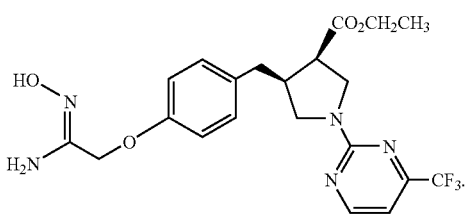

D

A mixture of Part C compound (246 mg; 0.567 mmol) and hydroxylamine (112 mg of a 50% solution in water; 1.70 mmol) in MeOH:H₂O (6 mL of a 2:1 solution) was heated to reflux for 5 h, after which volatiles were removed in vacuo. The residue was partitioned between EtOAc (30 mL) and H₂O (15 mL). The organic phase was washed with brine (40 mL), dried (MgSO₄) and concentrated in vacuo to provide crude Part D compound (208 mg, 79%) as an oil.

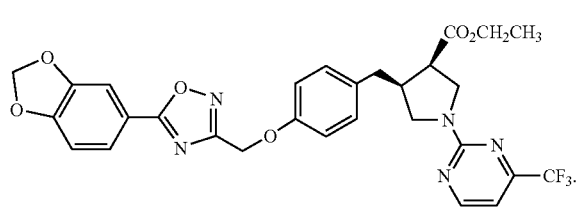

E

A mixture of Part D compound (30 mg; 0.0642 mmol), piperonyloyl chloride (23.6 mg; 0.128 mmol) in toluene (1 mL) was shaken at 115° C. for 6 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give the title compound (14 mg, 37%) as an oil.

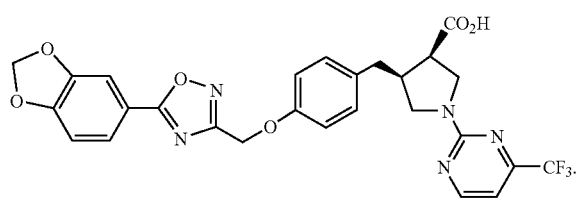

F

A solution of Part E compound (14 mg; 0.0235 mmol) in HOAc/concentrated HCl (1.5 mL of a 9:1 solution) was stirred at 70° C. for 17 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give the title compound (6.4 mg, 48%) as a white solid.

[M+H]⁺=570.0

EXAMPLES 247-250

Example 247 through 250 were prepared in a similar fashion to Example 246 (from Example 246 part D compound) using a variety of acid chlorides.

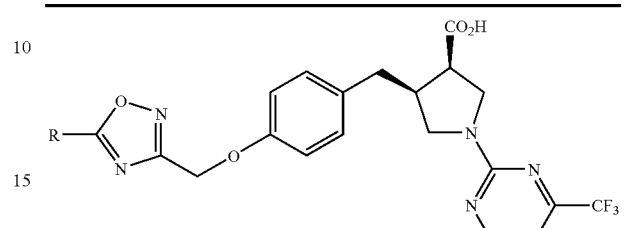

| Example # | R | [M + H]⁺ |
|---|---|---|
| 247 | (4-tert-butylphenyl) | 582.0 |
| 248 | (biphenyl-4-yl) | 602.1 |
| 249 | (4-trifluoromethoxyphenyl) | 609.9 |
| 250 | (3-ethoxyphenyl) | 570.4 |

EXAMPLE 251

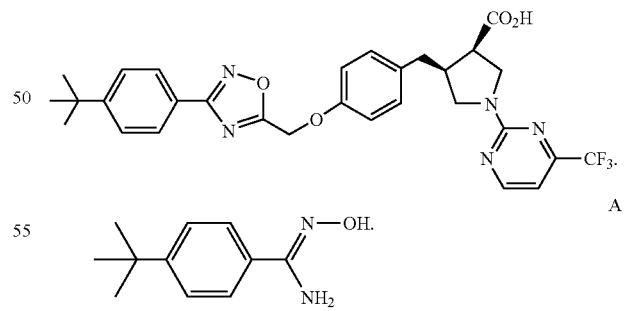

A

A mixture of 4-tert-butyl-benzonitrile (5.0 g; 31.4 mmol), hydroxylamine hydrochloride (3.27 g; 47.1 mmol) and K₂CO₃ (8.68 g; 62.8 mmol) in EtOH (170 mL) was stirred at reflux for 18 h, then was cooled to RT and filtered. The filtrate was concentrated in vacuo to provide crude Part A compound as a solid, which was used in the next step without further purification

EXAMPLE 252

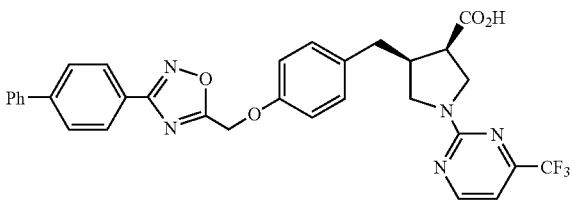
A

A mixture of 4-biphenylcarbonitrile (5.0 g; 27.9 mmol), hydroxylamine hydrochloride (2.9 g; 41.8 mmol) and $K_2CO_3$ (7.7 g; 55.8 mmol) in EtOH (150 mL) was stirred at reflux for 18 h, then was cooled to RT and filtered. The filtrate was concentrated in vacuo to provide crude Part A compound as a solid, which was used in the next step without further purification

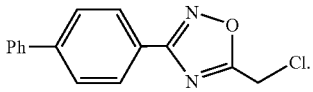
B

To a solution of crude Part A compound in $CH_2Cl_2$ (50 mL) at RT was added α-chloroacetyl chloride (2.7 mL; 33.5 mmol) followed by $Et_3N$ (4.7 mL; 33.5 mmol). The reaction mixture was stirred at RT for 2 h, after which volatiles were removed in vacuo and the residue was dissolved in toluene (80 mL). The reaction mixture was then heated and stirred at reflux for 13 h, after which the mixture was cooled to RT. The reaction was then partitioned between EtOAc (150 mL) and $H_2O$ (100 mL). The organic phase was washed with brine (200 mL), dried ($MgSO_4$) and concentrated in vacuo. The residue was chromatographed ($SiO_2$; continuous gradient from 100% hex to 100% EtOAc) to give Part B compound (431 mg; 5.7% for 2 steps) as a solid.

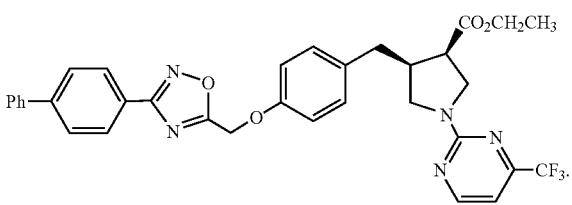

A mixture of Part B compound (27.5 mg; 0.102 mmol), Example 243 Part A compound (20 mg; 0.051 mmol) and $K_2CO_3$ (14.1 mg; 0.102 mmol) in $CH_3CN$ (1.2 mL) was stirred at 90° C. for 14 h, then was cooled to RT and partitioned between EtOAc (10 mL) and $H_2O$ (5 mL). The organic phase was washed with brine (20 mL), dried ($MgSO_4$) and concentrated in vacuo to provide crude Part B compound as an oil, which was used in the next step without further purification.

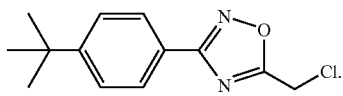
B

To a solution of crude Part A compound in $CH_2Cl_2$ (50 mL) at RT was added α-chloroacetyl chloride (2.97 mL; 37.3 mmol) followed by $Et_3N$ (5.2 mL; 37.3 mmol). The reaction mixture was stirred at RT for 2 h, after which volatiles were removed in vacuo and the residue was dissolved in toluene (80 mL). The reaction mixture was then heated at reflux for 12 h, then was cooled to RT and partitioned between EtOAc (150 mL) and $H_2O$ (100 mL). The organic phase was washed with brine (200 mL), dried ($MgSO_4$) and concentrated in vacuo. The residue was chromatographed ($SiO_2$; continuous gradient from 100% hex to 100% EtOAc) to give Part B compound (746 mg; 9.5% for 2 steps) as a solid.

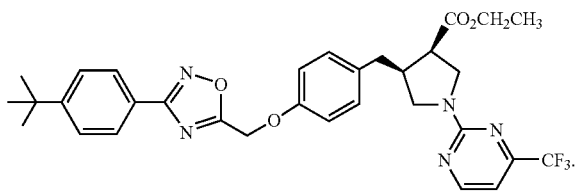
C

A mixture of Part B compound (25.5 mg; 0.102 mmol), Example 243 Part A compound (20 mg; 0.051 mmol) and $K_2CO_3$ (14.1 mg; 0.102 mmol) in $CH_3CN$ (1.2 mL) was stirred at 90° C. for 14 h, after which the reaction was partitioned between EtOAc (10 mL) and $H_2O$ (5 mL). The organic phase was washed with brine (20 mL), dried ($MgSO_4$) and concentrated in vacuo to provide crude Part B compound as an oil, which was used in the next step without further purification.

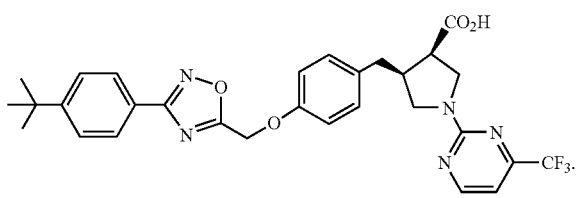
D

A solution of Part C compound in HOAc/concentrated HCl (1.2 mL of a 9:1 solution) was stirred at 70° C. for 17 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give the title compound (10.4 mg; 35%) as a white solid.

$[M+H]^+$=582.0

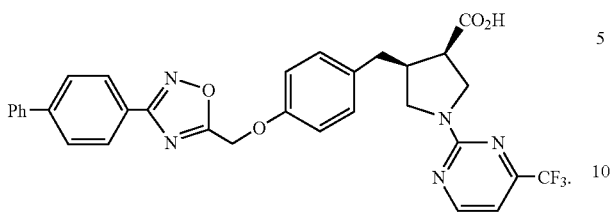

D

A solution of Part C compound in HOAc/concentrated HCl (1.2 mL of a 9:1 solution) was stirred at 70° C. for 17 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give the title compound (4.1 mg; 13%) as a white solid.

[M+H]$^+$=602.0

EXAMPLE 253

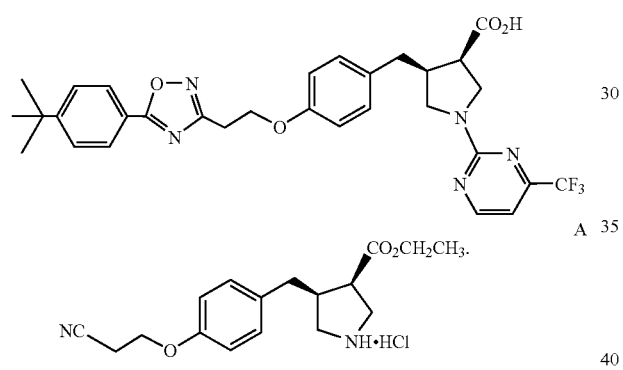

A solution of Example 51 Part B compound (329 mg; 0.82 mmol) and HCl (0.41 mL of a 4 M solution in dioxane; 1.64 mmol) in CH$_2$Cl$_2$ (5 mL) was stirred at RT for 3 h, then was concentrated in vacuo to give crude Part A compound (188 mg; 76%) as an oil.

A mixture of crude Part A compound (188 mg; 0.623 mmol) and 2-chloro-4-(trifluoromethyl)pyrimidine (0.150 mL; 1.25 mmol) and Et$_3$N (0.175 mL; 1.25 mmol) in toluene (6.2 mL) was stirred at 80° C. for 2 h, then was cooled to RT and partitioned between EtOAc (35 mL) and aqueous 1 M HCl (15 mL). The organic phase was washed with H$_2$O (2×35 mL) and brine (40 mL), dried (MgSO$_4$) and concentrated in vacuo. The residue was chromatographed (SiO$_2$; continuous gradient from 90% hex to 100% EtOAc) to give Part B compound (170 mg; 61%) as a colorless oil.

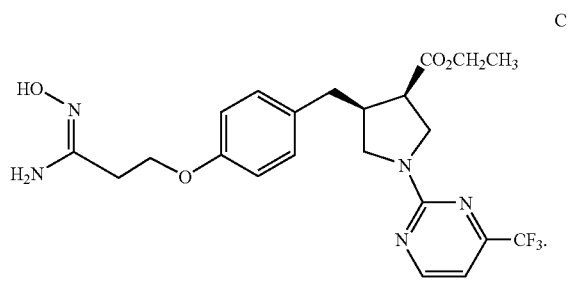

A mixture of Part B compound (170 mg; 0.379 mmol) and hydroxylamine (75 mg of a 50% solution in water; 1.138 mmol) in MeOH:H$_2$O (5 mL of a 2:1 solution) was heated at reflux for 5 h, then was cooled to RT and concentrated in vacuo. The residue was partitioned between EtOAc (30 mL) and H$_2$O (15 mL). The organic phase was washed with brine (40 mL), dried (MgSO$_4$) and concentrated in vacuo to provide crude Part C compound (149 mg, 82%) as an oil.

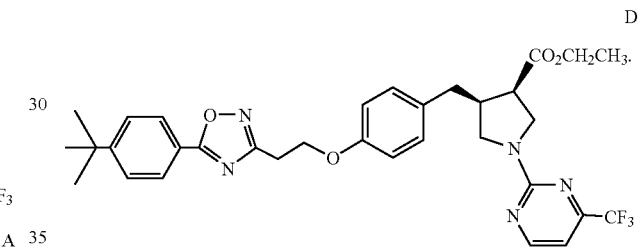

A mixture of Part C compound (28 mg; 0.0582 mmol), 4-tert-butylbenzoyl chloride (22.8 mg; 0.116 mmol) in toluene (1 mL) was shaken at 115° C. for 6 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give Part D compound (22 mg, 61%) as an oil.

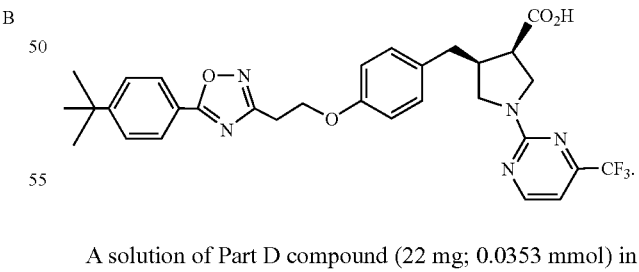

A solution of Part D compound (22 mg; 0.0353 mmol) in HOAc/concentrated HCl (1.3 mL of a 9:1 solution) was stirred at 70° C. for 16 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give the title compound (10.8 mg; 51%) as a white solid.

[M+H]$^+$=596.5

EXAMPLES 254-255

Examples 254-255 of the invention were prepared in a similar fashion to Example 253 (from Example 253 part C compound) using a variety of acid chlorides.

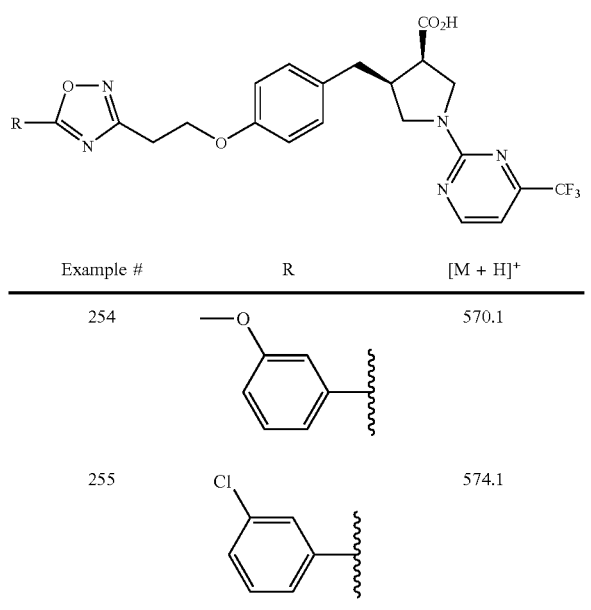

| Example # | R | [M + H]+ |
|---|---|---|
| 254 | —O-(3-methoxyphenyl) | 570.1 |
| 255 | Cl-(3-chlorophenyl) | 574.1 |

EXAMPLE 256

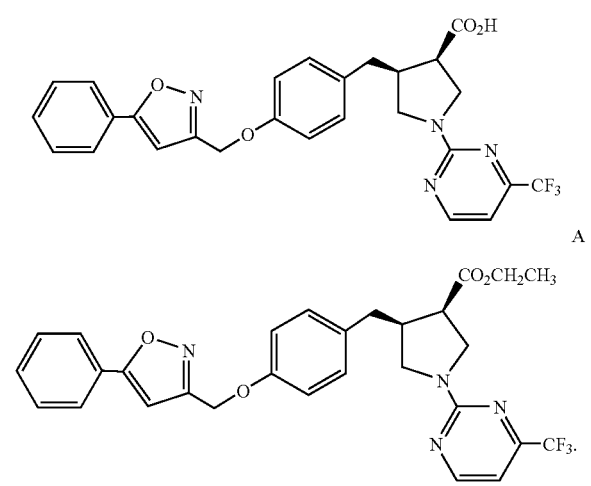

A

A mixture of 4-chloromethyl-5-phenylisoxazole (14.7 mg; 0.076 mmol), Example 243 Part A compound (15 mg; 0.038 mmol) and $K_2CO_3$ (10.5 mg; 0.076 mmol) in $CH_3CN$ (1 mL) was heated at 90° C. for 16 h, after which the reaction was partitioned between EtOAc (10 mL) and $H_2O$ (5 mL). The organic phase was washed with brine (20 mL), dried ($MgSO_4$) and concentrated in vacuo to provide crude Part A compound as an oil, which was used in the next step without further purification.

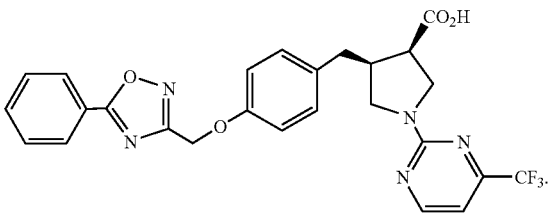

B

A solution of Part A compound and $LiOH \cdot H_2O$ (8.0 mg; 0.19 mmol) in THF (1.2 mL) and $H_2O$ (0.6 mL) was stirred at 60° C. for 12 h, then was cooled to RT and the pH was adjusted to ~2 with aqueous 1 N HCl. The mixture was partitioned between EtOAc (10 mL) and $H_2O$ (5 mL). The organic phase was washed with brine (20 mL), dried ($MgSO_4$) and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give two compounds. The compound with the shorter retention time was lyophilized from 1,4-dioxane to give the title compound (8.1 mg; 41% for 2 steps) as a white solid.

[M+H]+=525.3

The second compound (longer retention time) was determined to be the corresponding epimerized transisomer of Example 256. This compound was also lyophilized from 1,4-dioxane to give Example 257 (1.1 mg; 5.5% for steps) as a white solid.

EXAMPLE 257

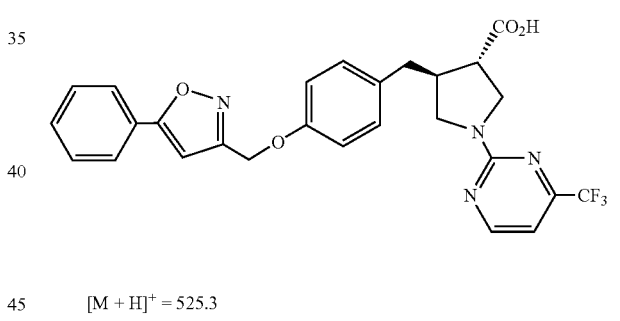

[M + H]+ = 525.3

EXAMPLE 258

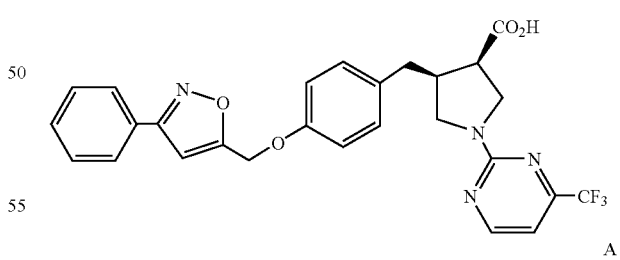

A

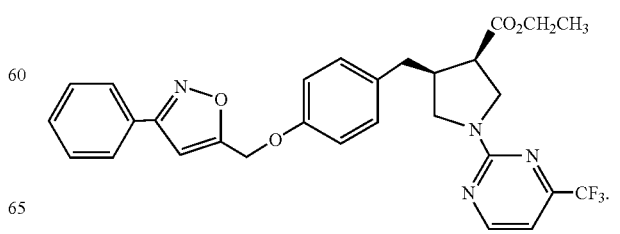

A mixture of 5-chloromethyl-3-phenylisoxazole (14.7 mg; 0.076 mmol), Example 243 Part A compound (15 mg; 0.038 mmol) and $K_2CO_3$ (10.5 mg; 0.076 mmol) in $CH_3CN$ (1 mL) was heated at 90° C. for 16 h, then was cooled to RT and partitioned between EtOAc (10 mL) and $H_2O$ (5 mL). The organic phase was washed with brine (20 mL), dried ($MgSO_4$) and concentrated in vacuo to provide crude Part A compound as an oil, which was used in the next step without further purification.

B

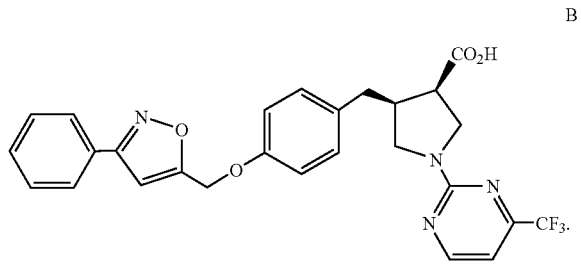

A solution of crude Part A compound and $LiOH.H_2O$ (8.0 mg; 0.19 mmol) in THF (1.2 mL) and $H_2O$ (0.6 mL) was stirred at 60° C. for 12 h, then was cooled to RT and the pH was adjusted to ~2 with aqueous 1 N HCl. The mixture was partitioned between EtOAc (10 mL) and $H_2O$ (5 mL). The organic phase was washed with brine (20 mL), dried ($MgSO_4$) and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give two compounds. The compound with the shorter retention time was lyophilized from 1,4-dioxane to give the title compound (4.0 mg; 20% for 2 steps) as a white solid.

$[M+H]^+=525.3$

The second compound (longer retention time) was determined to be the corresponding epimerized transisomer of Example 258. This compound was also lyophilized from 1,4-dioxane to give Example 259 (1.0 mg; 5.0% for 2 steps) as a white solid.

EXAMPLE 259

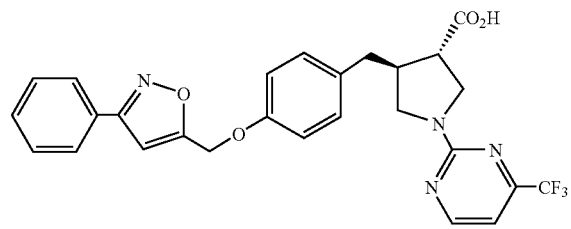

$[M + H]^+ = 525.3$

EXAMPLE 260

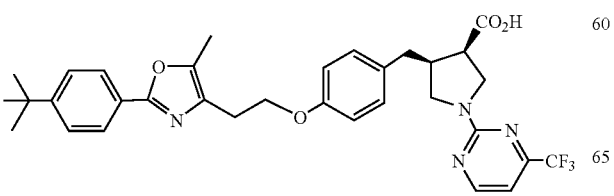

A

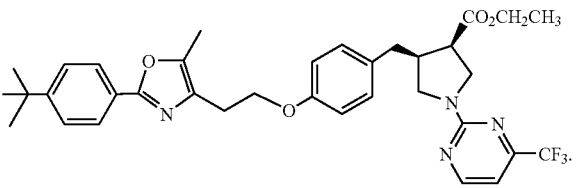

To a solution of Example 243 Part A compound (16 mg; 0.0405 mmol) in toluene (0.4 mL) were successively added Example 233 Part A compound (15.7 mg; 0.0608 mmol) and cyanomethylene tri-n-butylphosphorane (29.4 mg; 0.122 mmol). The reaction mixture was heated to 80° C. for 8 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give Part A compound (7.3 mg; 28%).

B

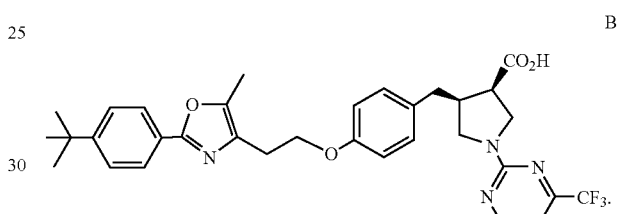

A solution of Part A compound (7.3 mg; 0.011 mmol) and $LiOH.H_2O$ (8.5 mg; 0.202 mmol) in THF (1.2 mL) and $H_2O$ (0.6 mL) was stirred at 60° C. for 15 h, then was cooled to RT and the pH was adjusted to ~2 with aqueous 1 N HCl. The mixture was partitioned between EtOAc (10 mL) and $H_2O$ (5 mL). The organic phase was washed with brine (20 mL), dried ($MgSO_4$) and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give two compounds. The compound with the shorter retention time was lyophilized from 1,4-dioxane to give the title compound (2.6 mg; 39%) as a white solid.

$[M+H]^+=609.5$

The second compound (longer retention time) was determined to be the corresponding epimerized transisomer of Example 260. This compound was also lyophilized from 1,4-dioxane to give Example 261 (1.2 mg; 4.9% for two steps) as a white solid.

EXAMPLE 261

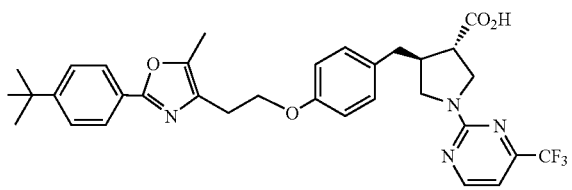

$[M + H]^+ = 609.4$

EXAMPLE 262

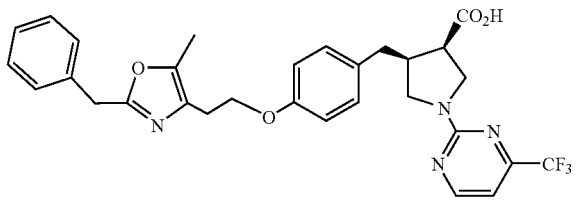

The title compound (4.8 mg; 21%) was prepared from Example 229 Part B compound (13.2 mg; 0.0608 mmol) and Example 243 Part A compound according to the procedure described for the synthesis of Example 261.

[M+H]$^+$=567.4

EXAMPLE 263

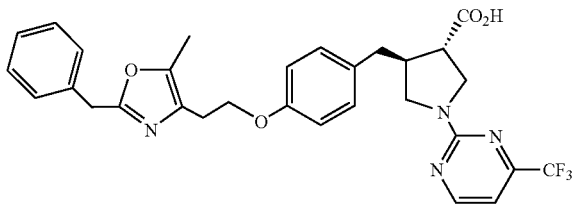

The title compound (1.2 mg; 5.2%) was obtained from Example 229 Part B compound (13.2 mg; 0.0608 mmol) and according to the general procedure described for the synthesis of Example 262.

[M+H]$^+$=567.4

EXAMPLE 264

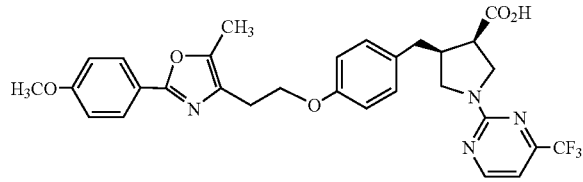

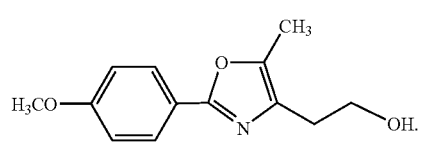

Part A compound was synthesized according to the general procedure described for the synthesis of Example 231 Part A compound except that 4-methoxybenzoyl chloride was used instead of 3-chlorobenzoyl chloride.

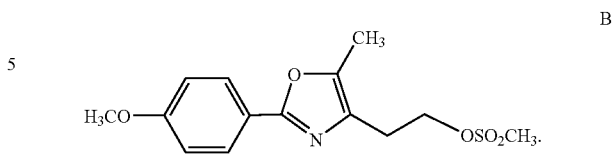

Part B compound was synthesized from Part A compound according to the general procedure described for the synthesis of Example 23 Part A compound.

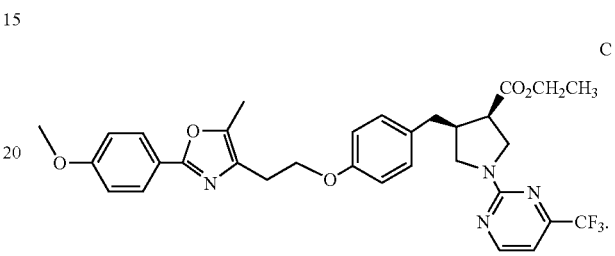

A mixture of Example 243 Part A compound (20 mg; 0.051 mmol), Part B compound (24 mg; 0.076 mmol) and K$_2$CO$_3$ (21 mg; 0.152 mmol) in CH$_3$CN (1.0 mL) was stirred at 90° C. for 22 h, then was cooled to RT and partitioned between EtOAc (10 mL) and H$_2$O (5 mL). The organic phase was washed with brine (20 mL), dried (MgSO$_4$) and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give Part C compound (14.5 mg; 47%).

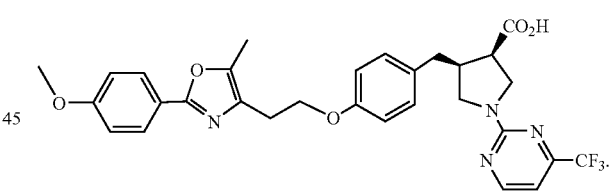

A solution of Part C compound (14.5 mg; 0.0238 mmol) in HOAc/concentrated HCl (1.2 mL of a 9:1 solution) was stirred at 75° C. for 18 h, then was cooled to RT and concentrated in vacuo. The residue was-purified by preparative HPLC (as described for Example 1 except that a continuous gradient from 30:70 Solvent A:Solvent B to 100% B over 10 min was used, followed by 4 min hold at 100% B) to give the title compound (7.3 mg; 53%) as a white solid.

[M+H]$^+$=583.2

EXAMPLES 265-267

Examples 265-267 of the invention were prepared in a similar fashion to Example 264 using appropriately substituted phenyl oxazole mesylates.

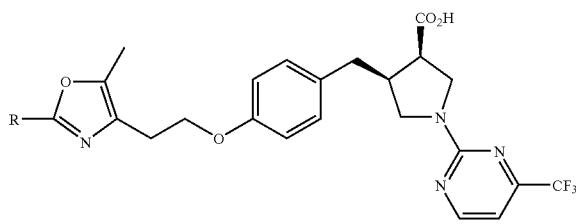

| Example # | R | [M + H]+ |
|---|---|---|
| 265 | 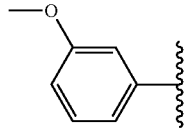 | 583.1 |
| 266 | 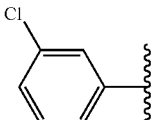 | 587.1 |
| 267 | 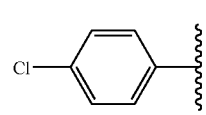 | 587.1 |

EXAMPLE 268

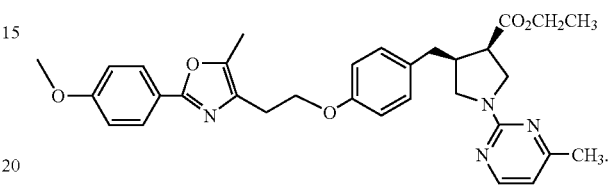

A mixture of Example 229 Part C compound (70 mg; 0.28 mmol)

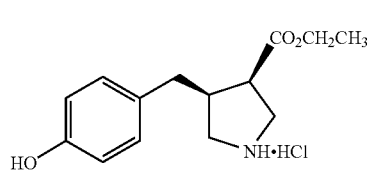

and 2-chloro-4-methyl-pyrimidine (36 mg; 0.28 mmol) and iPr₂NEt (97.5 μL; 0.56 mmol) in toluene (2.3 mL) was stirred at 80° C. for 2 h, then was cooled to RT and partitioned between EtOAc (15 mL) and aqueous 1 M HCl (10 mL). The organic phase was washed with H₂O (2×15 mL) and brine (20 mL), dried (MgSO₄) and concentrated in vacuo. The residue was chromatographed (SiO₂; continuous gradient from 90% hex to 100% EtOAc) to give Part A compound (82 mg; 86%) as a colorless oil.

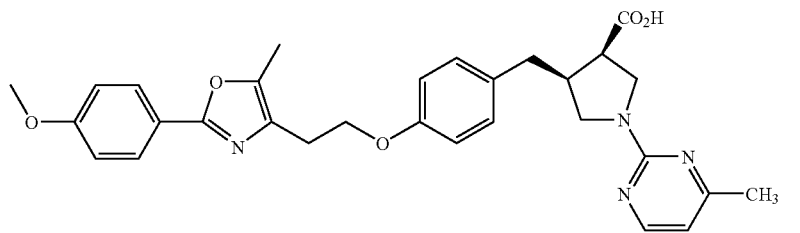

A mixture of Part A compound (15 mg; 0.044 mmol), Example 264 Part B compound (23.3 mg; 0.0748 mmol) and K₂CO₃ (10.9 mg; 0.0792 mmol) in CH₃CN (1.0 mL) was stirred at 90° C. for 30 h, then was cooled to RT and partitioned between EtOAc (10 mL) and H₂O (5 mL). The organic phase was washed with brine (20 mL), dried (MgSO₄) and concentrated in vacuo to give crude Part B compound, which was used in the next step without further purification.

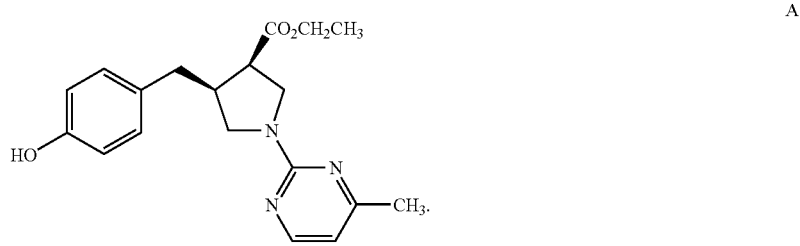

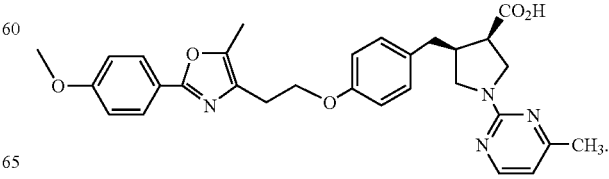

A solution of crude Part B compound in HOAc/concentrated HCl (1.0 mL of a 9:1 solution) was stirred at 75° C. for 18 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give the title compound (3.8 mg; 16% for 2 steps) as a white solid.

[M+H]$^+$=529.1

EXAMPLE 269-270

Example 269-270 of the invention were prepared in the same ways as Example 268 using appropriate mesylates (synthesized as for Example 264 Part B compound).

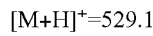

| Example # | R | [M + H]$^+$ |
|---|---|---|
| 269 | 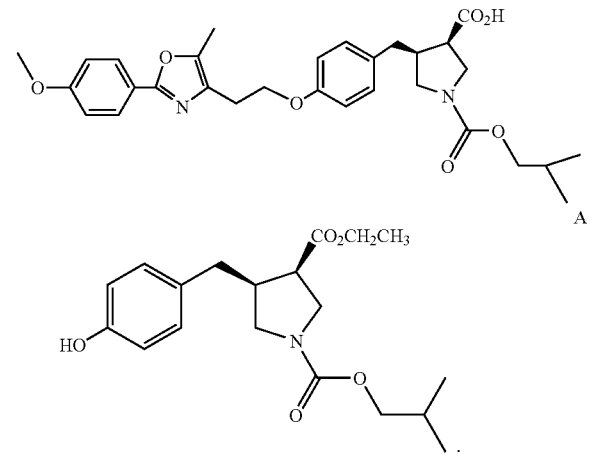 | 529.1 |
| 270 | | 533.1 |

EXAMPLE 271

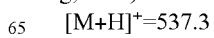

A mixture of Example 229 Part C compound (476 mg; 1.91 mmol),

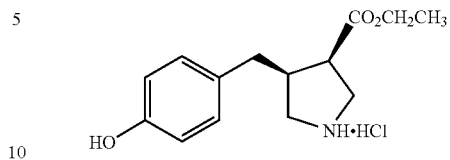

isobutyl chloroformate (248 μL; 1.91 mmol) and NaHCO$_3$ (241 mg; 2.87 mmol) in dioxane:H$_2$O (9.6 mL of a 2:1 solution) was stirred at RT for 3 h, then was partitioned between EtOAc (150 mL) and H$_2$O (100 mL). The organic phase was washed with brine (140 mL), dried (MgSO$_4$) and concentrated in vacuo. The residue was chromatographed (SiO$_2$; continuous gradient from 90% hex to 100% EtOAc) to give Part A compound (513 mg; 77%) as a colorless oil.

B

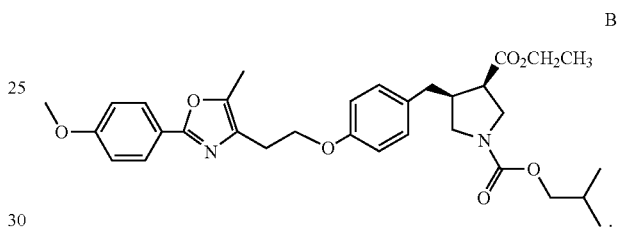

A mixture of Part A compound (20 mg; 0.057 mmol), Example 264 Part B compound (32 mg; 0.104 mmol) and K$_2$CO$_3$ (14.2 mg; 0.104 mmol) in CH$_3$CN (1.0 mL) was stirred at 90° C. for 30 h, then was cooled to RT and partitioned between EtOAc (10 mL) and H$_2$O (5 mL). The organic phase was washed with brine (20 mL), dried (MgSO$_4$) and concentrated in vacuo to give crude Part B compound, which was used in the next step without further purification.

C

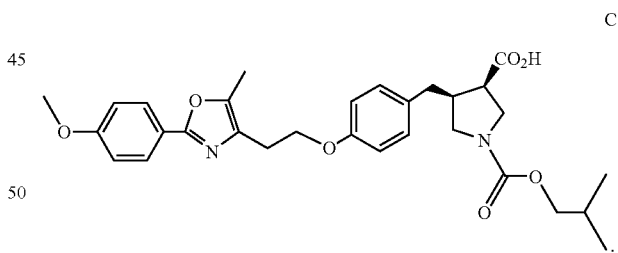

A solution of crude Part B compound in HOAc/concentrated HCl (1.0 mL of a 9:1 solution) was stirred at 75° C. for 18 h, then was cooled to RT and concentrated in vacuo. The residue was purified by preparative HPLC (as described for Example 1 except that a continuous gradient from 30:70 Solvent A:Solvent B to 100% B over 10 min was used, followed by 4 min hold at 100% B) to give two compounds. The compound with the shorter retention time was lyophilized from 1,4-dioxane to give the title compound (8.5 mg; 28%) as a white solid.

[M+H]$^+$=537.3

The second compound (longer retention time) was determined to be the corresponding epimerized transisomer of Example 271. This compound was also lyophilized from 1,4-dioxane to give Example 272 (5.8 mg; 19% for two steps) as a white solid.

EXAMPLE 272

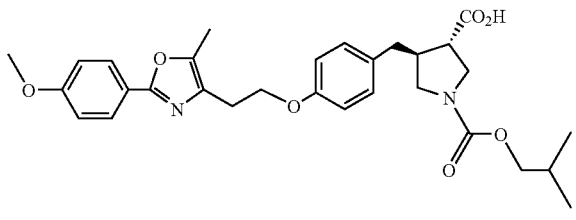

[M+H]⁺=537.2

EXAMPLE 273-274

Example 273 through 274 of the invention were prepared in a similar fashion to Example 272 using appropriately substituted phenyloxazole mesylates.

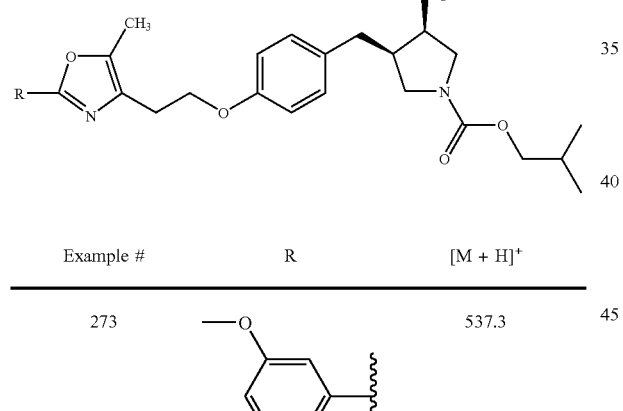

| Example # | R | [M + H]⁺ |
|---|---|---|
| 273 | 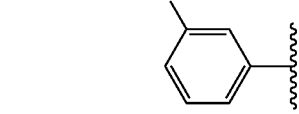 | 537.3 |
| 274 | 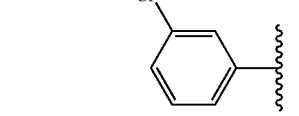 | 541.2 |

EXAMPLE 275-276

Example 275-276 of the invention were obtained in a similar fashion to Example 272. They were determined to be the corresponding epimerized trans-isomers of Examples 273-274.

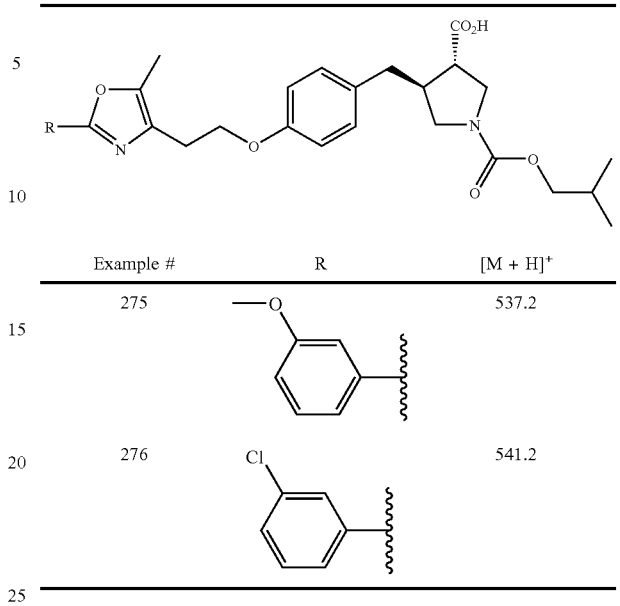

| Example # | R | [M + H]⁺ |
|---|---|---|
| 275 | 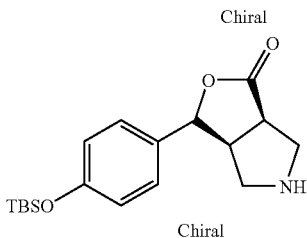 | 537.2 |
| 276 | | 541.2 |

EXAMPLE 277

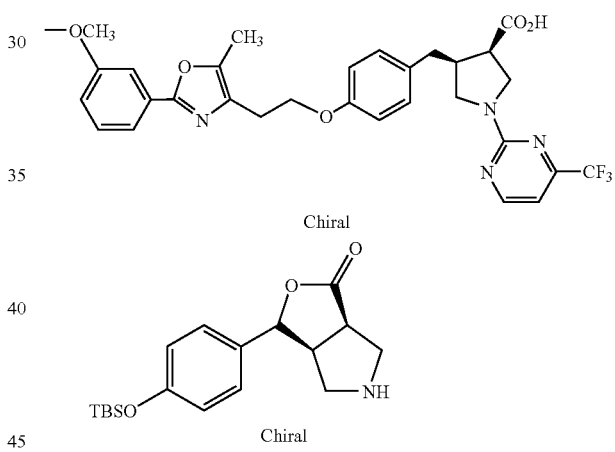

Example 184 Part D compound (200 mg; 0.46 mmol)

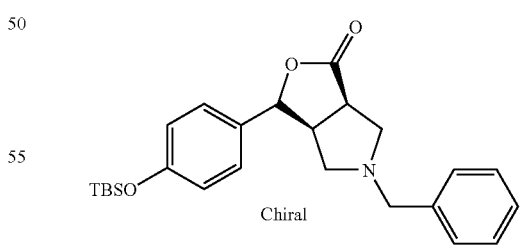

was stripped from from toluene (2×10 mL), dissolved in CH$_2$Cl$_2$ (10 mL), cooled to 0° C. and α-chloroethyl chloroformate (0.16 g, 1.2 mmol) was added. The solution was heated at 56° C. for 2 h, then cooled to RT and concentrated in vacuo. The residue was stripped from toluene, dissolved in MeOH (5 mL) and stirred for 2 h and concentrated in vacuo. The residue was chromatographed (SiO$_2$; 9:1

CH$_2$Cl$_n$:MeOH with 0.1% of NH$_4$OH) give Part A Compound as a clear oil (0.1 g; 66%)

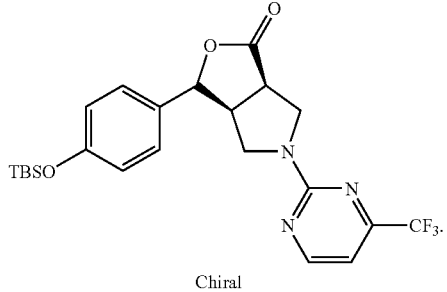

B

Chiral

To a solution of Part A Compound (0.1 , 0.3 mmol) in toluene (5 mL) was added 2-chloro-4-trifluoromethylpyrimidine (81 mg, 0.45 mmol) and iPr$_2$NEt (57 mg, 0.45 mmol). The solution was stirred for 5 h at 80° C., then cooled to RT and concentrated in vacuo. The residue was chromatographed (SiO$_2$; 4:1 EtOAc:hex) to give Part B compound as a clear oil (89 mg; 80%).

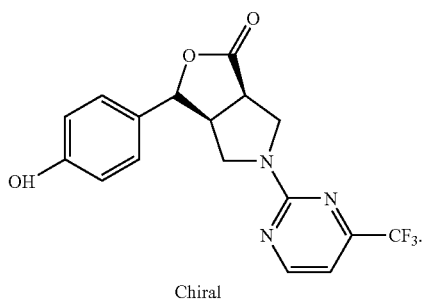

C

Chiral

A mixture of Part B compound (290 mg; 0.61 mmol) and tetrabutylammonium fluoride (1.22 mL of a 1 M solution in THF; 1.22 mmol) in THF (3.1 mL) was stirred at RT for 3 h, after which the reaction was partitioned between EtOAc (60 mL) and H$_2$O (30 mL). The organic phase was washed with brine (40 mL), dried (MgSO$_4$) and concentrated in vacuo. The residue was chromatographed (SiO$_2$; continuous gradient from 9:1 hex:EtOAc to 100% EtOAc) to give Part C compound (140 mg; 63%) as a colorless oil.

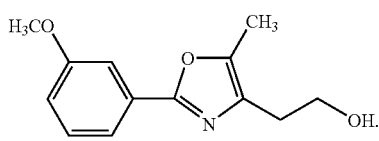

D

Part D compound was synthesized according to the general procedure described for the synthesis of Example 231 Part A compound except that 4-methoxybenzoyl chloride was used instead of 3-chlorobenzoyl chloride.

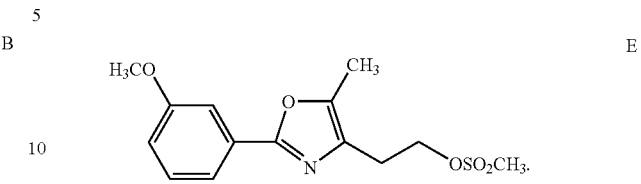

E

Part E compound was synthesized from Part D compound according to the general procedure described for the synthesis of Example 23 Part A compound.

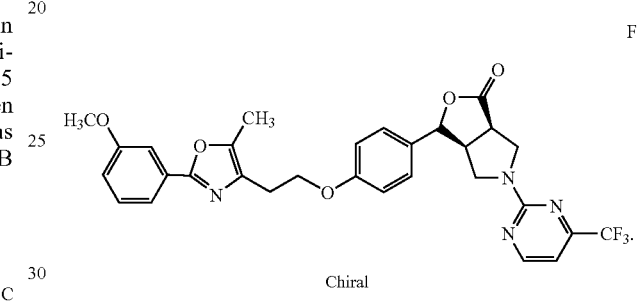

F

Chiral

A mixture of Part C compound (47 mg; 0.129 mmol), Part E compound (60 mg; 0.193 mmol) and K$_2$CO$_3$ (36 mg; 0.258 mmol) in CH$_3$CN (1.5 mL) was stirred at 90° C. for 18 h, then was cooled to RT and partitioned between EtOAc (10 mL) and H$_2$O (5 mL). The organic phase was washed with brine (20 mL), dried (MgSO$_4$) and concentrated in vacuo to give crude Part F compound, which was used in the next step without further purification.

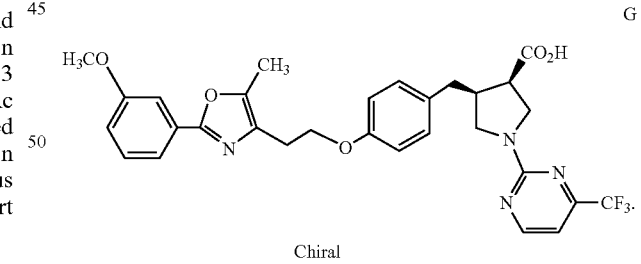

G

Chiral

A mixture of crude Part F compound and 10% Pd/C (8 mg) in MeOH (1.5 mL) was stirred under an atmosphere of H$_2$ (balloon) at RT for 18 h. The catalyst was filtered off (Celite®) and the filtrate was concentrated in vacuo; the residue was purified by preparative HPLC (as described for Example 1 except that a continuous gradient from 40:60 Solvent A:Solvent B to 100% B over 10 min was used, followed by 4 min-hold at 100% B) to give the title compound (3.0 mg; 4% for 2 steps) as a white solid. [M+H]$^+$=583.1

EXAMPLE 278

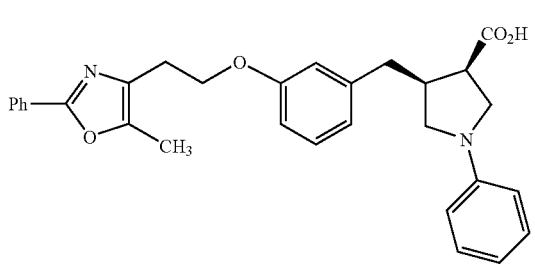

A mixture of Example 21 Part E compound (130 mg; 0.299 mmol), phenylboronic acid (50 mg; 0.41 mmol), Cu(OAc)$_2$ (5 mg; 0.027 mmol), 2,6 lutidine (0.5 mL) and molecular sieves (4 A) in toluene (2 mL) was stirred at RT for 24 h in air. At this point HPLC showed that product had been formed. The reaction mixture was filtered, and the filtrate was concentrated in vacuo. A solution of the residue in acetic acid/concentrated HCl (2 mL of a 3:1 solution) was stirred at 70° C. for 18 h. Volatiles were removed in vacuo and the residue was purified by preparative HPLC (as described for Example 1) to provide the title compound (28 mg; 19.4%) as an oil.

[M+H]$^+$=483.1, $[\alpha]_{CH2Cl2}^{589nm}$=−18.3° (c=1.0; 25° C.)

$^1$HNMR (CDCl$_3$): δ 8.03-8.01 (2H, dd, J=1.8 Hz), 7.56-7.48 (3H, m), 7.37-7.33 (2H, t, J=7.4 Hz), 7.26-7.24 (2H, m), 7.17-7.13 (2H, m), 6.71-6.75 (3H, m), 4.27-4.18 (2H, m), 4.11-4.06 (1H, m), 3.79-3.76 (1H, dd, J=4.4 Hz), 3.62-3.58 (1H, m), 3.47-3.42 (1H, t, J=10 Hz), 3.38-3.33 (1H, m), 3.14-3.07 (3H, m), 2.97-2.92 (1H, dd, J=6.1 Hz), 2.67-2.61 (1H, dd, J=4.8 Hz), 2.46 (3H, s)

EXAMPLE 279

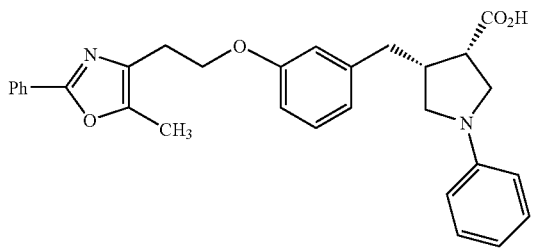

The titled compound (41 mg; 28.4%) was prepared from Example 21 Part E compound (using the same sequence as the synthesis of Example previous compound).

[M+H]+=483.1 $[\alpha]_{CH2Cl2}^{589nm}$=20°, (c=1.0; 25° C.)

$^1$HNMR (CDCl$_3$): δ 8.03-8.00 (2H, dd, J=1.8 Hz), 7.56-7.48 (3H, m), 7.37-7.33 (2H, t, J=7.4 Hz), 7.26-7.24 (2H, m), 7.17-7.13 (2H, m), 6.71-6.75 (3H, m), 4.27-4.18 (2H, m), 4.11-4.06 (1H, m), 3.79-3.76 (1H, dd, J=4.4 Hz), 3.62-3.58 (1H, m), 3.47-3.42 (1H, t, J=10 Hz), 3.38-3.34 (1H, m), 3.14-3.04 (3H, m), 2.98-2.93 (1H, dd, J=6.1 Hz), 2.62-2.56 (1H, dd, J=4.8 Hz), 2.44(3H, S)

EXAMPLE 280

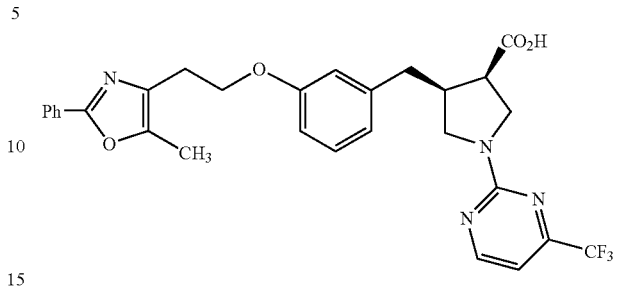

A mixture of Example 21 Part E compound (50 mg; 0.115 mmol), 2-Chloro-4-(trifluoromethyl)-pyrimidine (21 mg; 0.115 mmol), Et$_3$N (50 mg; 0.5 mmol) in toluene (3 mL) was stirred at 50° C. for 1 h in air. The reaction mixture was concentrated in vacuo. A solution of the residue in acetic acid/concentrated HCl (2 mL of a 3:1 solution) and stirred at 80° C. for 18 h. Volatiles were removed in vacuo and the residue was purified by preparative HPLC (as described for Example 1) to provide the title compound (60 mg; 90%) as a white solid.

[M+H]$^+$=553.3, $[\alpha]_{CH2Cl2}^{589nm}$=−37.7°; (c=1.25; 25° C.)

$^1$HNMR (CDCl$_3$): δ 8.55 (1H, s), 8.01-7.99 (2H, d, J=8 Hz), 7.53-7.46 (3H, m), 7.12-7.21 (1H, m), 6.84-6.69 (4H, m), 4.17-4.27 (2H, t, J=8 Hz), 3.98-4.08 (1H, m), 3.50-3.80 (3H, m), 3.18-3.30 (1H, m), 3.03-3.13 (2H, t, J=8 Hz), 2.77-2.96 (2H, m), 2.57-2.67 (1H, m), 2.44 (3H, s)

EXAMPLE 281

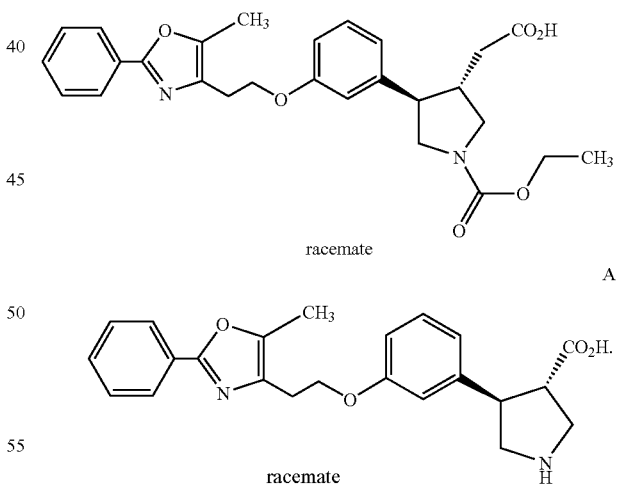

A mixture of Example 12 Part C compound (550 mg; 0.92 mmol) and 10% Pd/C (30 mg) in MeOH (10 mL) under an atmosphere of H$_2$ was stirred at RT for 2 h. At this point analytical HPLC showed that the reaction was complete. The catalyst was filtered off (using a pad of Celite®) and the filtrate was concentrated in vacuo to give crude Part A compound as an oil which was used in the next reaction without further purification.

B

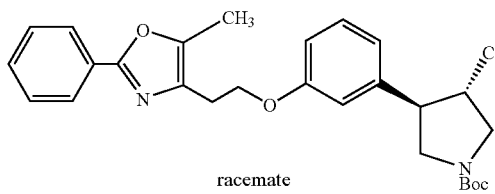

racemate

A mixture of crude Part A compound and di-tert butyl dicarbonate (300 mg; 1.3 mmol) in saturated aqueous NaHCO$_3$ (5 mL) and THF (5 mL) was stirred at RT for 2 h, then was partitioned between EtOAc and H$_2$O (20 mL each). The organic phase was concentrated in vacuo and the residue was purified by preparative HPLC (as described for Example 1) to give the title compound (237 mg; 52% for 2 steps) as an oil.

C

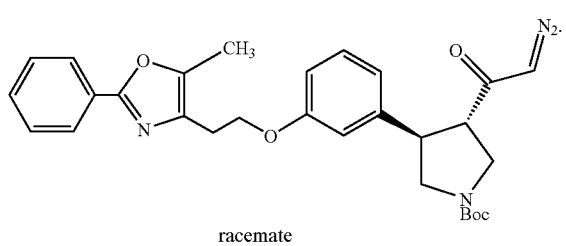

racemate

Step 1. Preparation of Diazomethane:

To a solution of aqueous KOH (40%; 2 mL) and diethyl ether (5 mL) was added 1-Methyl-3-nitro-1-nitrosoguanidine (176 mg; 1.2 mmol) slowly at 0° C. and the reaction was stirred at 0° C. for a further 30 min. The aqueous phase was removed and the top yellow organic phase containing diazomethane was dried with solid KOH (1 g) at 0° C. and was used for the next step without further purification.

Step 2. Preparation of Diazoketone:

To a solution of Part B compound (237 mg; 0.48 mmol) in THF (10 mL) and N-methylmorpholine (61 mg; 0.6 mmol) was cooled to −20° C. and added isobutyl chloroformate (82 mg; 0.6 mmol) over 5 min. The reaction was stirred at −20° C. for a further 30 min and then was added to the solution of CH$_2$N$_2$ (from Step 1) at 0° C. After stirring at 0° C. for 30 min, the reaction was stirred at RT for another 3 h, then was concentrated in vacuo; the residue was chromatographed (SiO$_2$; 3:1 Hex:EtOAc) to give Part C compound (150 mg; 60%) as an oil.

D

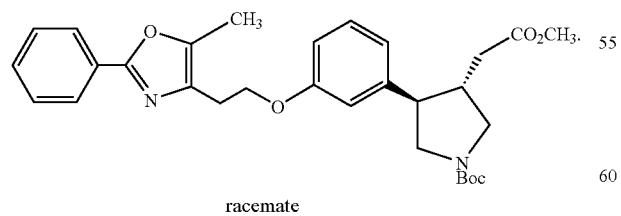

racemate

To a solution of Part C compound (150 mg; 0.29 mmol) in anhydrous MeOH (1 mL) was added a solution of silver benzoate (15 mg; 0.065 mmol) in Et$_3$N (0.7 mL) and the reaction was stirred at RT for 30 min, after which EtOAc (10 mL) was added. The solution was washed with 1N aqueous HCl (5 mL) and H$_2$O (5 mL×2), dried (Na$_2$SO$_4$) and concentrated in vacuo. The residue was chromatographed (SiO$_2$; 3:1 Hex:EtOAc) to give Part D compound (78 mg; 31%) as an oil.

E

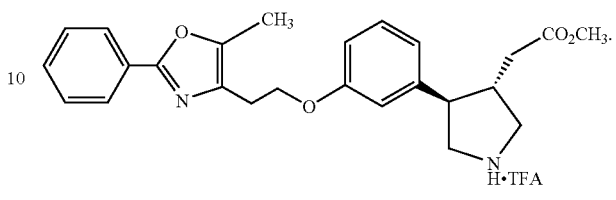

racemate

A solution of Part D compound (78 mg; 0.15 mmol) and TFA (1 mL) in CH$_2$Cl$_2$ (1 mL) was stirred at RT for 30 min. Volatiles were removed in vacuo and the residue was purified by preparative HPLC (as described for example 1) to give Part E compound (80 mg; 99%).

F

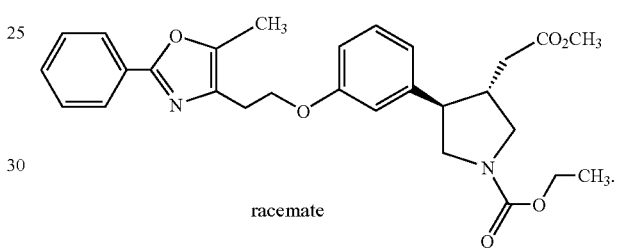

racemate

To a 0° C. solution of Part E compound (10 mg; 0.018 mmol) and DMAP (12 mg; 0.1 mmol) in CH$_2$Cl$_2$ (1 mL) was added dropwise ethyl chloroformate (4 μL; 0.032 mmol). The reaction mixture was allowed to warm to RT and stirred at RT for 3 h. At this point HPLC indicated that all starting material had been consumed. The solid was filtered through SiO$_2$ with Hex:EtOAc (3:1)and the filtrate was concentrated in vacuo to give the Cartg (SiO$_2$; Hex:EtOAc 3:1) to provide crude Part F compound as an oil.

G

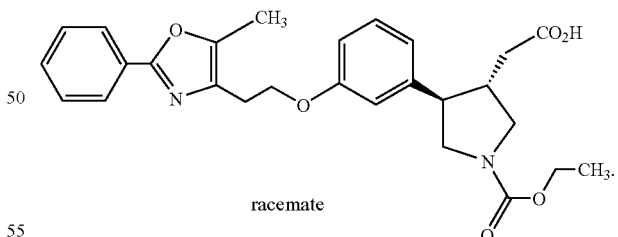

racemate

A solution of Part F compound in aqueous LiOH (1 mL of a 1 M solution) and THF (1 mL) was stirred at RT for 2 h; TLC indicated that the reaction was complete at this point. The reaction mixture was acidified with aqueous HCl (2 mL of a 1 M solution) and extracted with EtOAc (2×2 mL). The organic phase was washed with H$_2$O (2×2 mL) and concentrated in vacuo. The residue was purified by preparative HPLC (as described for Example 1) to provide the title compound (7.4 mg; 85.9%) as an oil.

[M+H]$^+$479.2

EXAMPLES 282-288

Examples 282 through 288 were prepared in a similar fashion to the previous Example using the appropriate chloroformates.

| Example # | R | [H + H]+ |
|---|---|---|
| 282 | (but-3-enyl) | 491.3 |
| 283 | (propyl) | 493.3 |
| 284 | (butyl) | 507.3 |
| 285 | (phenyl) | 527.2 |
| 286 | (4-fluorophenyl) | 545.2 |
| 287 | (4-methoxyphenyl) | 557.2 |
| 288 | (benzyl) | 541.2 |

EXAMPLE 289

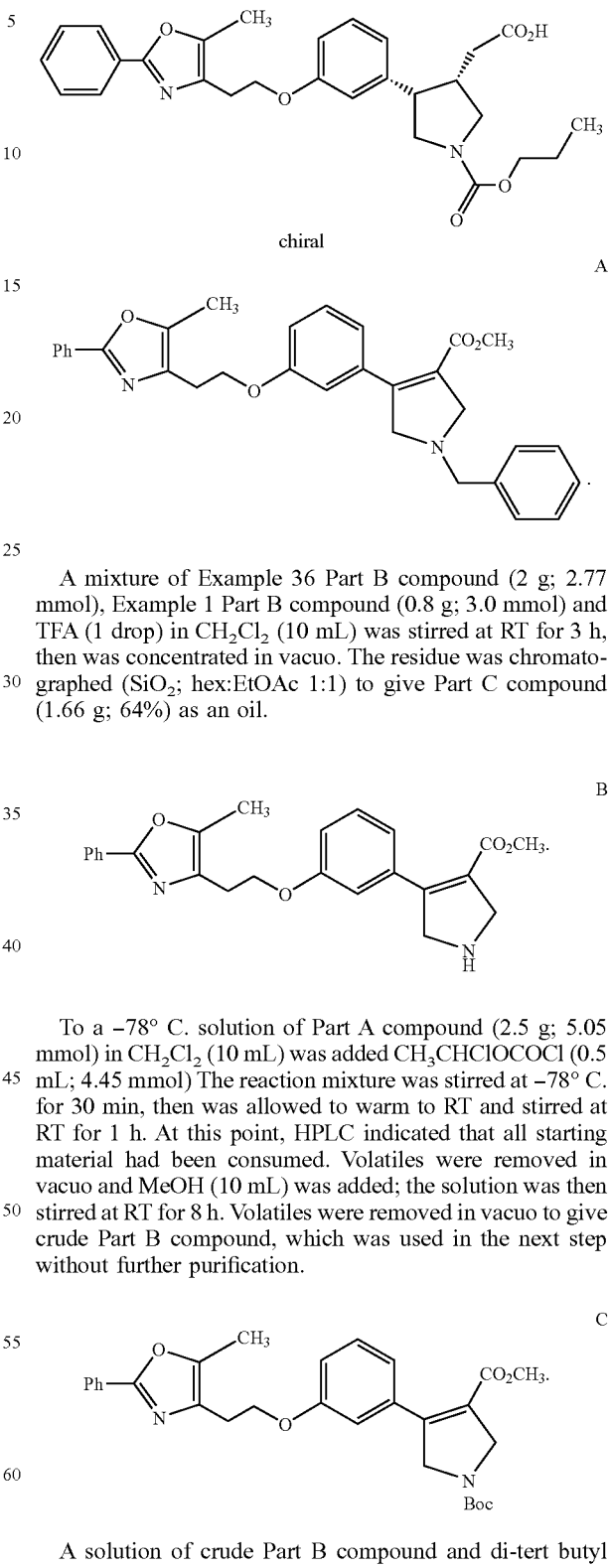

A mixture of Example 36 Part B compound (2 g; 2.77 mmol), Example 1 Part B compound (0.8 g; 3.0 mmol) and TFA (1 drop) in CH$_2$Cl$_2$ (10 mL) was stirred at RT for 3 h, then was concentrated in vacuo. The residue was chromatographed (SiO$_2$; hex:EtOAc 1:1) to give Part C compound (1.66 g; 64%) as an oil.

To a −78° C. solution of Part A compound (2.5 g; 5.05 mmol) in CH$_2$Cl$_2$ (10 mL) was added CH$_3$CHClOCOCl (0.5 mL; 4.45 mmol) The reaction mixture was stirred at −78° C. for 30 min, then was allowed to warm to RT and stirred at RT for 1 h. At this point, HPLC indicated that all starting material had been consumed. Volatiles were removed in vacuo and MeOH (10 mL) was added; the solution was then stirred at RT for 8 h. Volatiles were removed in vacuo to give crude Part B compound, which was used in the next step without further purification.

A solution of crude Part B compound and di-tert butyl dicarbonate (800 mg; 3.66 mmol) in saturated aqueous NaHCO$_3$ (10 mL) and THF (10 mL) was stirred at RT for 2 h, then was partitioned between EtOAc and H$_2$O (20 mL). The organic phase was concentrated in vacuo and the residue was chromatographed (SiO$_2$; Hex:EtOAc 3:1) to give Part C compound (2.1 g; 82% for two steps) as an oil.

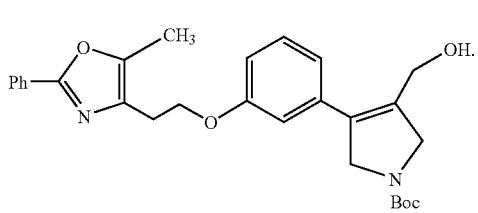

D

To a −70° C. solution of Part C compound (373 mg; 0.74 mmol) in anhydrous THF (3 mL) was added DIBALH (1.5 mL of a 1 M solution in hexane; 1.5 mmol) dropwise. The reaction was stirred at −70° C. for 20 min, then was warmed to RT and stirred at RT for 2 h, then re-cooled to −70° C. and quenched by dropwise addition of MeOH (1 mL). The mixture was allowed to warm to RT, aqueous Rochelle salt (10 mL of a 1 M solution) was added and stirring was continued for 1 h. The mixture was partitioned between H$_2$O and Et$_2$O (20 mL each). The aqueous phase was extracted with additional Et$_2$O (20 mL); the combined organic extracts were dried (Na$_2$SO$_4$) and concentrated in vacuo to give crude Part D compound, which was used in the next step without further purification.

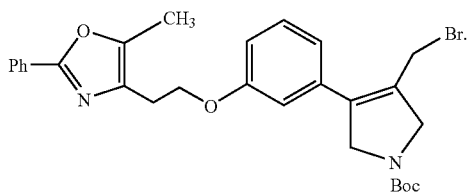

E

To a 0° C. solution of crude Part C compound and Ph$_3$P (232 mg; 0.89 mmol) in CH$_2$Cl$_2$ (1 mL) was added CBr$_4$ (294 mg; 0.89 mmol) potionwise. The reaction was allowed to warm to RT and stirred at RT for 2 h, then was concentrated in vacuo. The residue was chromatographed (SiO$_2$; hex:EtOAc 3:1) to give Part E compound (270 mg; 68% for two steps) as an oil.

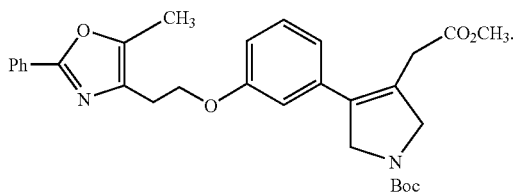

F

A mixture of Part E compound (270 mg; 0.5 mmol), (Ph$_3$P)$_4$Pd° (58 mg; 0.05 mmol) and KHCO$_3$ (200 mg; 2.0 mmol) in anhydrous MeOH (5 mL) in an autoclave was pressurized to 100 psi with carbon monoxide (vessel flushed 3× with CO). The reaction mixture was stirred at RT for 3 h, after which the CO gas was released and the mixture was filtered. The filtrate was concentrated in vacuo and the residue was chromatographed (SiO$_2$; 3:1 hex:EtOAc) to give Part F compound (150 mg; 56%) as an oil.

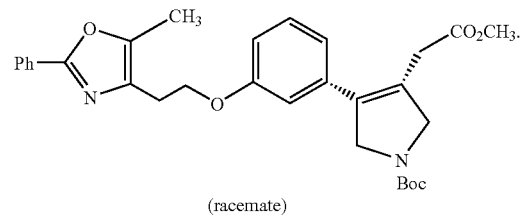

G (racemate)

A suspension of Part F compound (150 mg; 0.29 mmol) and 10% Pd/C (10 mg) in MeOH (5 mL) was stirred at RT under an atmosphere of H$_2$ (balloon) for 2 h. The catalyst was filtered off (Celite®) and the filtrate was concentrated in vacuo to give the Part G compound (147 mg; 56% for 2 steps) as an oil.

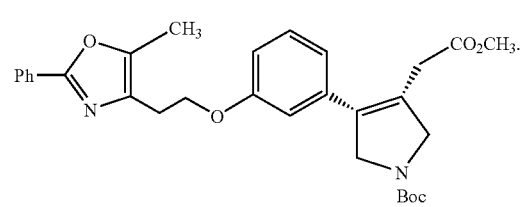

H (enantiomer #1; arbitrary absolute configuration)

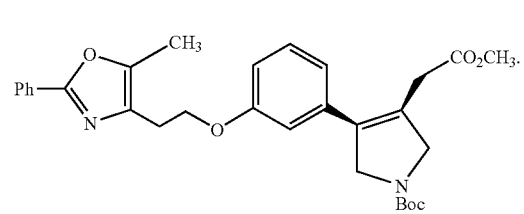

I (enantiomer #2; arbitrary absolute configuration)

The two enantiomers of racemic Part G compound (147 mg; 0.283 mmol) were separated by preparative HPLC using the following conditions: ChiralPAK@AS 5 cm×50 cm chiral column: flow rate=40 mL/min; isocratic conditions=93:7 isopropanol:hexane. Chiral analytical HPLC (Daicel Chiralcel AS 4.6×250 mm column): flow rate=1.5 mL/min; isocratic conditions =80:20 hexane:iPrOH; detector wavelength=220 nm.

Part G compound (Enantiomer I) was obtained (60 mg; 81.6%; retention time=4.64 min; ee>95%) as an oil.

Part H compound (Enantiomer II) was obtained (55 mg; 74.8%; retention time=6.29 min; ee>90%) as an oil.

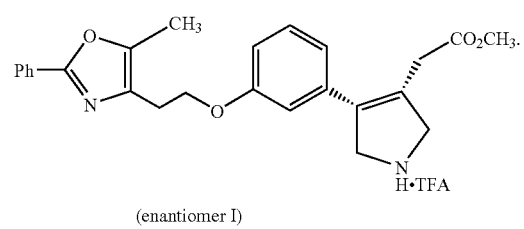

J (enantiomer I)

A solution of Part H compound (enantiomer I; 60 mg; 0.115 mmol) in TFA (0.5 mL) and CH$_2$Cl$_2$ (0.5 mL) was stirred at RT for 2.5 h, then was concentrated in vacuo to give crude Part J compound as an oil, which was used in the next step without further purification.

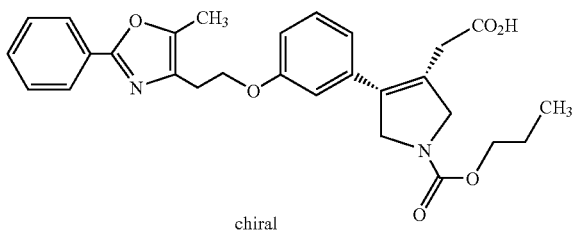

chiral

A mixture of crude Part J compound (0.038 mmol), DMAP (30 mg; 0.3 mmol) and n-propyl chloroformate (36 mg; 0.3 mmol) in $CH_2Cl_2$ (1 mL) was stirred at RT for 1 h, then was loaded onto a $SiO_2$ cartridge and flushed with EtOAc/Hexane (1:3) to give crude Part K compound.

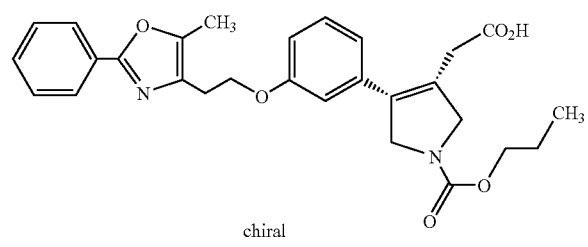

chiral

A solution of Part K compound in aqueous LiOH (1 mL of a 1 M solution) and THF (1 mL) was stirred at RT for 2 h; TLC indicated that the reaction was complete at this point. The reaction mixture was acidified with aqueous HCl (2 mL of a 1 M solution) and extracted with EtOAc (2 mL). The organic phase was washed with $H_2O$ (2×2 mL) and concentrated in vacuo. The residue was purified by preparative HPLC (as described for Example 1) to provide the title compound (28 mg; 95%) as an oil.

$[M+H]^+$=493.2, $[\alpha]_{CH2Cl2}^{589nm}$=25.5; (c=0.65; 25° C.)

$^1$HNMR (CDCl$_3$): δ 8.02-8.0 (2H, dd, J=8 Hz), 7.6-7.46 (3H, m), 7.23-7.19 (1H, t, J=12 Hz), 6.78-6.65 (3H, m), 4.3-4.07 (4H, m), 3.85-3.52 (4H, m), 3.20-3.1 (1H, m), 3.09-3.01(2H, t, J=6.2 Hz), 2.98-2.89 (1H, m), 2.44 (3H, s), 2.20-2.11 (1H, m), 1.96-1.85 (1H, m), 1.74-1.62 (2H, m), 0.97-0.95 (3H, m)

EXAMPLES 290-292

Example 290 was prepared from Example 289 Part J compound in the same way as Example 289 but using isobutyl chloroformate. Examples 2-3 were prepared from Example 289 Part I compound using the identical sequence as for the synthesis of Example 289 from Example 289 Part H compound, using n-propyl and isobutyl chloroformate respectively.

| Example # | Structure | [α] 589 nm in $CH_2Cl_2$ | $[M + H]^+$ |
|---|---|---|---|
| 290 | cis enantiomer #1 | 28.2 (c = 0.95) | 507.3 |
| 291 | cis enantiomer #2 | −21.3 (c = 0.95) | 493.3 |

| Example # | Structure | [α] 589 nm in CH$_2$Cl$_2$ | [M + H]$^+$ |
|---|---|---|---|
| 292 | *cis enantiomer #2* | −28.5 (c = 0.8) | 507.3 |

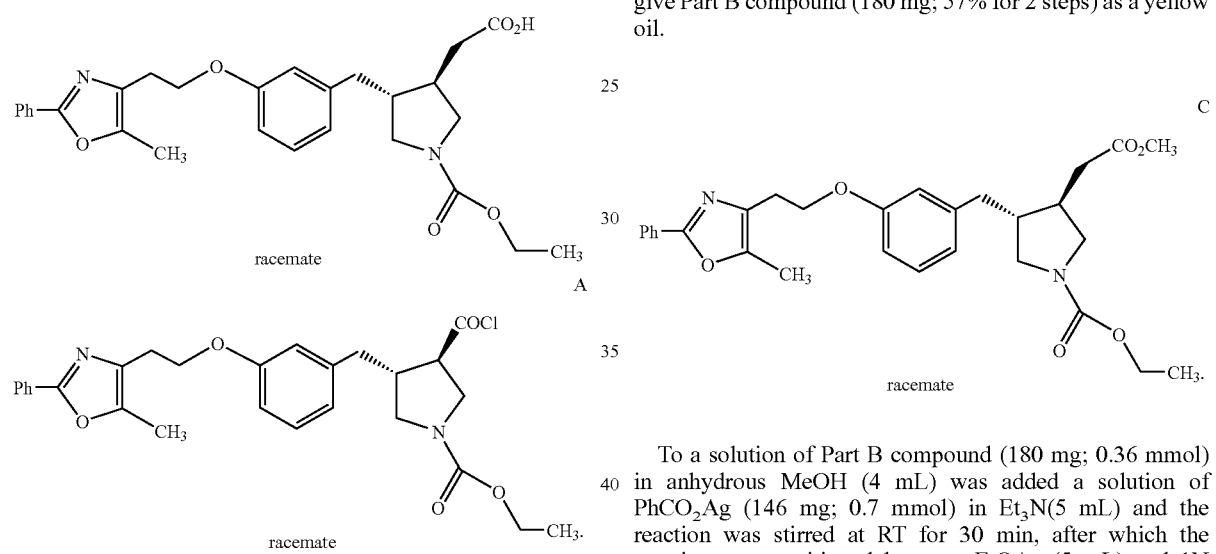

EXAMPLE 293

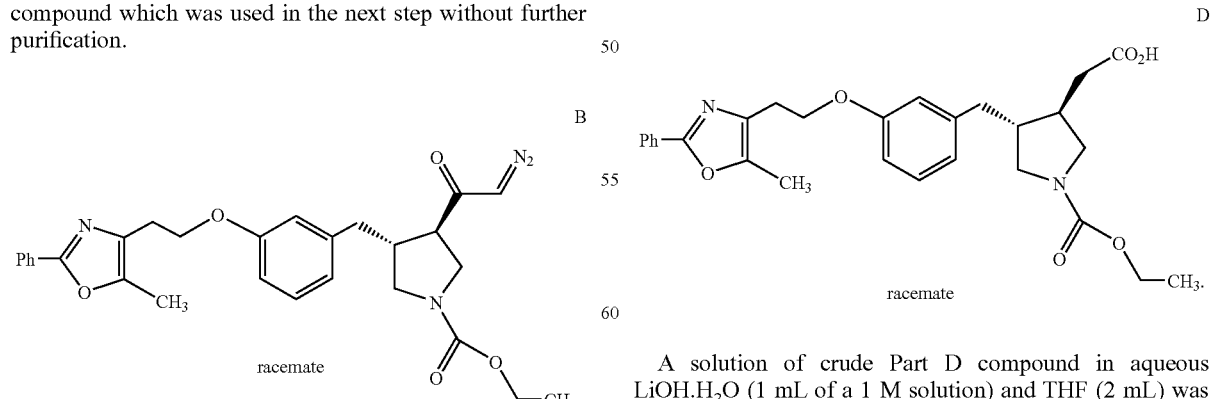

A mixture of Example 2 Part B compound (250 mg; 0.522 mmol), phosgene (5 mL of a 1M solution in CH$_2$Cl$_2$) and catalytic DMF was stirred at 60° C. in a sealed tube for 18 h, then was concentrated in vacuo to give crude Part A compound which was used in the next step without further purification.

To a 0° C. solution of Part A compound in CH$_2$Cl$_2$ (2 mL) was added diazomethane (prepared as for Example 281 Part C). The reaction was stirred at 0° C. for 30 min, then at RT for another 3 h. Volatiles were removed in vacuo and the residue was chromatographed. (SiO$_2$; Hex:EtOAc=3:1) to give Part B compound (180 mg; 57% for 2 steps) as a yellow oil.

To a solution of Part B compound (180 mg; 0.36 mmol) in anhydrous MeOH (4 mL) was added a solution of PhCO$_2$Ag (146 mg; 0.7 mmol) in Et$_3$N(5 mL) and the reaction was stirred at RT for 30 min, after which the reaction was partitioned between EtOAc (5 mL) and 1N aqueous HCl (5 mL×1). The organic phase was washed with H$_2$O (5 mL×2), dried (Na$_2$SO$_4$) and concentrated in vacuo to give crude Part C compound.

A solution of crude Part D compound in aqueous LiOH.H$_2$O (1 mL of a 1 M solution) and THF (2 mL) was stirred at RT for 3 h; TLC indicated that the reaction was complete at this point. The reaction mixture was acidified with aqueous HCl (2 mL of a 1 M solution) and extracted with EtOAc (2 mL). The organic phase was washed with H₂O (2×2 mL) and concentrated in vacuo. The residue was purified by preparative HPLC (as described for Example 1) to provide the title compound (160 mg; 90% for two steps) as an oil.

[M+H]⁺=493.2

¹HNMR (CDCl₃): δ 8.03-8.0 (2H, m), 7.56-7.51 (3H, m), 7.19-7.15 (1H, m), 6.76-6.70 (3H, m), 4.24-4.21 (2H, m), 4.12-4.07 (2H, q, J=7.0 Hz), 3.83-3.74 (1H, m), 3.53-3.41 (1H, m), 3.13-3.01 (4H, m), 2.83-2.77 (1H, m), 2.55-2.43 (2H, m), 2.40 (3H, s), 2.34-2.13 (3H, m), 1.27-1.19 (3H, m)

EXAMPLE 294

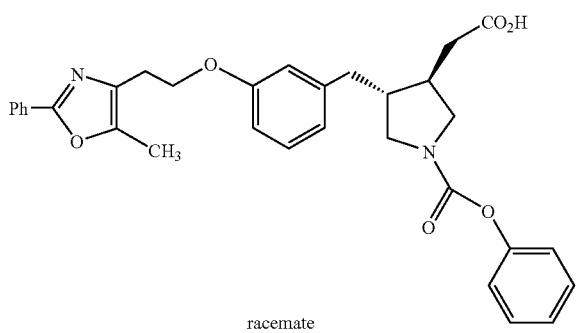

racemate

The title compound (16 mg; 32%) was prepared from Example 3 compound (using the same sequence as for the synthesis of Example 293 except that phenyl chloroformate was used instead of ethyl chloroformate).

[M+H]⁺=541.3

¹HNMR (CDCl₃): δ 8.03-8.00 (2H, m), 7.56-7.49 (3H, m), 7.33-7.28 (2H, m), 7.19-7.15 (2H, m), 7.08-7.05 (2H, m), 6.75-6.71 (3H, m), 4,25-4.23 (2H, t, J=5 Hz), 3.98-3.85 (1H, m), 3.70-3.58 (1H, m), 3.31-3.13 (2H, m), 3.11-3.09 (2H, t, J=5 Hz), 2.86-2.80 (1H, m), 2.61-2.57 (2H, m), 2.48 (3H, s), 2.34-2.13 (3H, m)

EXAMPLE 295

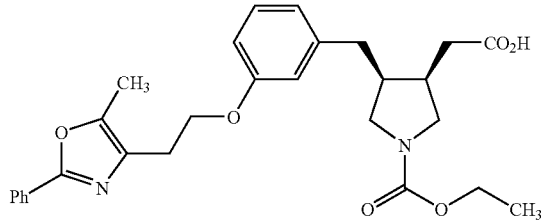

The title (15 mg; 42% yield overall for 3 steps) was prepared from Example 22 compound by the same sequence as for the synthesis of Example 293.

[M+H]⁺=493.2; [α]$_{CH2Cl2}^{589nm}$=−16.1° (c=0.6; 25° C.)

¹HNMR (CDCl₃): δ 8.03-8.02 (2H, m), 7.56-7.51 (3H, m), 7.19-7.15 (1H, m), 6.76-6.70 (3H, m), 4,25-4.22 (2H, t, J =5.72 Hz), 4.13-4.08 (2H, m), 3.57-3.53 (1H, m), 3.33-3.09 (6H, m), 2.75-2.07 (8H, m), 1.25-1.22 (3H, m)

EXAMPLE 296

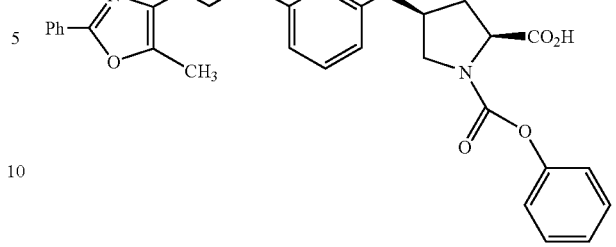

racemic cis

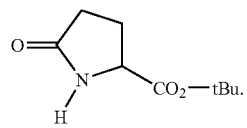

A

A solution of DL-pyroglutamic acid (5 g; 0.039 mol, HClO₄ (1.25 mL of a 70% solution) in tert-butyl acetate (60 mL) was stirred at RT for 18 h, then was poured into saturated aqueous NaHCO₃ (100 mL) and ice. The mixture was extracted with EtOAc (20 mL×3). The combined organic extracts were dried (Na₂SO₄) and concentrated in vacuo to give Part A compound as white crystals (4.36 g; 60.3%).

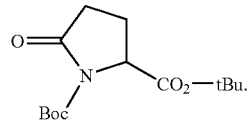

B

A mixture of Part A compound (4.36 g; 23.5 mmol); di-tert-butyl dicarbonate (10.7 g; 50 mmol) and DMAP (6.1 g; 50 mmol) in MeCN (20 mL) was stirred at RT for 18 h. Volatiles were removed in vacuo and the residue was chromatographed (SiO₂; Hex:EtOAc 1:1) to give part B compound (6.6 g; 98.4%) as an oil.

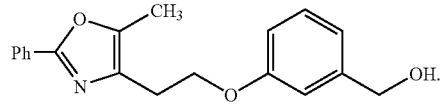

C

A mixture of 3-hydroxybenzyl alcohol(2 gm; 16 mmol), the mesylate Example 23 Part A compound (2.0 g; 7.11 mmol)

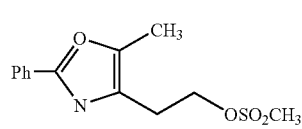

and K₂CO₃ (5.0 g; 36 mmol) in MeCN (100 mL) was stirred at 80° C. for 10 h. At this point LC/MS showed that the reaction was complete. The reaction was cooled to RT, solids were filtered off, and the filtrate was partitioned between EtOAc (100 mL) and aqueous 1 M HCl (10 mL). The organic phase was successively washed with 1 M NaOH (10 mL) and H₂O (50 mL)., dried (Na₂SO₄) and concentrated in vacuo. The residue was chromatographed (SiO₂; 2:1 Hex: EtOAc) to give Part C compound (2.15 g; 98%) as white crystals.

D

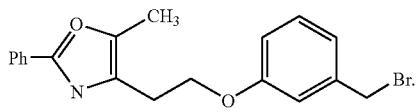

A mixture of Part C compound (2.15 g; 6.95 mmol), PBr₃ (10 mL of a 1 M solution in CH₂Cl₂) in CH₂Cl₂ (5 mL) was stirred at RT for 0.5 h. Volatiles were removed in vacuo. The residue was chromatographed (SiO₂; Hex:EtOAc 3:1) to give part D compound (2.0 g; 75%) as white crystals.

E

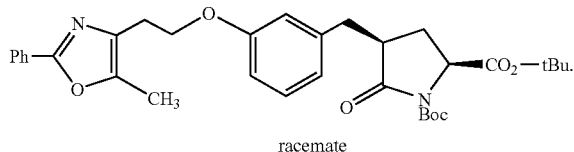
racemate

To a −74° C. solution of Part B compound (200 mg; 0.7 mmol) in THF (5 mL) was added LiN(TMS)₂ (1.2 mL of a 1 M solution in THF) dropwise. The reaction was stirred at −74° C. for 40 min, after which a solution of Part D compound (200 mg; 0.54 mmol) in THF (5 mL) was added dropwise at −60° C. The reaction mixture was stirred at −60° C. for 2 h, then was quenched by dropwise addition of saturated aqueous NH₄Cl (1 mL). The mixture was allowed to warm to RT, then extracted with EtOAc (2×10 mL). The combined organic extracts were washed with water, dried (Na₂SO₄), concentrated in vacuo and the crude residue was chromatographed (SiO2; Hex:EtAc 3:1) to give both the desired cis isomer (27 mg; 6.5%) Part E compound as well as the trans isomer Part F compound (8.7 mg; 2.4%) as oils.

Part F compound:

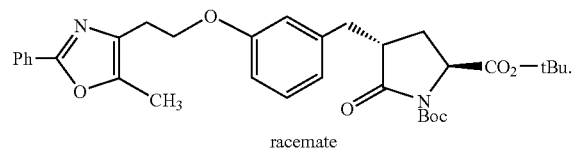
racemate

Part G compound:

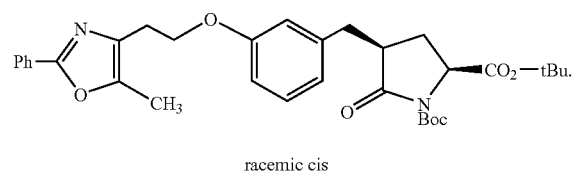
racemic cis

To a −74° C. solution of Part E compound (cis isomer; 27 mg; 0.047 mmol) in THF (5 mL) under N₂ was added LiEt₃BH (0.06 mL of a 1 M solution in THF). The reaction was stirred at −74° C. for 30 min, then was quenched by dropwise addition of saturated aqueous NaHCO₃ (1 mL) and one drop of H₂O₂. The mixture was allowed to warm to RT, then extracted with EtOAc (2×10 mL). The combined organic extracts were washed with water, dried (Na₂SO₄) and concentrated in vacuo. To a −74° C. solution of the crude product and Et₃SiH (7.5 μL; ; 1M solution in THF; 0.06 mmol) in CH₂Cl₂ (5 mL) was added BF₃.OEt₂ (7.6 μL; 0.06 mmol). The reaction was stirred at −74° C. for 30 min, after which more Et₃SiH (7.5 μL) and BF₃—OEt₂ (7.6 μL) was added. The reaction was warmed to RT and stirred at RT for another 30 min, after which it was quenched by dropwise addition of saturated aqueous NaHCO₃ (1 mL), then extracted with CH₂Cl₂ (2×10 mL). The combined organic extracts were dried with Na₂SO₄ and concentrated in vacuo. The residue was chromatographed (SiO₂; Hex:EtAc 2:1) to provide Part G compound (23 mg, 80%).

H

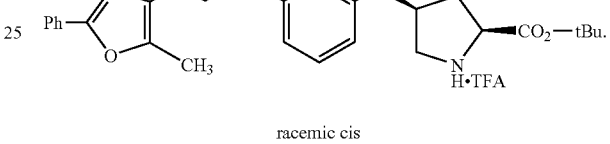
racemic cis

A solution of Part H compound and TFA (1 mL) in CH₂Cl₂ (1 mL) was stirred at RT for 1 h, after which volatiles were removed in vacuo to give crude Part H compound (15 mg; 79%), which was used in the next step without further purification.

I

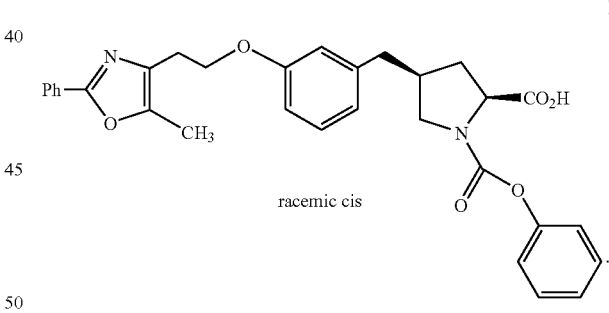
racemic cis

A solution of crude Part I compound, saturated aqueous NaHCO₃ (2 mL) and phenyl chloroformate (50 μL; 0.36 mmol) in THF (2 mL) was stirred at RT for 30 min, then was partitioned between EtOAc and H₂O (10 mL each). The organic phase was dried (MgSO₄) and concentrated in vacuo. The residue was purified by preparative HPLC (as described for Example 1) to provide the title compound (19 mg; 76.7%) as an oil.

[M+H]+=527.3

¹HNMR (CDCl₃): δ 7.98-7.94 (2H, m), 7.49-7.10 (9H, m), 6.75-6.68 (3H, m), 4.54-4.20 (3H, m), 3.88-3.74 (1H, m), 3.57-3.42 (1H, m), 3.02-2.99 (2H, t, J=5 Hz), 2.83-2.74 (2H, m), 2.58-2.50 (1H, m), 2.40-2.33 (4H, m), 2.02-1.92 (1H, m)

EXAMPLE 297

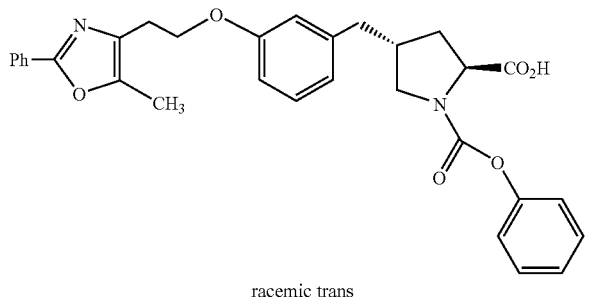

racemic trans

This trans isomer (6.6 mg; 83.5%) was prepared from Part F compound (using the same sequence as for the synthesis of previous Cis isomer).
[M+H]+=527.3
¹HNMR (CDCl₃): δ 8.03-7.98 (2H, m), 7.56-7.47 (3H, m), 7.35-7.27 (2H, m), 7.22-7.05 (4H, m), 6.75-6.69 (3H, m), 4.61-4.49 (1H, m), 4.23-4.20 (2H, t, J=8.0 Hz), 3.79-3.70 (1H, m), 3.29-3.20 (1H, m), 3.09-3.06 (2H, t, J=8 Hz), 2.78-2.60 (3H, m), 2.45 (3H, s), 2.40-1.92 (2H, m)

EXAMPLE 298

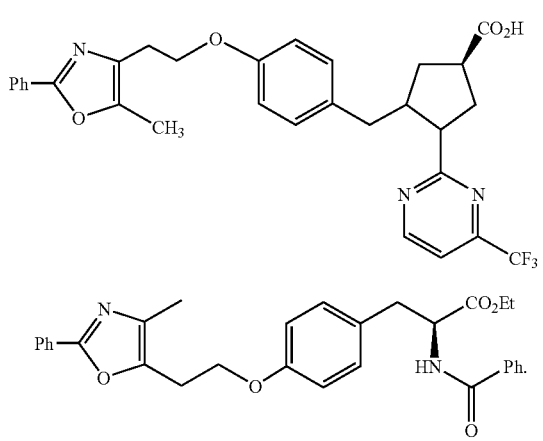

A mixture of N-benzoyl-L-tyrosine ethyl ester (1.0 g; 3.19 mmol), 5-phenyl-2-methyl-oxazole-4-ethanol (650 mg; 3.19 mmol) and cyanomethylene-tri-n-butylphosphorane (1.15 g; 4.79 mmol) in toluene (10 mL) was stirred at 70° C. for 3 h, then was concentrated in vacuo. The residue was chromatographed (SiO₂; Hex:EtAc 2:1) to provide Part A compound (1.28 g; 81%) as yellowish crystals.

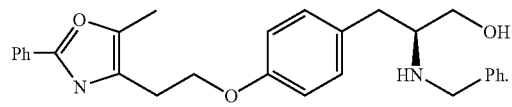

A solution of Part A compound (500 mg; 1.0 mmol), LiAlH₄ (2 mL of a 1 M solution in THF) in THF was stirred at 50° C. for 1 h, then MeOH (1 mL) was added slowly, follow by aqueous Rochelle salt (5 mL of a 1 M solution). The mixture was stirred at RT for 18 h and filtered. The filtrate was diluted with Et₂O (20 mL) and washed with H₂O (3×30 mL), dried (MgSO₄) and concentrated in vacuo to give Part B compound (394 mg; 89%) as white solid.

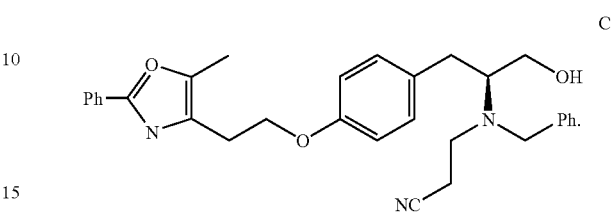

A solution of Part B compound (300 mg; 0.68 mmol), acrylonitrile (4.3 mL) and HOAc (41 µL) in EtOH (5 mL) was stirred at 75° C. for 30 h, then was cooled to RT and partitioned between EtOAc (20 mL) and aqueous NaOH (10 mL of a 1 M solution). The organic phase was washed with H₂O (2×30 mL), dried (MgSO₄) and concentrated in vacuo. The crude residue was chromatographed (SiO₂; 2:1 Hex: EtOAc) to give Part C compound (180 mg; 89%) as an oil.

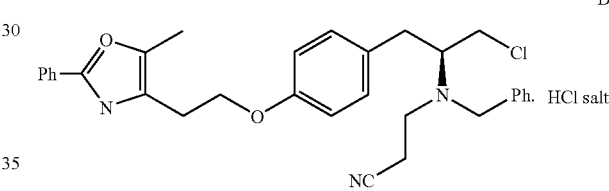

A mixture of Part C compound (182 mg; 0.367 mmol) and SOCl₂ (0.25 mL; 3.4 mmol) in CHCl₃ (5 mL) was heated at reflux for 30 min, then was cooled to RT. 100 mL Et₂O was added and the mixture was filtered; the recovered solids were dried in vacuo to give Part D compound (200 mg; 99%) as white solid.

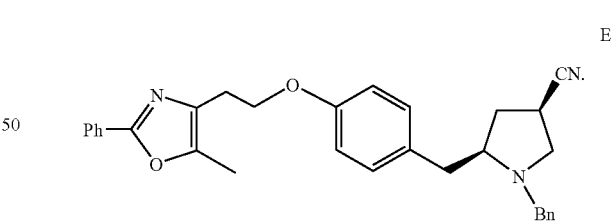

To a RT solution of Part D compound (200 mg; 0.36 mmol) in THF (5 mL) under N₂ was added dropwise NaN(TMS)₂ in THF (0.80 mL of a 1 M solution; 0.80 mmol). The reaction was stirred at RT for 1 h, then was quenched by addition of saturated aqueous NH₄Cl (1 mL). The mixture was extracted with EtOAc (10 mL). The organic phase was washed with water (2×10 mL), dried (Na₂SO₄) and concentrated in vacuo. The crude residue was chromatographed (SiO₂; 2:1 Hex:EtOAc) to give Part E compound (21 mg; 24%) as an oil in addition to the trans isomer Part F compound (21 mg; 24%)

Part F compound:

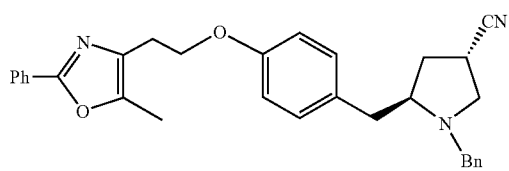

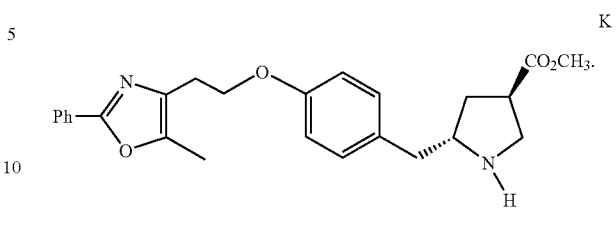

A mixture of Part E compound (21 mg; 0.044 mmol) in H$_2$SO$_4$—MeOH (10%; 2 mL) was stirred at 80° C. for 72 h, then was cooled to RT, the mixture was partitioned between EtOAc and H$_2$O (10 mL each). The organic phase was washed with H$_2$O (2×10 mL), dried (Na$_2$SO$_4$) and concentrated in vacuo. The crude residue was chromatographed (SiO$_2$; 1:1 Hex:EtOAc) to give Part G compound (20 mg; 89%) as an oil.

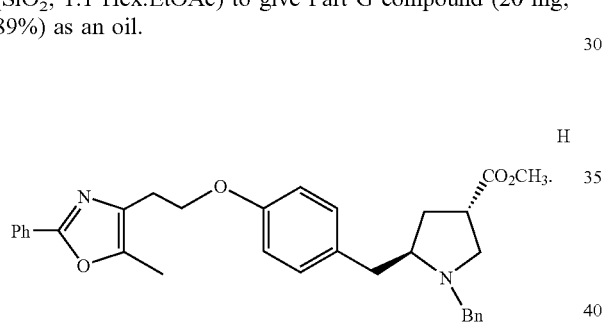

Part H compound (20 mg; 89%) was prepared from Part F compound (using the same procedure as the preparation of Part G compound from Part E compound) as an oil.

Part I compound (18-mg; 80%) and Part J compound (19 mg; 82%) were both prepared from N-benzoyl-D-tyrosine ethyl ester (using exactly the same sequence as the synthesis of Part G compound and Part H compound).

Part I compound:

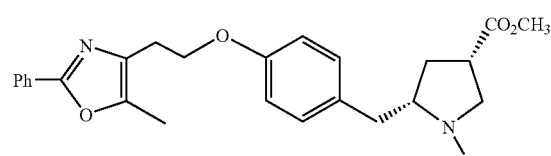

Part J compound:

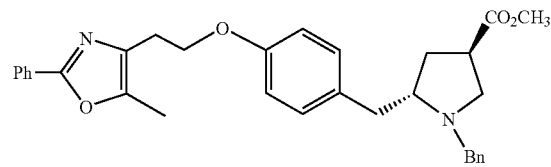

A solution of Part G compound (20 mg; 0.039 mmol) and CH$_3$CHClOCOCl (5 μL; 0.05 mmol) in CH$_2$Cl$_2$ (2 mL) was stirred at RT for 18 h. Volatiles were removed in vacuo and MeOH (2 mL) was added; the solution was then stirred at RT for 8 h. Volatiles were removed in vacuo and the residue was purified by preparative HPLC (YMC reverse-phase ODS 30×250 mm column; flow rate=25 mL/min; 30 min continuous gradient from 30:70 B:A to 100% B+10 min hold-time at 100% B, where solvent A=90:10:0.1H$_2$O:MeOH: TFA and solvent B=90:10:0.1 MeOH:H$_2$O:TFA) to provide Part K compound (16 mg; 80%) as a TFA salt.

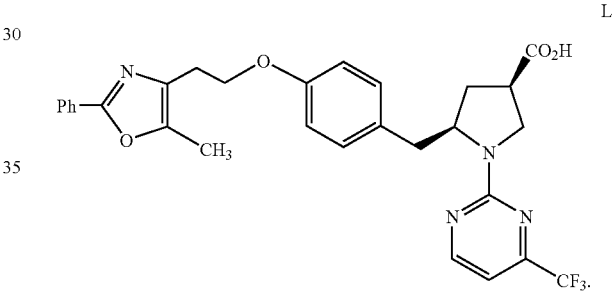

A mixture of Part K compound (16 mg; 0.038 mmol), 2-Chloro-4-(trifluoromethyl)-pyrimidine (10 mg; 0.04 mmol) and Et$_3$N (25 mg; 0.25 mmol) in toluene (2 mL) was stirred at 60° C. for 2 h, then was cooled to RT and concentrated in vacuo. A solution of the residue in HOAc/concentrated HCl (5 mL of a 3:1 solution) was stirred at 75° C. for 18 h. Volatiles were removed in vacuo and the residue was purified by preparative HPLC (as described for Example 1) to provide the title compound (5.4 mg; 30%) as a white solid.

[M+H]+=553.2

$^1$HNMR (CDCl$_3$): δ 8.50-8.49 (1H, d, J=4 Hz), 7.91-7.90 (2H, m), 7.40-7.30 (3H, m), 7.09-7.07 (2H, d, J=8 Hz), 6.78-6.73 (3H, m), 4.28 (1H, s, broad), 4.15-4.13 (2H, t, J=4 Hz), 4.00 (1H, s, br), 3.85 (1H, s, br), 3.28-3.26 (1H, d, J=8 Hz), 3.07-3.05 (1H, m), 2.98-2.92 (2H, t, J=4 Hz), 2.45 (1H, s, br), 2.32 (3H, s), 2.24-2.16 (2H, m)

Chiral analytical HPLC (Daicel Chiralcel AD 4.6×250 mm column): flow rate=1 mL/min; isocratic conditions=100:7 A:B, where A=heptane+0.1% TFA; B IPA+ 0.1% TFA; detector wavelength=220 nm; retention time=23 min; ee>90%

EXAMPLE 299

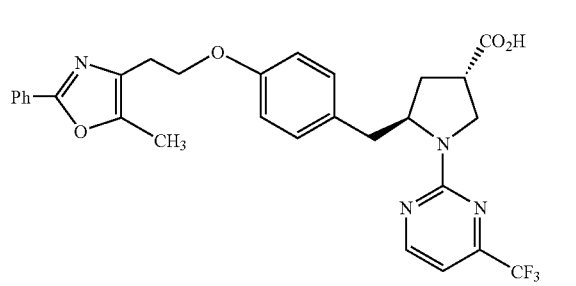

A

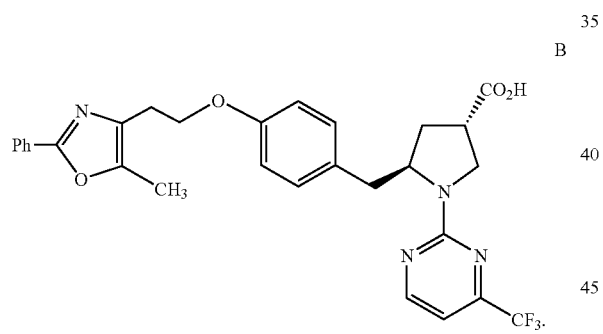

Part A compound was prepared from Example 298 Part H compound in exactly the same way as Example 298 Part K compound was prepared from Example 298 Part G compound.

B

The title compound (6.9 mg; 42% overall for 3 steps) was prepared from Part A compound in exactly the same way as Example 298 compound was prepared from Example 298 Part K compound.

[M+H]$^+$=553.3

$^1$HNMR (CDCl$_3$): δ 8.61-8.60 (1H, d, J=4 Hz), 8.03-8.01 (2H, d, J=8 Hz), 7.60-7.50 (3H, m), 7.12-7.10 (2H, d, J =8 Hz), 6.88-6.87 (1H, m), 6.82-6.81 (2H, d, J=8 Hz) 4.50 (1H, s, broad), 4.15-4.13 (2H, t, J=4.8 Hz), 3.82-3.81 (2H, d, J=7.0 Hz), 3.13-3.10 (4H, m), 2.61 (1H, s, broad), 2.48 (3H, s), 2.18-2.16 (2H, m)

Chiral analytical HPLC (Daicel Chiralcel OD 4.6×500 mm column): flow rate=1 mL/min; isocratic conditions=93:7 A:B, where A=heptane+0.1% TFA; B IPA+0.1% TFA; detector wavelength=220 nm; retention time=32 min; ee >90%

EXAMPLE 300

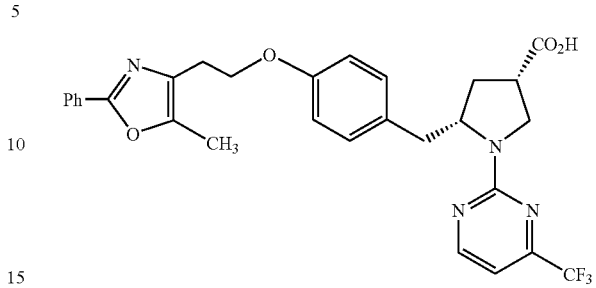

A

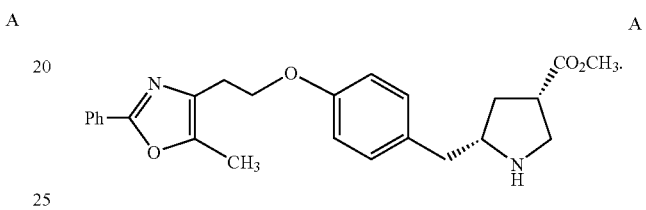

Part A compound was prepared from Example 298 Part I compound according to the method used to prepare Example 298 Part K compound from Example 298 Part G compound.

B

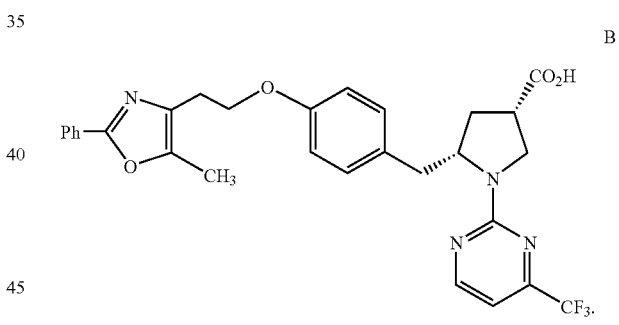

The title compound (11.7 mg; 66% overall for 3 steps) was prepared from Part A compound (using the same sequence as for the synthesis of Example 299 compound).

[M+H]$^+$=553.3

$^1$HNMR (CDCl$_3$): δ 8.57-8.56 (1H, d, J=4 Hz), 7.99-7.97 (2H, m), 7.44-7.38 (3H, m), 7.16-7.15. (2H, d, J=8 Hz), 6.83-6.82 (3H, m), 4.35 (1H, s, broad), 4.23-4.20 (2H, t, J=8 Hz), 4.07 (1H, s, broad), 3.94 (1H, s, broad), 3.36-3.33 (1H, d, J=8 Hz), 3.18-3.11 (1H, m), 3.02-3.00 (2H, m), 2.50 (1H, s, broad), 2.39 (3H, s), 2.30-2.20 (2H, m)

Chiral analytical HPLC (Daicel Chiralcel AD 4.6×250 mm column): flow rate=1 mL/min; isocratic conditions 90:10 A:B, where A=heptane+0.1% TFA; B IPA+0.1% TFA; detector wavelength=220 nm; retention time=13.45 min; ee>90%

EXAMPLE 301

A.

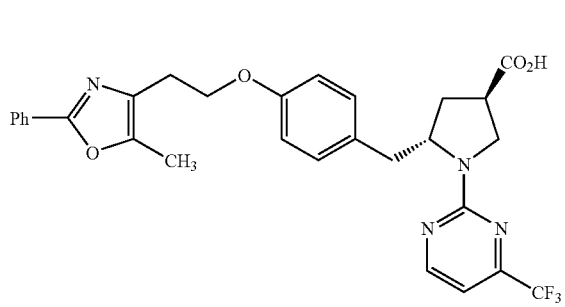

Part A compound was prepared from Example 298 Part J compound according to the method used to prepare Example 298 Part K compound from Example 298 Part G compound.

B.

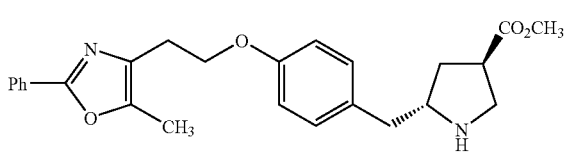

The title compound (4.4 mg; 50% overall for 3 steps) was prepared from Part A compound (using the same sequence as for the synthesis of Example 299).

[M+H]$^+$=553.3

$^1$HNMR (CDCl$_3$): δ 8.61-8.60 (1H, d, J=4 Hz), 8.03-8.01 (2H, d, J=8 Hz), 7.58-7.50 (3H, m), 7.12-7.10 (2H, d, J =8 Hz), 6.88-6.87 (1H, m), 6.83-6.81 (2H, d, J=8 Hz) 4.50 (1H, s, broad), 4.23-4.21 (2H, t, J=4.8 Hz), 3.82-3.81 (2H, d, J=7.0 Hz), 3.13-3.10 (4H, m), 2.61 (1H, s, broad), 2.47 (3H, s), 2.18-2.16 (2H, m)

Chiral analytical HPLC (Daicel Chiralcel OD 4.6×500 mm column): flow rate=1 mL/min; isocratic conditions=93:7 A:B, where A=heptane+0.1% TFA; B IPA+0.1% TFA; detector wavelength=220 nm; retention time=39 min; ee >90%

EXAMPLE 302

A.

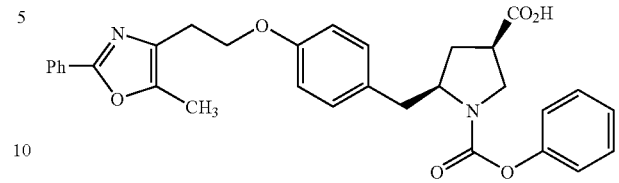

A suspension of Example 298 Part G compound (34 mg; 0.066 mmol) and Pd-Black (20 mg) in HCO$_2$H—MeOH (3 mL of a 9:1 solution) was stirred at RT for 1 h. The catalyst was filtered off and the filtrate was partitioned between EtOAc (5 mL) and aqueous NaOH (2 mL of a 1 M solution). The organic phase was washed with water, dried, (Na$_2$SO$_4$) and concentrated in vacuo to give Part A compound (27 mg; 97.2%) as an oil which was used in the next step without further purification.

B.

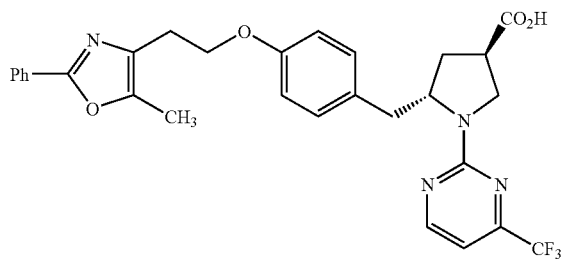

A mixture of Part A compound (18 mg; 0.042 mmol), DMAP (12 mg; 0.1 mmol) and phenyl chloroformate (15 μL; 0.12 mmol) in CH$_2$Cl$_2$ (1 mL) was stirred at RT for 2 h, then was partitioned between aqueous 1 N HCl and EtOAc. The organic phase was washed with H$_2$O and brine, dried (MgSO$_4$) and concentrated in vacuo. A mixture of the residual crude carbamate-ester in HOAc/concentrated HCl (5 mL of a 4:1 solution) was stirred at 80° C. for 18 h, then was cooled to RT and concentrated in vacuo. The mixture was partitioned between EtOAc and H$_2$O (5 mL each). The organic phase was concentrated in vacuo and the residue was purified by preparative HPLC (as described for Example 1) to give the title compound (11.6 mg; 71%) as a white solid.

[M+H]$^+$=527.1

$^1$HNMR (CDCl$_3$): δ 7.99-7.97 (2H, m), 7.47-7.43 (3H, m) 7.40-7.3 (2H, m), 7.25-7.10 (5H, m), 6.82-6.80 (2H, d, J=8 Hz), 4.50-4.10 (3H, m), 4.05-3.90 (1H, m), 3.75-3.63 (1H, m), 3.29-3.19 (1H, m), 3.18-3.01 (3H, m), 2.74-2.50 (1H, m), 2.40 (3H, s), 2.26-2.10 (2H, m)

Chiral analytical HPLC (Daicel Chiralcel OD 10 um 4.6×250 mm column): flow rate=1.0 mL/min; isocratic conditions=85:15 A:B, where A=hexane with 0.1% TFA; B=isopropanol with 0.1% TEA; detector wavelength=220 nm; retention time=12.39 min; ee>90%

EXAMPLE 303

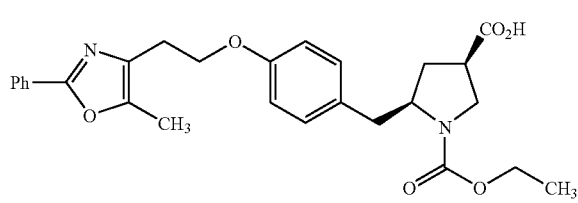

The title compound (12 mg; 78%) was prepared from Example 302 Part A compound (using the same sequence as for the synthesis of Example 302 except that ethyl chloroformate was used instead of phenyl chloroformate).

[M+H]⁺=479.2

¹HNMR (CDCl₃): δ 7.99-7.97 (2H, d, J=8 Hz), 7.52-7.45 (3H, m), 7.06 (2H, s), 6.80-6.78 (2H, d, J=8 Hz), 4.21-4.14 (4H, m), 4.01-3.79 (2H, m), 3.52-3.47 (1H, t, J=8 Hz), 3.32-2.85 (4H, m), 2.56-2.47 (1H, m), 2.42 (3H, s), 2.23-1.89 (2H, m), 1.30-1.27 (3H, t, J=8 Hz)

Chiral analytical HPLC (Daicel Chiralcel AD 10 um 4.6×250 mm column): flow rate=1.0 mL/min; isocratic conditions=90:10 A:B, where A=hexane with 0.1% TFA; B =isopropanol with 0.1% TFA; detector wavelength=220 nm; retention time=20.43 min; ee>90%

EXAMPLE 304

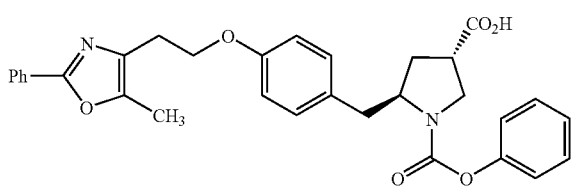

The title Compound (15.6 mg; 70%) was prepared from Example 299 Part A compound using the same sequence as for the synthesis of Example 302 from Example 302 Part A compound.

[M+H]⁺=527.1

¹HNMR (CDCl₃): δ 7.98-7.97 (2H, d, J=8 Hz), 7.45-7.29 (5H, m), 7.23-7.02 (5H, m), 6.85-6.82 (2H, d, J=8 Hz), 4.45-4.20 (3H, m), 3.82-3.56 (2H, m), 3.08-2.85 (4H, m), 2.62-2.80 (1H, m), 2.37 (3H, s), 2.13-2.03 (2H, m)

Chiral analytical HPLC (Daicel Chiralcel OD 10 um 4.6×250 mm column): flow rate=1.0 mL/min; isocratic conditions=85:15 A:B, where A=hexane with 0.1% TFA; B=isopropanol with 0.1% TFA; detector wavelength=220 nm; retention time=18.18 min; ee>90%

EXAMPLE 305

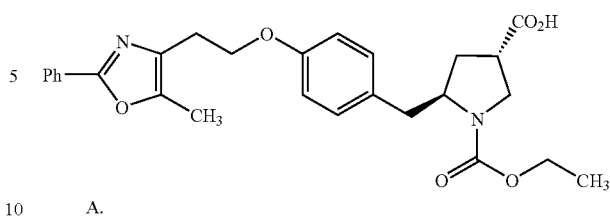

A.

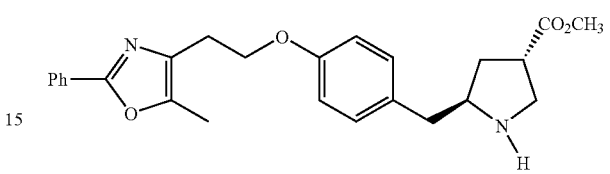

Part A compound (37 mg; 90%) was prepared from Example 298 Part H compound by the same procedure as the synthesis of Example 302 Part A compound from Example 298 Part G compound.

B.

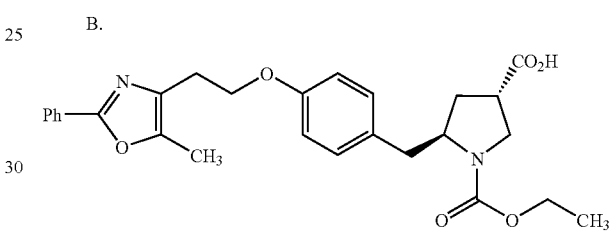

The title compound (16 mg; 79%) was prepared according to the same procedure as the synthesis of Example 303 from Example 302 Part A compound.

[M+H]⁺=479.2

¹HNMR (CDCl₃): δ 8.00-7.97 (2H, m), 7.50-7.45 (3H, m), 7.05 (2H, s), 6.81-6.79 (2H, d, J=8 Hz), 4.21-4.11 (5H, m), 3.65-3.48 (2H, m), 3.06-2.51 (5H, m), 2.42 (3H, s), 2.08-1.95 (2H, m), 1.29-1.26 (3H, t, J=4 Hz)

Chiral analytical HPLC (Daicel Chiralcel AD 10 um 4.6×250 mm column): flow rate=1.0 mL/min; isocratic conditions=90:10 A: B, where A=hex with 0.1% TFA; B=IPA with 0.1% TFA; detector wavelength=220 nm; retention time=27.23 min; ee>90%

EXAMPLE 306

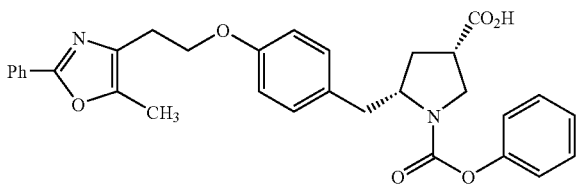

A.

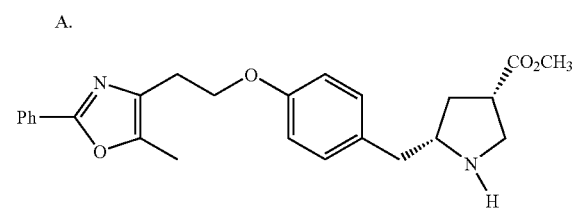

Part A compound (39 mg; 97%) was prepared from Example 298 Part I compound by the same procedure as Example Part A compound.

B.

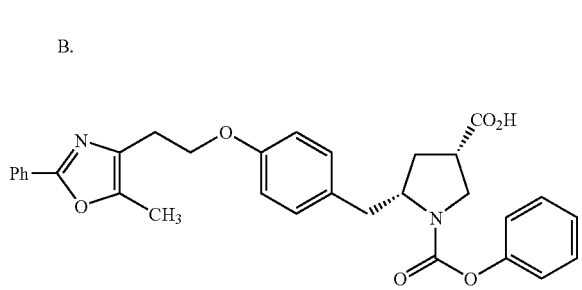

The title compound was prepared (12 mg; 47%) was prepared from Part A compound using the same procedure as for the synthesis of Example 302 from Example 302 Part A compound.

[M+H]$^+$=527.1

$^1$HNMR (CDCl$_3$): δ 7.99-7.97 (2H, m), 7.52-7.43 (3H, m), 7.40-7.30 (2H, m), 7.23-7.00 (5H, m), 6.87-6.72 (2H, d, J=8 Hz), 4.50-4.10 (3H, m), 4.05-3.90 (1H, m), 3.75-3.63 (1H, m), 3.29-3.19 (1H, m), 3.18-3.01 (3H, m), 2.74-2.50 (1H, m), 2.40 (3H, s), 2.26-2.10 (2H, m)

Chiral analytical HPLC (Daicel Chiralcel OD 10 um 4.6×250 mm column): flow rate=1.0 mL/min; isocratic conditions=85:15 A:B, where A=hexane with 0.1% TFA; B=iPrOH with 0.1% TFA; detector wavelength=220 nm; retention time=17.3 min; ee>90%

EXAMPLE 307

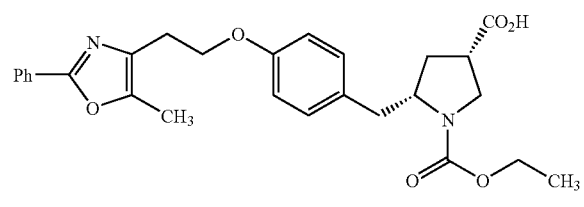

The title compound (14 mg; 64%) was prepared from Example 306 Part A compound as for Example 306, except that ethyl chlorformate was used instead of phenyl chloroformate.

[M+H]$^+$=479.2

$^1$HNMR (CDCl$_3$): δ 7.99-7.97 (2H, d, J=8 Hz), 7.52-7.45 (3H, m), 7.06 (2H, s), 6.80-6.78 (2H, d, J=8 Hz), 4.21-4.14 (4H, m), 4.01-3.79 (2H, m), 3.52-3.47 (1H, t, J=8 Hz), 3.32-2.85 (4H, m), 2.56-2.47 (1H, m), 2.42 (3H, s), 2.23-1.89 (2H, m), 1.30-1.27 (3H, t, J=8 Hz)

Chiral analytical HPLC (Daicel Chiralcel AD 10 um 4.6×250 mm column): flow rate=1.0 mL/min; isocratic conditions=90:10 A:B, where A=HEX with 0.1% TFA; B=IPA with 0.1% TFA; detector wavelength=220 nm; retention time=29.29 min; ee>90%

EXAMPLE 308

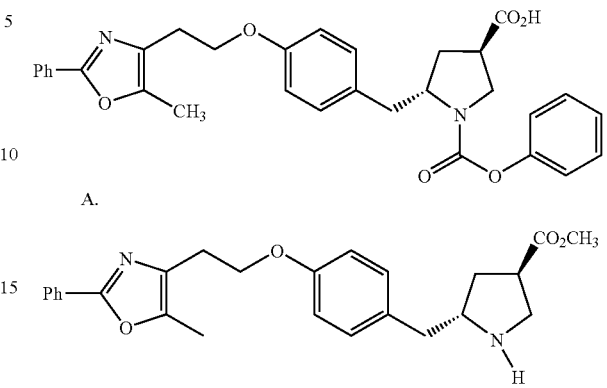

A.

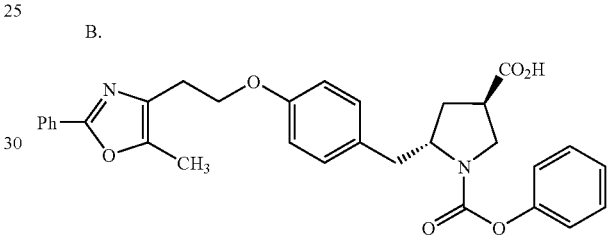

Part A compound (48 mg; 90%) was prepared from Example 298 Part J compound by the same procedure as the synthesis of Example 302 Part A compound.

B.

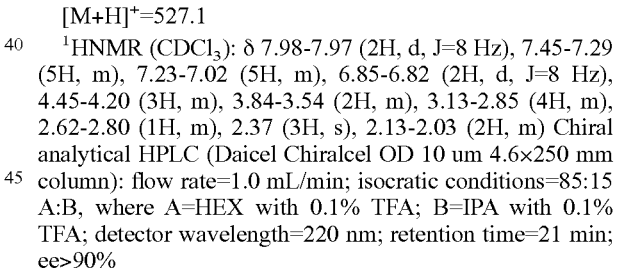

The title compound (26 mg; 86%) was prepared from Part A compound using the same procedure as the synthesis of Example 302 from Example 302 Part A compound.

[M+H]$^+$=527.1

$^1$HNMR (CDCl$_3$): δ 7.98-7.97 (2H, d, J=8 Hz), 7.45-7.29 (5H, m), 7.23-7.02 (5H, m), 6.85-6.82 (2H, d, J=8 Hz), 4.45-4.20 (3H, m), 3.84-3.54 (2H, m), 3.13-2.85 (4H, m), 2.62-2.80 (1H, m), 2.37 (3H, s), 2.13-2.03 (2H, m) Chiral analytical HPLC (Daicel Chiralcel OD 10 um 4.6×250 mm column): flow rate=1.0 mL/min; isocratic conditions=85:15 A:B, where A=HEX with 0.1% TFA; B=IPA with 0.1% TFA; detector wavelength=220 nm; retention time=21 min; ee>90%

EXAMPLE 309

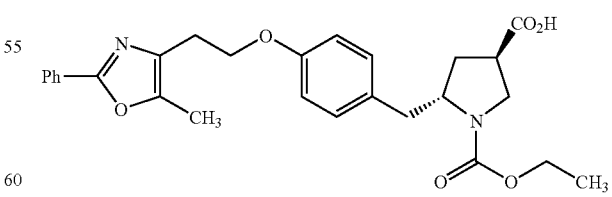

The title compound (18.4 mg; 67%) was prepared from Example 308 Part A compound as for Example 302, except that ethyl chlorformate was used instead of phenyl chloroformate.

[M+H]$^+$=479.2

¹HNMR (CDCl₃): δ 8.00-7.97 (2H, m), 7.50-7.45 (3H, m), 7.05 (2H, s), 6.81-6.79 (2H, d, J=8 Hz), 4.21-4.11 (5H, m), 3.65-3.48 (2H, m), 3.06-2.86 (4H, m), 2.51-2.69 (1H, m), 2.42 (3H, s), 2.08-1.95 (2H, m), 1.29-1.26 (3H, t, J=4 Hz)

Chiral analytical HPLC (Daicel Chiralcel AD 10 um 4.6×250 mm column): flow rate=1.0 mL/min; isocratic conditions=90:10 A:B, where A=HEX with 0.1% TFA; B=IPA with 0.1% TFA; detector wavelength=220 nm; retention time=29.50 min; ee>90%

EXAMPLE 310

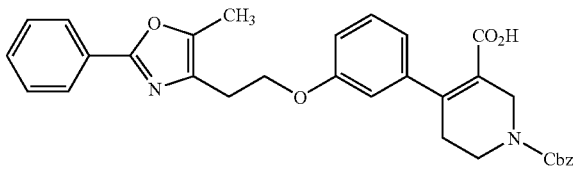

A.

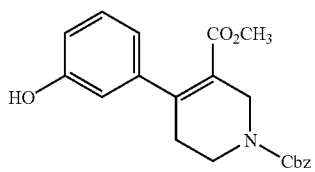

A mixture of tetrahydropyridine-3-carbomethoxyl triflate (0.58 g; 1.3 mmol)

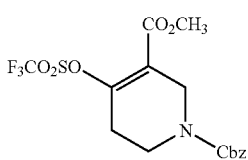

(prepared according to the procedure of Astles, P. C., et. al., PCT Int. Appl (2001), WO 0190101), 3-hydroxyphenyl-boronic acid (0.24 g; 1.7 mmol), (Ph₃P)₄Pd° (0.41 g; 0.35 mmol), and tetrabutylammonium bromide (0.57 g; 1.7 mmol) in dioxane (10 mL) was stirred for 5 h at 90° C., then was cooled to RT and concentrated in vacuo. The residue was partitioned between EtOAc and brine. The organic layer was dried (MgSO₄) and concentrated concentrated in vacuo. The residue was chromatogrphed (SiO₂; 9:1 hexane:EtOAc) to give Part A Compound (0.35 g; 70%).

B.

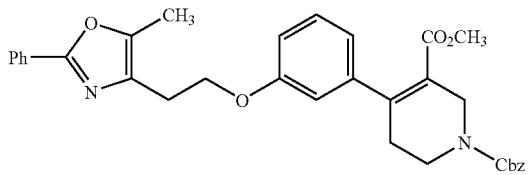

A mixture of Part A Compound (0.2 g 0.57 mmol), Example 23 Part A compound (0.19 g; 0.69 mmol) and K₂CO₃ (0.095 g; 0.69 mmol) in MeCN (10 mL) was stirred for 8 h at 80° C., then cooled to RT and concentrated in vacuo. The residue partitioned between EtOAc and brine. The organic layer was dried (MgSO₄) and concentrated in vacuo. The residue was chromatographed (SiO₂; 4:1 hex: EtOAc) to give Part B Compound (0.15 g; 50%) as an oil.

C.

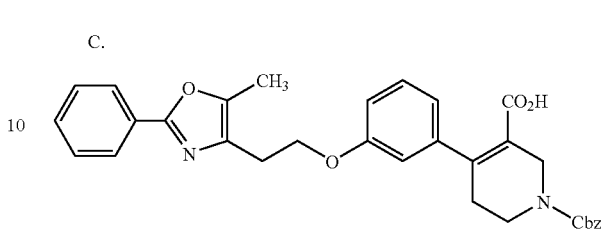

A solution of Part B Compound (0.1 g; 0.28 mmol) and aqueous KOH (2 mL of a 1 N solution) in MeOH (5 mL) was stirred at RT for 18 h, then was concentrated in vacuo. The residue was neutralized with aqueous 1 N HCl and extracted with EtOAc (3×). The combined organic extracts were dried (Na₂SO₄) and concentrate in vacuo to give the title compound.

[M+H]⁺=553.2

EXAMPLE 311

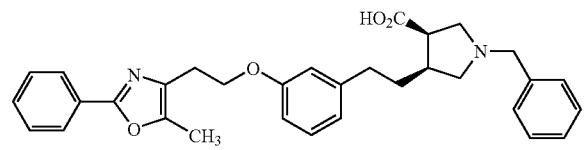

racemate

A

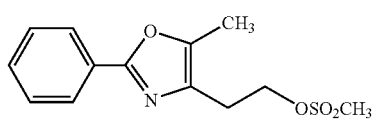

A mixture of 3-(3-hydroxyphenyl)-propionic acid methyl ester (3.12 g; 17.3 mmol), Example 23 Part A compound (4.86 g; 17.3 mmol)

and K₂CO₃ (4.9 g; 36 mmol) in MeCN (100 mL) was heated overnight at 90° C. in an oil bath. Volatiles were removed in vacuo, and the residue was partitioned between H₂O and EtOAc. The aqueous phase was extracted with EtOAc (2×) and the combined organic extracts were dried (MgSO₄) and concentrated in vacuo. The residue was chromatographed (SiO₂; continuous gradient from 100% hex to 100% EtOAc) to give a mixture of the product and unreacted phenol, which was washed repeatedly with aqueous 2N NaOH to furnish purified Part A compound (4.0 g; 63%) as a pale yellow solid.

[M+H]⁺=366.3

B.

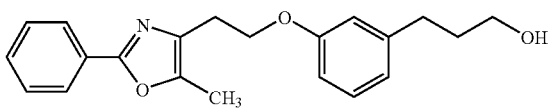

To a 0° C. solution of Part A compound (2.02 g; 5.55 mmol) in anhydrous THF (30 mL) was cautiously added portionwise solid LiAlH$_4$ (290 mg; 7.63 mmol). The reaction was allowed to warm to RT and stirred at RT overnight, then was cautiously quenched with excess aqueous 1 N HCl (30 mL). The mixture was extracted with EtOAc (2×). The combined organic extracts were washed with brine, dried (Na$_2$SO$_4$) and concentrated in vacuo to give Part B compound (1.90 g; 100% crude), which was used in the next reaction without further purification.

[M+H]$^+$=324.4

C.

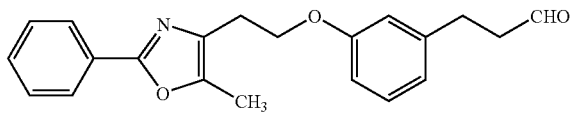

To a RT suspension of Dess-Martin periodinane (3.6 g; 8.5 mmol) in CH$_2$Cl$_2$ (50 mL) was added dropwise a solution of Part B compound (1.90 g; 5.64 mmol) in CH$_2$Cl$_2$ (10 mL) over 5 min. The reaction was stirred at RT for 4.5 h, then was concentrated in vacuo. The residue was chromatographed (SiO$_2$; continuous gradient from 100% hex to 100% EtOAc) to give Part C compound (1.70 g; 90%) as a colorless oil.

E.

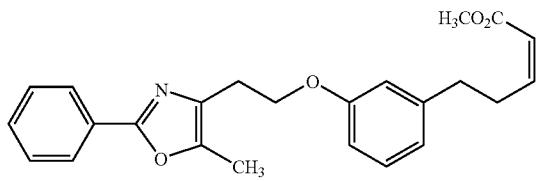

Reference: Sano, S.; Yokoyama, K.; Fukushima, M.; Yagi, T.; Nagao, Y. Chem. Commun. 1997, 6, 559-560

To a −78° C. suspension of NaH (65 mg of a 60% mixture; 1.63 mmol) in anhydrous THF (10 mL) under N$_2$ was added (CF$_3$CH$_2$O)$_2$P(O)CH$_2$CO$_2$CH$_3$ (380 µL; 1.79 mmol) dropwise. The solution was stirred at −78° C. for 10 min, after which a solution of Part C compound (343 mg; 1.02 mmol) in THF (5 mL) was added dropwise over 5 min. The reaction mixture was stirred for 6 h at −78° C. (a significant amount of Part C compound remained at this point), then was allowed to warm slowly to RT and stirred overnight at RT. Excess saturated aqueous NH$_4$Cl was added and the mixture was extracted with EtOAc (3×). The combined organic extracts were washed with brine, dried (Na$_2$SO$_4$), concentrated in vacuo, and the residue was chromatographed (SiO$_2$; continuous gradient from 100% hex to 100% EtOAc) to give the Z-isomer Part D compound (199 mg; 50%) as a colorless oil as well as the E-isomer Part E compound (86 mg; 22%) as a colorless oil.

Part D compound (Z-isomer) data:
$^1$H NMR (CDCl$_3$, 400 MHz) δ 2.27 (s, 3H), 2.62 (t. J=7.7 Hz, 2H), 2.83-2.90 (m, 4H), 3.58 (s, 3H), 4.14 (t, J=6.6 Hz, 2H), 5.69 (dt, J=11.4, 1.8 Hz, 1H), 6.12 (dt, J=11.4, 7.5 Hz, 1H), 6.6-6.72 (m, 3H), 7.08 (t, J=7.9, 1H), 7.28-7.35 (m, 3H), 7.89 (dd, J 7.9, 1.8 Hz, 2H).

E.

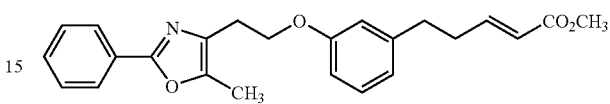

Part E compound (E-isomer) data:
$^1$H NMR (CDCl$_3$, 400 MHz) δ 2.29 (s, 3H), 2.38-2.46 (m, 2H), 2.64 (t. J=7.9 Hz, 2H), 2.90 (t, J=6.6 Hz, 2H), 3.63 (s, 3H), 4.16 (t, J=6.8 Hz, 2H), 5.75 (dt, J=15.8, 1.8 Hz, 1H), 6.6-6.7 (m, 3H), 6.90 (dt, J=15.4, 7.0 Hz, 1H), 7.1 (t, J=7.9, 1H), 7.3-7.4 (m, 3H), 7.90 (dd, J=7.9, 1.8 Hz, 2H).

F.

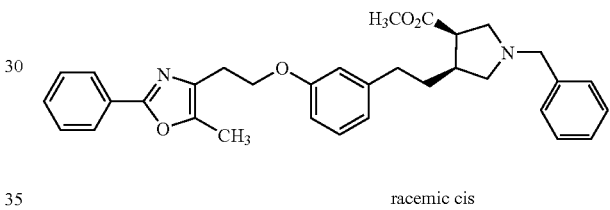

racemic cis

To a solution of Part D compound (126 mg; 0.32 mmol) in toluene (4 mL) were successively added Example 1 Part B compound (192 mg; 1.23 mmol) and TFA (4 drops). The reaction was stirred at RT for 2 h, after which more Example 1 Part B compound (100 mg) was added. Volatiles were removed in vacuo and the residue was chromatographed (SiO$_2$; continuous gradient from 100% hex to 100% EtOAc) to provide Part F compound (189 mg; contains some unreacted Example 1 Part B compound; 100%) as a colorless oil.

G.

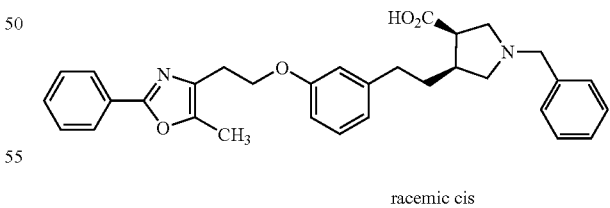

racemic cis

A mixture of Part F compound (24 mg; 0.046 mmol) in 20% aqueous HCl (0.25 mL) and HOAC (0.75 mL) was stirred at 80° C. for 3 h, after which volatiles were removed in vacuo. The residue was purified by preparative HPLC (YMC ODS 20×100 mm reverse phase column, 10 min. continuous gradient from 50:50 A:B to 100% B according to the procedure in Example 1), then lyophilized from dioxane to provide the title compound (7 mg; 25%) as a white solid.

[M+H]$^+$=511.6

EXAMPLE 312

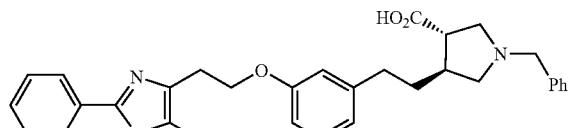
racemic trans

A.

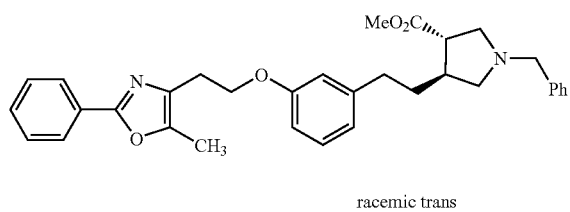
racemic trans

To a solution of Example 311 Part E compound (70 mg, 0.179 mmol) in toluene (3 mL) was added Example 1 Part B compound (0.4 g, 1.68 mmol) followed by TFA (2 drops). The mixture was stirred for 16 h at RT, evaporated in vacuo and the residue was chromatographed (SiO$_2$; 100% hex to 100% EtOAc) to afford Part A compound (34 mg, 36%) as a colorless oil.

[M+H]$^+$=525.5

B.

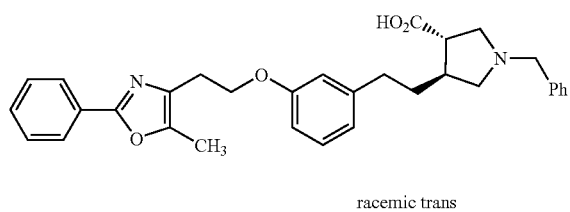
racemic trans

A solution of Part A compound (34 mg, 0.065 mmol) in 20% HCl:HOAc (1 mL of a 1:3 solution) was heated at 80° C. for 3 h, then cooled to RT and concentrated in vacuo. The residue was purified by preparative HPLC (YMC ODS 20×100 mm reverse phase column, 10 min continuous gradient from 70:30 A:B to 100% B, according to the conditions described for the purification of Example 1) and lyophilized from dioxane to afford the title compound (12.8 mg, 32%) as a white solid.

[M+H]$^+$=511.6

EXAMPLE 313

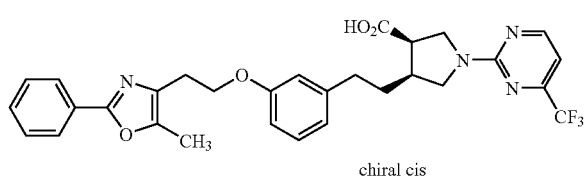
chiral cis

-continued

A.

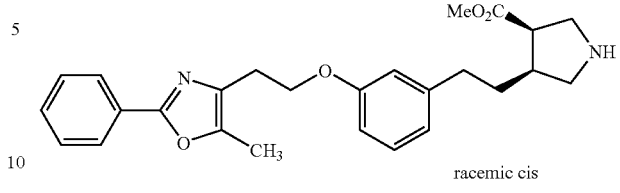
racemic cis

A mixture of Example 311 Part F compound (5.1 g, 9.7 mmol) in 30% HCOOH—MeOH (50 mL) and Pd black (1 g) was stirred at RT for 16 h. The catalyst was filtered off; the filtrate was evaporated in vacuo and the residue was partitioned between EtOAc and saturated aqueous NaHCO$_3$. The aqueous layer was extracted with EtOAc (×2) and the combined organic layers were washed with brine, dried (Na$_2$SO$_4$) and evaporated in vacuo to yield Part A compound (4.3 g; 9.9 mmol; 100%) as a colorless oil.

B.

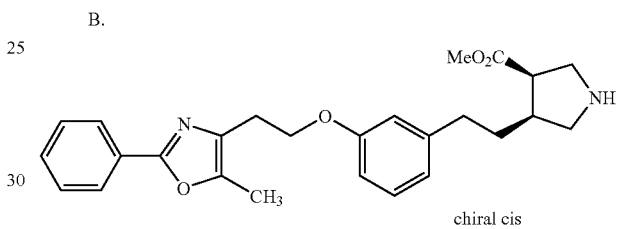
chiral cis

Part A compound (racemate) was separated into the two individual enantiomers by preparative HPLC (Chiralpak AD chiral column, 5 cm×50 cm, 20µ; isocratic 20% EtOH—MeOH (1:1)+85% heptane, flow rate=45 mL/min) to afford Part B compound (1.8 g; faster-eluting enantiomer) and Part C compound (2.0 g; slower-eluting enantiomer) as colorless oils. The absolute stereochemistry of the two enantiomers is arbitrarily assigned.

C.

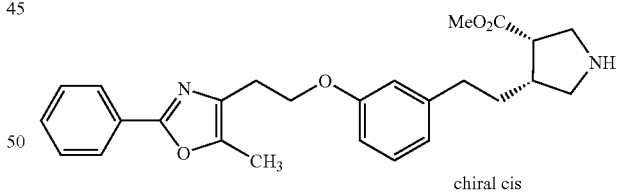
chiral cis

D.

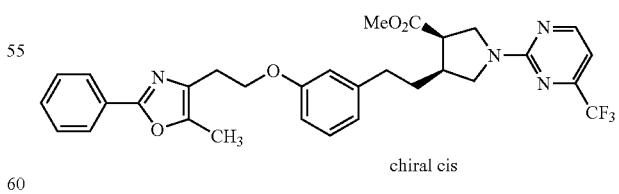
chiral cis

A mixture of Part B compound (20 mg, 0.046 mmol), 2-chloro-4-trifluoromethylpyrimidine (24 mg, 0.131 mmol) and iPr$_2$NEt (26 µL, 0.15 mmol) in 0.5 mL toluene was stirred at RT for 1 h, then was concentrated in vacuo. The residue was purified by preparative HPLC (YMC ODS 20×100 mm reverse phase column, 10 min continuous gradient from 20:80 A:B to 100% B according to the procedure in Example 1) to yield Part D compound (22 mg; 82%) as a colorless oil. The absolute stereochemistry of Part D compound is arbitrarily assigned.

[M+H]$^+$=581.4

E.

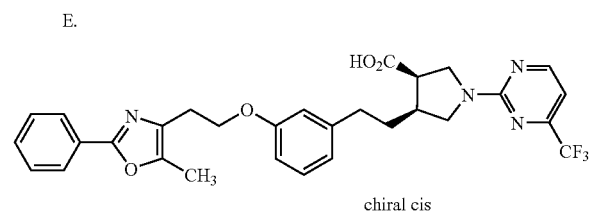

chiral cis

A solution of Part D compound (22 mg, 0.038 mmol) in 20% HCl:HOAc (1:3; 1 mL) was heated at 70° C. for 19 h, then was concentrated in vacuo. The residue was purified by preparative HPLC (Phenomenex LUNA 5 μ C18(2) 21.2× 100 mm reverse phase column, 10 min. continuous gradient from 20:80 A:B to 100% B as described in the general procedure in Example 1) to afford the title compound (13.5 mg, 63%) as a colorless oil.

[M+H]$^+$=567.4

EXAMPLE 314 racemic cis

The title compound (racemate) was prepared according to the sequence described for the synthesis of Example 318 using phenyl chloroformate and Example 313 Part A compound (racemate).

[M+H$^{+]}$=541.5

EXAMPLE 315 racemic cis

The title compound (racemate) was prepared using ethyl chloroformate and Example 313 Part A compound (racemic) according to the sequence described for the synthesis of Example 318.

[M+H]$^+$=493.5

EXAMPLE 316 chiral cis

The title compound was prepared in the same way as for Example 315, but using Example 313 Part B compound (chiral).

[M+H]$^+$=493.3

EXAMPLE 317 chiral cis

The title compound was synthesized in the same way as Example 316, but from Example 313 Part C compound and ethyl chloroformate.

[M+H]$^+$=493.3

EXAMPLE 318 chiral cis

A.

chiral cis

To a solution of Example 313 Part B compound (120 mg, 0.286 mmol) in CH$_2$Cl$_2$ (5 mL) was added Et$_3$N (80 μL, 0.575 mmol) followed by phenyl chloroformate (50 μL, 0.4 mmol) at RT. The reaction mixture was stirred for 3 h at RT, then was partitioned between CH$_2$Cl$_2$ (25 mL) and 1N aqueous HCl (20 mL). The organic phase was washed with brine, dried (Na$_2$SO$_4$) and concentrated in vacuo. The residue was chromatographed (SiO$_2$, continuous gradient from 100% hex to 100% EtOAc) to afford Part A compound (144 mg, 91%) as a colorless oil.

B.

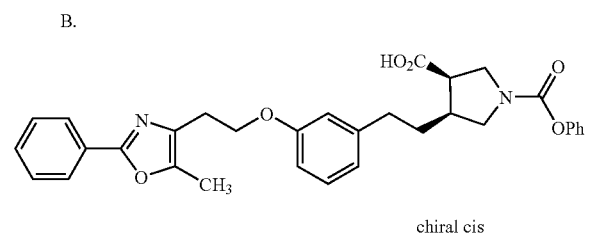

chiral cis

A solution of Part A compound (144 mg, 0.26 mmol) in 20% HCl:HOAc (3 mL of a 1:3 solution) was heated at 70° C. for 19 h, then was cooled to RT and concentrated in vacuo. The residue was purified by preparative HPLC (YMC ODS 20×100 mm reverse phase column, 10 min continuous gradient from 20:80 A:B to 100% B according to the general procedure for Example 1) afforded the title compound (135 mg, 96%) as a pale yellow solid. The absolute stereochemistry is arbitrarily assigned.

$[M+H]^+ = 541.38$

EXAMPLE 319

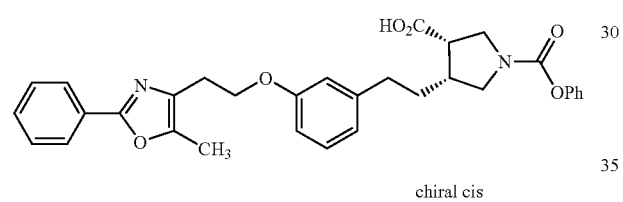

chiral cis

The title compound was prepared in the same manner as for the synthesis of Example 318 using Example 313 Part C compound and phenyl chloroformate. The absolute stereochemistry is arbitrarily assigned.

EXAMPLES 320-330

Examples 320-330 of the invention were prepared as part of a library using the same sequence for the preparation of Example 318 starting from racemic cis Example 313 Part A compound and an appropriate chloroformate.

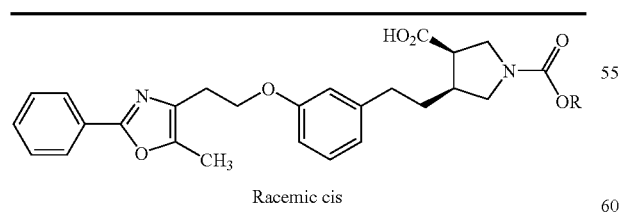

Racemic cis

| Example Number | R | $[M+H]^+$ |
|---|---|---|
| 320 | propyl | 507.6 |
| 321 | isopropyl-CH2 | 507.6 |
| 322 | n-butyl-CH2 | 521.6 |
| 323 | isobutyl | 521.6 |
| 324 | neopentyl | 535.6 |
| 325 | benzyl | 555.6 |
| 326 | 4-F-phenyl | 559.6 |
| 327 | 4-Cl-phenyl | 575.5 |
| 328 | 4-Br-phenyl | 619.5 |
| 329 | 4-Me-phenyl | 555.6 |
| 330 | 4-MeO-phenyl | 571.6 |

EXAMPLE 331

A.

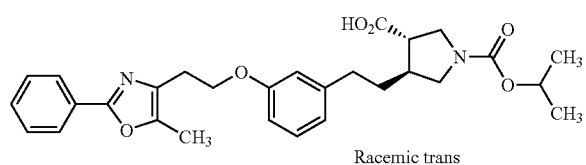

Racemic trans

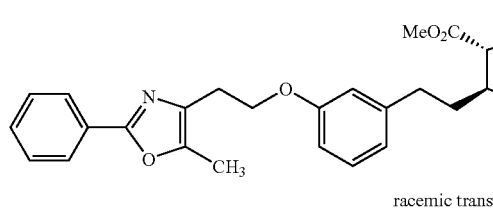

racemic trans

A mixture of Example 312 Part A compound (240 mg, 0.46 mmol) and Pd black (235 mg) in 30% HCOOH-MeOH (5 mL) was stirred at RT for 3.5 h. The catalyst was filtered off; the filtrate was concentrated in vacuo and partitioned between EtOAc and saturated aqueous NaHCO$_3$. The aqueous layer was extracted with EtOAc (×2) and the combined organic layers were washed with brine, dried (Na$_2$SO$_4$) and evaporated in vacuo to yield crude Part A compound (220 mg; 100%, purity ~92%) as a colorless oil.

B.

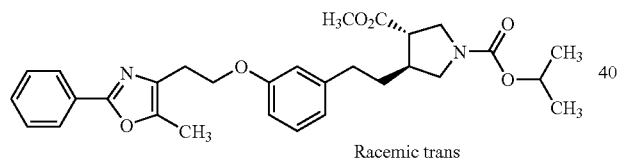

Racemic trans

Crude Part A compound (24 mg, 0.05 mmol) was reacted with isopropyl chloroformate (60 μL; 0.06 mmol), Et$_3$N (40 μL, 0.287 mmol) in CH$_2$Cl$_2$ (2 mL) as in Example 318 Part A compound to give Part B compound as an oil which was used in the next step without further purification.

C.

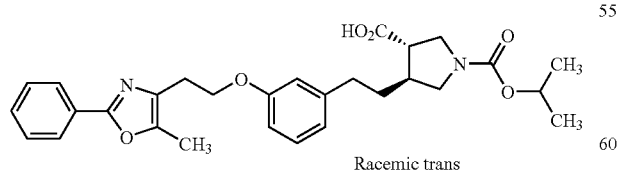

Racemic trans

Part B compound was hydrolyzed to the acid using the same procedure as for Example 318 Part B to give the title compound (3.6 mg; 14% for 3 steps) as a colorless solid.

EXAMPLES 332-339

Examples 332-339 of the invention were prepared as part of a library in using the same sequence as for the synthesis of Example 331 (from Example 331 Part A compound and appropriate chloroformates).

| Example Number | R | [M + H]$^+$ |
|---|---|---|
| 332 | n-butyl | 521.7 |
| 333 | isopropyl-CH$_2$ | 521.6 |
| 334 | t-butyl-CH$_2$ | 535.7 |
| 335 | 4-F-C$_6$H$_4$ | 559.6 |
| 336 | 4-Cl-C$_6$H$_4$ | 575.6 |
| 337 | 4-Br-C$_6$H$_4$ | 619.6 |
| 338 | 4-CH$_3$-C$_6$H$_4$ | 555.6 |
| 339 | 4-CH$_3$-C$_6$H$_4$-CH$_2$ | 571.6 |

EXAMPLE 340

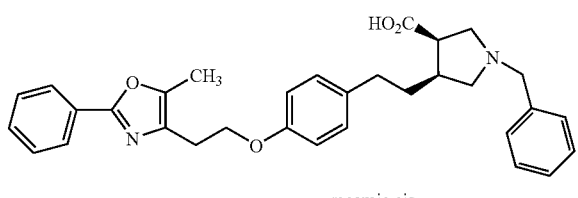

racemic cis

A.

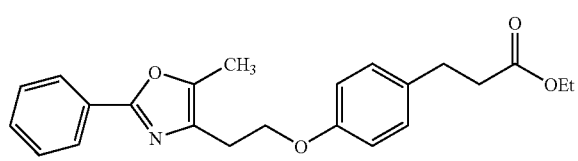

A mixture of 4-hydroxyphenylpropanoic acid ethyl ester (1.8 g; 9.28 mmol), Example 23 Part A compound (2.63 g; 9.36 mmol)

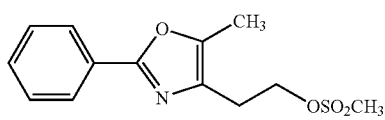

and $K_2CO_3$ (2.65 g; 19.2 mmol) in MeCN (50 mL) was heated overnight at 90° C. in an oil bath. Volatiles were removed in vacuo and the residue was partitioned between $H_2O$ and EtOAc. The aqueous phase was extracted with EtOAc (2×) and the combined organic extracts were dried ($MgSO_4$) and concentrated in vacuo. The residue was chromatographed ($SiO_2$; continuous gradient from 100% hex to 100% EtOAc) to give part A compound (1.9 g, 54%) as a white solid.

$[M+H]^+=380.3$

B.

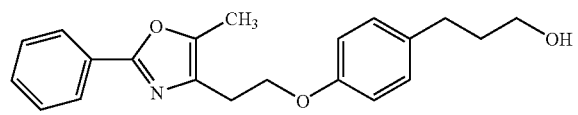

To a 0° C. solution of Part A compound (1.87 g; 5 mmol) in anhydrous THF (30 mL) was cautiously added portionwise solid $LiAlH_4$ (295 mg; 7.6 mmol). The reaction mixture was allowed to warm to RT, stirred at RT overnight, then was cautiously quenched with excess aqueous 1 N HCl. The mixture was extracted with EtOAc (2×). The combined organic extracts were washed with brine, dried ($Na_2SO_4$) and concentrated in vacuo. The residue was chromatographed ($SiO_2$; continuous gradient from 100% hex to 100% EtOAc) to give crude Part B compound (1.49 g; 88%) as a golden oil.

C.

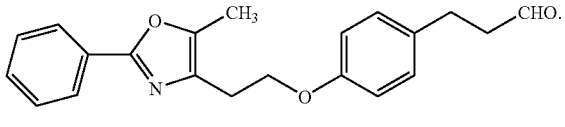

To a RT suspension of Dess-Martin periodinane (2.1 g; 4.95 mmol) in $CH_2Cl_2$ (30 mL) was-added dropwise a solution of Part B compound (1.49 g; 4.42 mmol) in $CH_2Cl_2$ (30 mL) over 5 min. The reaction was stirred at RT for 1 h, then was concentrated in vacuo. The residue was chromatographed ($SiO_2$; continuous gradient from 100% hex to 100% EtOAc) to give Part C compound (1.41 g; 95%) as a colorless solid.

D

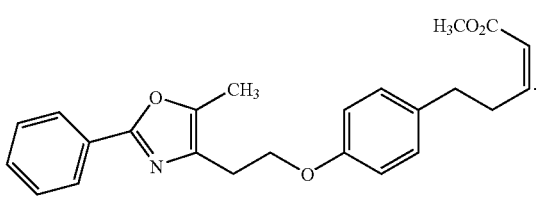

To a −78° C. suspension of NaH (340 mg of a 60% mixture; 8.5 mmol) in anhydrous THF (40 mL) under $N_2$ was added $(CF_3CH_2O)_2P(O)CH_2CO_2CH_3$ (2.2 mL; 10.41 mmol) dropwise. The solution was stirred at −78° C. for 10 min, after which a solution of Part C compound (1.41 g; 4.21 mmol) in THF (10 mL) was added dropwise over 5 min. The reaction mixture was then allowed to warm slowly to RT and stirred overnight at RT. Excess saturated aqueous $NH_4Cl$ was added and the mixture was extracted with EtOAc (3×). The combined organic extracts were washed with brine, dried ($Na_2SO_4$), concentrated in vacuo, and the residue was chromatographed ($SiO_2$; continuous gradient from 100% hex to 100% EtOAc) to give the Z-isomer Part D compound (1.16 g; 70.2%) as a colorless oil as well as the E-isomer Part E compound (209 mg; 12.7%) as a colorless solid.

LC-MS for Part D: $[M+H]^+=392.3$;

TLC: $R_f$ (7:3 hex: EtOAc) 0.43 (Part D compound, Z-isomer).

E

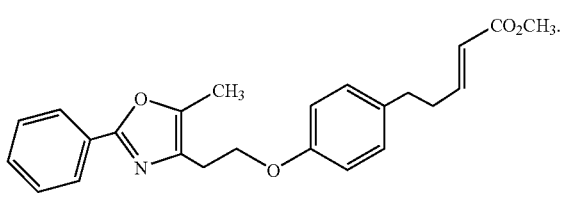

TLC: R_f (7:3 hex: EtOAc)=0.36 (Part E compound, E-isomer)

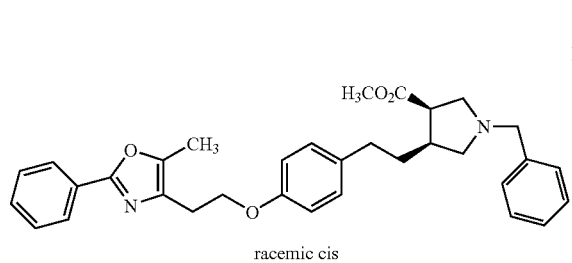

F racemic cis

To a solution of Part D compound (1.04 g, 2.66 mmol) in toluene (10 mL) was added Example 1 Part B compound (1.0 gm, 4.2 mmol) followed by TFA (5 drops). The mixture was stirred for 16 h at RT, concentrated in vacuo and the residue was chromatographed (SiO$_2$; continuous gradient from 100% hex to 100% EtOAc) to afford Part F compound (1.26 g, 91%) as a colorless oil.

[M+H]$^+$=525.4

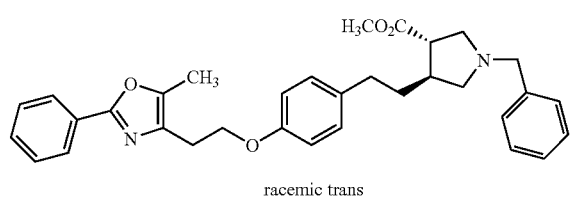

G racemic trans

Part G compound (trans isomer) was prepared (in a similar manner to Part F compound) from Part E compound (E-alkene) in quantitative yield.

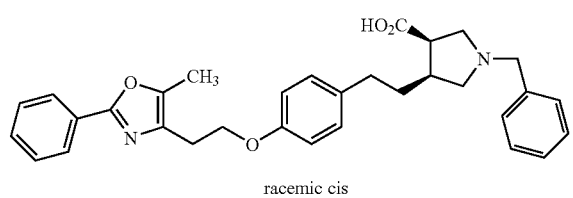

H racemic cis

A solution of Part F compound (11.8 mg, 0.023 mmol) in 20% HCl:HOAc (1 mL of a 1:3 solution) was heated at 75° C. for 3.5 h, then was cooled to RT and concentrated in vacuo. The residue was purified by preparative HPLC (Phenomenex LUNA 5 µ C18(2) 21.2×100 mm reverse phase column, 10 min continuous gradient from 30:70 A:B to 100% B according to the general procedure of Example 1) to afford the title compound (10.7 mg, 93%) as a colorless oil. [M+H]$^+$=511.4

EXAMPLE 341

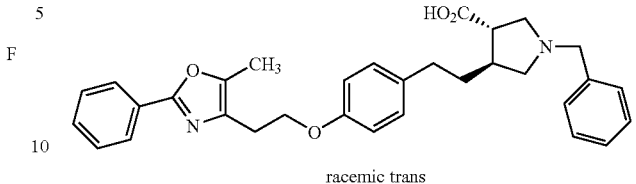

racemic trans

The title compound was prepared from the E-alkenyl ester Example 340 Part G compound (using the same procedure as for the synthesis of Example 340).

[M+H]$^+$=511.4

EXAMPLE 342

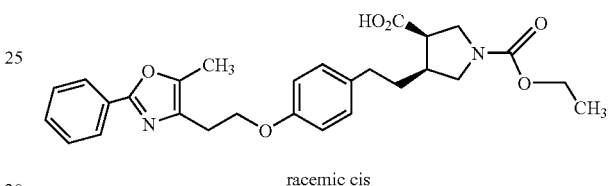

racemic cis

A

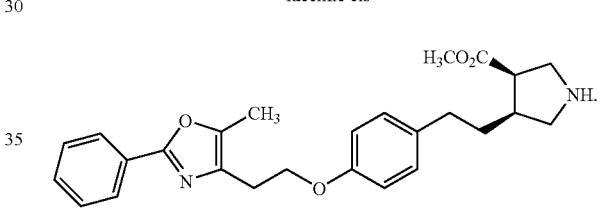

racemic cis

A mixture of Example 340 Part F compound (1.24 g, 2.36 mmol) and Pd black (164 mg) in 30% HCOOH—MeOH (12 mL) was stirred at RT for 16 h. The catalyst was filtered off; the filtrate was concentrated in vacuo, then partitioned between EtOAc and saturated aqueous NaHCO$_3$. The aqueous layer was extracted with EtOAc (×2) and the combined organic layers were washed with brine, dried (Na$_2$SO$_4$) and concentrated in vacuo to yield Part A compound (983 mg; 2.26 mmol, 96%) as a colorless oil.

[M+H]$^+$=435.4

B

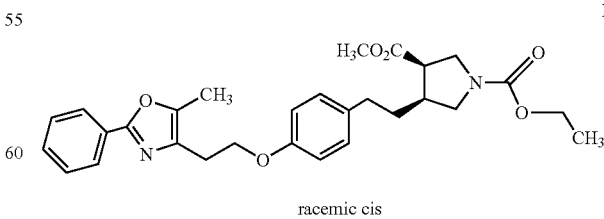

racemic cis

To a solution of Part A compound (20 mg, 0.11 mmol) in CH$_2$Cl$_2$ (0.5 mL) was added Et$_3$N (25 µL, 0.18 mmol) and ethyl chloroformate (20 µL, 0.21 mmol) and the mixture was stirred at RT for 2 h. Volatiles were removed in vacuo and the residue was purified by preparative HPLC (Phenomenex LUNA 5 μ C18(2) 21.2×100 mm reverse phase column, 10 min continuous gradient from 20:80 A:B to 100% B according to the general procedure in Example 1).
[M+H]⁺=507.3

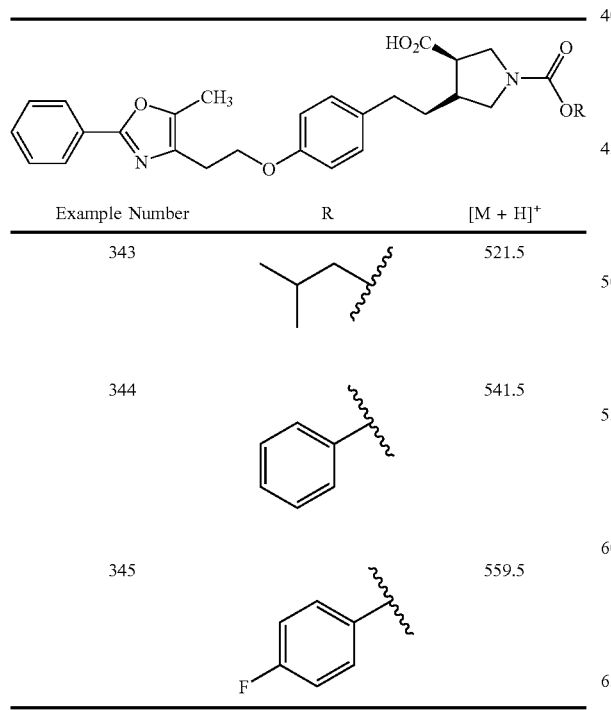

racemic cis

A solution of Part B compound in 20% HCl:HOAc (1 mL of a 1:3 solution) was heated at 75° C. overnight, then was cooled to RT and concentrated in vacuo. The residue was purified by preparative HPLC (YMC ODS 20×100 mm reverse phase column, 10 min continuous gradient from 20:80 A:B to 100% B according to the procedure in Example 1) afforded the title compound (14.6 mg; 64% for 2 steps).
[M+H]⁺=493.5

EXAMPLES 343-345

Examples 343-345 of the invention were prepared according to the general procedure described for the synthesis of Example 342 (using Example 342 Part A compound and appropriate chloroformates).

EXAMPLE 346

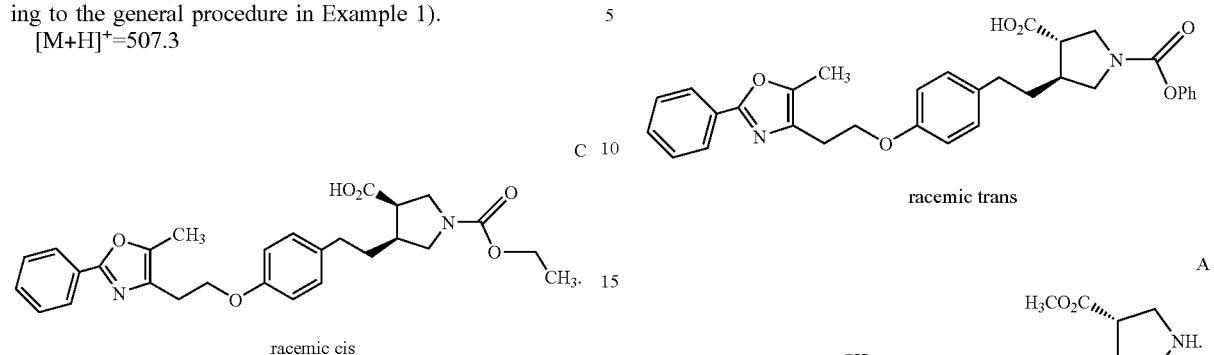

racemic trans

Part A compound was obtained by Pd black-catalyzed hydrogenolysis of Example 340 Part G compound following a procedure similar to Example 342 Part A.

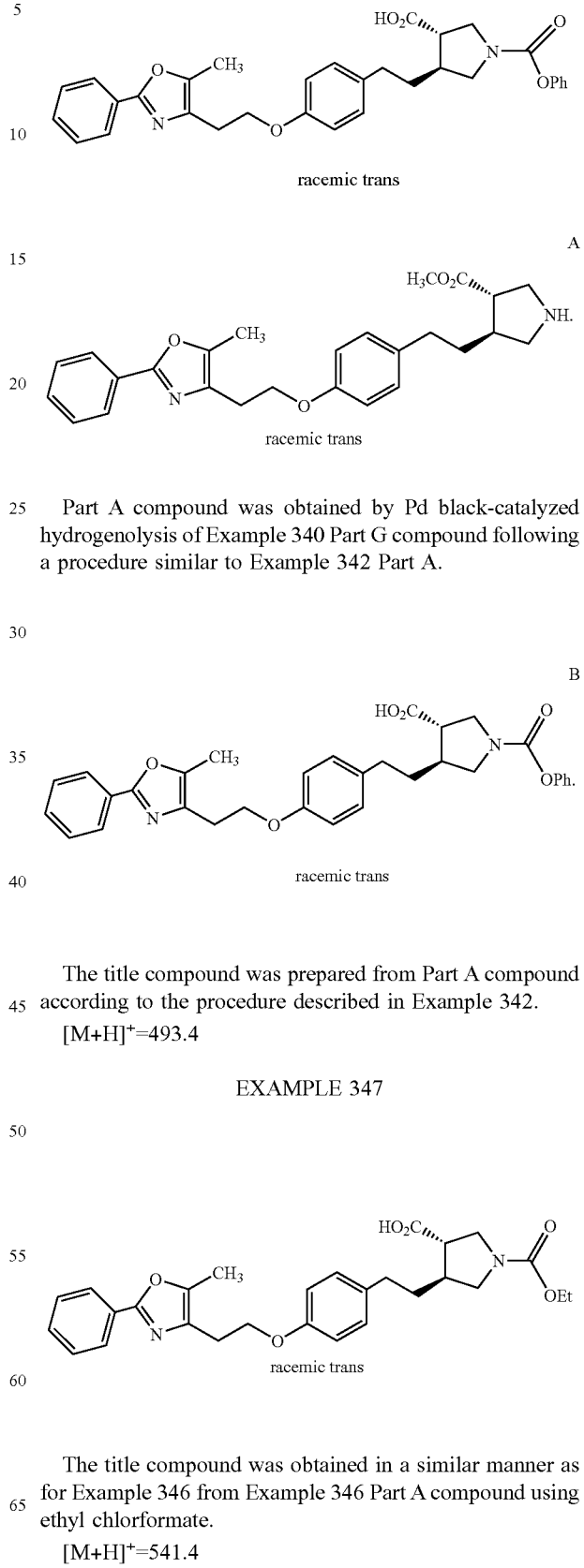

The title compound was prepared from Part A compound according to the procedure described in Example 342.
[M+H]⁺=493.4

EXAMPLE 347

The title compound was obtained in a similar manner as for Example 346 from Example 346 Part A compound using ethyl chlorformate.
[M+H]⁺=541.4

EXAMPLE 348 ENANTIOMER 1

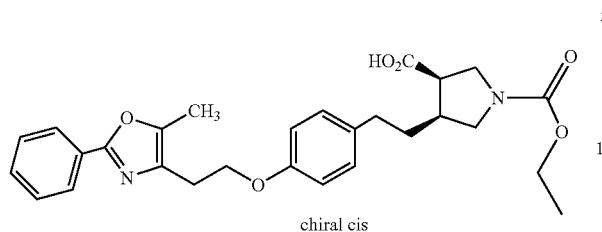
chiral cis

A

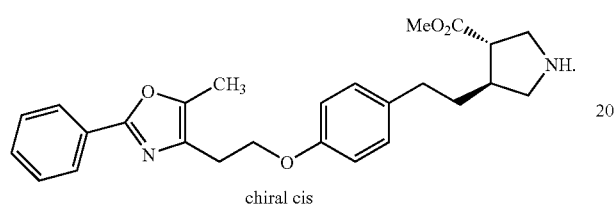
chiral cis

The two enantiomers of racemic Example 342 Part A compound (800 mg) were separated by preparative HPLC: Chiralpak AD chiral column; 5 cm×50 cm, 20μ; isocratic 15% EtOH-MeOH (1:1)+85% heptane+0.1% Et$_2$NH) to afford Part A compound (284 mg; faster-eluting enantiomer) and Part B compound (232 mg; slower-eluting enantiomer) as well as 71 mg of mixed fractions as colorless oils. The absolute stereochemistry of the two enantiomers is arbitrarily assigned.

B

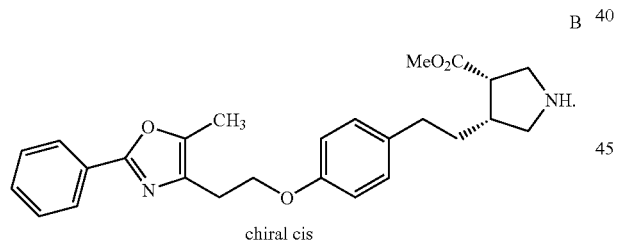
chiral cis

C

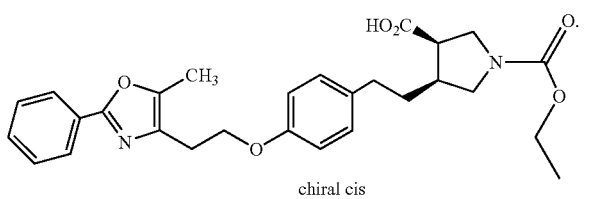
chiral cis

Example 348 was prepared according to the procedure in Example 342 from ethyl chloroformate and Part A compound.

[M+H$^+$]=493.3

EXAMPLE 349 (ENANTIOMER 2)

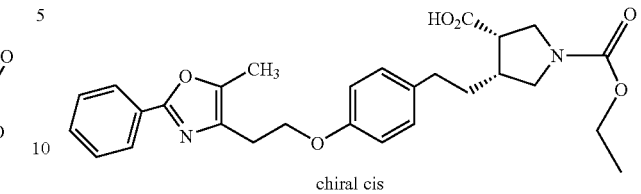
chiral cis

The title compound was prepared according to the procedure in Example 342 from ethyl chloroformate and Part B compound.

[M+H]$^+$=493.3

EXAMPLE 350

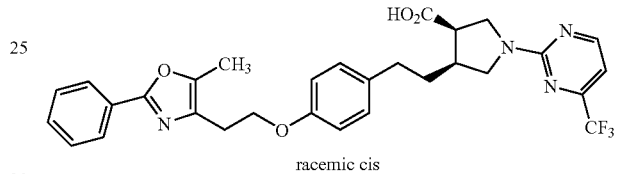
racemic cis

A

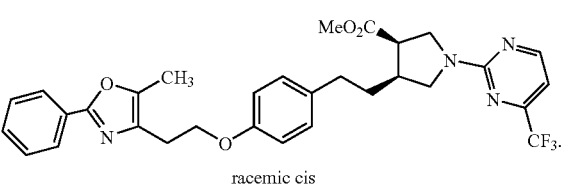
racemic cis

A solution of Example 342 Part A compound (20 mg, 0.046 mmol), 2-chloro-4-trifluoromethylpyrimidine (30 mg, 0.166 mmol) and iPr$_2$NEt (26 μL, 0.15 mmol) in CH$_2$Cl$_2$ (0.5 mL) were stirred at RT overnight, then was concentrated in vacuo. The residue was purified by preparative HPLC (Phenomenex LUNA 5 μ C18(2) 21.2×100 mm reverse phase column, 10 min continuous gradient from 20:80 A:B to 100% B according to the general procedure described in Example 1) to yield Part A compound as a colorless oil which was used in the next step without further purification.

[M+H]$^+$=581.4

B

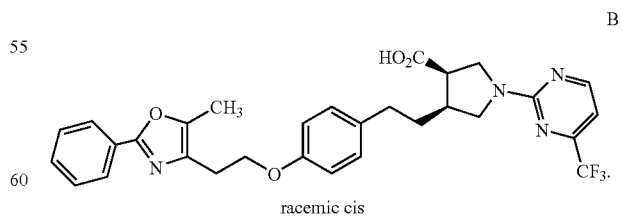
racemic cis

A solution of Part A compound in 20% HCl:HOAc (1 mL of a 1:3 solution) was heated at 75° C. for 19 h, then was cooled to RT and concentrated in vacuo. The residue was purified by preparative HPLC (YMC ODS 20×100 mm reverse phase column, 10 min continuous gradient from 20:80 A:B to 100% B according to the procedure described in Example 1) to afford the title compound (5.2 mg, 20% for 2 steps) as a colorless oil.

[M+H]⁺=567.4

EXAMPLE 351

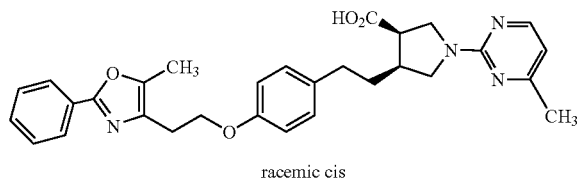

racemic cis

The title compound was prepared in a similar manner as for the synthesis of Example 350 using Example 174 Part A compound.

[M+H]⁺=513.5

EXAMPLE 352

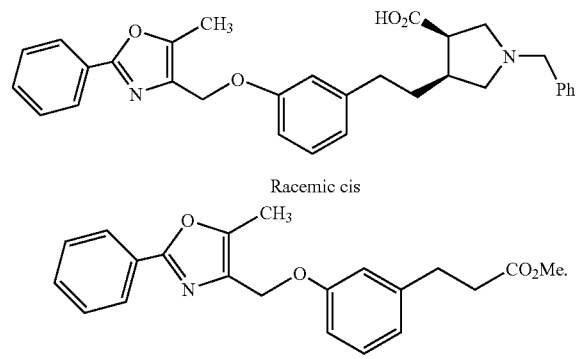

Racemic cis

A mixture of 3-(3-hydroxyphenyl)-propionic acid methyl ester (3.2 g, 17.83 mmol), K₂CO₃ (4.9 g, 35.5 mmol), Example 89 Part B compound (3.72 g, 17.93 mmol) in CH₃CN (50 mL) was heated at 80° C. for 16 h, then was cooled to RT and filtered. The filtrate was concentrated in vacuo and partitioned between EtOAc and H₂O. The aqueous layer was extracted with EtOAc (×2) and the combined organic layers were washed with brine, dried (Na₂SO₄), filtered and evaporated in vacuo. The residue was chromatographed (SiO₂; continuous gradient from 100% hex to 100% EtOAc) to afford Part A compound (4.26 g, 68%) as a golden oil.

[M+H]⁺=352.3

To a 0° solution of Part B compound (4.3 g, 12.1 mmol) in THF (50 mL) was added LiAlH₄ (600 mg, 15.8 mmol) and the reaction was allowed to warm to RT and stirred at RT for-16 h. The mixture was then quenched cautiously with 1N aqueous HCl, extracted with EtOAc (×2), washed with brine, dried (Na₂SO₄) and evaporated in vacuo. The residue was chromatographed (SiO₂; continuous gradient 100% hex to 100% EtOAc) to afford Part B compound (3.3 gm, 84%) as a colorless solid.

[M+H]⁺=324.4

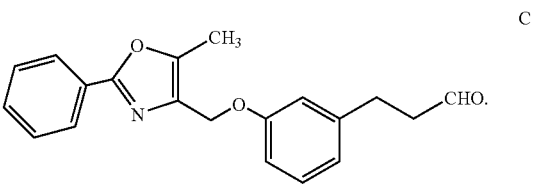

To a dispersion of Dess-Martin reagent (5.0 g, 11.8 mmol) in CH₂Cl₂ (25 mL) was added a solution of Part B compound (3.3 g, 10.2 mmol) in CH₂Cl₂ (35 mL) dropwise at RT and the resulting mixture was allowed to stir at RT for 1 h. The mixture was then evaporated in vacuo and the residue was chromatographed (SiO₂; 100% hex to 100% EtOAc) to yield Part C compound (2.69 g, 82%) as a golden oil.

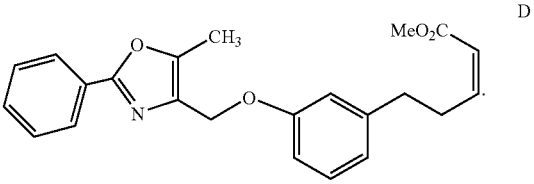

A suspension of NaH (60% dispersion in oil, 670 mg, 16.75 mmol) in THF (100 mL) was stirred at RT for 15 min and then cooled to −78° C. [Bis-(2,2,2-trifluoroethoxy)-phosphoryl]-acetic acid methyl ester (4.5 mL, 21.3 mmol) was added and the mixture was stirred for 20 min at −78° C. A solution of Part C compound (2.69 gm, 8.38 mmol) in THF (20 mL) was then added dropwise to the −78° C. reaction. The reaction was allowed to warm to RT and stirred at RT for 16 h, then was quenched with aqueous NH₄Cl. The aqueous phase was extracted with EtOAc (×2); the combined organic layers were washed with brine, dried (Na₂SO₄) and evaporated in vacuo. The residue was chromatographed (SiO₂; continuous gradient from 100% hex to 100% EtOAc; 3 times) to afford Part D compound (Z-alkene; 2.22 g, 70%) and Part E compound (E-alkene; 0.346 g, 11%).

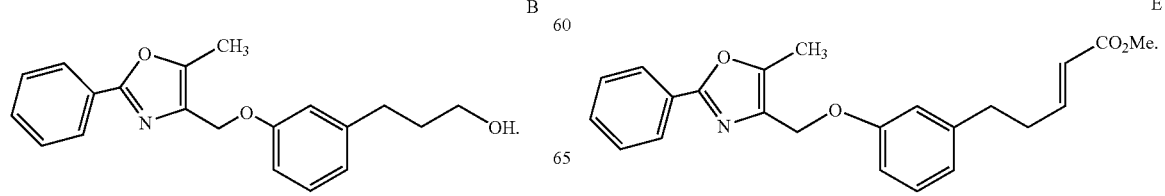

-continued

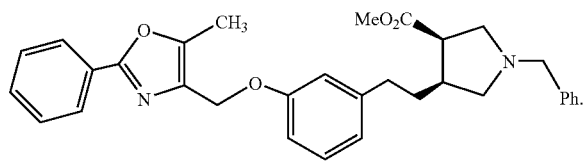
F

To a solution of Part D compound (2.22 g, 5.88 mmol) in toluene (20 mL) was added Example 1 Part B compound (2.14 gm, 9 mmol) followed by TFA (5 drops). The mixture was stirred for 16 h at RT, evaporated in vacuo and the residue was chromatographed (SiO$_2$; 100% hex to 100% EtOAc) to afford Part F compound (3.0 g, 100%) as a colorless oil.

[M+H]$^+$=511.6

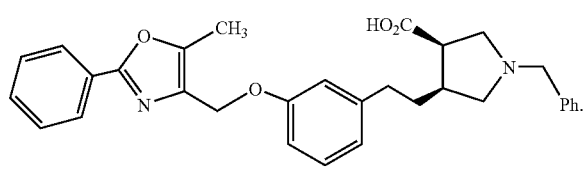
G

Racemic cis

A solution of Part F compound (51 mg, 0.1 mmol) in 20% HCl:HOAc (3 mL of a 1:3 solution) was heated at 70° C. for 5 h, then was cooled to RT and concentrated in vacuo. The residue was purified by preparative HPLC (YMC ODS 20×100 mm reverse phase column, 10 min continuous gradient from 70:30 A:B to 100% B according to the general procedure in Example 1) to afford the title compound (0.8 mg, 1.6%) as a colorless oil.

[M+H]$^+$=497.4

EXAMPLE 353

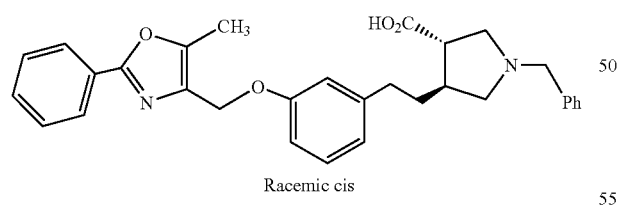

Racemic cis

A

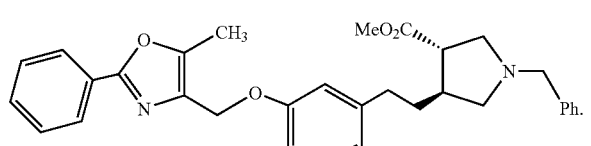

To a solution of Example 352 Part E compound (346 mg, 0.92 mmol) in toluene (5 mL) was added Example 1 Part B compound (387 mg, 1.63 mmol) followed by TFA (5 drops). The mixture was stirred for 16 h at RT, evaporated in vacuo and the residue was chromatographed (SiO$_2$; 100% hex to 100% EtOAc) to afford Part A compound (414 mg, 88%) as a colorless oil.

[M+H]$^+$=511.6

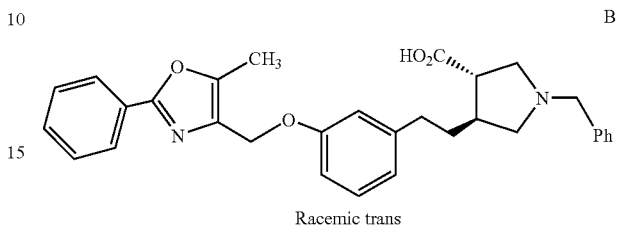
B

Racemic trans

A solution of Part A compound (16 mg, 0.03 mmol) in 20% HCl:HOAc (2 mL of a 1:3 solution) was heated at 70° C. for 5 h, then was cooled to RT and concentrated in vacuo. The residue was purified by preparative HPLC (YMC ODS 20×100 mm reverse phase column, 10 min continuous gradient from 70:30 A:B to 100% B according to the general procedure in Example 1) to afford the title compound (1.5 mg, 10%) as a colorless oil.

[M+H]$^+$=497.4

EXAMPLE 354

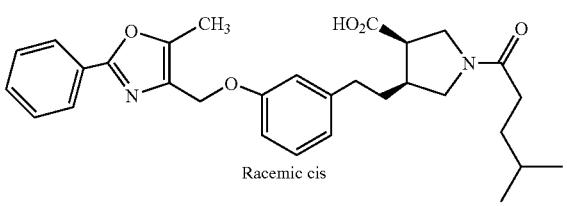

Racemic cis

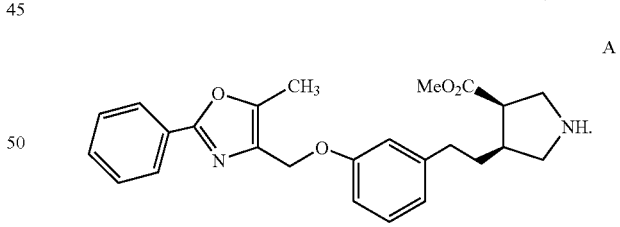
A

A mixture of Example 352 Part F compound (514 mg, 1 mmol) and Pd black (392 mg) in 30% HCO$_2$H—MeOH (5 mL) was stirred at RT for 16 h. The reaction mixture was filtered, evaporated in vacuo and partitioned between EtOAc and saturated aqueous NaHCO$_3$. The aqueous layer was extracted with EtOAc (×2) and the combined organic layers were washed with brine, dried (Na$_2$SO$_4$) and concentrated in vacuo to yield crude Part A compound (369 mg; 0.88 mmol, 88%) as a colorless oil.

[M+H]$^+$=421.3

B

To a solution of Part A compound (44 mg, 0.11 mmol) in CH₂Cl₂ (2 mL) was added Et₃N (50 μL, 0.36 mmol) and isobutyl chloroformate (35 μL, 0.27 mmol) and the mixture was stirred at RT for 1 h. The mixture was then evaporated in vacuo and purified by preparative HPLC (YMC ODS 20×100 mm reverse phase column, 10 min continuous gradient from 20:80 A:B to 100% B according to the general procedure described in Example 1) to give Part A compound. [M+H]⁺=521.5

C

A solution of Part B compound in 20% HCl:HOAc (1 mL of a 1:3 solution) was heated at 70° C. for 3 h, then was cooled to RT and concentrated in vacuo. The residue was purified by preparative HPLC (YMC ODS 20×100 mm reverse phase column, 10 min continuous gradient from 30:70 A:B to 100% B according to the general procedure described in Example 1) to afford the title compound (3.3 mg; 6% for 2 steps) as a colorless oil.
[M+H]⁺=507.5

EXAMPLES 355-357

Examples 355-357 of the invention (cis-disubstituted pyrrolidine compounds) were prepared in the same manner as for Example 356:

| Example Number | R | [M + H]⁺ |
|---|---|---|
| 355 | (propyl) | 479.5 |
| 356 | (phenyl) | 527.5 |
| 357 | (4-fluorophenyl) | 545.5 |

EXAMPLE 358

Racemic trans

A

A mixture of Example 353 Part A compound (395 mg, 0.78 mmol) in 30% HCOOH—MeOH (5 mL) and Pd black (318 mg) was stirred at at RT under for 16 h. The reaction mixture was filtered; the filtrate was concentrated in vacuo and partitioned between EtOAc and saturated aqueous NaHCO₃. The aqueous layer was extracted with EtOAc (×2) and the combined organic layers were washed with brine, dried (Na₂SO₄) and concentrated in vacuo to give crude Part A compound (294 mg; 0.7 mmol, 90%) as a golden oil.
[M+H]⁺=421.3

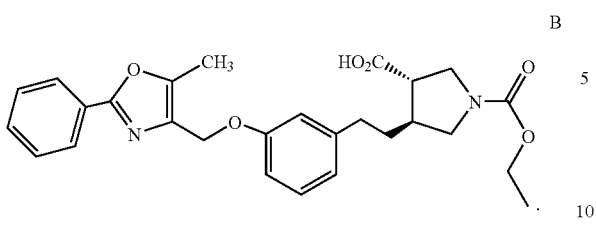

The title compound was prepared from Part A compound in the same manner as for the synthesis of Example 354 in 5% yield for 2 steps.
[M+H]⁺=479.1

EXAMPLES 359-361

The following compounds of the invention were prepared according to the same procedure as Example 354 starting from Example 358 Part A compound.

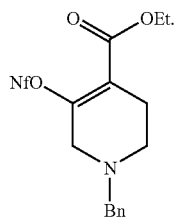

Racemic trans

| Example Number | R | [M + H]+ |
|---|---|---|
| 361 | isobutyl | 507.1 |
| 362 | benzyl | 527.1 |
| 363 | 4-fluorobenzyl | 545.1 |

EXAMPLE 362

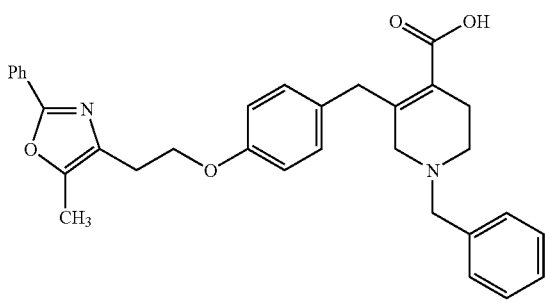

To a 0° C. solution of ethyl 1-benzyl-3-oxo-4-piperidine carboxylate hydrochloride (5.0 g, 16.77 mmol) in MeOH (16 mL) was added aqueous $K_2CO_3$ (2.55 g, 18.47 mmol; in 26 mL $H_2O$). The mixture was stirred at 0° C. for 10 min, then was extracted with $CH_2Cl_2$ (4×30 mL). The combined organic extracts were dried ($K_2CO_3$) and concentrated in vacuo to give the corresponding free base (3.5 g, 80%). The β-keto ester free base (1.37 g, 5.22 mmol) was stripped from toluene (2×), dissolved in anhydrous THF (50 mL) and cooled to −70° C. under Ar. KN(TMS)₂ in toluene (13.5 mL of a 0.5 M solution) was added dropwise. After stirring at −70° C. for 15 min, 1,1,2,2,3,3,4,4,4-Nonafluoro-1-butane-sulfonyl fluoride (1.28 mL, 6.78 mmol) was added. The reaction was allowed to warm to RT and stirred overnight at RT, then was washed with saturated aqueous NH₄Cl (200 mL). The aqueous layer was extracted with Et₂O (3×50 mL). The combined organic extracts were dried (Na₂SO₄) and concentrated in vacuo to give Part A compound as a brown oil (2.84 g, 100%), which was used in the next step without further purification.
[M+H]⁺=544.4
¹H NMR (400 MHz, CDCl₃) δ 7.26 (m, 5H), 4.21 (q, J=7.0 Hz, 2H), 3.59 (s, 2H), 3.12 (s, 2H), 2.58 (m, 2H), 2.52 (m, 2H), 1.24 (t, J=7.0 Hz, 3H)

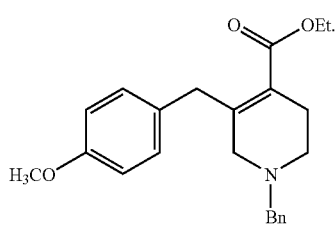

To a solution of Bis(dibenzylideneacetone)palladium (0) [Pd(dba)₂] (0.18 g, 0.31 mmol) and 1,1'-Bis(diphenyl-phosphino)ferrocene (dppf) (0.18 g, 0.31 mmol) in anhydrous THF (21 mL) under Ar was added 4-methoxybenzyl zinc chloride (25.0 ml, 11.5 mmol, 0.5 M in THF) at RT. The reagent mixture was stirred at RT for 20 min. A solution of Part A Compound (2.84 g, 5.22 mmol; stripped from anhydrous toluene 3× before use) in dry THF (20 mL) was added slowly to the Pd catalyst/organozinc reagent mixture. The mixture was heated at 65° C. under Ar for 12 h, cooled to RT, and partitioned between CH₂Cl₂ (70 mL) and saturated aqueous NaHCO₃. Solids were filtered off, and the aqueous phase was extracted with CH₂Cl₂ (4×30 mL). The combined organic extracts were dried (K₂CO₃) and concentrated in vacuo. The residue was chromatographed (SiO₂; 85:15 hexane:EtOAc) to afford Part B compound as a light yellow oil (1.37 g, 72%).
[M+H]⁺=366.5

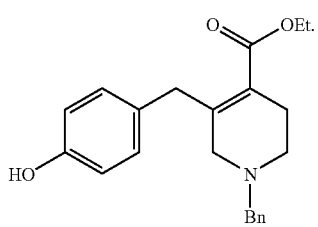

To a 0° C. solution of compound B (1.0 g, 2.74 mmol) in CH$_2$Cl$_2$ (15 mL) was added dropwise BBr$_3$ in CH$_2$Cl$_2$ (6.5 mL of a 1.0 M solution; 6.49 mmol). The mixture was stirred at 0° C. for 2 h. EtOH (1 mL) and saturated aqueous NaHCO$_3$ (10 mL) were subsequently added to quench the reaction. The aqueous phase was further extracted with CH$_2$Cl$_2$ (3×10 mL). The combined organic extracts were dried (Na$_2$SO$_4$) and concentrated in vacuo. The residue was chromatographed (SiO$_2$; 4:1 hex:EtOAc) to afford Part C compound (0.59 g, 61%) as light yellow solid.

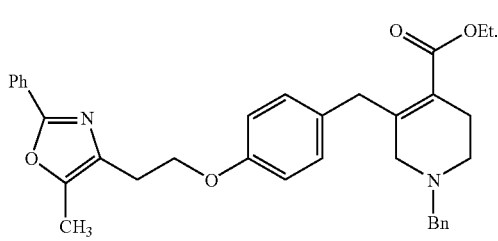

Part C compound (0.264 g, 0.753 mmol) and Example 23 Part A compound (0.265 g, 0.942 mmol) were stripped from dry toluene (3×), then were dissolved in anhydrous MeCN (7.5 mL); finally anhydrous K$_2$CO$_3$ (0.13 g, 0.942 mmol) was added. The reaction was stirred at 90° C. overnight. Additional Example 23 Part A compound was added until all Part C compound was consumed. Volatiles were removed in vacuo and the residue was dissolved in water (15 mL) and extracted with CH$_2$Cl$_2$ (3×15 mL). The combined organic extracts were dried (K$_2$CO$_3$) and concentrated in vacuo. The residue was chromatographed (SiO$_2$; 4:1 hex:EtOAc) to give compound D (0.202 g, 50%) as a light yellow oil.

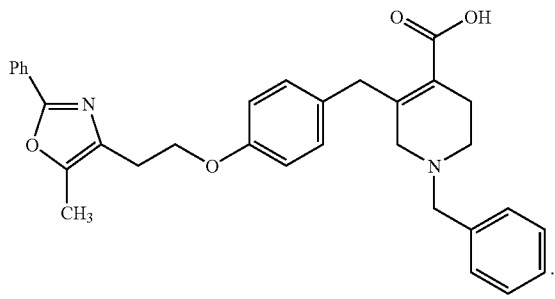

A solution of Part D compound in HCl/HOAc (1 mL of a conc. HCl:HOAc solution; 20:80 v/v) was heated at 90° C. in a sealed tube for 8 h, then cooled to RT. Volatiles were removed in vacuo, and the residue was purified by prepara- tive HPLC (YMC S5 ODS 20×250 mm column; continuous gradient from 50:50 solvent A:B to 100% solvent B; where solvent A=90:10:0.1H$_2$O:CH$_3$CN:TFA; solvent B=90:10: 0.1 CH$_3$CN:H$_2$O:TFA) and lyophilized from CH$_3$CN/H$_2$O to give the title compound (5.6 mg, 50%) as the TFA salt (light yellow oil).

[M+H]$^+$ (electrospray)=509.0

EXAMPLE 363

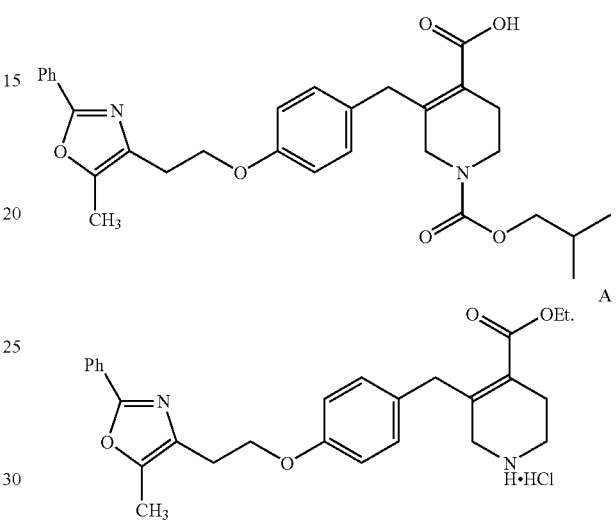

Example 362 Part D Compound (40 mg, 0.0745 mmol) and Proton Sponge [1,8-bis(dimethylamino)naphthalene] (2.0 mg) were stripped from dry toluene (2×), then dissolved in CH$_2$Cl$_2$ (1 mL). To this 0° C. solution was added dropwise α-chloroethyl chloroformate (21 μL, 0.186 mmol). The reaction mixture was allowed to warm to RT, then heated at 40° C. under Ar for 1 h. Volatiles were removed in vacuo; MeOH (1 mL) was added, and the mixture was heated at 50° C. for 1 h, then cooled to RT. Volatiles were removed in vacuo to afford crude Part A compound as a light yellow oil, which was used in the next reaction without further purifi- cation.

[M+H]$^+$=447.5

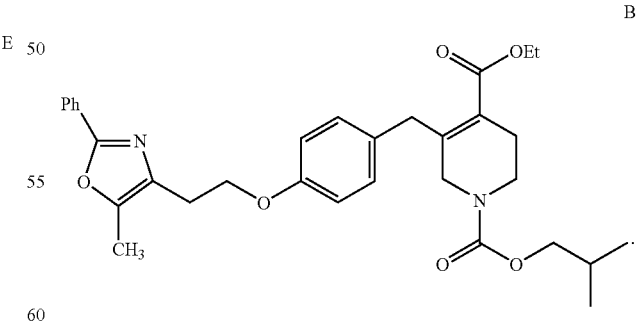

To a solution of Part A compound (ca 0.0745 mmol) in 1,4-dioxane/H$_2$O (2.0 mL of a 1:1 solution) were succes- sively added isobutyl chloroformate (15.0 μL, 0.064 mmol) and NaHCO$_3$ (25.0 mg, 0.298 mmol). The mixture was stirred at RT for 1 h, then was partitioned between water (3 mL) and CH$_2$Cl$_2$ (5 mL). The aqueous phase was extracted with CH$_2$Cl$_2$ (2×5 mL). The combined organic extracts were dried (Na$_2$SO$_4$) and concentrated in vacuo. The residue was chromatographed (SiO$_2$; 3:1 hex:EtOAc) to give Part B compound as a colorless oil (32.5 mg, 80%).

[M+H]$^+$=547.2

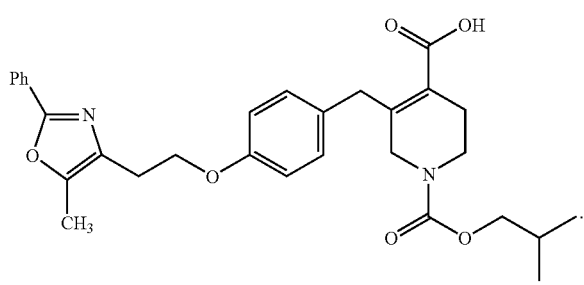

A solution of Part B Compound (32.5 mg, 0.0595 mmol) in 20% HCl/HOAc (2.0 mL of a conc HCl:HOAc solution; 20:80 v/v) was heated at 110° C. in a sealed tube for 2 h, then cooled to R.T. Volatiles were removed in vacuo, and the residue was purified by preparative HPLC (YMC S5 ODS 20 mm×100 mm column; continuous gradient from 70% A:30% B to 100% B for 10 min; flow rate=20 mL/min, where A=90:10:0.1H$_2$O:MeOH:TFA and where B=90:10:0.1 MeOH:H$_2$O:TFA) to give the title compound (15.4 mg; 50%) as a colorless solid.

[M+H]$^+$=519.0

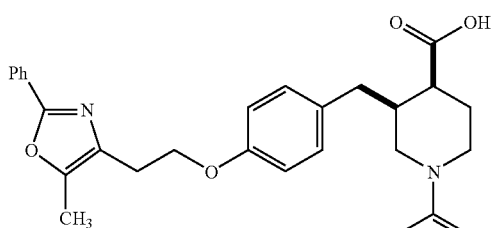

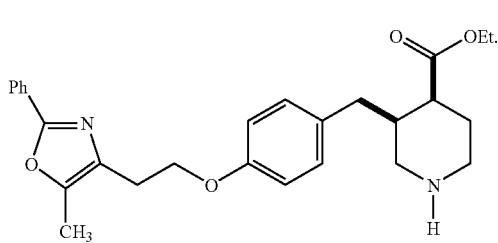

A mixture of Example 362 Part D Compound (0.26 g, 0.48 mmol) and 10% Pd/C (0.1 g) in HOAc (4.8 mL) was stirred overnight under an atmosphere of H$_2$ (60 psi pressure). The catalyst was filtered off, and the filtrate was concentrated in vacuo to afford crude Part A compound as a light yellow oil (0.117 g, 54%), which was used in the next step without further purification.

[M+H]$^+$=449.5

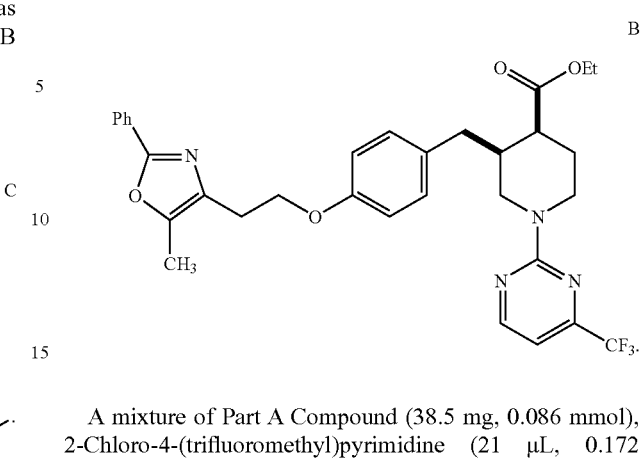

A mixture of Part A Compound (38.5 mg, 0.086 mmol), 2-Chloro-4-(trifluoromethyl)pyrimidine (21 μL, 0.172 mmol) and iPr$_2$NEt (40 μL, 0.215 mmol) in dry toluene (1 mL) was heated at 100° C. for 3 h. Volatiles were removed in vacuo, and the residue was purified by preparative HPLC (YMC S5 ODS 20 mm×100 mm column; continuous gradient from 70% A:30% B to 100% B for 10 min; flow rate=20 mL/min, where A=90:10:0.1H$_2$O:MeOH:TFA and where B=90:10:0.1 MeOH:H$_2$O:TFA) to give Part B compound (22.2 mg, 44% yield) as a white solid.

[M+H]$^+$=595.6

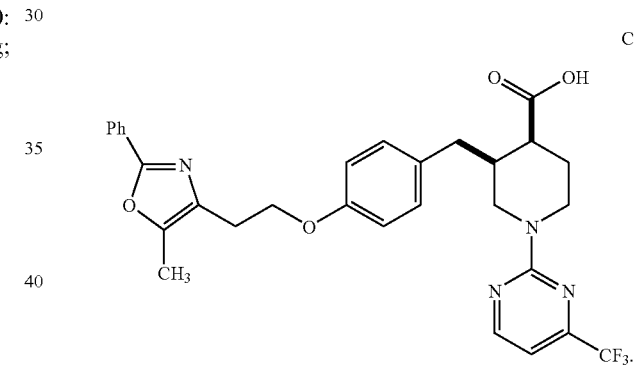

Part B Compound (22.2 mg, 0.0373 mmol) was: 1) deprotected using the standard HCl/HOAc/110° C. procedure and 2) purified by preparative HPLC, both as for Example 363 Part C. The title compound was obtained as a white solid (12.6 mg, 60%).

[M+H]$^+$=567.0

EXAMPLE 365

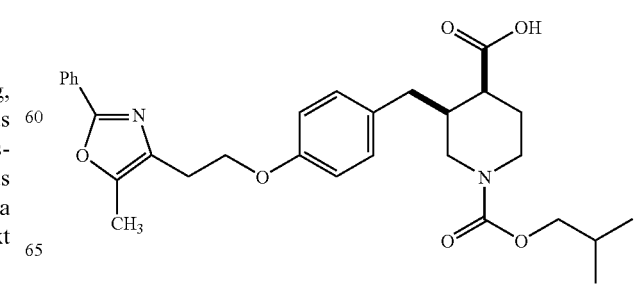

-continued

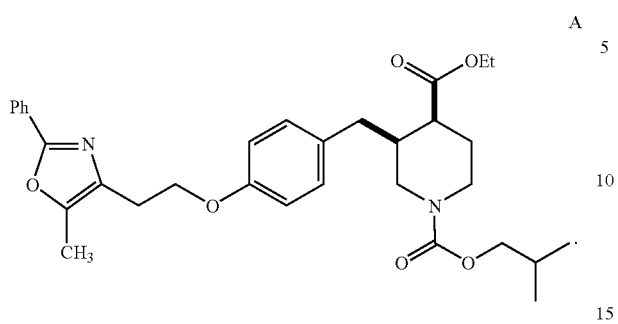

A

To a solution of Example 364 Part A compound (35.5 mg, 0.0793 mmol) in 1,4 dioxane/H$_2$O (2.0 mL of a 1:1 solution) were added isobutyl chloroformate (15.0 μL, 0.111 mmol) and NaHCO$_3$ (27.0 mg, 0.317 mmol). The mixture was stirred at RT for 1 h, then water (3 mL) was added. The aqueous phase was extracted with CH$_2$Cl$_2$ (3×5 mL). The combined organic extracts were dried (Na$_2$SO$_4$) and concentrated in vacuo to give crude Part A compound.

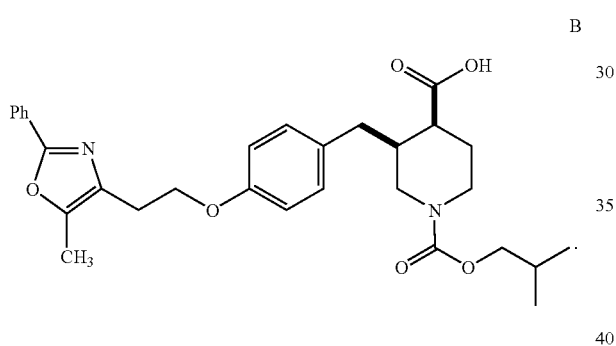

B

Crude Part A Compound was: 1) deprotected using the same HCl/HOAc/110° C. procedure and 2) purified by preparative HPLC both as for Example 363 Part C. The title compound was obtained as a white solid (20.6 mg, 50% yield). [M+H]$^+$=521.1

EXAMPLE 366

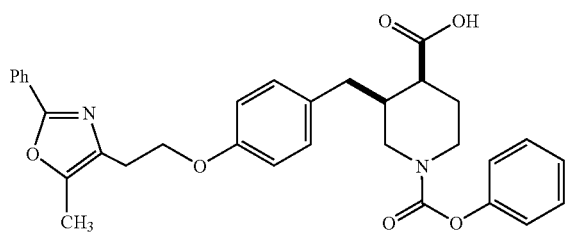

Example 364 Part A compound (20 mg, 0.045 mmol) was reacted with phenyl chloroformate (8.5 μL, 0.067 mmol), followed by the acid-mediated hydrolysis of the ester (both steps as for Example 365) to give the title compound (12.0 mg, 50% yield) as a white solid.

[M+H]$^+$=541.0

EXAMPLE 367

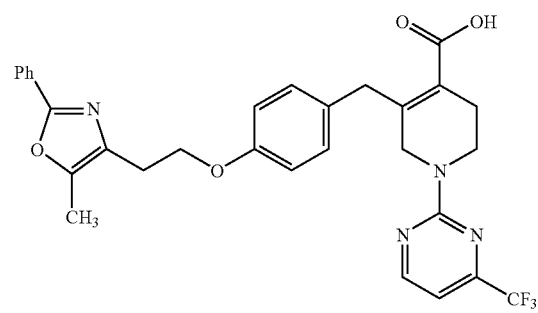

Example 363 Part A compound (76.7 mg; 0.171 mmol) was reacted with 2-chloro-4-(trifluoromethyl)pyrimidine (41.7 μL; 0.342 mmol), followed by acid-mediated hydrolysis (both steps following the general procedures described in Example 365) to give the title compound (29 mg; 30%) as white solid.

[M+H]$^+$=565.0

EXAMPLE 369

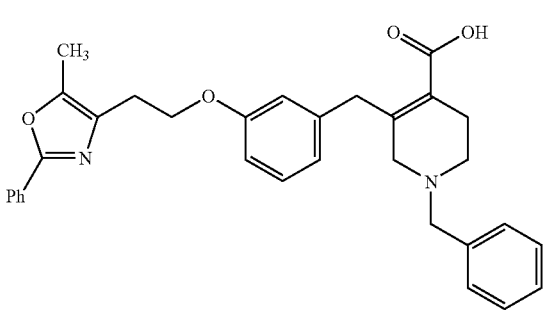

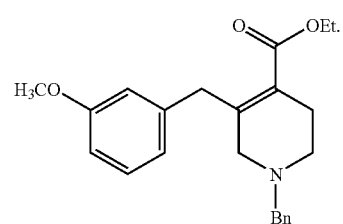

A 3-methoxybenzylzinc chloride (15 mL of a 0.5 M solution in THF, 7.47 mmol) was reacted with Example 362 Part A compound (1.85 g, 3.40 mmol) according the general procedure described for the preparation of Example 362 Part B compound to give Part A compound (0.972 g, 78%) as a light yellow oil.

[M+H]$^+$=366.5

$^1$H NMR (400 MHz, CDCl$_3$) δ 7.24-6.69 (m, 6H), 6.66-6.63 (m, 3H), 4.10 (q, J=7.1 Hz, 2H), 3.69 (s, 3H), 3.68 (s, 2H), 3.41 (s, 2H), 2.90 (s, 2H), 2.46-2.40 (m, 4H), 1.16 (t, J=7.1 Hz, 3H)

$^{13}$C NMR (400 MHz, CDCl$_3$) δ 167.6, 159.5, 145.0, 140.7, 137.7, 129.1, 128.8, 128.1, 127.0, 124.1, 121.0, 114.3, 111.3, 61.7, 60.1, 56.8, 55.0, 48.9, 38.1, 26.9, 14.1

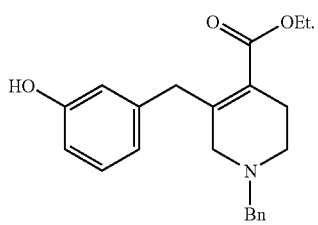

Part A Compound was subjected to BBr₃ deprotection using the general procedure described for Example 362 Part C compound. Part B compound (42%) was isolated as a brown oil.

[M+H]⁺=352.4

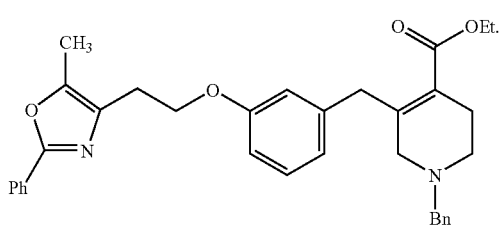

Part C compound was prepared from Part B compound as a light yellow oil (50%) following the general procedure described for the synthesis of Example 362 Part D compound.

[M+H]⁺=537.7

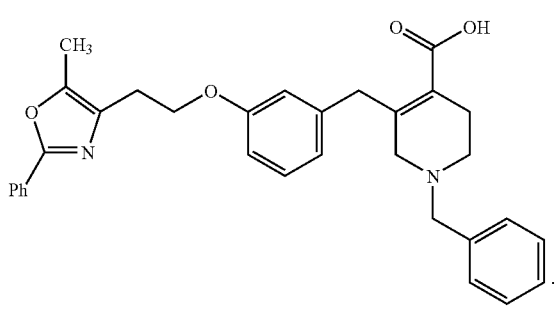

The title compound was obtained from Part C compound following the general procedure described in Example 362 Part E compound. The title compound (50%) was obtained as a brown solid.

[M+H]⁺=509.0

EXAMPLE 370

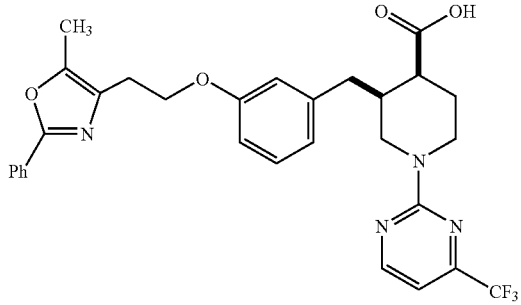

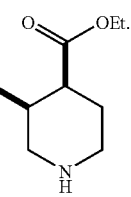

A mixture of Example 369 Part A compound (0.824 g, 2.25 mmol) and 10% Pd-C (1.65 g) in HOAc (23 mL) was stirred overnight under an atmosphere of H₂ (80 psi pressure). The catalyst was filtered off and volatiles were removed in vacuo to give Part A compound as a brown oil, which was used in the next step without further purification.

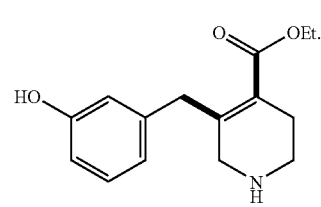

To a 0° C. solution of crude Part A compound in CH₂Cl₂ (23,mL) was added BBr₃ (11.7 mL, 11.7 mmol, 1 M in CH₂Cl₂ added slowly over 15 min. The reaction was stirred at 0° C. for 1 h, then was quenched with MeOH (1 mL) and saturated aqueous NaHCO₃ (10 mL). The organic layer was separated; the aqueous layer was extracted with CH₂Cl₂ (3×15 mL). The combined organic extracts were concentrated in vacuo to give crude Part B compound as a brown oil.

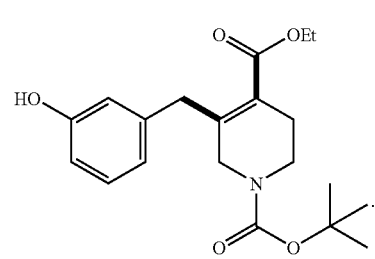

To a solution of Part B compound in 1,4-dioxane-H₂O (20 mL, 1:1 v/v) was added di-tert-butyl dicarbonate (0.419 g, 1.91 mmol) and NaHCO₃ (0.322 g, 3.83 mmol). The mixture was stirred at RT for 1 h, then was partitioned between H₂O and EtOAc (15 mL each). The aqueous layer was extracted with EtOAc (2×15 mL) and the combined organic extracts were dried (Na₂SO₄), and concentrated in vacuo. The residue was chromatographed (SiO₂; stepwise gradient from 4:1 to 65:35 hex:EtOAc) to give the title compound as a colorless oil (0.413 g, 51% yield over 3 steps).

[M+H]⁺=364.4

¹H NMR (400 MHz, CDCl₃) δ 7.05 (t, J=7.5 Hz, 1H), 6.65-6.61 (m, 3H), 4.11 (m, 2H), 3.92 (m, 1H), 3.78 (m, 1H), 2.90-2.86 (m, 2H), 2.60-2.17 (m, 4H), 1.75 (m, 2H), 1.38 (s, 9H), 1.23 (t, 7.1 Hz, 3H)

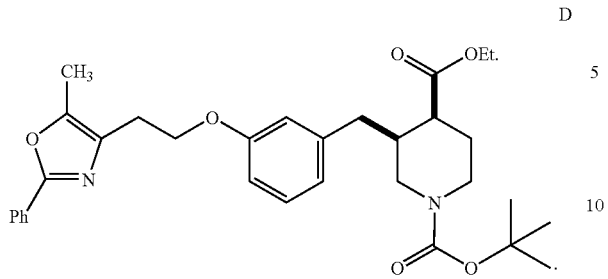

Part C compound (0.413 g, 1.13 mmol) and 2-(5-methyl-2-phenyloxazole-4-yl)ethanol (0.255 g, 1.25 mmol) were stripped from dry toluene (3×). To a mixture of these two compounds in dry toluene (12 mL) was added $Bu_3PCHCN$ (0.302 g, 1.25 mmol). The mixture was heated at 50° C. under Ar for 2 h, cooled to RT and volatiles were removed in vacuo. The residue was chromatographed ($SiO_2$; 5:1 to 7:3 hex:EtOAc) to give Part D compound as a colorless oil (0.370 g, 60%).

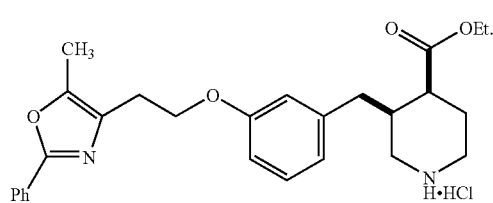

To a 0° C. solution of MeOH (4.0 mL) was slowly added acetyl chloride (1.2 mL). The mixture was stirred at 0° C. for 1 h, then was added to Part D compound (50 mg, 0.091 mmol). The mixture was stirred at 0° C. for 15 min and then was allowed to warm to RT. Volatiles were removed in vacuo to give crude Part E compound (41.1 mg, 93%), which was used in the next reaction without further purification. $[M+H]^+=449.5$

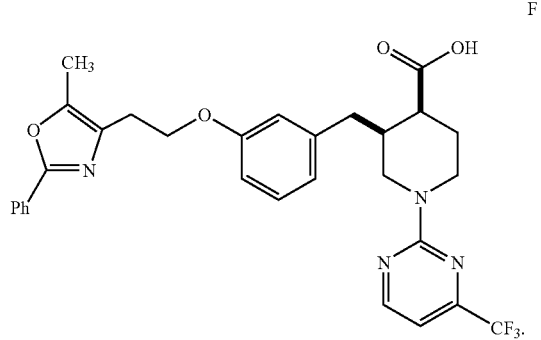

Part E compound was reacted with 2-chloro-4-(trifluoromethyl)pyrimidine using the procedure described in Example 364. The crude product from this reaction was subjected to acid-mediated hydrolysis and preparative HPLC (as for Example 363) to afford the title compound as a white solid (27% for 2 steps). $[M+H]^+=567.4$

EXAMPLE 371

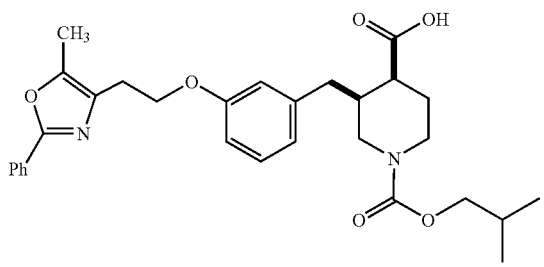

Example 370 Part E compound was reacted with iso-butyl chloroformate followed by acid-mediated hydrolysis and preparative HPLC purification (as described for Example 363) to afford the title compound as a white solid.
$[M+H]^+=521.3$

EXAMPLE 372

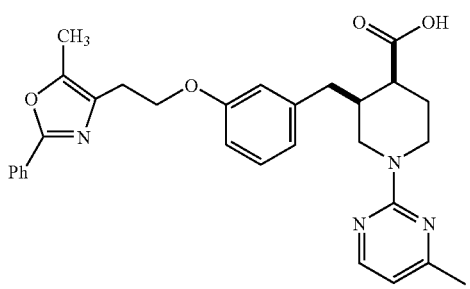

Example 370 Part E compound was reacted with 2-chloro-4-methylpyrimidine (Example 174 Part A compound) according to the general procedure described in Example 364 Part B compound. The crude product was subjected to acid hydrolysis and HPLC purification (as for Example 363) to afford the title compound as a white solid (30% yield for two steps). $[M+H]^+=513.4$

EXAMPLE 373

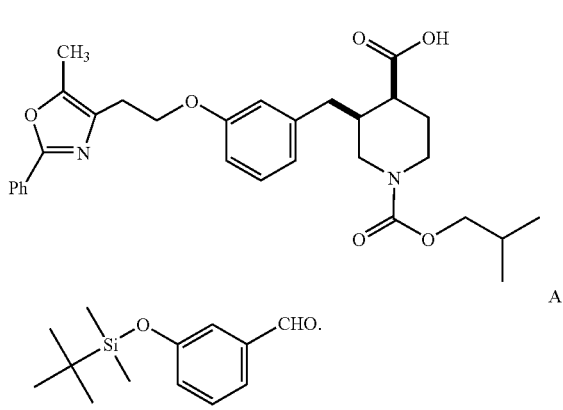

A mixture of 3-hydroxybenzaldehyde (3.59 g, 28.51 mmol), t-butyldimethylsilyl chloride (5.1 g, 32.79 mmol) and imidazole (3.92 g, 57.02 mmol) in DMF (50 mL) was stirred at RT for 2 h, then was partitioned between saturated aqueous NH₄Cl (100 mL) and Et₂O (50 mL). The aqueous phase was extracted with Et₂O (2×50 mL); the combined organic extracts were washed with H₂O (2×50 mL), brine (50 mL), dried (Na₂SO₄), and concentrated in vacuo to afford Part A Compound as a yellow oil (6.74 g, 100% yield).

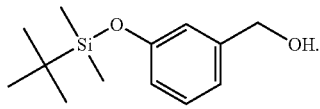
B

To a 0° C. solution of Part A compound (6.74 g; 28.5 mmol) in MeOH (100 mL) was added NaBH₄ (2.37 g, 62.7 mmol) portionwise over 10 min, and the reaction was stirred at 0° C. for 1 h. Saturated aqueous NH₄Cl (100 mL) was added, and the mixture was extracted with EtOAc (3×50 mL). The combined organic extracts were washed with H₂O (2×50 mL), brine (50 mL), dried (Na₂SO₄), and concentrated in vacuo to afford Part B compound as a yellow oil (7.41 g, 100%).

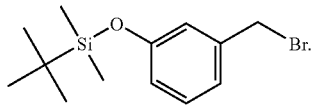
C

To a 0° C. solution of Part B compound (7.41 g; 28.5 mmol) and Ph₃P (9.44 g, 35.6 mmol) in CH₂Cl₂ (56 mL) was added CBr₄ (11.94 g, 35.6 mmol) portionwise over 10 min. The mixture was warmed to RT over 40 min, then was concentrated to ⅕ of the original volume and hexane (60 mL) was added. The precipitate was filtered off and rinsed with hexane. The combined filtrate and rinses were concentrated in vacuo, and the residue was chromatographed (SiO₂; 95:5 hex:EtOAc) to give Part C compound (10.2 g, 100%) as a colorless oil.

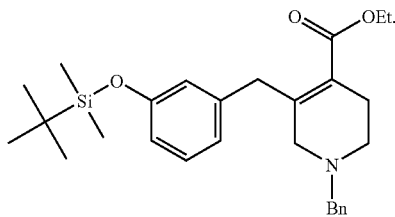
D

To a 0° C. solution of Rieke zinc (23 mL of an activated zinc powder suspension in THF [containing 5 g of Zn per 100 mL THF], 17.8 mmol) in THF (18 mL) was added a solution of Part C compound (4.10 g, 13.7 mmol) in THF (18 mL) under Ar. The mixture was stirred at RT for 3 h; excess zinc was filtered off under Ar and the benzylzinc solution was added to a mixture of 1,1'-Bis(diphenylphosphino)ferrocene (dppf) (0.156 g, 0.274 mmol) and Bis(dibenzylideneacetone)palladium (0) [Pd(dba)₂] (0.157 g, 0.274 mmol) under Ar. The mixture was stirred at RT for 30 min, after which a solution of Example 362 Part A compound (2.47 g, 4.56 mmol) in THF (18 mL) was added dropwise. The mixture was heated to 65° C. for 12 h, then cooled to RT. Saturated aqueous NaHCO₃ (60 mL) was added; solids were filtered off, and the cake was rinsed with Et₂O. The aqueous phase was extracted with Et₂O (3×30 mL). The combined organic extracts/rinses were dried (Na₂SO₄), concentrated in vacuo, and chromatographed (SiO₂; 85:15 hexane:EtOAc) to afford Part D compound as a light yellow oil (0.982 g, 46%).

[M+H]⁺=466.7

¹H NMR (400 MHz, CDCl₃) δ 7.17 (m, 5H), 7.02 (t, J=Hz, 1H), 6.70 (m, 1H), 6.60 (m, 2H), 4.11 (q, J=7.0 Hz, 2H), 3.66 (s, 2H), 3.40 (s, 2H), 2.88 (s, 2H), 2.60-2.39 (m, 4H), 1.15 (t, J=7.0 Hz, 3H), 0.89 (s, 9H), 0.10 (s, 6H)

¹³C NMR (400 MHz, CDCl₃) δ 167.7, 155.6, 145.2, 140.6, 137.9, 129.1, 128.8, 128.1, 121.7, 120.2, 117.8, 61.8, 60.1, 57.0, 49.0, 38.0, 27.0, 25.7, 18.2, 14.2

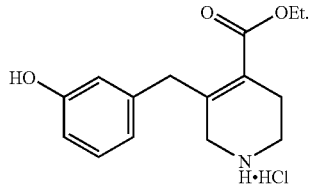
E

To a 0° C. solution of Part D compound (0.391 g, 0.842 mmol) and Proton-sponge (3 mg) in CH₂Cl₂ (8 mL) was slowly added α-chloroethyl chloroformate (0.233 mL, 2.10 mmol). The mixture was heated at 40° C. for 1 h; volatiles were removed in vacuo, and a solution of the residue in MeOH (8 mL) was heated at 40° C. for 1 h. Volatiles were removed in vacuo to afford Part E compound as a yellow oil, which was used in the next reaction without further purification. [M+H]⁺=261.3

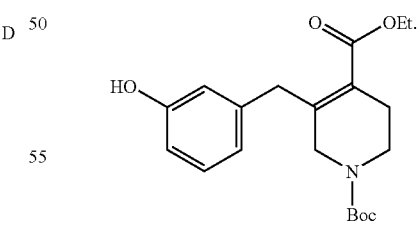
F

To a solution of compound E in 1,4-dioxane/H₂O (10 mL of a 1:1 v/v solution) was added di-tert-butyl dicarbonate (0.165 g, 0.758 mmol) and NaHCO₃ (0.212 g, 2.53 mmol). The mixture was stirred at RT for 2 h, then was partitioned between H₂O (20 mL) and CH₂Cl₂ (15 mL). The aqueous phase was extracted with CH₂Cl₂ (2×15 mL). The combined organic extracts were dried (Na₂SO₄), concentrated in vacuo, and chromatographed (SiO$_2$; 4:1 hex:EtOAc) to give Part F compound as a colorless oil (0.218 g, 72% yield over 2 steps). [M+H]$^+$=362.4

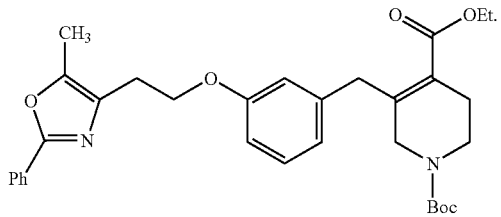

G

Part F Compound (0.218 g, 0.603 mmol) and 2-(5-methyl-2-phenyloxazole-4-yl)ethanol (0.184 g, 0.904 mmol) were stripped from dry toluene (3×), then were dissolved in dry toluene (6 mL). Bu$_3$PCHCN (0.20 mL, 0.905 mmol) was added dropwise and the mixture was heated at 60° C. under Ar for 2 h, then was cooled to RT. Volatiles were removed in vacuo, and the residue was chromatographed (SiO$_2$; gradient from 5:1 to 7:3 hex: EtOAc) to afford Part G compound as a colorless oil (0.297 g, 90%).

[M+H]$^+$=547.7

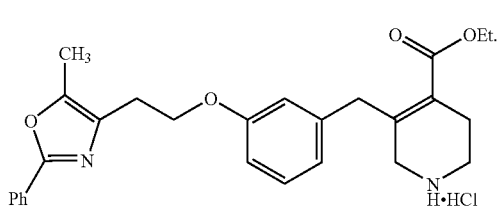

H

Part G compound was deprotected (removal of N-Boc group) using the AcCl/MeOH procedure described in Example 370 (Part E) to give Part H compound (0.263 g; 100% yield) as an oil.

[M+H]$^+$447.5

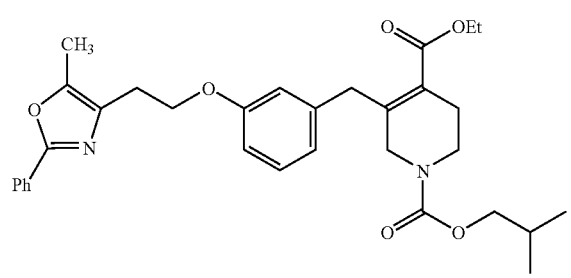

I

Part H compound (39.1 mg; 0.081 mmol) was reacted (as for Example 363) with isobutyl chloroformate (11.6 μL, 0.090 mmol) to give compound I (44.5 mg; 100%) as a light yellow oil, which was used in the next reaction without further purification. [M+H]$^+$=547.6

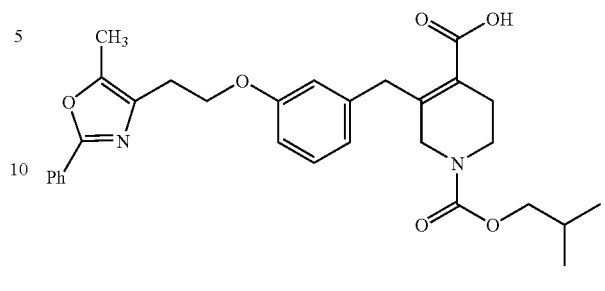

J

Part I Compound (22.2 mg; 0.040 mmol) was hydrolyzed under acid (20% HCl/HOAc) conditions as described in Example 362 Part E. The crude product was purified by preparative HPLC (YMC S5 ODS 20×250 mm column; continuous gradient from 50:50 solvent A:B to 100% solvent B; where solvent A=90:10:0.1 H$_2$O:CH$_3$CN:TFA; solvent B=90:10:0.1 CH$_3$CN:H$_2$O:TFA) to afford the title compound (38%) as a white solid. [M+H]$^+$=519.2

$^1$H NMR (400 MHz, CD$_3$OD) δ 7.96 (m, 2H), 7.47 (m, 3H), 7.16 (t, J=7.4 Hz, 1H), 6.83-6.80 (m, 3H), 4.21 (t, J=6.7 Hz, 2H), 3.89-3.50 (m, 8H), 2.97 (t, J=6.7 Hz, 2H), 2.47 (s, 2H), 2.38 (s, 3H), 2.00-1.60 (m, 1H), 0.92-0.71 (br., 6H)

$^{13}$C NMR (100.6 MHz, CD$_3$OD) δ 169.2, 159.5, 158.5, 155.3, 140.1, 131.6, 130.2, 129.1, 128.5, 125.7, 124.6, 120.9, 114.8, 112.1, 71.4, 66.0, 46.3, 40.0, 37.2, 27.5, 26.0, 25.6, 18.4, 9.6

EXAMPLES 374-380

Examples 374-380 of the invention were prepared according to the general procedures described for the syntheses of Examples 363, 364, 370 and 373.

| Example No | R | [M + H]+ |
|---|---|---|
| 374 | phenyl carbonate | 539.2 |
| 375 | ethyl carbonate | 491.2 |
| 376 | 4-(trifluoromethyl)pyrimidin-2-yl | 565.0 |

-continued

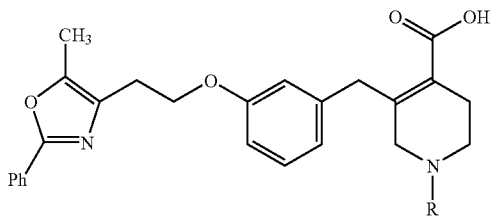

| Example No | R | [M + H]+ |
|---|---|---|
| 377 | 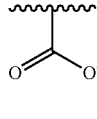 | 553.2 |
| 378 | 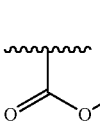 | 569.1 |
| 379 | 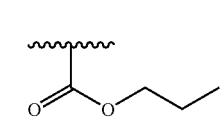 | 505.1 |
| 380 | 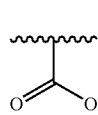 | 519.6 |

EXAMPLE 381

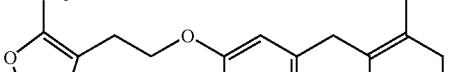

A solution of Example 373 Part I compound (24 mg, 0.044 mmol), LiOH.H$_2$O (4.2 mg, 0.175 mmol) and MeOH (1 drop) in THF-H$_2$O (1.5 mL, 2:1 v/v) was stirred at RT for 3 h. The reaction was acidified to pH 2 with 1 N aqueous HCl, then was extracted with EtOAc (3×5 mL). The combined organic extracts were concentrated in vacuo and the residue was purified by preparative HPLC (YMC S5 ODS 20×250 mm column; continuous gradient from 50:50 solvent A:B to 100% solvent B; where solvent A=90:10: 0.1H$_2$O:CH$_3$CN:TFA; solvent B=90:10:0.1 CH$_3$CN:H$_2$O: TFA) to give the title compound (11.9 mg, 52%) as a white solid.

[M+H]$^+$=519.2

$^1$H NMR (400 MHz, CD$_3$OD) δ 7.95 (m, 2H), 7.46 (m, 3H), 7.18 (t, J=7.9 Hz, 1H), 6.85-6.66 (m, 4H), 4.22 (br. S, 2H), 4.95-4.85 (m, 3H), 3.40 (m, 3H), 2.98 (t, J=6.6 Hz, 2H), 2.90 (m, 1H), 2.38 (s, 3H), 2.10-1.73 (m, 3H), 0.94 (d, J=6.6 Hz, 3H), 0.84 (d, J=6.6 Hz, 3H)

$^{13}$C NMR (125.7 MHz, DMSO-d$_6$, t=100° C.) δ 174.4, 159.2, 159.0, 153.2, 145.2, 141.5, 133.4, 130.3, 129.7, 129.3, 128.0, 126.1, 123.7, 121.9, 116.0, 115.3, 113.1, 71.9, 70.0, 40.7, 40.2, 39.6, 28.0, 26.4, 25.0, 19.2, 10.2

EXAMPLES 382-389

Examples 382-389 of the invention were prepared according to the procedures described for the synthesis of Example 373 and Example 381.

| Example No. | Structure | [M + H]+ |
|---|---|---|
| 382 | 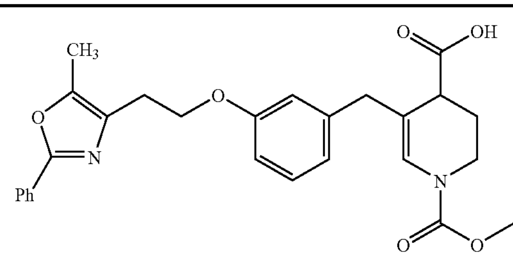 | 477.0 |
| 383 | 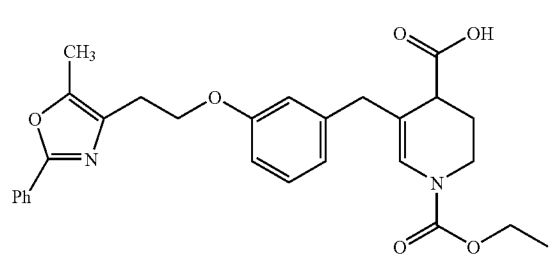 | 491.2 |

-continued

| Example No. | Structure | [M + H]+ |
|---|---|---|
| 384 | 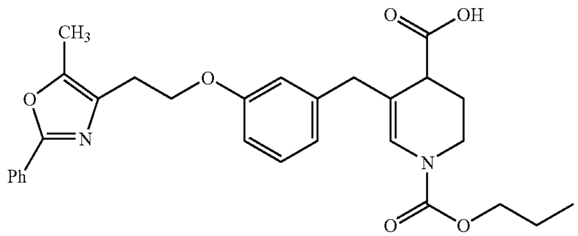 | 505.1 |
| 385 | 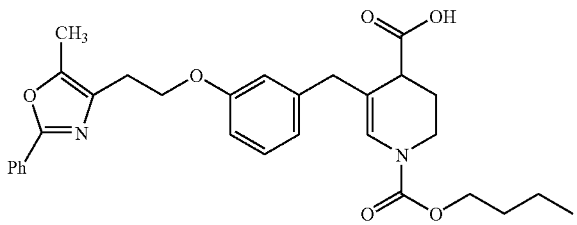 | 519.1 |
| 386 | 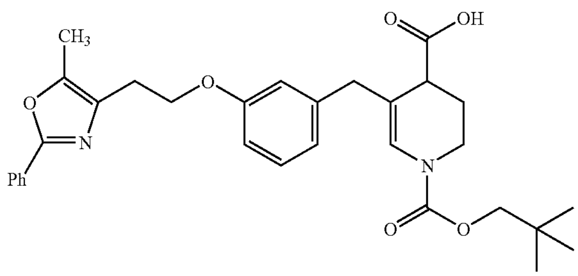 | 533.1 |
| 387 | 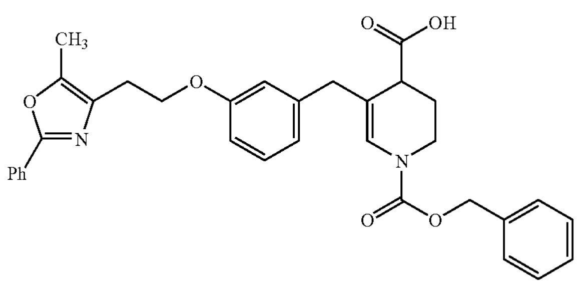 | 553.2 |
| 388 | 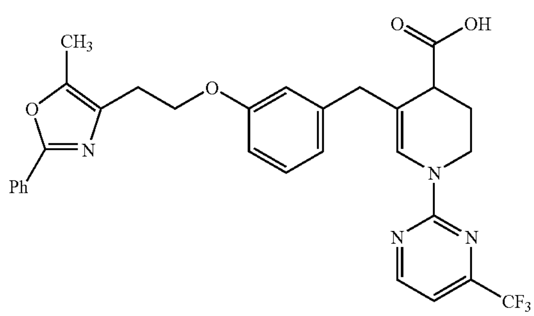 | 565.1 |
| 389 | 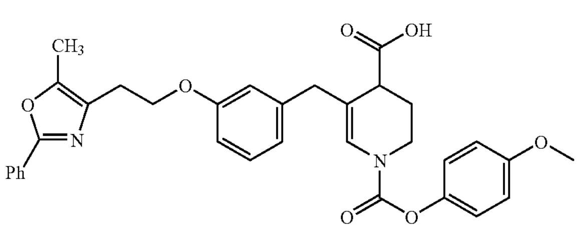 | 569.1 |

EXAMPLE 390

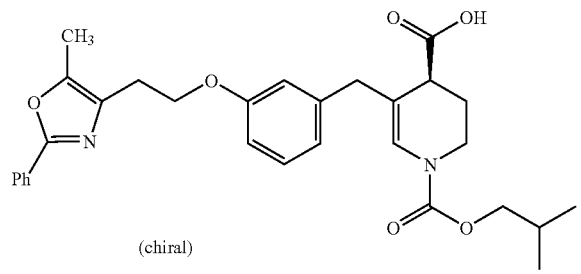

(chiral)

The two individual enantiomers of Example 381 (racemate; 50 mg) were separated by preparative HPLC (Chiralpak® AD chiral column; 5 cm×50 cm, 20μ, Chiral Technologies Inc; isocratic solvent system: 6% i-PrOH/heptane; Flow rate=40 mL/min). The faster eluting fraction (single enantiomer) was characterized as Example 390 (absolute stereochemistry arbitrarily assigned): retention time=45 min; 22.5 mg, white solid, 90% recovery, >99% e.e., $[M+H]^+=519.2$, $[\alpha]_{24}^D=-108.8°$ (c=0.358 g/100 mL, MeCN).

The slower eluting fraction (single enantiomer), was characterized as Example 391 (absolute stereochemistry arbitrarily assigned): retention time=60 min; 17.6 mg, white solid, 70% recovery, >99% e.e.). $[M+H]^+=519.2$, $[\alpha]_{24}^D=+100.3°$ (c=0.50 g/100 mL, MeCN)

EXAMPLE 391

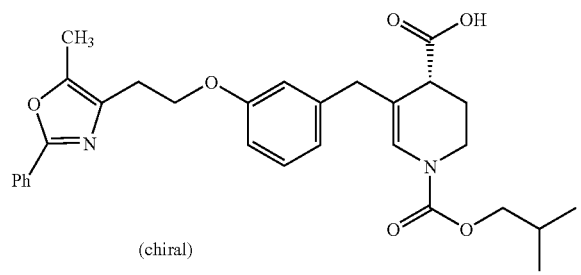

(chiral)

EXAMPLE 392

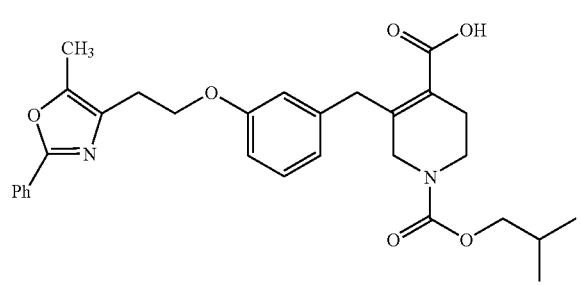

-continued

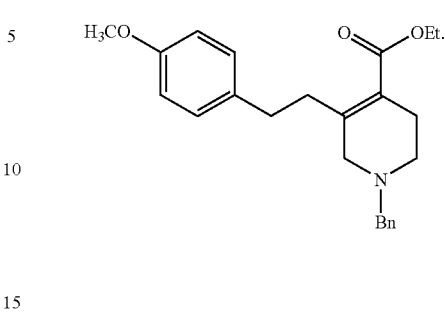

A

To a 0° C. solution of $ZnCl_2$ in THF (12.65 mL of a 1 M solution, 12.65 mmol) was added 4-methoxyphenethyl magnesium chloride in THF (19.5 mL of a 0.5 M solution, 9.73 mmol) dropwise. After stirring for 40 min at 0° C., bis (dibenzylideneacetone)palladium (0) $[Pd(dba)_2]$ (0.153 g, 0.265 mmol) and 1,1'-bis(diphenylphosphino)ferrocene (dppf) (0.152 g, 0.265 mmol) were added. The reagent mixture was stirred at RT for 10 min, after which a solution of Example 362 Part A compound (2.4 g, 4.42 mmol) in THF (18 mL) was added dropwise. The reaction was heated at 65° C. for 12 h, then cooled to RT and concentrated in vacuo. The residue was partitioned between $CH_2Cl_2$ (80 mL) and saturated aqueous $NaHCO_3$ (40 mL) The aqueous phase was extracted with $CH_2Cl_2$ (4×30 mL). The combined organic extracts were dried ($K_2CO_3$), concentrated in vacuo and the residue was chromatographed ($SiO_2$; 85:15 hex:EtOAc) to afford Part A compound as a light yellow oil (0.989 g, 59%). $[M+H]^+=380.5$ $^1H$ NMR (400 MHz, $CDCl_3$) δ 7.35-7.24 (m, 5H), 7.15 (d, J=7.9 Hz, 2H), 6.83 (d, J=7.4 Hz, 2H), 4.21 (q, J=7.0 Hz, 2H), 3.76 (s, 3H), 3.58 (s, 2H), 3.03 (s, 2H), 2.73-2.47 (m, 8H), 1.30 (t, J=7.0 Hz, 3H)

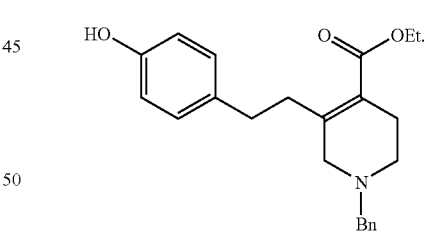

B

To a 0° C. solution of Part A compound (0.483 g, 1.273 mmol) in $CH_2Cl_2$ (13 mL) was added dropwise $BBr_3$ in $CH_2Cl_2$ (3.2 mL of a 1.0 M solution; 3.20 mmol). The mixture was stirred at 0° C. for 1.5 h. EtOH (1 mL) and saturated aqueous $NaHCO_3$ (10 mL) were subsequently added to quench the reaction. The aqueous phase was further extracted with $CH_2Cl_2$ (3×10 mL). The combined organic extracts were dried $Na_2SO_4$ and concentrated in vacuo. The residue was chromatographed ($SiO_2$; 3:1 hex:EtOAc) to afford Part B compound (0.443 g, 95%) as a light yellow solid.

C

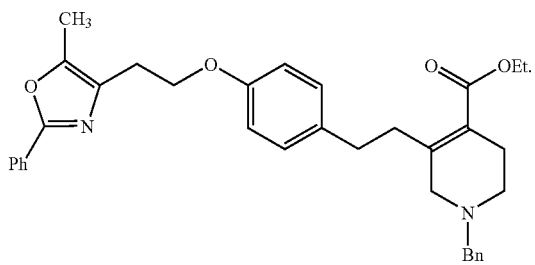

Part B compound (0.443 g, 1.212 mmol) and Example 23 Part A compound (0.426 g, 1.516 mmol) were stripped from dry toluene (3×), then were dissolved in anhydrous MeCN (12 mL) and anhydrous $K_2CO_3$ (0.503 g, 3.63 mmol) was added. The reaction mixture was stirred at 90° C. overnight. Additional Example 23 Part A compound (0.341 g, 1.21 mmol) was added, and the reaction was kept at 90° C. for another 4 h. Volatiles were removed in vacuo, and the residue was dissolved in water (15 mL) and extracted with $CH_2Cl_2$ (3×15 mL) The combined organic extracts were dried ($K_2CO_3$) and concentrated in vacuo. The residue was chromatographed ($SiO_2$; 4:1 hex:EtOAc) to afford Part C compound (0.400 g, 60%) as a light yellow oil.

D

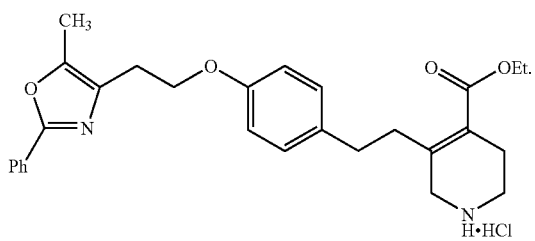

Part C Compound (0.216 g, 0.394 mmol) and Proton Sponge [1,8-bis(dimethylamino)naphthalene] (4.0 mg) were stripped from dry toluene (2×), then dissolved in $CH_2Cl_2$ (4 mL). To this 0° C. solution was added dropwise α-chloroethyl chloroformate (0.10 mL, 0.906 mmol). The reaction was allowed to warm to RT, then heated to 40° C. under Ar for 1 h. Volatiles were removed in vacuo; MeOH (4 mL) was added, and the mixture was heated at 50° C. for 1 h. Volatiles were removed in vacuo to afford crude Part D compound (0.156 g, 80% yield) as a light yellow oil, which was used in the next step without further purification. [M+H]$^+$=461.5

E

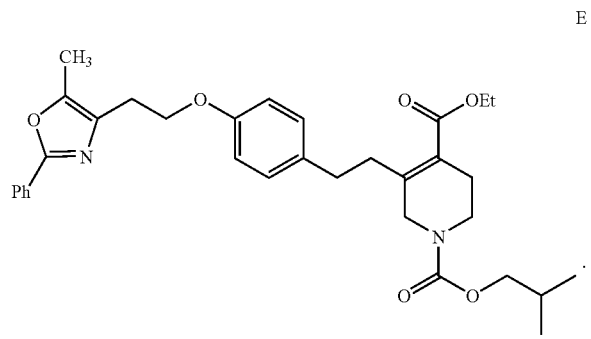

Part E compound was prepared from Part D compound and isobutyl chloroformate according to the procedure described for the synthesis of Example 363 Part B compound.

F

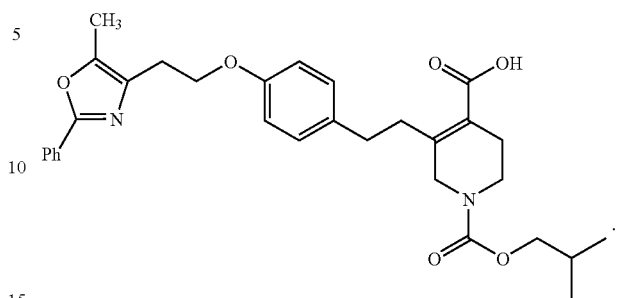

The title compound (white solid; 60% overall for 2 steps) was prepared from Part E compound by acid-mediated hydrolysis followed by purification by preparative HPLC according to the procedure described for the synthesis of Example 363.
[M+H]$^+$=533.5

EXAMPLE 393

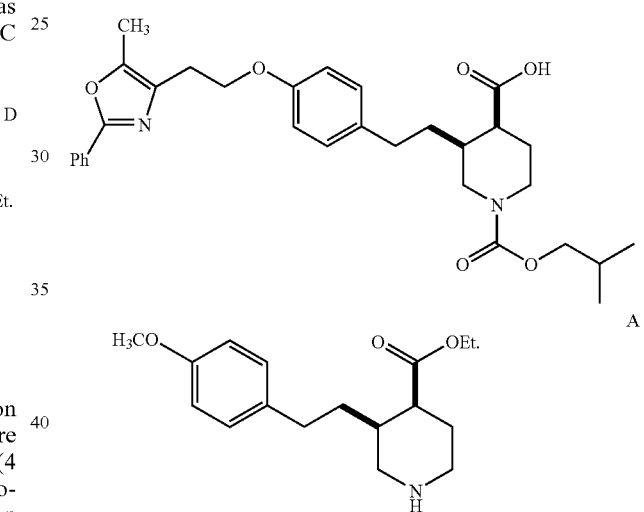

A

A mixture of Example 392 Part A Compound (0.506 g, 1.33 mmol) and 10% Pd/C (1.02 g) in HOAc (14 mL) was stirred under an atmosphere of $H_2$ (80 psi pressure) overnight, after which the catalyst was filtered off. The filtrate was concentrated in vacuo to give crude Part A compound as a brown oil.

B

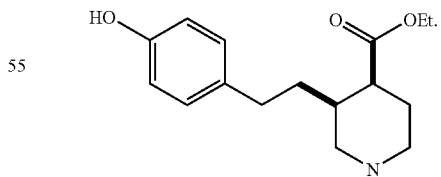

To a 0° C. solution of crude Part A compound in $CH_2Cl_2$ (13 mL) was added $BBr_3$ (4.0 mL, 4.0 mmol, 1 M in $CH_2Cl_2$) dropwise over ~15 min. The mixture was stirred at 0° C. for 1 h. MeOH (1 mL) and saturated aqueous $NaHCO_3$ (10 mL) was added slowly to quench the reaction, which was partitioned between water and $CH_2Cl_2$. The aqueous layer was extracted with $CH_2Cl_2$ (2×15 mL). The combined organic extracts were concentrated under reduced pressure to afford crude Part B compound as a brown oil.

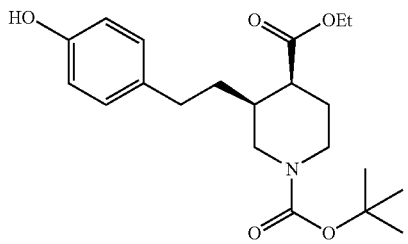

C

A solution of crude Part B compound, di-tert-butyl dicarbonate (0.291 g, 1.334 mmol) and NaHCO$_3$ (0.448 g, 5.33 mmol) in 1,4-dioxane-H$_2$O (13.4 mL, 1:1 v/v) was stirred at RT for 1 h, then was partitioned between H$_2$O and EtOAc (15 mL each). The aqueous phase was extracted with EtOAc (2×15 mL). The combined organic extracts were dried (Na$_2$SO$_4$) and concentrated in vacuo. The residue was chromatographed (SiO$_2$; 7:3 hex:EtOAc) to give Part C compound as a white solid (0.277 g, 55% yield over 3 steps).

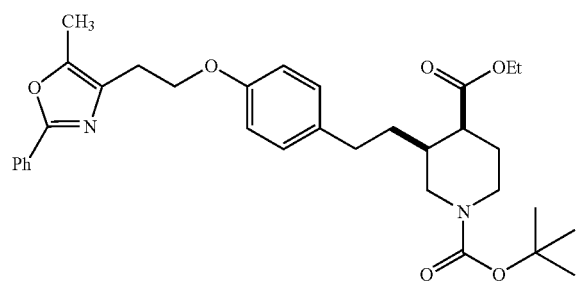

D

Part C Compound (0.277 g, 0.734 mmol) and 2-(5-methyl-2-phenyloxazole-4-yl)ethanol (0.224 g, 1.102 mmol) were stripped from dry toluene (3×), then were dissolved in dry toluene (7.4 mL) and Bu$_3$PCHCN (0.266 g, 1.102 mmol) was added. The mixture was heated at 50° C. under Ar for 2 h, then cooled to RT and volatiles were removed in vacuo. The residue was purified (SiO$_2$; 3:1 hex:EtOAc) to give Part D compound as a colorless oil (0.373 g, 90%).

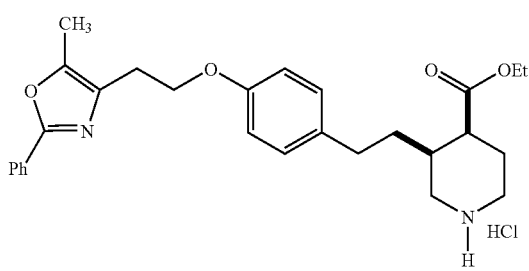

E

The deprotection of the N-Boc group of Part D compound (64 mg, 0.114 mmol) was carried out using the AcCl/MeOH procedure described for the synthesis of Example 370 Part E compound to give Part E compound (56.7 mg, 100%) as an oil.

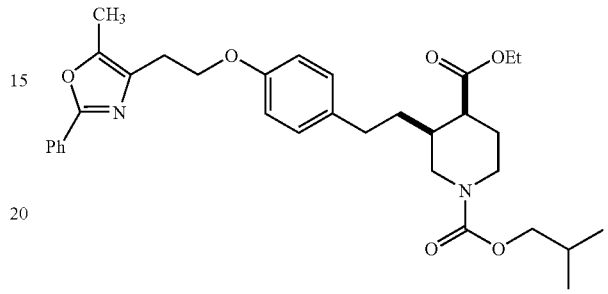

F

Part F compound was prepared from Part E compound and isobutyl chloroformate according to the procedure described for the synthesis of Example 363 Part B compound.

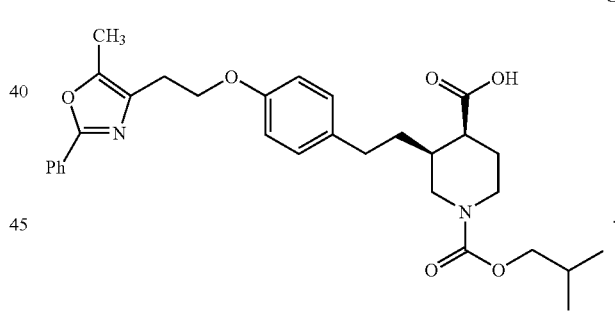

G

The title compound (white solid) was prepared from Part F compound by acid-mediated hydrolysis and purified by preparative HPLC according to the procedure described for the synthesis of Example 363.

[M+H]$^+$=535.4

EXAMPLES 394-399

Examples 394-399 of the invention were prepared according to the procedures described for the synthesis of Example 392 and Example 393. The N-pyrimidine compounds were synthesized using the procedure described for the synthesis of Example 364 Part B compound.

| Example No. | Structure | [M + H]+ |
|---|---|---|
| 394 | 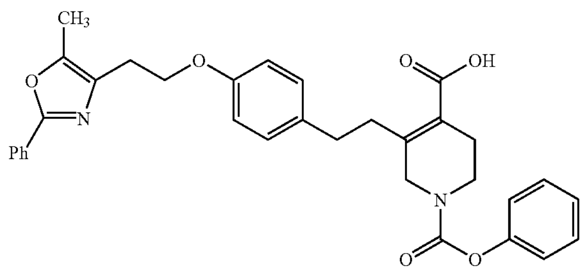 | 553.5 |
| 395 | 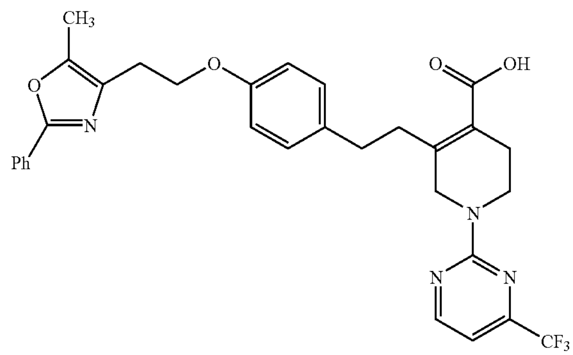 | 579.5 |
| 396 | 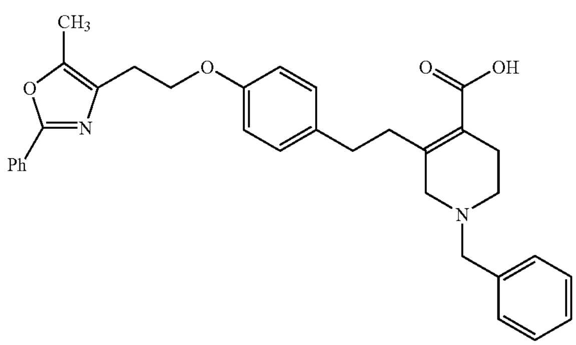 | 523.4 |
| 397 | 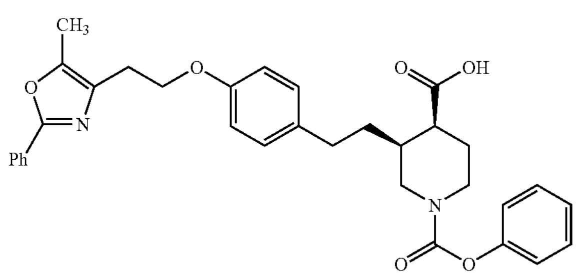 | 555.4 |
| 398 | 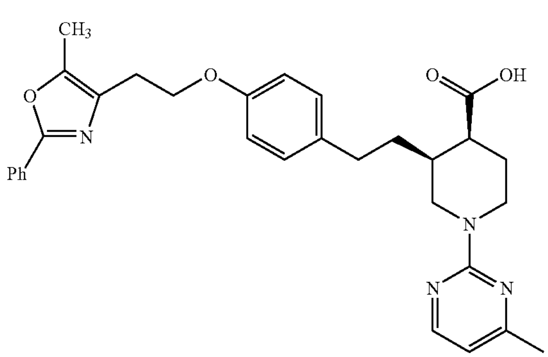 | 527.3 |

| Example No. | Structure | [M + H]+ |
|---|---|---|
| 399 | 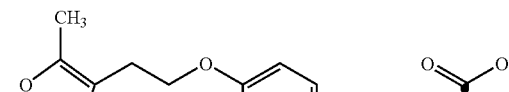 | 581.4 |

EXAMPLE 400

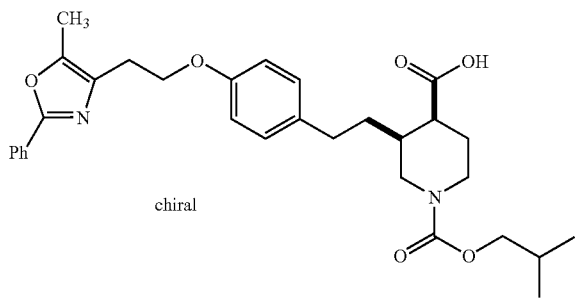

The two individual enantiomers of Example 393 (racemate; 30 mg) were separated by preparative HPLC: (Chiralcel® OJ chiral column; 2 cm×25 cm, Chiral Technologies Inc; isocratic solvent system: 15% EtOH-MeOH (1:1) with 0.1% TFA+85% heptane (0.1% TFA); flow rate=7 mL/min. The faster eluting fraction (enantiomer) was characterized as Example 400 (absolute stereochemistry arbitrarily assigned): retention time=45 min; 13.6 mg, white solid, 90% recovery, >99% e.e., [M+H]$^+$=535.1,

[α]$_{24}^D$=−10.3° (c=0.15 g/100 mL, MeCN).

The slower eluting fraction (enantiomer), was characterized as Example 401 (absolute stereochemistry arbitrarily assigned): retention time=72 min; 12.2 mg, white solid, 81% recovery, >99% e.e.). [M+H]$^+$=535.2,

[α]$_{24}^D$=+9.6° (c=0.54 g/100 mL, MeCN)

EXAMPLE 401

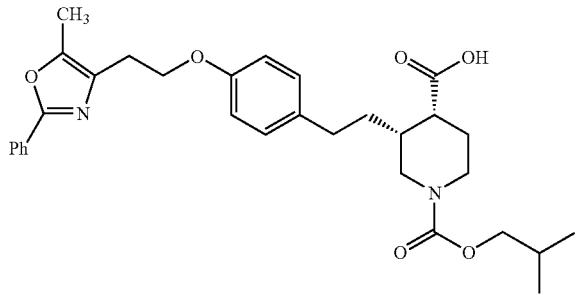

EXAMPLE 402

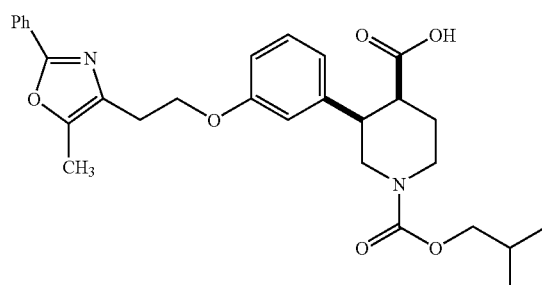

A

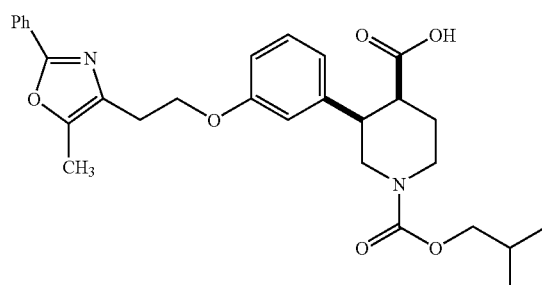

Example 362 Part A compound (1.93 g, 3.55 mmol) was reacted 3-methoxyphenyl magnesium chloride (7.8 mL, 1 M solution in THF, 7.8 mmol) according to the procedure described in Example 392 Part A to give Part A compound (0.745 g, 60%) as a light yellow oil.

[M+H]$^+$=352.4

$^1$H NMR (400 MHz, CDCl$_3$) δ 7.38-7.27 (m, 6H), 6.82 (m, 1H), 6.75-6.70 (m, 2H), 3.93 (q, J=7.1 Hz, 2H), 3.77 (s, 3H), 3.67 (s, 2H), 3.28 (s, 2H), 2.80-2.5.6 (m, 4H), 0.90 (t, J=7.1 Hz, 3H)

$^{13}$C NMR (100 MHz, CDCl$_3$) δ 168.1, 159.1, 144.4, 141.8, 137.3, 129.7, 129.0, 128.8, 128.2, 127.1, 125.5, 119.5, 112.8, 112.7, 61.8, 59.9, 58.1, 55.0, 48.8, 26.7, 13.4

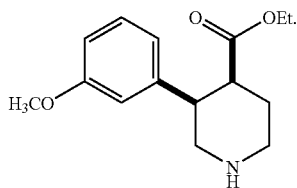

B

A mixture of Part A compound (0.241 g, 0.687 mmol) and 10% Pd/C (0.48 g) in HOAc (10 mL) mixture was stirred under an atmosphere of $H_2$ (80 psi) for 24 h. The catalyst was filtered off, and the filtrate was concentrated in vacuo to give crude Part B compound as a brown oil.

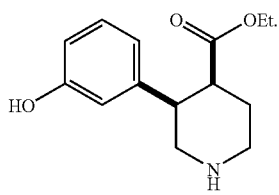

C

To a 0° C. solution of crude Part B compound in $CH_2Cl_2$ (6.8 mL) was slowly added $BBr_3$ (3.41 mL, 3.41 mmol, 1 M in $CH_2Cl_2$) over 15 min. The mixture was stirred at 0° C. for 1 h. MeOH (1 mL) and saturated aqueous $NaHCO_3$ (10 mL) were slowly added to quench the reaction. The aqueous layer was extracted with $CH_2Cl_2$ (3×10 mL). The combined organic extracts were concentrated in vacuo to give crude Part C compound as a brown oil.

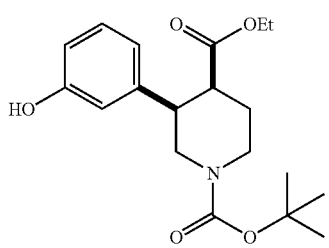

D

A solution of crude Part C compound, di-tert-butyl dicarbonate (0.151 g, 0.687 mmol) and $NaHCO_3$ (0.230 g, 2.74 mmol) in 1,4-dioxane-$H_2O$ (4.0 mL, 1:1 v/v) was stirred at RT for 1 h. $H_2O$ (15 mL) was added and the mixture was extracted with EtOAc (3×10 mL). The combined organic extracts were dried ($Na_2SO_4$) and concentrated in vacuo. The residue was chromatographed ($SiO_2$; 3:1 hex:EtOAc) to give Part D compound as a colorless oil (0.106 g, 45% yield over 3 steps).

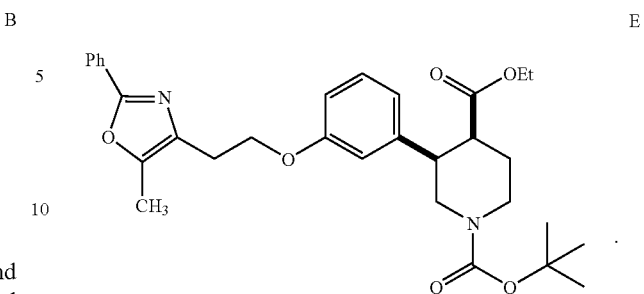

E

Part D Compound (0.105 g, 0.300 mmol) and 2-(5-methyl-2-phenyloxazole-4-yl)ethanol (0.092 g, 0.450 mmol) were stripped from dry toluene (3×), then were dissolved in dry toluene (3.0 mL) and $Bu_3PCHCN$ (0.108 g, 0.450 mmol) was added. The mixture was heated at 50° C. under Ar for 2 h, then cooled to RT and concentrated in vacuo. The residue was chromatographed ($SiO_2$; 3:1 hex: EtOAc) to give Part E compound as a colorless oil (0.119 g, 75%).

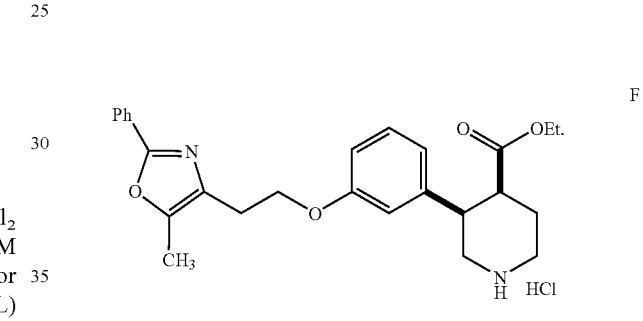

F

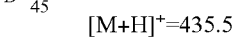

To MeOH (12.5 mL) at 0° C. was slowly added acetyl chloride (3.2 mL). The solution was stirred 0° C. for 1 h, then was added to Part E compound (0.119 g, 0.223 mmol). The mixture was stirred at 0° C. for 15 min and then gradually warmed to RT. Volatiles were removed in vacuo to give crude Part F compound (99.9 mg, 95%), which was used in the next reaction without further purification.

$[M+H]^+=435.5$

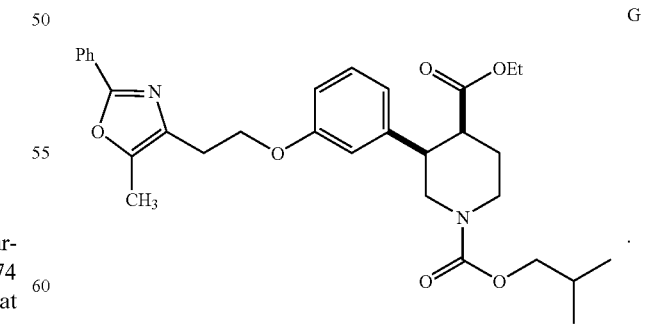

G

Part G compound was prepared from Part F compound and isobutyl chloroformate according to the procedure described for the synthesis of Example 363 Part B compound.

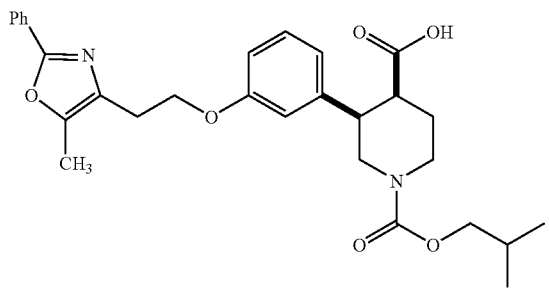

The title compound (white solid) was prepared from Part G compound by acid-mediated hydrolysis and purified by preparative HPLC according to the procedure described for the synthesis of Example 363.

[M+H]$^+$=507.2

EXAMPLES 403-405

Examples 403-405 of the invention were prepared according to the procedures described for the synthesis of Example 402. The N-pyrimidine compounds were synthesized using the procedure described for the synthesis of Example 364 Part B compound.

| Example No. | Structure | [M + H]+ |
|---|---|---|
| 403 | 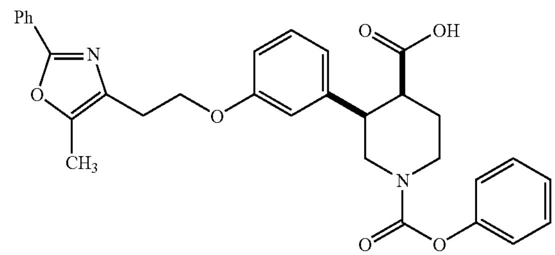 | 527.2 |
| 404 | 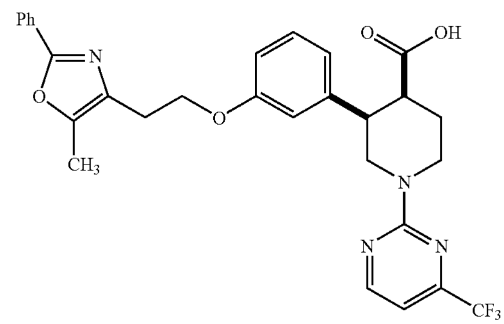 | 553.2 |
| 405 | 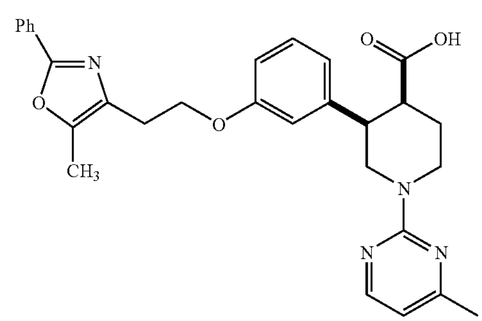 | 499.2 |

EXAMPLE 406

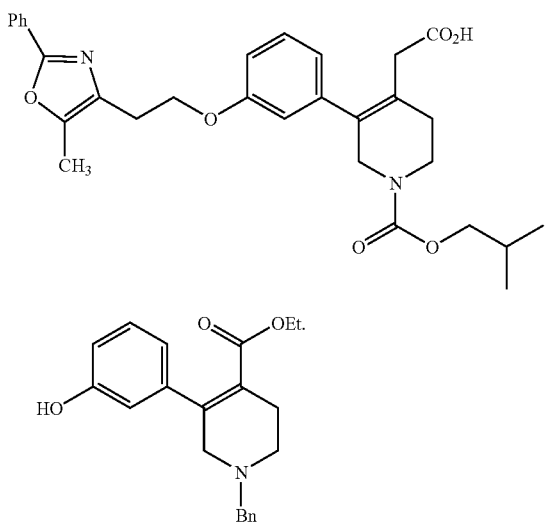

To a solution of Example 362 Part A Compound (1.68 g, 3.11 mmol) and 3-hydroxyphenylboronic acid (0.86 g, 6.22 mmol) in 1,4-dioxane (31 mL) were added Pd(PPh$_3$)$_4$ (1.08 g, 0.933 mmol), LiCl (0.263 g, 6.21 mmol), and aqueous K$_2$CO$_3$ (3.1 mL of a 2 M solution, 6.21 mmol). The mixture was heated at 115° C. under Ar for 12 h, then was cooled to RT. Precipitates were filtered off. H$_2$O (40 mL) was added, and the mixture was extracted with CH$_2$Cl$_2$ (3×20 mL). The combined organic extracts were dried (NaHCO$_3$) and concentrated in vacuo. The residue was chromatographed (SiO$_2$; 7:3 hex:EtOAc) to give Part A compound (1.03 g, 95%) as a colorless oil.

$^1$H NMR (500 MHz, CDCl$_3$) δ 8.33 (br s, 1H), 7.37-6.34 (m, 9H), 3.85 (q, t=7.0 Hz, 2H), 3.70 (s, 2H), 3.24 (s, 2H), 2.76 (m, 2H), 2.62 (m, 2H), 0.83 (t, J=7.0 Hz, 3H)

$^{13}$C NMR (125 MHz, CDCl$_3$) δ 168.3, 156.2, 144.2, 141.3, 135.4, 129.7, 129.2, 128.3, 127.6, 125.4, 118.7, 115.0, 114.0, 107.5, 103.0, 61.9, 60.3, 57.3, 48.8, 26.0, 13.3

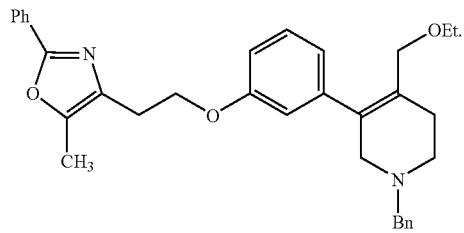

Part A compound (1.0 g, 2.97 mmol) and Example 23 Part A compound (1.04 g, 3.70 mmol) were stripped from dry toluene (3×), then were dissolved in anhydrous MeCN (30 mL); finally anhydrous K$_2$CO$_3$ (1.64 g, 11.86 mmol) was added. The reaction was stirred at 90° C. overnight. More Example 23 Part A compound (0.416 g, 1.48 mmol) was added and the mixture was stirred at 90° C. for another 4 h. Volatiles were removed in vacuo, and the residue was dissolved in water (30 mL) and extracted with CH$_2$Cl$_2$ (3×20 mL). The combined organic extracts were dried (K$_2$CO$_3$) and concentrated in vacuo. The residue was chromatographed (SiO$_2$; 7:3 hex:EtOAc) to give Part B compound (0.93 g, 60%) as a light yellow oil.

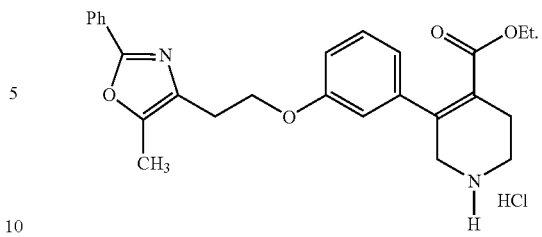

Part B compound (0.594 g; 1.14 mmol) was converted to Part C Compound using the procedure described in Example 373 Part E. Part C compound was obtained as an oil, which was used in the next step without further purification. [M+H]$^+$=433.5

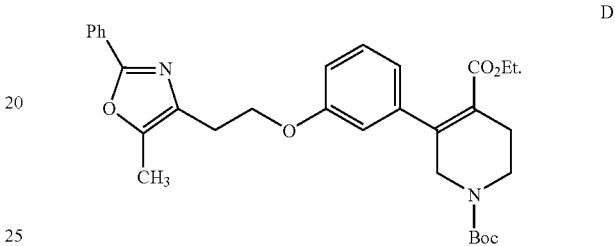

To a solution of Part C compound in 1,4-dioxane/H$_2$O (22 mL of a 1:1 v/v solution) was added di-tert-butyl dicarbonate (0.25 g, 1.137 mmol) and NaHCO$_3$ (0.24 g, 2.84 mmol). The mixture was stirred at RT for 2 h, then was partitioned between H$_2$O (20 mL) and CH$_2$Cl$_2$ (15 mL). The aqueous phase was extracted with CH$_2$Cl$_2$ (2×15 mL). The combined organic extracts were dried (Na$_2$SO$_4$), concentrated in vacuo, and chromatographed (SiO$_2$; 4:1 hex:EtOAc) to give Part D compound as a colorless oil (0.55 g, 91% yield over 2 steps). [M+H]$^+$=533.6

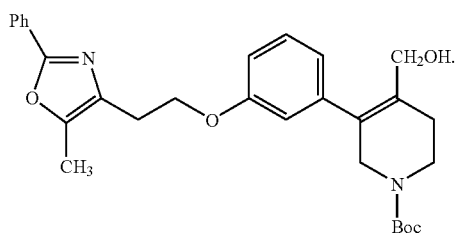

To a solution of Part D compound (0.55 g, 1.04 mmol) in THF (10 mL) at −78° C. was added LiAlH$_4$ in THF (1.56 mL of a 1 M solution, 1.56 mmol). The reaction was gradually warmed to 10° C. and stirred for 12 h. Saturated aqueous NH$_4$Cl solution (10 mL) was added; precipitates were filtered off. The aqueous phase was extracted with CH$_2$Cl$_2$ (3×10 mL). The combined organic extracts were dried (Na$_2$SO$_4$), concentrated in vacuo and chromatographed (SiO$_2$; 55:45 hex:EtOAc) to give Part E compound (0.389 g, 76%) as a white solid. [M+H]$^+$=491.6

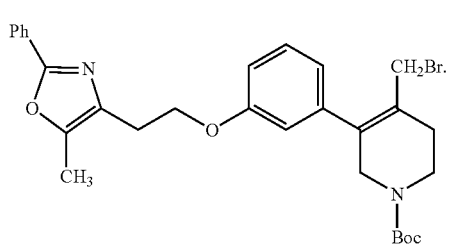

To a 0° C. solution of Part E Compound (0.389 g, 0.792 mmol) and PPh₃ (0.262 g, 0.991 mmol) in CH₂Cl₂ (8 mL) was added CBr₄ (0.332 g, 0.991 mmol) portionwise. The mixture was slowly warmed to RT and stirred at RT for 2 h. Volatiles were removed in vacuo, and the residue was chromatographed (SiO₂; continuous gradient from 90:10 to 85:15 hex:EtOAc)) to afford Part F compound (0.407 g, 93%) as a light yellow oil.

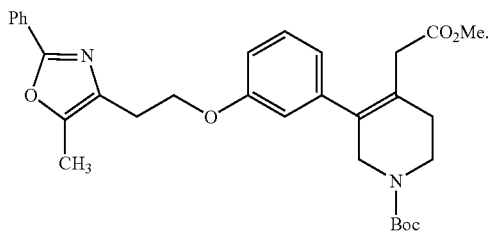

G

To a solution of Part F compound (0.371 g, 0.671 mmol) and (PPh₃P)₄Pd (0.155 g, 0.134 mmol) in MeOH (8 mL) was added KHCO₃ (0.268 g, 2.68 mmol) The mixture stirred at RT overnight under a pressure of 100 psi of CO gas in a stainless steel bomb. Volatiles were removed in vacuo and the residue was taken up in H₂O (10 mL) and extracted with CH₂Cl₂ (3×10 mL). The combined organic extracts were dried (Na₂SO₄), concentrated in vacuo, and chromatographed (4:1 hex:EtOAc) to afford Part G compound (0.218 g, 61%) as a colorless oil.

$[M+H]^+=533.6$

¹H NMR (400 MHz, CDCl₃) δ 7.91 (dd, J=2.0 & 7.9 Hz, 2H), 7.33 (m, 3H), 7.17 (s 1H), 7.16 (d, J=10.6 Hz, 1H), 6.76 (d, J=6.3 Hz, 1H), 6.68 (d, J=-6.3 Hz, 1H), 4.16 (t, J=6.6 Hz, 2H), 3.96 (s, 2H), 3.56 (s, 3H), 3.50 (t, J=5.5 Hz, 2H), 2.91 (m, 4H), 2.30 (s, 3H), 2.15 (br. s, 2H), 1.39 (s, 9H)

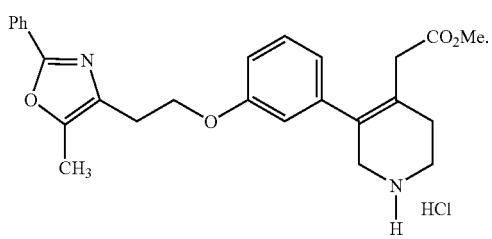

H

Compound G (0.218 g; 0.410 mmol) was subjected to the acetyl chloride/MeOH deprotection conditions (as for Example 402 Part F compound) for the deprotection of the N-Boc group to give Part H compound as the HCl salt (0.171 g; 89%). $[M+H]^+=433.5$

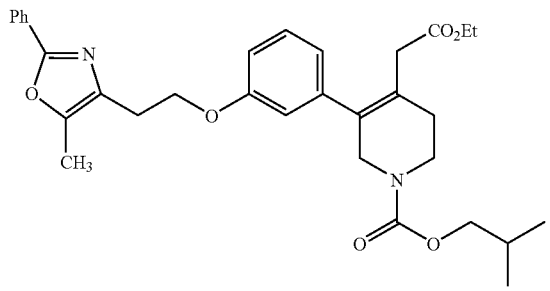

I

Part I compound was prepared from Part H compound and isobutyl chloroformate according to the procedure described for the synthesis of Example 363 Part B compound.

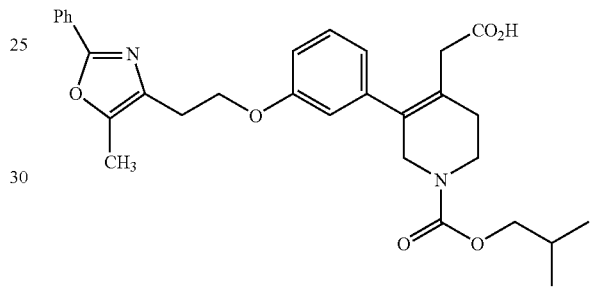

J

The title compound (white solid) was prepared from Part G compound by acid-mediated hydrolysis and purified by preparative HPLC according to the procedure described for the synthesis of Example 363.

$[M+H]^+=519.3$

EXAMPLES 407-408

Examples 407-408 of the invention were prepared according to the procedures described for the synthesis of Example 406. The N-pyrimidine compound was synthesized using the procedure described for the synthesis of Example 364 Part B compound.

| Example No | Structure | [M + H]+ |
|---|---|---|
| 407 | ![structure] | 539.2 |

-continued

| Example No | Structure | [M + H]+ |
|---|---|---|
| 408 | 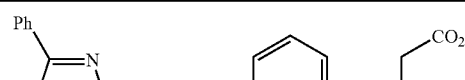 | 565.1 |

EXAMPLE 409

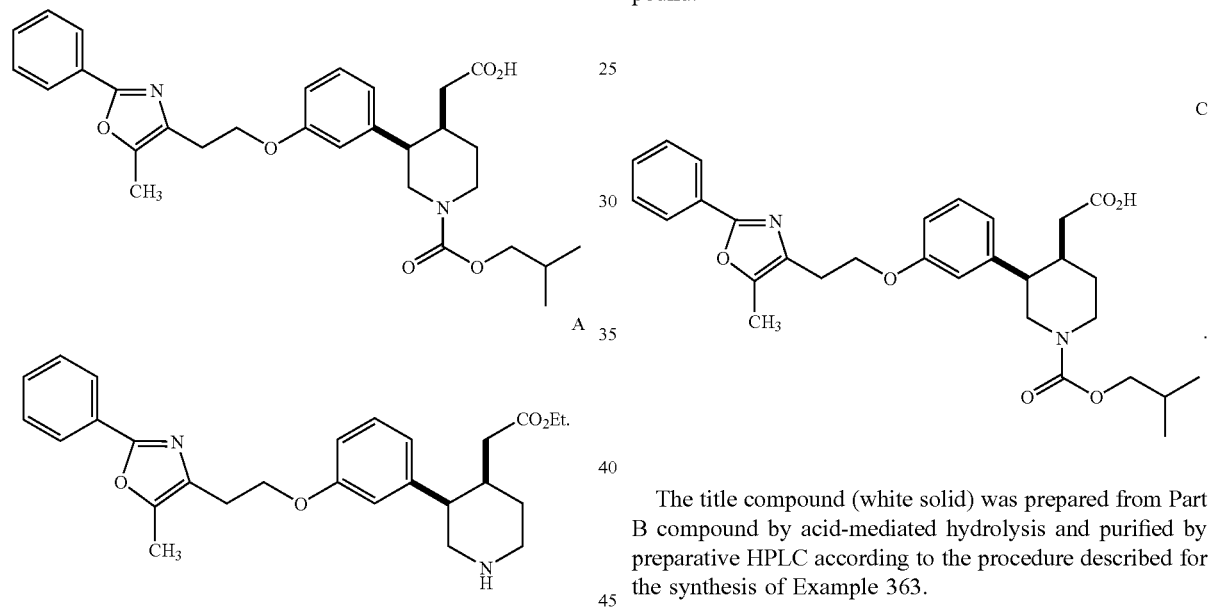

A mixture of Example 406 Part H compound (13.2 mg; 0.0282 mmol) and Pd/C (40 mg, 10%) in HOAc (10 mL) was stirred under an atmosphere of H$_2$ (60-70 psi) overnight to give Part A compound (12.2 mg; 100%).

Part B compound was prepared from Part A compound and isobutyl chloroformate according to the procedure described for the synthesis of Example 363 Part B compound.

The title compound (white solid) was prepared from Part B compound by acid-mediated hydrolysis and purified by preparative HPLC according to the procedure described for the synthesis of Example 363.

[M+H]$^+$=521.1

EXAMPLE 410

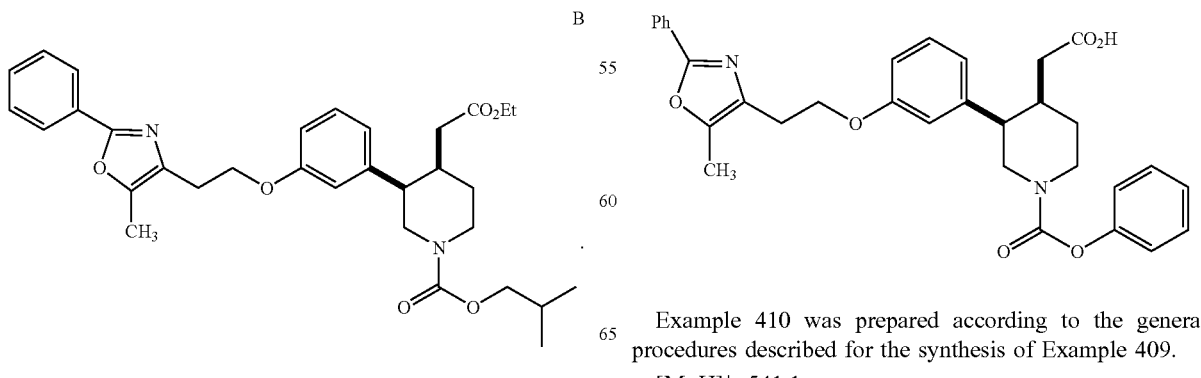

Example 410 was prepared according to the general procedures described for the synthesis of Example 409.

[M+H]$^+$=541.1

EXAMPLE 413

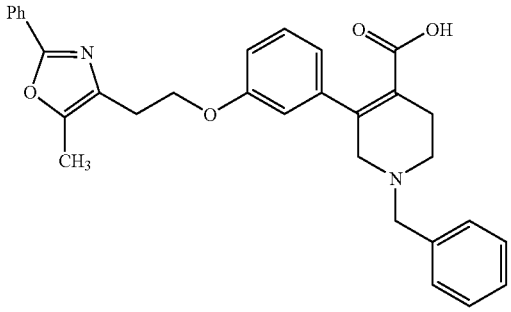

The title compound was prepared from Example 406 Part B compound by acid-mediated hydrolysis according to the procedure described for the synthesis of Example 363. The crude product was purified by preparative HPLC (also according to the procedure of Example 363) to give the title compound (10.7 mg, 56.7%) as a white solid.

$[M+H]^+=495.5$

EXAMPLE 414

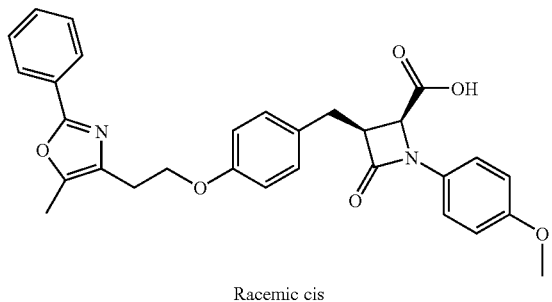

Racemic cis (Ref. Adlington, R. M. et al. *J. Med. Chem.* 2001, 44, 1491)

To a 45° C. mixture of Example 419 Part A compound (3.0 g, 10.93 mmol)

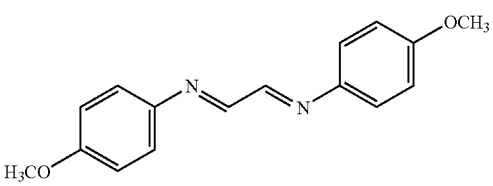

and $Et_3N$ (1.6 mL, 11.5 mmol) in dry toluene (70 mL) under $N_2$ was added dropwise a solution of 3-(4-benzyloxyphe-nyl)-propionyl chloride (prepared in the same manner as Example 419 Part E compound, but starting from 3-(4-hydroxyphenyl)propionic acid; 2.93 g in 5 mL toluene; 10.93 mmol) over 45 min. The solution was stirred at 45° C. for another 4 h, cooled to RT and aqueous HCl (9 mL of concentrated HCl in 66 mL $H_2O$) was added. The mixture was stirred at RT for 16 h, then extracted with EtOAc (200 mL). The combined organic extracts were dried ($Na_2SO_4$), concentrated in vacuo and the residue was chromatographed ($SiO_2$; continuous gradient using hex:EtOAc from 100% hex to 100% EtOAc) to give Part A compound (1.71 g, 39%) as a yellow solid.

$[M-H^+]=400.1$.

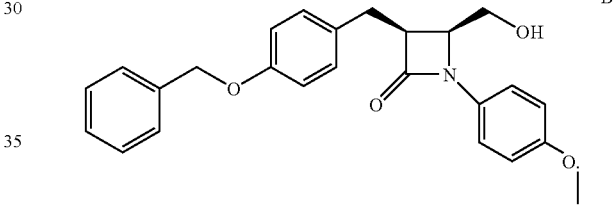

Racemic cis

A mixture of Part A compound (108 mg; 0.269 mmol) in THF (6 mL) and $LiBH_4$ (8 mg, 0.367 mmol) was stirred at RT overnight, then was partitioned between saturated aqueous $NaHCO_3$ and EtOAc. The aqueous phase was extracted with EtOAc and the combined organic extracts were washed with brine, dried ($Na_2SO_4$), and concentrated in vacuo. The residue was chromatographed ($SiO_2$; continuous gradient from 0 to 100% EtOAc-hexanes) to afford Part B compound as a white solid (60 mg, 55%). $[M+H]^+=404.3$.

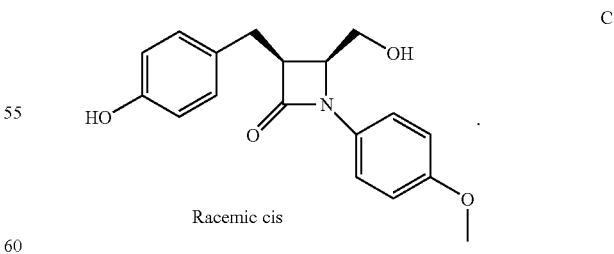

Racemic cis

A mixture of Part B compound (60 mg; 0.149 mmol) and 10% Pd/C (30 mg) in EtOAc (10 mL) was stirred under an atmosphere of $H_2$ (1 atm) at RT for 5 h. The catalyst was filtered off and the filtrate was concentrated in vacuo to give Part C compound (45 mg, 97%) as a colorless oil.

$[M+Na]^+=336.2$.

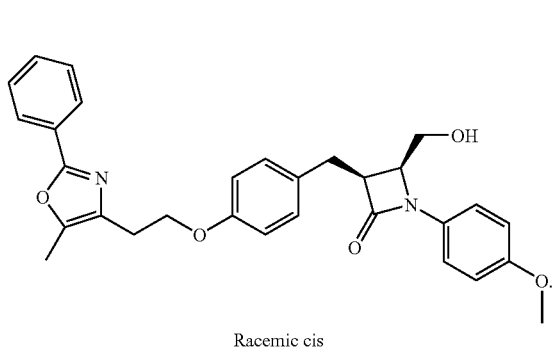

D

Racemic cis

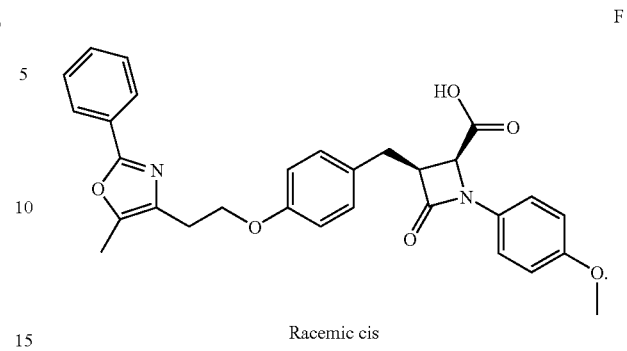

F

Racemic cis

A mixture of Part C compound (45 mg; 0.144 mmol), Example 23 Part A compound (62 mg; 0.22 mmol), and powdered K$_2$CO$_3$ (45 mg; 0.33 mmol) in CH$_3$CN (8 mL) was heated at reflux overnight, then cooled to RT and partitioned between EtOAc (25 mL) and H$_2$O (25 mL). The organic phase was washed with water, brine, dried (Na$_2$SO$_4$) and concentrated in vacuo. The residue was chromatographed (SiO$_2$; continuous gradient from 100% hex to 100% EtOAc) to give Part D compound (30 mg; 42%) as a colorless oil.

[M+H]$^+$=499.4.

To a solution of Part E compound (19 mg, 0.04 mmol) in acetone (1.5 mL) was added Jones reagent (4 drops). The reaction was stirred at RT for 3 h and then partitioned between water and EtOAc (20 mL each). The organic phase was washed with H$_2$O, brine, dried (Na$_2$SO$_4$) and concentrated in vacuo. The residue was purified by preparative HPLC (YMC reverse-phase ODS 20×100 mm column; flow rate=20 mL/min; 10 min continuous gradient from 70:30 B:A to 100% B, where solvent A=90:10:0.1 H$_2$O:MeOH:TFA and solvent B=90:10:0.1 MeOH:H$_2$O:TFA) to give the title compound (4.9 mg; 25%).

[M+H]$^+$=513.3

$^1$H NMR (400 MHz, CDCl$_3$) δ 2.38 (s, 3H), 2.87 (dd, J=14.9, 7.47 Hz, 1H), 2.95-3.1 (m, 3H), 3.75 (s, 3H), 3.7-3.8 (m, 1H), 4.05-4.15 (br. t, J=6.15 Hz, 2H), 4.58 (d, J=5.72 Hz, 1H), 6.69 (d, J=8.36 Hz, 2H), 6.82 (d, J=8.8 Hz, 2H), 7.01 (d, J=8.36 Hz, 2H), 7.27 (d, J=9.24 Hz, 2H), 7.35-7.45 (m, 3H), 7.92 (d, J=7.48 Hz, 2H).

ALTERNATIVE SEQUENCE: EXAMPLE 414

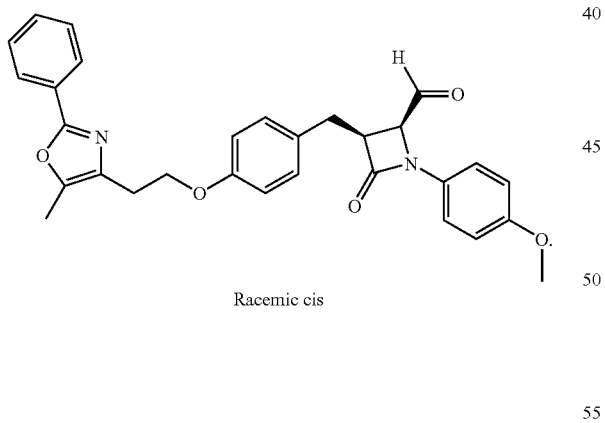

E

Racemic cis

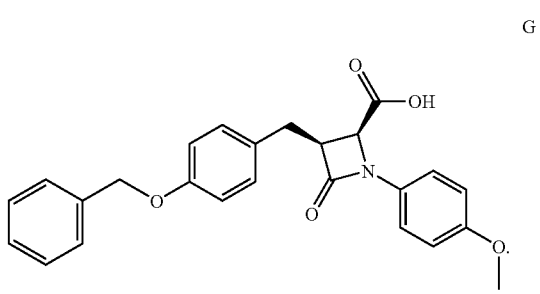

G

Racemic cis

To a dispersion of Dess-Martin periodinane (48 mg, 0.11 mmol) in CH$_2$Cl$_2$ (3 mL) was added dropwise a solution of Part D compound (30 mg, 0.06 mmol) in CH$_2$Cl$_2$ (3 mL) and the resulting mixture was stirred at RT for 7 h. Volatiles were removed in vacuo and the residue was chromatographed (SiO$_2$; continuous gradient from 100% hex to 100% EtOAc) to yield Part E compound (19.6 mg, 66%) as a pale yellow oil.

[M-H$^+$]=495.3.

To a solution of Example 414 Part A compound (979 mg, 2.44 mmol) in acetone (75 mL) was added Jones reagent (2.6 mL) dropwise. The reaction was stirred at RT for 0° C. for 1.5 h, concentrated in vacuo. The residue was partitioned between water and EtOAc (100 mL each). The organic phase was washed with H$_2$O, brine, dried (Na$_2$SO$_4$) and concentrated in vacuo to give the crude Part G compound (787 mg) which was used in the next step without further purification.

[M+H]$^+$=418.5.

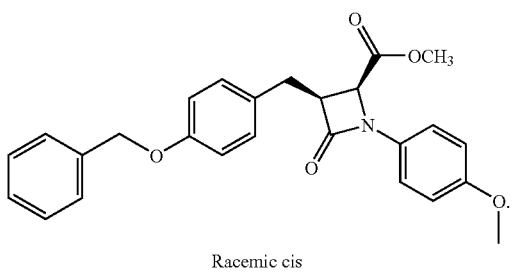

Racemic cis

To a 0° C. solution of the crude Part G compound in CH$_2$Cl$_2$:CH$_3$OH (1:1, 20 mL) was added TMSCHN$_2$ (3 mL of a 2M solution in hexanes, 6 mmol) dropwise and the mixture was stirred at 0° C. for 1 h. Volatiles were removed in vacuo and the residue was chromatographed (SiO$_2$; continuous gradient from 100% hex to 100% EtOAc) to give Part H compound (477 mg, 45% for 2 steps) as an off-white solid.
[M+H]$^+$=432.5.

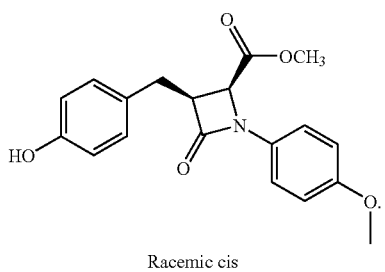

Racemic cis

A mixture of Part H compound (76 mg; 0.176 mmol) and 10% Pd/C (33 mg) in EtOAc (5 mL) was stirred overnight under an atmosphere of H$_2$ (1 atm) at RT. HPLC indicated incomplete conversion. More 10% Pd/C (37 mg) was added and the mixture was stirred for a further 2 h under H$_2$. The catalyst was filtered off and the filtrate was concentrated in vacuo to give Part I compound (49 mg, 81%) as a white solid.

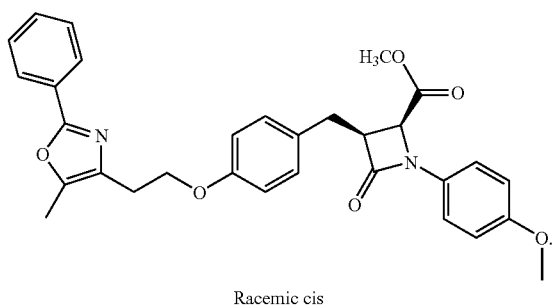

Racemic cis

A mixture of Part I compound (49 mg; 0.144 mmol), Example 23 Part A compound (65 mg; 0.23 mmol) and powdered K$_2$CO$_3$ (40 mg; 0.29 mmol) in CH$_3$CN (10 mL) was heated under reflux overnight, at which point HPLC indicated incomplete conversion. More Example 23 Part A compound (63 mg; 0.22 mmol) and K$_2$CO$_3$ (49 mg; 0.36 mmol) were added and the mixture heated at reflux for a further 12 h, then was cooled to RT and partitioned between EtOAc and H$_2$O (25 mL each). The aqueous phase was extracted with EtOAc (×2) and the combined organic extracts were washed with water, brine, dried (Na$_2$SO$_4$) and concentrated in vacuo. The residue was chromatographed (SiO$_2$; continuous gradient from 100% hexane to 100% EtOAc) to give Part J compound (68 mg; 83%) as a colorless oil.
[M+H]$^+$=526.8.

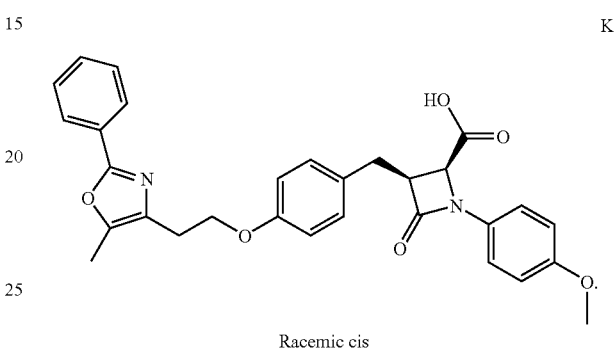

Racemic cis

A solution of Part H compound (67 mg, 0.127 mmol) and LiOH.H$_2$O (10 mg, 0.238 mmol) in H$_2$O (0.3 mL) in THF (1.2 mL) was stirred for 5 h at RT, then was partitioned between EtOAc (20 mL) and aqueous 1N HCl (10 mL). The aqueous phase was extracted with EtOAc (×2) and the combined organic extracts were washed with brine, dried (Na$_2$SO$_4$), and evaporated in vacuo to yield the title compound (60.5 mg; 93%) as a white solid.
[M+H]$^+$=513.4.

EXAMPLE 415

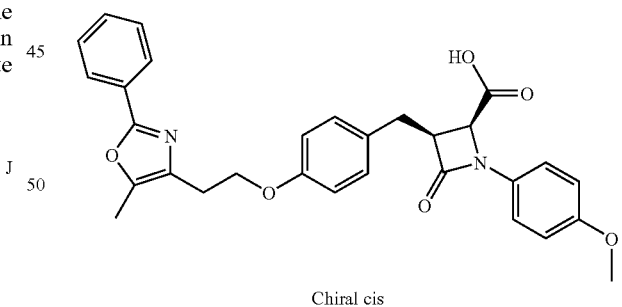

Chiral cis

The racemic Example 414 Part J compound (31 mg) was separated into the two individual enantiomers by preparative HPLC (Chiracel chiral AD 5×50 cm column; flow rate=45 mL/min; isocratic mobile phase 65:35 A:B, where solvent A=heptane+0.1% TFA and solvent B=isopropanol+0.1% TFA). The faster eluting fraction was concentrated in vacuo to give Example 415. [M+H]$^+$=513.4; [α]$_D$=−16.0° (c=0.075, CDCl$_3$, 24° C.); The absolute stereochemistry is arbitrarily assigned. The $^1$H NMR spectrum is identical to Example 414. Chiral analytical HPLC (Daicel Chiralcel AD 4.6×250 mm column, flow rate=1 mL/min; isocratic conditions=65:35 A:B, where A=heptane+0.1% TFA and B=IPA+0.1% TFA; detector wavelength=264 nm): retention time=9.91 min; ee=96%.

EXAMPLE 416

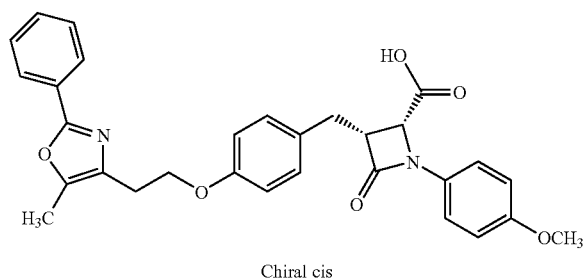

Chiral cis

The slower eluting fraction in the above separation was evaporated in vacuo to give Example 416. [M+H]$^+$=513.4; [α]$_D$=+20.77° (c=0.062, CDCl$_3$, 24° C.); Chiral analytical HPLC (Daicel Chiralcel AD 4.6×250 mm column, flow rate=1 mL/min; isocratic conditions=65:35 A:B, where A=heptane+0.1% TFA and B=IPA+0.1% TFA; detector wavelength=264 nm): retention time=15.96 min; ee=>99%. Absolute stereochemistry is arbitrarily assigned. $^1$H NMR: identical to Example 414.

EXAMPLE 417

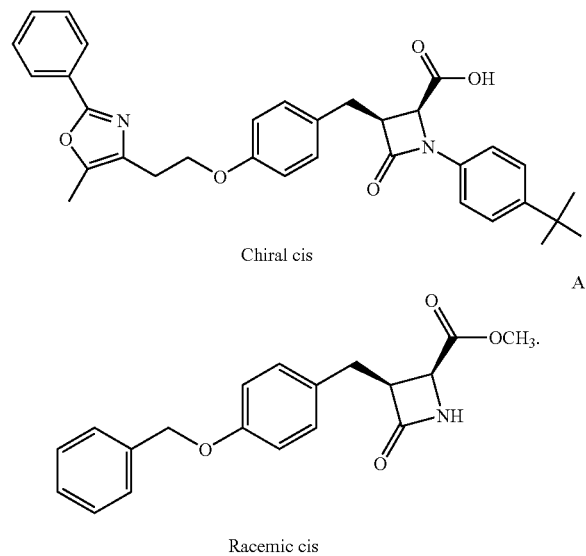

Chiral cis

A

Racemic cis

To a 0° C. solution of Example 414 Part H compound (366 mg; 0.85 mmol) in CH$_3$CN (15 mL) was added aqueous ammonium cerium nitrate (990 mg; 1.8 mmol in 5 mL H$_2$O). The reaction mixture was stirred at 0° C. for 3 h, then EtOAc (100 mL) was added. The organic phase was washed with saturated aqueous Na$_2$SO$_3$ (15 mL), dried (Na$_2$SO$_4$) and concentrated in vacuo. The residue was chromatographed (SiO$_2$; continuous gradient from 100% hex to 100% EtOAc) to give Part A compound (173 mg; 63%) as a yellow solid.

$^1$H NMR (400 MHz, CDCl$_3$) δ 2.81 (dd, J=15.4, 8.4 Hz, 1H), 3.00 (dd, J=14.9, 7.9 Hz, 1H), 3.62 (s, 3H), 3.83 (br. q, J=7.92 Hz, 1H), 4.28 (d, J=5.72 Hz, 1H), 4.98 (s, 2H), 6.14 (br. s, 1H), 6.89 (d, J=8.32 Hz, 2H), 7.12 (d, J=8.36 Hz, 2H), 7.26-7.43 (m, 5H); [M–H$^+$]=324.6

B

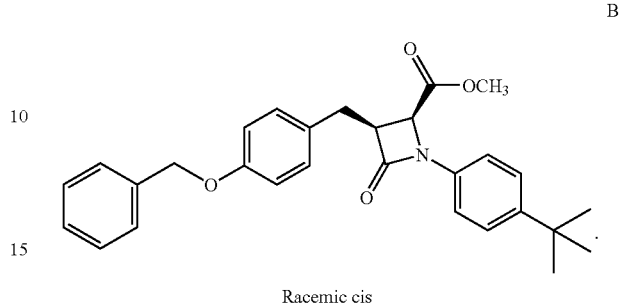

Racemic cis

To a solution of the Part A compound (57.7 mg, 0.178 mmol) in DCE (2.5 mL) was added p-t-butyl phenylboronic acid (66 mg, 0.37 mmol), Cu(OAc)$_2$ (34 mg 0.187), Et$_3$N (74 μL, 0.53 mmol), pyridine (55 μL, 0.68 mmol) and 4 Å molecular sieves (33 mg; pre-dried at 400° C. overnight). Air was allowed to pass into the reaction mixture, which was stirred at RT for 1.5 h. The volatiles were removed in vacuo and the residue was chromatographed (SiO$_2$; continuous gradient from 100% hex to 100% EtOAc) to give Part B compound (49 mg, 60%) as a colorless oil.

[M+H]$^+$=458.5.

C

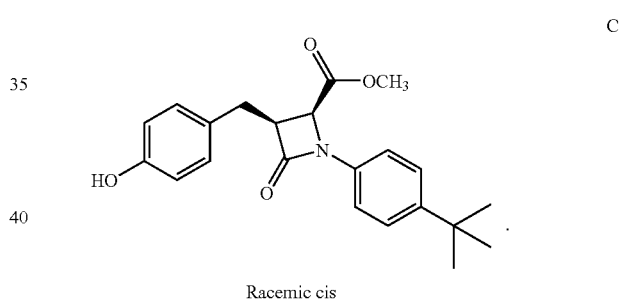

Racemic cis

A mixture of Part B compound and 10% Pd/C (49 mg) in EtOAc (5 mL) was stirred under an atmosphere of H$_2$ (1 atm) at RT for 2 h. The catalyst was filtered off and the filtrate was concentrated in vacuo to give Part C compound, which was used in the next step without further purification.

[M+H]$^+$=368.4.

D

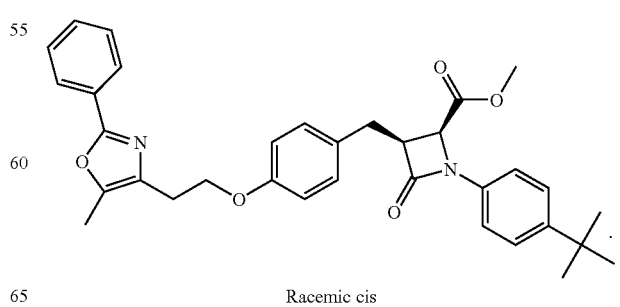

Racemic cis

A mixture of crude Part C compound, Example 23 Part A compound (65 mg; 0.23 mmol) and powdered K$_2$CO$_3$ (70 mg; 0.51 mmol) in CH$_3$CN (3 mL) was stirred at 95° C. for 16 h, then cooled to RT and partitioned between EtOAc (20 mL) and aqueous 1N HCl (10 mL). The aqueous layer was extracted with EtOAc (×2) and the combined organic extracts were washed with brine, dried (Na$_2$SO$_4$) and concentrated in vacuo. The residue was chromatographed (SiO$_2$; continuous gradient from 100% hex to 100% EtOAc) to afford Part D compound (50.3 mg, 85%) as a colorless oil.

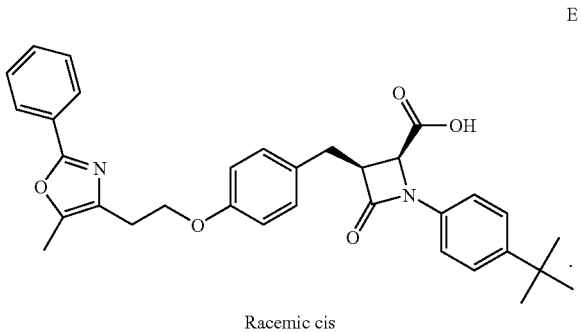

Racemic cis

A solution of Part D compound (50 mg, 0.091 mmol) and LiOH.H$_2$O (9 mg, 0.214 mmol) in H$_2$O (0.5 mL) and THF (3 mL) was stirred for 7 h at RT, then partitioned between EtOAc (20 mL) and aqueous 1N HCl (10 mL). The aqueous layer was extracted with EtOAc (×2) and the combined organic extracts were washed with brine, dried (Na$_2$SO$_4$), and concentrated in vacuo. The residue was purified by preparative HPLC (YMC reverse-phase ODS 20×100 mm column; flow rate=20 mL/min; 10 min continuous gradient from 60:40 B:A to 100% B, where solvent A=90:10:0.1 H$_2$O:MeOH:TFA and solvent B=90:10:0.1 MeOH:H$_2$O:TFA) to give Part E compound.

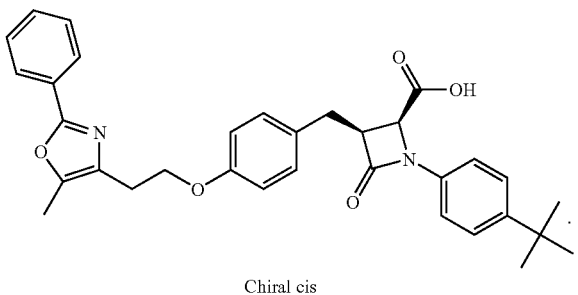

Chiral cis

Part E compound was separated into the two individual enantiomers by preparative HPLC (Chiracel chiral AD 5×50 cm column; flow rate=45 mL/min; isocratic mobile phase 85:15 A:B, where solvent A=Heptane+0.1% TFA and solvent B=IPA+0.1% TFA). The faster eluting fraction was evaporated in vacuo to give Example 417 (15 mg, 31% yield; 50% of theoretical recovery).

[M+H]$^+$=539.4.

Absolute stereochemistry is tentatively assigned.

$^1$H NMR: δ 1.21 (s, 9H), 2.33 (m, 3H), 2.82 (dd, J=14.94, 7.9 Hz, 1H), 2.92-3.05 (m, 3H), 3.72 (q, J=7.48 Hz, 1H), 3.95-4.1 (m, 2H), 4.54 (d, J=6.16 Hz, 1H), 6.64 (d, J=8.36 Hz, 2H), 6.96 (d, J=8.36 Hz, 2H), 7.18-7.4 (m, 7H), 7.86 (d, J=7.48 Hz, 2H), 9.98 (br. s, 1H).

Chiral analytical HPLC (Daicel Chiralcel AD 4.6×250 mm column, flow rate=1 mL/min; isocratic conditions 60:40 A:B, where A=heptane+0.1% TFA and B=IPA+0.1% TFA; detector wavelength=254 nm): retention time=10.96 min; ee=99%, Purity=85% (contained 15% transisomer).

EXAMPLE 418

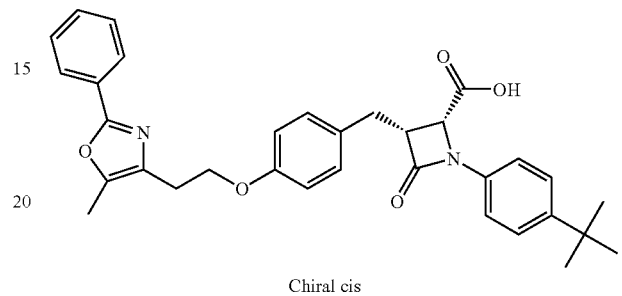

Chiral cis

The slower eluting fraction in the above separation was evaporated in vacuo to give Example 418 (8 mg, 16% yield; 50% of theoretical recovery).

[M+H]$^+$=539.4

Absolute stereochemistry is arbitrarily assigned. $^1$H NMR: Identical to Example 417.

Chiral analytical HPLC (Daicel Chiralcel AD 4.6×250 mm column, flow rate=1 mL/min; isocratic conditions=60:40 A:B, where A=heptane+0.1% TFA and B=IPA+0.1% TFA; detector wavelength=254 nm): retention time=21.84 min; ee=99%, Purity=99%.

EXAMPLE 419

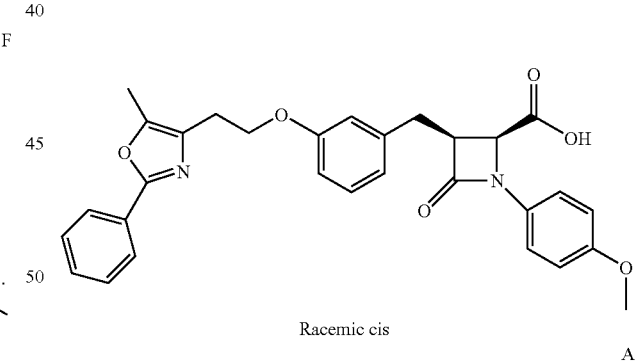

Racemic cis

To a solution of p-anisidine (12.3 g; 0.1 mol) in MeOH (60 mL) at 58° C. was added glyoxal (13.4 g, 40% solution in H$_2$O, 0.05 mol) over 2 min. The reaction mixture was stirred at 58° C. for another 2 min, then cooled to RT. The mixture was filtered to give Part A compound as a yellow solid (11.0 g, 82%).

B

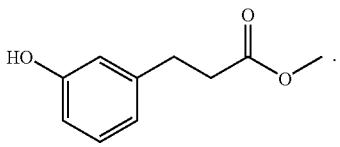

To a solution of 3-(3-hydroxyphenyl)propionic acid (18.5 g, 0.11 mol) in MeOH (150 mL) at RT was added concentrated $H_2SO_4$ (3 mL). The reaction mixture was stirred at 50° C. for 1 h. Volatiles were removed in vacuo and the residue was partitioned between saturated aqueous $NaHCO_3$ (70 mL) and EtOAc (400 mL). The organic phase was dried ($MgSO_4$) and concentrated in vacuo to give crude Part B compound (20.0 g, 99%) as an oil.

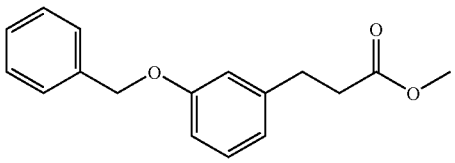

A mixture of Part B compound (20.0 g, 0.11 mol), benzyl bromide (13.5 ml, 0.113 mol) and powdered $K_2CO_3$ (22.7 g, 0.164 mol) in $CH_3CN$ (400 mL) was stirred at 70° C. for 12 h, then cooled to RT and filtered. The filtrate was concentrated in vacuo to give Part C compound (30.0 g; 100%) as an oil.

D

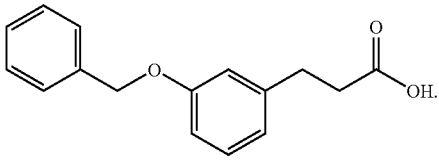

A solution of Part C compound (30 g, 0.111 mol) and aqueous LiOH (5.57 g in 300 mL $H_2O$, 0.132 mol) in THF (300 mL) was stirred at RT for 16 h, after which more $LiOH.H_2O$ (1.0 g, 0.238 mmol) was added. The reaction was stirred at RT for another 36 h, then acidified to pH 4 with concentrated HCl. Organic volatiles were removed in vacuo and the aqueous phase was extracted with EtOAc (2×100 mL). The combined organic extracts were dried ($MgSO_4$) and concentrated in vacuo to give Part D compound (28.1 g, 99%).

E

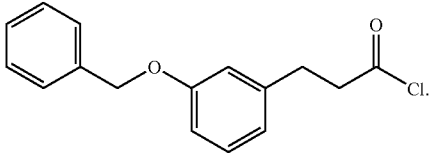

To a 0° C. solution of Part D compound (28.1 g, 0.111 mol) in $CH_2Cl_2$ (100 mL) were added DMF (0.5 mL) and oxalyl chloride (20 mL, 0.229 mol) over 75 min. The reaction was stirred at RT for 1 h. Volatiles were removed in vacuo and the residue was distilled (Kugelrohr; bp=200° C.@0.1 mm Hg) to give Part E compound (24.2 g; 80%) as a clear oil.

F

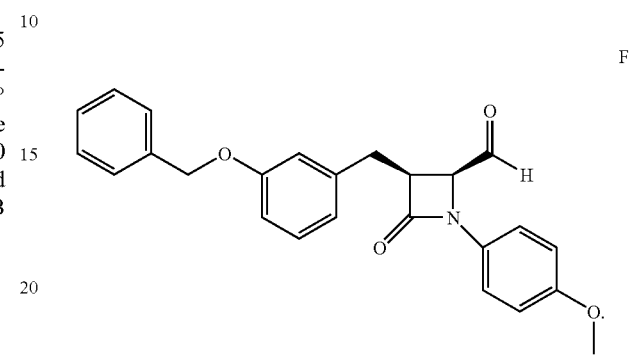

Racemic cis

Ref: Adlington, R. M. et al *J. Med. Chem.* 2001, 44, 1491

To a mixture of Part A compound (3.8 g, 0.014 mol) and $Et_3N$ (3.39 ml, 0.024 mol) in dry toluene (110 mL) at 40° C. under $N_2$ was added dropwise a solution of Part E compound (6.77 g in 5 mL toluene; 0.0247 mol) over 2.5 h. The reaction was stirred at 35-40° C. for another 1.5 h, then cooled to RT and aqueous HCl (20 mL of conc. HCl in 130 mL $H_2O$) was added. The mixture was stirred at RT for 16 h and extracted with EtOAc (250 mL). The combined organic extracts were dried ($Na_2SO_4$), concentrated in vacuo, and the residue was recrystallized from $Et_2O$ to give Part F compound. In addition, the combined mother liquors were concentrated in vacuo, and the residue was chromatographed ($SiO_2$; continuous gradient from 100% hex to 55:45 hex:EtOAc over 35 min, 55:45 hex:EtOAc for 10 min) to give additional Part F compound (combined recovery=4.03 g, 80%) as a solid. $^1H$ NMR (400 MHz, $CDCl_3$) δ 2.87(dd, J=14.4, 9.7 Hz, 1H), 3.30 (dd, J=9.7, 6.2 Hz, 1H), 3.77 (s, 3H), 4.02 (dt, J=9.7, 6.2 Hz, 1H), 4.56 (dd, J=6.2, 2.7 Hz, 1H), 5.05 (s, 2H), 6.86-7.50 (m, 13H), 9.60 (d, J=2.7 Hz, 1H);

$[M+H]^+=402.3$.

G

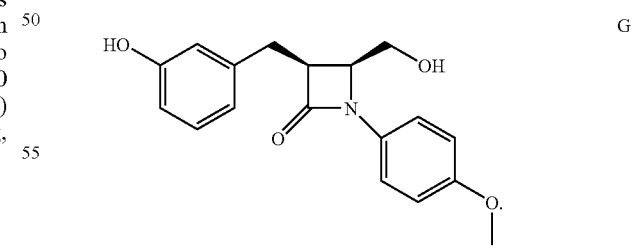

Racemic cis

A mixture of Part F compound (2.0 g, 4.98 mmol) and 10% Pd/C (1.85 g) in EtOAc (150 mL) was stirred under an atmosphere of $H_2$ (60 psi) at RT for 24 h, at which point the reaction was complete by HPLC. The catalyst was filtered off (Celite®) and the filtrate was concentrated in vacuo to give Part G compound (1.42 g, 91%) as a white foam.

H.

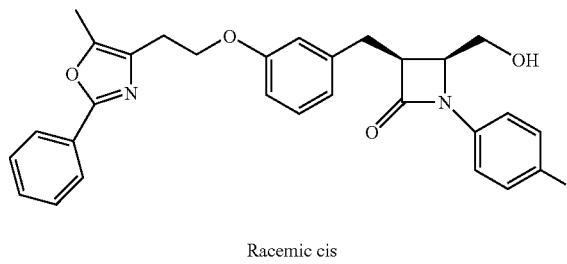

Racemic cis

A mixture of Part G compound (1.42 g; 4.53 mmol), Example 23 Part A compound (1.91 g; 6.79 mmol) and powdered K₂CO₃ (1.37 g; 9.93 mmol) in CH₃CN (40 mL) was stirred at 85° C. for 22 h. At this point analytical HPLC indicated that all starting material had been consumed. The reaction mixture was partitioned between Et₂O (200 mL) and H₂O (50 mL). The organic phase was washed with water (2×50 mL), dried (MgSO₄) and concentrated in vacuo. The residue was chromatographed (SiO₂; stepwise gradient from 5:1 to 2:1 hex:EtOAc) to give Part H compound (1.36 g; 60%) as a white foam.

I

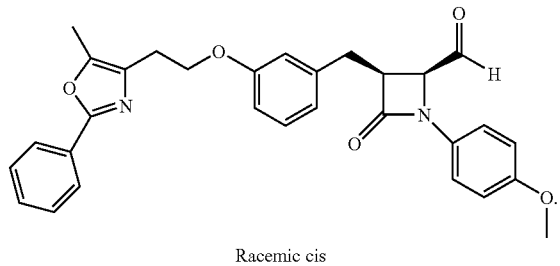

Racemic cis

To a mixture of Dess-Martin periodinane (116 mg; 0.27 mmol) in CH₂Cl₂ (1.3 mL) at RT was added a solution of Part H compound (100 mg; 0.20 mmol) in CH₂Cl₂ (1.3 mL). The reaction was stirred at RT for 30 min. Volatiles were removed in vacuo. The residue was chromatographed (SiO₂; 2:1 hex:EtOAc) to give Part I compound (96 mg; 96%) as an oil.

J

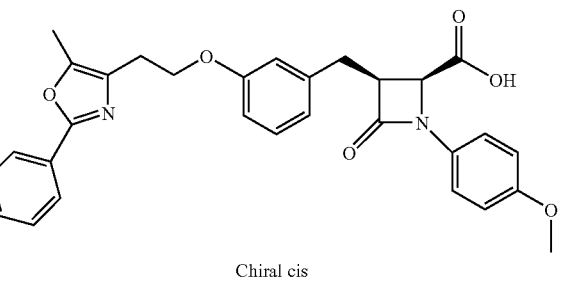

Racemic cis

To a 0° C. solution of Part I compound (96 mg, 2.23 mmol) in acetone (75 mL) was added Jones reagent (2.25 mL) dropwise. The reaction was stirred at RT for 30 min, after which volatiles were removed in vacuo and the residue was partitioned between water (60 mL) and EtOAc (200 mL). The organic phase was dried (MgSO₄) and concentrated in vacuo to give the crude product, which was filtered through SiO₂ (100% EtOAc). Volatiles were removed in vacuo and the residue was purified by preparative HPLC (YMC reverse-phase ODS 20×100 mm column; flow rate=20 mL/min; 10 min continuous gradient from 70:30 B:A to 100% B+10 min hold-time at 100% B, where solvent A=90:10:0.1H₂O:MeOH:TFA and solvent B=90:10:0.1 MeOH:H₂O:TFA) to give Example 419 (32 mg; 32%).

[M+H]⁺=513.4

¹H NMR (400 MHz, CDCl₃) δ 2.40 (s, 3H), 2.99 (t, J=8.7 Hz, 2H), 3.23 (dd, J=14.5, 12.3 Hz, 1H), 3.32 (dd, J=14.5, 3.5 Hz, 1H), 3.78 (s, 3H), 3.83-3.92 (m, 1H), 4.20-4.45 (m, 2H), 4.50 (d, J=5.7 Hz, 1H), 6.80-6.98 (m, 5H), 7.20-7.50 (m, 6H), 7.92-7.98 (m, 2H).

EXAMPLE 420

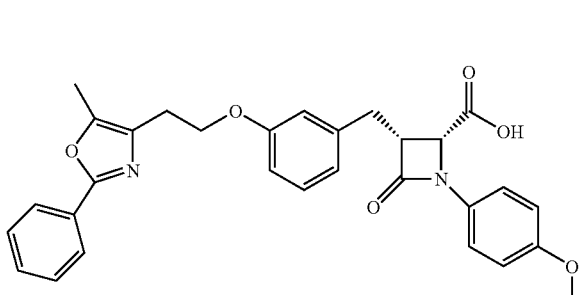

Chiral cis

The individual enantiomers of Example 419, Part J compound were separated by preparative HPLC (Chiracel chiral OD 5×50 cm column; flow rate=45 mL/min; isocratic mobile phase 70:30 A:B, where solvent A=Heptane+0.1% TFA and solvent B=isopropanol+0.1% TFA). The faster eluting fraction yielded Example 420. [M+H]⁺=513.2; [α]_D=−74.8° (c=0.16, CDCl₃, 25° C.); Absolute stereochemistry is tentatively assigned. ¹H NMR: identical to Example 419. Chiral analytical HPLC (Daicel Chiralcel AD 4.6×250 mm column): flow rate=1 mL/min; isocratic conditions=70:30 A:B, where A heptane+0.1% TFA and B=isopropanol+ 0.1% TFA; detector wavelength=264 nm; retention time=7.89 min; ee>99%.

EXAMPLE 421

Chiral cis

The slower eluting fraction from the above chiral separation (Example 420) yielded Example 421. (The isocratic mobile phase changed to 60:40 A:B after the faster eluting enantiomer came out, where solvent A=Heptane+0.1% TFA and solvent B IPA+0.1% TFA); [M+H]$^+$=513.4; [α]$_D$=+58.8° (c=0.16, CDCl$_3$, 25° C.); Absolute stereochemistry is tentatively assigned. $^1$H NMR: identical to Example 419.

An alternative method was developed for preparation of Examples 420 and 421.

A

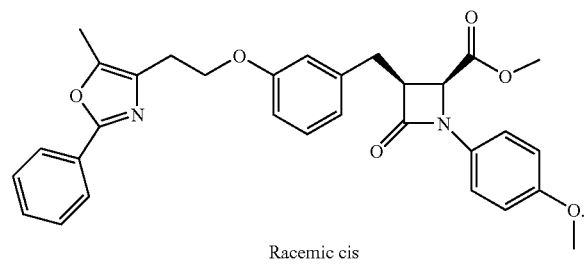

Racemic cis

To a 0° C. solution of Example 419, part J compound (800 mg, 1.56 mmol) in CH$_2$Cl$_2$/MeOH (8.3 mL/8.3 mL) was added a solution of TMSCHN$_2$ (3.7 mL of a 2M solution in hexane; 0.074 mmol). The mixture was stirred at RT for 30 min. Volatiles were removed in vacuo and the residue was chromatographed (SiO$_2$; continuous gradient from 100% hex to 60:40 hex:EtOAc over 30 min, 60:40 hex:EtOAc for 10 min) to give Part A compound (0.4 g, 49%). [M+H]$^+$=527.2.

B

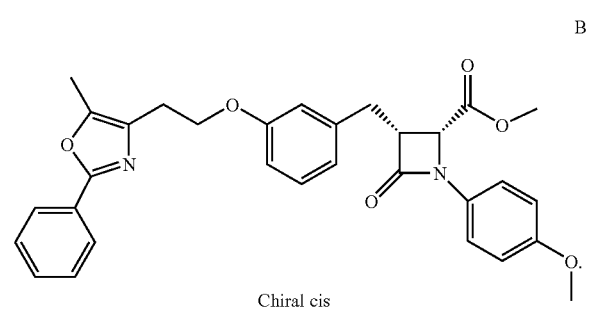

Chiral cis

The two enantiomers of the racemate (Part A compound) were separated by preparative HPLC (Chiralcel chiral OD 5×50 cm column; flow rate=45 mL/min; isocratic mobile phase 60:40 A:B, where solvent A=Heptane+0.1% TFA and solvent B=IPA+0.1% TFA). The faster eluting fraction yielded Part B compound and slowing eluting enatiomer afforded Part C compound below (the isocratic mobile phase changed to 20:80 A:B after fractions containing faster eluting enantiomer were collected, where solvent A=Heptane+0.1% TFA and solvent B=IPA+0.1% TFA). Chiral analytical HPLC (Daicel Chiralcel OD 4.6×250 mm column): flow rate=1.5 mL/min; isocratic conditions=60:40 A:B, where A=heptane and B=IPA, detector wavelength=264 nm; retention time=32.9 min;

C

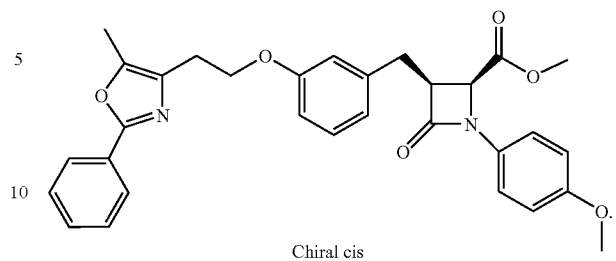

Chiral cis

Chiral analytical HPLC (Daicel Chiralcel OD 4.6×250 mm column): flow rate=1.5 mL/min; isocratic conditions=60:40 A:B, where A=heptane and B=IPA, detector wavelength=264 nm; retention time=42.7 min;

D

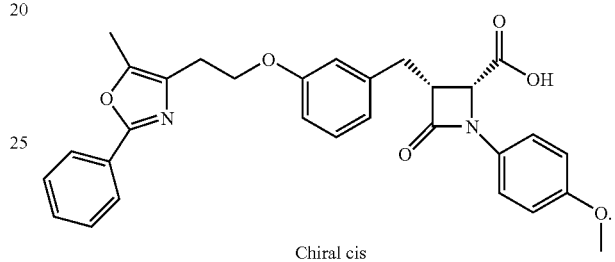

Chiral cis

To a solution of Part B compound (146 mg, 0.277 mmol) in THF (6 mL) was added a solution of aqueous LiOH (23.3 mg in 3 mL H$_2$O, 0.554 mmol). The reaction mixture was stirred at RT for 16 h after which it was acidified to pH 3 with excess aqueous 1 M HCl, then organic solvents were removed in vacuo. The residual aqueous phase was extracted with EtOAc (2×15 mL). The combined organic extracts were successively washed with H$_2$O and brine (50 mL each), dried (Na$_2$SO$_4$), filtered and concentrated in vacuo to give Example 421 compound as a white solid (120 mg ; 85%). [M+H]$^+$=513.2; [α]$_D$=+83.1° (c=0.16, CDCl$_3$, 25° C.).
$^1$H NMR: identical to Example 419.

Chiral analytical HPLC (Daicel Chiralcel AD 4.6×250 mm column): flow rate 1 mL/min; isocratic conditions=70:30 A:B, where A=heptane +0.1% TFA and B=IPA+0.1% TFA; detector wavelength=264 nm; retention time=12.9 min; ee>93%

E

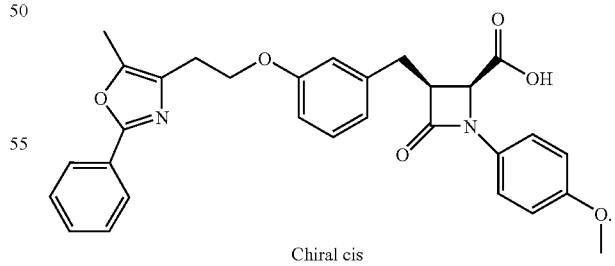

Chiral cis

A solution of Part C compound (90 mg, 0.171 mmol) in THF (4 mL) and aqueous LiOH (14.3 mg in 1.8 mL H$_2$O, 0.34 mmol) was stirred at RT for 16 h, then was acidified to pH 3 with excess aqueous 1 M HCl. The organic volatiles were removed in vacuo. The residual aqueous phase was extracted with EtOAc (2×15 mL). The combined organic extracts were successively washed with H$_2$O and brine (50 mL each), dried (Na$_2$SO$_4$) and concentrated in vacuo to give Example 420 compound as a white solid (70 mg ; 80%); [M+H]$^+$=513.2; [α]$_D$=−82.3° (c=0.18, CDCl$_3$, 25° C.).

$^1$H NMR: identical to Example 419.

Chiral analytical HPLC (Daicel Chiralcel AD 4.6×250 mm column): flow rate=1 mL/min; isocratic conditions=70:30 A:B, where A=heptane+0.1% TFA and B=IPA+0.1% TFA; detector wavelength=264 nm; retention time=8.0 min; ee>99%

EXAMPLE 422

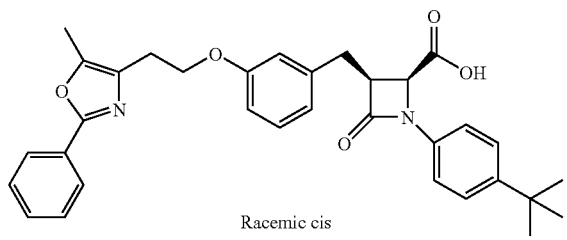

Racemic cis

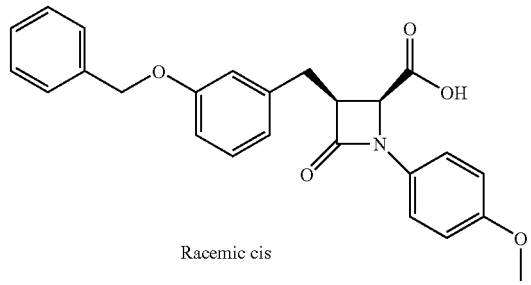

Racemic cis

To a 0° C. solution of Example 419, Part F compound (0.896 g, 2.23 mmol) in acetone (75 mL) was added Jones reagent (2.25 mL) dropwise. The reaction mixture was stirred at RT for 30 min. Volatiles were removed in vacuo and the residue was partitioned between water (60 mL) and EtOAc (200 mL). The organic phase was dried (MgSO$_4$) and concentrated in vacuo to give Part A compound which was used in the next step without further purification.

[M+H]$^+$=418.3.

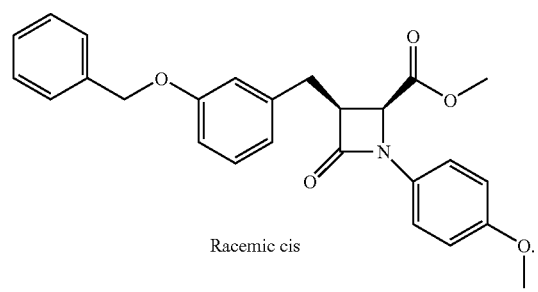

Racemic cis

To a 0° C. solution of Part A compound in CH$_2$Cl$_2$/MeOH (7 mL/7 mL) was added TMSCHN$_2$ in hexane (3 mL of a 2M solution). The reaction was stirred at RT for 30 min. Volatiles were removed in vacuo and the residue was chromatographed (SiO$_2$; continuous gradient from 100% hex to 50:50 hex:EtOAc over 30 min) to give Part B compound (0.60 g, 62%). [M+H]$^+$=432.4.

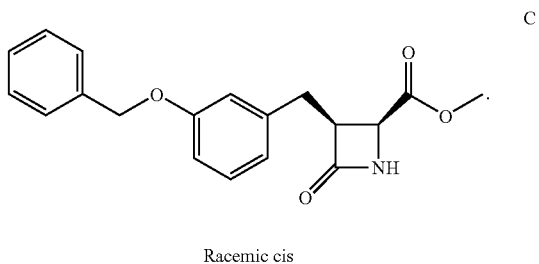

Racemic cis

To a 0° C. solution of Part B compound (0.60 g; 1.4 mmol) in CH$_3$CN (17 mL) was added a solution of ceric ammonium nitrate (1.5 g; 2.73 mmol) in H$_2$O (9.6 mL). The reaction mixture was stirred at 0° C. for 20 min, then EtOAc (150 mL) was added. The organic phase was washed with saturated aqueous sodium sulfite (15 mL), dried (MgSO$_4$) and concentrated in vacuo. The residue was chromatographed (SiO$_2$; stepwise gradient from 3:1 to 1:1 hex:EtOAc) to give Part C compound (0.342 g; 75%) as a colorless oil. $^1$H NMR (400 MHz, CDCl$_3$) δ 2.78 (dd, J=14.9, 8.4 Hz, 1H), 3.01 (dd, J=14.9, 7.5 Hz, 1H), 3.57 (s, 3H), 3.81 (m, 1H), 4.24 (d, J=5.7 Hz, 1H), 4.98 (bs, 1H), 5.03 (s, 2H), 6.70-6.85 (m, 3H), 7.13 (t, J=7.9 Hz, 1H), 7.25-7.40 (m, 5H); [M+H]$^+$=326.3.

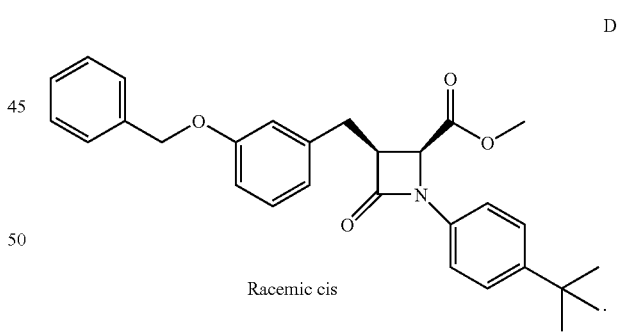

Racemic cis

To a solution of the Part C compound (27.9 mg, 0.086 mmol) in DCE (1.2 mL) was added p-tert-butyl phenylboronic acid (31.3 mg, 0.176 mmol), Cu(OAc)$_2$ (16 mg 0.088 mmol), Et$_3$N (35 μL, 0.25 mmol), pyridine (25 μL. 0.31 mmol) and 4 Å molecular sieves (150 mg; pre-dried at 400° C. overnight). Air was allowed to pass into the reaction mixture, which was stirred at RT for 1.5 h. Volatiles were removed in vacuo and the residue was chromatographed (SiO$_2$; 3:1 hex:EtOAc) to give Part D compound (38.6 mg, 98%). [M+H]$^+$=458.3.

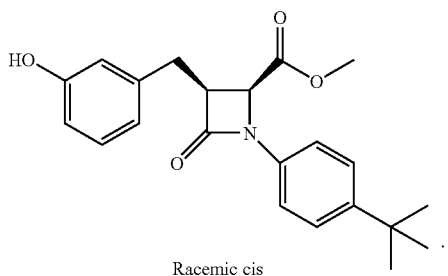

Racemic cis

A mixture of Part D compound (38.6 mg; 0.084 mmol) and 10% Pd/C (20 mg) in EtOAc (3 mL) was stirred under an atmosphere of $H_2$ (balloon) at RT for 3 h, at which point the reaction was complete by HPLC. The catalyst was filtered off (Celite®) and the filtrate was concentrated in vacuo to give Part E compound (20 mg, 65%) as a solid. $[M+H]^+=367.3$.

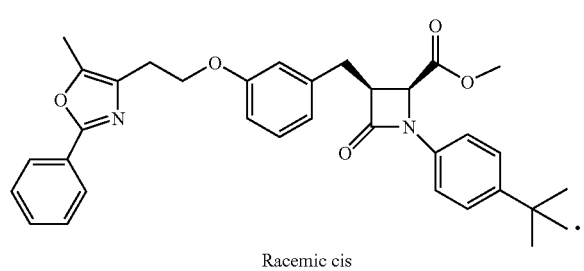

Racemic cis

A mixture of Part E compound (13.2 mg; 0.036 mmol), Example 23 Part A compound (30 mg; 0.107 mmol) and powdered $K_2CO_3$ (23 mg; 0.167 mmol) in $CH_3CN$ (1.5 mL) was stirred at 85° C. for 16 h, after which precipitates were filtered. The filtrate was concentrated in vacuo and the residue was chromatographed ($SiO_2$; stepwise gradient from 3:1 to 1.5:1 hex:EtOAc) to give Part F compound (11.1 mg; 56%) as an oil. $[M+H]^+=553.4$.

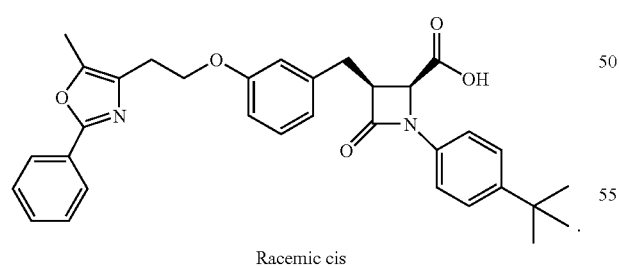

Racemic cis

A solution of Part F compound (11.1 mg, 0.019 mmol) and aqueous $LiOH \cdot H_2O$ (2 mg in 0.6 mL $H_2O$, 0.047 mmol) in THF (0.8 mL) was stirred at RT for 16 h, after which more $LiOH \cdot H_2O$ (2 mg, 0.047 mmol) was added. After stirring for another 24 h, the mixture was acidified to pH 4 with 1 M aqueous HCl. Volatiles were removed in vacuo and the residue was partitioned between water (2 mL) and EtOAc (6 mL). The organic phase was dried ($MgSO_4$) and concentrated in vacuo. The residue was purified by preparative HPLC (continuous gradient over 12 min from 75:25 A:B to 100% B; A=90:10:0.1$H_2O$:MeOH:TFA; B=90:10:0.1 MeOH:$H_2O$:TFA; flow rate=20 mL/min; detection at 220 nm; YMC ODS 20×100 mm column) to give Example 422 (2.08 mg; 19%) as a viscous oil. $[M+H]^+=539.2$.

EXAMPLES 423-427

Examples 423-427 were prepared in the same fashion as Example 422 (from Example 422, Part C compound) using the appropriately substituted phenyl boronic acids.

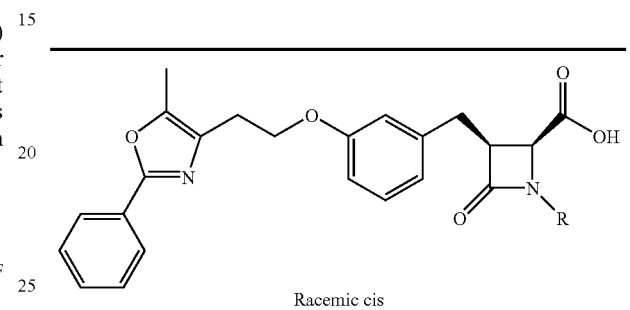

Racemic cis

| Example # | R | [M + H]+ |
|---|---|---|
| 423 | 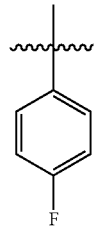 | 501.2 |
| 424 | 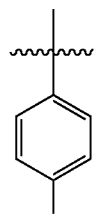 | 517.1 |
| 425 | 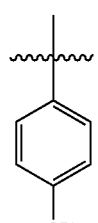 | 575.2 |
| 426 | 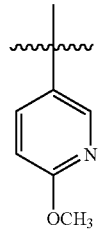 | 514.2 |

-continued

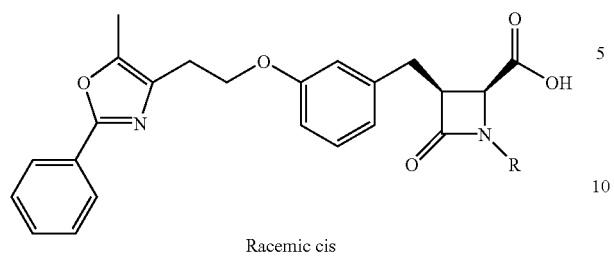

Racemic cis

| Example # | R | [M + H]+ |
|---|---|---|
| 427 | ![3-CF3-phenyl] | 551.1 |

EXAMPLE 428

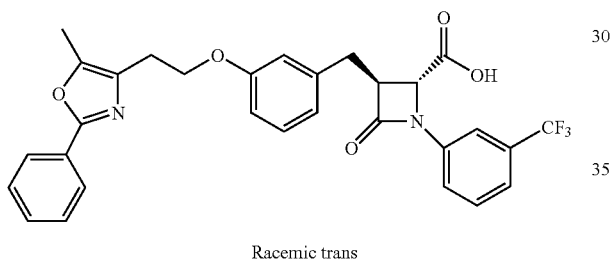

Racemic trans

During the preparation of Example 427, at the final hydrolysis step, a slower eluting side product was isolated by preparative HPLC and was determined to be the corresponding trans diastereomer (title compound). The epimerization was presumed to have occurred at the carboxylic acid stereocenter.

$^1$H NMR (400 MHz, CDCl$_3$) δ 2.24 (s, 3H), 2.86 (t, J=6.6 Hz, 2H), 3.00-3.15 (m, 2H), 3.60-3.63 (m, 1H), 4.15 (t, J=6.6 Hz, 2H), 4.36 (s, 1H), 6.68-6.85 (m, 3H), 7.10 (t, J=7.7 Hz, 1H), 7.25-7.50 (m, 6H), 7.55 (s, 1H), 7.85-7.90 (m, 2H); [M+H]$^+$=551.3.

EXAMPLE 429

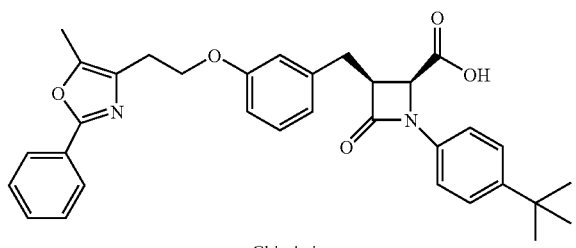

Chiral cis

-continued

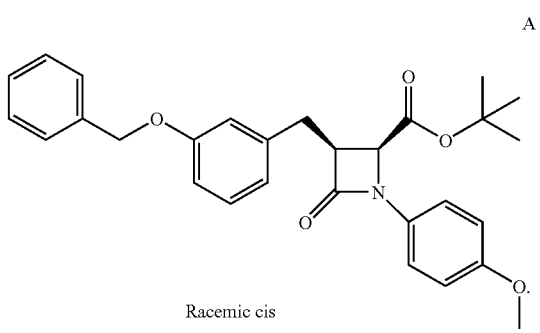

Racemic cis

To a 0° C. solution of Example 422, Part A compound (2.3 g, 5.73 mmol) in CH$_2$Cl$_2$ (9 mL) was added a solution of t-butyl 2,2,2,-trichloroacetimidate (3.55 mL, 19.8 mmol) and BF$_3$.OEt$_2$ (0.305 ml, 2.4 mmol). The mixture was stirred at RT for 2 h, after which excess solid NaHCO$_3$ was added and stirring was continued for 5 min. Solids were filtered off (Celite®) and the filtrate was concentrated in vacuo to give a residue which was chromatographed (SiO$_2$; continuous gradient from 100% hex to 75:25 hex:EtOAc over 25 min, hold at 75:25 hex:EtOAc for 15 min) to give Part A compound (1.66 g, 62%). [M+H]$^+$=474.5

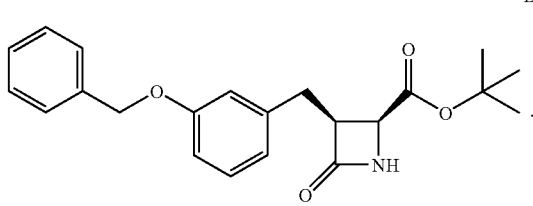

Racemic cis

To a 0° C. solution of Part A compound (1.78 g; 1.64 mmol) in CH$_3$CN (50 mL) was added aqueous ceric ammonium nitrate solution (4.12 g; 7.51 mmol in 28 mL of H$_2$O). The reaction mixture was stirred at 0° C. for 20 min, then was partitioned between EtOAc (250 mL) and saturated aqueous sodium sulfite (50 mL). The organic phase was dried (MgSO$_4$) and concentrated in vacuo. The residue was chromatographed (SiO$_2$; stepwise gradient from 3:1 to 2:1 hex:EtOAc) to give Part B compound (1.13 g; 82%) as a colorless oil. $^1$H NMR (400 MHz, CDCl$_3$) δ 1.40 (s, 9H), 2.93 (dd, J=15.4, 7.9 Hz, 1H), 3.06 (dd, J=14.9, 7.9 Hz, 1H), 3.83 (m, 1H), 4.24 (d, J=5.7 Hz, 1H), 5.01 (s, 2H), 6.02 (bs, 1H), 6.84 (dd, J=8.4, 2.2 Hz, 1H), 6.86 (d, J=7.9 Hz, 1H), 6.93 (s, 1H), 7.21 (t, J=7.9 Hz, 1H), 7.30-7.45 (m, 5H); [M+Na]$^+$=390.2.

C

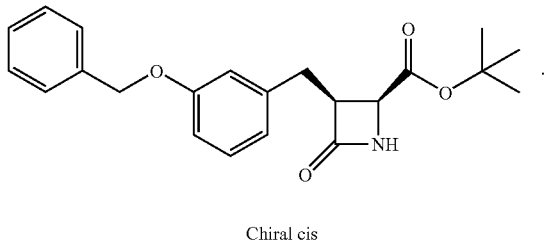

Chiral cis

The two enantiomers of racemic Part B compound were separated preparative HPLC (Chiralcel chiral AD 5×50 cm column; flow rate=45 mL/min; isocratic mobile phase 92:8 A:B for 60 min, 85:15 A:B for 60 min, 80:20 A:B for 60 min, 77:23 A:B for 60 min, where solvent A=Heptane+0.1% TFA and solvent B=isopropanol+0.1% TFA). The faster eluting fraction was designated as Part C compound. $[M+Na]^+=$ 390.2; $[\alpha]_D=+23.5°$ (c=0.41, CDCl$_3$, 25° C.).

Chiral analytical HPLC (Daicel Chiralcel AD 4.6×250 mm column): flow rate=1 mL/min; isocratic conditions=70:30 A:B, where A=heptane+0.1% TFA and B=IPA+0.1% TFA; detector wavelength=254 nm; retention time=9.43 min; ee>99%

D

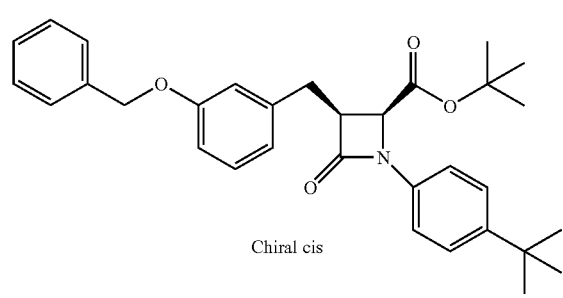

Chiral cis

The slower eluting fraction was designated as Part D compound. $[M+Na]^+=390.2$; $[\alpha]_D=-17.9°$ (c=0.45, CDCl$_3$, 25° C.). Chiral analytical HPLC (Daicel Chiralcel AD 4.6×250 mm column): flow rate=1 mL/min; isocratic conditions=70:30 A:B, where A=heptane+0.1% TFA and B=IPA+0.1% TFA; detector wavelength 254 nm; retention time=29.1 min; ee>97.5%

E

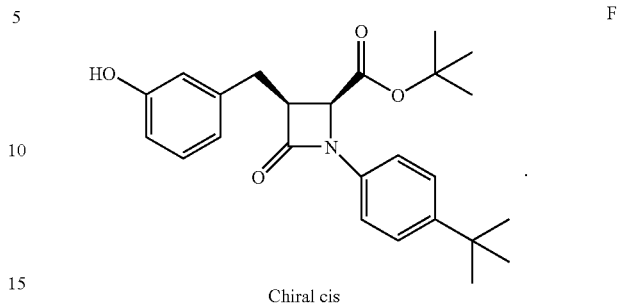

Chiral cis

To a solution of Part C compound (270 mg, 0.75 mmol) in DCE (12 mL) was added p-tert-butyl phenylboronic acid (377 mg, 2.11 mmol), Cu(OAc)$_2$ (160 mg, 0.88 mmol), Et$_3$N (0.511 μL, 3.67 mmol), pyridine (297 μL, 3.67 mmol) and 4 Å molecular sieves (200 mg; pre-dried at 400° C. overnight). Air was allowed to pass into the reaction mixture, which was stirred at RT for 5 h. The solid was filtered off (Celite®) and the filtrate was concentrated in vacuo to give a residue which was chromatographed (SiO$_2$; continuous gradient from 100% hex to 75:25 hex:EtOAc over 25 min, hold at 75:25 hex:EtOAc for 15 min) to give Part E compound (355 mg, 96%). $[M+H]^+=500.3$.

F

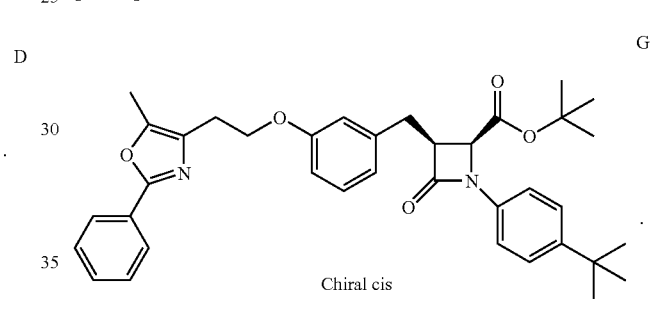

Chiral cis

A mixture of Part E compound (355 mg; 0.71 mmol) and 10% Pd/C (200 mg) in EtOAc (40 mL) was stirred under an atmosphere of H$_2$ (balloon) at RT for 3 h, at which point the reaction was complete by HPLC. The catalyst was filtered off (Celite®) and the filtrate was concentrated in vacuo to give a residue which was chromatographed (SiO$_2$; stepwise gradient from 4:1 to 3:1 hex:EtOAc to 1:1 hex:EtOAc) to give Part F compound as a white solid (254 mg, 87%). $[M+H]^+=410.4$.

G

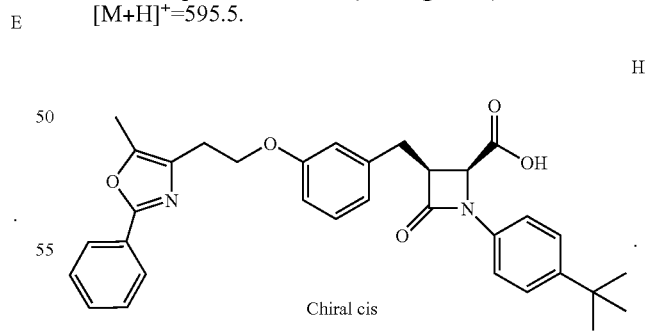

Chiral cis

A mixture of Part F compound (200 mg; 0.49 mmol), Example 23 Part A compound (302 mg; 1.07 mmol) and powdered K$_2$CO$_3$ (270 mg; 1.96 mmol) in CH$_3$CN (15 mL) was stirred at 85° C. for 22 h, then was cooled to RT and the precipitates were filtered off. The filtrate was concentrated in vacuo and the residue was chromatographed (SiO$_2$; continuous gradient from 100% hex to 66%:33% hex:EtOAc over 20 min, hold at 66%:33% hex:EtOAc over 15 min) to give Part G compound as a solid (246 mg, 84%). $[M+H]^+=595.5$.

H

Chiral cis

A solution of Part G compound (229 mg; 0.385 mmol) and TFA (5 mL) in CH$_2$Cl$_2$ (5 mL) was stirred at RT for 4 h. Volatiles were removed in vacuo and the residue was purified by preparative HPLC (Phenomenex reverse-phase Luna C18 5μ 30×250 mm column; flow rate=20 mL/min; 30 min continuous gradient from 80:20 B:A to 100% B+15 min hold time at 100% B, where solvent A=90:10:0.1 H$_2$O: MeOH:TFA and solvent B 90:10:0.1 MeOH:H$_2$O:TFA) to give the product, which was then chromatographed (SiO$_2$;

stepwise gradient from 15:1 to 10:1 CH₂Cl₂:MeOH) to give Example 429 as a white solid (145 mg; 70%). ¹H NMR (400 MHz, CDCl₃) δ 1.29 (s, 9H), 2.40 (S, 3H), 3.00 (t, J=7.9 Hz, 2H), 3.23 (dd, J=14.5, 11.8 Hz, 1H), 3.32 (dd, J=14.5, 3.6 Hz, 1H), 3.83-3.92 (m, 1H), 4.20-4.43 (m, 2H), 4.50 (d, J=5.7 Hz, 1H), 6.79 (dd, J=7.9, 2.2 Hz, 1H), 6.93 (d, J=7.9 Hz, 1H), 6.96 (s, 1H), 7.20-7.35 (m, 0.7H), 7.40-7.46 (m, 1H), 7.92-7.98 (m, 2H); [M+H]⁺=539.1. [α]$_D$=−76.2° (c=0.5, CDCl₃, 25° C.); Absolute stereochemistry is tentatively assigned.

Chiral analytical HPLC (Daicel Chiralcel AD 4.6×250 mm column): flow rate=1 mL/min; isocratic conditions=70:30 A:B, where A=heptane+0.1% TFA and B=IPA+0.1% TFA; detector wavelength=254 nm; retention time=7.96 min; ee>99%

EXAMPLE 430

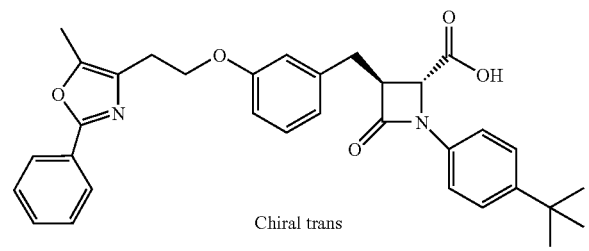

Chiral trans

During preparation of Example 429, a slower eluting side product was isolated by preparative HPLC and was determined to be the corresponding trans epimer (title compound). The epimerization was presumed to have occurred at the carboxylic acid stereocenter. Relative and absolute stereochemistry is tentatively assigned.

¹H NMR (400 MHz, CDCl₃) δ 1.27 (s, 9H), 2.51 (s, 3H), 3.02-3.13 (m, 3H), 3.35 (dd, J=15.9, 3.3 Hz, 1H), 3.73-3.80 (m, 1H), 3.83-3.92 (m, 1H), 4.20-4.30 (m, 2H), 6.74 (d, J=7.7 Hz, 1H), 6.82 (d, J=7.7 Hz, 1H), 6.90 (s, 1H), 7.19 (t, J=7.7 Hz, 1H), 7.25 (d, J=8.3 Hz, 2H), 7.33 (d, J=8.3 Hz, 2H), 7.50-7.61 (m, 3H), 8.05-8.09 (m, 2H); [M+H]⁺=539.2.

EXAMPLE 431

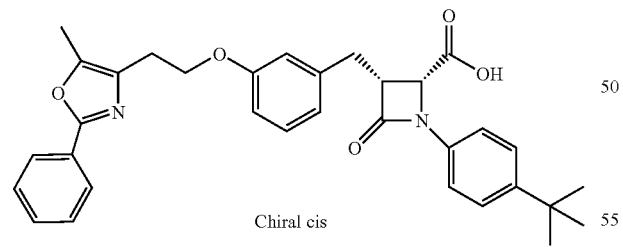

Chiral cis

The title compound was prepared as in Example 429 by starting from Example 429 Part D compound. ¹H NMR: identical to Example 11; [M+H]⁺=539.1; [α]$_D$=+62.0° (c=0.5, CDCl₃, 25° C.). The absolute stereochemistry is tentatively assigned.

Chiral analytical HPLC (Daicel Chiralcel AD 4.6×250 mm column): flow rate=1 mL/min; isocratic conditions 70:30 A:B, where A=heptane+0.1% TFA and B=isopropanol+0.1% TFA; detector wavelength 264 nm; retention time=9.25 min; ee=99.3%

EXAMPLES 432-435

Examples 432-435 were prepared in a similar fashion to Example 429 (from Example 429, Part F compound) using a variety of 2-substituted phenyl-5-methyl oxazole-4-ethanol mesylates (prepared according to general procedure in Example 231, Part A compound) during alkylation step.

Chiral cis

| Example # | R | [M + H]+ | Chiral HPLC Retention time (min)* |
|---|---|---|---|
| 432 | 3-chlorophenyl | 569.1 | 7.15 |
| 433 | 4-chlorophenyl | 569.1 | 8.94 |
| 434 | 3-methoxyphenyl (H₃CO-) | 573.1 | 8.34 |
| 435 | 4-methoxyphenyl (-OCH₃) | 573.0 | 11.18 |

*Chiral analytical HPLC (Daicel Chiralcel AD 4.6 × 250 mm column): flow rate = 1 mL/min; isocratic conditions = 70:30 A:B, where A = heptane + 0.1% TFA and B = isopropanol + 0.1% TFA; detector wavelength = 264 nm.

EXAMPLE 436

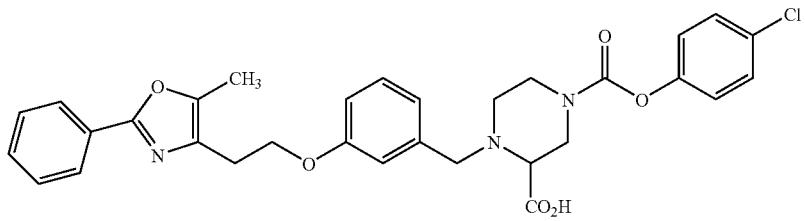

A

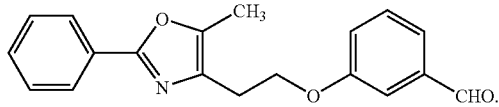

Part A compound was prepared exactly according to the method of Example 47 Part B compound except that 3-hydroxy-benzaldehyde was used in place of 4-hydroxybenzaldehyde.

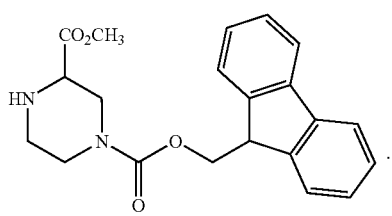

B

HCl gas was bubbled through a solution of N-1-Boc-N-4-Fmoc-2-piperazine carboxylic acid (5.0 g; 11 mmol) in MeOH (250 mL) at RT for 5 min. The reaction was stirred at RT for 5 h, then was concentrated in vacuo. The residue was partitioned between EtOAc and 1N aqueous NaOH. The organic phase was dried (MgSO$_4$) and concentrated in vacuo to give Part B compound (3.8 g; 95%) as an oil.

To a RT solution of Part B compound (1.0 g; 2.7 mmol) and Part A compound (840 mg; 2.7 mmol) in CH$_2$Cl$_2$ (150 mL) was added NaBH(OAc)$_3$ (930 mg; 4.4 mmol). The reaction was stirred at RT for 18 h and then washed with saturated aqueous NaHCO$_3$. The organic phase was dried (MgSO$_4$) and concentrated in vacuo to furnish Part C compound (1.74 g; 97%) as an oil.

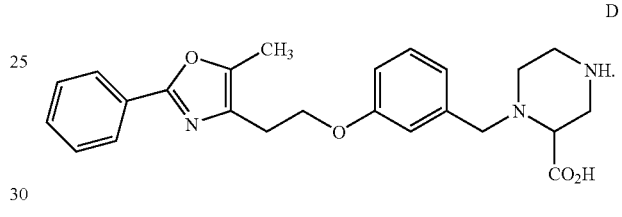

D

A solution of Part C compound (1.74 g; 2.65 mmol) and KOH (740 mg; 13.2 mmol) in MeOH/H$_2$O (40 mL of a 1:1 solution) was stirred at RT for 18 h. Volatiles were removed in vacuo, and the residue was purified by preparative HPLC (YMC reverse-phase ODS 30×250 mm column; detection at 220 nm; flow rate=25 mL/min; continuous gradient from 100% A to 100% B over 30 min+10 min hold time at 100% B, where A=90:10:0.1H$_2$O:MeOH:TFA and B=90:10:0.1 MeOH:H$_2$O:TFA) to provide Part D compound (510 mg; 40%) as an oil.

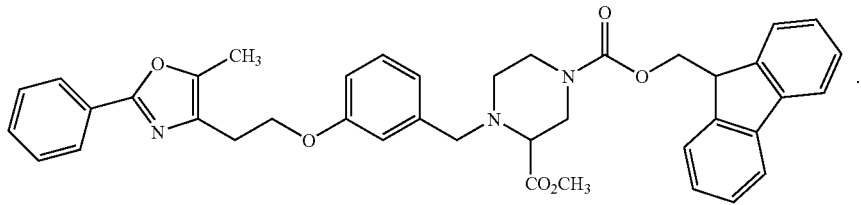

C

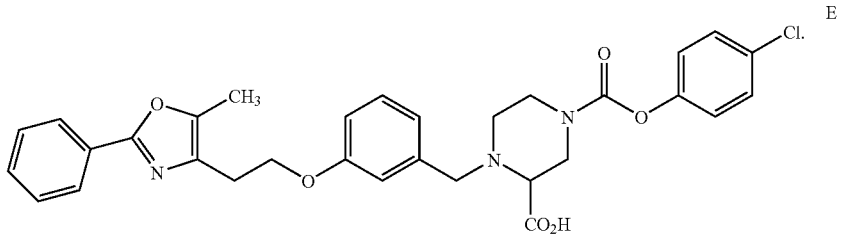

E

To a RT solution of Part D compound (50 mg; 0.11 mmol) and 4-chlorophenyl chloroformate (28 mg; 0.14 mmol) in CH$_2$Cl$_2$ (2 mL) was added Et$_3$N (70 µL; 0.52 mmol). The reaction was stirred at RT for 16 h and then was concentrated in vacuo. The residue was purified by preparative HPLC (YMC reverse-phase ODS 20×100 mm column; detection at 220 nm; flow rate=20 mL/min; continuous gradient from 100% A to 100% B over 30 min+10 min hold time at 100% B, where A=90:10:0.1H$_2$O:MeOH:TFA and B=90:10:0.1 MeOH:H$_2$O:TFA) to provide the title compound (28 mg; 44%) as a solid.
[M+H]$^+$=577.4

EXAMPLES 437-441

Examples 437-441 of the invention were prepared according to the general procedure described for the synthesis of Example 436.

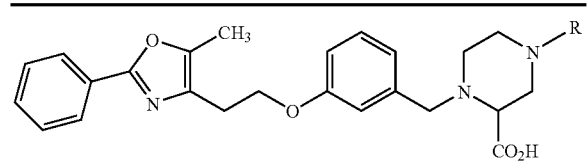

| Example # | R | [M + H]$^+$ |
|---|---|---|
| 437 | 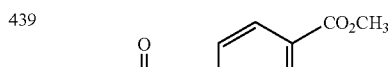 | 560.2 |
| 438 | 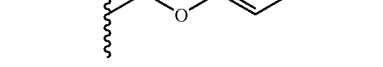 | 556.2 |
| 439 | 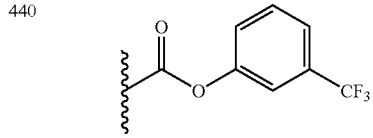 | 600.2 |
| 440 | 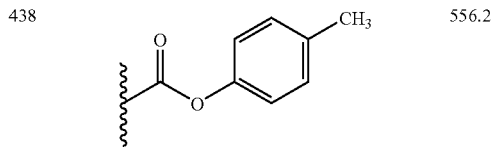 | 610.2 |

-continued

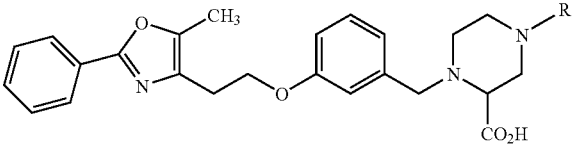

| Example # | R | [M + H]$^+$ |
|---|---|---|
| 441 |  | 592.2 |

EXAMPLE 442

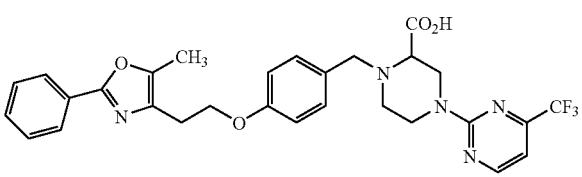

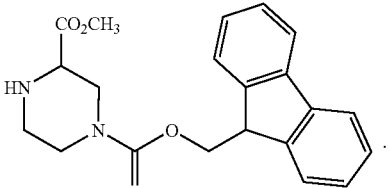

A

HCl gas was bubbled through a solution of N-1-Boc-N-4-Fmoc-2-piperazine carboxylic acid (2.0 g; 4.4 mmol) in MeOH (100 mL) at RT for 5 min. The reaction was stirred at RT for 3 h, then was concentrated in vacuo. The residue was partitioned between EtOAc and 1N aqueous NaOH. The organic phase was dried (MgSO$_4$) and concentrated in vacuo to give Part A compound (1.2 g; 75%) as an oil.

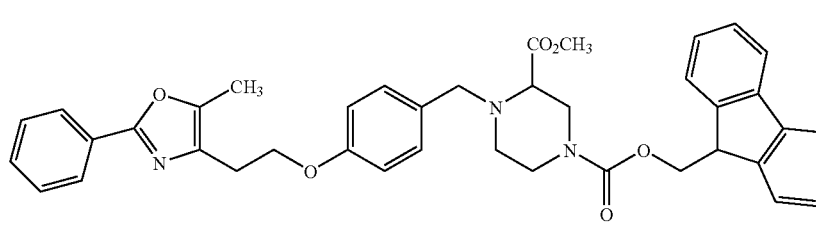

B

To a RT solution of Part A compound (1.1 g; 3.0 mmol) and Example 47 Part B compound (925 mg; 3.0 mmol)

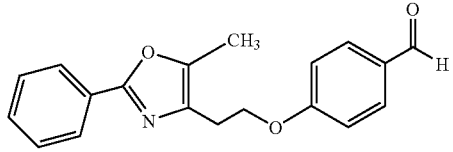

in CH$_2$Cl$_2$ (150 mL) was added NaBH(OAc)$_3$ (930 mg; 4.4 mmol) at RT. The reaction was stirred at RT for 18 h and then washed with saturated aqueous NaHCO$_3$. The organic phase was dried (MgSO$_4$) and concentrated in vacuo. The residue was purified by preparative HPLC (YMC reverse-phase ODS 20×100 mm column; detection at 220 nm; flow rate=20 mL/min; continuous gradient from 100% A to 100% B over 30 min+10 min hold time at 100% B, where A=90:10:0.1 H$_2$O:MeOH:TFA and B=90:10:0.1 MeOH:H$_2$O:TFA) to provide Part B compound (625 mg; 34%) as a solid.

C

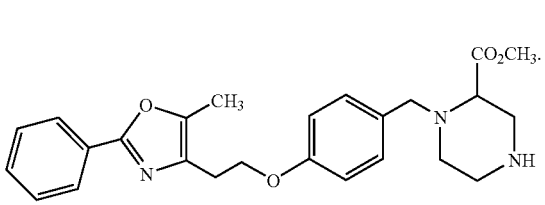

A solution of Part B compound (315 mg; 0.5 mmol) and pyrrolidine (1.0 mL; 12.0 mmol) in DMF (5 mL) was stirred at RT for 18 h. Volatiles were removed in vacuo, and the residue was purified by preparative HPLC (YMC reverse-phase ODS 30×250 mm column; detection at 220 nm; flow rate=25 mL/min; continuous gradient from 100% A to 100% B over 30 min+10 min hold time at 100% B, where A=90:10:0.1 H$_2$O:MeOH:TFA and B=90:10:0.1 MeOH:H$_2$O:TFA) to provide Part C compound (105 mg; 50%) as an oil.

D

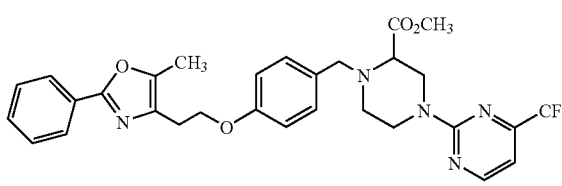

To a RT solution of Part C compound (20 mg; 0.05 mmol) and 2-chloro-4-(trifluoromethyl)-pyrimidine (8.5 mg; 0.05 mmol) in CH$_3$CN (2 mL) was added Cs$_2$CO$_3$ (15 mg; 0.05 mmol). The reaction mixture was stirred at 60° C. for 18 h and then was concentrated in vacuo to give the crude Part D compound, which was used in the next step without further purification.

E

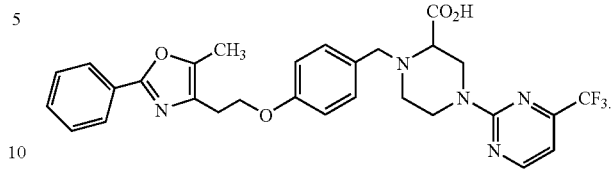

A solution of crude Part D compound was MeOH/H$_2$O (2 mL of a 1:1 solution) and KOH (5 mg, 0.09 mmol) was stirred at 60° C. for 18 h, then cooled to RT and concentrated in vacuo. The residue was purified by preparative HPLC (YMC reverse-phase ODS 20×100 mm column; detection at 220 nm; flow rate=20 mL/min; continuous gradient from 100% A to 100% B over 30 min+10 min hold time at 100% B, where A=90:10:0.1 H$_2$O:MeOH:TFA and B=90:10:0.1 MeOH:H$_2$O:TFA) to provide the title compound (13 mg; 50%) as a solid.

[M+H]$^+$=568.6

EXAMPLES 443-445

Examples 443-445 of the invention were prepared according to the general procedure described for the synthesis of Example 442.

| Example # | R | [M + H]$^+$ |
|---|---|---|
| 443 | 2-chloropyrimidin-4-yl | 535.2 |
| 444 | 3,5,6-trifluoro-4-methylpyridin-2-yl | 567.6 |
| 445 | pyrimidin-2-yl | 500.6 |

EXAMPLE 446

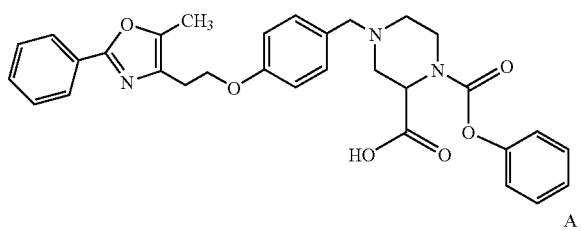

A

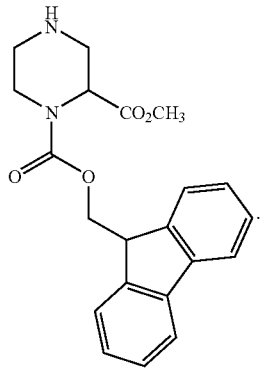

HCl gas was bubbled through a solution of N-4-Boc-N-1-Fmoc-2-piperazine carboxylic acid (1.0 g; 2.2 mmol) in MeOH (100 mL) at RT for 5 min. The reaction was stirred at RT for 2 h, then was concentrated in vacuo. The residue was partitioned between EtOAc and 1N aqueous NaOH. The organic phase was dried (MgSO$_4$) and concentrated in vacuo to give Part A compound (0.8 g; 99%) as an oil.

B

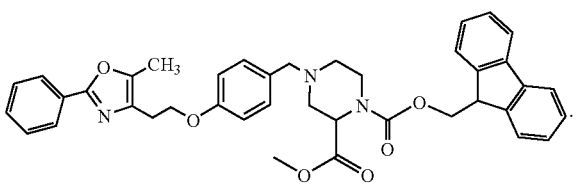

To a RT solution of Part A compound (800 mg; 2.2 mmol) and Example 47 Part B compound (670 mg; 2.2 mmol) in CH$_2$Cl$_2$ (100 mL) was added NaBH(OAc)$_3$ (1.5 g; 7.0 mmol). The reaction was stirred at RT for 48 h and then concentrated in vacuo. The residue was partitioned between EtOAc and saturated aqueous NaHCO$_3$. The organic phase was extracted, dried (MgSO$_4$) and concentrated in vacuo to furnish Part B compound (1.02 g; 73%) as an oil.

C

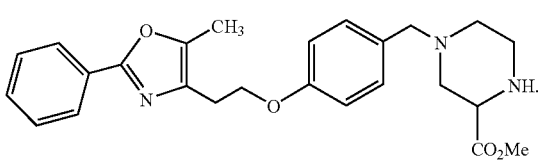

A solution of Part B compound (1.0 g; 1.6 mmol) and pyrrolidine (3.2 mL; 38.8 mmol) in DMF (15 mL) was stirred at RT for 18 h. Volatiles were removed in vacuo, and the residue was purified by preparative HPLC (Shimadzu VP reverse-phase ODS 20×250 mm column; detection at 254 nm; flow rate=20 mL/min; continuous gradient from 90% A to 100% B over 10 min+10 min hold time at 100% B, where A=90:10:0.1 H$_2$O:MeOH:TFA and B=90:10:0.1 MeOH:H$_2$O:TFA) to provide Part C compound (575 mg; 85%) as an oil.

D

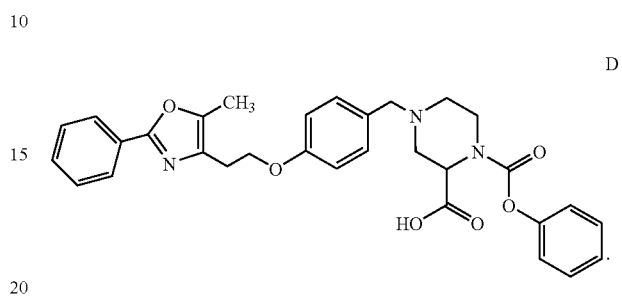

To a RT solution of Part C compound (21 mg; 0.05 mmol) and phenyl chloroformate (9.0 mg; 0.05 mmol) in CH$_2$Cl$_2$ (2 mL) was added Et$_3$N (30 μL; 0.21 mmol). The reaction was stirred at RT for 16 h and then was concentrated in vacuo. The residue was dissolved in MeOH (2.0 mL) and 2.0 mL of a 2.0M KOH solution was added. The reaction was stirred at RT for 8 h, then was concentrated in vacuo. The residue was purified by preparative HPLC (YMC reverse-phase ODS 20×100 mm column; detection at 220 nm, flow rate=20 mL/min; continuous gradient from 90% A to 100% B over 10 min+10 min hold time at 100% B, where A=90:10:0.1 H$_2$O:MeOH:TFA and B=90:10:0.1 MeOH:H$_2$O:TFA) to provide the title compound (4.0 mg; 15%) as a solid. [M+H]$^+$=542.6

EXAMPLES 447-460

Examples 447-460 of the invention were prepared according to the general procedures described for the synthesis of Example 446.

| Example # | R | [M + H]$^+$ |
|---|---|---|
| 447 | ethyl ester | 494.5 |
| 448 | 4-methoxyphenyl carbonate | 572.6 |

435

-continued

| Example # | R | [M + H]+ |
|---|---|---|
| 449 | (ethyl ketone) | 478.5 |
| 450 | (methyl ketone, gem-dimethyl) | 464.5 |
| 451 | (N-methyl-N-phenyl amide) | 555.6 |
| 452 | (benzoyl) | 526.6 |
| 453 | (4-methoxybenzoyl) | 556.6 |
| 454 | (4-fluorobenzoyl) | 560.6 |
| 455 | (4-methylbenzoyl) | 556.6 |
| 456 | (4-chlorobenzoyl) | 577 |
| 457 | (2-methoxyphenyl ester) | 572.6 |

436

-continued

| Example # | R | [M + H]+ |
|---|---|---|
| 458 | (2-naphthyl ester) | 592.6 |
| 459 | (4-methoxybenzyl) | 542.6 |
| 460 | H | 422 |

EXAMPLE 461

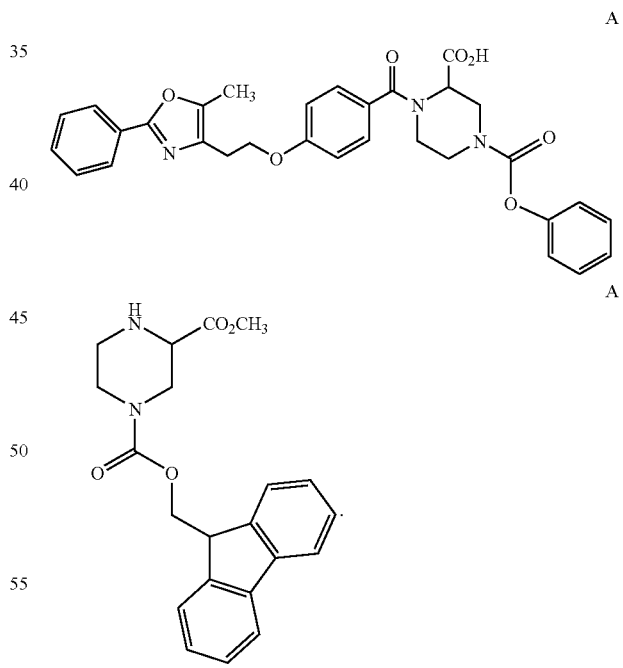

HCl gas was bubbled through a solution of N-1-Boc-N-4-Fmoc-2-piperazine carboxylic acid (4.0 g; 8.8 mmol) in MeOH (200 mL) at RT for 5 min. The reaction was stirred at RT for 2 h, then was concentrated in vacuo. The residue was partitioned between EtOAc and 1N aqueous NaOH. The organic phase was dried (MgSO$_4$) and concentrated in vacuo to give Part A compound (1.4 g; 42%) as an oil.

B

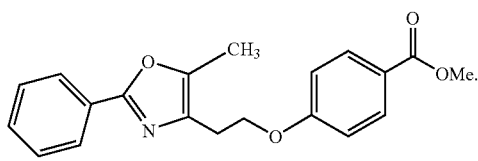

A solution of Example 23 Part A compound (1.1 g; 3.7 mmol), 4-hydroxy-benzoic acid methyl ester (570 mg; 3.7 mmol), and $K_2CO_3$ (515 mg; 3.7 mmol) in $CH_3CN$ (100 mL) was heated at 90° C. with stirring for 18 h. The reaction mixture was cooled to RT, and the solvent was removed in vacuo. The residue was partitioned between EtOAc and 1N NaOH. The organic phase was extracted, dried ($MgSO_4$) and concentrated in vacuo to give Part B compound (1.1 g; 91%).

C

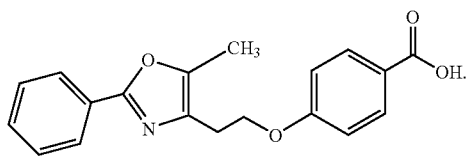

A solution of Part B compound (1.1 g; 3.3 mmol) and potassium hydroxide (1.8 g; 33 mmol) in 1:1 MeOH:$H_2O$ (100 mL) was stirred at RT for 18 h. The solvent was removed in vacuo, and the residue was partitioned between EtOAc and $H_2O$. The aqueous layer was brought to pH 5 using 1N HCl. The organic phase was extracted, dried ($MgSO_4$) and concentrated to give Part C compound (1.1 g; >99%).

D

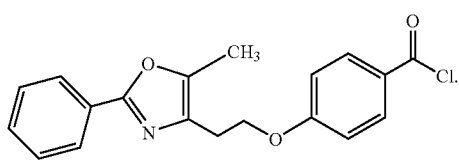

A solution of Part C compound (1.1 g; 3.4 mmol) and oxalyl chloride (1.5 mL; 17 mmol) in $CH_2Cl_2$ (100 mL) was stirred at RT for 18 h. A second portion of oxalyl chloride (1.5 mL; 17 mmol) was added to the reaction, and the mixture stirred at RT for an additional 18 h. The solvent was removed in vacuo to give Part D compound (1.16 g; >99%).

To a RT solution of Part A compound (1.25 g mg; 3.4 mmol) and Part D compound (1.16 g; 3.4 mmol) in $CH_2Cl_2$ (100 mL) was added $Et_3N$ (1.0 mL; 6.8 mmol). The reaction was stirred at RT for 18 h and then concentrated in vacuo. The residue was partitioned between EtOAc and saturated aqueous $NaHCO_3$. The organic phase was extracted, dried ($MgSO_4$) and concentrated in vacuo to give Part E compound (1.7 g; 75%) as an oil.

F

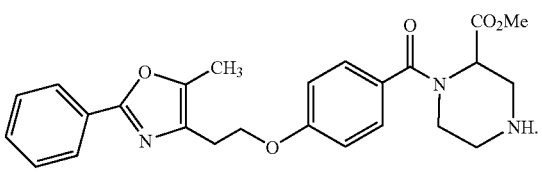

A solution of Part E compound (1.7 g; 2.5 mmol) and pyrrolidine (5.2 mL; 62.5 mmol) in DMF (10 mL) was stirred at RT for 18 h. Volatiles were removed in vacuo, and the residue was purified by preparative HPLC (Shimadzu VP reverse-phase ODS 20×250 mm column; detection at 254 nm; flow rate=20 mL/min; continuous gradient from 90:10 A:B to 100% B over 10 min+10 min hold time at 100% B, where A=90:10:0.1 $H_2O$:MeOH:TFA and B=90:10:0.1 MeOH:$H_2O$:TFA) to provide Part F compound (1.08 g; 96%) as an oil.

G

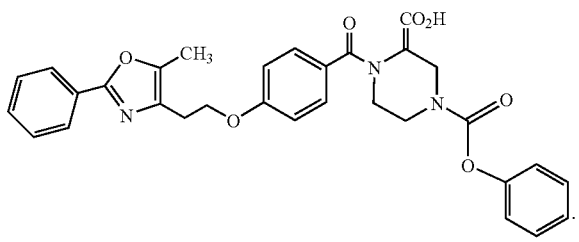

To a RT solution of Part F compound (50 mg; 0.11 mmol) and phenyl chloroformate (21 mg; 0.13 mmol) in $CH_2Cl_2$ (2 mL) was added $Et_3N$ (70 μL; 0.48 mmol). The reaction was stirred at RT for 16 h and then was concentrated in vacuo. The residue was dissolved in MeOH (2.0 mL) and aqueous KOH (2.0 mL of a 2 M solution) was added. The reaction stirred at RT for 8 h and then was concentrated in vacuo. The residue was purified by preparative HPLC (exactly as described in Part F) to provide the title compound (10.0 mg; 16%) as a solid.

[M+H]$^+$=556.6

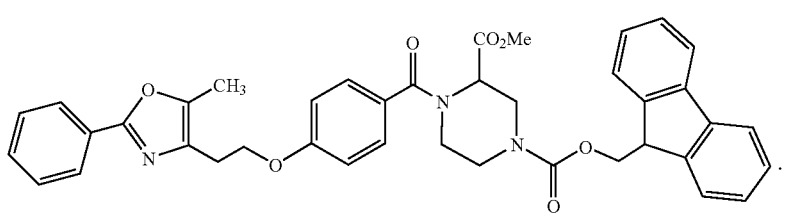

EXAMPLES 462-468

Examples 462-468 of the invention were prepared according to the general procedures described for the synthesis of Example 461.

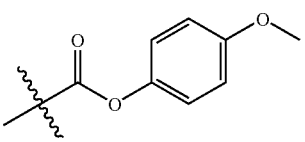

| Example No. | R | [M + H]⁺ |
|---|---|---|
| 462 | 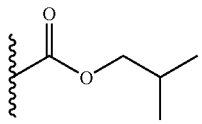 | 586.6 |
| 463 | 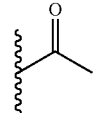 | 536.6 |
| 464 | 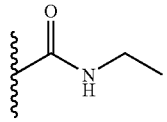 | 478.5 |
| 465 | 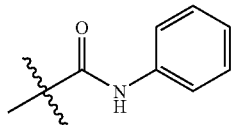 | 507.6 |
| 466 | 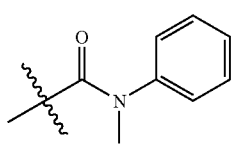 | 555.6 |
| 467 | 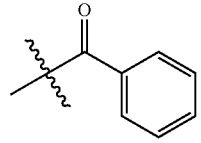 | 569.6 |
| 468 | 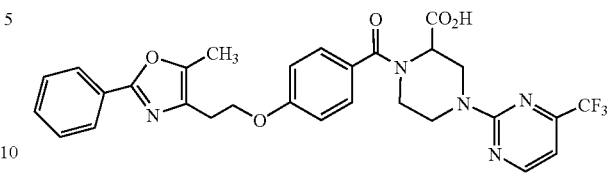 | 540.6 |

EXAMPLE 469

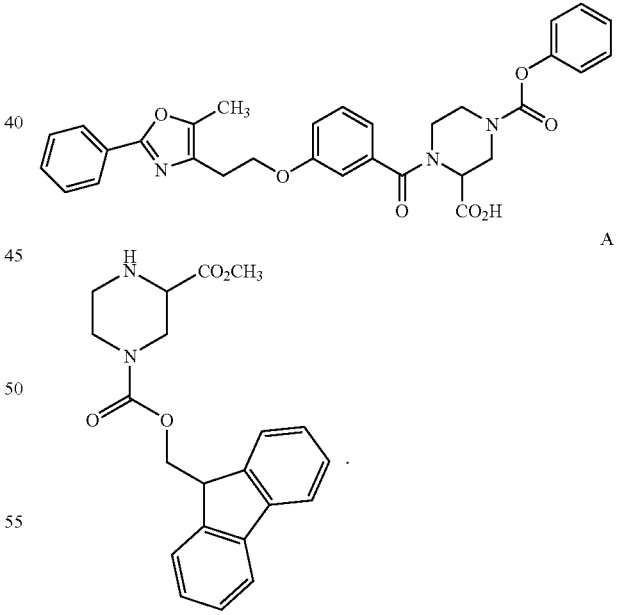

To a RT solution of Example 461 Part F compound (50 mg; 0.11 mmol) and 2-chloro-4-(trifluoromethyl)pyrimidine (21 mg; 0.11 mmol) in $CH_3CN$ (2 mL) was added $Cs_2CO_3$ (37 mg; 0.11 mmol). The reaction was stirred at RT for 16 h, then at 60° C. for 4 h and then was concentrated in vacuo. The residue was dissolved in MeOH (2.0 mL) and aqueous KOH (2.0 mL of a 2.0M solution) was added. The reaction was stirred at 60° C. for 18 h and was concentrated in vacuo. The residue was purified by preparative HPLC (YMC reverse-phase ODS 20×100 mm column; detection at 220 nm; flow rate=20 mL/min; continuous gradient from 90% A to 100% B over 10 min+10 min hold time at 100% B, where A=90:10:0.1 $H_2O$:MeOH:TFA and B=90:10:0.1 MeOH:$H_2O$:TFA) to provide the title compound (5.0 mg; 10%) as a solid.

$[M+H]^+=582.5$

EXAMPLE 470

HCl gas was bubbled through a solution of N-1-Boc-N-4-Fmoc-2-piperazine carboxylic acid (4.0 g; 8.8 mmol) in MeOH (200 mL) at RT for 5 min. The reaction was stirred at RT for 2 h, then was concentrated in vacuo. The residue was partitioned between EtOAc and 1N aqueous NaOH. The organic phase was dried ($MgSO_4$) and concentrated in vacuo to give Part A compound (1.4 g; 42%) as an oil.

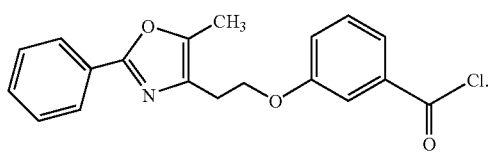
B

Part B compound was prepared according to the procedure described for the synthesis of Example 461 Parts B-D compounds, except that 3-hydroxy-benzoic acid methyl ester was used in place of 4-hydroxy-benzoic acid methyl ester.

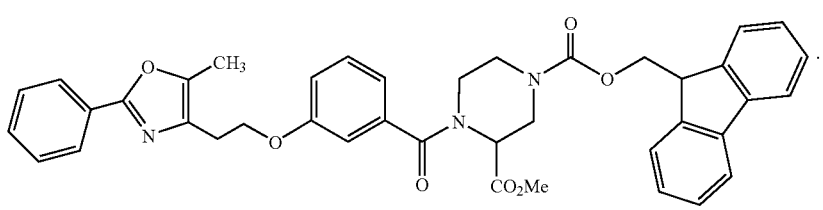
C

A RT solution of Part A compound (1.25 g mg; 3.4 mmol), Part B compound (1.16 g; 3.4 mmol) and Et₃N (1.0 mL; 6.8 mmol) in CH₂Cl₂ (100 mL) was stirred at RT for 18 h and then concentrated in vacuo. The residue was partitioned between EtOAc and saturated aqueous NaHCO₃. The organic phase was extracted, dried (MgSO₄) and concentrated in vacuo to furnish Part C compound (2.2 g; 99%) as an oil.

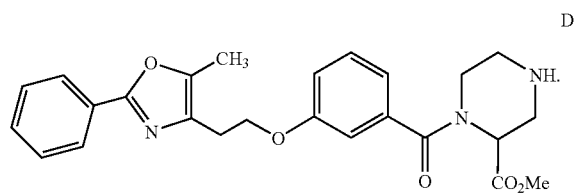
D

A solution of Part C compound (2.2 g; 3.3 mmol) and pyrrolidine (6.8 mL; 82.0 mmol) in DMF (10 mL) was stirred at RT for 18 h. Volatiles were removed in vacuo, and the residue was purified by preparative HPLC (Shimadzu VP reverse-phase ODS 20×250 mm column; detection at 254 nm; flow rate=20 mL/min; continuous gradient from 90% A to 100% B over 10 min+10 min hold time at 100% B, where A=90:10:0.1 H₂O:MeOH:TFA and B=90:10:0.1 MeOH:H₂O:TFA) to provide Part D compound (382 mg; 26%) as an oil.

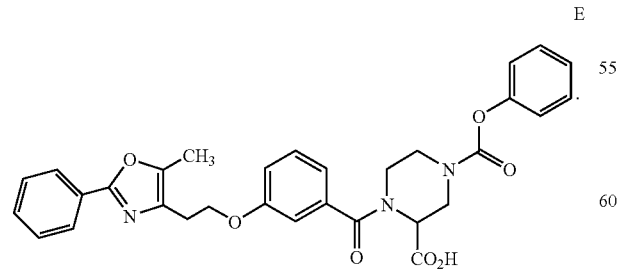
E

To a RT solution of Part D compound (40 mg; 0.09 mmol) and phenyl chloroformate (17 mg; 0.11 mmol) in CH₂Cl₂ (2 mL) was added Et₃N (60 µL; 0.39 mmol). The reaction was stirred at RT for 16 h and then was concentrated in vacuo.

The residue was dissolved in methanol (2.0 mL) and aqueous KOH (2.0 mL of a 2 M solution) was added. The reaction was stirred at RT for 8 h and was concentrated in vacuo. The residue was purified by preparative HPLC (as described for Part D compound) to provide the title compound (11.0 mg; 22%) as a solid. [M+H]⁺=556.6

EXAMPLES 471-477

Examples 471-477 of the invention were prepared according to the general procedures described for the synthesis of Example 470.

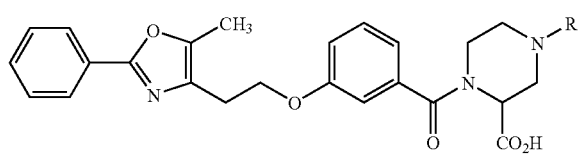

| Example # | R | [M + H]⁺ |
|---|---|---|
| 471 | 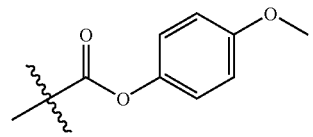 | 586.6 |
| 472 | 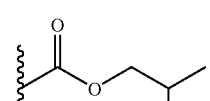 | 536.6 |
| 473 | 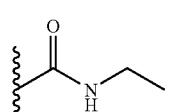 | 507.6 |
| 474 | | 555.6 |
| 475 | | 569.6 |

-continued

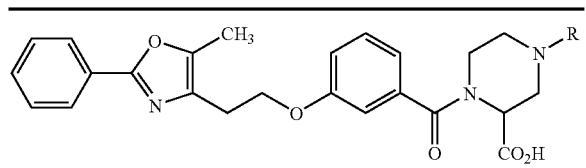

| Example # | R | [M + H]+ |
|---|---|---|
| 476 | 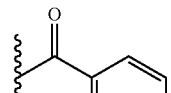 | 540.6 |
| 477 |  | 478.5 |

EXAMPLE 478

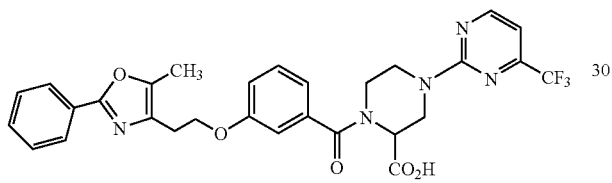

To a RT solution of Example 470 Part D compound (40 mg; 0.09 mmol) and 2-chloro-4-(trifluoromethyl)pyrimidine (17 mg; 0.09 mmol) in $CH_3CN$ (2 mL) was added $Cs_2CO_3$ (30 mg; 0.09 mmol). The reaction was stirred at RT for 18 h and then was concentrated in vacuo. The residue was dissolved in methanol (2.0 mL) and aqueous KOH (2.0 mL of a 2 M solution) was added. The reaction was stirred at RT for 18 h and was concentrated in vacuo. The residue was purified by preparative HPLC (YMC reverse-phase ODS 20×100 mm column; detection at 220 nm; flow rate=20 mL/min; continuous gradient from 90% A to 100% B over 10 min+10 min hold time at 100% B, where A=90:10:0.1 $H_2O$:MeOH:TFA and B=90:10:0.1 MeOH:$H_2O$:TFA) to provide the title compound (3.0 mg; 6%) as a solid. $[M+H]^+=582.5$

EXAMPLE 479

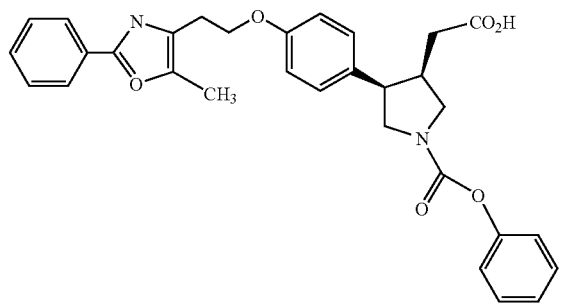

A

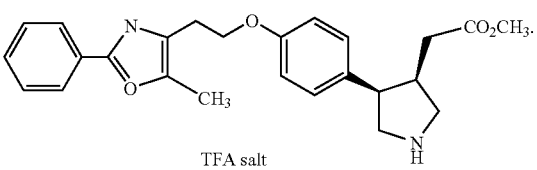

TFA salt

A solution of Example 242 Part A compound (65.6 mg; 0.126 mmol) in TFA (1 mL) and $CH_2Cl_2$ (4 mL) was stirred at RT for 1.5 h, then was concentrated in vacuo to give Part A compound as an oil (66 mg), which was used in the next step without further purification.

B

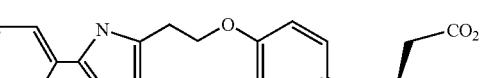

To a solution of Part A compound (9.4 mg, 0.0176 mmol) and $NaHCO_3$ (15 mg; 0.178 mmol) in $H_2O$ (0.7 mL) and THF (1 mL) was added phenyl chloroformate (15 mg, 0.0285 mmol). The reaction was stirred at RT for 2 h, then was partitioned between EtOAc and $H_2O$ (1 mL each). The organic phase was concentrated in vacuo to give Part B compound as an oil.

C

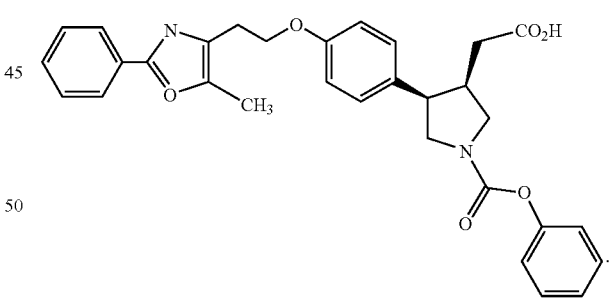

A mixture of Part B compound and $LiOH.H_2O$ (8 mg; 0.19 mmol) in THF/$H_2O$ (1 mL of a 1:1 solution) was stirred at RT for 16 h, after which the pH was adjusted to ~5 with aqueous 1 M HCl. The mixture was extracted with EtOAc (2 mL). The combined organic extracts were concentrated in vacuo and the residue was purified by preparative HPLC (YMC reverse-phase ODS 20×100 mm column; flow rate=20 mL/min; 10 min continuous gradient from 30:70 B:A to 100% B+5 min hold-time at 100% B, where solvent A=90:10:0.1 $H_2O$:MeOH:TFA and solvent B=90:10:0.1 MeOH:$H_2O$:TFA) to give the title compound (5.0 mg; 54%). $[M+H]^+=527.0$

EXAMPLES 480-486

Examples 480-486 of the invention were prepared in a similar fashion to the synthesis of Example 479 (from Example 479 Part A compound) using a variety of chloroformates.

| Example # | R | [M + H]⁺ |
|---|---|---|
| 480 | –C(O)OEt | 479.1 |
| 481 | –C(O)O-n-Pr | 493.1 |
| 482 | –C(O)O-i-Pr | 493.1 |
| 483 | –C(O)O-n-Bu | 507.1 |
| 484 | –C(O)O-i-Bu | 539.0 |
| 485 | –C(O)OCH₂Ph | 541.0 |
| 486 | –C(O)O(4-MeO-C₆H₄) | 557.0 |

EXAMPLE 487

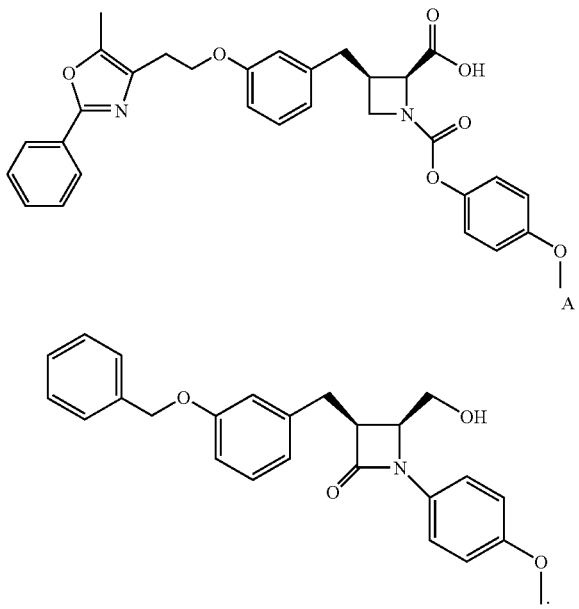

To a solution of Example 419 Part F compound (2.0 g, 4.99 mmol) in THF (60 mL) was added LiBH$_4$ (0.18 g 8.26 mmol) and MeOH (6 ml). The reaction was stirred at RT for 2 h. Volatiles were removed in vacuo and the residue was partitioned between saturated aqueous NaHCO$_3$ (20 mL) and EtOAc (250 mL). The organic phase was dried (MgSO$_4$) and concentrated in vacuo. The residue was chromatographed (SiO$_2$; continuous gradient from 92:8 hex:EtOAc to 65:35 hex:EtOAc over 40 min, 65:35 hex:EtOAc for 20 min) to give Part A compound (1.5 g, 75%) as a solid.

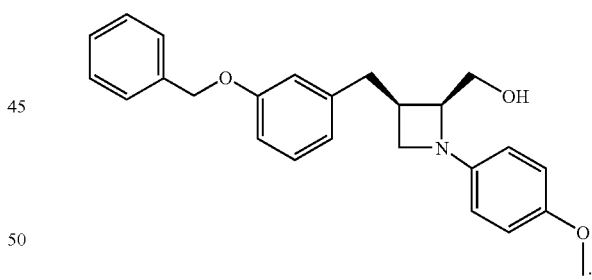

Monochloro-alane was prepared according to the literature procedure (Ref: Benito Alcaide et al, JOC 1999, 64, 9596). A solution of anhydrous AlCl$_3$ (400 mg, 3.1 mmol) in dry Et$_2$O (5 mL) was added to a well-stirred suspension of LiAlH$_4$ (118 mg, 1.73 mmol) in anhydrous Et$_2$O. The mixture was heated at reflux for 30 min and cooled to RT. An aliquot of this monochloro-alane solution in Et$_2$O (10 mL, ~3.1 mmol) was transferred via cannula into a solution of Part A compound (0.7 g, 1.73 mmol) in THF (21 mL) at RT. The mixture was stirred at RT for 1.5 h, then was partitioned between water (5 mL) and EtOAc (150 mL). The organic phase was dried (MgSO$_4$) and concentrated in vacuo; the residue was chromatographed (SiO$_2$; 3:2 hex:EtOAc) to give Part B compound (0.38 g; 56%) as a colorless oil, [M+H]⁺= 390.3.

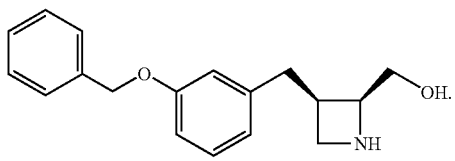

C

To a 0° C. solution of Part B compound (0.2 g; 0.52 mmol) in CH₃CN (3 mL) was added aqueous ceric ammonium nitrate (0.422 g in 2.1 mL H₂O; 0.77 mmol). The reaction was stirred at 0° C. for 30 min, then was partitioned between EtOAc (10 mL) and saturated aqueous sodium sulfite (5 mL). The organic phase was dried (MgSO₄) and concentrated in vacuo to give crude Part C compound as an oil.

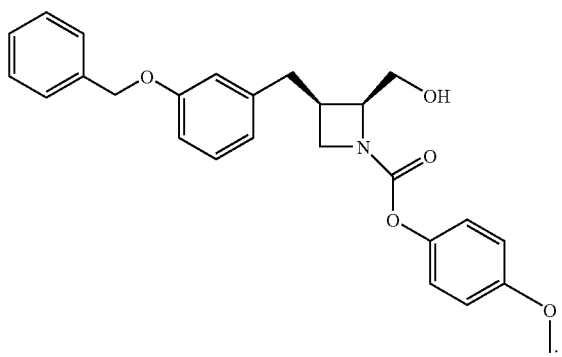

D

To a solution of Part C compound in THF (3 mL) was added aqueous NaHCO₃ (0.128 g in 2 mL H₂O; 1.52 mmol) and 4-methoxyphenyl chloroformate (0.1 ml, 0.67 mmol). The reaction mixture was stirred at RT for 30 min, then was partitioned between water (5 mL) and EtOAc (20 mL). The organic phase was dried (MgSO₄) and concentrated in vacuo; the residue was chromatographed (SiO₂; stepwise gradient from 2:1 to 1.5:1 hex:EtOAc) to give Part D compound (31.2 mg; 14% over 2 steps) as a colorless oil. [M+H]⁺=434.3.

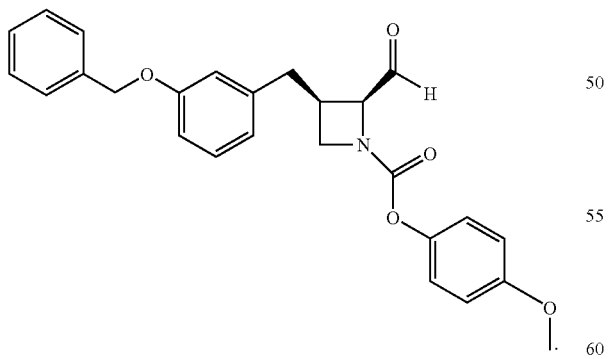

E

To a mixture of Dess-Martin periodinane(58 mg; 0.137 mmol) in CH₂Cl₂ (3 mL) at RT was added a solution of Part D compound (40 mg; 0.093 mmol). The reaction was stirred at RT for 30 h. Volatiles were removed in vacuo. The residue was chromatographed (SiO₂; 2:1 hex:EtOAc) to give Part E compound as an oil.

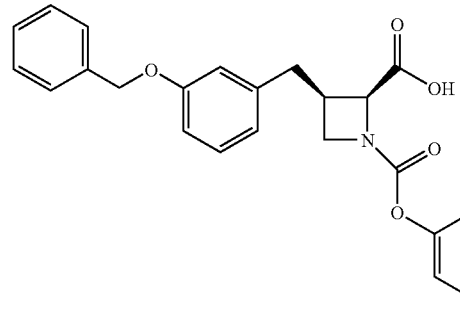

F

To a 0° C. solution of Part E compound in acetone (2 mL) was added Jones reagent (~3 drops). The reaction was stirred at RT for 30 min. Volatiles were removed in vacuo and the residue was partitioned between water (2 mL) and EtOAc (5 mL). The organic phase was dried (MgSO₄) and concentrated in vacuo to give crude Part F compound, which was used in the next step without further purification. [M+H]⁺= 448.3.

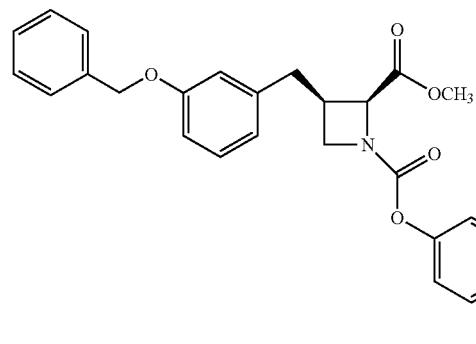

G

To a 0° C. solution of Part F compound in MeOH (1.5 mL) and CH₂Cl₂ (0.5 mL) was added TMSCHN₂ (0.2 mL of a 2M solution in hexane; 0.4 mmol). The reaction was stirred at RT for 2 h. Volatiles were moved in vacuo. The residue was chromatographed (SiO₂; stepwise gradient from 3:1 to 2:1 hex:EtOAc) to give Part G compound (30 mg; 70% over two steps) as an oil. [M+H]⁺=462.3

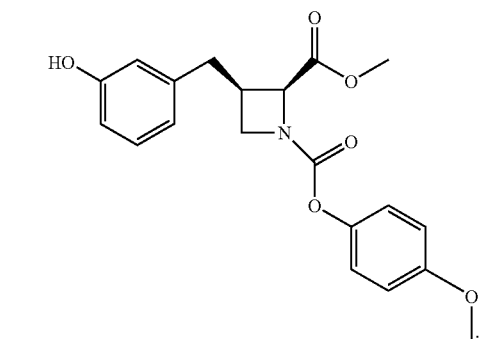

H

A mixture of Part G compound (30 mg; 0.065 mmol) and 10% Pd/C (8 mg) in EtOAc (3.5 mL) was stirred under an atmosphere of H₂ (balloon) at RT for 4 h, at which point the reaction was complete by HPLC. The catalyst was filtered off through Celite® and the filtrate was concentrated in vacuo to give crude Part H compound (17.0 mg, 71%) as a white solid which was used in the next step without further purification.

[M+H]⁺=372.6.

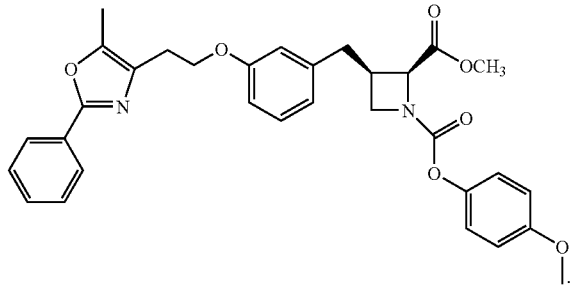

I

A mixture of Part H compound (17 mg; 0.045 mmol), Example 23 Part A compound (23 mg; 0.082 mmol) and powdered K₂CO₃ (16 mg; 0.115 mmol) in CH₃CN (2 mL) was stirred at 90° C. for 4 h, after which another portion of Example 23 Part A compound (20 mg; 0.082 mmol) was added. The reaction mixture was stirred at 90° C. for another 14 h, cooled to RT and filtered. The filtrate was concentrated in vacuo. The residue was chromatographed (SiO₂; stepwise gradient from 3:1 to 1:1 hex:EtOAc) to give Part I compound as an oil.

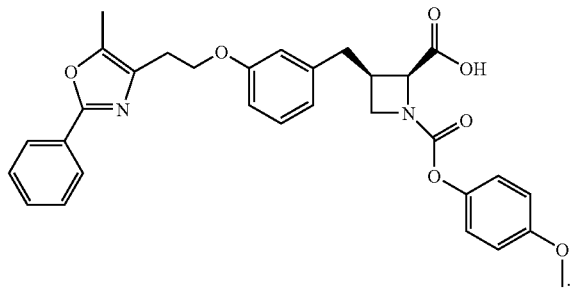

J

A solution of Part I compound and aqueous LiOH (4 mg in 0.6 mL H₂O, 0.095 mmol) in THF (1.5 mL) was stirred at RT for 6 h, then acidified to pH 4 by the addition of 1M aqueous HCl. Volatiles were removed in vacuo and the residue was partitioned between water (2 mL) and EtOAc (10 mL). The organic phase was dried (MgSO₄) and concentrated in vacuo. The residue was purified by preparative HPLC (continuous gradient from 70:30 A:B to 100% B; A=90:10:0.1 H₂O:MeOH:TFA; B=90:10:0.1 MeOH:H₂O: TFA; 12 min run @ 20 mL/min; detection at 220 nm; YMC ODS 20×100 mm column) to give the title compound (4.0 mg; 16%) as a viscous oil.

¹H NMR (400 MHz, CD₃OD) δ 2.28(3H, s), 2.55-2.65 (1H, m), 2.89-2.90 (3H, m), 3.2-3.3 (1H ,m), 3.69 (3H, s), 3.70-4.10 (2H, m), 4.14 (2H, t, J=6.6 Hz), 4.70-4.90 (1H, m), 6.60-7.10 (m, 8H), 7.35-7.40 (3H, m), 7.80-7.90 (2H, m)

[M+H]⁺=543.2

EXAMPLE 488

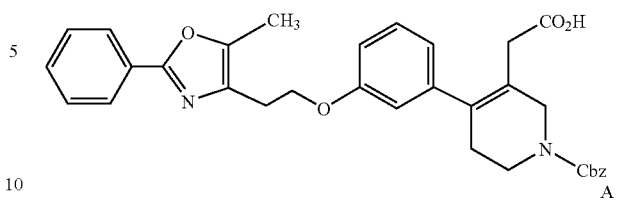

A

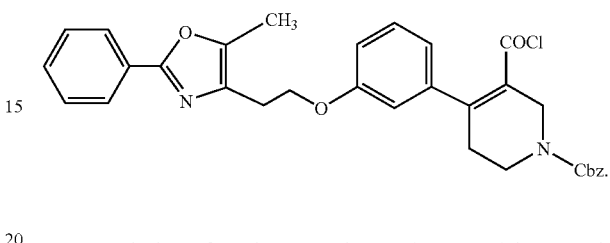

To a solution of crude Example 310 (~100 mg) in CH₂Cl₂ (5 mL) was added oxalyl chloride (1.4 mL of a 1 mL solution in CH₂Cl₂; 1.4 mmol) and one drop of DMF. The solution was stirred for 18 h at RT and then concentrated in vacuo to give Part A compound.

B

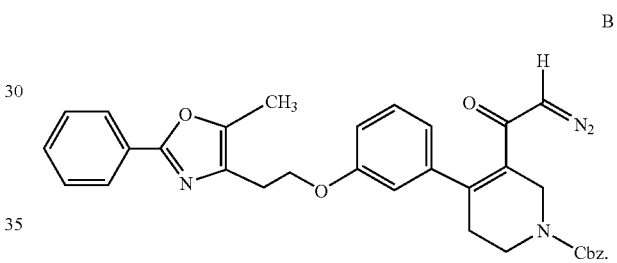

To a solution of diazomethane in 20 mL of Et₂O (prepared from 10 mL of 50% aqueous KOH and 1-methyl-3-nitro-1-nitrosoguanidine (0.411 g; 2.8 mmoL) in 20 mL of Et₂O at 0° C. according to the procedure described in Example 281 Part C), was added a solution of Part A compound in CH₂Cl₂ (2 mL) and Et₂O (10 mL). The solution was stirred for 4 h at RT and concentrated in vacuo. The residue was chromatographed (SiO₂; 4:1 hex:EtOAc) to give Part B compound.

C

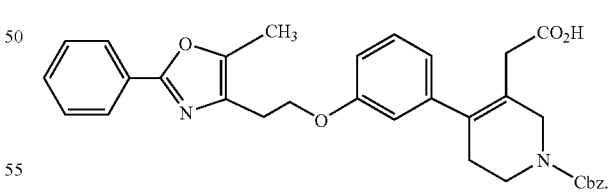

To a solution of Part B compound in MeOH (5 mL) was added silver benzoate (64 mg; 0.28 mmol) and Et₃N (0.2 mL) at RT. The mixture was stirred at RT for 4 h and then filtered. Aqueous 1 N KOH (2 mL) was added to the filtrate and the mixture was stirred for 3 h at RT, then was neutralized with 1 N HCl, concentrated in vacuo and partitioned between brine and EtOAc. The organic layer was washed with brine and concentrated in vacuo. The residue was purified by HPLC (YMC reverse-phase ODS 20×100 mm column; flow rate=20 mL/min; 10 min continuous gradient from 30:70 B:A to 100% B+5 min hold-time at 100% B, where solvent A=90:10:0.1 H$_2$O:MeOH:TFA and solvent B=90:10:0.1 MeOH:H$_2$O:TFA) to give the title compound (7 mg; 7%).

[M+H]$^+$=553.2

What is claimed is:

1. A compound having the structure

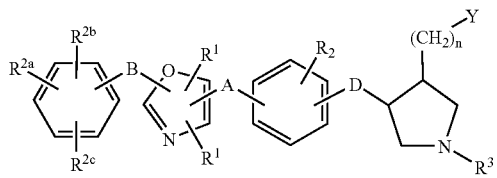

wherein

D is —CH= or C=O or (CH$_2$)$_m$ where m is 0, 1, 2 or 3;

n=0, 1 or 2;

A is (CH$_2$)$_x$ where x is 1 to 5; or A is (CH$_2$)$_x^1$, where x$^1$ is 1 to 5, with an alkenyl bond or an alkynyl bond embedded anywhere in the chain; or A is —(CH$_2$)$_x^2$—O—(CH$_2$)$_x^3$— where x$^2$ is 0 to 5 and x$^3$ is 0 to 5, provided that at least one of x$^2$ and x$^3$ is other than 0;

B is a bond or is (CH$_2$)$_x^4$ where x$^4$ is 1 to 5;

R$^1$ is H or alkyl;

R$^2$ is H, alkyl, alkoxy, halogen, amino or substituted amino;

R$^{2a}$, R$^{2b}$ and R$^{2c}$ may be the same or different and are selected from H, alkyl, alkoxy, halogen, amino, substituted amino or cyano;

R$^3$ is selected from H, arylalkyl, aryloxycarbonyl, alkyloxycarbonyl, alkynyloxycarbonyl, alkenyloxycarbonyl, alkylcarbonyl, aryl, heteroaryl, heteroaryloxycarbonyl, cycloheteroalkyloxycarbonyl, substituted aminocarbonyl, alkylaminocarbonyl, arylaminocarbonyl, alkoxyaryloxycarbonyl, arylalkyloxycarbonyl, alkylaryloxycarbonyl, arylalkylarylalkyl, aryloxyarylalkyl, haloalkoxyaryloxycarbonyl, alkoxycarbonylaryloxycarbonyl, aryloxyaryloxycarbonyl, arylalkenyloxycarbonyl, heteroaryloxyarylalkyl, alkylsulfonyl, alkenylsulfonyl, aryloxyarylalkyloxycarbonyl, arylalkylcarbonyl, aryloxyalkyloxycarbonyl, arylalkylsulfonyl, arylalkenylsulfonyl, heteroarylsulfonyl, arylsulfonyl, alkoxyarylalkyl, heteroarylalkoxycarbonyl, arylheteroarylalkyl, heteroarylalkyloxyarylalkyl, arylarylalkyl, arylalkenylarylalkyl, arylalkoxyarylalkyl, arylcarbonylarylalkyl, alkylaryloxyarylalkyl, heteroarylarylalkyl, heteroaryloxyarylalkyl, arylaminoarylalkyl, or aminocarbonylarylarylalkyl;

(CH$_2$)$_x$, (CH$_2$)$_x^1$, (CH$_2$)$_x^2$, (CH$_2$)$_x^3$, (CH$_2$)$_x^4$, (CH$_2$)$_m$, and (CH$_2$)$_n$ may be optionally substituted;

Y is CO$_2$R$^4$ where R$^4$ is H or alkyl, or Y is a C-linked 1-tetrazole, a phosphinic acid of the structure P(O)(OR$^{4a}$)R$^5$ where R$^{4a}$ is H, R$^5$ is alkyl or aryl, or a phosphonic acid of the structure P(O)(OR$^{4a}$)$_2$;

including all stereoisomers thereof, prodrug esters thereof, and pharmaceutically acceptable salts thereof.

2. The compound as defined in claim 1 wherein A is —CH$_2$)$_x^2$—O—.

3. The compound as defined in claim 1 wherein B is a bond.

4. The compound as defined in claim 1 wherein B is a bond and A is —(CH$_2$)$_x^2$—O—.

5. The compound as defined in claim 1 wherein B is a bond;

A is (CH$_2$)$_x^2$—O—;

R$^1$ is alkyl;

R$^{2a}$ is alkyl, alkoxy or halogen;

x$^2$ is 1 to 3;

D is —CH= or (CH$_2$)$_m$ where m is 0 or (CH$_2$)$_m$ is CH$_2$ or CH-alkyl;

(CH$_2$)$_n$ is a bond or CH$_2$;

R$^3$ is alkoxycarbonyl, aryl, heteroaryl, aryloxycarbonyl or arylalkyl;

Y is CO$_2$R$^4$; and n is 0.

6. The compound as defined in claim 1 selected from the group consisting of compounds having the structure

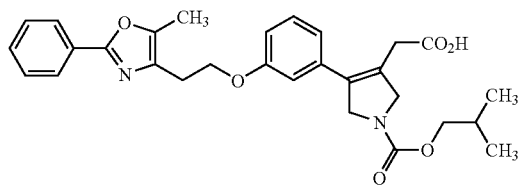

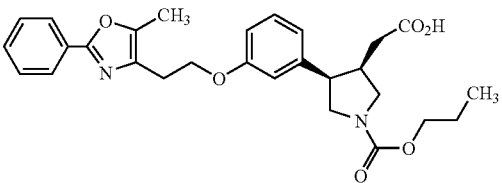

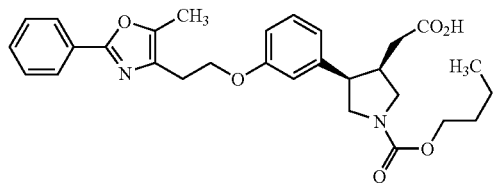

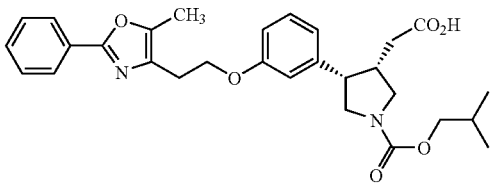

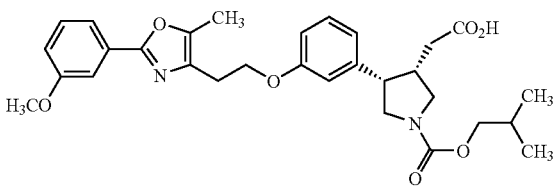

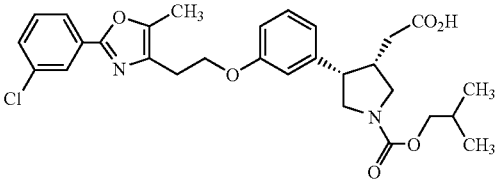

453
454
-continued
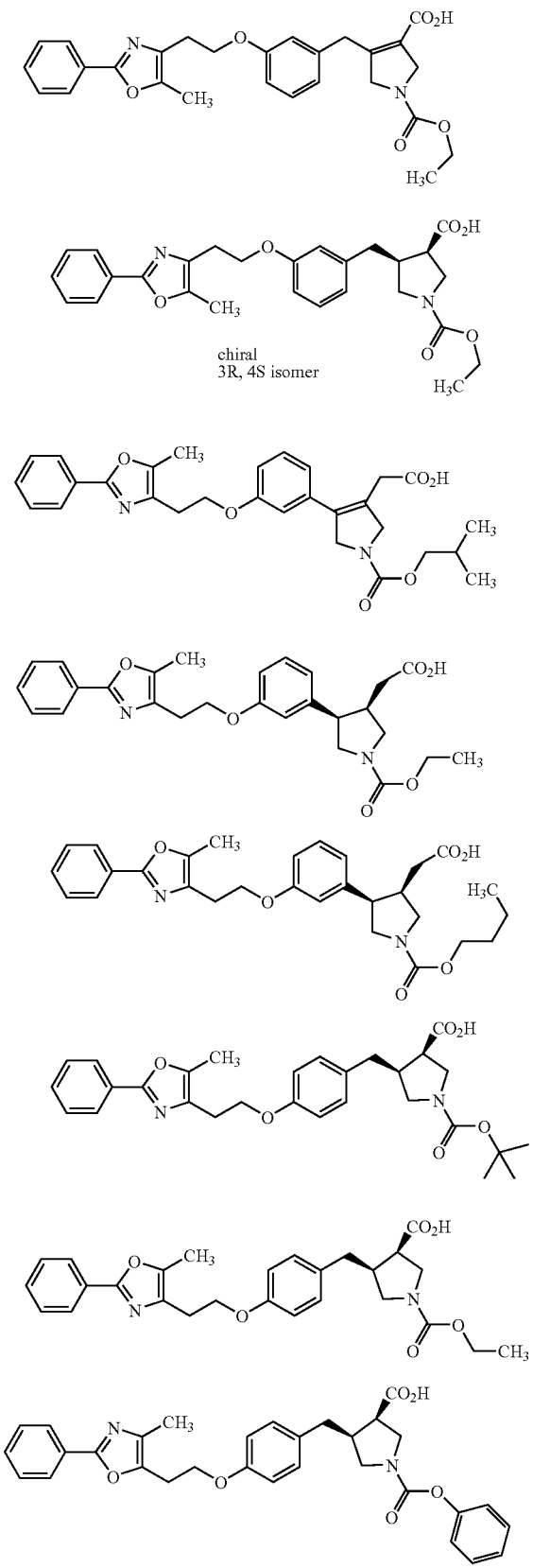
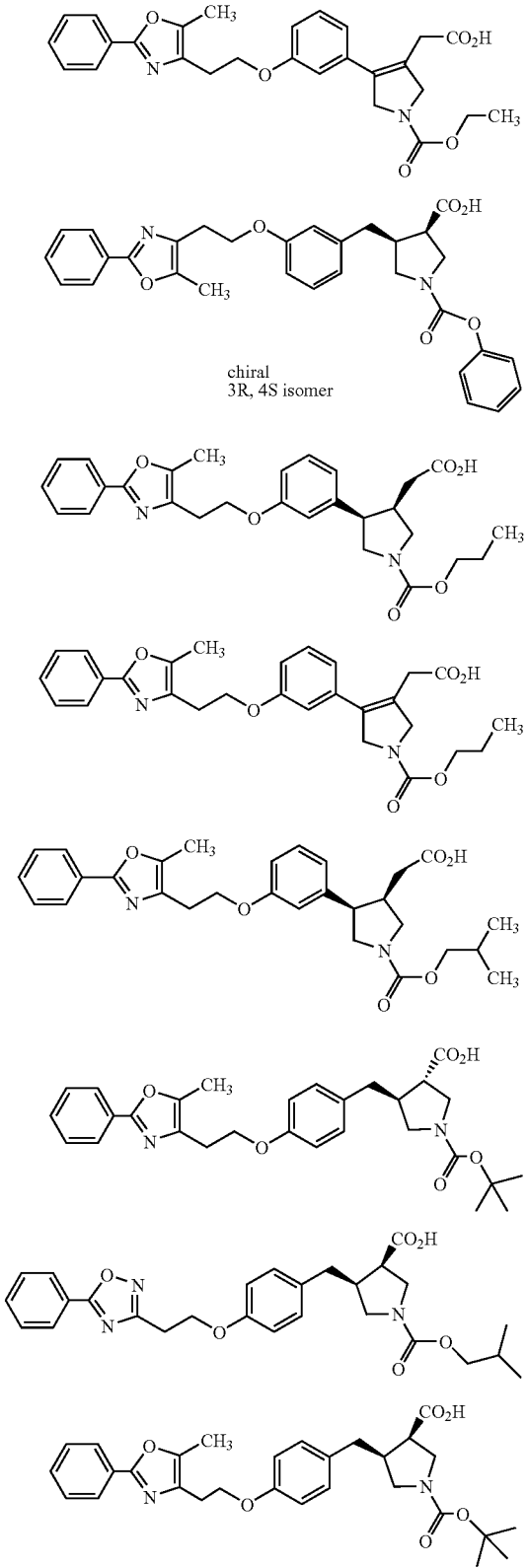

455
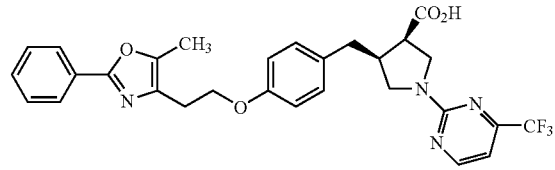
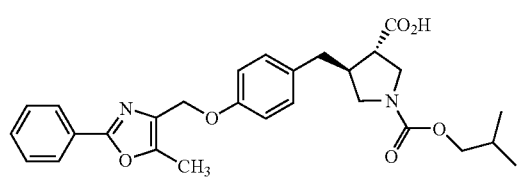
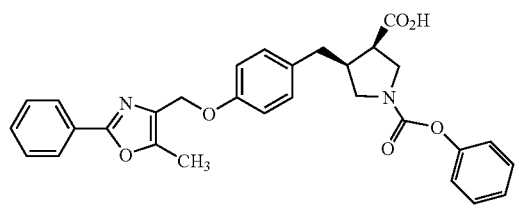
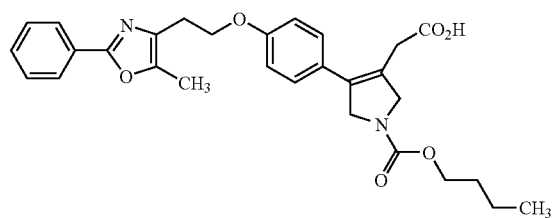
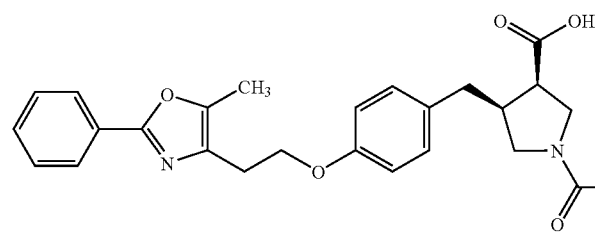
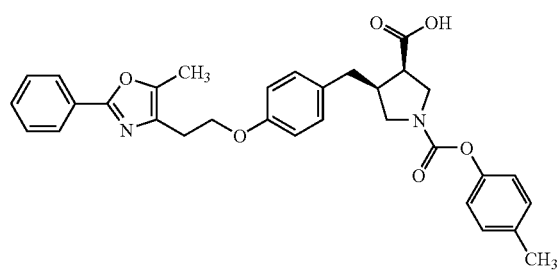
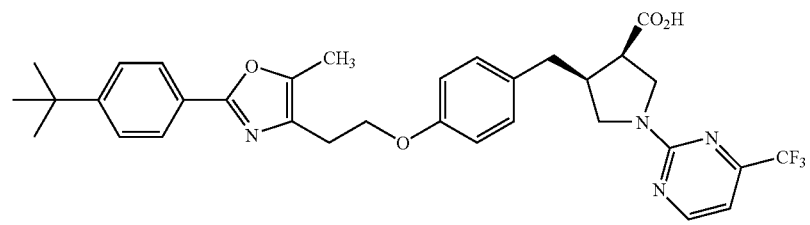
456
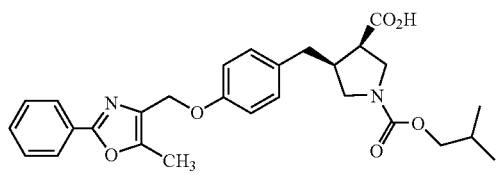
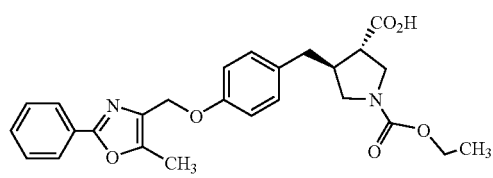
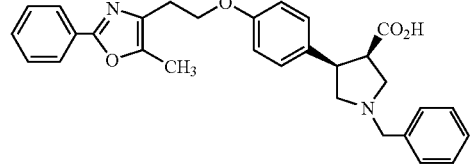
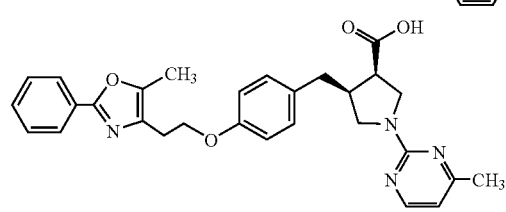
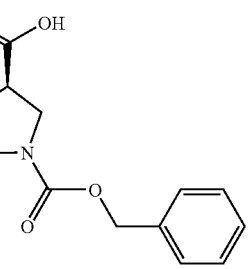
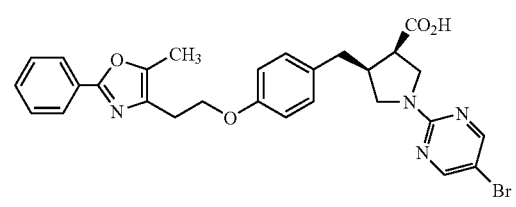
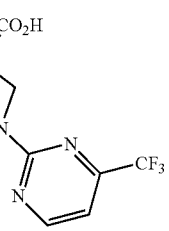

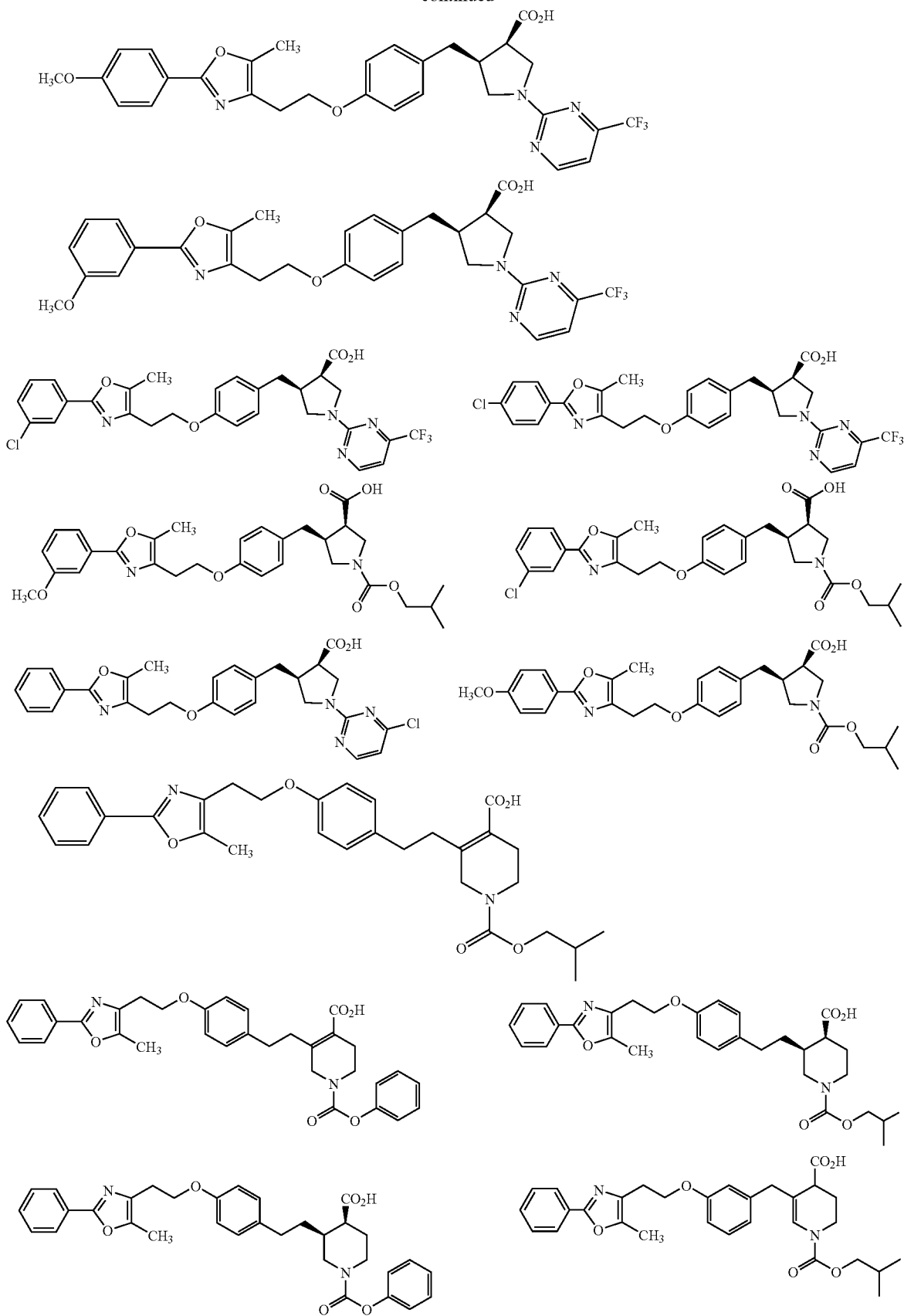

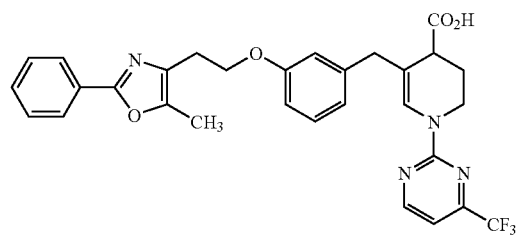
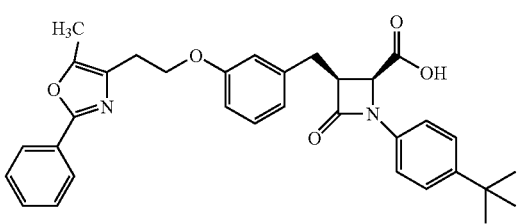
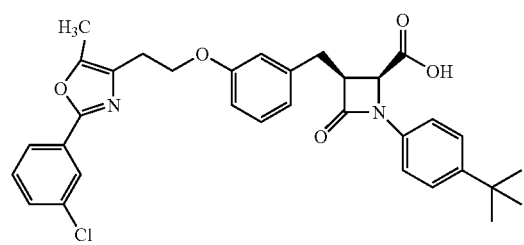
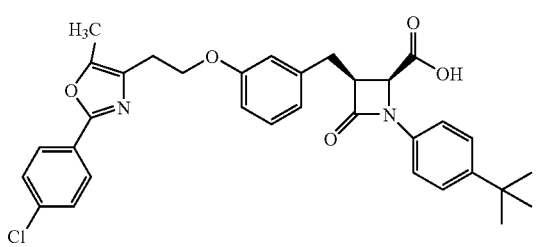
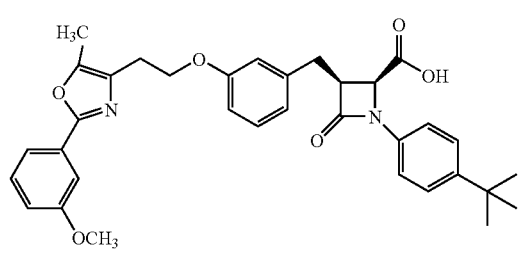
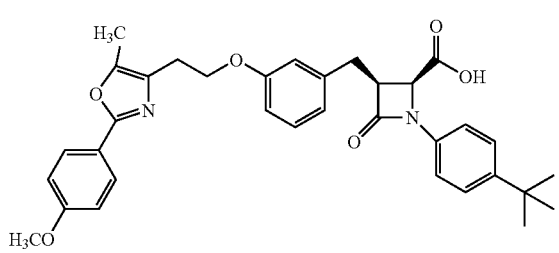
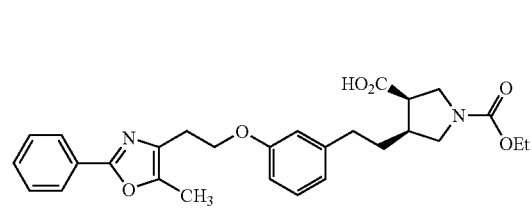
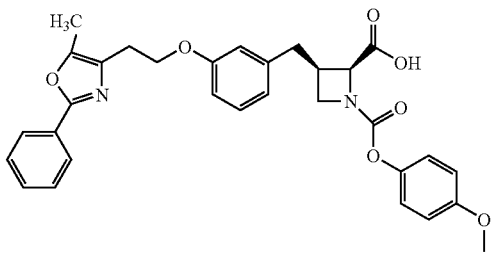
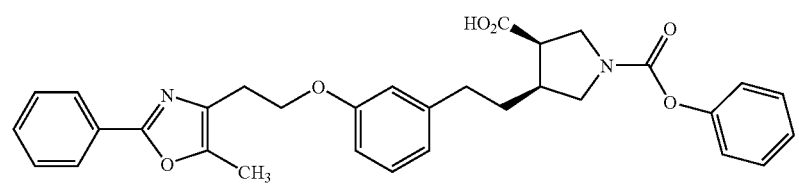
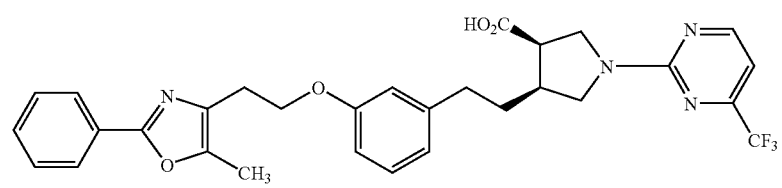
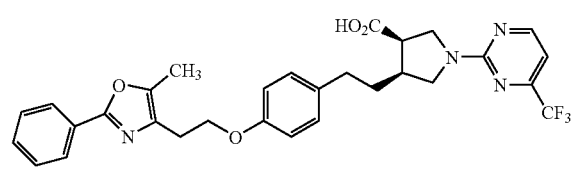
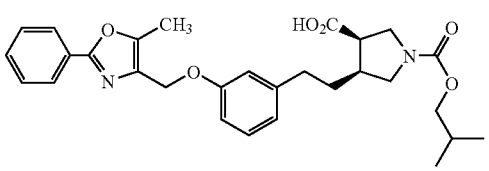

-continued

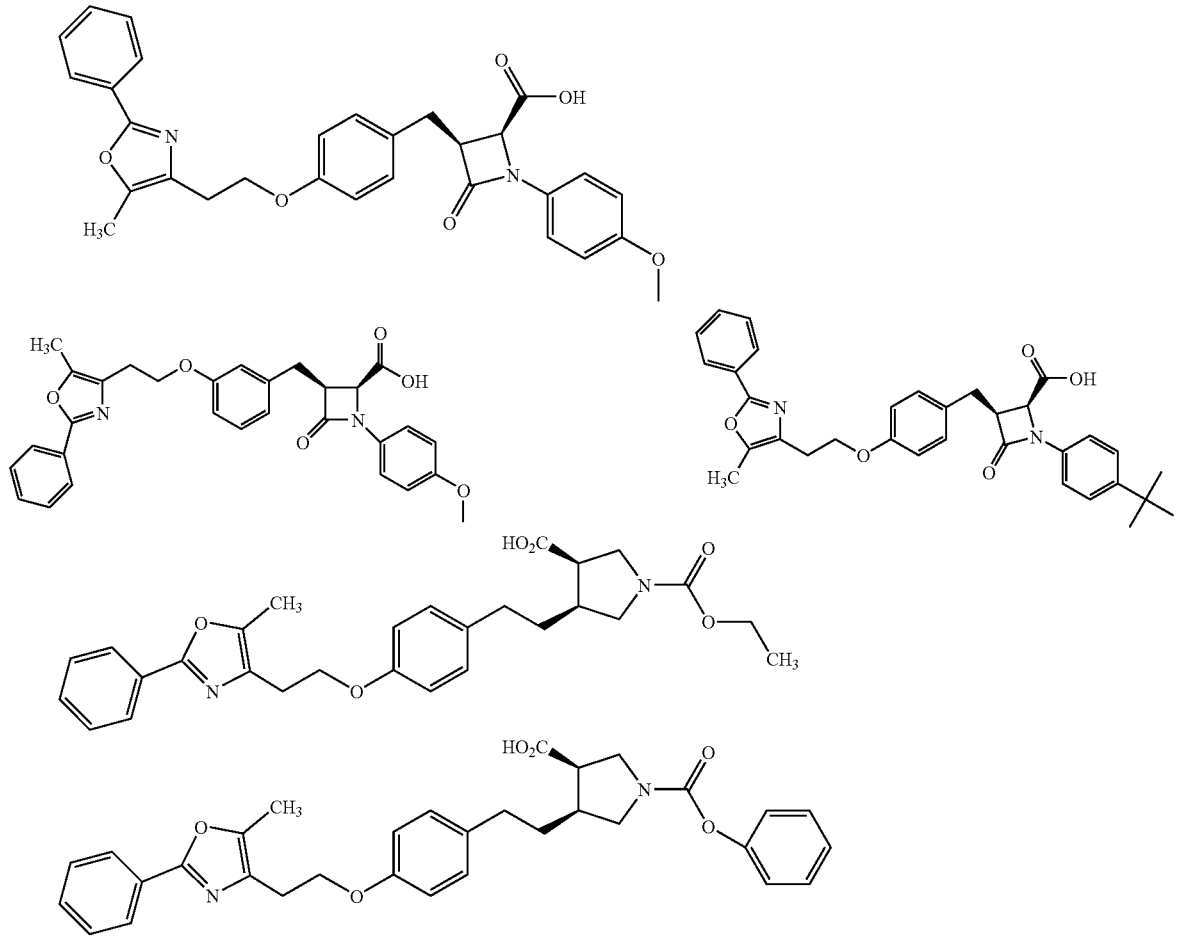

7. A pharmaceutical composition comprising a compound as defined in claim 1 and a pharmaceutically acceptable carrier therefor.

8. A method for treating diabetes, Type 2 diabetes, insulin resistance, hyperglycemia, hyperinsulinemia, elevated blood levels of fatty acids or glycerol, hyperlipidemia, obesity, hypertriglyceridemia, Syndrome X, or atherosclerosis, which comprises administering to a patient in need of such treatment a therapeutically effective amount of a compound as defined in claim 1.

9. A pharmaceutical composition comprising a compound as defined in claim and a lipid-lowering agent, an antidiabetic agent, an anti-obesity agent, an antihypertensive agent, a platelet aggregation inhibitor, or an antiosteoporosis agent.

10. The composition as defined in claim 9 wherein the antidiabetic agent is 1, 2, 3 or more of a biguanide; a sulfonyl urea; a glucosidase inhibitor; a PPAR γ agonist; a PPAR α/γ dual agonist; an SGLT2 inhibitor; a DP4 inhibitor; an a P2 inhibitor; an insulin sensitizer; a glucagon-like peptide-1 (GLP-1); insulin and/or a meglitinide; the anti-obesity agent is a beta 3 adrenergic agonist; a lipase inhibitor; a serotonin and/or dopamine reuptake inhibitor; a thyroid receptor agonist; a cannabinoid receptor-1 antagonist and/or an anorectic agent; the lipid lowering agent is an MTP inhibitor, an HMG CoA reductase inhibitor, a squalene synthetase inhibitor, a fibric acid derivative, an upregulator of LDL receptor activity, a lipoxygenase inhibitor, a farnesoid receptor (FXR) agonist, a liver X receptor (LXR) agonist, a CETP inhibitor or an ACAT inhibitor; the antihypertensive agent is an ACE inhibitor an angiotensin II receptor antagonist, a NEP/ACE inhibitor, a calcium channel blocker or a β-adrenergic blocker.

11. The composition as defined in claim 10 wherein the antidiabetic agent is 1, 2, 3 or more of metformin, glyburide, glimepiride, glipyride, glipizide, chlorpropamide, gliclazide, acarbose, miglitol, pioglitazone, rosiglitazone, balaglitazone, insulin, G1-262570, isaglitazone, JTT-501, NN-2344, L895645, YM-440, R-119702, AJ9677, repaglinide, nateglinide, KAD1129, AR-HO39242, GW-409544, KRP297, AZ-242, AC2993, LY315902, P32/98 and/or NVP-DPP-728A, the anti-obesity agent is orlistat, ATL-962, AJ9677, L750355, CP331648, sibutramine, topiramate, axokine, dexamphetamine, phentermine, phenylpropanolamine, rimonabant (SR-141716) and/or mazindol, the lipid lowering agent is pravastatin, lovastatin, simvastatin, atorvastatin, fluvastatin, itavastatin, visastatin, rosuvastatin, pitavastatin, fenofibrate, gemfibrozil, clofibrate, avasimibe, ezetimibe, TS-962, MD-700, cholestagel, niacin and/or LY295427, the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan, telinisartan or valsartan; amlodipine besylate, prazosin HCl, verapamil, nifedipine, nadolol, propranolol, carvedilol, or clonidine HCl, the platelet aggregation inhibitor is aspirin, clopidogrel, ticlopidine, dipyridamole or ifetroban.

* * * * *

UNITED STATES PATENT AND TRADEMARK OFFICE
CERTIFICATE OF CORRECTION

PATENT NO. : 7,279,485 B2  
APPLICATION NO. : 10/616365  
DATED : October 9, 2007  
INVENTOR(S) : Peter T. Cheng et al.

Page 1 of 1

It is certified that error appears in the above-identified patent and that said Letters Patent is hereby corrected as shown below:

In the Claims:

Claim 6, Col. 451, delete first compound.
Col. 453, delete first and third compounds.
Col. 454, delete first and fourth compounds.
Col. 455, delete fourth compound.
Col. 457, delete sixth, seventh and eighth compounds (last 3 compounds).
Col. 458, delete fourth and fifth compounds (last two compounds).
Col. 459, delete first, second and third compounds.
Col. 460, delete first, second, third and fourth compounds.
Col. 461, delete first and second compounds.
Col. 462, delete first compound.

Signed and Sealed this
Twelfth Day of July, 2011

David J. Kappos
*Director of the United States Patent and Trademark Office*